(12) United States Patent
Erion et al.

(10) Patent No.: US 7,514,419 B2
(45) Date of Patent: Apr. 7, 2009

(54) PHOSPHORUS-CONTAINING THYROMIMETICS

(75) Inventors: Mark D. Erion, Del Mar, CA (US); Hongjian Jiang, San Diego, CA (US); Serge H. Boyer, San Diego, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 173 days.

(21) Appl. No.: 11/137,773

(22) Filed: May 26, 2005

(65) Prior Publication Data

US 2006/0046980 A1 Mar. 2, 2006

Related U.S. Application Data

(63) Continuation-in-part of application No. PCT/US2004/039024, filed on Nov. 19, 2004.

(60) Provisional application No. 60/598,524, filed on Aug. 3, 2004, provisional application No. 60/523,830, filed on Nov. 19, 2003.

(51) Int. Cl.
  *A61K 31/66* (2006.01)
  *C07F 9/02* (2006.01)
(52) U.S. Cl. ......................... 514/140; 558/70
(58) Field of Classification Search .................. 558/70; 514/140
See application file for complete search history.

(56) References Cited

U.S. PATENT DOCUMENTS

| | | | |
|---|---|---|---|
| 3,120,551 A | 2/1964 | Goldschmidt et al. |
| 3,357,887 A | 12/1967 | Kagan et al. |
| 4,069,343 A | 1/1978 | Sellstedt et al. |
| 4,069,347 A | 1/1978 | McCarthy et al. |
| 4,423,227 A | 12/1983 | Batz et al. |
| 4,426,453 A | 1/1984 | Cree et al. |
| 4,554,290 A | 11/1985 | Boger et al. |
| 4,673,691 A | 6/1987 | Bachynsky et al. |
| 4,766,121 A | 8/1988 | Ellis et al. |
| 4,826,876 A | 5/1989 | Ellis et al. |
| 4,910,305 A | 3/1990 | Ellis et al. |
| 5,061,798 A | 10/1991 | Emmett et al. |
| 5,116,828 A | 5/1992 | Miura et al. |
| 5,158,978 A | 10/1992 | Rubin et al. |
| 5,232,946 A | 8/1993 | Hurnaus et al. |
| 5,284,971 A | 2/1994 | Walker et al. |
| 5,324,522 A | 6/1994 | Krenning et al. |
| 5,401,772 A | 3/1995 | Yokoyama et al. |
| 5,519,163 A * | 5/1996 | Gibbs et al. ................... 562/23 |
| 5,569,674 A | 10/1996 | Yokoyama et al. |
| 5,571,840 A | 11/1996 | Mayor et al. |
| 5,627,173 A | 5/1997 | Graeve et al. |
| 5,654,468 A | 8/1997 | Yokoyama et al. |
| 5,663,159 A | 9/1997 | Starrett, Jr. et al. |
| 5,741,803 A | 4/1998 | Pool et al. |
| 5,753,254 A | 5/1998 | Khan et al. |
| 5,854,282 A | 12/1998 | Mellin |
| 5,883,294 A | 3/1999 | Scanlan et al. |
| 5,922,775 A | 7/1999 | Kun et al. |
| 5,951,989 A | 9/1999 | Heymann |
| 6,107,517 A | 8/2000 | Scanlan et al. |
| 6,117,873 A | 9/2000 | Acklin et al. |
| 6,194,454 B1 | 2/2001 | Dow |
| 6,221,911 B1 | 4/2001 | Lavin et al. |
| 6,236,946 B1 | 5/2001 | Scanlan et al. |
| 6,266,622 B1 | 7/2001 | Scanlan et al. |
| 6,326,398 B1 | 12/2001 | Chiang et al. |
| 6,344,481 B1 | 2/2002 | Cornelius et al. |
| 6,361,992 B1 | 3/2002 | Szkudlinski et al. |
| 6,380,255 B1 | 4/2002 | Lavin et al. |
| 6,414,002 B1 | 7/2002 | Cheng et al. |
| 6,414,026 B1 | 7/2002 | Billingham |
| 6,441,015 B2 | 8/2002 | Aspnes et al. |
| 6,465,687 B1 | 10/2002 | Li et al. |
| 6,468,755 B1 | 10/2002 | Shoelson |
| 6,492,424 B1 | 12/2002 | Apelqvist et al. |
| 6,495,533 B1 * | 12/2002 | Matsui et al. ................ 514/120 |
| 6,534,676 B2 | 3/2003 | Morkin et al. |
| 6,545,015 B2 | 4/2003 | Cheng et al. |
| 6,545,018 B2 | 4/2003 | Chiang et al. |
| 6,555,582 B1 | 4/2003 | Schwartz et al. |
| 6,566,372 B1 | 5/2003 | Zhi et al. |
| 6,608,049 B2 | 8/2003 | Woltering et al. |
| 6,620,830 B2 | 9/2003 | Chiang |

(Continued)

FOREIGN PATENT DOCUMENTS

EP 0580550 A1 7/1993

(Continued)

OTHER PUBLICATIONS

Ryono et al., 2004, CAS: 927006.*
Ibbrhimi et al., 2000, CAS: 133:14000.*
Hopper et al.,, 1999, CAS: 130:332269.*
Auberson, Y.P. et al., "N-Phosphonoalkyl-5-Aminomethylquinoxaline-2,3-Diones: In Vivo Active AMPA and NMDA(Glycine) Antagonists," *Bioorg. Med. Chem. Lett.* 9:249-254, Elsevier Science Ltd. (1999).

(Continued)

*Primary Examiner*—Rei-tsang Shiao
(74) *Attorney, Agent, or Firm*—Arnold & Porter LLP

(57) ABSTRACT

The present invention relates to compounds of phosphonic acid-containing T3 mimetics and monoesters thereof, stereoisomers, pharmaceutically acceptable salts, co-crystals, and prodrugs thereof and pharmaceutically acceptable salts and co-crystals of the prodrugs, as well as their preparation and uses for preventing and/or treating metabolic diseases such as obesity, NASH, hypercholesterolemia and hyperlipidemia, as well as associated conditions such as atherosclerosis, coronary heart disease, impaired glucose tolerance, metabolic syndrome x and diabetes.

18 Claims, 13 Drawing Sheets

U.S. PATENT DOCUMENTS

| | | |
|---|---|---|
| 6,664,291 B2 | 12/2003 | Chiang et al. |
| 6,673,815 B2 | 1/2004 | Devasthale et al. |
| 6,680,340 B2 | 1/2004 | Cheng et al. |
| 6,689,896 B2 | 2/2004 | Kukkola |
| 6,716,877 B2 | 4/2004 | Morkin |
| 6,723,744 B2 | 4/2004 | Aspnes et al. |
| 6,727,271 B2 | 4/2004 | Cheng et al. |
| 6,747,048 B2 | 6/2004 | Zhang et al. |
| 6,787,652 B1 | 9/2004 | Dow et al. |
| 6,794,406 B2 | 9/2004 | Haning et al. |
| 6,806,381 B2 | 10/2004 | Chidambaram et al. |
| 6,825,201 B2 * | 11/2004 | Wang et al. ............ 514/254.06 |
| 6,831,102 B2 | 12/2004 | Hangeland |
| 6,852,706 B1 | 2/2005 | Heber-Katz |
| 6,875,782 B2 | 4/2005 | Cheng et al. |
| 6,982,348 B2 | 1/2006 | Kori et al. |
| 7,015,246 B2 | 3/2006 | Schmeck et al. |
| 2001/0051645 A1 | 12/2001 | Chiang et al. |
| 2001/0051657 A1 | 12/2001 | Chiang et al. |
| 2002/0006946 A1 | 1/2002 | Aspnes et al. |
| 2002/0045751 A1 | 4/2002 | Kukkola |
| 2002/0049226 A1 | 4/2002 | Chiang et al. |
| 2002/0107390 A1 | 8/2002 | Kukkola |
| 2002/0123521 A1 | 9/2002 | Lavin |
| 2003/0027862 A1 | 2/2003 | Haning et al. |
| 2003/0040535 A1 | 2/2003 | Aspnes et al. |
| 2003/0078288 A1 | 4/2003 | Haining et al. |
| 2003/0078289 A1 | 4/2003 | Aspnes et al. |
| 2003/0114521 A1 | 6/2003 | Chiang et al. |
| 2003/0153513 A1 | 8/2003 | Shiomi et al. |
| 2003/0166724 A1 | 9/2003 | Hangeland |
| 2004/0029187 A1 | 2/2004 | Palmer |
| 2004/0039028 A1 | 2/2004 | Zhang et al. |
| 2004/0077694 A1 | 4/2004 | Chiang et al. |
| 2004/0097589 A1 | 5/2004 | Yi-Lin et al. |
| 2004/0110951 A1 | 6/2004 | Chiang |
| 2004/0116387 A1 | 6/2004 | Malm et al. |
| 2004/0116391 A1 | 6/2004 | Piccariello et al. |
| 2004/0142868 A1 | 7/2004 | Sleeman |
| 2004/0152783 A1 | 8/2004 | Olon et al. |
| 2004/0157844 A1 | 8/2004 | Dow et al. |
| 2004/0219218 A1 | 11/2004 | Martino et al. |
| 2004/0220147 A1 | 11/2004 | Malm et al. |
| 2005/0004184 A1 | 1/2005 | Ryono et al. |
| 2005/0038122 A1 | 2/2005 | Hangeland |
| 2005/0054727 A1 | 3/2005 | Hangeland |
| 2005/0085541 A1 | 4/2005 | Shiohara et al. |

FOREIGN PATENT DOCUMENTS

| | | |
|---|---|---|
| EP | 0580550 A1 | 1/1994 |
| EP | 1 297 833 | 4/2003 |
| EP | 1 471 049 | 10/2004 |
| EP | 1 666 035 A1 | 6/2006 |
| WO | WO 89/08458 A1 | 9/1989 |
| WO | WO 90/08155 | 7/1990 |
| WO | WO 90/10636 | 9/1990 |
| WO | WO 91/06569 A1 | 5/1991 |
| WO | WO 91/11181 A1 | 8/1991 |
| WO | WO 95/00135 A1 | 1/1995 |
| WO | WO 95/24919 A1 | 9/1995 |
| WO | WO 96/05190 A1 | 2/1996 |
| WO | WO 96/40048 A2 | 12/1996 |
| WO | WO 97/21993 A2 | 6/1997 |
| WO | WO 98/07435 A1 | 2/1998 |
| WO | WO 98/41216 A1 | 9/1998 |
| WO | WO 98/57919 A1 | 12/1998 |
| WO | WO 99/00353 A1 | 1/1999 |
| WO | WO 99/26966 A2 | 6/1999 |
| WO | WO 99/29321 A1 | 6/1999 |
| WO | WO 99/38376 A1 | 8/1999 |
| WO | WO 99/45016 A1 | 9/1999 |
| WO | WO 99/62507 A1 | 12/1999 |
| WO | WO 00/00468 A1 | 1/2000 |
| WO | WO 00/07972 A1 | 2/2000 |
| WO | WO 00/39077 A2 | 7/2000 |
| WO | WO 00/51971 A1 | 9/2000 |
| WO | WO 00/52015 A1 | 9/2000 |
| WO | WO 00/58279 A1 | 10/2000 |
| WO | WO 01/13936 A1 | 3/2001 |
| WO | WO 01/18013 A1 | 3/2001 |
| WO | WO 01/36365 A2 | 5/2001 |
| WO | WO 01/60784 A1 | 8/2001 |
| WO | WO 01/72692 A1 | 10/2001 |
| WO | WO 01/79287 A2 | 10/2001 |
| WO | WO 01/94293 A2 | 12/2001 |
| WO | WO 01/98256 A1 | 12/2001 |
| WO | WO 02/03914 A2 | 1/2002 |
| WO | WO 02/04515 A1 | 1/2002 |
| WO | WO 02/05834 A2 | 1/2002 |
| WO | WO 02/11666 | 2/2002 |
| WO | WO 02/26752 A1 | 4/2002 |
| WO | WO 02/32408 A2 | 4/2002 |
| WO | WO 02/060374 A2 | 8/2002 |
| WO | WO 02/062780 A2 | 8/2002 |
| WO | WO 02/066017 A1 | 8/2002 |
| WO | WO 02/072528 A1 | 9/2002 |
| WO | WO 02/079181 A1 | 10/2002 |
| WO | WO 02/092550 A1 | 11/2002 |
| WO | WO 03/003013 A1 | 1/2003 |
| WO | WO 03/015771 A1 | 2/2003 |
| WO | WO 03/018515 A2 | 3/2003 |
| WO | WO 03/039456 A2 | 5/2003 |
| WO | WO 03/061557 A2 | 7/2003 |
| WO | WO 03/061567 | 7/2003 |
| WO | WO 03/070169 A2 | 8/2003 |
| WO | WO 03/075835 A2 | 9/2003 |
| WO | WO 03/084915 A1 | 10/2003 |
| WO | WO 03/094845 A2 | 11/2003 |
| WO | WO 03/099864 A1 | 12/2003 |
| WO | WO 03/105760 A2 | 12/2003 |
| WO | WO 2004/007430 A2 | 1/2004 |
| WO | WO 2004/014318 A2 | 2/2004 |
| WO | WO 2004/018421 A1 | 3/2004 |
| WO | WO 2004/026097 A2 | 4/2004 |
| WO | WO 2004/041208 A2 | 5/2004 |
| WO | WO 2004/065620 A2 | 8/2004 |
| WO | WO 2004/066929 A2 | 8/2004 |
| WO | WO 2004/067482 A2 | 8/2004 |
| WO | WO 2004/078947 A2 | 9/2004 |
| WO | WO 2004/091636 A1 | 10/2004 |
| WO | WO 2004/093799 A2 | 11/2004 |
| WO | WO 2004/103289 A2 | 12/2004 |
| WO | WO 2005/009433 A1 | 2/2005 |
| WO | WO 2005/016862 | 2/2005 |
| WO | WO 2005/027895 A2 | 3/2005 |
| WO | WO 2005/028488 A1 | 3/2005 |
| WO | WO 2005/042556 A1 | 5/2005 |
| WO | WO 2005/051298 A2 | 6/2005 |
| WO | WO 2005/123729 | 12/2005 |
| WO | WO 2006/128055 | 11/2006 |
| WO | WO 2006/128056 | 11/2006 |
| WO | WO 2006/128058 | 11/2006 |
| WO | WO 2007/009913 A1 | 1/2007 |

OTHER PUBLICATIONS

Blennemann, B., et al., "Tissue-Specific Regulation of Fatty Acid Synthesis by Thyroid Hormone," *Endocrinology* 130:637-643, The Endocrine Society (1992).

Collazo, A-M.G., et al., "Thyroid receptor ligands. Part 5: Novel bicyclic agonist ligands selective for the thyroid hormone receptor β" *Bioorg. Med. Chem. Lett.* 16:1240-1244, Elsevier Ltd. (Mar. 2006).

Danzi, S., et al., "Triiodothyronine-mediated myosin heavy chain gene transcription in the heart," *Am. J. Physiol. Heart Circ. Physiol.* 284:H2255-H2262, The American Physiological Society (Feb. 2003).

Erion, M.D., et al., "Design, Synthesis, and Characterization of a Series of Cytochrome $P_{450}$ 3A-Activated Prodrugs (HepDirect Prodrugs) Useful for Targeting Phosph(on)ate-Based Drugs to the Liver," *J. Am. Chem. Soc.* 126:5154-5163, American Chemical Society (Apr. 2004).

Erion, M.D., et al., "Liver-Targeted Drug Delivery Using HepDirect Prodrugs" *J. Pharmacol. Exper. Ther.* 312:554-560, American Society for Pharmacology and Experimental Therapeutics (Feb. 2005).

Goglia, F., "Biological Effects of 3,5-Diiodothyronine ($T_2$)," *Biochemistry (Moscow)* 70:164-172, Consultants Bureau (Feb. 2005).

Grover, G.J., et al., "Selective thyroid hormone receptor-β activation: A strategy for reduction of weight, cholesterol, and lipoprotein (a) with reduced cardiovascular liability," *PNAS* 17:10067-10072, National Academy of Sciences (Aug. 2003).

Hume, J.R., et al., "Anion Transport in Heart," *Physiological Reviews* 80:31-81, The American Physiological Society (2000).

Sass, D.A., et al., "Nonalcoholic Fatty Liver Disease: A Clinical Review," *Dig. Dis. Sci.* 50:171-180 Springs Science Business Media, Inc. (Jan. 2005).

Webb, P., et al., "Design of thyroid hormone receptor antagonists from first principles," *J. Steroid Biochem. Molec. Biol.* 83:59-73, Elsevier Science Ltd. (Dec. 2003).

Ye, L., et al., "Thyroid Receptor Ligands. 1. Agonist Ligands Selective for the Thyroid Receptor $β_1$," *J. Med. Chem.* 46:1580-1588, American Chemical Society (Apr. 2003).

Amma, L.L., et al., "Distinct Tissue-Specific Roles for Thyroid Hormone Receptors β and α1 in Regulation of Type 1 Deiodinase Expression," *Mol. Endocrinol.* 15:467-475, The Endocrine Society (2001).

Anderson, S.N., et al., "Activation of Electrophilic Aromatic Substitution by the Substituent $-CH_2Co(dmgH)_2py$. Products of Reaction of Benzylcobaloximes with Halogens in Acetic Acid," *J. Chem. Soc. Perkin Trans. II* 311-318, Royal Society of Chemistry (1972).

Annett, R.G., et al., "Enzymatically catalysed decarboxylation of β-carboxyaspartic acid (Asa)," *Can. J. Chem.* 68:886-887, NRC Research Press (1990).

Antons, K.A., et al., "Clinical Perspectives of Statin-Induced Rhabdomyolysis," *Am. J. Med.* 119:400-409, Excerpta Medica (May 2006).

Apriletti, J.W., et al., "Molecular and Structural Biology of Thyroid Hormone Receptors," *Clin. Exp. Pharmacol. Physiol.* 25:S2-S11, Blackwell Science Asia (1998).

Archer, S.J., et al., "Hepatitis C Virus NS3 Protease Requires Its NS4A Cofactor Peptide for Optimal Binding of a Boronic Acid Inhibitor as Shown by NMR," *Chem. Biol.* 9:79-92, Elsevier Science Ltd. (Jan. 2002).

Arnold, S., et al., "3,5-Diiodothyronine binds to subunit Va of cytochrome-c oxidase and abolishes the allosteric inhibition of respiration by ATP," *Eur. J. Biochem.* 252:325-330, Blackwell Science Ltd. (1998).

Arnold, L.A., et al., "Discovery of Small Molecule Inhibitors of the Interaction of the Thyroid Hormone Receptor with Transcriptional Coregulators," *J. Biol. Chem.* 280:43048-43055, American Society for Biochemistry and Molecular Biology (Dec. 2005).

Auerbach, B.J., et al., "Comparative Effects of HMG-CoA reductase inhibitors on apo B production in the casein-fed rabbit: Atorvastatin versus Lovastatin," *Atherosclerosis* 115:173-180, Elsevier Science Ltd. (1995).

Ayajiki, K., et al., "Endothelial and Neuronal Functions in Cerebral and Temporal Arteries from Monkeys Fed a High Cholesterol Diet," *J. Cardiovascular Pharmacol.* 40:456-466, Lippincott Williams & Wilkins (Sep. 2002).

Ball, S.G., et al., "3,5-Diiodo-L-thyronine ($T_2$) has selective thyromimetic effects in vivo and in vitro," *J. Mol. Endocrinol.* 19:137-147, Society for Endocrinology (1997).

Baxter, J.D., et al., "Structure-Based Design and Synthesis of a Thyroid Homone Receptor (TR) Antagonist," *Endocrinology* 143:517-524, Endocrine Society (Feb. 2002).

Beg, M.A.A. and Clark, H.C., "Chemistry of the Trifluoromethyl Group, Part III. Phenyltrifluoromethylphospine and Related Compounds," *Can. J. Chem.* 39:564-570, NRC Research Press (1962).

Beg, M.A.A. and Clark, H.C., "Chemistry of the Trifluoromethyl Group, Part IV. Diphenyltrifluoromethylphophine and Complex Formation by Phenyltrifluoromethylphospines," *Can. J. Chem.* 40:283-288, NRC Research Press (1962).

Benayoud, F. and Hammond, G.B., "An expedient synthesis of (α,α-difluoroprop-2-ynyl) phosphonate esters," *Chem. Commun.* 1447-1448, Royal Society of Chemistry (1996).

Bianco, A.C., et al., "Biochemistry, Cellular and Molecular Biology, and Physiolgical Roles of the Iodothyronine Selenodeiodinases," *Endocrine Rev.* 2338-39, The Endocrine Society (Feb. 2002).

Bilger, C., et al., "A Convenient One-Pot Synthesis of Aralkyl Bromides and Iodides by Reductive Halogenation of Aromatic Carbonyl Compounds," *Synthesis* 902-904, Georg Thieme Verlag (1988).

Bobyleva, V., et al., "Decrease in mitochondrial energy coupling by thyroid hormones: a physiological effect rather than a pathological hyperthyroidism consequence," *FEBS Lett.* 430:409-413, Elsevier Science Ltd. (1998).

Bocan, T.M.A., et al., "HMG-CoA reductase and ACAT inhibitors act synergistically to lower plasma cholesterol and limit atherosclerotic lesion development in the cholesterol-fed rabbit," *Atherosclerosis* 139:21-30, Elsevier Science Ltd. (1998).

Bogardus, J.B. and Higuchi, T., "Kinetics and Mechanism of Hydrolysis of Labile Quaternary Ammonium Derivatives of Tertiary Amines," *J. Pharm. Sci.* 71:729-735, Wiley (1982).

Bohmer, V. and Vogt, W., "7.(o-Hydroxyphenyl)methylphosphonic acids: Synthesis and Potentiometric Determination of their pKa Values," *Helvetica Chimica Acta* 76:139-149, Verlag Helvetica Chimica Acta (1993).

Boyd, E.A., et al., "Facile Synthesis of Functionalised Phenylphosphinic Acid Derivatives," *Tetrahedron Lett.* 37:1651-1654, Elsevier Science Ltd. (1996).

Boyd, E.A. and Regan, A.C., "Synthesis of γ-Keto-substituted Phosphinic Acids from Bis(trimethylsilyl)phosphonite and α,β-Unsaturated Ketones," *Tetrahedron Lett.* 332:813-816, Elsevier Science Ltd. (1992).

Briel, D., et al., "3-Amino-5-phenoxythiophenes: Syntheses and Structure-Function Studies of a Novel Class of Inhibitors of Cellular L-Triiodothyronine Uptake," *J. Med. Chem.* 42:1849-1854, American Chemical Society (1999).

Brown, K., et al., "Accelerator Mass Spectrometry for Biomedical Research," *Meth. Enzymol.* 402:423-443, Academic Press (Nov. 2005).

Christian, M.S. and Trenton, N.A., "Evaluation of thyroid function in neonatal and adult rats: The neglected endocrine mode of action," *Pure Appl. Chem.* 75:2055-2068, International Union of Pure and Applied Chemistry (Nov. 2003).

Cimmino, M., et al., "Demonstration of in vivo metabolic effects of 3,5-di-iodothyronine," *J. Endocrinol.* 149:319-325, Society for Endocrinology (1996).

Clutterbuck, P.W. and Cohen, J.B., "The Aryl and Alkyl Sulphonamides," *J. Chem. Soc.* 123:2507-2515, Royal Society of Chemistry (1923).

Columbano, A., et al., "The Thyroid Hormone Receptor-β Agonist GC-1 Induces Cell Proliferation in Rat Liver and Pancreas," *Endocrinology* 147:3211-3218, Endocrine Society (Mar. 2006).

Corrie, J.E.T. and Trentham, D.R., "Synthetic, Mechanistic and Photochemical Studies of Phosphate Esters of Substituted Benzoins," *J. Chem. Soc. Perkin Trans. 1*: 2409-2417, Chemical Society (1992).

Crimmins, M.T., et al., "Asymmetric Aldol Additions: Use of Titanium Tetrachloride and (-)-Sparteine for the Soft Enolization of N-Acyl Oxazolidinones, Oxazolidinethiones, and Thiazolidinethiones," *J. Org. Chem.* 66:894-902, American Chemical Society (2001).

Croxall, W.J., et al., "Organic Reactions with Boron Fluoride. XI. The Condensation of Propylene with m-and p-Hydroxybenzoic acids," *J. Am. Chem. Soc.* 57:1549-1551, American Chemical Society (1935).

Database Beilstein, (Online), Beilstein Registry No. 7222862, 6 pages, Beilstein Institute for Organic Chemistry, Frankfurt-Main, DE.

Database Beilstein, (Online), Beilstein Registry No. 7505261, 2 pages, Beilstein Institute for Organic Chemistry, Frankfurt-Main, DE.

Database Beilstein, (Online), Beilstein Registry No. 6636402, 4 pages, Beilstein Institute for Organic Chemistry, Frankfurt-Main, DE.

Database CAplus, Chemical Abstract Service, Columbus Ohio, Enrion, M.D., et al., "Preparation of phosphonic acid-containing liver-selective thyromimetics effective against metabolic diseases," WO 2005-0512986, 16 pages (created Jun. 2005).

Davis, R. and Untch, K.G., "Direct one-step Conversion of Alcohols into Nitriles," *J. Org. Chem.* 46:2985-2987, American Chemical Society (1981).

Davis, P.J., et al., "Comparison of the mechanisms of nongenomic actions of thyroid hormone and steroid hormones," *J. Endocrinol. Invest.* 25: 377-388, Italian Society of Endocrinology (Apr. 2002).

De Brabandere, V.I., et al., "Isotope Dilution-Liquid Chromatography/Electrospray Ionization-Tandem Mass Spectrometry for the Determination of Serum Thyroxine as a Potential Reference Method," *Rapid Commun. Mass Spectrometry* 12:1099-1103, Wiley (1998).

De Sandro, V., et al., "Comparison of the Effects of Propylthiouracil, Amiodarone, Diphenylhydantoin, Phenobarbital, and 3-Methylcholanthrene on Hepatic and Renal T4 Metabolism and Thyroid Gland Function in Rats," *Toxicol. Appl. Pharmacol.* 111:263-278, Academic Press (1991).

Demori, I., et al., "3,-5-diiodothyronine Mimics the Effect of Triiodothyronine on Insulin-like growth Factor Binding Protein-4 Expression in Cultured Rat Hepatocytes," *Horm. Metab. Res.* 36:679-685, Georg Thieme Verlag (Oct. 2004).

Depréle, S. and Montchamp, J.-L., "A novel and convenient preparation of hypophosphite esters," *J. Organometallic Chem.* 646-644:154-163, Elsevier Science Ltd. (Aug. 2002).

Dhawan, B. and Redmore, D., "1,2-Alkanediol Bis(Dihydrogen Phosphates)," *Synth. Commun.* 18:327-331, Georg Thieme Verlag (1988).

Dingwall, J.G., et al., "Diethoxymethylphosphonites and Phospinates. Intermediates for the Synthesis of α,β-and γ-Aminoalkylphosphonous Acids," *Tetrahedron* 45:3787-3808, Pergamon Press (1989).

DiStefano III, J.J. and Feng, D., "Comparative Aspects of the Distrubution, Metabolism, and Excretion of Six Iodothyronines in the Rat," *Endocrinology* 123:2514-2525, Endocrine Society (1988).

Docter, R., et al., "Inhibition of Uptake of Thyroid Hormone into Rat Hepatocytes by Preincubation with N-Bromoacetyl-3,3',5-Triiodothyronine," *Endocrinology* 123:1520-1525, The Endocrine Society (1988).

Dow, R.L., et al., "Discovery of a Novel Series of 6-Azauracil-Based Thyroid Hormone Receptor Ligands: Potent, TRβ Subtype-Selective Thyromimetics," *Bioorg. Med. Chem. Lett.* 13:379-382, Elsevier Science Ltd. (Nov. 2003).

Drechsler, U. and Hanack, M., "An Easy Route from Catechols to Phthalonitriles," *Synett* 1207-1208, Georg Thieme Verlag (1998).

Earle, M.J., et al., "The first high yield green route to a pharmaceutical in a room temperature ionic liquid," *Green Chem.* 2:261-262, Royal Society of Chemistry (2000).

Ebdrup, S., et al., "Structure-activity relationship for aryl and heteroarly boronic acid inhibitors of homone-sensitive lipase," *Bioorg. Med. Chem.* 13:2305-2312, Elsevier Science Ltd. (Jan. 2005).

Edwards, M.L., et al., "Difluoromethyldiphenylphosphine oxide. A new reagent for conversion of carbonyl compounds to 1,1 -difluoroolefins," *Tetrahedron Lett.* 31:5571-5574, Elsevier Science Ltd. (1990).

Eisch, J.J., et al., "Rearrangement and Cleavage of [(Aryloxy)methyl]silanes by Organolithium Reagents: Conversion of Phenols into Benzylic Alcohols," *J. Org. Chem.* 47:5051-5056, American Chemical Society (1982).

Ekins, R., "Validity of Analog Free Thyroxin Immunoassays" *Clin. Chem.* 33:2137-2152, American Association For Clinical Chemistry (1987).

Fabiano, E., et al., "A Simple Conversion of Alcohols into Amines," *Synthesis* 190-192, Georg Thieme Verlag (1987).

Faergemann, J., et al., "Dose-Response Effects of Tri-iodothyroacetic Acid (Triac) and other Thyroid Hormone Analogues on Glucocorticoid-Induced Skin Atrophy in the Haired Mouse," *Acta Derm. Venereol.* 82:179-183, Society for the Publication of Acta Dermato-Venereologica (Mar. 2002).

Farquhar, D., et al., "Biologically-Cleavable Phosphate Protective Groups: 4-Acyloxy-1,3,2-Dioxaphosphorinaanes as Neutral Latent Precursors of Dianionic Phosphates," *Tetrahedron Lett.* 36:655-658, Elsevier Science Ltd. (1995).

Feinstein, S., et al., "Submitral Atheromatous Lesions in Monkey and Man", *Clin. Cardiol.* 6:109-115, John Wiley & Sons, Inc. (1983).

Feng, W., et al., "Hormone-Dependent Coactivator Binding to a Hydrophobic Cleft on Nuclear Receptors," *Science* 280:1747-1749, American Association for the Advancement of Science (1998).

Field, L.D. and Wilkinson, M.P., "A new Synthesis of 1,2-Bis(Bis(Trifluoromethyl)Phosphino)ethane," *Tetrahedron Lett.* 33:7601-7604, Elsevier Science Ltd. (1992).

Fieser, L.F. and Ardao, M.I., "Investigation of the Chemical Nature of Gonyleptidine," *J. Am. Chem. Soc.* 78:774-781, American Chemical Society (1956).

Fleischmann, K., et al., "Synthesis of HR 916 B: The First Technically Feasible Route to the 1-(Pivaloyloxy)ethyl Esters of Cephalosporins," *Liebigs Ann.* 1735-1741, Verlag Chemie (1996).

Fong, T.-L., et al., "Hyperthyroidism and Hepatic Dsfunction," *J. Clin. Gastroenterol.* 14:240-244, Raven Press (1992).

Freitas, F.R.S., et al., "Spared bone mass in rats treated with thyroid hormone receptor TRβ-selective compound GC-1," *Am. J. Physiol. Endocrinol. Metab.* 285:E1135-E1141, American Physiological Society (Sep. 2003).

Freitas, F.R.S., et al., "The Thyroid Hormone Receptor β-Specific Agonist GC-1 Selectivity Affects the Bone Development of Hypothyroid Rats," *J. Bone Mineral Res.* 20:294-304, American Society for Bone and Mineral Research (Nov. 2004).

Froestl, W., et al., "Phosphinic Acid Analogues of GABA. 1. New Potent and Selective $GABA_B$ Agonists," *J. Med. Chem.* 38:3297-3312, American Chemical Society (1995).

Froestl, W., et al., "Phosphinic Acid Analogues of GABA. 2. Selective, Orally Active $GABA_B$ Antagonists," *J. Med. Chem.* 38:3313-3331, American Chemical Society (1995).

Gallagher, M.J. and Honegger, H., "Organophosphorus Intermediates. VI. The Acid-Catalysed Reaction of Trialkyl Orthoformates with Phosphinic Acid," *Aust. J. Chem.* 33:287-294, Commonwealth Scientific And Industrial Research Organization (1980).

Gilman, H. and Calloway, N.O., "Super-Aromatic Properties of Furan. II. The Friedel-Crafts Reaction," *J. Am. Chem. Soc.* 55:4197-4205, American Chemical Society (1933).

Goglia, F., et al., "In Vitro binding of 3,5-di-iodo-L-thyronine to rat liver mitochondria," *J. Mol. Endocrinol.* 13: 275-282, Society for Endocrinology (1994).

Goglia, F., "Biological Effects of 3,5-Diiodothyronine ($T_2$)," *Biochemistry (Moscow)* 70:164-172, Pleiades Publishing, Inc. (Feb. 2005).

Goglia, F., et al., "Interaction of diiodothyronines with isolated cytochrome *c* oxidase," *FEBS Lett.* 346:295-298, Elsevier Science Ltd. (1994).

Goodrich, P., et al., "Kinetic Study of the Metal Triflate Catalyzed Benzoylation of Anisole in an Ionic Liquid," *Ind. Eng. Chem. Res.* 45:6640-6647, American Chemical Society (Sep. 2006).

Goswami, A., et al., "Inhibition by coumadin anticoagulants of enzymatic outer ring monodeiodination of iodothyronines," *Biochem. Biophys. Res. Commun.* 104:1231-1238, Academic Press (1982).

Goya, R.G., et al., "Effects of Growth Hormone and Thyroxine on Thymulin Secretion in Aging Rats," *Neuroendocrinology* 58:338-343, S. Karger AG, Basel (1993).

Greco, M.N., et al., "Discovery of Potent, Selective, Orally Active, Nonpeptide Inhibitors of Human Mast Cell Chymase," *J. Med. Chem.* 50:1727-1730, American Chemical Society (Mar. 2007).

Gregory, R.B. and Berry, M.N., "On the thyroid hormone-induced increase in respiratory capacity of isolated rat hepatocytes," *Biochim. Biophys. Acta* 1098:61-67, Elsevier Science Ltd. (1991).

Gronemeyer, H., et al., "Principles for Modulation of the Nuclear Receptor Superfamily" *Nature Reviews, Drug Discovery* 3:950-964, Nature Publishing Group (Nov. 2004).

Grover, G.J., et al., "Development of the Thyroid Homone Receptor β-Subtype Agonist KB-141: A Strategy for Body Weight Reduction and Lipid Lowering with Minimal Cardiac Side Effects," *Cardiovascular Drug Rev. 23*:133-148, Blackwell Publishing (Nov. 2005).

Guernik, S., et al., "A novel system consisting of Rh-DuPHOS and ionic liquid for asymmetric hydrogenations," *Chem. Commun.* 2314-2315, Royal Society of Chemistry (2001).

Hadváry, P. and Weller, T., "202. Conformationally Restricted Analogs of Platelet-Activating Factor (PAF)," *Helvetica Chimica Acta 69*:1862-1871, Verlag Helvetica Chimica Acta (1986).

Hashimoto, A., et al., "Design and synthesis of complementing ligands for mutant thyroid hormone receptor TRβ(R320H): a tailor-made approach toward the treatment of resistance to thyroid hormone," *Bioorg. Med. Chem. 13*:3627-3639, Elsevier Science Ltd. (Jun. 2005).

Hayakawa, Y., et al., "A General Approach to Nuceloside 3'- and 5'-Monophosphates," *Tetrahedron Lett. 28*:2259-2262, Elsevier Science Ltd. (1987).

Hedfors, Å., et al., "Thyroid Receptor Ligands. 3. Design and Synthesis of 3,5-Dihalo-4-alkoxyphenylalkanoic Acids as Indirect Antagonistis of the Thyroid Hormone Receptor," *J. Med. Chem. 48*:3114-3117, American Chemical Society (May 2005).

Heimberg, M., et al., "Plasma Lipoproteins and Regulation of Heptic Metabolism of Fatty Acids in Altered Thyroid States," *Endocrine Rev. 6*:590-607, Endocrine Society (1985).

Hennemann, G., et al., "Carrier-Mediated Transport of Thyroid Hormone into Rat Hepatocytes is Rate-Limiting in Total Cellular Uptake and Metabolism," *Endocrinology 119*:1870-1872, Endocrine Society (1986).

Hennemann, G., "Notes on the History of Cellular Uptake and Deiodination of Thyroid Hormone," *Thyroid 15*:753-756, Mary Ann Liebert Publishers (Aug. 2005).

Holý, A., "Phosphonomethyoxyalkyl Analogs of Nucleotides," *Curr. Pharm. Des. 9*:2567-2592, Bentham Science Publishers (Dec. 2003).

Horst, C., et al., "3,5-Di-iodo-L-thyronine suppresses TSH in rats in vivo and in rat pituitary fragments in vitro," *J. Endocrinol. 145*:291-297, Society for Endocrinology (1995).

Horst, C., et al., "Rapid Stimulation of hepatic oxygen consumption by 3,5-di-iodo-L-thyronine," *Biochem. J. 261*:945-950, Portland Press (1989).

Howarth, J., et al., "Sodium Borohydride Reduction of Aldehydes and Ketones in the Recyclable Ionic Liquid [BMIM]PF$_6$," *Synth. Commun. 31*:2935-2938, Taylor & Francis (2001).

Huddleston, J.G., et al., "Characterization and comparison of hydrophilic and hydrophobic room temperature ionic liquids incorporating the imidazolium cation," *Green Chem. 3*:156-164, Royal Society of Chemistry (2001).

Hum, G., et al., "Synthesis of [Difluoro-(3-alkenylphenyl)-methyl]-phosphonic Acids on Non-crosslinked Polystyrene and Their Evaluation as Inhibitors of PTP1B," *Bioorg. Med. Chem. Lett. 12*:3471-3474, Elsevier Science Ltd. (Aug. 2002).

Hunter, D.H., et al., "Crown ether catalysis of decarboxylation and decarbalkoxylation of β-keto acids and malonates: a synthetic application," *Can. J. Chem. 58*:2271-2277, NRC Research Press (1980).

Ichikawa, K., et al., "Mechanism of liver-selective thyromimetic activity of SK&F L-94901: evidence for the presence of a cell-type-specific nuclear iodothyronine transport process," *J. Endocrinol. 165*:391-397, Society for Endocrinology (2000).

Ing, H.R., "The Pharmacology of Homologous Series," *Fortschritte der Arzneimittelforschung. Progress in drug research. Progrès des recherches pharmaceutiques 20*:306-309, Birkhäuser Verlag (1964).

Iyer, S. and Liebesking, L.S., "Regiospecific Synthesis of 2-Methoxy-3-methyl-1,4-benzoquinones from Maleoylcobalt Complexes and Alkynes via Lewis Acid Catalysis. A Highly Convergent Route to Isoquinoline Quinones," *J. Am. Chem. Soc. 109*:2759-2770, American Chemical Society (1987).

Jepson, E.M., "Thyroxine analogues as hypocholesterolemic agents," *Am. Heart J. 67*:422-424, Mosby (1964).

Johnson, E.O., et al., "Experimentally-induced hyperthyroidism is associated with activation of the rat hypothalamic-pituitay-adrenal axis," *Eur. J. Endocrinol. 153*:177-185, BioScientifica Ltd (Jul. 2005).

Jones, P.B. and Porter, N.A., "2-Aroylbenzoyl Serine Proteases: Photoreversible Inhibition or Photoaffinity Labeling?," *J. Am. Chem. Soc. 121*:2753-2761, American Chemical Society (1999).

Jorgensen, E.C., "Thyroid Hormones and Analogs. II. Structure-Activity Relationships," in: *Hormonal Proteins and Peptides*, Li, C.H., eds., Academic Press, New York, NY, pp. 107-204 (1978).

Jorgensen, E.C., "Thyroid Hormones and Analogs. I. Synthesis, Physical Properties and Theoretical Calculations," in: *Hormonal Proteins and Peptides*, Li, C.H., eds., Academic Press, New York, NY, pp. 56-105 (1978).

Jorgensen, E.C. and Murray, W.J., "Thyroxine Analogs. 22. Thyromimetic Activity of Halogen-Free Derivatives of 3,5-Dimethyl-L-Thyronine," *J. Med. Chem. 17*:434-439 (1974).

Kadenbach, B., et al., "Mitochondrial Energy Metabolsim is Regulated via Nuclear-Coded Subunits of Cytochrome *C* Oxidase," *Free Radical Biol. Med. 29*:211-221, Elsevier Science Ltd. (2000).

Kazemifard, A.G., et al., "Identification and quantitation of sodium-thyroxine and its degradation products by LC using electrochemical and MS detection," *J. Pharm. Biomed. Anal. 25*:697-711, Elsevier Science Ltd. (2001).

Kennedy, J.A., et al., "Influence of Imipramine on the Hypothalamic/Pituitary/Thryoid Axis of the Rat," *Metabolism 46*:1429-1434, W.B. Saunders (1997).

Kennedy, J.F, et al., "Isolation of thyroxine-binding globulin (TBG) by immunoadsorption chromatography: some physical and immunochemical characteristics of TBG," *Clinica Chimica Acta 129*:251-261, Elsevier Science Ltd. (1983).

Knölker, H.-J. and Filali, S., "Transition Metal Complexes in Organic Synthesis, Part 69. Total Synthesis of the *Amaryllidaceae* Alkaloids Anhydrolycorinone and Hippadine Using Iron-and Palladium-Mediated Coupling Reactions," *Synlett* 1752-1754, Georg Thieme Verlag (Jun. 2003).

Kobayashi, H., et al., "Organization of Nucleosides Supported by Boronic-Acid-Appended Poly(L-lysine): Creation of a Novel RNA Mimic," *Bull. Chem. Soc. Jpn. 74*:1311-1317, The Chemical Society of Japan (2001).

Koehler, K., et al., "Thyroid Receptor Ligands, 6. A High Affinity "Direct Antagonist" Selective for the Thyroid Hormone Receptor," *J. Med. Chem. 49*:6635-6637, American Chemical Society (Oct. 2006).

Koerner, D., et al., "Binding of Selected Iodothyronine Analogues to Receptor Sites of Isolated Rat Hepatic Nuclei," *J. Biol.Chem. 250*:6417-6423, American Society for Biochemistry and Molecular Biology (1975).

Krause, B.R., et al., "Opposite effects of bezafibrate and gemfibrozil in both normal and hypertriglyceridemic rats," *Atherosclerosis 127*:91-101, Elsevier Science Ltd. (1996).

Kvetny, J., "3,5-T$_2$ Stimulates Oxygen Consumption, But Not Glucose Uptake in Human Mononuclear Blood Cells," *Horm. Metab. Res. 24*:322-325, Georg Thieme Verlag (1992).

Lacoste, A.M., et al., "Research Regarding Aminoalkylphosphonic Acids. II.—Iodine Derivatives of the Phosphonic Analog of Tyrosine," *Bull. Soc. Chim. Biol. 49*:1827-1835, Masson Et Cie (1967).

Lacoste, A.-M., et al., "Biochemistry—Synthesis and biological properties of the phosphonic analog of thyroxine," *C. R. Acad. Sci. Paris 267*:1890-1892, Gauthier Villars Editeur (1968).

Lacoste, A.-M., et al., "Endocrinology. Action of the phosphonic analog of thyroxine on post-embryonic development of the tadpole of *Rana dalmatina* Bon," *Biol. Soc. Bordeaux* 1684-1689 (1967).

Lanni, A., et al., "Specific Binding sites for 3,3'-diiodo-L-thyronine (3,3'-T$_2$) in rat liver mitochondria," *FEBS Lett. 351*:237-240, Elsevier Science Ltd. (1994).

Lanni, A., et al., "Effect of 3,3'-di-iodothyronine and 3,5-di-iodothyronine on rat liver mitochondria," *J. Endocrinol. 136*:59-64, Society for Endocrinology (1993).

Lanni, A., et al., "Effect of 3,3'-diiodothyronine and 3,5-diiodothyronine on rat liver oxidative capacity," *Mol. Cell. Endocrinol. 86*:143-148, Elsevier Scientific Publishers Ireland (1992).

Lanni, A., et al., "Rapid stimulation in vitro of rat liver cytochrome oxidase activity by 3,5-diiodo-1-thyronine and by 3,3'-diiodo-L-thyronine," *Mol. Cell. Endocrinol. 99*:89-94, Elsevier Science Ltd. (1994).

Lanni, A., et al., "Expression of uncoupling protein-3 and mitochondrial activity in the transition from hypothyroid to hyperthyroid state in rat skeletal muscle," *Febs Lett.* 444:250-254, Elsevier Science Ltd. (1999).

Lanni, A., et al., "Calorigenic effect of diiodothyronines in the rat," *J. Physiol.* 494:831-837, Blackwell Publishing (1996).

Laskorin, B.N., et al., "Preparation and Investigation of the Steric Structure of Sterically Hindered α-oxo Phosphoryl Compounds," *Zhurnal Obshchei Khimii* 44:1716-1720, Rossiiskaya Akademiya Nauk (1974).

Lee, S.-G., et al., "Microwave-assisted Kabachnik-Fields Reaction in Ionic Liquid," *Bull. Korean Chem. Soc.* 23:667-668, The Korean Chemical Society (Mar. 2002).

Lee, Y.-P., et al., "Effects of Thyroid Hormones on the Guinea Pig," *Endocrinology* 86:241-250, The Endocrine Society (1970).

Leonard, J.L. and Rosenberg, I.N., "Iodothyronine 5'-Deiodinase from Rat Kidney: Substrate Specificity and the 5'-Deiodination of Reverse Triiodothryonine," *Endocrinology* 107:1376-1383, The Endocrine Society (1980).

Leonard, J.L. and Rosenberg, I.N., "Thyroxine 5'-Deiodinase Activity of Rat Kidney: Observations on Activation by Thiols and Inhibition by Proylthiouracil," *Endocrinology* 103:2137-2144, The Endocrine Society (1978).

Lewis, D.S., "Effects of dietary cholestrol on adipose tissue lipoprotein lipase in the baboon," *Biochim. Biophys. Acta* 879:44-50, Elsevier Science Ltd. (1986).

Li, Y.-L., et al., "Thyroid receptor ligands. Part 4: 4'-amido bioisosteric ligands selective for the thyroid hormone receptor beta," *Bioorg. Med. Chem. Lett.* 16:884-886, Elsevier Science Ltd. (Feb. 2006).

Liddle, C., et al., "Separate and Interactive Regulation of Cytochrome P450 3A4 by Triiodothyronine, Dexamethasone, and Growth Hormone in Cultured Hepatocytes," *J. Clin. Endocrinol. Metab.* 83:2411-2416, The Endocrine Society (1998).

Lin, C.-C., et al., "Pharmacokinetics of Pradefovir and PMEA in Healthy Volunteers After Oral Dosing of Pradefovir," *J. Clin. Pharmacol.* 45:1250-1258, Sage Science Press (Nov. 2005).

Linsel-Nitschke, P. and Tall, A.R., "HDL as a Target in the Treatment of Atherosclerotic Cardiovascular Disease," *Nature Reviews, Drug Discovery* 4:193-205, Nature Publishing Group (Mar. 2005).

Liotta, D., et al., "A Simple, Inexpensive Procedure for the Large-Scale Production of Alkyl Quinones," *J. Org. Chem.* 48:2932-2933, American Chemical Society (1983).

Lombardi, A., et al., "Characterization of the binding of 3, 3'-di-iodo-L-thyronine to rate liver mitochondria," *J. Endocrinol.* 154:119-124, Society for Endocrinology (1997).

Lombardi, A., et al., "Effect of 3,5-di-iodo-L-thyronine on the mitochondrial energy-transduction apparatus," *Biochem. J.* 330:521-526, Portland Press (1998).

Lukashev, N.V., et al., "Palladium-Catalyzed Cross-Coupling Reactions of Organocopper Derivatives of Methylphosphonic Esters and Amides with Aryl and Hetaryl Iodides," *Russian J. Gen. Chem.* 71:172-178, Kluwer Academic Publishers (2001).

Mackenzie, P.I., et al., "Regulation of UDP Glucuronosyltransferase Genes," *Curr. Drug Metab.* 4:249-257, Bentham Science Publishers (Jun. 2003).

Mains, R.E. and Eipper, B.A., "Tissue Culture of Primary Rat Anterior Pituitary Cells" in *Regulatory Peptides: From Molecular Biology to Function*, Costa, E., Trabucchi, M., eds., Raven Press, New York City, NY, pp. 1-8 (1982).

Makinen, M.W. and Lee, C.-P., "Biochemical Studies of Skeletal Muscle Mitochondria: I. Microanalysis of Cytochrome Content, Oxidative and Phosphorylative Activities of Mammalian Skeletal Muscle Mitochondria," *Arch. Biochem. Biophys.* 126:75-82, Academic Press (1968).

Malevannaya, R.A., et al., "(Dialkoxyphosphinyl) Acetic Acids and Some of Their Analogs," *Zhurnal Obshchei Khimii* 41:1426-1434, Rossiiskaya Akademiya Nauk (1971).

Marcune, B.F., et al., "Selective displacement of aryl fluorides with hydroquinone: synthesis of 4-phenoxyphenols" *Tetrahedron Lett.* 46:7823-7826, Elsevier Science Ltd. (Nov. 2005).

Marimuthu, A., et al., "TR Surfaces and Conformations Required to Bind Nuclear Receptor Corepressor" *Mol. Endocrinol.* 16:271-286, The Endocrine Society (Feb. 2002).

Matsui, T., et al., "Discovery of Novel Phosphonic Acid Derivatives as New Chemical Leads for Inhibitors of TNF-α Production," *Bioorg. Med. Chem.* 10:3807-3815, Elsevier Science Ltd. (Aug. 2002).

McClain, R.M., "Mechanistic considerations for the relevance of animal data on thyroid neoplasia to human risk assessment," *Mutation Res.* 333:131-142, Elsevier Science Ltd. (1995).

Mertins, K., et al., "Transition-Metal-Catalyzed Benzylation of Arenes and Heteroarenes," *Angew. Chem. Int. Ed.* 44:238-242, Wiley-VCH Verlag GmbH & Co. (Dec. 2004).

Middleton, W.J., "New Fluorinating Reagents. Dialkylaminosulfur Fluorides," *J. Org. Chem.* 40:574-578, American Chemical Society (1975).

Miyabara, E.H., et al., "Thyroid hormone receptor-β-selective agonist GC-24 spares skeletal muscle type I to II fiber shift," *Cell Tissue Res.* 321:233-241, Springer-Verlag (Aug. 2005).

Mocchegiani, E., et al., "Neuroendocrine-thymus interactions. I. In vitro modulation of thymic factor secretion by thyroid hormones," *J. Endocrinol. Invest.* 13:139-147, Italian Society of Endocrinology (1990).

Moreno, M., et al., "How the thyroid controls metabolism in the rat: different roles for triiodothyronine and diiodothyronines," *J. Physiol.* 505:529-538, Cambridge Univ. Press (1997).

Morkin, E., et al., "Pilot Studies on the Use of 3, 5-Diiodothyropropionic Acid, a Thyroid Hormone Analog, in the Treatment of Congestive Heart Failure," *Cardiology* 97:218-225, S. Karger AG, Basel (Jul. 2002).

Moscioni, A.D. and Gartner, L.M., "Thryoid Hormone and Hepatic UDP-Glucuronosyl Transferase Activity: Contrary Effects in Rat and Mouse," *Res. Commun. Chem. Pathol. Pharmacol.* 39:445-462, Pjd Publications Ltd. (1983).

Murphy-Jolly, M.B., et al., "The synthesis of tris(perfluoroalkyl)phosphines," *Chem. Commun.* 4479-4480, Royal Society of Chemistry (Aug. 2005).

Nabeshima, T., et al., "Rate-accelerating Metal Ion Effects on Decarboxylation of α-Keto Acids by a Thiazolium Ion bearing a Metal Binding Site," *J. Chem. Soc. Chem. Commun.* 373-374, Royal Society of Chemistry (1991).

Ness, G.C., et al., "Effects of L-Triiodothyronine and the Thyromimetic L-94901 on Serum Lipoprotein Levels and Hepatic Low-Density Lipoprotein Receptor, 3-Hydroxy-3-methylglutaryl Coenzyme A Reductase, and Apo A-I Gene Expression," *Biochem. Pharmacol.* 56:121-129, Elsevier Science Ltd. (1998).

Nguyen, N.-H., et al., "Hammett Analysis of Selective Thyroid Hormone Receptor Modulators Reveals Structural and Electronic Requirements for Homone Antagonists," *J. Am. Chem. Soc.* 127:4599-4608, American Chemical Society (Mar. 2005).

Nishinaga, et al., "Model Reactions for the Biosynthesis of Thyroxine. XII. The Nature of a Thyroxine Precursor Formed in the Synthesis of Thyroxine from Diiodotyrosine and Its Keto Acid Analog," *Biochemistry* 7:388-397, American Chemical Society (1968).

Nurtdinov, S.Kh., et al., "Reactions of Alkylphohphonous Dichlorides with Carboxylic Acid Chlorides," *Zhurnal Obshchei Khimii* 41:2486-2490, Rossiiskaya Akademiya Nauk (1971).

Ocasio, Cory A., and Scanlan, T.S., "Clinical prospects for new thyroid hormone analogues" *Curr. Opin. Endocrinol. Diabetes* 12:363-370, Lippincott Williams & Wilkins (Oct. 2005).

Ocasio, Cory A., and Scanlan, T.S., "Design and characterization of a thyroid hermone receptor α (TRα)-Specific Agonist," *ACS Chem. Biol.* 1:585-593, American Chemical Society (Oct. 2006).

O'Reilly, Ian, and Murphy, M.P., "Studies on the rapid stimulation of mitochondrial respiration by thyroid hormones." *Acta Endocrinol.* 127:542-546, Romanian Society for Endocrinology (1992).

O'Reilly, Ian, and Murphy, M.P., "Treatment of hypothyroid rats with $T_2$ (3,5-di-iodo-L-thyronine) rapidly stimulates respiration in subsequently isolated mitochondria," *Biochem. Soc. Trans.* 20:59S, Portland Press (1991).

Osuka, A., et al., "Synthesis of Arenephosphonates by Copper(I) Iodide-Promoted Arylation of Phoshite Anions," *Synthesis* 69-71, George Thieme Verlag-Stuttart (1983).

Pan, S.-Y., et al., "Bifendate treatment attenuates hepatic steatosis in cholesterol/bile salt- and high-fat diet-induced hypercholesterolemia in mice," *Eur. J. Pharmacol.* 552:170-175 Elsevier Science Ltd. (Dec. 2006).

Panne, P., et al., "Cyanide initiated perfluoroorganylations with perfluoroorgano silicon compounds" *J. Fluorine Chem.* 112:283-286 Elsevier Science Ltd. (2001).

Pétervári, E., et al., "Hyperphagia of hyperthyroidism: Is neuropeptide Y involved?" *Regulatory Peptides* 131:103-110, Elsevier Science Ltd. (Nov. 2005).

Prashad, M., "Phosphonate vs. Phosphinate Elimination during Olefination of Aldehydes," *Tetrahedron Lett.* 34:1585-1588, Elsevier Science Ltd. (1993).

Psarra, A.-M.G., et al., "The mitochondrion as a primary site of action of steroid and thyroid hormones: Presence and action of steroid and thyroid hormone receptors in mitochondria of animal cells." *Mol. Cell. Endocrinol.* 246:21-33, Elsevier Science Ltd. (Feb. 2006).

Pue, M.A., et al., "The disposition of SK&F L-94901, a selective thyromimetic in rat, dog and cynomolgus monkey," *Eur. J. Drug Metab. Pharmacokinetics* 14:209-219, Edition Medecine Et Hygiene (1989).

Radominska-Pandya, A., et al., "A Historical Overview of the Heterologous Expression of Mammalian UDP-Glucuronosyltransferase Isoforms Over the Past Twenty Years," *Curr. Drug Metab.* 6:141-160, Bentham Science Publishers Ltd. (Apr. 2005).

Rai, R., and Katzenellenbogen, J.A., "Effect on Conformational Mobility and Hydrogen-Bonding Interactions on the Selectivity of Some Guanidinoaryl-Substituted Mechanism-Based Inhibitors of Trypsin-like Serine Proteases," *J. Med. Chem.* 35:4297-4305, American Chemical Society (1992).

Rashid, S., et al., "Effect of Atorvastatin on High-Density Lipoprotein Apolipoprotein A-I Production and Clearance in the New Zealand White Rabbit," *Circulation* 106:2955-2960, Lippincott Williams & Wilkins (Dec. 2002).

Razumov, A.I. and Gazizov, M.B., "Reactivity of Organophosphorus Carbonyl-Containing Compounds IV. Synthesis, Properties, and Structure of Acylphosphinic Esters," *Zhurnal Obshchei Khimii* 37:2738-2742, Rossiiskaya Akademiya Nauk (1967).

Ren, S.G., et al., "Dose-Response Relationship Between Thyroid Hormone and Growth Velocity in Cynomolgus Monkeys," *J. Clin. Endocrinol. Metab.* 66:1010-1013, The Endocrine Society (1988).

Ribeiro, R.C.J., et al., "X-ray Crystallographic and Functional Studies of Thyroid Hormone Receptor," *J. Steroid Biochem. Molec. Biol.* 65:133-141, Pergamon Press (1998).

Rooda, S.J.E., et al., "Metabolism of Triiodothyronine in Rat Hepatocytes," *Endocrinology* 125:2187-2197, The Endocrine Society (1989).

Ross, J. and Xiao, J., "Friedel-Crafts acylation reactions using metal triflates in ionic liquid," *Green Chem.* 4:129-133, Royal Society of Chemistry (Feb. 2002).

Ruhlandt-Senge, K. and Englich, U., "Synthesis and characterization of the first discrete potassium thiolates displaying three different coordination spheres at potassium in one molecule," *Chem. Commun.* 147-148, Royal Society of Chemistry (1996).

Saitoh, H. and Aungst, B.J., "Improvement of the Intestinal Absorption of a Peptidomimetic, Boronic Acid Thrombin Inhibitor Possibly Utilizing the Oligopeptide Transporter," *Pharm. Res.* 16:1786-1789, Plenum Publishing Corporation (1999).

Sakamoto, T., et al., "Cross-Coupling of N-Heteroaryl Halides with Active Methylene Compounds in the Presence of Tetrakis(triphenylphosphine)palladium," *Chem. Pharm. Bull.* 36:1664-1668, Pharmaceutical Society of Japan (1988).

Sakamoto, T., et al., "Palladium-Catalyzed Condensation of Aryl Halides with Phenylsulfonylacetonitrile and Diethyl Cyanomethylphosphonate," *Chem. Pharm. Bull.* 38:1513-1517, Pharmaceutical Society of Japan (1990).

Samuels, H.H., et al., "Depletion of L-3,5,3'-Triiodothyronine and L-Thyroxine in Euthyroid Calf Serum for Use in Cell Culture Studies of the Action of Thyroid Hormone," *Endocrinology* 105:80-85, The Endocrine Society (1979).

Sano, M. and Yamatera, H., "Potential Energy Surface of $[Cu(H_2O)_6]^{2+}$ and $[Zn(H_2O)_6]^{2+}$ Derived From Ab Initio MO Calculations," *Chem. Lett.* 1495-1496, The Chemical Society of Japan (1980).

Saulnier, M.G., et al., "Microwave-assisted synthesis of primary amine HX salts from halides and 7M ammonia in methanol," *Tetrahedron Lett.* 45:397-399, Elsevier Science Ltd. (Jan. 2004).

Schlosser, M. and Geneste, H., "The Organometallic Route to Benzylamine Type Monoamine Oxidase Inhibitors," *Tetrahedron* 54:10119-10124, Pergamon Press (1998).

Schmitt, L., et al., "Synthesis of Arylalkylmonofluorophosphonates as *Myo*-Inositol monophosphatase Ligands," *Tetrahedron Lett.* 39:4009-4012, Elsevier Science Ltd. (1998).

Schröder-van der Elst, J.P., et al., "Effects of 5,5'-diphenylhydantoin on the thyroid status in rats," *Eur. J. Endocrinol.* 134:221-224, BioScientifica Ltd (1996).

Selenkow, H.A. and Asper, Jr., S.P., "Biological Activity of Compounds Structurally Related to Thyroxine," *Physiol. Rev.* 35:426-474, American Physiological Society (1955).

Shi, Y., et al., "Mutant-Selective Thyromimetics for the Chemical Rescue of Thyroid Hormone Receptor Mutants Associated with Resistance to Thyroid Hormone," *Biochemistry* 44:4612-4626, American Chemical Society (Mar. 2005).

Smith, C.L. and O'Malley, B.W., "Coregulator Function: A Key to Understanding Tissue Specificity of Selective Receptor Modulators," *Endocrine Rev.* 25:45-71, The Endocrine Society (Feb. 2004).

Soldin, S.J., et al., "The measurement of free thyroxine by isotope dilution tandem mass spectrometry," *Clinica Chimica Acta* 358:113-118, Elsevier Science Ltd. (Aug. 2005).

Song, K., et al., "Induction of angiotensin converting enzyme and angiotensin II receptors in the atherosclerotic aorta of high-cholesterol fed *Cynomolgus* monkeys," *Atherosclerosis* 138:171-182, Elsevier Science Ltd. (1998).

Stanton, J.L., et al., "Synthesis and Biological Activity of Phenoxyphenyl Oxamic Acid Derivatives Related to L-Thyronine," *Bioorg. Med. Chem. Lett.* 10:1661-1663, Elsevier Science Ltd (2000).

Sterling, K. and Brenner, M.A., "Thyroid Hormone Action: Effect of Triiodothyronine on Mitochondrial Adenine Nucleotide Translocase In Vivo and In Vitro," *Metabolism* 44:193-199, W.B. Saunders (1995).

Tai, S.S.-C., et al., "Candidate Reference Method for Total Thyroxine in Human Serum: Use of Isotope-Dilution Liquid Chromatography-Mass Spectrometry with Electrospray Ionization," *Clin. Chem.* 48:637-642, American Association For Clinical Chemistry (Jan. 2002).

Takayama, S., et al., "Antithyroid Effects of Propylthiouracil and Sulfamonomethoxine in Rats and Monkeys," *Toxicol. Applied Pharmacol.* 82:191-199, Academic Press (1986).

Tal, D.M. and Karlish, S.J.D., "Synthesis of a Novel Series of Arylmethylisothiouronium Derivatives," *Tetrahedron* 51:3823-3830, Pergamon Press (1995).

Taylor, A.H., et al., "Beneficial Effects of a Novel Thyromimetic on Lipoprotein Metabolism," *Mol. Pharmacol.* 52:542-547, American Society for Pharmacology and Experimental Therapeutics (1997).

Taylor, S.D., et al., "Synthesis of Aryl(DifluoromethylenePhosphonates) via Electrophilic Fluorination of α-Carbanions of Benzylic Phosphonates with N-Fluorobenzenesulfonimide," *Tetrahedron* 54:1691-1714, Pergamon Press (1998).

Thienpont, L.M., et al., "Isotope Dilution-Gas Chromatography/Mass Spectrometry and Liquid Chromatography/Electrospray Ionization-Tandem Mass Spectrometry for the Determination of Triiodo-L-Thyronine in Serum," *Rapid Commun. Mass Spectrometry* 13:1924-1931, John Wiley & sons, Ltd (1999).

Thornber, C.W., "Isosterism and Molecular Modification in Drug Design," *Chem. Soc. Rev.* 8:563-580, Chemical Society (1979).

Togashi, M., et al., "Conformational adaptation of nuclear receptor ligand binding domains to agonists: Potential for novel approaches to ligand design," *J. Steroid Biochem. Mol. Biol.* 93:127-137, Elsevier Science Ltd. (Feb. 2005).

Tomilov, A.P., et al., "Electrochemical synthesis of diethyl fluoromethanephosphonate," *J. Fluorine Chem.* 82:39-41, Elsevier Science Ltd. (1997).

Toussaint, O., et al., "The Copper(I)-Catalyzed Decarboxylation of Malonic Acids: A New Mild and Quantitative Method," *Synthesis* 1029-1031, Georg Thieme Verlag (1986).

Trost, S.U., et al., "The Thyroid Hormone Receptor-β-Selective Agonist GC-1 Differentially Afftects Plasma Lipids and Cardiac Activity," *Endocrinology* 141:3057-3064, The Endocrine Society (2000).

Tsuchimoto, T., et al., "Scandium(III) Triflate Catalyzed Friedel-Crafts Alkylation Reactions," *J. Org. Chem.* 62:6997-7005, American Chemcial Society (1997).

Underwood, A.H., et al., "A thyromimetic that decreases plasma cholesterol levels without increasing cardiac activity," *Nature* 324:425-429, Nature Publishing Group (1986).

Van Rompacy, K., et al., "A versatile synthesis of 2-substituted 4-amino-1,2,4,5-tetrahydro-2-benzazepine-3-ones," *Tetrahedron* 59:4421-4432, Pergamon Press (Apr. 2003).

Vaughan, M.K., et al., "Chronic Exposure to Short Photoperiod Inhibits Free Thyroxine Index and Plasma Levels of TSH, $T_4$, Triiodothyronine ($T_3$) and Cholesterol in Female Syrian Hamsters," *Comp. Biochem. Physiol.* 71A:615-618, Pergamon Press Ltd. (1982).

Veer, G.V.D.S., et al., "Temperature Effects on Free-Thyroxine Measurements: Analytical and Clinical Consequences," *Clin. Chem.* 38:1327-1331, American Association For Clinical Chemistry (1992).

Verd, J.C., et al., "Different effect of simvastatin and atorvastatin on key enzymes involved in VLDL synthesis and catabolism in high fat/cholestrol fed rabbits," *Br. J. Pharmacol.* 127:1479-1485, Nature Publishing Group (1999).

Villicev, C.M., et al., "Thyroid hormone receptor β-specific agonist GC-1 increases energy expenditure and prevents fat-mass accumulation in rats," *J. Endocrinol.* 193:21-29, Society for Endocrinology (Jan. 2007).

Visser, T.J., et al., "Deiodination of Thyroid Hormone by Human Liver," *J. Clin. Endocrinol. Metab.* 67:17-24, The Endocrine Society (1988).

Walker, D.M., et al., "Design and Synthesis of γ-Oxygenated Phosphinothricins as Inhibitors of Gluamine Synthetase," *J. Chem. Soc. Perkin Trans.* 1 659-666, Royal Society of Chemistry (1990).

Wang, B., et al., "Effects of triiodo-thyronine on angiotensin-induced cardiomyocyte hypertrophy: reversal of increased β-myosin heavy chain gene expression," *Can. J. Physiol. Pharmacol.* 84:935-941, NRC Research Press (Aug. 2006).

Wang, R., et al., "Salsalate Administration—A Potential Pharmacological Model of the Sick Euthyroid Syndrome," *J. Clin. Endocrinol. Metab.* 83:3095-3099, Endocrine Society (1998).

Waschbüsch, R., et al., "A high yielding synthesis of diethyl-1-fluoromethylphosphonate in pure form," *C. R. Acad. Sci. Paris, t. I, Série II c 1*:49-52, Elsevier Science Ltd. (1998).

Wasserscheid, P. and Keim, W., "Ionic Liquids-New "Solutions" for Transition Metal Catalysis," *Angew Chem. Int. Ed.* 39:3772-3789, Wiley-VCH Verlag GmbH (2000).

Wechter, W.J., et al., "Hypocholesterolemic Agents. Thyroalkanols," *J. Med. Chem.* 8:474-478, American Chemical Society (1965).

Wells, P.G., et al., "Effect of thyrotoxicosis on liver blood flow and propranolol disposition after long-term dosing," *Clin. Pharmacol. Ther.* 33:603-608, Nature Publishing Group (1983).

Welton, T., "Room-Temperature Ionic Liquids. Solvents for Synthesis and Catalysis," *Chem. Rev.* 99:2071-2083, American Chemical Society (1999).

Wibom, R., et al., "A sensitive method for measuring ATP-formation in rat muscle mitochondria," *Scand. J. Clin. Lab. Invest.* 50:143-152, Taylor & Francis Health Sciences (1990).

Wienand, A., et al., "Design, Synthesis and Biological Evaluation of Selective Boron-containing Thrombin Inhibitors," *Bioorg. Med. Chem.* 7:1295-1307, Elsevier Science Ltd. (1999).

Willnow, T.E. and Herz, J., "Animal models for disorders of hepatic lipoprotein metabolism," *J. Mol. Med.* 73:213-220, Springer-Verlag (1995).

Winder, W.W., et al., "Effects of thyroid hormone administration on skeletal muscle mitochondria," *Am. J. Physiol.* 228:1341-1345, American Physiological Society (1975).

Wondisford, F.E., "Unlikely partners in weight loss?," *Cell Metab.* 3:81-82, Cell Press (Feb. 2006).

Wu, K.-M. and Farrelly, J.G., "Preclinical Development of New Drugs that Enhance Thyroid Hormone Metabolism and Clearance: Inadequacy of Using Rats as an Animal Model for Predicting Human Risks in an IND and NDA," *Am. J. Therap.* 13:141-144, Lippincott Williams & Wilkins (Mar./Apr. 2006).

Wu, Y., et al., "Removal of Thiazolidinethione Auxiliaries with Benzyl Alcohol Mediated by DMAP," *J. Org. Chem.* 69:6141-6144, American Chemical Society (May 2004).

Xu, L., et al., "Heck Reaction in Ionic Liquids and the in Situ Identification of N-Heterocyclic Carbene Complexes of Palladium," *Organometallics* 19:1123-1127, American Chemical Society (2000).

Yang, W., et al., "Boronic Acid Compounds as Potential Pharmaceutical Agents," *Med. Res. Rev.* 23:346-368, Wiley Periodicals, Inc. (May 2003).

Yang, C. and Pittman, Jr., C.U., "Reductions of Organic Functional Groups Using $NaBH_4$ or $NaBH_4/LiCl$ in Diglyme at 125 to 162° C," *Synth. Commun.* 28:2027-2041, Georg Thieme Verlag (1998).

Yen, P.M., "Physiological and Molecular Basis of Thyroid Hormone Action," *Physiol. Rev.* 81:1097-1142, American Physiological Society (2001).

Yoshihara, H.A.I., et al., "Structural Determinants of Selective Thyromimetics" *J. Med. Chem.* 46:3152-3161, American Chemical Society (Jul. 2003).

Yoshioka, R., et al., "The Optical Resolution and Asymmetric Transformation of DL-p-Hydroxyphenylglycine with (+)-1-Phenylethanesulfonic Acid," *Bull. Chem. Soc. Jpn.* 60:649-652, The Chemical Society of Japan (1987).

Yu, K.-L., et al., "Concerning the Phosphorylation of Vicinal Diols," *Synth. Commun.* 18:465-468, Taylor & Francis, Inc. (1988).

Zalkow, L.H., et al., "Studies in the Synthesis of Camptothecin. An Efficient Synthesis of 2,3-Dihydro-1H-pyrrolo[3,4-b]quinoline," *J. Chem. Soc.* 3551-3554, Royal Society of Chemistry (1971).

Zenker, N. and Jorgensen, E.C., "Thyroxine Analogs. I. Synthesis of 3,5-Diiodo-4-(2'-alkylphenoxy)-DL-phenylalanines," *J. Am. Chem. Soc.* 81:4643-4647, American Chemical Society (1959).

Zhang, N. and Casida, J.E., "Novel Irreversible Butyrylcholinesterase Inhibitors: 2-Chloro-1-(substituted-phenyl)ethylphosphonic Acids," *Bioorg. Med. Chem.* 10:1281-1290, Elsevier Science Ltd. (Nov. 2002).

Zhang, J. and Lazar, M.A., "The Mechanism of Action of Thyroid Hormones," *Annu. Rev. Physiol.* 62:439-466, Annual Reviews (2000).

Baxter, J.D., et al., "Selective activation of thyroid hormone signaling pathways by GC-1: a new approach to controlling cholesterol and body weight," *Trends Endocrinol. Metab.* 15:154-157, Elsevier Ltd. (2004).

International Search Report for International Application No. PCT/US04/39024, International Search Authority, Alexandria, VA, mailed Jul. 5, 2005.

Edmundson, R.S., et al., "Cyclic Organophosphorus Compounds. Part 23. Configurational Assignments in the 4-Phenyl-1,3,2$\lambda^5$-dioxaphosphorinane Series. X-Ray Molecular Structure of cis-2-Benzylamino-4-phenyl-1,3,2-dioxaphosphorinane 2-Oxide," *J. Chem. Res. Synop.* 5:122-123, Science Reviews, Ltd. (1989).

Webb, P., et al., "Design of thyroid hormone receptor antagonists from first principles," *J. Steroid Biochem.* 46:59-73, Elsevier Science (Dec. 2002).

Ye, L., et al., "Thyroid Receptor Ligands. 1. Agonist Ligands Selective for the Thyroid Receptor $\beta_1$," *J. Med. Chem.* 46:1580-1588, American Chemical Society (Apr. 2003).

International Search Report for International Application No. PCT/US2006/020607, mailed on Mar. 28, 2007, European Patent Office, Netherlands.

U.S. Appl. No. 11/816,774, inventors Erion, et al., filed Aug. 21, 2007.

U.S. Appl. No. 11/842,067, inventors Erion, et al., filed Aug. 20, 2007.

U.S. Appl. No. 10/580,134, inventors Erion, M., et al., filed May 19, 2006.

* cited by examiner

T3 Binding Assay Results

T3 Binding Assay Results

Compound 17 Binding Assay Results

Compound 17 Binding Assay Results

Compound 7 Binding Assay Results

Compound 7 Binding Assay Results

Dose Response of Cholesterol to Compound 17 in Cholesterol Fed Rats

Dose Response of Cholesterol to Compound 7 in Cholesterol Fed Rats

Effect of Compound 17 on Heart Weight in Cholesterol Fed Rats

Effect of Compound 7 on Heart Weight in Cholesterol Fed Rats

Effect of Compound 17 on Cardiac GPDH Activity in Cholesterol Fed Rats

Effect of Compound 7 on Cardiac GPDH Activity in Cholesterol Fed Rats

Effect of Compound 13-1-*cis* (●) and Compound 18 (○) on Cholesterol in Cholesterol Fed Rats

PHOSPHORUS-CONTAINING THYROMIMETICS

FIELD OF THE INVENTION

The present invention is directed toward phosphonic acid-containing compounds and monoesters thereof that are thyroid receptor ligands, pharmaceutically acceptable salts, and to prodrugs of these compounds as well as their preparation and uses for preventing and/or treating metabolic diseases such as obesity, NASH, hypercholesterolemia and hyperlipidemia as well as associated conditions such as atherosclerosis, coronary heart disease, impaired glucose tolerance and diabetes. The invention is also related to the liver specific delivery of thyroid receptor ligands and the use of these compounds for the prevention and treatment of diseases responsive to modulation of T3-responsive genes in the liver.

BACKGROUND OF THE INVENTION

The following description of the background is provided to aid in understanding, but is not admitted to be, or to describe, prior art. All publications and their cited references are incorporated by reference in their entirety.

Thyroid hormones (TH) are synthesized in the thyroid in response to thyroid stimulating hormone (TSH), which is secreted by the pituitary gland in response to various stimulants (e.g., thyrotropin-releasing hormone (TRH) from the hypothalamus). Thyroid hormones are iodinated O-aryl tyrosine analogues excreted into the circulation primarily as 3,3',5,5'-tetraiodothyronine (T4). T4 is rapidly deiodinated in local tissues by thyroxine 5'-deiodinase to 3,3',5'-triiodothyronine (T3), which is the most potent TH. T3 is metabolized to inactive metabolites via a variety of pathways, including pathways involving deiodination, glucuronidation, sulfation, deamination, and decarboxylation. Most of the circulating T4 and T3 is eliminated through the liver.

THs have profound physiological effects in animals and humans. Hyperthyroidism is associated with increased body temperature, general nervousness, weight loss despite increased appetite, muscle weakness and fatigue, increased bone resorption and enhanced calcification, and a variety of cardiovascular changes, including increased heart rate, increased stroke volume, increased cardiac index, cardiac hypertrophy, decreased peripheral vascular resistance, and increased pulse pressure. Hypothyroidism is generally associated with the opposite effects.

The biological activity of THs is mediated largely through thyroid hormone receptors (TRs). TRs belong to the nuclear receptor superfamily, which, along with its common partner, the retinoid X receptor, form heterodimers that act as ligand-inducible transcription factors. Like other nuclear receptors, TRs have a ligand binding domain and a DNA binding domain and regulate gene expression through ligand-dependent interactions with DNA response elements (thyroid response elements, TREs). Currently, the literature shows that TRs are encoded by two distinct genes (TRα and TRβ), which produce several isoforms through alternative splicing (Williams, *Mol. Cell Biol.* 20(22):8329-42 (2000); Nagaya et al., *Biochem. Biophys. Res. Commun.* 226(2):426-30 (1996)). The major isoforms that have so far been identified are TRα-1, TRα-2, TRβ-1 and TRβ-2. TRα-1 is ubiquitously expressed in the rat with highest expression in skeletal muscle and brown fat. TRβ-1 is also ubiquitously expressed with highest expression in the liver, brain and kidney. TRβ-2 is expressed in the anterior pituitary gland and specific regions of the hypothalamus as well as the developing brain and inner ear. In the rat and mouse liver, TRβ-1 is the predominant isoform (80%). The TR isoforms found in human and rat are highly homologous with respect to their amino acid sequences which suggest that each serves a specialized function.

TSH is an anterior pituitary hormone that regulates thyroid hormone production. TSH formation and secretion is in turn regulated by the hypothalamic TRH. TSH controls the uptake of iodide by the thyroid, the subsequent release of iodinated thyronines from thyroglobulin (e.g., T3, T4) as well as possibly the intrapituitary conversion of circulating T4 to T3. Compounds that mimic T3 and T4 can negatively regulate both TSH and TRH secretion resulting in suppression of TSH levels and decreased levels of T3 and other iodinated thyronines. Negative regulation of TSH is postulated based on co-transfection and knockout studies (Abel et al., *J. Clin. Invest.* 104:291-300 (1999)) to arise through activation of the thyroid receptor TRY, possibly the isoform TRβ-2, which is highly expressed in the pituitary.

The most widely recognized effects of THs are an increase in metabolic rate, oxygen consumption and heat production. T3 treatment increases oxygen consumption in isolated perfused liver and isolated hepatocytes. (Oh et al., *J. Nutr.* 125 (1):112-24 (1995); Oh et al., *Proc. Soc. Exp. Biol. Med.* 207(3): 260-7 (1994)) Liver mitochondria from hyperthyroid rats exhibit increased oxygen consumption (Carreras et al., *Am. J. Physiol. Heart Circ. Physiol.* 281(6):H2282-8 (2001) and higher activities of enzymes in the oxidative pathways (Dummler et al., *Biochem. J.* 317(3):913-8 (1996), Schmehl et al., *FEBS Lett.* 375(3):206-10 (1995), Harper et al., *Can. J. Physiol. Pharmacol.* 72(8):899-908 (1994)). Conversely, mitochondria from hypothyroid rats show decreased oxygen consumption. Increased metabolic rates are associated with increased mitochondrial biogenesis and the associated 2- to 8-fold increase in mitochondrial mRNA levels. Some of the energy produced from the increased metabolic rate is captured as ATP (adenosine 5'-triphosphate), which is stored or used to drive biosynthetic pathways (e.g., gluconeogenesis, lipogenesis, lipoprotein synthesis). Much of the energy, however, is lost in the form of heat (thermogenesis), which is associated with an increase in mitochondrial proton leak possibly arising from TH-mediated effects on mitochondrial membrane, uncoupling proteins, enzymes involved in the inefficient sn-glycerol 3-phosphate shuttle such as mitochondrial sn-glycerol 3-phosphate dehydrogenase (mGPDH), and/or enzymes associated with proton leakage such as the adenine nucleotide transporter (ANT), $Na^+/K^+$-ATPase, $Ca^{2+}$-ATPase and ATP synthase.

THs also stimulate metabolism of cholesterol to bile acids. Hyperthyroidism leads to decreased plasma cholesterol levels, which is likely due to increased hepatic LDL receptor expression. Hypothyroidism is a well-established cause of hypercholesterolemia and elevated serum LDL. L-T3 is known to lower plasma cholesterol levels. The effects of T3 are attributed to TRβ since TRβ-deficient mice are resistant to T3-induced reduction in cholesterol levels. The effects on cholesterol levels have been postulated to result from direct effects on LDL receptor expression, enzymes involved in conversion of cholesterol to bile acids such as the rate-limiting enzyme cholesterol 7α-hydroxylase (CYP7A) and/or possibly enzymes involved in cholesterol synthesis such as HMG CoA reductase. In addition, THs are known to affect levels of other lipoproteins linked to atherosclerosis. THs stimulate apo AI and the secretion of apo AI in HDL while reducing apo B100. Accordingly, one would expect T3 and T3 mimetics to inhibit the atherosclerotic process in the cholesterol fed animal.

THs simultaneously increase de novo fatty acid synthesis and oxidation through effects on enzymes such as ACC, FAS, and spot-14. THs increase circulating free fatty acids (FFA) levels in part by increasing production of FFAs from adipose tissue via TH-induced lipolysis. In addition, THs increase mitochondrial enzyme levels involved in FFA oxidation, e.g., carnitine palmitoyltransferase 1 (CPT-1) and enzymes involved in energy storage and consumption.

The liver represents a major target organ of THs. Microarray analysis of hepatic gene expression from livers of hypothyroid mice and mice treated with T3 showed changes in mRNA levels for 55 genes (14 positively regulated and 41 negatively regulated) (Feng et al., *Mol. Endocrinol.* 14(7): 947-55 (2000). Others have estimated that approximately 8% of the hepatic genes are regulated by T3. Many of these genes are important to both fatty acid and cholesterol synthesis and metabolism. T3 is also known to have other effects in liver, including effects on carbohydrates through increased glycogenolysis and gluconeogenesis and decreased insulin action.

The heart is also a major target organ of THs. THs lower systemic vascular resistance, increase blood volume and produce inotropic and chronotropic effects. Overall TH results in increased cardiac output, which may suggest that T3 or T3 mimetics might be of use to treat patients with compromised cardiac function (e.g., patients undergoing coronary artery bypass grafting (CABG) or cardiac arrest) (U.S. Pat. No. 5,158,978). The changes in cardiac function are a result of changes in cardiac gene expression. Increased protein synthesis and increased cardiac organ weight are readily observed in T3-treated animals and represent the side effect of T3 that limits therapeutic use. TRβ knockout mice exhibit high TSH and T4 levels and increased heart rate suggesting that they retain cardiac sensitivity and therefore that the cardiac effects are via TRα. TRα knockouts exhibit reduced heart rates.

THs also play a role in the development and function of brown and white adipose tissue. Both TRα and TRβ are expressed in brown adipose tissue (BAT). THs induce differentiation of white adipose tissue (WAT) as well as a variety of lipogenic genes, including ACC, FAS, glucose-6-phosphate dehydrogenase and spot-14. Overall THs play an important role in regulating basal oxygen consumption, fat stores, lipogenesis and lipolysis (Oppenheimer et al., *J. Clin. Invest.* 87(1):125-32 (1991)).

TH has been used as an antiobesity drug for over 50 years. In the 1940s TH was used alone, whereas in the 1950s it was used in combination with diuretics and in the 1960s in combination with amphetamines. Hyperthyroidism is associated with increased food intake but is also associated with an overall increase in the basal metabolic rate (BMR). Hyperthyroidism is also associated with decreased body weight (ca. 15%) whereas hypothyroidism is associated with a 25-30% increase in body weight. Treating hypothyroidism patients with T3 leads to a decrease in body weight for most patients but not all (17% of the patients maintain weight).

The effectiveness of TH treatment is complicated by the need for supraphysiological doses of T3 and the associated side effects, which include cardiac problems, muscle weakness and erosion of body mass. Long-term therapy has also been associated with bone loss. With these side effects, the medical community has tended to use thyroxine at low doses as an adjunct to dietary treatments. At these doses, TH has little effect on body weight or BMR.

The effectiveness of T3 to induce weight loss may be attenuated by defects in TH action. In comparison to normal animals, higher T3 doses were required in ob/ob mice to affect oxygen consumption, which was only observed in muscle, with no changes in liver and BAT. (Oh et al., *J. Nutr.* 125(1):112-24 (1995); Oh et al., *Proc. Soc. Exp. Biol. Med.* 207(3):260-7 (1994)). These effects were at least partially attributed to decreased uptake of T3 by the liver.

T3 analogues have been reported. Many were designed for use as cholesterol-lowering agents. Analogues that lower cholesterol and various lipoproteins (e.g., LDL cholesterol and Lp(a)) without generating adverse cardiac effects have been reported (e.g., Underwood et al., *Nature* 324:425-9 (1986)). In some cases the improved therapeutic profile is attributed to increased specificity for the TR-β wherein other cases it may be due to enhanced liver distribution. (Stanton et al., *Bioorg. Med. Chem. Lett.* 10(15):1661-3 (2000); Dow et al., *Bioorg. Med. Chem. Lett.* 13(3):379-82 (2003)).

T3 and T3 mimetics are thought to inhibit atherosclerosis by modulating the levels of certain lipoproteins known to be independent risk factors or potential risk factors of atherosclerosis, including low density lipoprotein (LDL)-cholesterol, high density lipoprotein (HDL)-cholesterol, apoAI, which is a major apoprotein constituent of high density lipoprotein (HDL) particles and lipoprotein (a) or Lp(a).

Lp(a) is an important risk factor, elevated in many patients with premature atherosclerosis. Lp(a) is considered highly atherogenic (de Bruin et al., *J. Clin. Endocrinol. Metab.* 76:121-126 (1993)). In man, Lp(a) is a hepatic acute phase protein that promotes the binding of LDL to cell surfaces independent of LDL receptors. Accordingly, Lp(a) is thought to provide supplementary cholesterol to certain cells, e.g., cells involved in inflammation or repair. Lp(a) is an independent risk factor for premature atherosclerosis. Lp(a) is synthesized in the liver.

Apolipoprotein AI or apoAI is the major component of HDL, which is an independent risk factor of atherosclerosis. apoAI is thought to promote the efflux of cholesterol from peripheral tissues and higher levels of HDL (or apoAI) result in decreased risk of atherosclerosis.

Hyperthyroidism worsens glycemic control in type 2 diabetics. TH therapy is reported to stimulate hepatic gluconeogenesis. Enzymes specific to gluconeogenesis and important for controlling the pathway and its physiological role of producing glucose are known to be influenced by TH therapy. Phosphoenolpyruvate carboxykinase (PEPCK) is upregulated by TH (Park et al, *J. Biol. Chem.* 274:211 (1999)) whereas others have found that glucose 6-phosphatase is upregulated (Feng et al., *Mol. Endocrinol.* 14:947 (2000)). TH therapy is also associated with reduced glycogen levels.

TH therapy results in improved non insulin stimulated and insulin stimulated glucose utilization and decreased insulin resistance in the muscle of ob/ob mice. (Oh et al., *J. Nutr.* 125:125 (1995)).

There is still a need for novel thyromimetics that can be used to modulate cholesterol levels, to treat obesity, and other metabolic disorders especially with reduced undesirable effects.

SUMMARY OF THE INVENTION

Figure 1A:
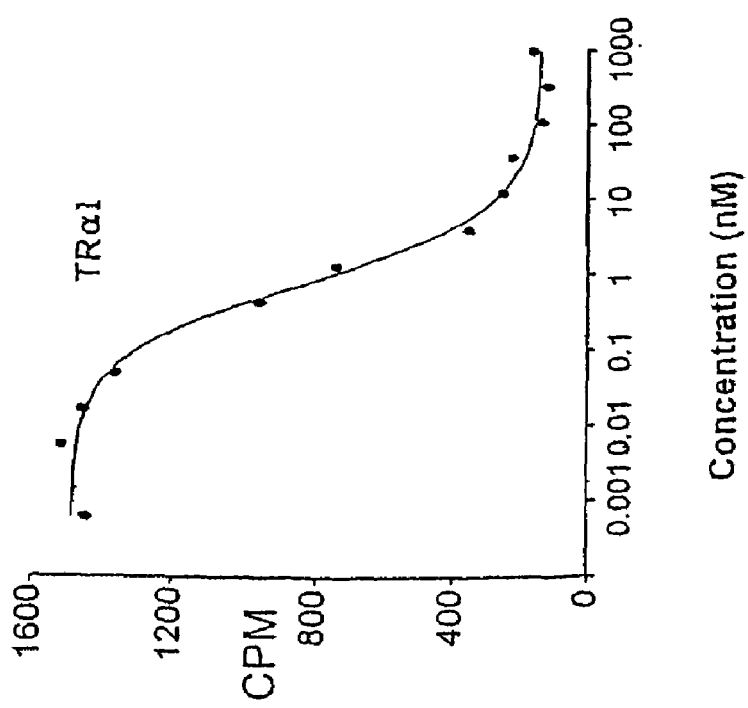
FIG. 1a depicts the binding of T3 to the TRα1 receptor using a homologous displacement reaction.

The present invention relates to phosphonic acid- and phosphonic acid monoester-containing compounds that bind to thyroid receptors in the liver. Activation of these receptors results in modulation of gene expression of genes regulated by thyroid hormones. The present invention also relates to pharmaceutically acceptable salts and co-crystals, prodrugs, and pharmaceutically acceptable salts and co-crystals of these prodrugs of these compounds. The compounds can be used to treat diseases and disorders including metabolic diseases. In one aspect, the phosphonic acid- and phosphonic acid monoester-containing compounds are useful for improving efficacy, improving the therapeutic index, e.g., decreasing non-liver related toxicities and side effects, or for improving liver selectivity, i.e., increasing distribution of an active drug to the liver relative to extrahepatic tissues and more specifically increasing distribution of the an active drug to the nucleus of liver cells relative to the nucleus of extrahepatic tissue cells (including heart, kidney and pituitary). Prodrugs of the phosphonic acid- and phosphonic acid monoester-containing compounds are useful for increasing oral bioavailability and sustained delivery of the phosphorus-containing compounds.

In another aspect, the present invention relates to compounds of Formula I, II, III, VIII, and X. The compounds of Formula I, II, III, VIII, and X may be an active form or a prodrug thereof. Further included are pharmaceutically acceptable salts, including but not limited to acid addition salts and physiological salts, and co-crystals of said compounds of Formula I, II, III, VIII, and X. Further included in the present invention are prodrugs of compounds of Formula I, II, III, VIII, and X that are active forms, and pharmaceutically acceptable salts, including but not limited to acid addition salts and physiological salts, and co-crystals thereof. Further included are methods of making and using the compounds of the present invention.

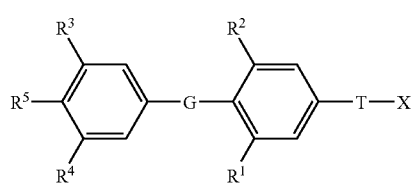

Formula I

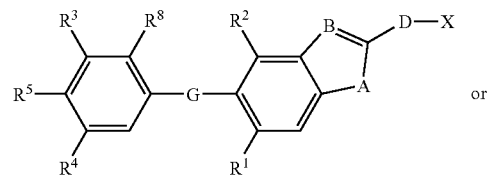

Formula II or

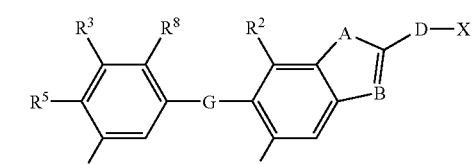

Formula III

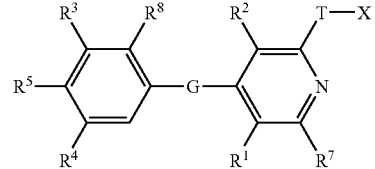

Formula VIII

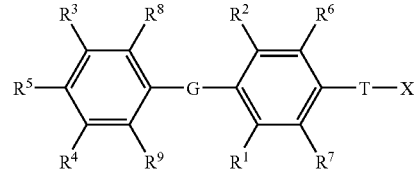

Formula X $(Ar^1)-G-(Ar^2)-T-X$

Some of the compounds of Formula I, II, III, VIII, and X have asymmetric centers. Thus included in the present invention are racemic mixtures, enantiomerically enriched mixtures, diastereomeric mixtures, including diastereomeric enriched mixtures, and individual stereoisomers of the compounds of Formula I, II, III, VIII, and X and prodrugs thereof.

Definitions

As used herein, the following terms are defined with the following meanings, unless explicitly stated otherwise.

T groups that have more than one atom are read from left to right wherein the left atom of the T group is connected to the phenyl group bearing the $R^1$ and $R^2$ groups, and the right atom of the T group is linked to the phosphorus atom in X. For example, when T is —O—CH$_2$— or —N(H)C(O)— it means -phenyl-O—CH$_2$—P(O)YR$^{11}$Y'R$^{11}$ and -phenyl-N(H)C(O)—P(O)YR$^{11}$Y'R$^{11}$.

The term "alkyl" refers to a straight or branched or cyclic chain hydrocarbon radical with only single carbon-carbon bonds. Representative examples include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted. Alkyl groups are $C_1$-$C_{12}$.

The term "aryl" refers to aromatic groups which have 5-14 ring atoms and at least one ring having a conjugated pi electron system and includes carbocyclic aryl, heterocyclic aryl and biaryl groups, all of which may be optionally substituted.

Carbocyclic aryl groups are groups which have 6-14 ring atoms wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups which have 5-14 ring atoms wherein 1 to 4 heteroatoms are ring atoms in the aromatic ring and the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "biaryl" represents aryl groups which have 5-14 atoms containing more than one aromatic ring including both fused ring systems and aryl groups substituted with other aryl groups. Such groups may be optionally substituted. Suitable biaryl groups include naphthyl and biphenyl.

The term "optionally substituted" or "substituted" includes groups substituted by one to six substituents, independently selected from lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halo, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, sulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, and lower arylalkyloxyalkyl.

"Substituted aryl" and "substituted heteroaryl" refers to aryl and heteroaryl groups substituted with 1-3 substituents. These substituents are selected from the group consisting of lower alkyl, lower alkoxy, lower perhaloalkyl, halo, hydroxy, and amino.

The term "-aralkyl" refers to an alkylene group substituted with an aryl group. Suitable aralkyl groups include benzyl, picolyl, and the like, and may be optionally substituted. "Heteroarylalkyl" refers to an alkylene group substituted with a heteroaryl group.

The term "alkylaryl-" refers to an aryl group substituted with an alkyl group. "Lower alkylaryl-" refers to such groups where alkyl is lower alkyl.

The term "lower" referred to herein in connection with organic radicals or compounds respectively refers to 6 carbon atoms or less. Such groups may be straight chain, branched, or cyclic.

The term "higher" referred to herein in connection with organic radicals or compounds respectively refers to 7 carbon atoms or more. Such groups may be straight chain, branched, or cyclic.

The term "cyclic alkyl" or "cycloalkyl" refers to alkyl groups that are cyclic of 3 to 10 carbon atoms, and in one aspect are 3 to 6 carbon atoms Suitable cyclic groups include norbornyl and cyclopropyl. Such groups may be substituted.

The term "heterocyclic", "heterocyclic alkyl" or "heterocycloalkyl" refer to cyclic groups of 3 to 10 atoms, and in one aspect are 3 to 6 atoms, containing at least one heteroatom, in a further aspect are 1 to 3 heteroatoms. Suitable heteroatoms include oxygen, sulfur, and nitrogen. Heterocyclic groups may be attached through a nitrogen or through a carbon atom in the ring. The heterocyclic alkyl groups include unsaturated cyclic, fused cyclic and spirocyclic groups. Suitable heterocyclic groups include pyrrolidinyl, morpholino, morpholinoethyl, and pyridyl.

The terms "arylamino" (a), and "aralkylamino" (b), respectively, refer to the group —NRR' wherein respectively, (a) R is aryl and R' is hydrogen, alkyl, aralkyl, heterocycloalkyl, or aryl, and (b) R is aralkyl and R' is hydrogen, aralkyl, aryl, alkyl or heterocycloalkyl.

The term "acyl" refers to —C(O)R where R is alkyl, heterocycloalkyl, or aryl.

The term "carboxy esters" refers to —C(O)OR where R is alkyl, aryl, aralkyl, cyclic alkyl, or heterocycloalkyl, all optionally substituted.

The term "carboxyl" refers to —C(O)OH.

The term "oxo" refers to =O in an alkyl or heterocycloalkyl group.

The term "amino" refers to —NRR' where R and R' are independently selected from hydrogen, alkyl, aryl, aralkyl and heterocycloalkyl, all except H are optionally substituted; and R and R' can form a cyclic ring system.

The term "-carboxylamido" refers to —CONR$_2$ where each R is independently hydrogen or alkyl.

The term "-sulphonylamido" or "-sulfonylamido" refers to —S(=O)$_2$NR$_2$ where each R is independently hydrogen or alkyl.

The term "halogen" or "halo" refers to —F, —Cl, —Br and —I.

The term "alkylaminoalkylcarboxy" refers to the group alkyl-NR-alk-C(O)—O— where "alk" is an alkylene group, and R is a H or lower alkyl.

The term "sulphonyl" or "sulfonyl" refers to —SO$_2$R, where R is H, alkyl, aryl, aralkyl, or heterocycloalkyl.

The term "sulphonate" or "sulfonate" refers to —SO$_2$OR, where R is —H, alkyl, aryl, aralkyl, or heterocycloalkyl.

The term "alkenyl" refers to unsaturated groups which have 2 to 12 atoms and contain at least one carbon-carbon double bond and includes straight-chain, branched-chain and cyclic groups. Alkenyl groups may be optionally substituted. Suitable alkenyl groups include allyl. "1-alkenyl" refers to alkenyl groups where the double bond is between the first and second carbon atom. If the 1-alkenyl group is attached to another group, e.g., it is a W substituent attached to the cyclic phosphonate, it is attached at the first carbon.

The term "alkynyl" refers to unsaturated groups which have 2 to 12 atoms and contain at least one carbon-carbon triple bond and includes straight-chain, branched-chain and cyclic groups. Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, e.g., it is a W substituent attached to the cyclic phosphonate, it is attached at the first carbon.

The term "alkylene" refers to a divalent straight chain, branched chain or cyclic saturated aliphatic group. In one aspect the alkylene group contains up to and including 10 atoms. In another aspect the alkylene group contains up to and including 6 atoms. In a further aspect the alkylene group contains up to and including 4 atoms. The alkylene group can be either straight, branched or cyclic.

The term "acyloxy" refers to the ester group —O—C(O)R, where R is H, alkyl, alkenyl, alkynyl, aryl, aralkyl, or heterocycloalkyl.

The term "aminoalkyl-" refers to the group NR$_2$-alk- wherein "alk" is an alkylene group and R is selected from —H, alkyl, aryl, aralkyl, and heterocycloalkyl.

The term "alkylaminoalkyl-" refers to the group alkyl-NR-alk- wherein each "alk" is an independently selected alkylene, and R is H or lower alkyl. "Lower alkylaminoalkyl-" refers to groups where the alkyl and the alkylene group is lower alkyl and alkylene, respectively.

The term "arylaminoalkyl-" refers to the group aryl-NR-alk- wherein "alk" is an alkylene group and R is —H, alkyl, aryl, aralkyl, or heterocycloalkyl. In "lower arylaminoalkyl-", the alkylene group is lower alkylene.

The term "alkylaminoaryl-" refers to the group alkyl-NR-aryl- wherein "aryl" is a divalent group and R is —H, alkyl, aralkyl, or heterocycloalkyl. In "lower alkylaminoaryl-", the alkyl group is lower alkyl.

The term "alkoxyaryl-" refers to an aryl group substituted with an alkyloxy group. In "lower alkyloxyaryl-," the alkyl group is lower alkyl.

The term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "alkoxy-" or "alkyloxy-" refers to the group alkyl-O—.

The term "alkoxyalkyl-" or "alkyloxyalkyl-" refer to the group alkyl-O-alk- wherein "alk" is an alkylene group. In "lower alkoxyalkyl-," each alkyl and alkylene is lower alkyl and alkylene, respectively.

The term "alkylthio-" refers to the group alkyl-S—.

The term "alkylthioalkyl-" refers to the group alkyl-5-alk- wherein "alk" is an alkylene group. In "lower alkylthioalkyl-" each alkyl and alkylene is lower alkyl and alkylene, respectively.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The term "amido" refers to the $NR_2$ group next to an acyl or sulfonyl group as in $NR_2$—C(O)—, RC(O)—$NR^1$—, $NR_2$—S(=O)$_2$— and RS(=O)$_2$—$NR^1$—, where R and $R^1$ include —H, alkyl, aryl, aralkyl, and heterocycloalkyl.

The term "carboxamido" refer to $NR_2$—C(O)— and RC(O)—$NR^1$—, where R and $R^1$ include —H, alkyl, aryl, aralkyl, and heterocycloalkyl. The term does not include urea, —NR—C(O)—NR—.

The terms "sulphonamido" or "sulfonamido" refer to $NR_2$—S(=O)$_2$— and RS(=O)$_2$—$NR^1$—, where R and $R^1$ include —H, alkyl, aryl, aralkyl, and heterocycloalkyl. The term does not include sulfonylurea, —NR—S(=O)$_2$—NR—.

The term "carboxamidoalkylaryl" and "carboxamidoaryl" refers to an aryl-alk-$NR^1$—C(O), and ar-$NR^1$—C(O)-alk-, respectively where "ar" is aryl, "alk" is alkylene, $R^1$ and R include H, alkyl, aryl, aralkyl, and heterocycloalkyl.

The term "sulfonamidoalkylaryl" and "sulfonamidoaryl" refers to an aryl-alk-$NR^1$—S(=O)$_2$—, and ar-$NR^1$—S(=O)$_2$—, respectively where "ar" is aryl, "alk" is alkylene, $R^1$ and R include —H, alkyl, aryl, aralkyl, and heterocycloalkyl.

The term "hydroxyalkyl" refers to an alkyl group substituted with one —OH.

The term "haloalkyl" refers to an alkyl group substituted with halo.

The term "cyano" refers to —C≡N.

The term "nitro" refers to —$NO_2$.

The term "acylalkyl" refers to an alkyl-C(O)-alk-, where "alk" is alkylene.

The term "aminocarboxamidoalkyl-" refers to the group $NR_2$—C(O)—N(R)-alk- wherein R is an alkyl group or H and "alk" is an alkylene group. "Lower aminocarboxamidoalkyl-" refers to such groups wherein "alk" is lower alkylene.

The term "heteroarylalkyl" refers to an alkylene group substituted with a heteroaryl group.

The term "perhalo" refers to groups wherein every C—H bond has been replaced with a C-halo bond on an aliphatic or aryl group. Suitable perhaloalkyl groups include —$CF_3$ and —$CFCl_2$.

The term "carboxylic acid moiety" refers to a compound having a carboxylic acid group (—COOH), and salts thereof, a carboxylic acid ester, or a carboxylic acid surrogate.

The term "surrogates of carboxylic acid" refers to groups that possess near equal molecular shapes and volumes as carboxylic acid and which exhibit similar physical and biological properties. Examples of surrogates of carboxylic acid include, but are not limited to, tetrazole, 6-azauracil, acylsulphonamides, thiazolidinedione, hydroxamic acid, oxamic acid, malonamic acid, and carboxylic acid amides. Because phosphorus-containing thyromimetics (e.g., phosphonic acid-, phosphonic acid monoester-, and phosphinic acid-containing compounds) have a markedly different biological activity as compared to carboxylic acid-containing thyromimetics, phosphonic acid, phosphonic acid monoester, and phosphinic acid are not considered to be surrogates of carboxylic acid in these compounds.

The term "co-crystal" as used herein means a crystalline material comprised of two or more unique solids at room temperature, each containing distinctive physical characteristics, such as structure, melting point and heats of fusion. The co-crystals of the present invention comprise a co-crystal former H-bonded to a compound of the present invention. The co-crystal former may be H-bonded directly to the compound of the present invention or may be H-bonded to an additional molecule which is bound to the compound of the present invention. The additional molecule may be H-bonded to the compound of the present invention or bound ionically to the compound of the present invention. The additional molecule could also be a second API. Solvates of compounds of the present invention that do not further comprise a co-crystal former are not "co-crystals" according to the present invention. The co-crystals may however, include one or more solvate molecules in the crystalline lattice. That is, solvates of co-crystals, or a co-crystal further comprising a solvent or compound that is a liquid at room temperature, is included in the present invention as a co-crystal.

The co-crystals may also be a co-crystal between a co-crystal former and a salt of a compound of the present invention, but the compound of the present invention and the co-crystal former are constructed or bonded together through hydrogen bonds. Other modes of molecular recognition may also be present including, pi-stacking, guest-host complexation and van der Waals interactions. Of the interactions listed above, hydrogen-bonding is the dominant interaction in the formation of the co-crystal, (and a required interaction according to the present invention) whereby a non-covalent bond is formed between a hydrogen bond donor of one of the moieties and a hydrogen bond acceptor of the other.

Crystalline material comprised of solid compound of the present invention and one or more liquid solvents (at room temperature) are included in the present invention as "solvates." A "hydrate" is where the solvent is water. Other forms of the present invention include, but are not limited to, anhydrous forms and de-solvated solvates.

The ratio of the compound of the present invention to co-crystal former or solvent may be specified as stoichiometric or non-stoichiometric. 1:1, 1.5:1, 1:1.5, 2:1, 1:2, and 1:3 ratios of API:co-crystal former/solvent are examples of stoichiometric ratios.

The term "binding" means the specific association of the compound of interest to the thyroid hormone receptor. One method of measuring binding in this invention is the ability of the compound to inhibit the association of $^{125}$I-T3 with a mixture of thyroid hormone receptors using nuclear extracts or purified or partially purified thyroid hormone receptor (for example, alpha or beta) in a heterologous assay.

The term "energy expenditure" means basal or resting metabolic rate as defined by Schoeller et al., *J Appl Physiol.* 53(4):955-9 (1982). Increases in the resting metabolic rate can be also be measured using increases in $O_2$ consumption and/or $CO_2$ efflux and/or increases in organ or body temperature.

The phrase "therapeutically effective amount" means an amount of a compound or a combination of compounds that ameliorates, attenuates or eliminates one or more of the symptoms of a particular disease or condition or prevents, modifies, or delays the onset of one or more of the symptoms of a particular disease or condition.

The term "pharmaceutically acceptable salt" includes salts of compounds of Formula I and its prodrugs derived from the combination of a compound of this invention and an organic or inorganic acid or base. Suitable acids include acetic acid, adipic acid, benzenesulfonic acid, (+)-7,7-dimethyl-2-oxobicyclo[2.2.1]heptane-1-methanesulfonic acid, citric acid, 1,2-ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfinuric acid, 2-naphthalenesulfonic acid, nitric acid, oleic acid, 4,4'-methylenebis[3-hydroxy-2-naphthalenecarboxylic acid], phosphoric acid, polygalacturonic acid, stearic acid, succinic acid, sulfuric acid, sulfosalicylic acid, tannic acid, tartaric acid, terphthalic acid, and p-toluenesulfonic acid.

The term "patient" means an animal.

The term "animal" includes birds and mammals. In one embodiment a mammal includes a dog, cat, cow, horse, goat, sheep, pig or human. In one embodiment the animal is a human. In another embodiment the animal is a male. In another embodiment the animal is a female.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, $R_2$N—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of the present invention fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, and/or pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

The term "phosphonate prodrug" refers to compounds that breakdown chemically or enzymatically to a phosphonic acid or phosphinic acid group or a monoester thereof in vivo. As employed herein the term includes, but is not limited to, the following groups and combinations of these groups:

Acyloxyalkyl esters which are well described in the literature (Farquhar et al., *J. Pharm. Sci.* 72:324-325 (1983)).

Other acyloxyalkyl esters are possible in which a cyclic alkyl ring is formed. These esters have been shown to generate phosphorus-containing nucleotides inside cells through a postulated sequence of reactions beginning with deesterification and followed by a series of elimination reactions (e.g., Freed et al., *Biochem. Pharm,* 38:3193-3198 (1989)).

Another class of these double esters known as alkyloxycarbonyloxymethyl esters, as shown in formula A, where R is alkoxy, aryloxy, alkylthio, arylthio, alkylamino, and arylamino; R', and R" are independently —H, alkyl, aryl, alkylaryl, and heterocycloalkyl have been studied in the area of β-lactam antibiotics (Nishimura et al., *J. Antibiotics* 40(1): 81-90 (1987); for a review see Ferres, H., *Drugs of Today,* 19:499 (1983)). More recently Cathy, M. S. et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

Formula A

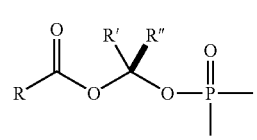

wherein R, R', and R" are independently H, alkyl, aryl, alkylaryl, and alicyclic (see WO 90/08155; WO 90/10636).

Other acyloxyalkyl esters are possible in which a cyclic alkyl ring is formed such as shown in formula B. These esters have been shown to generate phosphorus-containing nucleotides inside cells through a postulated sequence of reactions beginning with deesterification and followed by a series of elimination reactions (e.g., Freed et al., *Biochem. Pharm.* 38:3193-3198 (1989)).

Formula B

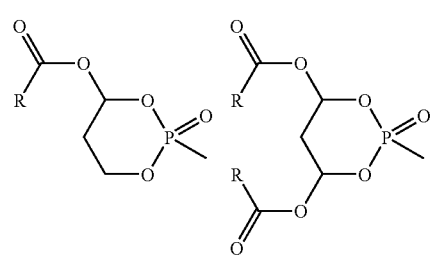

wherein R is —H, alkyl, aryl, alkylaryl, alkoxy, aryloxy, alkylthio, arylthio, alkylamino, arylamino, or cycloalkyl.

Aryl esters have also been used as phosphonate prodrugs (e.g., DeLambert et al., *J. Med. Chem.* 37(7):498-511 (1994); Serafinowska et al., *J. Med. Chem.* 38(8):1372-9 (1995). Phenyl as well as mono and poly-substituted phenyl proesters have generated the parent phosphonic acid in studies conducted in animals and in man (Formula C). Another approach has been described where Y is a carboxylic ester ortho to the phosphate (Khamnei et al., *J. Med. Chem.* 39:4109-15 (1996)).

Formula C

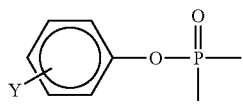

wherein Y is —H, alkyl, aryl, alkylaryl, alkoxy, acyloxy, halogen, amino, alkoxycarbonyl, hydroxy, cyano, and heterocycloalkyl.

Benzyl esters have also been reported to generate the parent phosphonic acid. In some cases, using substituents at the para-position can accelerate the hydrolysis. Benzyl analogs with 4-acyloxy or 4-alkyloxy group [Formula D, X=—H, OR or O(CO)R or O(CO)OR] can generate the 4-hydroxy compound more readily through the action of enzymes, e.g., oxidases, esterases, etc. Examples of this class of prodrugs are described in Mitchell et al., *J. Chem. Soc. Perkin Trans. I* 2345 (1992); WO 91/19721.

Formula D

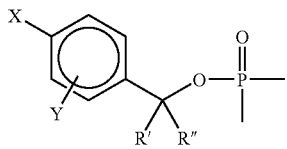

wherein X and Y are independently —H, alkyl, aryl, alkylaryl, alkoxy, acyloxy, hydroxy, cyano, nitro, perhaloalkyl, halo, or alkyloxycarbonyl; and R' and R" are independently —H, alkyl, aryl, alkylaryl, halogen, and cyclic alkyl.

Thio-containing phosphonate proesters may also be useful in the delivery of drugs to hepatocytes. These proesters contain a protected thioethyl moiety as shown in formula E. One or more of the oxygens of the phosphonate can be esterified. Since the mechanism that results in de-esterification requires the generation of a free thiolate, a variety of thiol protecting groups are possible. For example, the disulfide is reduced by a reductase-mediated process (Puech et al., *Antiviral Res.* 22:155-174 (1993)). Thioesters will also generate free thiolates after esterase-mediated hydrolysis Benzaria, et al., *J. Med. Chem.* 39(25):4958-65 (1996)). Cyclic analogs are also possible and were shown to liberate phosphonate in isolated rat hepatocytes. The cyclic disulfide shown below has not been previously described and is novel.

Formula E

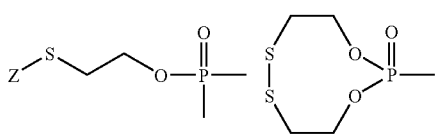

wherein Z is alkylcarbonyl, alkoxycarbonyl, arylcarbonyl, aryloxycarbonyl, or alkylthio.

Other examples of suitable prodrugs include proester classes exemplified by Biller and Magnin (U.S. Pat. No. 5,157,027); Serafinowska et al., *J. Med. Chem.* 38(8):1372-9 (1995); Starrett et al., *J. Med. Chem.* 37:1857 (1994); Martin et al. *J. Pharm. Sci.* 76:180 (1987); Alexander et al., *Collect. Czech. Chem. Commun.* 59:1853 (1994); and EP 0 632 048 A1. Some of the structural classes described are optionally substituted, including fused lactones attached at the omega position (formulae E-1 and E-2) and optionally substituted 2-oxo-1,3-dioxolenes attached through a methylene to the phosphorus oxygen (formula E-3) such as:

E-1

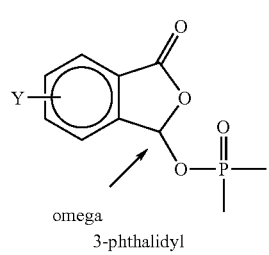

omega
3-phthalidyl

E-2

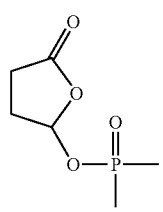

2-oxotetrahydrofuran-5-yl

E-3

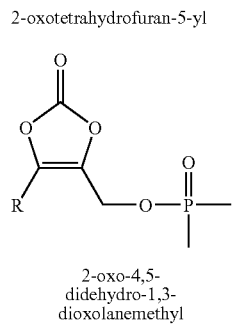

2-oxo-4,5-
didehydro-1,3-
dioxolanemethyl wherein R is —H, alkyl, cycloalkyl, or heterocycloalkyl; and wherein Y is —H, alkyl, aryl, alkylaryl, cyano, alkoxy, acyloxy, halogen, amino, heterocycloalkyl, and alkoxycarbonyl.

The prodrugs of Formula E-3 are an example of "optionally substituted heterocycloalkyl where the cyclic moiety contains a carbonate or thiocarbonate."

Propyl phosphonate proesters can also be used to deliver drugs into hepatocytes. These proesters may contain a hydroxyl and hydroxyl group derivatives at the 3-position of the propyl group as shown in formula F. The R and X groups can form a cyclic ring system as shown in formula F. One or more of the oxygens of the phosphonate can be esterified.

Formula F

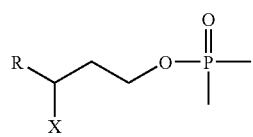

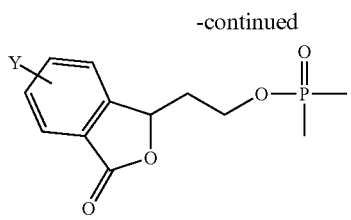

wherein R is alkyl, aryl, heteroaryl;

X is hydrogen, alkylcarbonyloxy, alkyloxycarbonyloxy; and

Y is alkyl, aryl, heteroaryl, alkoxy, alkylamino, alkylthio, halogen, hydrogen, hydroxy, acyloxy, amino.

Phosphoramidate derivatives have been explored as phosphate prodrugs (e.g., McGuigan et al., *J. Med. Chem.* 42:393 (1999) and references cited therein) as shown in Formula G and H.

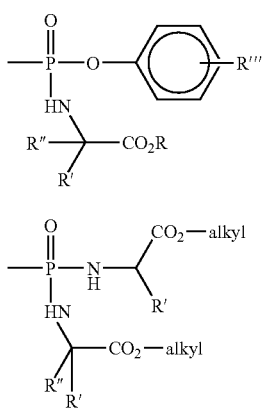

Formula G

Formula H

Cyclic phosphoramidates have also been studied as phosphonate prodrugs because of their speculated higher stability compared to non-cyclic phosphoramidates (e.g., Starrett et al., *J. Med. Chem.* 37:1857 (1994)).

Another type of phosphoramidate prodrug was reported as the combination of S-acyl-2-thioethyl ester and phosphoramidate (Egron et al., *Nucleosides Nucleotides* 18:981 (1999)) as shown in Formula J:

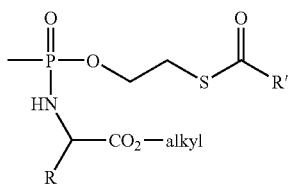

Formula J

Other prodrugs are possible based on literature reports such as substituted ethyls, for example, bis(trichloroethyl) esters as disclosed by McGuigan, et al., *Bioorg Med. Chem. Lett.* 3:1207-1210 (1993), and the phenyl and benzyl combined nucleotide esters reported by Meier, C. et al., *Bioorg. Med. Chem. Lett.* 7:99-104 (1997).

The structure

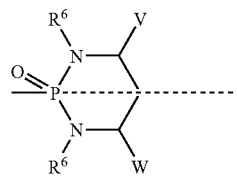

has a plane of symmetry running through the phosphorus-oxygen double bond when $R^6=R^6$, V=W, and V and W are either both pointing up or both pointing down. The same is true of structures where each —$NR^6$ is replaced with —O—.

The term "cyclic phosphonate ester of 1,3-propane diol", "cyclic phosphonate diester of 1,3-propane diol", "2 oxo $2\lambda^5$ [1,3,2] dioxaphosphonane", "2 oxo [1,3,2] dioxaphosphonane", "dioxaphosphonane" refers to the following:

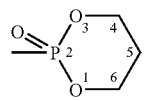

The phrase "together V and Z are connected via an additional 3-5 atoms to form a cyclic group containing 5-7 atoms, optionally containing 1 heteroatom, substituted with hydroxy, acyloxy, alkylthiocarbonyloxy, alkoxycarbonyloxy, or aryloxycarbonyloxy attached to a carbon atom that is three atoms from both Y groups attached to the phosphorus" includes the following:

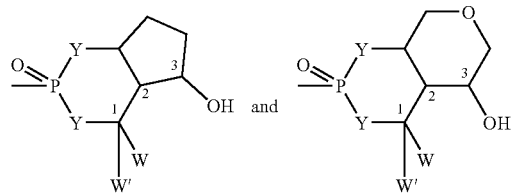

The structure shown above (left) has an additional 3 carbon atoms that forms a five member cyclic group. Such cyclic groups must possess the listed substitution to be oxidized.

The phrase "together V and Z are connected via an additional 3-5 atoms to form a cyclic group, optionally containing one heteroatom, that is fused to an aryl group attached at the beta and gamma position to the Y attached to the phosphorus" includes the following:

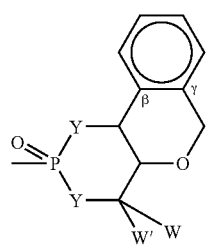

The phrase "together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus" includes the following:

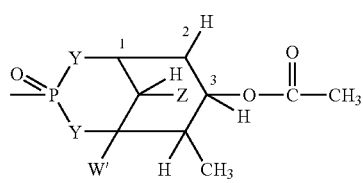

The structure above has an acyloxy substituent that is three carbon atoms from a Y, and an optional substituent, —CH$_3$, on the new 6-membered ring. There has to be at least one hydrogen at each of the following positions: the carbon attached to Z; both carbons alpha to the carbon labeled "3"; and the carbon attached to "OC(O)CH$_3$" above.

The phrase "together W and W' are connected via an additional 2-5 atoms to form a cyclic group, optionally containing 0-2 heteroatoms, and V must be aryl, substituted aryl, heteroaryl, or substituted heteroaryl" includes the following:

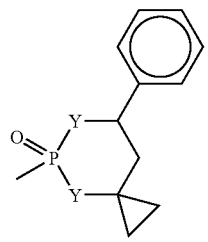

The structure above has V=aryl, and a spiro-fused cyclopropyl group for W and W'.

The term "cyclic phosphon(amid)ate" refers to

where Y is independently —O— or —NR$^V$—. The carbon attached to V must have a C—H bond. The carbon attached to Z must also have a C—H bond.

The naming of the compounds is done by having the ring bearing the groups R$^5$ and R$^3$ be a substituent on the ring bearing the R$^1$ and R$^2$ groups. The naming of the prodrugs is done by having the diaryl system with its linker T (Formula I or III) or D (Formula II) be a substituent on the phosphorus atom contained in X. For example:

[3-R$^1$-5-R$^2$-4-(4'-R$^5$-3'-R$^3$-benzyl)phenoxy]methylphosphonic acid represents the formula:

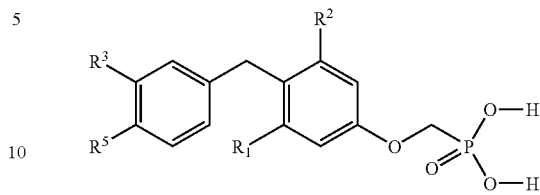

[3-R$^1$-5-R$^2$-4-(4'-R$^5$-3'-R$^3$-phenoxy)phenoxy]methylphosphonic acid represents the formula:

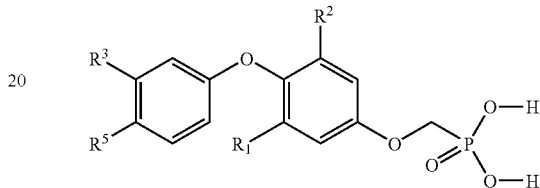

N-[3-R$^1$-5-R$^2$-4-(4'-R$^5$-3'-R$^3$-phenoxy)phenyl]carbamoylphosphonic acid represents the formula:

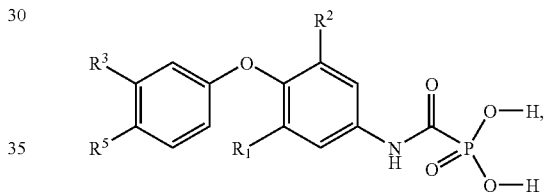

2-[(3-R$^1$-5-R$^2$-4-(4'-R$^5$-3'-R$^3$-benzyl)phenoxy)methyl]-4-aryl-2-oxo-2λ$^5$-[1,3,2]-dioxaphosphonane:

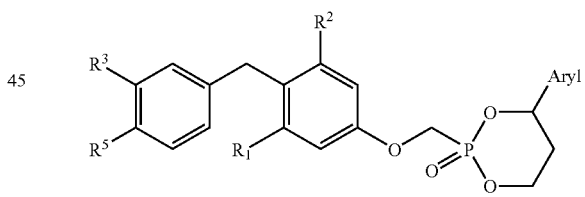

2-[(3-R$^1$-5-R$^2$-4-(4'-R$^5$-3'-R$^3$-phenoxy)phenoxy)methyl]-4-aryl-2-oxo-2λ$^5$-[1,3,2]-dioxaphosphonane:

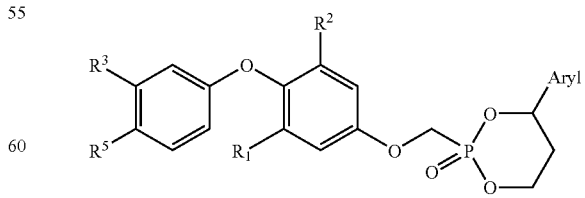

The term "cis" stereochemistry refers to the spatial relationship of the V group and the carbon attached to the phosphorus atom on the six-membered ring. The formula below shows a cis stereochemistry.

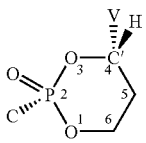

The term "trans" stereochemistry refers to the spatial relationship of the V group and the carbon, attached to the phosphorus atom, on the six-membered ring. The formula below shows a trans-stereochemistry.

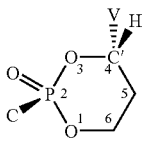

The formula below shows another trans-stereochemistry.

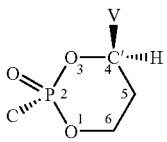

The terms "S-configuration", "S-isomer" and "S-prodrug" refers to the absolute configuration S of carbon C''. The formula below shows the S-stereochemistry.

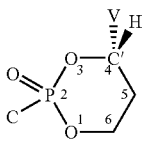

The terms "R-configuration", "R-isomer" and "R-prodrug" refers to the absolute configuration R of carbon C''. The formula below shows the R-stereochemistry.

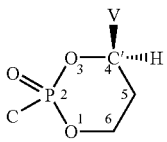

The term "percent enantiomeric excess (% ee)" refers to optical purity. It is obtained by using the following formula:

$$\frac{[R]-[S]}{[R]+[S]} \times 100 = \%\ R - \%\ S$$

where [R] is the amount of the R isomer and [S] is the amount of the S isomer. This formula provides the % ee when R is the dominant isomer.

The term "enantioenriched" or "enantiomerically enriched" refers to a sample of a chiral compound that consists of more of one enantiomer than the other. The extent to which a sample is enantiomerically enriched is quantitated by the enantiomeric ratio or the enantiomeric excess.

The term "liver" refers to liver organ.

The term "enhancing" refers to increasing or improving a specific property.

The term "liver specificity" refers to the ratio:

$$\frac{[\text{drug or a drug metabolite in liver tissue}]}{[\text{drug or a drug metabolite in blood or another tissue}]}$$

as measured in animals treated with the drug or a prodrug. The ratio can be determined by measuring tissue levels at a specific time or may represent an AUC based on values measured at three or more time points.

The term "phosphorus-containing compounds" refers to compounds that contain $PO_3H_2$, $PO_3^{2-}$, $PO_2HR$, $PO_2R^{1-}$, and monoesters thereof.

The term "inhibitor of fructose-1,6-biphosphatase" or "FBPase inhibitor" refers to compounds that inhibit FBPase enzyme activity and thereby block the conversion of fructose 1,6-bisphosphate, the substrate of the enzyme, to fructose 6-phosphate. These compounds have an $IC_{50}$ of equal to or less than 50 µM on human liver FBPase measured according to the procedure found in U.S. Pat. No. 6,489,476.

The term "increased or enhanced liver specificity" refers to an increase in the liver specificity ratio in animals treated with a compound of the present invention and a control compound. In one embodiment the test compound is a phosphonic acid compound of the present invention and in another embodiment the test compound is a prodrug thereof. In one embodiment the control compound is a phosphorus-containing compound of the present invention. In another embodiment the control compound is the corresponding carboxylic acid derivative of the phosphorus-containing test compound.

The term "enhanced oral bioavailability" refers to an increase of at least 50% of the absorption of the dose of the parent drug, unless otherwise specified. In an additional aspect the increase in oral bioavailability of the prodrug (compared to the parent drug) is at least 100%, that is a doubling of the absorption. Measurement of oral bioavailability usually refers to measurements of the prodrug, drug, or drug metabolite in blood, plasma, tissues, or urine following oral administration compared to measurements following systemic administration of the compound administered orally.

The terms "treating" or "treatment" of a disease includes a slowing of the progress or development of a disease after onset or actually reversing some or all of the disease affects. Treatment also includes palliative treatment.

The term "preventing" includes a slowing of the progress or development of a disease before onset or precluding onset of a disease.

The term "thyroid hormone receptors" (TR) refers to intracellular proteins located in cell nuclei that, following the binding of thyroid hormone, stimulate transcription of specific genes by binding to DNA sequences called thyroid hormone response elements (TREs). In this manner TR regulates the expression of a wide variety of genes involved in metabolic processes (e.g., cholesterol homeostasis and fatty acid oxidation) and growth and development in many tissues, including liver, muscle and heart. There are at least two forms of TR; TR alpha (on chromosome 17) and TR beta (on chromosome 3). Each of these isoforms also has two main isoforms: TR alpha-1 and TR alpha-2; and TR beta-1 and TR beta-2, respectively. TRs are high affinity receptors for thyroid hormones, especially triiodothyronine.

The term "ACC" refers to acetyl CoA carboxylase.

The term "FAS" refers to fatty acid synthase.

The term "spot-14" refers to a 17 kilodalton protein expressed in lipogenic tissues and is postulated to play a role in thyroid hormone stimulation of lipogenesis. (Campbell, M C et al., *Endocrinology* 10:1210 (2003).

The term "CPT-1" refers to carnitine palmitoyltransferase-1.

The term "CYP7A" refers to cholesterol 7-alpha hydroxylase, which is a membrane-bound cytochrome P450 enzyme that catalyzes the 7-alpha-hydroxylation of cholesterol in the presence of molecular oxygen and NADPH-ferrihemoprotein reductase. CYP7A, encoded by CYP7, converts cholesterol to 7-alpha-hydroxycholesterol which is the first and rate-limiting step in the synthesis of bile acids.

The term "apoAI" refers to Apolipoprotein AI found in HDL and chylomicrons. It is an activator of LCAT and a ligand for the HDL receptor.

The term "mGPDH" refers to mitochondrial glycerol-3-phosphate dehydrogenase.

The term "hypercholesterolemia" refers to presence of an abnormally large amount of cholesterol in the cells and plasma of the circulating blood.

The term "hyperlipidemia" or "lipemia" refers to the presence of an abnormally large amount of lipids in the circulating blood.

The term "atherosclerosis" refers to a condition characterized by irregularly distributed lipid deposits in the intima of large and medium-sized arteries wherein such deposits provoke fibrosis and calcification. Atherosclerosis raises the risk of angina, stroke, heart attack, or other cardiac or cardiovascular conditions.

The term "obesity" refers to the condition of being obese. Being obese is defined as a body mass index (BMI) of 30.0 or greater; and extreme obesity is defined at a BMI of 40 or greater. "Overweight" is defined as a body mass index of 25.0 to 29.9 (This is generally about 10 percent over an ideal body weight)

The term "coronary heart disease" or "coronary disease" refers to an imbalance between myocardial functional requirements and the capacity of the coronary vessels to supply sufficient blood flow. It is a form of myocardial ischemia (insufficient blood supply to the heart muscle) caused by a decreased capacity of the coronary vessels.

The terms "fatty liver" and "liver steatosis" are interchangeable and refer to a disease or disorder characterized by significant lipid deposition in the liver hepatocytes (parenchyma cells). Simple fatty liver or liver steatosis is not associated with any other liver abnormalities such as scarring or inflammation. Fatty liver or liver steatosis is a common in patients who are very overweight or have diabetes mellitus.

The term "NonAlcoholic SteatoHepatitis (NASH) refers to a disease or disorder characterized by inflammation of the liver in combination with fatty liver. NASH is a possible diagnosis when other causes of liver inflammation such as hepatitis B and C viruses, autoimmune disorders, alcohol, drug toxicity, and the accumulation of copper (Wilson's Disease) or iron (hemochromatosis) are excluded.

The term "NonAlcoholic Fatty Liver Disease (NAFLD) refers to a wide spectrum of liver disease ranging from (and including) simple fatty liver (steatosis) to nonalcoholic steatohepatitis (NASH), to cirrhosis (advanced scarring of the liver). All of the stages of NAFLD have fatty liver in common.

In NASH, fat accumulation is associated with varying degrees of inflammation (hepatitis) which may lead to scarring (fibrosis) of the liver.

Steatosis can be most readily diagnosed with noninvasive imaging modalities, such as ultrasound, magnetic resonance imaging, or computed tomography as examples, or following a percutaneous biopsy. Using ultrasound as an example of a noninvasive imaging diagnosis tool: the sonographic findings of diffuse fatty change include a diffuse hyperechoic echotexture (bright liver), increased liver echotexture compared with the kidneys, vascular blurring, and deep attenuation (Yajima et al., *Tohoku J Exp Med* 139(1):43-50 (1983)). Using percutaneous biopsy, the histological features of NAFLD are indistinguishable from those of alcohol-induced liver disease, of which, predominant macrovesicular steatosis alone in >33% of hepatocytes will be used as the definition. Other histologic features, such as varying amounts of cytologic ballooning and spotty necrosis, scattered mixed neutrophilic-lymphocytic inflammation, glycogen nuclei, Mallory's hyaline, and perisinusoidal fibrosis may be present, but are not required for a diagnosis of NAFLD.

The term "nephrotic syndrome" refers to a condition of heavy glomerular proteinuria which is associated with hyperlipidemia, increased risk of cardiovascular disease, and deterioration of renal function. The nephrotic dyslipidemia is marked by hypercholesterolemia, hypertriglyceridemia, and elevated plasma concentration and impaired clearance of LDL, VLDL, and IDL. These abnormalities are largely a result of dysregulation of the key enzymes and receptors involved in lipid metabolism, including LDL receptor deficiency, lecithin-cholesterol acyl transferase (LCAT) deficiency, elevated plasma cholesterol ester transfer protein, diminished HDL receptor, dysregulation of HMG-CoA reductase and 7α-hydroxylase, diminished catabolism of apo B-100, increased production of Lp(a), downregulation of lipoprotein lipase VLDL receptor and hepatic lipase, and upregulation of hepatic acyl-coenzyme A:diacylglycerol acyltransferase, acetyl-coenzyme A carboxylase, and fatty acid synthase.

The term "chronic renal failure" refers to a chronic kidney condition that leads to abnormalities of lipid metabolism and marked alteration of plasma lipid profile. The typical dyslipidemia associated with chronic renal failure includes hypertriglyceridemia, elevated level and impaired clearance of VLDL, IDL, and LDL, inappropriately reduced HDL cholesterol, and impaired maturation of cholesterol-poor HDL-3 to cardioprotective cholesterol ester-rich HDL-2. The primary mechanisms for the dyslipidemia include downregulation of lipoprotein lipase, VLDL receptor, hepatic triglyceride lipase, and LCAT.

The term "diabetes" refers to a heterogeneous group of disorders that share glucose intolerance in common. It refers to disorders in which carbohydrate utilization is reduced and that of lipid and protein enhanced; and may be characterized by hyperglycemia, glycosuria, ketoacidosis, neuropathy, or nephropathy.

The term "non-insulin-dependent diabetes mellitus" (NIDDM or type 2 diabetes) refers to a heterogeneous disorder characterized by impaired insulin secretion by the pancreas and insulin resistance in tissues such as the liver, muscle and adipose tissue. The manifestations of the disease include one or more of the following: impaired glucose tolerance, fasting hyperglycemia, glycosuria, increased hepatic glucose output, reduced hepatic glucose uptake and glycogen storage, reduced whole body glucose uptake and utilization, dyslipidemia, fatty liver, ketoacidosis, microvascular diseases such as retinopathy, nephropathy and neuropathy, and macrovascular diseases such as coronary heart disease.

The term "impaired glucose tolerance (IGT)" refers to a condition known to precede the development of overt type 2 diabetes. It is characterized by abnormal blood glucose excursions following a meal. The current criteria for the diagnosis of IGT are based on 2-h plasma glucose levels post a 75 g oral glucose test (144-199 mg/dL). Although variable from population to population studied, IGT progresses to full blown NIDDM at a rate of 1.5 to 7.3% per year, with a mean of 3-4% per year. Individuals with IGT are believed to have a 6 to 10-fold increased risk in developing NIDDM. IGT is an independent risk factor for the development of cardiovascular disease.

The term "insulin resistance" is defined clinically as the impaired ability of a known quantity of exogenous or endogenous insulin to increase whole body glucose uptake and utilization. As insulin regulates a wide variety of metabolic processes in addition to glucose homeostasis (e.g., lipid and protein metabolism), the manifestations of insulin resistance are diverse and include one or more of the following: glucose intolerance, hyperinsulinemia, a characteristic dyslipidemia (high triglycerides; low high-density lipoprotein cholesterol, and small, dense low-density lipoprotein cholesterol), obesity, upper-body fat distribution, fat accumulation in the liver (non-alcoholic fatty liver disease), NASH (non-alcoholic steatohepatitis), increased hepatic glucose output, reduced hepatic glucose uptake and storage into glycogen, hypertension, and increased prothrombotic and antifibrinolytic factors. This cluster of cardiovascular-metabolic abnormalities is commonly referred to as "The Insulin Resistance Syndrome" or "The Metabolic Syndrome" and may lead to the development of type 2 diabetes, accelerated atherosclerosis, hypertension or polycystic ovarian syndrome.

The Metabolic Syndrome" or "Metabolic Syndrome X" is characterized by a group of metabolic risk factors in one person. They include:
Central obesity (excessive fat tissue in and around the abdomen)
Atherogenic dyslipidemia (blood fat disorders—mainly high triglycerides and low HDL cholesterol—that foster plaque buildups in artery walls)
Raised blood pressure (130/85 mmHg or higher)
Insulin resistance or glucose intolerance (the body can't properly use insulin or blood sugar)
Prothrombotic state (e.g., high fibrinogen or plasminogen activator inhibitor [−1] in the blood)
Proinflammatory state (e.g., elevated high-sensitivity C-reactive protein in the blood)

According to the present invention, "Metabolic Syndrome" or "Metabolic Syndrome X" is identified by the presence of three or more of these components:
Central obesity as measured by waist circumference:
Men: Greater than 40 inches
Women: Greater than 35 inches
Fasting blood triglycerides greater than or equal to 150 mg/dL
Blood HDL cholesterol:
Men: Less than 40 mg/dL
Women: Less than 50 mg/dL
Blood pressure greater than or equal to 130/85 mmHg
Fasting glucose greater than or equal to 110 mg/dL The term "thyroid responsive element" or "TRE" refers to an element that usually consists of directly repeated half-sites with the consensus sequence AGGTCA. (Harbers et al., *Nucleic Acids Res.* 24(12):2252-2259 (1996)). TREs contain two half-sites of the AGGTCA motif which can be arranged as direct repeats, inverted repeats, or everted repeats.

The term "thyroid responsive genes" refers to genes whose expression is affected by triiodothyronine (Menjo et al., *Thyroid* 9(9):959-67 (1999); Helbing et al., *Mol. Endocrinol.* 17(7):1395-409 (2003)).

The term "TSH" or "thyrotropin" refers to the thyroid stimulating hormone.

The term "atherogenic proteins" refers to proteins that induce, stimulate, enhance or prolong atherosclerosis and diseases related to atherosclerosis, including but not limited to coronary heart disease. Atherogenic proteins include apoAI and Lp(a).

The term "thyroid hormone, or TH" includes for example natural iodinated thyronines from thyroglobulin (e.g., T3, T4), as well as drugs such as Levothyroxine sodium which is the sodium salt of a levorotatory isomer of T4 and a commonly used drug as replacement therapy in hypothyroidism. Other uses include the treatment of simple nonendemic goiter, chronic lymphocytic thyroiditis and thyrotropin-dependent thyroid carcinoma. Liothyronine sodium is the sodium salt of a levorotatory isomer of T3. Liotrix is a 4:1 mixture of levothyroxine and liothronine. Thyroid is a preparation derived from dried and defatted thyroid glands of animals.

The term "thyromimetic" or "T3 mimetic" as used herein, is intended to cover any moiety which binds to a thyroid receptor and acts as an agonist, antagonist or partial agonist/antagonist of T3. The thyromimetic may be further specified as an agonist, an antagonist, a partial agonist, or a partial antagonist. The thyromimetics of the present invention presumably bind the T3 binding site and can inhibit T3 binding to a thyroid hormone receptor utilizing a heterologous displacement reaction. Thyromimetics of the present invention that can produce one of or more of the effects mediated by naturally occurring L-triiodothyronine in a target tissue or cell would be considered an agonist or partial agonist. Thyromimetics of the present invention that can inhibit one of more of the effects mediated by naturally occurring L-triiodothyronine in a target tissue or cell would be considered an antagonist, partial agonist, or inverse agonist.

The term "metabolic disease" includes diseases and conditions such as obesity, diabetes and lipid disorders such as hypercholesterolemia, hyperlipidemia, hypertriglyceridemia as well as disorders that are associated with abnormal levels of lipoproteins, lipids, carbohydrates and insulin such as metabolic syndrome X, diabetes, impaired glucose tolerance, atherosclerosis, coronary heart disease, cardiovascular disease.

The term "mitochondrial biogenesis" or "mitochondrialgenesis" refers to the rate at which nascent mitochondria are synthesized. Mitochondrial biogenesis that occurs during cell replication provides enough new mitochondria for both the parent and daughter cells. Mitochondrial biogenesis that occurs in the absence of cell replication leads to an increase in the number of mitochondria within a cell.

As used herein, the term "significant" or "statistically significant" means a result (i.e. experimental assay result) where the p-value is $\leq 0.05$ (i.e. the chance of a type I error is less than 5%) as determined by an art-accepted measure of statistical significance appropriate to the experimental design.

All references cited herein are incorporated by reference in their entirety.

DETAILED DESCRIPTION OF THE INVENTION

The present invention relates to methods of preventing or treating metabolic diseases with phosphonic acid- or phosphonic acid monoester-containing compounds, pharmaceutically acceptable salts and prodrugs thereof, and pharmaceutically acceptable salts of the prodrugs, where the phosphonic acid- or phosphonic acid monoester-containing compounds bind to a thyroid hormone receptor.

Thyroid hormones and thyroid hormone mimetics bind to thyroid hormone receptors in the nucleus of cells and can change expression levels of genes encoding proteins that play an important role in metabolic diseases. Metabolic diseases that can be prevented or treated with thyroid hormone mimetics include obesity and lipid disorders such as hypercholesterolemia, hyperlipidemia, and hypertriglyceridemia as described in further detail below. Other metabolic diseases that can be prevented or treated with thyroid hormone mimetics include fatty liver/steatosis, NAFLD, NASH, diabetes, impaired glucose tolerance, and insulin resistance. Conditions associated with these diseases, such as atherosclerosis, coronary artery disease, and heart failure, can also be treated with these thyroid hormone receptor binding compounds.

Prior to the discoveries of the present invention, phosphonic acids were thought to be a poor replacement for carboxylic acids based on differences in geometry, size, and charge. Phosphonic acids can also show reduced binding affinities against enzymes that utilize or bind the analogous carboxylic acid. Phosphonic acids can also display differences in cellular and in vivo potency, oral bioavailability, pharmacokinetics, metabolism, and safety. T3 and previously reported T3 mimetics contain a carboxylic acid thought to be important for binding and activation of T3 responsive genes. The carboxylic acid may also be important in the transport and distribution of these compounds through various transport proteins. Transport proteins can enhance transport of certain compounds, particularly negatively charged compounds, to the nucleus.

Prior to the discoveries of the present invention it was therefore unclear whether replacement of a carboxylic acid with a phosphonic acid would produce a compound that is efficacious as a T3 mimetic because of the following:

1. it was not known whether a T3 mimetic with a phosphonic acid in place of the carboxylic acid would be transported into liver cell across the cellular membrane;
2. if the phosphonic acid containing T3 mimetic were transported across the cellular membrane of liver cells, it was not known whether the compound would be transported across the nuclear membrane into the nucleus;
3. if the phosphonic acid containing T3 mimetic were transported across both the cellular membrane and the nuclear membrane of the liver cell, it was not known if the compound would bind to the TR receptor with a great enough affinity to be efficacious;
4. if the phosphonic acid containing T3 mimetic were transported across both the cellular membrane and the nuclear membrane of the liver cell, and bound to the TR receptor with sufficient affinity for receptor activity, it was not known whether the compound would act as an agonist or antagonist of receptor activity;
5. if the phosphonic acid containing T3 mimetic were transported across both the cellular membrane and the nuclear membrane of the liver cell, and bound to the TR receptor with sufficient affinity for receptor activation, and acted as an agonist of receptor activity, it was unknown whether the compound would have a high enough tissue selectivity and have a therapeutic index great enough to be efficacious in treating the diseases and disorders described herein while avoiding undesired side-effects involving the heart.
6. finally, even if the if the phosphonic acid containing T3 mimetic were transported across both the cellular membrane and the nuclear membrane of the liver cell, and bound to the TR receptor with sufficient affinity for receptor activation, and acted as an agonist of receptor activity, and had a high enough tissue selectivity and had a therapeutic index great enough to be efficacious in treating the diseases and disorders described herein while avoiding undesired side-effects involving the heart, it was not known if the compounds of the present invention would be rapidly cleared from the blood by the kidneys thereby making the compound less useful as a drug compound.

Thus, it was unexpected when the present Inventors discovered that the phosphonic acid and phosphonic acid monoester T3 mimetic compounds of the present invention are capable of being effectively transported across the cellular membrane into liver cells and across the nuclear membrane where they bind the thyroid receptors and activate thyroid hormone responsive genes. Further, surprisingly the present Inventors discovered that the compounds of the present invention bind to the thyroid receptors with sufficient binding affinity to be effective in activating the receptors. Still further surprisingly, the present Inventors discovered that the compounds of the present invention act as agonists rather than antagonists and are thus effective in activating thyroid hormone responsive genes and for the uses described herein, such as lowering cholesterol. Still further surprisingly, the present Inventors discovered that the compounds of the present invention are effective in activating thyroid hormone responsive genes and for the uses described herein, such as lowering cholesterol, even for compounds of the present invention that bind to the thyroid hormone receptors with reduced affinity as compared to the corresponding carboxylic acid derivative. Still further surprisingly, the present Inventors discovered that the compounds of the present invention have a high enough tissue selectivity and have a therapeutic index great enough to be efficacious in treating the diseases and disorders described herein while avoiding undesired side-effects involving the heart. Still further surprisingly, the present Inventors have shown that, while phosphonic acid di-lower alkyl ester-containing thyromimetics are inactive, phosphonic acid mono-lower alkyl ester-containing compounds have similar activity to phosphonic acid-containing compounds.

It is well known that many phosphonic acids in the blood are quickly cleared by the kidneys thereby greatly diminishing their usefulness as drugs in many cases. When the Inventors of the present invention discovered that prodrugs of the compounds of the present invention were excreted into the blood stream as active phosphonic acids after being processed in the liver, it was not known whether the active compound would be quickly cleared by the kidneys or whether the phosphonic acid would be re-absorbed or transported into the liver. It was therefore unexpected when the present Inventors discovered that the active phosphonic acid compounds of the present invention were not rapidly cleared by the kidneys. It was also unexpected when the present Inventors discovered that the active phosphonic acid compounds of the present invention were re-absorbed or transported back into the liver. In fact, it was surprisingly found that the liver was the main mode of clearance of compounds tested.

In one aspect, the phosphonic acid- or phosphonic acid monoester-containing compounds, pharmaceutically acceptable salts and prodrugs thereof, and pharmaceutically acceptable salts of the prodrugs used in these methods bind to at least one thyroid hormone receptor with an Ki of $\leq 100$ nM relative to T3, or ≦90 nM, ≦80 nM, ≦70 nM, ≦60 nM, ≦50 nM, ≦40 nM, ≦30 nM, ≦20 nM, ≦10 nM, ≦50 nM, ≦1 nM, ≦0.5 nM. Thyroid hormone receptor binding is readily determined using assays described in the literature. For example, nuclear extracts from animal livers can be prepared according to the methods described by Yokoyama et al. (*J. Med. Chem.* 38:695-707 (1995)). Binding assays can also be performed using purified thyroid hormone receptors. For example, using the methods used by Chiellini et al. (*Bioorg. Med. Chem.* $^{10}$:333-346 (2002)), competition ligand binding affinities are determined using $^{125}$I-T3 and the human thyroid receptors TRα1 and TRβ1. The latter methods advantageously enable determination of thyroid receptor selectivity. Methods described in Example A were used to determine the binding of compounds of this invention.

In another aspect, the phosphonic acid- or phosphonic acid monoester-containing compounds, pharmaceutically acceptable salts and prodrugs thereof, and pharmaceutically acceptable salts of the prodrugs used in these methods cause at least a 50%, 2 fold, 3 fold, 4 fold, 6 fold or 8 fold increase or decrease in the expression of one or more thyroid hormone-responsive genes. Changes in gene expression can be detected in cells or in vivo. Prodrugs of the phosphonic acid- or phosphonic acid monoester-containing compounds can increase cellular uptake but in some cases are poorly converted to the phosphonic acid or monoester due to low levels of the enzymes required for the conversion. Changes in gene expression in vivo require either the phosphonic acid of the invention to be taken up by the tissue following administration or for the prodrug remain intact after administration long enough to distribute to the target organ and cell. Following distribution to the cell, enzymes responsible for cleaving the prodrug must act on the prodrug and convert it to the phosphonic acid or phosphonic acid monoester. The compound must then be able to be transported to the nucleus. If a portion of the compound is excreted from the cell it must be retransported back across the cellular membrane and nuclear membrane. The prodrugs of the present invention that are activated in the liver and excreted by the liver as phosphonic acid compounds are retransported back across the cellular and nuclear membrane and into the nucleus. Despite being excreted from the liver and having to be retransported into the nucleus and despite having reduced potency in vivo, the phosphonic acid- or phosphonic acid monoester-containing compounds and their prodrugs led to surprisingly potent biological activity. This surprisingly high biological activity is attributed to the ability of the compounds of the present invention to modulate genes known to be regulated by T3. For example, mGPDH increased >1.5-fold in the liver of an animal administered a 1 mg/kg dose of the drug.

The liver is a major target organ of thyroid hormone with an estimated 8% of the hepatic genes regulated by thyroid hormone. Quantitative fluorescent-labeled cDNA microarray hybridization was used to identify thyroid-responsive genes in the liver as shown in Table 1 below (Feng et al., *Mol. Endocrinol.* 14:947-955 (2000)). Hepatic RNA from T3-treated and hypothyroid mice were used in the study. Thyroid hormone treatment affected the expression of 55 genes from the 2225 different mouse genes sampled with 14 increasing >2-fold and 41 decreasing >60%.

| Function Clone ID | Genes | Accession No. | Fold |
|---|---|---|---|
| List of Hepatic Genes Regulated by T3 Determined by cDNA Microarray Analyses ||||
| Carbohydrate and fatty acid metabolism, and insulin action ||||
| 580906 | Spot 14 gene | X95279 | 8.8 |
| 523120 | Glucose-6-phosphatase | U00445 | 3.8 |
| 615159 | Carbonyl reductase (Cbr1) | U31966 | 3.3 |
| 571409 | Insulin-like growth factor binding protein 1 precursor | X81579 | 3.0 |
| 481636 | Fatty acid transport protein (FATP) | U15976 | 1.8 |
| 550993 | Cyp4a-10 | X69296 | 0.3 |
| 583329 | PHAS-II | U75530 | 0.3 |
| 616283 | Serine/threonine kinase (Akt2) | U22445 | 0.3 |
| 583333 | Putative transcription factor of the insulin gene | X17500 | 0.3 |
| 533177 | Nuclear-encoded mitochondrial acyltransferase | L42996 | 0.2 |
| 608607 | Glycerophosphate dehydrogenase | J02655 | 0.3 |
| Cell proliferation, Replication ||||
| 614275 | B61 | U26188 | 2.3 |
| 597868 | Bcl-3 | M90397 | 2.5 |
| 493127 | Kinesin-like protein (Kip1p) | AF131865 | 2.0 |
| 582689 | Chromodomain-helicase-DNA binding protein CHD-1 | P40201 | 0.4 |
| 524471 | NfiB1-protein (exon 1-12) | Y07685 | 0.3 |
| 516208 | Putative ATP-dependent RNA helicase PL10 | J04847 | 0.3 |
| 558121 | Murine vik5variant in the kinase | S53216 | 0.1 |
| 573247 | C11 protein | X81624 | 0.3 |
| 522108 | Thymic stromal stimulating factor | D43804 | 0.3 |
| 613942 | Ubiquitin-activating enzyme E1 X | D10576 | 0.3 |
| Signal transduction ||||
| 573046 | β-2 Adrenergic receptor | X15643 | 3.4 |
| 583258 | Protein kinase C inhibitor (mPKCl) | U60001 | 2.1 |
| 616040 | Inhibitory G protein of adenylate cyclase, α chain | M13963 | 0.3 |
| 583353 | Terminal deoxynucleotidyltransferase | 04123 | 0.3 |
| 550956 | Rho-associated, coiled-coil forming protein kinase p160 | U58513 | 0.2 |
| 582973 | Protein kinase C, Θ type | AB011812 | 0.3 |
| 442989 | Protein kinase ζ | M94632 | 0.5 |
| 607870 | Lamin A | D13181 | 0.3 |

List of Hepatic Genes Regulated by T3 Determined by cDNA Microarray Analyses

| Function Clone ID | Genes | Accession No. | Fold |
|---|---|---|---|
| | Glycoprotein synthesis | | |
| 375144 | α-2,3-Sialyltransferase | D28941 | 0.3 |
| 481883 | β-Galactoside α 2,6-sialyltransferase | D16106 | 0.3 |
| | Cellular immunity | | |
| 615872 | T-complex protein 1, d subunit | P80315 | 0.3 |
| 618426 | H-2 class I histocompatibility antigen | Q61147 | 0.3 |
| 614012 | FK506-binding protein (FKBP65) | L07063 | 0.3 |
| 604923 | FK506-binding protein (FKBP23) | AF040252 | 0.2 |
| | Cytoskeletal protein | | |
| 374030 | Myosin binding protein H (MyBP-H) | U68267 | 2.2 |
| 613905 | AM2 receptor | X67469 | 0.3 |
| 616518 | Cytoskeletal β-actin | X03672 | 0.3 |
| 614948 | Actin, α cardiac | M15501 | 0.3 |
| 607364 | Skeletal muscle actin | M12866 | 0.3 |
| 597566 | Capping protein a-subunit | G565961 | 0.3 |
| 483226 | Actin, γ-enteric smooth muscle | M26689 | 0.3 |
| | Others | | |
| 552837 | Major urinary protein 2 precursor | M27608 | 3.9 |
| 521118 | β-Globin | AB020013 | 2.3 |
| 493218 | α-Globin | L75940 | 2.7 |
| 585883 | Putative SH3-containing protein SH3P12 | AF078667 | 0.3 |
| 615239 | Membrane-type matrix metalloproteinase | X83536 | 0.2 |
| 402408 | ece1 (endothelin-converting enzyme) | W78610 | 0.2 |
| 635768 | α-Adaptin | P17426 | 0.3 |
| 634827 | Glucose regulated protein 78 | D78645 | 0.3 |
| 616189 | Lupus la protein homolog | L00993 | 0.3 |
| 588337 | EST | AI646753 | 0.4 |
| 335579 | Virus-like (VL30) retrotransposon BVL-1 | X17124 | 0.3 |
| 557037 | TGN38B | D50032 | 0.3 |
| 597390 | Mitochondrial genome | L07096 | 0.4 |
| 616563 | Arylsulfatase A | X73230 | 0.3 |

Genes reported to be affected by thyroid hormone are identified using a variety of techniques include microarray analysis. Studies have identified genes that are affected by T3 and T3 mimetics that are important in metabolic diseases.

T3-responsive genes in the liver include genes affecting lipogenesis, including spot 14, fatty acid transport protein, malic enzyme, fatty acid synthase (Blennemann et al., *Mol. Cell. Endocrinol.* 110(1-2):1-8 (1995)) and CYP4A. HMG CoA reductase and LDL receptor genes have been identified as affecting cholesterol synthesis and as being responsive to T3. CPT-1 is a T3-responsive gene involved in fatty acid oxidation. Genes affecting energy expenditure, including mitochondrial genes such as mitochondrial sn-glycerol 3-phosphate dehydrogenase (mGPDH), and/or enzymes associated with proton leakage such as the adenine nucleotide transporter (ANT), $Na^+/K^+$-ATPase, $Ca^{2+}$-ATPase and ATP synthase are also T3-responsive genes. T3-responsive genes affecting glycogenolysis and gluconeogenesis include glucose 6-phosphatase and PEPCK.

Thyroid hormone-responsive genes in the heart are not as well described as the liver but could be determined using similar techniques as described by Feng et al. Many of the genes described to be affected in the heart are the same as described above for the liver. Common genes evaluated include mitochondrial sn-glycerol 3-phosphate dehydrogenase (mGPDH), and myosin heavy and light chains (Danzi et al., *Thyroid* 12(6):467-72 (2002)).

Compounds used in the methods bind to thyroid receptors and produce a change in some hepatic gene expression. Evidence for agonist activity is obtained using standard assays described in the literature. One assay commonly used entails a reporter cell assay wherein cells, e.g., HeLa cells, Hek293 cells, or Chinese hamster ovary cells, are transfected with an expression vector for human TRα1 or TRβ1 and subsequently with a reporter vector encoding a secreted form of alkaline phosphatase whose expression is under the control of a thyroid hormone response element. Agonist activity is measured by exposing the cells to the compounds, especially phosphorus-containing prodrugs of the compounds that are cleaved to the phosphonic acid, phosphinic acid, or monoester by cell homogenates, followed by determining alkaline phosphatase activity in the cell culture medium using a chemiluminescent assay (Grover et al., *Proc. Natl. Acad. Sci. U.S.A.* 100(17):10067-72 (2003)).

In one aspect, the phosphonic acid- or phosphonic acid monoester-containing thyromimetics and their prodrugs and salts are useful in preventing or treating arteriosclerosis by modulating levels of atherogenic proteins, e.g., Lp(a), apoAI, apoAII, LDL, HDL. Clinically overt hypothyroidism is associated with accelerated and premature coronary atherosclerosis and subclinical hypothyroidism is considered a condition with an increased risk for these diseases (Vanhaelst et al. and Bastenie et al., *Lancet* 2 (1967)).

T3 and T3 mimetics modulate atherogenic proteins in a manner that could prove beneficial for patients at risk to develop atherosclerosis or patients with atherosclerosis or diseases associated with atherosclerosis. T3 and T3 mimetics are known to decrease Lp(a) levels, e.g., in the monkey, with 3,5-dichloro-4-[4-hydroxy-3-(1-methylethyl)phenoxy]benzeneacetic acid (Grover et al., *Proc. Natl. Acad. Sci. U.S.A.* 100:10067-10072 (2003)). In human hepatoma cells, the T3 mimetic CGS23425 ([[4-[4-hydroxy-3-(1-methylethyl)phenoxy]-3,5-dimethylphenyl]amino]oxo acetic acid) increased apoAI expression via thyroid hormone receptor activation (Taylor et al., *Mol. Pharm.* 52:542-547 (1997)).

Thus in one aspect, the phosphonic acid- or phosphonic acid monoester-containing thyromimetics, their salts and prodrugs can be used to treat or prevent atherosclerosis, coronary heart disease and heart failure because such compounds are expected to distribute to the liver (Examples F and H) and modulate the expression and production of atherogenic proteins.

In another aspect, the phosphonic acid- or phosphonic acid monoester-containing thyromimetics and their prodrugs and salts are useful for preventing and/or treating metabolic diseases such as obesity, hypercholesterolemia and hyperlipidemia and conditions such as atherosclerosis, coronary heart disease, heart failure, nephrotic syndrome, and chronic renal failure without affecting thyroid function, thyroid production of circulating iodinated thyronines such as T3 and T4, and/or the ratio of T3 to T4. Compounds previously reported that contain a carboxylic acid moiety, e.g., GC-1 ([4-[[4-hydroxy-3-(1-methylethyl)phenyl]methyl]-3,5-dimethylphenoxy] acetic acid) (Trost et al., *Endocrinology* 141:3057-3064 (2000)) and 3,5-Dichloro-4-[4-hydroxy-3-(1-methylethyl)phenoxy] benzeneacetic acid (Grover et al., *Proc. Natl. Acad. Sci. U.S.A.* 100:10067-10072 (2003)) report that these TRβ-selective compounds dose-dependently lower cholesterol and TSH levels. Effects on cholesterol and TSH occur at the same dose or at doses stated to be not pharmacologically different (e.g., 2-fold).

Particularly useful T3 mimetics in these methods would minimize effects on thyroid function, thyroid production of circulating iodinated thyronines such as T3 and T4, and/or the ratio of T3 to T4. Unlike prior T3 mimetics, the compounds or the present invention distribute more readily to the liver and result in pharmacological effects at doses that do not adversely affect thyroid function, thyroid production of circulating iodinated thyronines such as T3 and T4, and/or the ratio of T3 to T4. In one embodiment the compounds of the present invention have a therapeutic index, defined as the difference between the dose at which a significant effect is observed for a use disclosed herein, e.g., lowering cholesterol, and the dose at which a significant decrease in T3 or significant decrease in T4, or significant change in the ratio of T3 to T4 is observed, is at least 50 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold or at least 10000 fold. In one embodiment, rather than a significant amount, the amount of change in T3 or T4 is a decrease selected from at least 5%, 10%, 15%, 20%, 25% or at least 30% of circulating levels.

In one embodiment, the phosphonic acid- or phosphonic acid monoester-containing thyromimetics and their prodrugs and salts are useful for significantly lowering cholesterol levels without having a significant effect on TSH levels. In another embodiment, the compounds of the present invention significantly lower cholesterol levels without lowering TSH levels by more than 30%, 25%, 20%, 15%, 10%, or 5%.

Side effects associated with TH-based therapies limit their use for treating obese patients and according to the Physician's Desk Reference (PDR) T3 is now contraindicated for patients with obesity. 3,5-dichloro-4-[4-hydroxy-3-(1-methylethyl)phenoxy] benzeneacetic acid and other T3 mimetics are reported to result in weight loss in animals, e.g., rodent models and monkeys. Weight loss from these compounds may arise from their effects on the liver as well as peripheral tissues. TH is known to have a multitude of effects outside of the liver that could result in increased metabolism and weight loss. TH plays an important role in the development and function of brown and white adipose tissue. TH can induce WAT differentiation, proliferation and intracellular lipid accumulation. TH induces lipogenic genes in WAT such as glucose-6-phosphate dehydrogenase, fatty acid synthase and spot-14. TH also regulates lipolysis in fat to produce weight loss in a coordinated manner, i.e., lipolysis in fat to free fatty acids followed by free fatty acid utilization in tissues, e.g., liver, muscle and heart.

Weight loss through administration of liver-specific T3 analogues requires that the increased oxygen consumption in the liver resulting from T3 is sufficient to result in net whole body energy expenditure. The liver's contribution to energy expenditure is estimated to be 22% based on oxygen consumption measurements. (Hsu, A et al. *Am. J. Clin. Nutr.* 77(6):1506-11(2003)). Thus, the compounds of the present invention may be used to maintain or reduce weight in an animal.

Mitochondria are the fuel source for all cellular respiration. The synthesis of new mitochondria is a complex process which requires over 1000 genes (Goffart et al., *Exp. Physiol.* 88(1):33-40 (2003)). The mechanisms which control mitochondrial biogenesis are not well defined, but are known to include exercise (Jones et al., *Am. J. Physiol. Endocrinol. Metab.* 284(1):E96-101 (2003)), overexpression of PGC-1 (Lehman et al., *J. Clin. Invest.* 106(7):847-56 (2000)) or AMP activated protein kinase (Bergeron et al., *Am. J. Physiol. Endocrinol. Metab.* 281(6):E1340-6 (2001)). An increase in mitochondrial density leads to a greater rate of energy expenditure. Thyroid hormone has been shown to play a key role in mitochondrial biogenesis by increasing expression of nuclear respiratory factor-1 and PGC-1 (Weitzel et al., *Exp. Physiol.* 88(1):121-8 (2003)).

Compounds which increase the expression of NRF-1 and/or PGC-1 could lead to an increase in mitochondrial density within a cell. Such an increase would cause the cell to have a higher rate of energy expenditure. Methods to analyze NRF-1 and PGC-1 include immunoblotting with specific antibodies, or analysis of mRNA levels. Compounds that caused increases in NRF-1 or PGC-1 would therefore lead to a greater energy expenditure. Even small increases in energy expenditure over long periods of time (weeks to years) could cause a decrease in weight under isocaloric circumstances. Further methods for assessing mitochondrial biogenesis include the analysis of mitochondrial proteins such as cytochrome c and cytochrome c oxidase, either by immunoblotting or analysis of mRNA levels. Mitochondrial density can also be measured by counting the number of mitochondria in electron micrographs.

In one aspect, phosphonic acid- or phosphonic acid monoester-containing thyromimetics and their prodrugs and salts may be used to cause weight loss or prevent weight gain without side effects. It may be advantageous to use compounds that result in high liver specificity (Examples F and G). In one aspect, compounds that result in increased levels of genes associated with oxygen consumption, e.g., GPDH (Example B), are particularly useful in weight loss and controlling weight gain. In another aspect, compounds that show weight loss at doses that do not affect cardiac function, e.g., heart rate, force of systolic contraction, duration of diastolic relaxation, vascular tone, or heart weight, may be particularly useful in weight loss and controlling weight gain. In a further aspect, compounds that cause weight loss without affecting thyroid function, thyroid production of circulating iodinated thyronines such as T3 and T4, and/or the ratio of T3 to T4 are particularly useful.

Besides their use in obesity and weight control, phosphonic acid- or phosphonic acid monoester-containing thyromimetics and their prodrugs and salts may be used to treat diabetes and related conditions like impaired glucose tolerance, insulin resistance and hyperinsulinemia.

Patients with type 2 diabetes "T2DMs" exhibit chronic high blood glucose levels. High fasting blood glucose in T2DMs is related to the overproduction of glucose by a pathway in the liver known as the gluconeogenesis pathway. Throughput in this pathway is controlled in part by enzymes in the pathway such as PEPCK, fructose 1,6-bisphosphatase and glucose 6-phosphatase as well as by hormones such as insulin, which can influence the expression and activities of these enzymes. T3 is known to worsen diabetes. While the reason T3 worsens diabetes is not known, T3's effect on increasing the gene expression of PEPCK and glucose-6-phosphatase may be the cause of increased glucose levels. T3 is known to increase lipolysis of triglyceride pools in fat and to increase circulating levels of free fatty acids. (K. S. Park, et al., *Metabolism* 48(10):1318-21 (1999)) T3's effect on free fatty acid levels may also be responsible for the negative effect on diabetes because high free fatty acid levels enhance flux through the gluconeogenesis pathway.

Compounds of this invention, while they mimic T3, result in preferential activation of liver T3 genes, are not expected to increase lipolysis in peripheral tissues which is expected to avoid the T3-induced higher circulating levels of free fatty acids and their effects on increasing gluconeogenesis flux and decreasing insulin sensitivity. Increased hepatic insulin sensitivity will decrease PEPCK and glucose 6-phosphatase gene expression thus reducing gluconeogenesis. TR activation in the liver should also decrease liver fat content, which in turn is expected to improve diabetes and steatohepatitis (e.g., NASH), thus providing another use for the compounds of the present invention. A decrease in liver fat content is associated with increased hepatic insulin sensitivity (Shulman, 2000) and accordingly should improve glycemic control in type 2 diabetics through decreased glucose production and enhanced glucose uptake. The overall effect on the patient will be better glycemic control, thus providing another use for the compounds of the present invention.

TH also stimulates GLUT-4 transporter expression in skeletal muscle which produces concomitant increases in basal glucose uptake. Studies in obese, insulin-resistant Zucker rats showed that TH therapy induces GLUT-4 expression in skeletal muscle and total amelioration of the hyperinsulinemia, although plasma glucose levels were moderately elevated (Torrance et al. *Endocrinology* 138:1204 (1997)). Thus another embodiment of the present invention relates to the use of compounds of the present invention to prevent or treat hyperinsulinemia.

TH therapy results in increased energy expenditure. Increased energy expenditure can result in increased weight loss, which in turn can result in improved glycemic control. Diet and exercise are often used initially to treat diabetics. Exercise and weight loss increase insulin sensitivity and improve glycemia. Thus, further uses of the compounds of the present invention include increasing energy expenditure, increasing insulin sensitivity and improving glycemia.

In one aspect, the phosphonic acid- or phosphonic acid monoester-containing compounds of the present invention are useful for increasing levels of genes associated with gluconeogenesis (Example B). In another aspect, the compounds of the present invention are useful for decreasing hepatic glycogen levels. Further, compounds of the present invention result in amelioration of hyperinsulinemia and/or decreased glucose levels in diabetic animal models at doses that do not affect cardiac function, e.g., heart rate, force of systolic contraction, duration of diastolic relaxation, vascular tone, or heart weight. In a further aspect, compounds of the present invention result in amelioration of hyperinsulinemia and/or decreased glucose levels in diabetic animal models at doses that do not affect thyroid function, thyroid production of circulating iodinated thyronines such as T3 and T4, and/or the ratio of T3 to T4.

As discussed above, the previous use of T3 and T3 mimetics to treat metabolic diseases have been limited by the deleterious side-effects on the heart. Previous attempts to overcome this limitation have focused on selectively targeting the liver over the heart using T3 mimetics that selectively bind TRβ over TRα. Because the heart expresses mainly TRα, previous investigators have attempted to increase the therapeutic index of T3 mimetics by increasing the selectively of the compounds for TRβ which is expressed in the liver. Previous attempts have not focused on T3 mimetics that selectively distribute to the liver over the heart or at least have not been successful. Thus, rather than selecting for a particular tissue or organ, previous work has been directed to discovering T3 mimetics that act selectively at the receptor level after the drug is non-selectively distributed to both heart and liver tissue. It was therefore unexpected when the present Inventors discovered that the phosphonic acid- or phosphonic acid monoester-compounds of the present invention selectively distributed to the liver over the heart. The selective distribution to the liver over the heart was also found with prodrugs, that although were processed in the liver, were excreted from the liver into the blood stream as active phosphonic acid or monoester compounds. Thus the compounds of the present invention are able to selectively target the liver and thereby increase the therapeutic index as compared to T3 and T3 mimetics containing a carboxylic acid. The compounds of the present invention can therefore be dosed at levels that are effective in treating metabolic and other disorders where the liver is the drug target without significantly negatively affecting heart function.

Because of the selectivity of the phosphonic acid- or phosphonic acid monoester-containing compounds of the present invention for the liver over the heart, it is not necessary for the compound to have greater selectivity for TRβ over TRα, although this may be desired. In fact, surprisingly some of the compounds of the present invention selectively bind TRα over TRβ and are highly effective for the uses disclosed herein without having the negative side-effects normally associated with TRα selective compounds. Thus, included as an embodiment of the present invention are compounds of Formula I, II, III, and VIII that selectively bind TRβ over TRα by at least 5 fold, 10 fold, 20 fold, 30 fold, 40 fold, 50 fold, 60 fold, 70 fold, 80 fold, 90 fold, 100 fold, 200 fold, 300 fold, 400 fold or at least 500 fold, and compounds of Formula I, II, III, and VIII that selectively bind TRα over TRβ by at least 5 fold, 10 fold, 20 fold, 30 fold, 40 fold, 50 fold, 60 fold, 70 fold, 80 fold, 90 fold, 100 fold, 200 fold, 300 fold, 400 fold or at least 500 fold.

Changes in the therapeutic index are readily determined using assays and methods well described in the literature. Genes in extrahepatic tissues are monitored using methods well understood by those skilled in the art. Assays include using cDNA microarray analysis of tissues isolated from treated animals. The sensitivity of the heart to T3 makes analysis of T3-responsive genes in the heart as well as the functional consequences of these changes on cardiac properties one further strategy for evaluating the therapeutic index of the compounds of the present invention. Cardiac genes measured include mGPDH and myosin heavy and light chain. One method of measuring the effects of T3 mimetics on the heart is by the use of assays that measure T3 mediated myosin heavy chain gene transcription in the heart. Compounds of the present invention were tested using the methods described in Examples B, D, and I.

In one embodiment the compounds of the present invention have a therapeutic index, defined as the difference between the dose at which a significant effect is observed for a use disclosed herein, e.g., lowering cholesterol, and the dose at which a significant effect on a property or function, as disclosed herein (e.g., heart rate), is observed, is at least 50 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold or at least 10000 fold. Examples of said use disclosed herein includes but is not limited to reducing lipid levels, increasing the ratio of HDL to LDL or apoAI to LDL, reducing weight or preventing weight gain, maintaining or improving glycemic control, lowering blood glucose levels, increasing mitochondrial biogenesis, increasing expression of PGC-1, AMP activated protein kinase or nuclear respiratory factor, inhibiting hepatic gluconeogenesis or for the treatment or prevention of a disease or disorder selected from the group consisting of atherosclerosis, hypercholesterolemia, hyperlipidemia, obesity, fatty liver/steatosis, NASH, NAFLD, nephrotic syndrome, chronic renal failure, insulin resistance, diabetes, metabolic syndrome X, impaired glucose tolerance, hyperlipidemia, coronary heart disease, thyroid disease, thyroid cancer, depression, glaucoma, cardiac arrhythmias, heart failure, and osteoporosis. Examples wherein the property or function is a cardiac property/function include but are not limited to cardiac hypertrophy (heart weight to body weight ratio), heart rate, and various hemodynamic parameters, including systolic and diastolic arterial pressure, end systolic left ventricular pressure and maximal speeds of contraction and relaxation.

A variety of methods are described that provide a means for evaluating the functional consequences of T3-cardiac action, including measurement of cardiac hypertrophy (heart weight to body weight ratio), heart rate, and various hemodynamic parameters, including systolic and diastolic arterial pressure, end-systolic left ventricular pressure and maximal speeds of contraction and relaxation using methods described by Trost et al., (*Endocrinology* 141:3057-64 (2000)). Compounds of the present invention were tested using the methods described in Examples B, D, and I.

Other methods are also available to assess the therapeutic index including effects on muscle wasting and bone density. Compounds of the present invention were tested using the methods described in Examples C and G.

The therapeutic index is determined by administering to animals a wide range of doses and determining the minimal dose capable of inducing a response in the liver relative to the dose capable of inducing a response in the heart.

Phosphonic acids are often poorly transported into cultured cells. Accordingly, cell reporter assays, while often useful for confirming agonist activity, may not provide a suitable indication of potency. Thus, evidence of agonist activity is often more readily obtained in vivo for compounds of the present invention. In vivo assays include but are not limited to treating animals with phosphorus-containing compounds of the invention or a prodrug thereof and monitoring the expression of T3-responsive genes in the liver or the functional consequences of changes of T3-responsive genes.

In one aspect, compounds useful in the novel methods bind to thyroid receptors and produce changes in the expression of two or more hepatic genes. Animals used for testing compounds useful in the methods include normal rats and mice, animals made hypothyroid using methods well described in the literature, including thyroid hormone receptor knockout mice (e.g., TR$\alpha^{-/-}$ such as those used in Grover et al., 2003), or animals exhibiting high cholesterol (e.g., high cholesterol fed rat or hamster), obesity and/or diabetes (e.g., fa/fa rat, Zucker diabetic fatty rat, ob/ob mice, db/db mice, high fat fed rodent). (Liureau et al., *Biochem. Pharmacol.* 35(10):1691-6 (1986); Trost et al., *Endocrinology* 141(9):3057-64 (2000); and Grover et al., 2003). The drug or prodrug is administered by a variety of routes including by bolus injection, oral, and continuous infusion (Examples B, D and I). Animals are treated for 1-28 days and the liver, heart and blood are isolated. Changes in gene transcription relative to vehicle treated animals and T3-treated animals are determined using northern blot analysis, RNAase protection or reverse-transcription and subsequent PCR. While methods are available for monitoring changes in thousands of hepatic genes, only a small number need to be monitored to demonstrate the biological effect of compounds in this invention. Typically, genes such as spot-14, FAS, mGPDH, CPT-1, and LDL receptor are monitored. Changes of >1.5 fold in two or more genes is considered proof that the compound modulates T3-responsive genes in vivo. Alternative methods for measuring changes in gene transcription include monitoring the activity or expression level of the protein encoded by the gene. For instance, in cases where the genes encode enzyme activities (e.g., FAS, mGPDH), direct measurements of enzyme activity in appropriately extracted liver tissue can be made using standard enzymological techniques. In cases where the genes encode receptor functions (e.g., the LDL receptor), ligand binding studies or antibody-based assays (e.g., Western blots) can be performed to quantify the number of receptors expressed. Depending on the gene, TR agonists will either increase or decrease enzyme activity or increase or decrease receptor binding or number.

The functional consequences of changing the expression levels of hepatic genes responsive to T3 is many-fold and readily demonstrated using assays well described in the literature. Administering phosphonic acid- or phosphonic acid monoester-containing compounds that bind to a TR to animals can result in changes in lipids, including hepatic and/or plasma cholesterol levels; changes in lipoprotein levels including LDL-cholesterol, lipoprotein a (Lp(a)); changes in hepatic glycogen levels; and changes in energy expenditure as measured by changes in oxygen consumption and in some cases animal weight. For example, the effect on cholesterol is determined using cholesterol fed animals such as normal rats and hamsters, or TR$\alpha^{-/-}$ knockout mice. Cholesterol is measured using standard tests. Compounds of the present invention were tested using the methods described in Example D and I. Hepatic glycogen levels are determined from livers isolated from treated animals. Compounds of the present invention were tested using the methods described in Examples D and E. Changes in energy expenditure are monitored by measuring changes in oxygen consumption (MVo$_2$). A variety of methods are well described in the literature and include measurement in the whole animal using Oxymax chambers (U.S. Pat. No. 6,441,015). Livers from treated rats can also be evaluated (Fernandez et al., *Toxicol. Lett.* 69(2):205-10 (1993)) as well as isolated mitochondria from liver (Carreras et al., *Am. J. Physiol. Heart Circ. Physiol.* 281(6):

H2282-8 (2001)). Hepatocytes from treated rats can also be evaluated (Ismail-Beigi F et al., *J Gen Physiol*. 73(3):369-83 (1979)). Compounds of the present invention were tested using the methods described in Examples C and G.

Phosphonic acid- or phosphonic acid monoester-containing compounds that bind to a TR modulate expression of certain genes in the liver resulting in effects on lipids (e.g., cholesterol), glucose, lipoproteins, and triglycerides. Such compounds can lower cholesterol levels which is useful in the treatment of patients with hypercholesterolemia. Such compounds can lower levels of lipoproteins such as Lp(a) or LDL and are useful in preventing or treating atherosclerosis and heart disease in patients. Such compounds can raise levels of lipoproteins such as apoAI or HDL and are useful in preventing or treating atherosclerosis and heart disease in patients. Such compounds can cause a reduction in weight. Such compounds can lower glucose levels in patients with diabetes.

Another aspect are compounds that in the presence of liver cells or microsomes results in compounds of Formula I, II, III, VIII, and X wherein X is phosphonic acid or phosphonic acid monoester.

Also provided are methods of reducing plasma lipid levels in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter, is enantiomerically enriched or diastereomerically enriched, or a stereoisomer covered later. In another embodiment said compound is administered as a racemic mixture. In another embodiment said compound is administered as an enantiomerically enriched mixture. In another embodiment said compound is a administered as a diastereomerically enriched mixture. In still another embodiment said compound is administered as an individual stereoisomer.

Also provided are methods of reducing plasma lipid levels in an animal wherein the lipid is cholesterol, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VII, and X or a prodrug thereof comprises a stereocenter. In another embodiment said compound is administered as a racemic mixture. In another embodiment said compound is administered as an enantiomerically enriched mixture. In another embodiment said compound is administered as a diastereomeric mixture. In still another embodiment said compound is administered as an individual stereoisomer. In one embodiment said methods of reducing cholesterol results in a lowering of total cholesterol. In one embodiment said methods of reducing cholesterol results in a reduction of high density lipoprotein (HDL). In one embodiment said methods of reducing cholesterol results in a reduction of low density lipoprotein (LDL). In one embodiment said methods of reducing cholesterol results in a reduction of very low density lipoprotein (VLDL). In another embodiment said LDL is reduced to a greater extent than said HDL. In another embodiment said VLDL is reduced to a greater extent than said HDL. In another embodiment said VLDL is reduced to a greater extent than said LDL.

In one embodiment of the method of reducing lipids, the lipid is triglycerides. In one embodiment said lipid is liver triglycerides. In another embodiment said lipid is in the form of a lipoprotein. In another embodiment said lipoprotein is Lp(a). In another embodiment said lipoprotein is apoAII.

Also provided are methods of increasing the ratio of HDL to LDL, HDL to VLDL, LDL to VLDL, apoAI to LDL or apoAI to VLDL in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII and X, or a prodrug thereof comprises a stereocenter. In another embodiment said compound is administered as a racemic mixture. In another embodiment said compound is administered as an enantiomerically enriched mixture. In another embodiment said compound is administered as a diastereomeric mixture. In still another embodiment said compound is administered as an individual stereoisomer.

Also provided are methods of treating hyperlipidemia or hypercholesterolemia in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VII and X, or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of preventing or treating atherosclerosis in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of reducing fat content in the liver or of preventing or treating fatty liver/steatosis, NASH or NAFLD in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of preventing or treating nephrotic syndrome or chronic renal failure in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of reducing weight or preventing weight gain in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of preventing or treating obesity in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of preventing or treating coronary heart disease in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of maintaining or improving glycemic control in an animal being treated with a T3 mimetic, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is administered as a diastereomeric mixture. In still another embodiment said compound is administered as an individual stereoisomer. In one embodiment said glycemic control is maintained after said animal is treated for at least 14 days with said compound. In another embodiment said glycemic control is improved by 28 days in an animal treated with said compound.

Also provided are methods of lowering blood glucose levels in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of preventing or treating diabetes, insulin resistance, metabolic syndrome X or impaired glucose tolerance in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of preventing or treating altered energy expenditure in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of preventing or treating a liver disease responsive to modulation of T3-responsive genes in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of preventing or treating thyroid disease, thyroid cancer, depression, glaucoma, cardiac arrhythmias, heart failure, or osteoporosis in an animal, the method comprising the step of administering to a patient an amount of a compound of Formula I, II, III, VIII, and X or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of increasing mitochondrial biogenesis in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of increasing expression of PGC-1, AMP activated protein kinase or nuclear respiratory factor in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are methods of inhibiting hepatic gluconeogenesis in an animal, the method comprising the step of administering to a patient an amount of a compound of Formula I, II, III, VIII, and X, a prodrug thereof, or a pharmaceutically acceptable salt or co-crystal thereof. In one embodiment said compound is an active form. In another embodiment said compound is a prodrug. In another embodiment said compound of Formula I, II, III, VIII, and X or a prodrug thereof comprises a stereocenter. In another embodiment said compound is administered as a racemic mixture. In another embodiment said compound is administered as an enantiomerically enriched mixture. In another embodiment said compound is a administered as a diastereomeric mixture. In still another embodiment said compound is administered as an individual stereoisomer.

Also provided are kits for reducing lipid levels, increasing the ratio of HDL to LDL or apoAI to LDL, reducing weight or preventing weight gain, maintaining or improving glycemic control, lowering blood glucose levels, increasing mitochondrial biogenesis, increasing expression of PGC-1, AMP activated protein kinase or nuclear respiratory factor, inhibiting hepatic gluconeogenesis, or for the prevention or treatment of a disease or disorder for which a compound of the present invention is effective in preventing or treating, the kits comprising:

a) a pharmaceutical composition comprising a compound of Formula I, II, III, VIII, or X or a prodrug thereof; and b) at least one container for containing said pharmaceutical composition.

Also provided are pharmaceutical compositions comprising a compound of Formula I and a pharmaceutically acceptable excipient, carrier or diluent. Also provided are pharmaceutical compositions comprising a first pharmaceutical compound selected from Formula I, Formula II, Formula III, Formula VIII, or Formula X or a prodrug thereof and a second pharmaceutical compound of the same Formula but wherein said first and second pharmaceutical compounds are not the same molecules. Also provided are pharmaceutical compositions comprising a first pharmaceutical compound selected from Formula I, Formula II, Formula III, Formula VIII, or Formula X or a prodrug thereof and a second pharmaceutical compound selected from Formula I, Formula II, Formula III, Formula VIII, Formula X or a prodrug thereof, but wherein said first and said second pharmaceutical compounds are not both from the same Formula. Also provided are pharmaceutical compositions comprising a first pharmaceutical compound selected from Formula I, Formula II, Formula III, Formula VIII, or Formula X or a prodrug thereof and a second pharmaceutical compound that is not a compound selected from Formula I, Formula II, Formula III, Formula VIII, or Formula X or a prodrug thereof.

Also provided are pharmaceutical compositions comprising a first compound of the present invention and a second compound useful for reducing lipid levels, increasing the ratio of HDL to LDL or apoAI to LDL, reducing weight or preventing weight gain, maintaining or improving glycemic control, lowering blood glucose levels, increasing mitochondrial biogenesis, increasing expression of PGC-1, AMP activated protein kinase or nuclear respiratory factor, inhibiting hepatic gluconeogenesis or for the treatment or prevention of atherosclerosis, hyperlipidemia, hypercholesterolemia, obesity, fatty liver/steatosis, NASH, NAFLD, nephrotic syndrome, chronic renal failure, insulin resistance, diabetes, metabolic syndrome X, impaired glucose tolerance, hyperlipidemia, coronary heart disease, thyroid disease, thyroid cancer, depression, glaucoma, cardiac arrhythmias, heart failure, or osteoporosis. In one embodiment, a composition comprising said first and second compound is a single unit dose. In another embodiment, said unit does is in the form of a tablet, hard capsule or soft gel capsule.

Also provided are pharmaceutical compositions of the present invention having an oral bioavailability of at least 20%, 25%, 30%, 35%, 40%, 45%, 50%, 55%, 60%, 65%, 70% 75% or at least 80%.

Also provided are kits for the prevention or treatment of a disease or disorder for which a compound of the present invention is effective in preventing or treating, the kits comprising:

a) a first pharmaceutical composition comprising a compound of Formula I, II, III, VIII, or X or a prodrug thereof;

b) a second pharmaceutical composition comprising an additional compound useful for the treatment or prevention of a disease or disorder for which a compound of the present invention is effective in preventing or treating; and
c) at least one container for containing said first or second or both first and second pharmaceutical composition.

Also provided are kits for reducing lipid levels, increasing the ratio of HDL to LDL or apoAI to LDL, reducing weight or preventing weight gain, maintaining or improving glycemic control, lowering blood glucose levels, increasing mitochondrial biogenesis, increasing expression of PGC-1, AMP activated protein kinase or nuclear respiratory factor, inhibiting hepatic gluconeogenesis or for the treatment or prevention of a disease or disorder selected from the group consisting of atherosclerosis, hyperlipidemia, hypercholesterolemia, obesity, fatty liver/steatosis, NASH, NAFLD, nephrotic syndrome, chronic renal failure, insulin resistance, diabetes, metabolic syndrome X, impaired glucose tolerance, hyperlipidemia, coronary heart disease, thyroid disease, thyroid cancer, depression, glaucoma, cardiac arrhythmias, heart failure, and osteoporosis, the kits comprising:
a) a first pharmaceutical composition comprising a compound of Formula I, II, III, VIII, or X or a prodrug thereof;
b) a second pharmaceutical composition comprising an additional compound useful for reducing lipid levels, increasing the ratio of HDL to LDL or apoAI to LDL, reducing weight or preventing weight gain, maintaining or improving glycemic control, lowering blood glucose levels, increasing mitochondrial biogenesis, increasing expression of PGC-1, AMP activated protein kinase or nuclear respiratory factor, inhibiting hepatic gluconeogenesis or for the treatment or prevention of atherosclerosis, hyperlipidemia, hypercholesterolemia, obesity, fatty liver/steatosis, NASH, NAFLD, nephrotic syndrome, chronic renal failure, insulin resistance, diabetes, metabolic syndrome X, impaired glucose tolerance, hyperlipidemia, coronary heart disease, thyroid disease, thyroid cancer, depression, glaucoma, cardiac arrhythmias, heart failure, or osteoporosis; and
c) at least one container for containing said first or second or both first and second pharmaceutical composition.

Also provided are methods for reducing lipid levels, increasing the ratio of HDL to LDL or apoAI to LDL, reducing weight or preventing weight gain, maintaining or improving glycemic control, lowering blood glucose levels, increasing mitochondrial biogenesis, increasing expression of PGC-1, AMP activated protein kinase or nuclear respiratory factor, inhibiting hepatic gluconeogenesis or for the treatment or prevention of atherosclerosis, hyperlipidemia, hypercholesterolemia, obesity, fatty liver/steatosis, NASH, NAFLD, nephrotic syndrome, chronic renal failure, insulin resistance, diabetes, metabolic syndrome X, impaired glucose tolerance, hyperlipidemia, coronary heart disease, thyroid disease, thyroid cancer, depression, glaucoma, cardiac arrhythmias, heart failure, or osteoporosis the methods comprising the step of administering to a patient a therapeutically effective amount of 1) a first pharmaceutical composition comprising a compound of Formula I, II, III, VIII, or X or a prodrug thereof, and 2) a second pharmaceutical composition, wherein said second pharmaceutical composition is either another compound of Formula I, II, III, VIII, or X or a prodrug thereof, or is not another compound of Formula I, II, III, VIII, or X or a prodrug thereof.

Also provided are methods for reducing lipid levels, increasing the ratio of HDL to LDL or apoAI to LDL, reducing weight or preventing weight gain, maintaining or improving glycemic control, lowering blood glucose levels, increasing mitochondrial biogenesis, increasing expression of PGC-1, AMP activated protein kinase or nuclear respiratory factor, inhibiting hepatic gluconeogenesis or for the treatment or prevention of atherosclerosis, hyperlipidemia, hypercholesterolemia, obesity, fatty liver/steatosis, NASH, NAFLD, nephrotic syndrome, chronic renal failure, insulin resistance, diabetes, metabolic syndrome X, impaired glucose tolerance, hyperlipidemia, coronary heart disease, thyroid disease, thyroid cancer, depression, glaucoma, cardiac arrhythmias, heart failure, or osteoporosis the methods comprising the step of administering to a patient a therapeutically effective amount of 1) a first pharmaceutical composition comprising a compound of Formula I, II, III, VIII, or X or a prodrug thereof and 2) an second pharmaceutical composition that is effective alone for reducing lipid levels, increasing the ratio of HDL to LDL or apoAI to LDL, reducing weight or preventing weight gain, maintaining or improving glycemic control, lowering blood glucose levels, increasing mitochondrial biogenesis, increasing expression of PGC-1, AMP activated protein kinase or nuclear respiratory factor, inhibiting hepatic gluconeogenesis or for the treatment or prevention of atherosclerosis, hyperlipidemia, hypercholesterolemia, obesity, fatty liver/steatosis, NASH, NAFLD, nephrotic syndrome, chronic renal failure, insulin resistance, diabetes, metabolic syndrome X, impaired glucose tolerance, hyperlipidemia, coronary heart disease, thyroid disease, thyroid cancer, depression, glaucoma, cardiac arrhythmias, heart failure, or osteoporosis.

Also provided is the use of a compound of the present invention for the manufacture of a medicament for reducing lipid levels, increasing the ratio of HDL to LDL or apoAI to LDL, reducing weight or preventing weight gain, maintaining or improving glycemic control, lowering blood glucose levels, increasing mitochondrial biogenesis, increasing expression of PGC-1, AMP activated protein kinase or nuclear respiratory factor, inhibiting hepatic gluconeogenesis or for the treatment or prevention of atherosclerosis, hyperlipidemia, hypercholesterolemia, obesity, fatty liver/steatosis, NASH, NAFLD, nephrotic syndrome, chronic renal failure, insulin resistance, diabetes, metabolic syndrome X, impaired glucose tolerance, hyperlipidemia, coronary heart disease, thyroid disease, thyroid cancer, depression, glaucoma, cardiac arrhythmias, heart failure, or osteoporosis.

Also provided are compounds that selectively distribute to the liver. In one embodiment, the compounds have at least 10 fold, 25 fold, 50 fold, 75 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold 6000 fold, 7000 fold, 8000 fold, 9000 fold, 10,000 fold, 20,000 fold, 30,000 fold, 40,000 fold or 50,000 fold greater selectivity. In one embodiment the selectivity for the liver is compared to the heart. In another embodiment the selectivity for the liver is compared to the pituitary. In another embodiment the selectivity for the liver is compared to the kidney.

Also provided are phosphonic acid- or phosphonic acid monoester-containing T3 mimetics or prodrug thereof that have improved liver selectivity as compared to a corresponding compound where the phosphorus-containing group is replaced with a carboxylic acid, but wherein the corresponding compound is otherwise identical. In one embodiment, the phosphonic acid- or phosphonic acid monoester-containing compound (or prodrug thereof) has at least 10 fold, 25 fold, 50 fold, 75 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold 6000 fold, 7000 fold, 8000 fold, 9000 fold, 10,000 fold, 20,000 fold, 30,000 fold, 40,000 fold or 50,000 fold greater selectivity for the liver as compared to the corresponding carboxylic acid compound. In one embodiment the liver selectivity is relative to the heart. In another embodiment the liver selectivity is relative to the kidney. In another embodiment the liver selectivity is relative to the pituitary.

Also provided are phosphonic acid- or phosphonic acid monoester-containing T3 mimetics or prodrug thereof that have a decreased Ki as compared to a corresponding compound where the phosphorus-containing group is replaced with a carboxylic acid, but wherein the corresponding compound is otherwise identical. In one embodiment, the phosphonic acid- or phosphonic acid monoester-containing compound has at least 2 fold, 5 fold, 7 fold, 10 fold, 25 fold, or 50 fold lower Ki than the corresponding carboxylic acid derivative compound (wherein Ki is measured relative to T3). In another embodiment, the Ki of the phosphonic acid- or phosphonic acid monoester-containing compound is $\leq 150$ nM $\leq 100$ nM, $\leq 90$ nM, $\leq 80$ nM, $\leq 70$ nM, $\leq 60$ nM, $\leq 50$ nM, $\leq 40$ nM, $\leq 30$ nM, relative to T3. For purposes of clarity, it is noted that binding affinity increases as the numerical value of Ki decreases, i.e., there is an inverse relationship between Ki and binding affinity. In another embodiment the phosphonic acid- or phosphonic acid monoester-containing compound has the same Ki as the corresponding carboxylic acid derivative. In another embodiment the phosphonic acid- or phosphonic acid monoester-containing compound has a greater Ki than the corresponding carboxylic acid derivative.

Also provided are compounds of the present invention that bind at least one thyroid hormone receptor with an Ki of $\leq 100$ nM, $\leq 90$ nM, $\leq 80$ nM, $\leq 70$ nM, $\leq 60$ mM, $\leq 50$ nM, $\leq 40$ nM, $\leq 30$ mM, $\leq 20$ nM, $\leq 10$ nM, $\leq 50$ nM, $\leq 1$ nM, or $\leq 0.5$ nM relative to T3. In one embodiment said thyroid hormone receptor is TR$\alpha$. In one embodiment said thyroid hormone receptor is TR$\beta$. Also provided are compounds that bind at least one thyroid hormone receptor with an Ki of $\geq 100$ nM, $\geq 90$ nM, $\geq 80$ nM, $\geq 70$ nM, $\geq 60$ nM, $\geq 50$ nM, $\geq 40$ nM, $\geq 30$ nM, $\geq 20$ nM, $\geq 10$ nM, $\geq 50$ nM, $\geq 1$ nM, or $\geq 0.5$ nM relative to T3, but in each case $\leq 150$ nM. In one embodiment said thyroid hormone receptor is TR$\alpha$. In one embodiment said thyroid hormone receptor is TR$\beta$. In one embodiment said thyroid hormone receptor is TR$\alpha$1. In one embodiment said thyroid hormone receptor is TR$\beta$1. In one embodiment said thyroid hormone receptor is TR$\alpha$2. In one embodiment said thyroid hormone receptor is TR$\beta$2.

Novel methods described herein describe the use of phosphonic acid- or phosphonic acid monoester-containing compounds that bind to TRs. In one aspect, novel compounds described below include compounds of Formula I, II, III, VIII, and X. The compounds of the present invention can be used in the methods described herein.

Novel Compounds of the Invention

The novel compounds of the invention are phosphonic acid- or phosphonic acid monoester-containing compounds that bind to and activate thyroid receptors in the liver. The present invention relates to compounds of Formula I, II, III, VIII, and X, including stereoisomers and mixtures of stereoisomers thereof, pharmaceutically acceptable salts thereof, co-crystals thereof, and prodrugs (including stereoisomers and mixtures of stereoisomers thereof) thereof, and pharmaceutically acceptable salts and co-crystals of the prodrugs.

Importantly, lower alkyl esters (either diesters or monoesters) of phosphonic acid are not prodrug moieties as the phosphoester bond is not cleaved in vivo. Thus, the phosphonic acid monoester-containing compounds of the invention are not themselves prodrugs. The compounds can be made into prodrugs as disclosed above.

The compounds of the present invention may be either crystalline, amorphous or a mixture thereof. Compositions comprising a crystalline form a compound of the present invention may contain only one crystalline form of said compound or more than one crystalline form. For example, the composition may contain two or more different polymorphs. The polymorphs may be two different polymorphs of the free form, two or more polymorphs of different co-crystal forms, two or more polymorphs of different salt forms, a combination of one or more polymorphs of one or more co-crystal forms and one or more polymorphs of the free form, a combination of one or more polymorphs of one or more salt forms and one or more polymorphs of the free form, or a combination of one or more polymorphs of one or more co-crystal forms and one or more polymorphs of one or more salt forms.

Pharmaceutically acceptable base addition salts of the compounds herein are included in the present invention. Pharmaceutically acceptable base addition salts refer to those salts which retain the biological effectiveness and properties of the free acids, which are not biologically or otherwise undesirable. These salts are prepared from addition of an inorganic base or an organic base to the free acid. Salts derived from inorganic bases include, but are not limited to, sodium, potassium, lithium, ammonium, calcium, magnesium, zinc, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

Pharmaceutically acceptable acid addition salts of the compounds herein having a base functional group (e.g., a prodrug whereby the phosphorus-containing group is protected with a group comprising a base functional group) are also included in the present invention. Pharmaceutically acceptable acid addition salts refer to those salts which retain the biological effectiveness and properties of the free base, which are not biologically or otherwise undesirable. These salts are prepared from addition of an inorganic acid or an organic acid to the free base. Salts derived from inorganic acids include, but are not limited to, acistrate, hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthylate, mesylate, glucoheptonate, lactobionate, laurylsulphonate. bromide, fumarate, pamoate, glucouronate, hydroiodide, iodide, sulfate, xinofoate and chloride salts The compounds of the present invention may be pure or substantially pure or have a purity of at least 75%, 80%, 85%, 90%, 91%, 92%, 93%, 94%, 95%, 96%, 97%, 98%, 99% or purity at least 99.5%. The compounds may also be part of a pharmaceutically acceptable composition. The compounds may also be part of a biological material or sample. Thus, included in the present invention are cells and tissues comprising a compound of the present invention. The cells or tissues can be in vivo, ex vivo or in vitro. Examples include liver or liver cells (e.g., hepatocytes), blood, gastric fluid (simulated or actual), intestinal fluid (simulated or actual), and urine.

In one aspect the invention relates to a phosphonic acid- or phosphonic acid monoester-containing thyromimetic compound of Formula X:

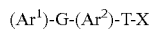

wherein:

$Ar^1$ and $Ar^2$ are aryl groups;

G is an atom or group of atoms that links $Ar^1$ and $Ar^2$ through a single C, S, O, or N atom;

T is an atom or group of atoms linking $Ar^2$ to X through 1-4 contiguous atoms or is absent;

X is a phosphonic acid, phosphonic acid monoester, or a prodrug thereof.

In one embodiment the compound has a Ki $\leqq$150 nM. Another embodiment includes a pharmaceutical composition comprising the compound and a at least one excipient. In another embodiment the pharmaceutical composition has a bioavailability of at least 15%. In another embodiment the compound is crystalline. In another embodiment the pharmaceutical composition is a unit dose.

In one embodiment, when the compound of Formula X is a compound of Formula I wherein G is —O—, T is —$CH_2$—, $R^1$ and $R^2$ are each bromo, $R^3$ is iso-propyl, $R^4$ is hydrogen, and $R^5$ is —OH, then X is not $P(O)(OH)_2$ or $P(O)(OCH_2CH_3)_2$. In another embodiment, when the compound of Formula X is a compound of Formula I wherein G is —O—, T is —$(CH_2)_{0-4}$—, $R^1$ and $R^2$ are independently halogen, alkyl of 1 to 3 carbons, and cycloalkyl of 3 to 5 carbons, $R^3$ is alkyl of 1 to 4 carbons or cycloalkyl of 3 to 7 carbons, $R^4$ is hydrogen, and $R^5$ is —OH, then X is not —$P(O)(OH)_2$ or —P(O)(O-lower alkyl)$_2$. In another embodiment, when the compound of Formula X is a compound of Formula I wherein G is —O—, $R^5$ is —NHC(O)$R^e$, —NHS(=O)$_{1-2}R^e$, —NHC(S)NH($R^h$), or —NHC(O)NH($R^h$), T is —$(CH_2)_m$—, —CH=CH—, —O$(CH_2)_{1-2}$—, or —NH$(CH_2)_{1-2}$—, then X is not —P(O)(OH)$_2$ or —P(O)(OH)NH$_2$. In another embodiment, when the compound of Formula X is a compound of Formula III wherein G is —O—, T is —NH—$CH_2$—, $R^1$ and $R^2$ are each chloro, $R^3$ is iso-propyl, $R^4$ is hydrogen, $R^7$ is fluoro, and $R^5$ is —OH, then X is not P(O)(OH)$_2$, P(O)(OH)(OCH$_3$) or P(O)(OCH$_3$)$_2$. In another embodiment, when the compound of Formula X is a compound of Formula III wherein G is selected from the group consisting of —O—, —S—, —S(=O)—, —S(=O)$_2$—, —CH$_2$—, —C(O)— and —NR$^b$—; T is -A-B— where A is selected from the group consisting of —NR$^b$—, —O—, —CH$_2$— and —S— and B is selected from the group consisting of a bond and substituted or unsubstituted $C_1$-$C_3$ alkyl; $R^3$ is selected from the group consisting of halogen, trifluoromethyl, substituted or unsubstituted $C_1$-$C_6$ alkyl, substituted or unsubstituted aryl, substituted or unsubstituted heteroaryl, aryloxy, substituted amide, sulfone, sulfonamide and $C_3$-$C_7$ cycloalkyl, wherein said aryl, heteroaryl or cycloalkyl ring(s) are attached or fused to the aromatic; $R^4$ is selected from the group consisting of hydrogen, halogen, substituted or unsubstituted $C_1$-$C_6$ alkyl, substituted or unsubstituted aryl, and substituted or unsubstituted heteroaryl; $R^1$ and $R^2$ are each independently selected from the group consisting of halogen, substituted or unsubstituted $C_1$-$C_4$ alkyl, and substituted or unsubstituted $C_3$-$C_5$ cycloalkyl; $R^7$ is selected from the group consisting of hydrogen, halogen, amino, hydroxyl, —O—$C_1$-$C_4$ alkyl, —SH and —S—$C_1$-$C_4$ alkyl; and $R^5$ is selected from the group consisting of hydroxyl, optionally substituted —O$C_1$-$C_6$ alkyl, and —OC(O)R$^e$; then X is not —P(O)(OH)$_2$.

In another aspect the invention relates to a method of improving liver versus heart selectivity or for increasing the therapeutic index of a thyromimetic compound of Formula Y:

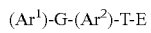

wherein:

$Ar^1$ and $Ar^2$ are aryl groups;

G is an atom or group of atoms that links $Ar^1$ and $Ar^2$ through a single C, S, O, or N atom;

T is an atom or group of atoms linking $Ar^2$ to E through 1-4 contiguous atoms or is absent;

E is a functional group or moiety with a pKa$\leqq$7.4, is carboxylic acid (COOH) or esters thereof, sulfonic acid, tetrazole, hydroxamic acid, 6-azauracil, thiazolidinedione, acylsulfonamide, or other carboxylic acid surrogates known in the art or a prodrug thereof, or an atom or group of atoms containing an O or N that binds the thyroid hormone binding pocket of a TR$\alpha$ or TR$\beta$, but wherein E is not a —P(O)(OH)$_2$ or ester thereof;

comprising the step of replacing E with a phosphonic acid, phosphonic acid monoester, or a prodrug thereof. In one embodiment the compound has a Ki $\leqq$150 nM. Another embodiment includes a pharmaceutical composition comprising the compound and a at least one excipient. In another embodiment the pharmaceutical composition has a bioavailability of at least 15%. In another embodiment the compound is crystalline. In another embodiment the pharmaceutical composition is a unit dose.

In another aspect the invention relates to a method of designing a thyromimetic compound with improved liver versus heart selectivity or improved therapeutic index comprising the steps of:

obtaining a formula for a thyromimetic of Formula Y:

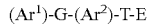

wherein:

$Ar^1$ and $Ar^2$ are aryl groups;

G is an atom or group of atoms that links $Ar^1$ and $Ar^2$ through a single C, S, O, or N atom;

T is an atom or group of atoms linking $Ar^2$ to E through 1-4 contiguous atoms or is absent;

E is a functional group or moiety with a pKa$\leqq$7.4, is carboxylic acid (COOH) or esters thereof, sulfonic acid, tetrazole, hydroxamic acid, 6-azauracil, thiazolidinedione, acylsulfonamide, or other carboxylic acid surrogates known in the art or a prodrug thereof, or an atom or group of atoms containing an O or N that binds the thyroid hormone binding pocket of a TR$\alpha$ or TR$\beta$, but wherein E is not a —P(O)(OH)$_2$ or ester thereof;

comprising the step of replacing E with a phosphonic acid, phosphonic acid monoester, or a prodrug thereof; and synthesizing a compound of Formula X wherein X is phosphonic acid, phosphonic acid monoester, or a prodrug thereof. In one embodiment the compound has a Ki$\leqq$150 nM. Another embodiment includes a pharmaceutical composition comprising the compound and a at least one excipient. In another embodiment the pharmaceutical composition has a bioavailability of at least 15%. In another embodiment the compound is crystalline. In another embodiment the pharmaceutical composition is a unit dose.

In one aspect, the invention relates to a compound of Formula I:

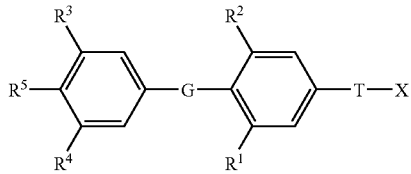

wherein:

G is selected from the group consisting of —O—, —S—, —Se—, —S(=O)—, —S(=O)$_2$—, —CH$_2$—, —CF$_2$—, —CHF—, —C(O)—, —CH(OH)—, —NH—, and —N(C$_1$-C$_4$ alkyl)-, or CH$_2$ linked to any of the preceding groups;

T is selected from the group consisting of —(CR$^a{}_2$)$_k$—, —CR$^b$=CR$^b$—(CR$^a{}_2$)$_n$—, —(CR$^a{}_2$)$_n$—CR$^b$=CR$^b$—, (CR$^a{}_2$)—CR$^b$=CR$^b$—(CR$^a{}_2$)$_k$—, —O(CR$^b{}_2$) (CR$^a{}_2$)$_n$—, —S(CR$^b{}_2$)(CR$^a{}_2$)$_n$—, —N(R$^c$)(CR$^b{}_2$) (CR$^a{}_2$)$_n$—, —N(R$^b$)C(O)(CR$^a{}_2$)$_n$—, —(CR$^a{}_2$)$_n$CH (NR$^b$R$^c$)—, —C(O)(CR$^a{}_2$)$_m$—, —(CR$^a{}_2$)$_m$C(O)—, —(CR$^a{}_2$)C(O)(CR$^a{}_2$)$_n$—, —(CR$^a{}_2$)$_n$C(O)(CR$^a{}_2$)—, —C(O)NH(CR$^b{}_2$)(CR$^a{}_2$)$_p$—, and —(CH$_2$)$_n$C(O)N(R$^b$) C(R$^a$)$_2$—;

k is an integer from 0-4;
m is an integer from 0-3;
n is an integer from 0-2;
p is an integer from 0-1;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and optionally substituted —C$_1$-C$_4$ alkyl;

Each R$^c$ is independently selected from the group consisting of hydrogen, optionally substituted —C$_1$-C$_4$ alkyl, optionally substituted —C(O)—C$_1$-C$_4$ alkyl, and —C(O)H;

R$^1$ and R$^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano;

R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_m$ aryl, optionally substituted —(CR$^a{}_2$)$_m$cycloalkyl, optionally substituted —(CR$^a{}_2$)$_m$heterocycloalkyl, —OR$^d$, —SR$^d$, —S(=O)R$^e$, —S(=O)$_2$R$^e$, —S(=O)$_2$NR$^f$R$^g$, —C(O)NR$^f$R$^g$, —C(O)OR$^h$, —C(O)R$^e$, —N(O) C(O)R$^e$, —N(R$^b$)C(O)NR$^f$R$^g$, —N(R$^b$)S(=O)$_2$R$^e$, —N(R$^b$)S(=O)$_2$NR$^f$R$^g$, and —NR$^f$R$^g$;

Each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, optionally substituted —(CR$^b{}_2$)$_n$heterocycloalkyl, and —C(O)NR$^f$R$^g$;

Each R$^e$ is optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_n$aryl, optionally substituted —(CR$^a{}_2$)$_n$cycloalkyl, and optionally substituted —(CR$^a{}_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl, or R$^f$ and R$^g$ may together form an optionally substituted heterocyclic ring, which may contain a second heterogroup selected from the group of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl;

R$^5$ is selected from the group consisting of —OH, optionally substituted —OC$_1$-C$_6$ alkyl, —OC(O)R$^e$, —OC(O) OR$^h$, —F, —NHC(O)R$^e$, —NHS(=O)R$^e$, —NHS (=O)$_2$R$^e$, —NHC(=S)NH(R$^h$), and —NHC(O)NH (R$^h$); or R$^3$ and R$^5$ are taken together along with the carbons they are attached to form an optionally substituted ring of 5 to 6 atoms with 0-2 unsaturations, not including the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

X is P(O)YR$^{11}$Y'R$^{11}$;

Y and Y' are each independently selected from the group consisting of —O—, and —NR$^v$—;

when Y and Y' are both —O—, R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR$^z{}_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy; and when Y and Y' are both —NR$^v$—, then R$^{11}$ attached to —NR$^v$— is independently selected from the group consisting of —H, —[C(R$^z$)$_2$]$_q$—COOR$^y$, —C(R$^x$)$_2$ COOR$^y$, —[C(R$^z$)$_2$]$_q$—C(O)SR$^y$, and -cycloalkylene-COOR$^y$; and when Y is —O— and Y' is NR$^v$, then R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted-alkylaryl, —C(R$^z$)$_2$OC(O)NR$^z{}_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy; and R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

but if both R$^{11}$ are alkyl, at least one is higher alkyl;

and both R$^{11}$ are not —H;

or when Y and Y' are independently selected from —O— and —NR$^v$—, then R$^{11}$ and R$^{11}$ together form a cyclic group comprising -alkyl-S-S-alkyl-, or R$^{11}$ and R$^{11}$ together are the group:

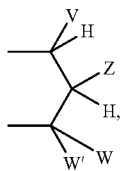

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or or together V and Z are connected via an additional 3-5 atoms to form a cyclic group, wherein 0-1 atoms are heteroatoms and the remaining atoms are carbon or carbon substituted by hydrogen, and said cyclic group is fused to an aryl group at the beta and gamma position to the Y attached to the phosphorus;

or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon or carbon substituted by hydrogen, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH=CR$^z_2$)OH, —CH(C≡CR$^z$)OH, —R$^z$, —NR$^z_2$, —OCO$_2$R$^y$, —OCO$_2$R$^y$, —SCO$_2$R$^y$, —SCO$_2$R$^y$, —NHCOR$^z$, —NHCO$_2$R$^y$, —CH$_2$NHaryl, —(CH$_2$)$_q$—OR$^z$, and —(CH$_2$)$_q$—SR$^z$;

q is an integer 2 or 3;

Each R$^z$ is selected from the group consisting of R$^y$ and —H;

Each R$^y$ is selected from the group consisting of alkyl, aryl, heterocycloalkyl, and aralkyl;

Each R$^x$ is independently selected from the group consisting of —H, and alkyl, or together R$^x$ and R$^x$ form a cycloalkyl group;

Each R$^v$ is selected from the group consisting of —H, lower alkyl, acyloxyalkyl, alkoxycarbonyloxyalkyl, and lower acyl;

with the provisos that:

a) V, Z, W, W' are not all —H; and b) when Z is —R$^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In another aspect, the invention relates to a compound of Formula I:

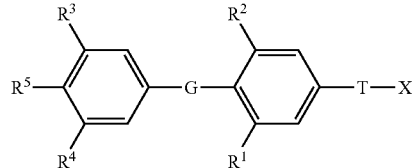

wherein:

G is selected from the group consisting of —O—, —S—, —Se—, —S(=O)—, —S(=O)$_2$—, —CH$_2$—, —CF$_2$—, —CHF—, —C(O)—, —CH(OH)—, —NH—, and —N(C$_1$-C$_4$ alkyl)-, or CH$_2$ linked to any of the preceding groups;

T is selected from the group consisting of —(CR$^a_2$)$_k$—, —CR$^b$=CR$^b$—(CR$^a_2$)$_n$—, —(CR$^a_2$)$_n$—CR$^b$=CR$^b$—, —(CR$^a_2$)—CR$^b$=CR$^b$—(CR$^a_2$)—, —O(CR$^b_2$)(CR$^a_2$)$_n$, —S(CR$^b_2$)(CR$^a_2$)$_n$—, —N(R$^c$)(CR$^b_2$)(CR$^a_2$)$_n$—, —N(R$^b$)C(O)(CR$^a_2$)$_n$—, —(CR$^a_2$)$_n$CH(NR$^b$R$^c$)—, —C(O)(CR$^a_2$)$_m$—, —(CR$^a_2$)$_m$C(O)—, —(CR$^a_2$)C(O)(CR$^a_2$)$_n$—, —(CR$^a_2$)$_n$C(O)(CR$^a_2$)—, —C(O)NH(CR$^b_2$)(CR$^a_2$)$_p$—, and —(CH$_2$)$_n$C(O)N(R$^b$)C(R$^a$)$_2$—;

k is an integer from 0-4;

m is an integer from 0-3;

n is an integer from 0-2;

p is an integer from 0-1;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and optionally substituted —C$_1$-C$_4$ alkyl;

Each R$^c$ is independently selected from the group consisting of hydrogen and optionally substituted —C$_1$-C$_4$ alkyl, optionally substituted —C(O)—C$_1$-C$_4$ alkyl, and —C(O)H;

$R^1$ and $R^2$ are each independently selected from the group consisting of halogen, optionally substituted —$C_1$-$C_4$ alkyl, optionally substituted —S—$C_1$-$C_3$ alkyl, optionally substituted —$C_2$-$C_4$ alkenyl, optionally substituted —$C_2$-$C_4$ alkynyl, —$CF_3$, —$OCF_3$, optionally substituted-O—$C_1$-$C_3$ alkyl, and cyano;

$R^3$ and $R^4$ are each independently selected from the group consisting of hydrogen, halogen, —$CF_3$, —$OCF_3$, cyano, optionally substituted —$C_1$-$C_{12}$ alkyl, optionally substituted —$C_2$-$C_{12}$ alkenyl, optionally substituted —$C_2$-$C_{12}$alkynyl, optionally substituted —$(CR^a{}_2)_m$aryl, optionally substituted —$(CR^a{}_2)_m$cycloalkyl, optionally substituted —$(CR^a{}_2)_m$heterocycloalkyl, —$OR^d$, —$SR^d$, —S(=O)$R^c$, —S(=O)$_2R^e$, —S(=O)$_2$N$R^fR^g$, —C(O)N$R^fR^g$, —C(O)O$R^h$, —C(O)$R^e$, —N($R^b$)C(O)$R^e$, —N($R^b$)C(O)N$R^fR^g$, —N($R^b$)S(=O)$_2R^e$, —N($R^b$)S(=O)$_2$N$R^fR^g$, and —N$R^fR^g$;

Each $R^d$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b{}_2)_n$aryl, optionally substituted —$(CR^b{}_2)_n$cycloalkyl, optionally substituted —$(CR^b{}_2)_n$heterocycloalkyl, and —C(O)N$R^fR^g$;

Each $R^e$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a{}_2)_n$aryl, optionally substituted —$(CR^a{}_2)_n$cycloalkyl, and optionally substituted —$(CR^a{}_2)_n$heterocycloalkyl;

$R^f$ and $R^g$ are each independently selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b{}_2)_n$aryl, optionally substituted —$(CR^b{}_2)_n$Cycloalkyl, and optionally substituted —$(CR^b{}_2)_n$heterocycloalkyl, or $R^f$ and $R^g$ may together form an optionally substituted heterocyclic ring, which may contain a second heterogroup selected from the group consisting of O, N$R^c$, and S, wherein said optionally substituted heterocyclic ring may be substituted with 0-4 substituents selected from the group consisting of optionally substituted —$C_1$-$C_4$ alkyl, —O$R^b$, oxo, cyano, —$CF_3$, optionally substituted phenyl, and —C(O)O$R^h$;

Each $R^h$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b{}_2)_n$aryl, optionally substituted —$(CR^b{}_2)_n$cycloalkyl, and optionally substituted —$(CR^b{}_2)_n$heterocycloalkyl;

$R^5$ is selected from the group consisting of —OH, optionally substituted —O$C_1$-$C_6$ alkyl, —OC(O)$R^e$, —OC(O)O$R^h$, —F, —NHC(O)$R^e$, —NHS(=O)$R^e$, —NHS(=O)$_2R^e$, —NHC(=S)NH($R^h$), and —NHC(O)NH($R^h$); or $R^3$ and $R^5$ are taken together along with the carbons they are attached to form an optionally substituted ring of 5 to 6 atoms with 0-2 unsaturations, not including the unsaturation on the ring to which $R^3$ and $R^5$ are attached, including 0 to 2 heteroatoms independently selected from —N$R^h$—, —O—, and —S—, with the proviso that when there are 2 heteroatoms in the ring and both heteroatoms are different than nitrogen then both heteroatoms have to be separated by at least one carbon atom;

X is P(O)Y$R^{11}$Y'$R^{11}$;

Y and Y' are each independently selected from the group consisting of —O—, and —N$R^v$—;

when Y and Y' are both —O—, $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —C($R^z$)$_2$OC(O)N$R^z{}_2$, —N$R^z$—C(O)—$R^y$, —C($R^z$)$_2$—OC(O)$R^y$, —C($R^z$)$_2$—O—C(O)O$R^y$, —C($R^z$)$_2$OC(O)S$R^y$, -alkyl-S—C(O)$R^y$, -alkyl-S-S-alkylhydroxy, and -alkyl-S-S-S-alkylhydroxy;

when Y and Y' are both —N$R^v$—, then $R^{11}$ attached to —N$R^v$— is independently selected from the group consisting of —H, —[C($R^z$)$_2$]$_q$—COO$R^y$, —C($R^x$)$_2$COO$R^y$, —[C($R^z$)$_2$]$_q$—C(O)S$R^y$, and -cycloalkylene-COO$R^y$;

when Y is —O— and Y' is N$R^v$, then $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —C($R^z$)$_2$OC(O)N$R^z{}_2$, —N$R^z$—C(O)—$R^y$, —C($R^z$)$_2$—OC(O)$R^y$, —C($R^z$)$_2$—O—C(O)O$R^y$, —C($R^z$)$_2$OC(O)S$R^y$, -alkyl-S—C(O)$R^y$, -alkyl-S-S-alkylhydroxy, and -alkyl-S-S-S-alkylhydroxy; and $R^{11}$ attached to —N$R^v$— is independently selected from the group consisting of —H, —[C($R^z$)$_2$]$_q$—COO$R^y$, —C($R^x$)$_2$COO$R^y$, —[C($R^z$)$_2$]$_q$—C(O)S$R^y$, and -cycloalkylene-COO$R^y$;

or when Y and Y' are independently selected from —O— and —N$R^v$—, then $R^{11}$ and $R^{11}$ together form a cyclic group comprising -alkyl-S-S-alkyl-, or together $R^{11}$ and $R^{11}$ are the group:

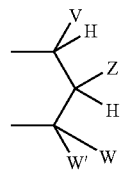

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or or together V and Z are connected via an additional 3-5 atoms to form a cyclic group, wherein 0-1 atoms are heteroatoms and the remaining atoms are carbon or carbon substituted by hydrogen, and said cyclic group is fused to an aryl group at the beta and gamma position to the Y attached to the phosphorus;

or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon or carbon substituted by hydrogen, and V must be aryl, substituted aryl, heteroaryl, or substituted heteroaryl;

Z is selected from the group consisting of —$CHR^zOH$, —$CHR^zOC(O)R^y$, —$CHR^zOC(S)R^y$, —$CHR^zOC(S)OR^y$, —$CH^zOC(O)SR^y$, —$CHR^zOCO_2R^y$, —$OR^z$, —$SR^z$, —$CHR^zN_3$, —$CH_2aryl$, —$CH(aryl)OH$, —$CH(CH=CR^z{}_2)OH$, —$CH(C\equiv CR^z)OH$, —$R^z$, —$NR^z{}_2$, —$OCOR^y$, —$OCO_2R^y$, —$SCOR^y$, —$SCO_2R^y$, —$NHCOR^z$, —$NHCO_2R^y$, —$CH_2NHaryl$, —$(CH_2)_q$—$OR^z$, and —$(CH_2)_q$—$SR^z$;

q is an integer 2 or 3;

Each $R^z$ is selected from the group consisting of $R^y$ and —H;

Each $R^y$ is selected from the group consisting of alkyl, aryl, heterocycloalkyl, and aralkyl;

Each $R^x$ is independently selected from the group consisting of —H, and alkyl, or together $R^x$ and $R^x$ form a cycloalkyl group;

Each $R^v$ is selected from the group consisting of —H, lower alkyl, acyloxyalkyl, alkoxycarbonyloxyalkyl, and lower acyl;

with the provisos that:
a) when G is —O—, T is —$CH_2$—, $R^1$ and $R^2$ are each chloro, $R^3$ is phenyl, $R^4$ is hydrogen, and $R^5$ is —OH, then X is not $P(O)(OH)(OCH_2CH_3)$;
b) when G is —O—, T is —$CH_2$—, $R^1$ and $R^2$ are each bromo, $R^3$ is iso-propyl, $R^4$ is hydrogen, and $R^5$ is —OH, then X is not $P(O)(OH)_2$ or $P(O)(OCH_2CH_3)_2$;
c) V, Z, W, W' are not all —H; and
d) when Z is —$R^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In another aspect, the invention relates to a compound of Formula I:

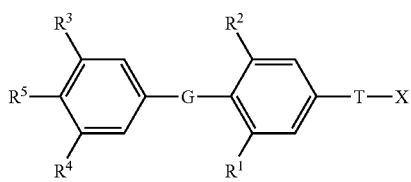

wherein:
G is selected from the group consisting of —O—, —S—, —Se—, —S(=O)—, —$S(=O)_2$—, —$CH_2$—, —$CF_2$—, —CHF—, —C(O)—, —CH(OH)—, —NH—, and —$N(C_1\text{-}C_4\text{alkyl})$-, or $CH_2$ linked to any of the preceding groups;

T is selected from the group consisting of —$(CR^a{}_2)_k$—, —$CR^b=CR^b$—$(CR^a{}_2)_n$—, —$(CR^a{}_2)_n$—$CR^b=CR^b$—, —$(CR^a{}_2)$—$CR^b=CR^b$—$(CR^a{}_2)$—, $O(CR^b{}_2)(CR^a{}_2)$, —$S(CR^b{}_2)(CR^a{}_2)_n$—, —$N(R^c)(CR^b{}_2)(CR^a{}_2)_n$—, —$N(R^b)C(O)(CR^a{}_2)_n$—, —$(CR^a{}_2)_nCH(NR^bR^c)$—, —$C(O)(CR^a{}_2)_m$—, —$(CR^a{}_2)_mC(O)$—, —$(CR^a{}_2)C(O)(CR^a{}_2)_n$—, —$(CR^a{}_2)_nC(O)(CR^a{}_2)$—, —$C(O)NH(CR^b{}_2)(CR^a{}_2)_p$—, and —$(CH_2)_nC(O)N(O)C(R^a)_2$—;

k is an integer from 0-4;
m is an integer from 0-3;
n is an integer from 0-2;
p is an integer from 0-1;

Each $R^a$ is independently selected from the group consisting of hydrogen, optionally substituted —$C_1$-$C_4$ alkyl, halogen, —OH, optionally substituted —O—$C_1$-$C_4$ alkyl, —$OCF_3$, optionally substituted —S—$C_1$-$C_4$ alkyl, —$NR^bR^c$, optionally substituted —$C_2$-$C_4$ alkenyl, and optionally substituted —$C_2$-$C_4$ alkynyl; with the proviso that when one $R^a$ is attached to C through an O, S, or N atom, then the other $R^a$ attached to the same C is a hydrogen, or attached via a carbon atom;

Each $R^b$ is independently selected from the group consisting of hydrogen and optionally substituted —$C_1$-$C_4$ alkyl;

Each $R^c$ is independently selected from the group consisting of hydrogen, optionally substituted —$C_1$-$C_4$ alkyl, optionally substituted —C(O)—$C_1$-$C_4$ alkyl, and —C(O)H;

$R^1$ and $R^2$ are each independently selected from the group consisting of halogen, optionally substituted —$C_1$-$C_4$ alkyl, optionally substituted —S—$C_1$-$C_3$ alkyl, optionally substituted —$C_2$-$C_4$ alkenyl, optionally substituted —$C_2$-$C_4$ alkynyl, —$CF_3$, —$OCF_3$, optionally substituted-O—$C_1$-$C_3$ alkyl, and cyano;

$R^3$ and $R^4$ are each independently selected from the group consisting of hydrogen, halogen, —$CF_3$, —$OCF_3$, cyano, optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a{}_2)_m$aryl, optionally substituted —$(CR^a{}_2)_m$cycloalkyl, optionally substituted $(CR^a{}_2)_m$heterocycloalkyl, —$OR^d$, —$SR^d$, —$S(=O)R^e$, —$S(=O)_2R^e$, —$S(=O)_2NR^fR^g$, —$C(O)NR^fR^g$, —$C(O)OR^h$, —$C(O)R^e$, —$N(R^b)C(O)R^e$, —$N(R^b)C(O)NR^fR^g$, —$N(R^b)S(=O)_2R^e$, —$N(R^b)S(=O)_2NR^fR^g$, and —$NR^fR^g$;

Each $R^d$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b{}_2)_n$aryl, optionally substituted —$(CR^b{}_2)_n$cycloalkyl, optionally substituted —$(CR^b{}_2)_n$heterocycloalkyl, and —$C(O)NR^fR^g$;

Each $R^e$ is optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a{}_2)_n$aryl, optionally substituted —$(CR^a{}_2)_n$cycloalkyl, and optionally substituted —$(CR^a{}_2)_n$heterocycloalkyl;

$R^f$ and $R^g$ are each independently selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —(CR$^b_2$)$_n$aryl, optionally substituted —(CR$^b_2$)$_n$cycloalkyl, and optionally substituted —(CR$^b_2$)heterocycloalkyl, or R$^f$ and R$^g$ may together form an optionally substituted heterocyclic ring, which may contain a second heterogroup selected from the group of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl;

R$^5$ is selected from the group consisting of —OH, optionally substituted —OC$_1$-C$_6$ alkyl, —OC(O)R$^e$, —OC(O)OR$^h$, —F, —NHC(O)R$^e$, —NHS(═O)R$^e$, —NHS(═O)$_2$R$^e$, —NHC(═S)NH(R$^h$), and —NHC(O)NH(R$^h$); or R$^3$ and R$^5$ are taken together along with the carbons they are attached to form an optionally substituted ring of 5 to 6 atoms with 0-2 unsaturations, not including the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

X is P(O)YR$^{11}$Y'R$^{11}$;

Y and Y' are each independently selected from the group consisting of —O—, and —NR$^v$—;

when Y and Y' are both —O—, R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR$^z_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy;

when Y and Y' are both —NR$^v$—, then R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

when Y is —O— and Y' is NR$^v$, then R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR$^z_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy; and R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

or when Y and Y' are independently selected from —O— and —NR$^v$—, then R$^{11}$ and R$^{11}$ together form a cyclic group comprising -alkyl-S-S-alkyl-, or together R$^{11}$ and R$^{11}$ are the group:

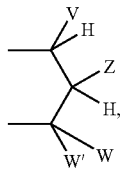

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or or together V and Z are connected via an additional 3-5 atoms to form a cyclic group, wherein 0-1 atoms are heteroatoms and the remaining atoms are carbon or carbon substituted by hydrogen, and said cyclic group is fused to an aryl group at the beta and gamma position to the Y attached to the phosphorus;

or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon or carbon substituted by hydrogen, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH═CR$^z_2$)OH, —CH(C≡CR$^z$)OH, —R$^z$, —NR$^z_2$, —OCOR$^y$, —OCO$_2$R$^y$, —SCOR$^y$, —SCO$_2$R$^y$, —NHCOR$^z$, —NHCO$_2$R$^y$, —CH$_2$NHaryl, —(CH$_2$)$_q$OR$^z$, and —(CH$_2$)$_q$—SR$^z$;

q is an integer 2 or 3;

Each R$^z$ is selected from the group consisting of R$^y$ and —H;

Each R$^y$ is selected from the group consisting of alkyl, aryl, heterocycloalkyl, and aralkyl;

Each R$^x$ is independently selected from the group consisting of —H, and alkyl, or together R$^x$ and R$^x$ form a cycloalkyl group;

Each $R^v$ is selected from the group consisting of —H, lower alkyl, acyloxyalkyl, alkoxycarbonyloxyalkyl, and lower acyl;

with the provisos that:

a) when G is —O—, —S—, —Se—, —S(=O)—, —S(=O)$_2$—, —CH$_2$—, —C(O)—, —NH— and, T is —(CH$_2$)$_{0-4}$— or —C(O)NH(CR$^b_2$)—, $R^1$ and $R^2$ are independently chosen from the group consisting of hydrogen, halogen, —C$_1$-C$_4$ alkyl, $R^3$ is —C(O)NR$^{25}$R$^{26}$, —CH$_2$—NR$^{25}$R$^{26}$, —NR$^{25}$—C(O)R$^{26}$, —OR$^{27}$, R$^{28}$, or

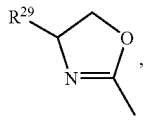

$R^4$ is hydrogen, halogen, cyano or alkyl, and $R^5$ is —OH, $R^{25}$ and $R^{26}$ are each independently selected from the group consisting of hydrogen, aryl, heteroaryl, alkyl, cycloalkyl, aralkyl or heteroaralkyl, $R^{27}$ is aryl, heteroaryl, alkyl, aralkyl, or heteroaralkyl, $R^{28}$ is aryl, heteroaryl, or cycloalkyl, $R^{29}$ is hydrogen, aryl, heteroaryl, alkyl, aralkyl, heteroaralkyl, then X is not —P(O)(OH)$_2$, or —P(O)(O-lower alkyl)$_2$;

b) when G is —O—, —S—, —Se—, —S(=O)—, —S(=O)$_2$—, —CH$_2$—, —CF$_2$—, —C(O)—, —NH— and, T is —C(O)NH(CR$^b_2$)—, $R^1$ and $R^2$ are independently halogen, cyano, —C$_1$-C$_4$ alkyl, $R^3$ is halogen, —C$_1$-C$_6$ alkyl, —C$_2$-C$_6$ alkynyl, —C$_4$-C$_7$ cycloalkenyl, —C$_3$-C$_7$ cycloalkoxy, —S(=O)$_2$(NR$^{14}$R$^{15}$), —N(R$^{16}$)S(=O)$_2$R$^{17}$, —SR$^{17}$, —S(=O)R$^{17}$, —S(=O)$_2$R$^{17}$, —C(O)R$^{16}$, or —CR$^{18}$(OR$^{16}$)R$^{19}$, $R^4$ is halogen, cyano or alkyl, and $R^5$ is —OH, optionally substituted —OC$_1$-C$_6$ alkyl, aroyl or alkanoyl, $R^{14}$, $R^{15}$, $R^{16}$, $R^{18}$ and $R^{19}$ are independently selected from the group consisting of hydrogen, alkyl, cycloalkyl, aryl, heteroalkyl, arylalkyl, and heteroarylalkyl, or $R^{14}$ and $R^{15}$ may be joined so as to comprise a chain of 3 to 6 methylene groups to form a ring of 4 to 7-membered in size, $R^{17}$ is selected from the group consisting of alkyl, cycloalkyl, aryl, heteroalkyl, arylalkyl, and heteroarylalkyl, then X is not —P(O)(OH)$_2$ or —P(O)(O-lower alkyl)$_2$;

c) when G is O and T is —(CH$_2$)$_k$—, $R^1$ and $R^2$ are independently halogen, alkyl of 1 to 3 carbons, $R^3$ is alkyl of 1 to 4 carbons or cycloalkyl of 3 to 7 carbons, $R^4$ is hydrogen, $R^5$ is OH, then X is not phosphonic acid or a lower alkyl ester thereof;

d) when G is O, T is —(CH$_2$)$_{1-3}$— or —(CH$_2$)$_{1-2}$—CH(R$^{aa}$), $R^{aa}$ is —OH, —NH$_2$, —NH(C$_{1-4}$alkyl), —NH(C$_{2-4}$alkenyl), or —NH(C$_{2-4}$alkynyl), $R^4$ is hydrogen, $R^1$ and $R^2$ are independently selected from halogen, C$_1$ alkyl substituted with 1, 2, or 3 hydrogen, fluorine, or a bioisosteric equivalent, C$_{1-4}$ alkyl and CF$_3$, and $R^3$ and $R^5$ are taken together along with the carbon atoms to which they are attached to form a five member heterocyclic ring of formula -A-C(R$^{bb}$)=B— wherein A, attached where the $R^5$ group is attached, is selected from —O—, —S—, and —NR$^h$—, B is selected from —CH—, and —N—, R$^{bb}$ is selected from C$_{6-10}$aryl, C$_{5-9}$heteroaryl, or C$_{1-4}$alkyl, then X is not phosphonic acid, phosphamic acid, or a lower alkyl ester or acyloxyalkyl ester thereof;

e) when G is O, $R^4$ is hydrogen, $R^3$ is selected from hydrogen, halogen, cyano, C$_{6-10}$aryl, C$_{5-10}$heteroaryl, C$_{1-10}$alkyl, C$_{3-8}$cycloalkyl, C$_{2-10}$alkenyl, C$_{2-10}$alkynyl, and $R^5$ is —NHC(O)R$^e$, —NHS(=O)R$^e$, —NHS(=O)$_2$R$^e$, —NHC(=S)NH(R$^h$) or —NHC(O)NH(R$^h$), T is —(CH$_2$)$_{1-2}$—, —CH=CH—, —O(CH$_2$)$_{1-2}$—, or —NH(CH$_2$)$_{1-2}$—, then X is not phosphonic acid or phosphamic acid or a lower alkyl ester thereof;

f) when G is —CH$_2$—O—, wherein the oxygen atom is attached to the ring bearing the T group, T is —(CH$_2$)$_{1-2}$CH(R$^{cc}$), R$^{cc}$ is —OH, —SH, —NH$_2$, or —NH(C$_{1-4}$), $R^1$ and $R^2$ are each independently selected from chlorine, bromine, C$_{1-4}$ alkyl, C$_{2-4}$ alkenyl, and C$_{2-4}$ alkynyl, then X is not phosphonic acid or phosphamic acid or a lower alkyl ester thereof;

g) V, Z, W, W' are not all —H; and h) when Z is —R$^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In one aspect, G is —O—. In another aspect, G is —CH$_2$—. In yet another aspect, G is selected from the group consisting of —O— and —CH$_2$—. In another aspect, G is —S—. In a further aspect, G is —S(=O)—. In another aspect, G is —S(=O)$_2$—. In a further aspect, G is —CH$_2$—. In another aspect, G is —CF$_2$—. In a further aspect, G is —CHF—. In another aspect, G is —C(O)—. In another aspect, G is —CH(OH)—. In a further aspect, G is —NH—. In another aspect, G is —N(C$_1$-C$_4$ alkyl)-. In yet another aspect, G is selected from the group consisting of —O—, —S— and —CH$_2$—.

In one aspect, T is —CH$_2$—. In another aspect, T is —(CH$_2$)$_{0-4}$—. In another aspect, T is selected from the group consisting of —(CH$_2$)$_m$—, —CH=CH—, —O(CH$_2$)$_{1-2}$—, and —NH(CH$_2$)$_{1-2}$—. In yet another aspect, T is selected from the group consisting of —(CR$^a_2$)$_n$—, —O(CR$^b_2$)(CR$^a_2$)$_p$—, —N(R$^c$)(CR$^b_2$)(CR$^a_2$)$_p$—, —S(CR$^b_2$)(CR$^a_2$)$_p$—, —NR$^b$(CO)—, and —CH$_2$CH(NR$^c$R$^b$)—. In another aspect, T is —CH$_2$CH(NH$_2$)—. In another aspect, T is —N(H)C(O)—. In a further aspect, T is —OCH$_2$—. In another aspect, T is —CH$_2$CH$_2$—. In yet another aspect, T is —CH$_2$CH(NH$_2$)—. In another aspect, T is —N(H)C(O)—.

In a further aspect, T is —(CR$^a_2$)$_k$—. In another aspect, T is —CR$^b$=CR$^b$—(CR$^a_2$)$_n$—. In a further aspect, T is —(CR$^a_2$)$_n$—CR$^b$=CR$^b$—. In another aspect, T is —(CR$^a_2$)—CR$^b$=CR$^b$—(CR$^a_2$)—. In a further aspect, T is —O(CR$^b_2$)(CR$^a_2$)$_n$— or —NH(CR$^b_2$)(CR$^a_2$)$_p$—. In another aspect, T is —S(CR$^b_2$)(CR$^a_2$)$_n$—. In a further aspect, T is —N(R$^c$)(CR$^b_2$)(CR$^a_2$)$_n$—. In another aspect, T is —N(R$^b$)C(O)(CR$^a_2$)$_n$—. In a further aspect, T is —(CR$^a_2$)$_n$CH(NR$^b$R$^c$)—. In another aspect, T is —C(O)(CR$^a_2$)$_m$—. In a further aspect, T is —(CR$^a_2$)$_m$C(O)—. In another aspect, T is —(CR$^a_2$)C(O)(CR$^a_2$)$_n$—. In a further aspect, T is —(CR$^a_2$)$_n$C(O)(CR$^a_2$)—. In yet another aspect, T is —C(O)NH(CR$^b_2$)(CR$^a_2$)$_p$—.

In one aspect k is 0. In a further aspect, k is 1. In an additional aspect, k is 2. In a further aspect, k is 3. In yet another aspect, k is 4. In one aspect m is 0. In a further aspect, m is 1. In an additional aspect, m is 2. In a further aspect, m is 3. In one aspect n is 0. In a further aspect, n is 1. In an additional aspect, n is 2. In one aspect, p is 0. In another aspect, p is 1.

In one aspect, each R$^a$ is hydrogen with the proviso that when one R$^a$ is attached to C through an O, S, or N atom, then the other R$^a$ attached to the same C is a hydrogen, or attached via a carbon atom. In another aspect, each R$^a$ is optionally substituted —C$_1$-C$_4$ alkyl with the proviso that when one R$^a$ is attached to C through an O, S, or N atom, then the other R$^a$ attached to the same C is a hydrogen, or attached via a carbon atom. In a further aspect, each $R^a$ is halogen with the proviso that when one $R^a$ is attached to C through an O, S, or N atom, then the other $R^a$ attached to the same C is a hydrogen, or attached via a carbon atom. In another aspect, each $R^a$ is —OH with the proviso that when one $R^a$ is attached to C through an O, S, or N atom, then the other $R^a$ attached to the same C is a hydrogen, or attached via a carbon atom. In a further aspect, each $R^a$ is optionally substituted —O—$C_1$-$C_4$ alkyl with the proviso that when one $R^a$ is attached to C through an O, S, or N atom, then the other $R^a$ attached to the same C is a hydrogen, or attached via a carbon atom. In another aspect, each $R^a$ is —$OCF_3$ with the proviso that when one $R^a$ is attached to C through an O, S, or N atom, then the other $R^a$ attached to the same C is a hydrogen, or attached via a carbon atom. In a further aspect, each $R^a$ is optionally substituted —S—$C_1$-$C_4$ alkyl with the proviso that when one $R^a$ is attached to C through an O, S, or N atom, then the other $R^a$ attached to the same C is a hydrogen, or attached via a carbon atom. In another aspect, each $R^a$ is —$NR^bR^c$ with the proviso that when one $R^a$ is attached to C through an O, S, or N atom, then the other $R^a$ attached to the same C is a hydrogen, or attached via a carbon atom. In a further aspect, each $R^a$ is optionally substituted —$C_2$-$C_4$ alkenyl with the proviso that when one $R^a$ is attached to C through an O, S, or N atom, then the other $R^a$ attached to the same C is a hydrogen, or attached via a carbon atom. In another aspect, each $R^a$ is optionally substituted —$C_2$-$C_4$ alkynyl with the proviso that when one $R^a$ is attached to C through an O, S, or N atom, then the other $R^a$ attached to the same C is a hydrogen, or attached via a carbon atom.

In one aspect, $R^b$ is hydrogen. In an additional aspect, $R^b$ is optionally substituted —$C_1$-$C_4$ alkyl.

In one aspect, $R^c$ is hydrogen. In another aspect, $R^c$ is optionally substituted —$C_1$-$C_4$ alkyl. In a further aspect, $R^c$ is optionally substituted —C(O)—$C_1$-$C_4$ alkyl. In yet another aspect, $R^c$ is —C(O)H.

In one aspect, $R^1$ and $R^2$ are each bromo. In another aspect, $R^1$ and $R^2$ are independently selected from the group consisting of hydrogen, halogen, alkyl of 1 to 3 carbons, and cycloalkyl of 3 to 5 carbons. In another aspect, $R^1$ and $R^2$ are independently halogen, alkyl of 1 to 3 carbons, and cycloalkyl of 3 to 5 carbons, In a further aspect, $R^1$ and $R^2$ are the same and are selected from the group consisting of halogen, —$C_1$-$C_4$ alkyl, —$CF_3$, and cyano. In an additional aspect, $R^1$ and $R^2$ are different and are selected from the group consisting of halogen, —$C_1$-$C_4$ alkyl, —$CF_3$, and cyano. In one aspect, $R^1$ and $R^2$ are each independently selected from the group consisting of halogen, —$C_1$-$C_4$ alkyl, —$CF_3$, and cyano. In another aspect, $R^1$ and $R^2$ are each independently selected from the group consisting of iodo, bromo, chloro, methyl, and cyano. In another aspect, $R^1$ and $R^2$ are each iodo. In one aspect, $R^1$ and $R^2$ are both alkyl. In one aspect, $R^1$ and $R^2$ are each methyl. In a further aspect, $R^1$ and $R^2$ are each chloro. In another aspect, $R^1$ and $R^2$ are each independently selected from the group consisting of iodo, bromo, chloro, and methyl. In an additional aspect, $R^1$ and $R^2$ are each halogen. In another aspect, $R^1$ and $R^2$ are not both halogen. In another aspect, $R^1$ and $R^2$ are each optionally substituted —$C_1$-$C_4$ alkyl. In a further aspect, $R^1$ and $R^2$ are each optionally substituted —S—$C_2$-$C_3$ alkyl. In another aspect, $R^1$ and $R^2$ are each optionally substituted —$C_2$-$C_4$ alkenyl. In a further aspect, $R^1$ and $R^2$ are each optionally substituted —$C_2$-$C_4$ alkynyl. In another aspect, $R^1$ and $R^2$ are each —$CF_3$. In a further aspect, $R^1$ and $R^2$ are each —$OCF_3$. In another aspect, $R^1$ and $R^2$ are each optionally substituted-O—$C_1$-$C_3$ alkyl. In a further aspect, $R^1$ and $R^2$ are each cyano.

In yet another aspect, $R^3$ and $R^4$ are each hydrogen. In another aspect, $R^3$ and $R^4$ are each halogen. In a further aspect, $R^3$ and $R^4$ are each —$CF_3$. In another aspect, $R^3$ and $R^4$ are each —$OCF_3$. In a further aspect, $R^3$ and $R^4$ are each cyano. In another aspect, $R^3$ and $R^4$ are each optionally substituted —$C_1$-$C_{12}$ alkyl. In a further aspect, $R^3$ and $R^4$ are each optionally substituted —$C_2$-$C_{12}$ alkenyl. In another aspect, $R^3$ and $R^4$ are each optionally substituted —$C_2$-$C_{12}$ alkynyl. In a further aspect, $R^3$ and $R^4$ are each optionally substituted —$(CR^a{}_2)_n$aryl. In another aspect, $R^3$ and $R^4$ are each optionally substituted —$(CR^a{}_2)_n$cycloalkyl. In a further aspect, $R^3$ and $R^4$ are each optionally substituted —$(CR^a{}_2)_n$heterocycloalkyl. In another aspect, $R^3$ and $R^4$ are each —$OR^d$. In another aspect, $R^3$ and $R^4$ are each —$SR^d$. In a further aspect, $R^3$ and $R^4$ are each —S(=O)$R^e$. In another aspect, $R^3$ and $R^4$ are each —S(=O)$_2R^e$. In a further aspect, $R^3$ and $R^4$ are each —S(=O)$_2NR^fR^g$. In another aspect, $R^3$ and $R^4$ are each —C(O)$NR^fR^g$. In a further aspect, $R^3$ and $R^4$ are each —C(O)$OR^h$. In another aspect, $R^3$ and $R^4$ are each —C(O)$R^e$. In a further aspect, $R^3$ and $R^4$ are each —N($R^b$)C(O)$R^e$. In another aspect, $R^3$ and $R^4$ are each —N($R^b$)C(O)$NR^fR^g$. In a further aspect, $R^3$ and $R^4$ are each —N($R^b$)S(=O)$_2R^e$. In another aspect, $R^3$ and $R^4$ are each —N($R^b$)S(=O)$_2NR^fR^g$. In a further aspect, $R^3$ and $R^4$ are each —$NR^fR^g$.

In one aspect, $R^4$ is selected from the group consisting of hydrogen, halogen, —$C_1$-$C_4$ alkyl, cyano and $CF_3$. In another aspect, $R^4$ is not hydrogen. In a further aspect, $R^4$ is selected from the group consisting of hydrogen and halogen. In another aspect, $R^4$ is selected from the group consisting of hydrogen and iodo. In a further aspect, $R^4$ is hydrogen.

In another aspect, each $R^d$ is optionally substituted —$C_1$-$C_2$ alkyl. In a further aspect, each $R^d$ is optionally substituted —$C_2$-$C_{12}$ alkenyl. In another aspect, each $R^d$ is optionally substituted —$C_2$-$C_{12}$ alkynyl. In a further aspect, each $R^d$ is optionally substituted —$(CR^b{}_2)_n$aryl. In another aspect, each $R^d$ is optionally substituted —$(CR^b{}_2)_n$cycloalkyl. In a further aspect, each $R^d$ is optionally substituted —$(CR^b{}_2)_n$heterocycloalkyl. In another aspect, each $R^d$ is —C(O)$NR^fR^g$.

In an additional aspect, $R^e$ is optionally substituted —$C_1$-$C_{12}$ alkyl. In another aspect, $R^e$ is optionally substituted —$C_2$-$C_{12}$ alkenyl. In a further aspect, $R^e$ is optionally substituted —$C_2$-$C_{12}$ alkynyl. In another aspect, $R^e$ is optionally substituted —$(CR^a{}_2)_n$aryl. In a further aspect, $R^e$ is optionally substituted —$(CR^a{}_2)$cycloalkyl. In another aspect, $R^e$ is optionally substituted —$(CR^a{}_2)_n$heterocycloalkyl.

In one aspect, $R^f$ and $R^g$ are each hydrogen. In an additional aspect, $R^f$ and $R^g$ are each optionally substituted —$C_1$-$C_{12}$ alkyl. In another aspect, $R^f$ and $R^g$ are each optionally substituted —$C_2$-$C_{12}$ alkenyl. In an additional aspect, $R^f$ and $R^g$ are each optionally substituted —$C_2$-$C_{12}$ alkynyl. In a further aspect, $R^f$ and $R^g$ are each optionally substituted —$(CR^b{}_2)_n$aryl. In an additional aspect, $R^f$ and $R^g$ are each optionally substituted —$(CR^b{}_2)_n$cycloalkyl. In another aspect, $R^f$ and $R^g$ are each optionally substituted —$(CR^b{}_2)_n$heterocycloalkyl.

In an additional aspect, $R^f$ and $R^g$ may together form an optionally substituted heterocyclic ring, which may contain a second heterogroup which is O. In another aspect, $R^f$ and $R^g$ may together form an optionally substituted heterocyclic ring, which may contain a second heterogroup which is $NR^c$. In another aspect, $R^f$ and $R^g$ may together form an optionally substituted heterocyclic ring, which may contain a second heterogroup which is S. In one aspect, $R^f$ and $R^g$ may together form an unsubstituted heterocyclic ring, which may contain a second heterogroup. In another aspect, the optionally substituted heterocyclic ring may be substituted with 1 substituent selected from the group consisting of optionally substituted —$C_1$-$C_4$ alkyl, —$OR^b$, oxo, cyano, —$CF_3$, optionally substituted phenyl, and —C(O)OR$^h$. In further aspect, the optionally substituted heterocyclic ring may be substituted with 2 substituents selected from the group consisting of optionally substituted —C$_1$-C$_4$ alkyl, —OR$^b$, oxo, cyano, —CF$_3$, optionally substituted phenyl, and —C(O)OR$^h$. In another aspect, the optionally substituted heterocyclic ring may be substituted with 3 substituents selected from the group consisting of optionally substituted —C$_1$-C$_4$ alkyl, —OR$^b$, oxo, cyano, —CF$_3$, optionally substituted phenyl, and —C(O)OR$^h$. In a further aspect, the optionally substituted heterocyclic ring may be substituted with 4 substituents selected from the group consisting of optionally substituted —C$_1$-C$_4$ alkyl, —OR$^b$, oxo, cyano, —CF$_3$, optionally substituted phenyl, and —C(O)OR$^h$.

In a further aspect, R$^h$ is optionally substituted —C$_1$-C$_{12}$ alkyl. In another aspect, R$^h$ is optionally substituted —C$_2$-C$_{12}$ alkenyl. In a further aspect, R$^h$ is optionally substituted —C$_2$-C$_{12}$ alkynyl. In another aspect, R$^h$ is optionally substituted —(CR$^b_2$)$_n$aryl. In a further aspect, R$^h$ is optionally substituted —(CR$^b_2$)$_n$cycloalkyl. In another aspect, R$^h$ is optionally substituted —(CR$^b_2$)$_n$heterocycloalkyl.

In one aspect, R$^5$ is —OH. In another aspect, R$^5$ is selected from the group consisting of —OH, —OC(O)R$^e$, —OC(O)OR$^h$, —F, and —NHC(O)R$^e$. In a further aspect, R$^5$ is selected from the group consisting of —OH and —OC(O)R$^e$. In an additional aspect, R$^5$ is optionally substituted —OC$_1$-C$_6$ alkyl. In another aspect, R$^5$ is —OC(O)R$^e$. In a further aspect, R$^5$ is —OC(O)OR$^h$. In another aspect, R$^5$ is —F. In another aspect, R$^5$ is —NHC(O)R$^e$. In a further aspect, R$^5$ is —NHS(=O)R$^e$. In another aspect, R$^5$ is —NHS(=O)$_2$R$^e$. In a further aspect, R$^5$ is —NHC(=S)NH(R$^h$). In another aspect, R$^5$ is —NHC(O)NH(R$^h$).

In one aspect, R$^3$ is selected from the group consisting of halogen, optionally substituted —C$_1$-C$_6$ alkyl, —CF$_3$, cyano, —C(O)NR$^f$R$^g$, optionally substituted (CR$^a_2$)$_n$aryl, —SO$_2$NR$^f$R$^g$, and —SO$_2$R$^e$. In another aspect, R$^3$ is isopropyl or 4-fluorobenzyl. In a further aspect, R$^3$ is alkyl of 1 to 4 carbons or cycloalkyl of 3 to 7 carbons. In yet another aspect, R$^3$ is selected from the group consisting of halogen, optionally substituted —C$_1$-C$_6$ alkyl, optionally substituted —CH$_2$aryl, optionally substituted —CH(OH)aryl, —C(O)-amido, —S(=O)$_2$-amido, wherein the amido group is selected from the group consisting of phenethylamino, piperidinyl, 4-methylpiperizinyl, morpholinyl, cyclohexylamino, anilinyl, and indolinyl, and —SO$_2$R$^e$ wherein R$^e$ is selected from the group consisting of phenyl, 4-chlorophenyl, 4-fluorophenyl, and 4-pyridyl. In another aspect, R$^3$ is iodo. In yet another aspect, R$^3$ is selected from the group consisting of iodo, bromo, optionally substituted —C$_1$-C$_6$ alkyl, optionally substituted —CH$_2$aryl, optionally substituted —CH(OH)aryl, —C(O)-amido, —S(=O)$_2$-amido, wherein the amido group is selected from the group consisting of phenethylamino, piperidinyl, 4-methypiperizinyl, morpholinyl, cyclohexylamino, anilinyl, and indolinyl, and —SO$_2$R$^e$ wherein R$^e$ is selected from the group consisting of phenyl, 4-chlorophenyl, 4-fluorophenyl, and 4-pyridyl. In one aspect, R$^3$ is —CH(OH)(4-fluorophenyl).

In one aspect, X is —P(O)YR$^{11}$Y'R$^{11}$.

In one aspect, X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][—OR$^{11}$], and —P(O)[—OCH(V)CH$_2$CH$_2$O—], wherein V is selected from the group consisting of optionally substituted aryl, aryl, heteroaryl, and optionally substituted heteroaryl. In another aspect, is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—OCH$_2$CH$_2$SC(O)Me]$_2$, —P(O)[—N(H)CR$^z_2$C(O)OR$^y$]$_2$, —P(O)[—N(H)CR$^z_2$C(O)OR$^y$][—OR$^{11}$] and —P(O)[—OCH(V)CH$_2$CH$_2$O—], wherein V is selected from the group consisting of optionally substituted aryl, aryl, heteroaryl, and optionally substituted heteroaryl. In another aspect, X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—Oalk-SC(O)R$^y$]$_2$, —P(O)[—N(H)CR$^z_2$C(O)OR$^y$]$_2$, —P(O)[—N(H)CR$^z_2$C(O)OR$^y$][—OR$^{11}$] and —P(O)[—OCH(V)CH$_2$CH$_2$O—], wherein V is selected from the group consisting of optionally substituted aryl, aryl, heteroaryl, and optionally substituted heteroaryl. In one aspect, X is selected from the group consisting of —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][—OR$^{11}$], —P(O)[—OCH(V)CH$_2$CH$_2$O—], —P(O)(OH)(OR$^{11}$), —P(O)(OR$^e$)(OR$^e$), —P(O)[—OCR$^z_2$OC(O)R$^y$](OR$^e$), —P(O)[—OCR$^z_2$OC(O)OR$^y$](OR$^e$), and —P(O)[—N(H)CR$^z_2$C(O)OR$^y$](OR$^{11}$), wherein V is selected from the group consisting of optionally substituted aryl, aryl, heteroaryl, and optionally substituted heteroaryl. In another aspect, X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][—OR$^{11}$], —P(O)[—OCH(V)CH$_2$CH$_2$O—], —P(O)(OH)(OR$^{11}$), —P(O)(OR$^e$)(OR$^e$), —P(O)[—OCR$^z_2$OC(O)R$^y$](OR$^e$), —P(O)[—OCR$^z_2$OC(O)OR$^y$](OR$^e$), —P(O)[—N(H)CR$^z_2$C(O)OR$^y$](OR$^e$), and —P(O)(OH)(NH$_2$), wherein V is selected from the group consisting of optionally substituted aryl, aryl, heteroaryl, and optionally substituted heteroaryl.

In one aspect, X is selected from the group consisting of —PO$_3$H$_2$, —P(O)[—OCH$_2$OC(O)-t-butyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$][3,4-methylenedioxyphenyl], —P(O)[—N(H)C(CH$_3$)$_2$C(O)OCH$_2$CH$_3$][3,4-methylenedioxyphenyl], —P(O)[—O—CH$_2$CH$_2$S—C(O)CH$_3$]$_2$, and —P(O)[—OCH(3-chlorophenyl)CH$_2$CH$_2$O—]. In a further aspect, X is selected from the group consisting of —PO$_3$H$_2$, —P(O)[—OCH$_2$OC(O)-t-butyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$][3,4-methylenedioxy-phenyl], —P(O)[—N(H)C(CH$_3$)$_2$C(O)OCH$_2$CH$_3$][3,4-methylenedioxyphenyl], and —P(O)[—OCH(3-chlorophenyl)CH$_2$CH$_2$O-]. In another aspect, X is —PO$_3$H$_2$. In yet another aspect, X is selected from the group consisting of —P(O)[—OCH$_2$OC(O)-t-butyl]$_2$ and —P(O)[—OCH$_2$OC(O)-i-propyl]$_2$. In another aspect, X is selected from the group consisting of —PO$_3$H$_2$, —P(O)[—OCH$_2$OC(O)-t-butyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$][3,4-methylenedioxyphenyl], —P(O)[—N(H)C(CH$_3$)$_2$C(O)OCH$_2$CH$_3$][3,4-methylenedioxyphenyl], —P(O)[—OCH(3-chlorophenyl)CH$_2$CH$_2$O—], —P(O)[—OCH(pyrid-4-yl)CH$_2$CH$_2$O—], —P(O)(OH)(OCH$_3$), —P(O)(OH)(OCH$_2$CH$_3$), —P(O)[—OCH$_2$OC(O)-t-butyl](OCH$_3$), —P(O)[—OCH$_2$OC(O)O-i-propyl](OCH$_3$), —P(O)[—OCH(CH$_3$)OC(O)-t-butyl](OCH$_3$), —P(O)[—OCH(CH$_3$)OC(O)O-i-propyl](OCH$_3$), —P(O)[—N(H)CH(CH$_3$)C(O)OCH$_2$CH$_3$](OCH$_3$), —P(O)[—N(H)C(CH$_3$)$_2$C(O)OCH$_2$CH$_3$](OCH$_3$), and —P(O)(OH)(NH$_2$).

In one aspect, X is selected from the group consisting of —P(O)[—OCH$_2$OC(O)O-ethyl]$_2$ and —P(O)[—OCH$_2$OC(O)O-i-propyl]$_2$. In another aspect, X is selected from the group consisting of —P(O)[—N(H)CH(CH$_3$)C(O)

OCH$_2$CH$_3$]$_2$ and —P(O)[—N(H)C(CH$_3$)$_2$C(O)OCH$_2$CH$_3$]$_2$. In a further aspect, X is —P(O)[—OCH$_2$CH$_2$SC(O)Me]$_2$. In another aspect, X is selected from the group consisting of —P(O)[—N(H)CH(CH$_3$)C(O)OCH$_2$CH$_3$] [3,4-methylenedioxyphenyl] and —P(O)[—N(H)C(CH$_3$)$_2$C(O)OCH$_2$CH$_3$] [3,4-methylenedioxyphenyl]. In a further aspect, X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][—OR$^{11}$] and —P(O)[—OCH(V)CH$_2$CH$_2$O—], wherein V is selected from the group consisting of optionally substituted aryl, aryl, heteroaryl, and optionally substituted heteroaryl. In another aspect, X is selected from the group consisting of —PO$_3$H$_2$, —P(O)[—OCH$_2$OC(O)-t-butyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$] [3,4-methylenedioxyphenyl], —P(O)[—N(H)C(CH$_3$)$_2$C(O)OCH$_2$CH$_3$] [3,4-methylenedioxyphenyl], and —P(O)[—OCH(3-chlorophenyl)CH$_2$CH$_2$O-].

In another aspect, X is —P(O)YR$^{11}$Y'R$^{11}$ wherein Y and Y' are each independently selected from —O— and —NR$^v$—; together R$^{11}$ and R$^{11}$ are the group:

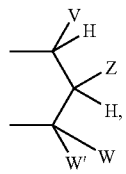

wherein

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkylthiocarbonyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus; or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus; or together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl; or or together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC( O)SR$^y$, —CHR$^z$OCO$_2$R$^y$, —OR$^z$, —SR$^z$, —CHR$^z$N$_3$, —CH$_2$aryl, —CH(aryl)OH, —CH(CH═CR$^z_2$)OH, —CH(C≡CR$^z$)OH, —R$^z$, —NR$^z_2$, —OCOR$^y$, —OCO$_2$R$^y$, —SCOR$^y$, —SCO$_2$R$^y$, —NHCOR$^z$, —NHCO$_2$R$^y$, —CH$_2$NHaryl, —(CH$_2$)$_q$—OR$^z$, and —(CH$_2$)$_q$—SR$^z$;

q is an integer 2 or 3;

with the provisos that:

a) V, Z, W, W' are not all —H; and b) when Z is —R$^z$, then at least one of V, W, and W' is not —H, alkyl, aralkyl, or heterocycloalkyl;

Each R$^z$ is selected from the group consisting of R$^y$ and —H;

Each R$^y$ is selected from the group consisting of alkyl, aryl, heterocycloalkyl, and aralkyl; and Each R$^v$ is selected from the group consisting of —H, lower alkyl, acyloxyalkyl, alkoxycarbonyloxyalkyl, and lower acyl.

In one aspect, V is optionally substituted aryl. In another aspect, V is selected from the group consisting of 3-chlorophenyl, 4-chlorophenyl, 3-bromophenyl, 3-fluorophenyl, pyrid-4-yl, pyrid-3-yl and 3,5-dichlorophenyl.

In one aspect, the relative stereochemistry between the V-group substituent and T on the dioxaphosphonane ring is cis. In another aspect, the cis dioxaphosphonane ring has R stereochemistry at the carbon where V is attached. In another aspect, the cis dioxaphosphonane ring has S stereochemistry at the carbon where V is attached.

In one aspect R$^{11}$ is not hydrogen.

In one aspect, X is —P(O)YR$^{11}$Y'', wherein Y'' is —C$_1$-C$_6$ alkyl. In one aspect, Y'' is selected from the group consisting of methyl, ethyl, propyl, isopropyl, butyl, isobutyl, and tert-butyl. In another aspect, X is PO$_2$H$_2$, P(O)(OH)(R$^z$), —P(O)[—OCR$^z_2$OC(O)R$^y$](R$^z$), —P(O)[—OCR$^z_2$OC(O)OR$^y$](R$^z$), —P (O)[—N(H)CR$^z_2$C(O)OR$^y$](R$^z$), —P(O)[—N(H)CR$^z_2$C(O)OR$^y$][—OR$^{11}$], or —P(O)(OH)[—N(H)CR$^z_2$C(O)OR$^y$]. In a further aspect, X is —P(O)(OH)(CH$_3$), —P(O)(OH)(CH$_2$CH$_3$), —P(O)(OH)(isopropyl), or —P(O)(OH)(t-butyl).

In a further aspect when G is —O—, T is —CH$_2$—, R$^1$ and R$^2$ are each bromo, R$^3$ is iso-propyl, and R$^5$ is —OH, then R$^4$ is not hydrogen. In another aspect, when G is —O—, T is —(CH$_2$)$_{0-4}$—, R$^1$ and R$^2$ are independently selected from the group consisting of halogen, alkyl of 1 to 3 carbons, and cycloalkyl of 3 to 5 carbons, R$^3$ is alkyl of 1 to 4 carbons or cycloalkyl of 3 to 7 carbons, and R$^5$ is —OH, then R$^4$ is not hydrogen; and wherein when G is —O—, R$^5$ is selected from the group consisting of NHC(O)R$^e$, —NHS(═O)$_{1-2}$R$^e$, —NHC(═S)NH(R$^h$), and —NHC(O)NH(R$^h$), T is selected from the group consisting of —(CH$_2$)$_m$—, —CH═CH—, —O(CH$_2$)$_{1-2}$—, and —NH(CH$_2$)$_{1-2}$—, then R$^4$ is not hydrogen. In a further aspect for the compounds of Formula I, G is selected from the group consisting of —O— and —CH$_2$—; T is selected from the group consisting of —(CR$^a_2$)$_n$, —O(CR$^b_2$)(CR$^a_2$)$_p$—, —N(R$^c$)(CR$^b_2$)(CR$^a_2$)$_p$—, —S(CR$^b_2$)(CR$^a_2$)$_p$—, —NR$^b$(CO)—, and —CH$_2$CH(NR$^c$R$^b$)—; R$^1$ and R$^2$ are each independently selected from the group consisting of halogen, —C$_1$-C$_4$ alkyl, —CF$_3$, and cyano; R$^4$ is selected from the group consisting of hydrogen, halogen, —C$_1$-C$_4$ alkyl, cyano and CF$_3$; R$^5$ is selected from the group consisting of —OH, —OC(O)R$^e$, —OC(O)OR$^h$, —F and —NHC(O)R$^e$; R$^3$ is selected from the group consisting of halogen, optionally substituted —C$_1$-C$_6$ alkyl, —CF$_3$, cyano, —C(O)NR$^f$R$^g$, optionally substituted —(CR$^a_2$)$_n$aryl, —SO$_2$NR$^f$R$^g$, and —SO$_2$R$^e$; and X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—Oalk-SC(O)R$^y$]$_2$, —P(O)[—N(H)CR$^z_2$C(O)OR$^y$]$_2$, —P(O)[—N(H)CR$^z_2$C(O)OR$^y$][—OR$^{11}$] and —P(O)[—OCH(V)CH$_2$CH$_2$O—], wherein V is selected from the group consisting of optionally substituted aryl, aryl, heteroaryl, and optionally substituted heteroaryl.

In another aspect, G is selected from the group consisting of —O— and —CH$_2$—; T is selected from the group consisting of —(CR$^a_2$)$_n$-, —O(CR$^b_2$)(CR$^a_2$)$_p$—, —N(R$^c$)(CR$^b_2$)(CR$^a_2$)$_p$—, —S(CR$^b_2$)(CR$^a_2$)$_p$—, —NR$^b$(CO)—, and —CH$_2$CH(NR$^c$R$^b$)—; R$^1$ and R$^2$ are each independently selected from the group consisting of halogen, —C$_1$-C$_4$ alkyl, —CF$_3$, and cyano; R$^4$ is selected from the group consisting of hydrogen, halogen, —C$_1$-C$_4$ alkyl, cyano and CF$_3$; R$^5$ is selected from the group consisting of —OH, —OC(O)R$^e$, —OC(O)OR$^b$, —F and —NHC(O)R$^e$; R$^3$ is selected from the group consisting of halogen, optionally substituted —C$_1$-C$_6$ alkyl, —CF$_3$, cyano, —C(O)NR$^f$R$^g$, optionally substituted —(CR$^a_2$)$_n$aryl, —SO$_2$NR$^f$R$^g$, and —SO$_2$R$^e$; and X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][—OR$^{11}$] and —P(O)[—OCH(V)CH$_2$CH$_2$O—], wherein V is selected from the group consisting of optionally substituted aryl, aryl, heteroaryl, and optionally substituted heteroaryl.

In an additional aspect, G is selected from the group consisting of —O— and —CH$_2$—; T is —CH$_2$CH(NH$_2$)—; R$^1$ and R$^2$ are each independently selected from the group consisting of iodo, bromo, chloro, methyl, and cyano; R$^4$ is hydrogen; R$^5$ is selected from the group consisting of —OH and —OC(O)R$^e$; R$^3$ is selected from the group consisting of halogen, optionally substituted —C$_1$-C$_6$ alkyl, optionally substituted —CH$_2$aryl, optionally substituted —CH(OH)aryl, —C(O)-amido wherein the amido group is selected from the group consisting of phenethylamino, piperidinyl, 4-methypiperizinyl, morpholinyl, cyclohexylamino, anilinyl, and indolinyl, —S(=O)$_2$-amido wherein the amido group is selected from the group consisting of phenethylamino, piperidinyl, 4-methypiperizinyl, morpholinyl, cyclohexylamino, anilinyl, and indolinyl, and —SO$_2$R wherein R is selected from the group consisting of phenyl, 4-chlorophenyl, 4-fluorophenyl, and 4-pyridyl, and X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][OR$^e$] and —P(O)[—OCR$^z$(aryl)CH$_2$CH$_2$O—].

In another aspect, when G is —O—, T is —CH$_2$—, R$^1$ and R$^2$ are bromo, R$^3$ is iso-propyl, R$^5$ is —OH, and X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][OR$^e$] and —P(O)[—OCR$^z$(aryl)CH$_2$CH$_2$O—], then R$^4$ is not hydrogen.

In one aspect for the compounds of Formula I, G is —O—; T is —CH$_2$CH(NH$_2$)—; R$^1$ and R$^2$ are each iodo; R$^4$ is selected from the group consisting of hydrogen and iodo; R$^5$ is —OH; and R$^3$ is iodo; and X is selected from the group consisting of —PO$_3$H$_2$, —P(O)[—OCR$_{z2}$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][OR$^e$] and —P(O)[—OCR$^z$(aryl)CH$_2$CH$_2$O—].

In another aspect G is —O—; T is —CH$_2$CH(NH$_2$)—; R$^1$ and R$^2$ are each iodo; R$^4$ is selected from the group consisting of hydrogen and iodo; R$^5$ is —OH; R$^3$ is iodo; and X is selected from the group consisting of —PO$_3$H$_2$, —P(O)[—OCH$_2$OC(O)-t-butyl]$_2$, —P(O)[—OCH$_2$OC(O)O-i-Propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$] [3,4-methylenedioxyphenyl], —P(O)[—N(H)C(CH$_3$)$_2$C(O)OCH$_2$CH$_3$] [3,4-methylenedioxyphenyl], and —P(O)[—OCH(3-chlorophenyl)CH$_2$CH$_2$O-].

In a further aspect for compounds of Formula I, G is selected from the group consisting of —O— and —CH$_2$—; T is —N(H)C(O)—; R$^1$ and R$^2$ are each independently selected from the group consisting of iodo, bromo, chloro, methyl, and cyano; R$^4$ is selected from the group consisting of hydrogen, iodo, 4-chlorophenyl, and cyclohexyl; R$^5$ is selected from the group consisting of —OH and —OC(O)R$^e$; R$^3$ is selected from the group consisting of hydrogen, iodo, bromo, optionally substituted —C$_1$-C$_6$ alkyl, optionally substituted —CH$_2$aryl, optionally substituted —CH(OH)aryl, —C(O)-amido wherein the amido group is selected from the group consisting of phenethylamino, piperidinyl, 4-methypiperizinyl, morpholinyl, cyclohexylamino, anilinyl, and indolinyl, —S(=O)$_2$-amido wherein the amido group is selected from the group consisting of phenethylamino, piperidinyl, 4-methypiperizinyl, morpholinyl, cyclohexylamino, anilinyl, and indolinyl, and —SO$_2$R wherein R is selected from the group consisting of phenyl, 4-chlorophenyl, 4-fluorophenyl, and 4-pyridyl; and X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—N(H) CR$^z_2$C(O)OR$^y$]$_2$, —P(O)[—N(H)CR$^z_2$C(O)OR$^y$][OR$^e$] and —P(O)[—OCR$^z$(aryl)CH$_2$CH$_2$O—].

An additional aspect is when G is —O—; T is —N(H)C(O)—; R$^1$ and R$^2$ are methyl; R$^4$ is hydrogen; R$^5$ is —OH; R$^3$ is —CH(OH)(4-fluorophenyl); and X is selected from the group consisting of —PO$_3$H$_2$, —P(O)[—OCR$^z_2$OC(O)R$^y$]$_2$, —P(O) [—OC$^z_2$OC(O)OR$^y$]$_2$, —P(O)[—N(H)CR$^z_2$C(O)OR$^y$]$_2$, —P(O)[—N(H)CR$^z_2$C(O)OR$^y$][OR$^e$] and —P(O)[—OCR$^z$(aryl)CH$_2$CH$_2$O—].

In an additional aspect, G is —O—; T is —N(H)C(O)—; R$^1$ and R$^2$ are each methyl; R$^4$ is hydrogen; R$^5$ is —OH; R$^3$ is —CH(OH)(4-fluorophenyl); and X is selected from the group consisting of —PO$_3$H$_2$, —P(O)[—OCH$_2$OC(O)-t-butyl]$_2$, —P(O)[—OCH$_2$OC(O)O-i-Propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$] [3,4-methylenedioxyphenyl], —P(O)[—N(H)C(CH$_3$)$_2$C(O)OCH$_2$CH$_3$] [3,4-methylenedioxyphenyl], and —P(O)[—OCH(3-chlorophenyl)CH$_2$CH$_2$O-].

In a further aspect G is selected from the group consisting of —O— and —CH$_2$—; T is —OCH$_2$—; R$^1$ and R$^2$ are each independently selected from the group consisting of iodo, bromo, chloro, methyl, and cyano; R$^4$ is selected from the group consisting of hydrogen, iodo, 4-chlorophenyl, and cyclohexyl; R$^5$ is selected from the group consisting of —OH and —OC(O)R$^e$; R$^3$ is selected from the group consisting of hydrogen, iodo, bromo, optionally substituted lower alkyl, optionally substituted —CH$_2$aryl, optionally substituted —CH(OH)aryl, —C(O)-amido wherein the amido group is selected from the group consisting of phenethylamino, piperidinyl, 4-methypiperizinyl, morpholinyl, cyclohexylamino, anilinyl, and indolinyl, —S(=O)$_2$-amido wherein the amido group is selected from the group consisting of phenethylamino, piperidinyl, 4-methypiperizinyl, morpholinyl, cyclohexylamino, anilinyl, and indolinyl, and —SO$_2$R wherein R is selected from the group consisting of phenyl, 4-chlorophenyl, 4-fluorophenyl, and 4-pyridyl; and X is selected from the group consisting of —PO$_3$H$_2$, —P(O)[—OCR$^z_2$OC(O)R$^y$]$_2$, —P(O)[—OCR$^z_2$OC(O)OR$^y$]$_2$, P(O)[—N(H)CR$^z_2$C(O)OR$^y$]$_2$, —P(O)[—N(H)CR$^z_2$C(O)OR$^y$][OR$^e$] and —P(O)[—OCR$^z$(aryl)CH$_2$CH$_2$O—].

In another aspect G is —$CH_2$—; T is —$OCH_2$—; $R^1$ and $R^2$ are each methyl; $R^4$ is hydrogen; $R^5$ is —OH; $R^3$ is iso-propyl; and X is selected from the group consisting of —$PO_3H_2$, —P(O)[—$OCR^z{}_2OC(O)R^y$]$_2$, —P(O)[—$OCR^z{}_2OC(O)OR^y$]$_2$, —P(O)[—$N(H)CR^z{}_2C(O)OR^y$]$_2$, —P(O)[—N(H)$CR^z{}_2C(O)OR^y$][$OR^e$] and —P(O)[—$OCR^z$(aryl)$CH_2CH_2O$—].

In another aspect, G is —$CH_2$—; T is —$OCH_2$—; $R^1$ and $R^2$ are each methyl; $R^4$ is hydrogen; $R^5$ is —OH; $R^3$ is iso-propyl; and X is selected from the group consisting of —$PO_3H_2$, —P(O)[—$OCH_2OC(O)$-t-butyl]$_2$, —P(O)[—$OCH_2OC(O)O$-i-propyl]$_2$, —P(O)[—$N(H)CH(CH_3)C(O)OCH_2CH_3$]$_2$, —P(O)[—$N(H)C(CH_3)_2C(O)OCH_2CH_3$]$_2$, —P(O)[—$N(H)CH(CH_3)C(O)OCH_2CH_3$] [3,4-methylenedioxyphenyl], —P(O)[—$N(H)C(CH_3)_2C(O)OCH_2CH_3$] [3,4-methylenedioxyphenyl], and —P(O)[—OCH(3-chlorophenyl)$CH_2CH_2O$—].

In a further aspect, G is selected from the group consisting of —O— and —$CH_2$—; T is —$CH_2$—; $R^1$ and $R^2$ are each independently selected from the group consisting of iodo, bromo, chloro, methyl, and cyano; $R^4$ is selected from the group consisting of hydrogen, iodo, 4-chlorophenyl, and cyclohexyl; $R^5$ is selected from the group consisting of —OH and —OC(O)$R^e$; $R^3$ is selected from the group consisting of hydrogen, iodo, bromo, optionally substituted lower alkyl, optionally substituted —$CH_2$aryl, optionally substituted —CH(OH)aryl, —C(O)-amido wherein the amido group is selected from the group consisting of phenethylamino, piperidinyl, 4-methypiperizinyl, morpholinyl, cyclohexylamino, anilinyl, and indolinyl, —S(=O)$_2$-amido wherein the amido group is selected from the group consisting of phenethylamino, piperidinyl, 4-methypiperizinyl, morpholinyl, cyclohexylamino, anilinyl, and indolinyl, and —$SO_2R$ wherein R is selected from the group consisting of phenyl, 4-chlorophenyl, 4-fluorophenyl, and 4-pyridyl; and X is selected from the group consisting of —$PO_3H_2$, —P(O)[—$OCR^z{}_2OC(O)R^y$]$_2$, —P(O) [—$OCR^z{}_2OC(O)OR^y$]$_2$, —P(O)[—$N(H)CR^z{}_2C(O)OR^y$]$_2$, —P(O)[—$N(H)CR^z{}_2C(O)OR^y$][$OR^e$] and —P(O)[—$OCR^z$(aryl)$CH_2CH_2O$—].

In additional aspects, when G is —O—, T is —$CH_2$—, $R^1$ and $R^2$ are each bromo, $R^3$ is iso-propyl, $R^5$ is —OH; and X is selected from the group consisting of —$PO_3H_2$, —P(O)[—$OCR^z{}_2OC(O)R^y$]$_2$, —P(O)[—$OCR^z{}_2OC(O)OR^y$]$_2$, —P(O)[—$N(H)CR^z{}_2C(O)OR^y$]$_2$, —P(O)[—$N(H)CR^z{}_2C(O)OR^y$][$OR^e$] and —P(O)[—$OCR^z$(aryl)$CH_2CH_2O$—], then $R^4$ is not hydrogen.

In another aspect, G is —O—; T is —$CH_2$—; $R^1$ and $R^2$ are each chloro; $R^4$ is hydrogen; $R^5$ is —OH; $R^3$ is i-propyl; and X is selected from the group consisting of —$PO_3H_2$, —P(O) [—$OCR^z{}_2OC(O)R^y$]$_2$, —P(O)[—$OCR^z{}_2OC(O)OR^y$]$_2$, —P(O)[—$N(H)CR^z{}_2C(O)OR^y$]$_2$, —P(O)[—$N(H)CR^z{}_2C(O)OR^y$][$OR^e$] and —P(O)[—$OCR^z$(aryl)$CH_2CH_2O$—].

In another aspect, G is —O—; T is —$CH_2$—; $R^1$ and $R^2$ are each chloro; $R^4$ is hydrogen; $R^5$ is —OH; $R^3$ is i-propyl; and X is selected from the group consisting of —$PO_3H_2$, —P(O)[—$OCH_2OC(O)$-t-butyl]$_2$, —P(O)[—$OCH_2OC(O)O$-i-propyl]$_2$, —P(O)[—$N(H)CH(CH_3)C(O)OCH_2CH_3$]$_2$, —P(O)[—$N(H)C(CH_3)_2C(O)OCH_2CH_3$]$_2$, —P(O)[—$N(H)CH(CH_3)C(O)OCH_2CH_3$] [3,4-methylenedioxyphenyl], —P(O)[—$N(H)C(CH_3)_2C(O)OCH_2CH_3$] [3,4-methylenedioxyphenyl], and —P(O)[—OCH(3-chlorophenyl)$CH_2CH_2O$—].

In additional aspects for compounds of Formula I, G is selected from the group consisting of —O— and —$CH_2$—; T is —$CH_2CH_2$—; $R^1$ and $R^2$ are each independently selected from the group consisting of iodo, bromo, chloro, methyl, and cyano; $R^4$ is selected from the group consisting of hydrogen, iodo, 4-chlorophenyl, and cyclohexyl; $R^5$ is selected from the group consisting of —OH and —OC(O)$R^e$; $R^3$ is selected from the group consisting of hydrogen, iodo, bromo, optionally substituted lower alkyl, optionally substituted —$CH_2$aryl, optionally substituted —CH(OH)aryl, —C(O)-amido wherein the amido group is selected from the group consisting of phenethylamino, piperidinyl, 4-methypiperizinyl, morpholinyl, cyclohexylamino, anilinyl, and indolinyl, —S(=O)$_2$-amido wherein the amido group is selected from the group consisting of phenethylamino, piperidinyl, 4-methypiperizinyl, morpholinyl, cyclohexylamino, anilinyl, and indolinyl, and —$SO_2R$ wherein R is selected from the group consisting of phenyl, 4-chlorophenyl, 4-fluorophenyl, and 4-pyridyl; and X is selected from the group consisting of —$PO_3H_2$, —P(O)[—$OCR^z{}_2OC(O)R^y$]$_2$, —P(O) [—$OCR^z{}_2OC(O)OR^y$]$_2$, —P(O)[—$N(H)CR^z{}_2C(O)OR^y$]$_2$, —P(O)[—$N(H)CR^z{}_2C(O)OR^y$][$OR^e$] and —P(O)[—$OCR^z$(aryl)$CH_2CH_2O$—].

In a further aspect, G is —O—; T is —$CH_2CH_2$—; $R^1$ and $R^2$ are each chloro; $R^4$ is hydrogen; $R^5$ is —OH; $R^3$ is iso-propyl; and X is selected from the group consisting of —$PO_3H_2$, —P(O)[—$OCR^z{}_2OC(O)R^y$]$_2$, —P(O) [—$OCR^z{}_2OC(O)OR^y$]$_2$, —P(O)[—$N(H)CR^z{}_2C(O)OR^y$]$_2$, —P(O)[—$N(H)CR^z{}_2C(O)OR^y$][$OR^e$] and —P(O)[—$OCR^z$(aryl)$CH_2CH_2O$—].

In another aspect, G is —O—; T is —$CH_2CH_2$—; $R^1$ and $R^2$ are each chloro; $R^4$ is hydrogen; $R^5$ is —OH; $R^3$ is iso-propyl; and X is selected from the group consisting of —$PO_3H_2$, —P(O)[—$OCH_2OC(O)$-t-butyl]$_2$, —P(O) [—$OCH_2OC(O)O$-i-propyl]$_2$, —P(O)[—$N(H)CH(CH_3)C(O)OCH_2CH_3$]$_2$, —P(O)[—$N(H)C(CH_3)_2C(O)OCH_2CH_3$]$_2$, —P(O)[—$N(H)CH(CH_3)C(O)OCH_2CH_3$] [3,4-methylenedioxyphenyl], —P(O)[—$N(H)C(CH_3)_2C(O)OCH_2CH_3$] [3,4-methylenedioxyphenyl], and —P(O)[—OCH(3-chlorophenyl)$CH_2CH_2O$—].

In an additional aspect, G is —$CH_2$—; T is —$OCH_2$—; $R^1$ and $R^2$ are each methyl; $R^4$ is hydrogen; $R^5$ is —OH; $R^3$ is iso-propyl; and X is —$PO_3H_2$. In a further aspect, G is —$CH_2$—; T is —$OCH_2$—; $R^1$ and $R^2$ are each methyl; $R^4$ is hydrogen; $R^5$ is —OH; $R^3$ is iso-propyl; and X is selected from the group consisting of —P(O)[—$OCH_2OC(O)$-t-butyl]$_2$ and —P(O)[—$OCH_2OC(O)$-i-propyl]$_2$. In another aspect, G is —$CH_2$—; T is —$OCH_2$—; $R^1$ and $R^2$ are each methyl; $R^4$ is hydrogen; $R^5$ is —OH; $R^3$ is iso-propyl; and X is selected from the group consisting of —P(O)[—$OCH_2OC(O)O$-ethyl]$_2$ and —P(O)[—$OCH_2OC(O)O$-i-propyl]$_2$. In an additional aspect, G is —$CH_2$—; T is —$OCH_2$—; $R^1$ and $R^2$ are each methyl; $R^4$ is hydrogen; $R^5$ is —OH; $R^3$ is iso-propyl; and X is selected from the group consisting of —P(O)[—$N(H)CH(CH_3)C(O)OCH_2CH_3$]$_2$ and —P(O)[—$N(H)C(CH_3)_2C(O)OCH_2CH_3$]$_2$. In additional aspects, G is —$CH_2$—; T is —$OCH_2$—; $R^1$ and $R^2$ are methyl; $R^4$ is hydrogen; $R^5$ is —OH; $R^3$ is iso-propyl; and X is —P(O)[—$OCH_2CH_2SC(O)$Me]$_2$, or X is —P(O)[—$N(H)C(CH_3)C(O)OCH_2CH_3$][3,4-methylenedioxyphenyl], or X is —P(O)[—$N(H)C(CH_3)_2C(O)OCH_2CH_3$][3,4-methylenedioxyphenyl].

In another aspect, G is —O—, T is —$(CH_2)_{0-4}$—, $R^1$ and $R^2$ are independently selected from the group consisting of hydrogen, halogen, alkyl of 1 to 3 carbons, and cycloalkyl of 3 to 5 carbons, $R^3$ is alkyl of 1 to 4 carbons or cycloalkyl of 3 to 7 carbons, and $R^5$ is —OH, then $R^4$ is not hydrogen; and wherein when G is —O—, $R^5$ is selected from the group consisting of NHC(O)$R^e$, —NHS(=O)$_{1-2}R^e$, —NHC(S)NH($R^h$), and —NHC(O)NH($R^h$), T is selected from the group consisting of —$(CH_2)_n$—, —CH=CH—, —$O(CH_2)_{1-2}$—, and —$NH(CH_2)_{1-2}$—, then $R^4$ is not hydrogen.

In an additional aspect, G is —CH$_2$—; T is —OCH$_2$—; R$^1$ and R$^2$ are each methyl; R$^4$ is hydrogen; R$^5$ is —OH; R$^3$ is iso-propyl; and X is —P(O)YR$^{11}$Y'R$^{11}$; wherein Y and Y' are each independently selected from —O— and —NR$^v$—; together R$^{11}$ and R$^{11}$ are the group:

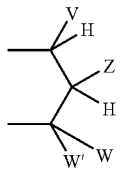

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl; or together V and Z are connected via an additional 3-5 atoms to form a cyclic group containing 5-7 atoms, wherein 0-1 atoms are heteroatoms and the remaining atoms are carbon, substituted with hydroxy, acyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus; or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus; or together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl; or together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH=CR$^z{}_2$)OH, —CH(C≡CR$^z{}_2$)OH, —R$^z$, —NR$^z{}_2$, —OCOR$^y$, —OCO$_2$R$^y$, —SCOR$^y$, —SCO$_2$R$^y$, —NHCOR$^z$, —NHCO$_2$R$^y$, —CH$_2$NHaryl, —(CH$_2$)$_q$—OR$^z$, and —(CH$_2$)$_q$—SR$^z$;

q is an integer 2 or 3;

with the provisos that:

a) V, Z, W, W' are not all —H; and b) when Z is —R$^z$, then at least one of V, W, and W' is not —H, alkyl, aralkyl, or heterocycloalkyl;

Each R$^z$ is selected from the group consisting of R$^y$ and —H;

Each R$^y$ is selected from the group consisting of alkyl, aryl, heterocycloalkyl, and aralkyl;

Each R$^x$ is independently selected from the group consisting of —H, and alkyl, or together R$^x$ and R$^x$ form a cycloalkyl group;

Each R$^v$ is selected from the group consisting of —H, lower alkyl, acyloxyalkyl, alkoxycarbonyloxyalkyl, and lower acyl. In a further aspect V is aryl. In an additional aspect Z is hydrogen, W is hydrogen, and W' is hydrogen. In an additional aspect, V is 3-chlorophenyl, 4-chlorophenyl, 3-bromophenyl, 3-fluorophenyl, pyrid-4-yl, pyrid-3-yl or 3,5-dichlorophenyl. In a further aspect the relative stereochemistry between the substituents on the dioxaphosphonane ring is cis.

In another aspect, each R$^a$ is independently selected from the group consisting of hydrogen, optionally substituted —C$_1$-C$_2$ alkyl, halogen, —OH, optionally substituted —O—C$_1$-C$_2$ alkyl, —OCF$_3$, optionally substituted —S—C$_1$-C$_2$ alkyl, —NR$^b$R$^c$, optionally substituted —C$_2$ alkenyl, and optionally substituted —C$_2$ alkynyl;

Each R$^b$ is independently selected from the group consisting of hydrogen, optionally substituted —C$_1$-C$_2$ alkyl;

Each R$^c$ is independently selected from the group consisting of hydrogen, optionally substituted —C$_1$-C$_4$ alkyl, and optionally substituted —C(O)—C$_1$-C$_2$ alkyl, —C(O)H;

Each R$^d$ is selected from the group consisting of optionally substituted —C$_1$-C$_6$ alkyl, optionally substituted —C$_2$-C$_6$ alkenyl, optionally substituted —C$_2$-C$_6$ alkynyl, optionally substituted —(CR$^b{}_2$)$_n$phenyl, optionally substituted —(CR$^b{}_2$)$_n$monocyclic-heteroaryl, optionally substituted —(CR$^b{}_2$)$_n$—C$_3$-C$_6$-cycloalkyl, optionally substituted —(CR$^b{}_2$)$_n$—C$_4$-C$_5$-heterocycloalkyl, and —C(O)NR$^f$R$^g$;

Each R$^e$ is selected from the group consisting of optionally substituted —C$_1$-C$_6$ alkyl, optionally substituted —C$_2$-C$_6$ alkenyl, optionally substituted —C$_2$-C$_6$ alkynyl, optionally substituted —(CR$^b{}_2$)$_n$phenyl, optionally substituted —(CR$^b{}_2$)$_n$monocyclic-heteroaryl, optionally substituted —(CR$^b{}_2$)$_n$—C$_3$-C$_6$-cycloalkyl, optionally substituted —(CR$^b{}_2$)$_n$—C$_4$-C$_5$-heterocycloalkyl;

R$^f$ and R$^g$ are each independently selected from the group consisting of hydrogen, optionally substituted —C$_1$-C$_6$ alkyl, optionally substituted —C$_2$-C$_6$ alkenyl, optionally substituted —C$_2$-C$_6$ alkynyl, optionally substituted —(CR$^b{}_2$)$_n$phenyl, optionally substituted —(CR$^b{}_2$)$_n$monocyclic-heteroaryl, optionally substituted —(CR$^b{}_2$)$_n$—C$_3$-C$_6$-cycloalkyl, optionally substituted —(CR$^b{}_2$)$_n$—C$_4$-C$_5$-heterocycloalkyl, or R$^f$ and R$^g$ may together form an optionally substituted heterocyclic ring, which may contain a second heterogroup selected from the group of O, NR$^b$, and S, wherein said optionally substituted heterocyclic ring may be substituted with 0-2 substituents selected from the group consisting of optionally substituted —C$_1$-C$_2$ alkyl, —OR$^b$, oxo, cyano, —CF$_3$, optionally substituted phenyl, and —C(O)OR$^h$;

Each R$^h$ is optionally substituted —C$_1$-C$_{16}$ alkyl, optionally substituted —C$_2$-C$_{16}$ alkenyl, optionally substituted —C$_2$-C$_{16}$ alkynyl, optionally substituted —(CR$^b{}_2$)$_n$phenyl, optionally substituted —(CR$^b{}_2$)$_n$monocyclic-heteroaryl, optionally substituted —(CR$^b{}_2$)$_n$—C$_3$-C$_6$-cycloalkyl, optionally substituted —(CR$^b{}_2$)$_n$—C$_4$-C$_5$-heterocycloalkyl.

In a further aspect, each R$^a$ is independently selected from the group consisting of hydrogen, methyl, fluoro, chloro, —OH, —O—CH$_3$, —OCF$_3$, —SCH$_3$, —NHCH$_3$, —N(CH$_3$)$_2$;

Each R$^b$ is independently selected from the group consisting of hydrogen, and methyl;

Each R$^c$ is independently selected from the group consisting of hydrogen, methyl, —C(O)CH$_3$, —C(O)H;

Each R$^d$ is selected from the group consisting of optionally substituted —C$_1$-C$_4$ alkyl, optionally substituted —C$_2$-C$_4$ alkenyl, optionally substituted —C$_2$-C$_4$ alkynyl, optionally substituted —(CH$_2$)$_n$phenyl, optionally substituted —(CH$_2$)$_n$ monocyclic-heteroaryl, optionally substituted —(CH$_2$)$_n$— C$_3$-C$_6$-cycloalkyl, optionally substituted —(CH$_2$)$_n$—C$_4$-C$_5$-heterocycloalkyl, and —C(O)NR$^f$R$^g$;

Each R$^e$ is selected from the group consisting of optionally substituted —C$_1$-C$_4$ alkyl, optionally substituted —C$_2$-C$_4$ alkenyl, optionally substituted —C$_2$-C$_4$ alkynyl, optionally substituted —(CH$_2$)$_n$phenyl, optionally substituted —(CH$_2$)$_n$ monocyclic-heteroaryl, optionally substituted —(CH$_2$)$_n$— C$_3$-C$_6$-cycloalkyl, optionally substituted —(CH$_2$)$_n$—C$_4$-C$_5$-heterocycloalkyl;

R$^f$ and R$^g$ are each independently selected from the group consisting of hydrogen, optionally substituted —C$_1$-C$_4$ alkyl, optionally substituted —C$_2$-C$_4$ alkenyl, optionally substituted —C$_2$-C$_4$ alkynyl, optionally substituted —(CH$_2$)nphenyl, optionally substituted —(CH$_2$)$_n$monocyclic-heteroaryl, optionally substituted —(CH$_2$)$_n$—C$_3$-C$_6$-cycloalkyl, optionally substituted —(CH$_2$)$_n$—C$_4$-C$_5$-heterocycloalkyl, or R$^f$ and R$^g$ may together form an optionally substituted heterocyclic ring, which may contain a second heterogroup selected from the group of O, NR$^b$, and S, wherein said optionally substituted heterocyclic ring may be substituted with 0-2 substituents selected from the group consisting of optionally substituted methyl, —OR$^b$, oxo, cyano, —CF$_3$, optionally substituted phenyl, and —C(O)OR$^h$;

Each R$^h$ is optionally substituted —C$_1$-C$_4$ alkyl, optionally substituted —C$_2$-C$_4$ alkenyl, optionally substituted —C$_2$-C$_4$ alkynyl, optionally substituted —(CH$_2$)$_n$phenyl, optionally substituted —(CH$_2$)nmonocyclic-heteroaryl, optionally substituted —(CH$_2$)$_n$—C$_3$-C$_6$-cycloalkyl, optionally substituted —(CH$_2$)$_n$—C$_4$-C$_5$-heterocycloalkyl.

Each of the individual species of compounds of Formula I which can be generated by making all of the above permutations may be specifically set forth as for inclusion or may be specifically excluded from the present invention.

In one aspect, the invention relates to a compound of Formula II:

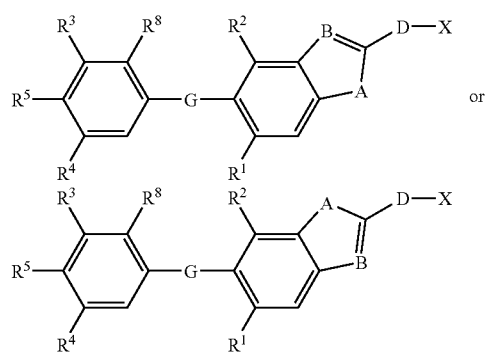

wherein:

A is selected from the group consisting of —NR$^i$—, —O—, and —S—;

B is selected from the group consisting of CR$^b$—, and —N—;

R$^i$ is selected from the group consisting of hydrogen, —C(O)C$_1$-C$_4$ alkyl, and —C$_1$-C$_4$ alkyl;

R$^b$ is selected from the group consisting of hydrogen and optionally substituted —C$_1$-C$_4$ alkyl;

G is selected from the group consisting of —O—, —S—, —Se—, —S($=$O)—, —S($=$O)$_2$—, —CH$_2$—, —CF$_2$—, —CHF—, —C(O)—, —CH(OH)—, —NH—, and —N(C$_1$-C$_4$ alkyl)-, or CH$_2$ linked to any of the preceding groups;

D is selected from the group consisting of a bond, —(CR$^a$$_2$)—, and —C(O)—;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

R$^1$ and R$^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano;

R$^8$ is selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a$$_2$)aryl, C(O)aryl, C(O)alkyl and cyano;

R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a$$_2$)$_m$aryl, optionally substituted —(CR$^a$$_2$)$_m$cycloalkyl, optionally substituted —(CR$^a$$_2$)$_m$heterocycloalkyl, —OR$^d$, —SR$^d$, —S($=$O)R$^e$, —S($=$O)$_2$R$^e$, —S($=$O)$_2$NR$^f$R$^g$, —C(O)NR$^f$R$^g$, —C(O)OR$^h$, —C(O)R$^e$, —N(R$^b$)C(O)R$^e$, —N(R$^b$)C(O)NR$^f$R$^g$, —N(R$^b$)S($=$O)$_2$R$^e$, —N(R$^b$)S($=$O)$_2$NR$^f$R$^g$, and —NR$^f$R$^g$;

Each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b$$_2$) aryl, optionally substituted —(CR$^b$$_2$)$_n$ cycloalkyl, optionally substituted —(CR$^b$$_2$)$_n$heterocycloalkyl, and —C(O)NR$^f$R$^g$;

Each R$^e$ is selected from the group consisting of optionally substituted —C$_1$-C$_1$ alkyl, optionally substituted —C$_2$-C$_{12}$ alkenyl, optionally substituted —C$_2$-C$_{12}$ alkynyl, optionally substituted —(CR$^a$$_2$)$_n$aryl, optionally substituted —(CR$^a$$_2$)$_n$ cycloalkyl, and optionally substituted —(CR$^a$$_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b$$_2$)$_n$aryl, optionally substituted —(CR$^b$$_2$)$_n$cycloalkyl, and optionally substituted —(CR$^b$$_2$)$_n$heterocycloalkyl, or R$^f$ and R$^g$ may together form an optionally substituted heterocyclic ring, which may contain a second heterogroup selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b$$_2$)$_n$aryl, optionally substituted —(CR$^b$$_2$)$_n$ cycloalkyl, and optionally substituted —(CR$^b$$_2$)$_n$heterocycloalkyl; or $R^3$ and $R^8$ are taken together along with the carbon atoms to which they are attached to form an optionally substituted ring of 5 to 6 atoms with 0-2 unsaturations, not including the unsaturation on the ring to which $R^3$ and $R^8$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom; or $R^8$ and G are taken together along with the carbon atoms to which they are attached to form an optionally substituted ring comprising —CH=CH—CH=, —N=CH—CH=, —CH=N—CH= or —CH=CH—N=;

$R^5$ is selected from the group consisting of —OH, optionally substituted —$OC_1$-$C_6$ alkyl, —OC(O)$R^e$, —OC(O)O$R^h$, —F, —NHC(O)$R^e$, —NHS(=O)$R^e$, —NHS(=O)$_2R^e$, —NHC(=S)NH($R^h$), and —NHC(O)NH($R^h$); or $R^3$ and $R^5$ are taken together along with the carbons they are attached to form an optionally substituted ring of 5 to 6 atoms with 0-2 unsaturations, not including the unsaturation on the ring to which $R^3$ and $R^5$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom;

X is P(O)Y$R^{11}$Y'$R^{11}$;

Y and Y' are each independently selected from the group consisting of —O—, and —$NR^v$—;

when Y and Y' are both —O—, $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —C($R^z$)$_2$OC(O)$NR^z_2$, —$NR^z$—C(O)—$R^y$, —C($R^z$)$_2$—OC(O)$R^y$, —C($R^z$)$_2$—O—C(O)O$R^y$, —C($R^z$)$_2$OC(O)S$R^y$, -alkyl-S—C(O)$R^y$, -alkyl-S-S-alkylhydroxy, and -alkyl-S-S-S-alkylhydroxy;

when Y and Y' are both —$NR^v$—, then $R^{11}$ attached to —$NR^v$— is independently selected from the group consisting of —H, —[C($R^2$)$_2$]$_q$—COO$R^y$, —C($R^x$)$_2$COO$R^y$, —[C($R^z$)$_2$]$_q$—C(O)S$R^y$, and -cycloalkylene-COO$R^y$;

when Y is —O— and Y' is $NR^v$, then $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —C($R^z$)$_2$OC(O)$NR^z_2$, —$NR^z$—C(O)—$R^y$, —C($R^z$)$_2$—OC(O)$R^y$, —C($R^z$)$_2$—O—C(O)O$R^y$, —C($R^z$)$_2$OC(O)S$R^y$, -alkyl-S—C(O)$R^y$, -alkyl-S-S-alkylhydroxy, and -alkyl-S-S-S-alkylhydroxy; and $R^{11}$ attached to —$NR^v$— is independently selected from the group consisting of —H, —[C($R^z$)$_2$]$_q$—COO$R^y$, —C($R^x$)$_2$COO$R^y$, —[C($R^z$)$_2$]$_q$—C(O)S$R^y$, and -cycloalkylene-COO$R^y$;

but if both $R^{11}$ are alkyl, at least one is higher alkyl;

and both $R^{11}$ are not —H;

or when Y and Y' are independently selected from —O— and —$NR^v$—, then $R^{11}$ and $R^{11}$ together form a cyclic group comprising -alkyl-S-S-alkyl-, or together $R^{11}$ and $R^{11}$ are the group:

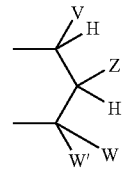

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or or together V and Z are connected via an additional 3-5 atoms to form a cyclic group, wherein 0-1 atoms are heteroatoms and the remaining atoms are carbon or carbon substituted by hydrogen, and said cyclic group is fused to an aryl group at the beta and gamma position to the Y attached to the phosphorus;

or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl;

or together W and W' are connected via an additional 2-5 atoms to form a cyclic group, wherein $O_2$ atoms are heteroatoms and the remaining atoms are carbon or carbon substituted by hydrogen, and V must be aryl, substituted aryl, heteroaryl, or substituted heteroaryl;

Z is selected from the group consisting of —CHR$^z$OH, —CHR$^z$OC(O)$R^y$, CHR$^z$OC(S)$R^y$, —CHR$^z$OC(S)O$R^y$, —CHR$^z$OC(O)S$R^y$, —CHR$^z$OCO$_2R^y$, —O$R^z$, —S$R^z$, —CHR$^z$N$_3$, —$CH_2$aryl, —CH(aryl)OH, —CH(CH=CR$^z_2$)OH, —CH(C≡CR$^z$)OH, —$R^z$, —$NR^z_2$, —OCOR$^y$, —OCO$_2R^y$, —SCOR$^y$, —SCO$_2R^y$, —NHCOR$^z$, —NHCO$_2R^y$, —$CH_2$NHaryl, —(CH$_2$)$_q$—O$R^z$, and —(CH$_2$)$_q$—S$R^z$;

q is an integer 2 or 3;

Each $R^z$ is selected from the group consisting of $R^y$ and —H;

Each $R^y$ is selected from the group consisting of alkyl, aryl, heterocycloalkyl, and aralkyl;

Each $R^x$ is independently selected from the group consisting of —H, and alkyl, or together $R^x$ and $R^x$ form a cycloalkyl group;

Each $R^v$ is selected from the group consisting of —H, lower alkyl, acyloxyalkyl, alkoxycarbonyloxyalkyl, and lower acyl;

with the provisos that:

a) V, Z, W, W' are not all —H; and b) when Z is —$R^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In another aspect, the invention relates to a compound of Formula II:

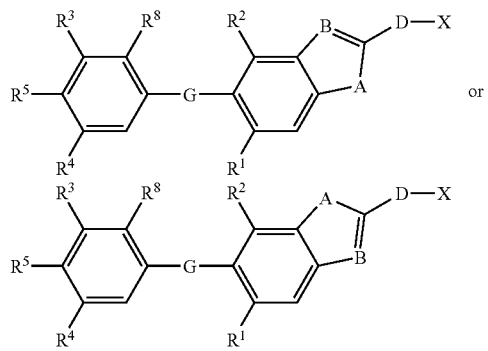

wherein:

A is selected from the group consisting of —NR$^i$—, —O—, and —S—;

B is selected from the group consisting of CR$^b$—, and —N—;

R$^i$ is selected from the group consisting of hydrogen, —C(O)C$_1$-C$_4$ alkyl, and —C$_1$-C$_4$ alkyl;

R$^b$ is selected from the group consisting of hydrogen and optionally substituted —C$_1$-C$_4$ alkyl;

G is selected from the group consisting of —O—, —S—, —Se—, —S(=O)—, —S(=O)$_2$—, —CH$_2$—, —CF$_2$—, —CHF—, —C(O)—, —CH(OH)—, —NH—, and —N(C$_1$-C$_4$ alkyl)-, or CH$_2$ linked to any of the preceding groups;

D is selected from the group consisting of a bond, —(CR$^a_2$)—, and —C(O)—;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

R$^1$ and R$^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano;

R$^8$ is selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a_2$)aryl, C(O)aryl, C(O)alkyl and cyano;

R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)aryl, optionally substituted —(CR$^a_2$)$_n$cycloalkyl, optionally substituted —(CR$^a_2$)$_n$heterocycloalkyl, —OR$^d$, —SR$^d$, —S(=O)R$^e$, —S(=O)$_2$R$^e$, —S(=O)$_2$NR$^f$R$^g$, —C(O)NR$^f$R$^g$, —C(O)OR$^h$, —C(O)R$^e$, —N(R$^b$)C(O)R$^e$, —N(R$^b$)C(O)NR$^f$R$^g$, —N(R$^b$)S(=O)$_2$R$^e$, —N(R$^b$)S(=O)$_2$NR$^f$R$^g$, and —NR$^f$R$^g$;

Each R$^d$ is selected from the group consisting of optionally substituted —C$_1$-C$_{12}$ alky, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, optionally substituted —(CR$^b_2$)$_n$heterocycloalkyl, and —C(O)NR$^f$R$^g$;

Each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_n$aryl, optionally substituted —(CR$^a_2$)$_n$cycloalkyl, and optionally substituted —(CR$^a_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl, or R$^f$ and R$^g$ may together form an optionally substituted heterocyclic ring, which may contain a second heterogroup selected from the group consisting of O, NR$^e$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl; or R$^3$ and R$^8$ are taken together along with the carbon atoms to which they are attached to form an optionally substituted ring of 5 to 6 atoms with 0-2 unsaturations, not including the unsaturation on the ring to which R$^3$ and R$^8$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom; or R$^8$ and G are taken together along with the carbon atoms to which they are attached to form an optionally substituted ring comprising —CH=CH—CH=, —N=CH—CH=, —CH=N—CH= or —CH=CH—N=;

R$^5$ is selected from the group consisting of —OH, optionally substituted —OC$_1$-C$_6$ alkyl, —OC(O)R$^e$, —OC(O)OR$^h$, —F, —NHC(O)R$^e$, —NHS(=O)R$^e$, —NHS(=O)$_2$R$^e$, —NHC(=S)NH(R$^h$), and —NHC(O)NH(R$^h$); or R$^3$ and R$^5$ are taken together along with the carbons they are attached to form an optionally substituted ring of 5 to 6 atoms with 0-2 unsaturations, not including the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

X is P(O)YR$^{11}$Y'R$^{11}$;

Y and Y' are each independently selected from the group consisting of —O—, and —NR$^v$—;

when Y and Y' are both —O—, R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR$^z$$_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy;

when Y and Y' are both —NR$^v$—, then R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

when Y is —O— and Y' is NR$^v$, then R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR$^z$$_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy; and R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

or when Y and Y' are independently selected from —O— and —NR$^v$—, then R$^{11}$ and R$^{11}$ together form a cyclic group comprising -alkyl-S-S-alkyl- to form a cyclic group, or together R$^{11}$ and R$^{11}$ are the group:

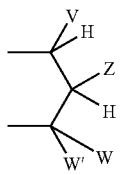

wherein:
V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or or together V and Z are connected via an additional 3-5 atoms to form a cyclic group, wherein 0-1 atoms are heteroatoms and the remaining atoms are carbon or carbon substituted by hydrogen, and said cyclic group is fused to an aryl group at the beta and gamma position to the Y attached to the phosphorus;

or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon or carbon substituted by hydrogen, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH=CR$^z$$_2$)OH, —CH(C≡CR$^z$)OH, —R$^z$, —NR$^z$$_2$, —OCOR$^y$, —OCO$_2$R$^y$, —SCOR$^y$, —SCO$_2$R$^y$, —NHCOR$^z$, —NHCO$_2$R$^y$, —CH$_2$NHaryl, —(CH$_2$)$_q$—OR$^z$, and —(CH$_2$)$_q$—SR$^z$;

q is an integer 2 or 3;
Each R$^z$ is selected from the group consisting of R$^y$ and —H;
Each R$^y$ is selected from the group consisting of alkyl, aryl, heterocycloalkyl, and aralkyl;
Each R$^x$ is independently selected from the group consisting of —H, and alkyl, or together R$^x$ and R$^x$ form a cycloalkyl group;
Each R$^v$ is selected from the group consisting of —H, lower alkyl, acyloxyalkyl, alkoxycarbonyloxyalkyl, and lower acyl;
with the provisos that:
a) V, Z, W, W' are not all —H; and
b) when Z is —R$^z$, then at least one of V, W, and W' is not —H, alkyl, aralkyl, or heterocycloalkyl;
and pharmaceutically acceptable salts and prodrugs thereof and pharmaceutically acceptable salts of said prodrugs.

In another aspect, G is selected from the group consisting of —O— and —CH$_2$—. In one aspect, G is —O—. In another aspect, G is —S—. In another aspect, G is —S(=O)—. In a further aspect, G is —S(=O)$_2$—. In another aspect, G is —CH$_2$—. In a further aspect, G is —CF$_2$—. In another aspect, G is —CHF—. In a further aspect, G is —C(O)—. In another aspect, G is —CH(OH)—. In another aspect, G is —NH—. In a further aspect, G is —N(C$_1$-C$_4$ alkyl)—.

In a further aspect, D is selected from the group consisting of a bond and —CH$_2$—. In another aspect D is a bond. In a further aspect D is —(CR$^a$$_2$)—. In another aspect D is —C(O)—.

In yet another aspect A is selected from —NH—, —NMe—, —O—, and —S—. In one aspect, A is —NR$^i$—. In another aspect, A is –O—. In a further aspect, A is —S—.

In a further aspect, B is selected from —CH—, CMe—, and —N—. In another aspect, B is —CR$^b$—. In a further aspect, B is —N—.

In one aspect, R$^i$ is hydrogen, —C(O)C$_1$-C$_4$ alkyl. In another aspect, R$^i$ is —C$_1$-C$_4$ alkyl. In a further aspect, R$^i$ is —C$_1$-C$_4$-aryl.

In one aspect, R$^b$ is hydrogen. In another aspect, R$^b$ is optionally substituted —C$_1$-C$_4$ alkyl.

In another aspect, R$^a$ is hydrogen with the proviso that when one R$^a$ is attached to C through an O, S, or N atom, then the other R$^a$ attached to the same C is a hydrogen, or attached via a carbon atom. In a further aspect, R$^a$ is optionally substituted —C$_1$-C$_4$ alkyl with the proviso that when one R$^a$ is attached to C through an O, S, or N atom, then the other R$^a$ attached to the same C is a hydrogen, or attached via a carbon atom. In another aspect, R$^a$ is halogen with the proviso that when one R$^a$ is attached to C through an O, S, or N atom, then the other R$^a$ attached to the same C is a hydrogen, or attached via a carbon atom. In a further aspect, R$^a$ is —OH with the proviso that when one R$^a$ is attached to C through an O, S, or N atom, then the other R$^a$ attached to the same C is a hydrogen, or attached via a carbon atom. In another aspect, Ra is optionally substituted —O—$C_1$-$C_4$ alkyl with the proviso that when one $R^a$ is attached to C through an O, S, or N atom, then the other $R^a$ attached to the same C is a hydrogen, or attached via a carbon atom. In another aspect, $R^a$ is —$OCF_3$ with the proviso that when one $R^a$ is attached to C through an O, S, or N atom, then the other $R^a$ attached to the same C is a hydrogen, or attached via a carbon atom. In a further aspect, $R^a$ is optionally substituted —S—$C_1$-$C_4$ alkyl with the proviso that when one $R^a$ is attached to C through an O, S, or N atom, then the other $R^a$ attached to the same C is a hydrogen, or attached via a carbon atom. In another aspect, $R^a$ is —$NR^b R^c$ with the proviso that when one $R^a$ is attached to C through an O, S, or N atom, then the other $R^a$ attached to the same C is a hydrogen, or attached via a carbon atom. In further aspect, $R^a$ is optionally substituted —$C_2$-$C_4$ alkenyl with the proviso that when one $R^a$ is attached to C through an O, S, or N atom, then the other $R^a$ attached to the same C is a hydrogen, or attached via a carbon atom. In another aspect, $R^a$ is optionally substituted —$C_2$-$C_4$ alkynyl with the proviso that when one $R^a$ is attached to C through an O, S, or N atom, then the other $R^a$ attached to the same C is a hydrogen, or attached via a carbon atom.

In one aspect, $R^1$ and $R^2$ are the same and are selected from the group consisting of halogen, —$C_1$-$C_4$ alkyl, —$CF_3$, and cyano. In another aspect, $R^1$ and $R^2$ are different and are selected from the group consisting of halogen, —$C_1$-$C_4$ alkyl, —$CF_3$, and cyano. In an additional aspect, $R^1$ and $R^2$ are each halogen. In another aspect, $R^1$ and $R^2$ are not both halogen. In another aspect, $R^1$ and $R^2$ are each optionally substituted —$C_1$-$C_4$ alkyl. In a further aspect, $R^1$ and $R^2$ are each optionally substituted —S—$C_1$-$C_3$ alkyl. In another aspect, $R^1$ and $R^2$ are each optionally substituted —$C_2$-$C_4$ alkenyl. In a further aspect, $R^1$ and $R^2$ are each optionally substituted —$C_2$-$C_4$ alkynyl. In another aspect, $R^1$ and $R^2$ are each —$CF_3$. In a further aspect, $R^1$ and $R^2$ are each —$OCF_3$. In another aspect, $R^1$ and $R^2$ are each optionally substituted-O—$C_1$-$C_3$ alkyl. In a further aspect, $R^1$ and $R^2$ are each cyano.

In yet another aspect, $R^3$ and $R^4$ are each hydrogen. In another aspect, $R^3$ and $R^4$ are each halogen. In a further aspect, $R^3$ and $R^4$ are each —$CF_3$. In another aspect, $R^3$ and $R^4$ are each —$OCF_3$. In a further aspect, $R^3$ and $R^4$ are each cyano. In another aspect, $R^3$ and $R^4$ are each optionally substituted —$C_1$-$C_{12}$ alkyl. In a further aspect, $R^3$ and $R^4$ are each optionally substituted —$C_2$-$C_{12}$ alkenyl. In another aspect, $R^3$ and $R^4$ are each optionally substituted —$C_2$-$C_{12}$ alkynyl. In a further aspect, $R^3$ and $R^4$ are each optionally substituted —$(CR^a_2)_m$aryl. In another aspect, $R^3$ and $R^4$ are each optionally substituted —$(CR^a_2)_m$cycloalkyl. In a further aspect, $R^3$ and $R^4$ are each optionally substituted —$(CR^a_2)_m$heterocycloalkyl. In another aspect, $R^3$ and $R^4$ are each —$OR^d$. In another aspect, $R^3$ and $R^4$ are each —$SR^d$. In a further aspect, $R^3$ and $R^4$ are each —$S(=O)R^e$. In another aspect, $R^3$ and $R^4$ are each —$S(=O)_2R^e$. In a further aspect, $R^3$ and $R^4$ are each —$S(=O)_2NR^f R^g$. In another aspect, $R^3$ and $R^4$ are each —$C(O)NR^f R^g$. In a further aspect, $R^3$ and $R^4$ are each —$C(O)OR^h$. In another aspect, $R^3$ and $R^4$ are each —$C(O)R^e$. In a further aspect, $R^3$ and $R^4$ are each —$N(R^e)C(O)R^e$. In another aspect, $R^3$ and $R^4$ are each —$N(R^b)C(O)NR^f R^g$. In a further aspect, $R^3$ and $R^4$ are each —$N(O)S(=O)_2R^e$. In another aspect, $R^3$ and $R^4$ are each —$N(R^b)S(=O)_2NR^f R^g$. In a further aspect, $R^3$ and $R^4$ are each —$NR^f R^g$. In an additional aspect, $R^4$ is selected from the group consisting of hydrogen, halogen, —$C_1$-$C_4$ alkyl, cyano and $CF_3$. In an additional aspect, $R^4$ is hydrogen. In an additional aspect, $R^3$ is selected from the group consisting of halogen, optionally substituted —$C_1$-$C_6$ alkyl, —$CF_3$, cyano, —$C(O)NR^f R^g$, optionally substituted —$(CR^a_2)_n$aryl, —$SO_2NR^f R^g$, and —$SO_2R^e$. In an additional aspect, $R^3$ is isopropyl or 4-fluorobenzyl.

In another aspect, each $R^d$ is optionally substituted —$C_1$-$C_{12}$ alkyl. In a further aspect, each $R^d$ is optionally substituted —$C_2$-$C_{12}$ alkenyl. In another aspect, each $R^d$ is optionally substituted —$C_2$-$C_{12}$ alkynyl. In a further aspect, each $R^d$ is optionally substituted —$(C_1$-$C_2)_n$aryl. In another aspect, each $R^d$ is optionally substituted —$(CR^b_2)_n$cycloalkyl. In a further aspect, each $R^d$ is optionally substituted —$(CR^b_2)_n$heterocycloalkyl. In another aspect, each $R^d$ is —$C(O)N^f R^g$.

In an additional aspect, $R^e$ is optionally substituted —$C_1$-$C_{12}$ alkyl. In another aspect, $R^e$ is optionally substituted —$C_2$-$C_{12}$ alkenyl. In a further aspect, $R^e$ is optionally substituted —$C_2$-$C_{12}$ alkynyl. In another aspect, $R^e$ is optionally substituted —$(CR^a_2)_n$aryl. In a further aspect, $R^e$ is optionally substituted —$(CR^a_2)_n$cycloalkyl. In another aspect, $R^e$ is optionally substituted —$(CR^a_2)_n$heterocycloalkyl.

In one aspect, $R^f$ and $R^g$ are each hydrogen. In an additional aspect, $R^f$ and $R^g$ are each optionally substituted —$C_1$-$C_{12}$ alkyl. In another aspect, $R^f$ and $R^g$ are each optionally substituted —$C_2$-$C_{12}$ alkenyl. In an additional aspect, $R^f$ and $R^g$ are each optionally substituted —$C_2$-$C_{12}$ alkynyl. In a further aspect, $R^f$ and $R^g$ are each optionally substituted —$(CR^b_2)_n$aryl. In an additional aspect, $R^f$ and $R^g$ are each optionally substituted —$(CR^b_2)_n$cycloalkyl. In another aspect, $R^f$ and $R^g$ are each optionally substituted —$(CR^b_2)_n$heterocycloalkyl.

In an additional aspect, $R^f$ and $R^g$ may together form an optionally substituted heterocyclic ring, which may contain a second heterogroup which is O. In another aspect, $R^f$ and $R^g$ may together form an optionally substituted heterocyclic ring, which may contain a second heterogroup which is $NR^c$. In another aspect, $R^f$ and $R^g$ may together form an optionally substituted heterocyclic ring, which may contain a second heterogroup which is S. In one aspect, $R^f$ and $R^g$ may together form an unsubstituted heterocyclic ring, which may contain a second heterogroup. In another aspect, the optionally substituted heterocyclic ring may be substituted with 1 substituent selected from the group consisting of optionally substituted —$C_1$-$C_4$ alkyl, —$OR^b$, oxo, cyano, —$CF_3$, optionally substituted phenyl, and —$C(O)OR^h$. In further aspect, the optionally substituted heterocyclic ring may be substituted with 2 substituents selected from the group consisting of optionally substituted —$C_1$-$C_4$ alkyl, —$OR^b$, oxo, cyano, —$CF_3$, optionally substituted phenyl, and —$C(O)OR^h$. In another aspect, the optionally substituted heterocyclic ring may be substituted with 3 substituents selected from the group consisting of optionally substituted —$C_1$-$C_4$ alkyl, —$OR^b$, oxo, cyano, —$CF_3$, optionally substituted phenyl, and —$C(O)OR^e$. In a further aspect, the optionally substituted heterocyclic ring may be substituted with 4 substituents selected from the group consisting of optionally substituted —$C_1$-$C_4$ alkyl, —$OR^b$, oxo, cyano, —$CF_3$, optionally substituted phenyl, and —$C(O)OR^h$.

In a further aspect, $R^h$ is optionally substituted —$C_1$-$C_{12}$ alkyl. In another aspect, $R^h$ is optionally substituted —$C_2$-$C_{12}$ alkenyl. In a further aspect, $R^h$ is optionally substituted —$C_2$-$C_{12}$ alkynyl. In another aspect, $R^h$ is optionally substituted —$(CR^b_2)_n$aryl. In a further aspect, $R^h$ is optionally substituted —$(CR^b_2)_n$cycloalkyl. In another aspect, $R^h$ is optionally substituted —$(CR^b_2)_n$heterocycloalkyl.

In another aspect, $R^5$ is selected from the group consisting of —OH, —$OC(O)R^e$, —$OC(O)OR^h$, —F, and —$NHC(O)R^e$. In another aspect, $R^5$ is —OH. In an additional aspect, $R^5$ is optionally substituted —$OC_1$-$C_6$ alkyl. In another aspect, $R^5$ is —$OC(O)R^e$. In a further aspect, $R^5$ is —$OC(O)OR^h$. In another aspect, $R^5$ is —F. In another aspect, $R^5$ is —$NHC(O)R^e$. In a further aspect, $R^5$ is —$NHS(=O)R^e$. In another aspect, R⁵ is —NHS(=O)₂Rᵉ. In a further aspect, R⁵ is —NHC(=S)NH(Rʰ). In another aspect, R⁵ is —NHC(O)NH(Rʰ).

In a further aspect, X is selected from the group consisting of —PO₃H₂, —P(O)[—OCR$^z$₂OC(O)R$^y$]₂, —P(O)[—OCR$^z$₂OC(O)OR$^y$]₂, —P(O)[—N(H) CR$^z$₂C(O)OR$^y$]₂, —P(O)[—N(H)CR$^z$₂C(O)OR$^y$][—OR¹¹], and —P(O)[—OCH(V)CH₂CH₂O—], wherein V is selected from the group consisting of optionally substituted aryl, aryl, heteroaryl, and optionally substituted heteroaryl. In another aspect, X is selected from the group consisting of —P(O)[—OCR$^z$₂OC(O)R$^y$]₂, —P(O)[—OCR$^z$₂OC(O)OR$^y$]₂, —P(O)[—N(H)CR$^z$₂C(O)OR$^y$]₂, —P(O)[—N(H)CR$^z$₂C(O)OR$^y$][—ORᵉ], —P(O)[—OC H(V)CH₂CH₂O—], —P(O)(OH)(OR¹¹), —P(O)(ORᵉ)(ORᵉ), —P(O)[—OCR$^z$₂OC(O)R$^y$](ORᵉ)—P(O)[—OCR$^z$₂OC(O)OR$^y$](ORᵉ), and —P(O)[—N(H)CR$^z$₂C(O)OR$^y$](ORᵉ), wherein V is selected from the group consisting of optionally substituted aryl, aryl, heteroaryl, and optionally substituted heteroaryl. In a further aspect, X is selected from the group consisting of —PO₃H₂, —P(O)[—OCR$^z$₂OC(O)R$^y$]₂, —P(O)[—OCR$^z$₂OC(O)OR$^y$]₂, —P(O)[—N(H)CR$^z$₂C(O)OR$^y$]₂, —P(O)[—N(H)CR$^z$₂C(O)OR$^y$][—OR¹¹], —P(O)[—OCH(V)CH₂CH₂O—], —P(O)(OH)(ORᵉ), —P(O)(ORᵉ)(ORᵉ), —P(O)[—OCR$^z$₂OC(O)R$^y$](ORᵉ), —P(O)[—OCR$^z$₂OC(O)OR$^y$](ORᵉ), and —P(O)[—N(H)CR$^z$₂C(O)OR$^y$](ORᵉ), wherein V is selected from the group consisting of optionally substituted aryl, aryl, heteroaryl, and optionally substituted heteroaryl. In a further aspect, wherein X is selected from the group consisting of —PO₃H₂, —P(O)[—OCH₂OC(O)-t-butyl]₂, —P(O)[—OCH₂OC(O)O-i-propyl]₂, —P(O)[—N(H)CH(CH₃)C(O)OCH₂CH₃]₂, —P(O)[—N(H)C(CH₃)₂C(O)OCH₂CH₃]₂, —P(O)[—N(H)CH(CH₃)C(O)OCH₂CH₃] [3,4-methylenedioxyphenyl], —P(O)[—N(H)C(CH₃)₂C(O)OCH₂CH₃] [3,4-methylenedioxyphenyl], —P(O)[—OCH(3-chlorophenyl)CH₂CH₂O-], —P(O)[—OCH(pyrid-4-yl)CH₂CH₂O—], —P(O)(OH)(OCH₃), —P(O)(OH)(OCH₂CH₃), —P(O)[—OCH₂OC(O)-t-butyl](OCH₃), —P(O)[—OCH₂OC(O)O-i-propyl](OCH₃), —P(O)[—OCH(CH₃)OC(O)-t-butyl] (OCH₃), —P(O)[—OCH(CH₃)OC(O)O-i-propyl](OCH₃), —P(O)[—N(H)CH(CH₃)C(O)OCH₂CH₃](OCH₃), —P(O)[—N(H)C(CH₃)₂C(O)OCH₂CH₃](OCH₃), and —P(O)(OH)(NH₂).

In one aspect, G is selected from the group consisting of —O— and —CH₂—; D is selected from the group consisting of a bond and —CH₂—; A is selected from the group consisting of —NH—, —NMe—, —O—, and —S—; B is selected from the group consisting of —CH—, —CMe—, and —N—; R¹ and R² are each independently selected from the group consisting of halogen, —C₁-C₄ alkyl, —CF₃, and cyano; R⁴ is selected from the group consisting of hydrogen, halogen, —C₁-C₄ alkyl, cyano and CF₃; R⁵ is selected from the group consisting of —OH, —OC(O)Rᵉ, —OC(O)ORʰ, —F, and —NHC(O)Rᵉ; R³ is selected from the group consisting of halogen, optionally substituted —C₁-C₆ alkyl, —CF₃, cyano, —C(O)NR$^f$R$^g$, optionally substituted —(CR$^a$₂)$_n$aryl, —SO₂NR$^f$R$^g$, and —SO₂Rᵉ; and X is selected from the group consisting of —PO₃H₂, —P(O)[—OCR$^z$₂OC(O)R$^y$]₂, —P(O)[—OCR$^z$₂OC(O)OR$^y$]₂, —P(O)[—N(H)CR$^z$₂C(O)OR$^y$]₂, —P(O)[—N(H)CR$^z$₂C(O)OR$^y$][—OR¹¹] and —P(O)[—OCH(V)CH₂CH₂O—], wherein V is selected from the group consisting of optionally substituted aryl, aryl, heteroaryl, and optionally substituted heteroaryl. In another aspect, G is selected from the group consisting of —O— and —CH₂; D is selected from the group consisting of a bond and —CH₂—; A is selected from the group consisting of —NH—, —NMe—, —O—, and —S—; B is selected from the group consisting of —CH—, —Cme— and —N—; R¹ and R² are each independently selected from the group consisting of iodo, bromo, chloro, methyl, and cyano; R⁴ is selected from the group consisting of hydrogen and halogen; R⁵ is selected from the group consisting of —OH and —OC(O)Rᵉ; and R³ is selected from the group consisting of halogen, optionally substituted —C₁-C₆ alkyl, optionally substituted —CH₂aryl, optionally substituted —CH(OH)aryl, —C(O)-amido, —S(=O)₂-amido, wherein the amido group is selected from the group consisting of phenethylamino, piperidinyl, 4-methylpiperizinyl, morpholinyl, cyclohexylamino, anilinyl, and indolinyl, and —SO₂Rᵉ wherein Rᵉ is selected from the group consisting of phenyl, 4-chlorophenyl, 4-fluorophenyl, and 4-pyridyl. In yet another aspect, G is —O—; D is a bond; A is selected from the group consisting of —NH— and —NMe—; B is selected from the group consisting of —CH— and —CMe—; R¹ and R² are each bromo; R⁴ is selected from the group consisting of hydrogen and iodo; R⁵ is —OH; and R³ is isopropyl.

In another aspect, G is —O—; D is a bond; A is selected from the group consisting of —NH— and —NMe—; B is selected from the group consisting of —CH— and —CMe—; R¹ and R² are each bromo; R⁴ is selected from the group consisting of hydrogen and iodo; R⁵ is —OH; R³ is isopropyl, and X is selected from the group consisting of —PO₃H₂, —P(O)[—OCH₂OC(O)-t-butyl]₂, —P(O)[—OCH₂OC(O)O-i-propyl]₂, —P(O)[—N(H)CH(CH₃)C(O)OCH₂CH₃]₂, —P(O)[—N(H)C(CH₃)₂C(O)OCH₂CH₃]₂, —P(O)[—N(H)CH(CH₃)C(O)OCH₂CH₃] [3,4-methylenedioxyphenyl], —P(O)[—N(H)C(CH₃)₂C(O)OCH₂CH₃] [3,4-methylenedioxyphenyl], and —P(O)[—OCH(3-chlorophenyl)CH₂CH₂O—].

In a further aspect, G is —O—; D is a bond; A is —O—; B is selected from the group consisting of —CH— and —Cme—; R¹ and R² are each bromo; R⁴ is selected from the group consisting of hydrogen and iodo; R⁵ is —OH; and R³ is isopropyl. In another aspect, G is —O—; D is a bond; A is —O—; B is selected from the group consisting of —CH— and —CMe—; R¹ and R² are each bromo; R⁴ is selected from the group consisting of hydrogen and iodo; R⁵ is —OH; R³ is isopropyl, X is selected from the group consisting of —PO₃H₂, —P(O)[—OCH₂OC(O)-t-butyl]₂, —P(O)[—OCH₂OC(O)O-i-propyl]₂, —P(O)[—N(H)CH(CH₃)C(O)OCH₂CH₃]₂, —P(O)[—N(H)C(CH₃)₂C(O)OCH₂CH₃]₂, —P(O)[—N(H)CH(CH₃)C(O)OCH₂CH₃] [3,4-methylenedioxyphenyl], —P(O)[—N(H)C(CH₃)₂C(O)OCH₂CH₃] [3,4-methylenedioxyphenyl], and —P(O)[—OCH(3-chlorophenyl)CH₂CH₂O—].

In another aspect, X is —P(O)YR¹¹Y'R¹¹ wherein Y and Y' are each independently selected from —O— and —NR$^v$—; together R¹¹ and R¹¹ are the group:

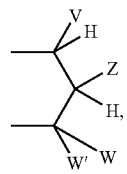

wherein

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkylthiocarbonyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus; or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus; or together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl; or or together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH=CR$^z{}_2$)OH, —CH(C=CR$^z$)OH, —R$^z$, —NR$^z{}_2$, —OCOR$^y$, —OCO$_2$R$^y$, —SCOR$^y$, —SCO$_2$R$^y$, —NHCOR$^z$, —NHCO$_2$R$^y$, —CH$_2$NHaryl, —(CH$_2$)$_q$—OR$^z$, and —(CH$_2$)$_q$—SR$^z$;

q is an integer 2 or 3;

with the provisos that:

a) V, Z, W, W' are not all —H; and b) when Z is —R$^z$, then at least one of V, W, and W' is not —H, alkyl, aralkyl, or heterocycloalkyl;

Each R$^z$ is selected from the group consisting of R$^y$ and —H;

Each R$^y$ is selected from the group consisting of alkyl, aryl, heterocycloalkyl, and aralkyl; and Each R$^v$ is selected from the group consisting of —H, lower alkyl, acyloxyalkyl, alkoxycarbonyloxyalkyl, and lower acyl.

In one aspect, V is optionally substituted aryl. In another aspect, V is selected from the group consisting of 3-chlorophenyl, 4-chlorophenyl, 3-bromophenyl, 3-fluorophenyl, pyrid-4-yl, pyrid-3-yl and 3,5-dichlorophenyl.

In one aspect, the relative stereochemistry between the V-group substituent and T on the dioxaphosphonane ring is cis. In another aspect, the cis dioxaphosphonane ring has R stereochemistry at the carbon where V is attached. In another aspect, the cis dioxaphosphonane ring has S stereochemistry at the carbon where V is attached.

In one aspect R$^{11}$ is not hydrogen.

In one aspect, X is —P(O)YR$^{11}$Y'', wherein Y'' is —C$_1$-C$_6$ alkyl. In one aspect, Y'' is selected from the group consisting of methyl, ethyl, propyl, isopropyl, butyl, isobutyl, and tert-butyl. In another aspect, X is PO$_2$H$_2$, P(O)(OH)(R$^z$), —P(O)[—OCR$^z{}_2$OC(O)R$^y$](R$^z$), —P(O)[—OCR$^z{}_2$OC(O)OR$^y$](R$^z$), —P(O)[—N(H)CR$^z{}_2$C(O)OR$^y$](R$^z$), —P(O)[—N(H)CR$^z{}_2$C(O)OR$^y$][—OR$^{11}$], or —P(O)(OH)[—N(H)CR$^z{}_2$C(O)OR$^y$].

In a further aspect, X is —P(O)(OH)(CH$_3$), —P(O)(OH)(CH$_2$CH$_3$), —P(O)(OH)(isopropyl), or —P(O)(OH)(t-butyl).

In an additional aspect, X is —PO$_3$H$_2$.

Each of the individual species of compounds of Formula II which can be generated by making all of the above permutations may be specifically set forth as for inclusion or may be specifically excluded from the present invention.

In another aspect, the invention relates to a compound of Formula III:

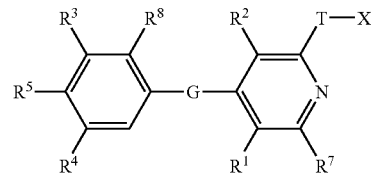

wherein:

G is selected from the group consisting of —O—, —S—, —Se—, —S(=O)—, —S(=O)$_2$—, —CH$_2$—, —CF$_2$—, —CHF—, —C(O)—, —CH(OH)—, —NH—, and —N(C$_1$-C$_4$ alkyl)-, or CH$_2$ linked to any of the preceding groups;

T is selected from the group consisting of —(CR$^a{}_2$)$_k$—, —CR$^b$=CR$^b$—(CR$^a{}_2$)$_n$—, —(CR$^a{}_2$)$_n$—CR$^b$=CR$^b$—, —(CR$^a{}_2$)—CR$^b$=CR$^b$—(CR$^a{}_2$)$_k$—, —O(CR$^b{}_2$)(CR$^a{}_2$)$_n$—, —S(CR$^b{}_2$)(CR$^a{}_2$)$_n$—, —N(R$^c$)(CR$^b{}_2$)(CR$^a{}_2$)$_n$—, —N(R$^b$)C(O)(CR$^a{}_2$)$_n$—, —(CR$^a{}_2$)$_n$CH(NR$^b$R$^c$)—, —C(O)(CR$^a{}_2$)$_m$—, —(CR$^a{}_2$)$_m$C(O)—, —(CR$^a{}_2$)C(O)(CR$^a{}_2$)$_n$—, —(CR$^a{}_2$)$_n$C(O)(CR$^a{}_2$)—, —C(O)NH(CR$^b{}_2$)(CR$^a{}_2$)$_p$—, and —(CH$_2$)$_n$C(O)N(R$^b$)C(R$^a$)$_2$—;

k is an integer from 0-4;

m is an integer from 0-3;

n is an integer from 0-2;

p is an integer from 0-1;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and optionally substituted —C$_1$-C$_4$ alkyl;

Each R$^c$ is independently selected from the group consisting of hydrogen and optionally substituted —C$_1$-C$_4$ alkyl, optionally substituted —C(O)—C$_1$-C$_4$ alkyl, and —C(O)H;

R$^1$ and R$^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano;

R$^8$ is selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a{}_2$)aryl, C(O)aryl, C(O)alkyl and cyano;

R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_m$aryl, optionally substituted —(CR$^a_2$)$_m$cycloalkyl, optionally substituted —(CR$^a_2$)$_m$heterocycloalkyl, —OR$^d$, —SR$^d$, —S(=O)R$^e$, —S(=O)$_2$R$^e$, —S(=O)$_2$NR$^f$R$^g$, —C(O)NR$^f$R$^g$, —C(O)OR$^h$, —C(O)R$^e$, —N(R$^b$)C(O)R$^e$, —N(R$^b$)C(O)NR$^f$R$^g$, —N(R$^b$)S(=O)$_2$R$^e$, —N(R$^b$)S(=O)$_2$NR$^f$R$^g$, and —NR$^f$R$^g$;

Each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, optionally substituted —(CR$^b_2$)$_n$heterocycloalkyl, and —C(O)NR$^f$R$^g$;

Each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_n$aryl, optionally substituted —(CR$^a_2$)$_n$cycloalkyl, and optionally substituted —(CR$^a_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)aryl, optionally substituted —(CR$^b_2$)$_n$cycloalkyl, and optionally substituted —(CR$^b_2$)$_n$heterocycloalkyl, or R$^f$ and R$^g$ may together form an optionally substituted heterocyclic ring, which may contain a second heterogroup selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl; or R$^3$ and R$^8$ are taken together along with the carbon atoms to which they are attached to form an optionally substituted ring of 5 to 6 atoms with 0-2 unsaturations, not including the unsaturation on the ring to which R$^3$ and R$^8$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom; or R$^8$ and G are taken together along with the carbon atoms to which they are attached to form an optionally substituted ring comprising —CH=CH—CH=, —N=CH—CH=, —CH=N—CH= or —CH=CH—N=;

R$^5$ is selected from the group consisting of —OH, optionally substituted —OC$_1$-C$_6$ alkyl, —OC(O)R$^e$, —OC(O)OR$^h$, —F, —NHC(O)R$^e$, —NHS(=O)R$^e$, —NHS(=O)$_2$R$^e$, —NHC(=S)NH(R$^h$), and —NHC(O)NH(R$^h$); or R$^3$ and R$^5$ are taken together along with the carbons they are attached to form an optionally substituted ring of 5 to 6 atoms with 0-2 unsaturations, not including the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

R$^7$ is selected from the group consisting of hydrogen, halogen, amino, hydroxyl, —O—C$_1$-C$_4$ alkyl, —SH and —S—C$_1$-C$_4$ alkyl;

X is P(O)YR$^{11}$Y'R$^{11}$;

Y and Y' are each independently selected from the group consisting of —O—, and —NR$^v$—;

when Y and Y' are both —O—, R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR$^z_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy;

when Y and Y' are both —NR$^v$—, then R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

when Y is —O— and Y' is NRV, then R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR$^z_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy; and R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

but if both R$^{11}$ are alkyl, at least one is higher alkyl;

and both R$^{11}$ are not —H;

or when Y and Y' are independently selected from —O— and —NR$^v$—, then R$^{11}$ and R$^{11}$ together form a cyclic group comprising -alkyl-S-S-alkyl-, or together R$^{11}$ and R$^{11}$ are the group:

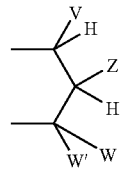

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl; or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon or carbon substituted by hydrogen, and said cyclic group is fused to an aryl group at the beta and gamma position to the Y attached to the phosphorus; or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus; or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon or carbon substituted by hydrogen, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH=CR$^z_2$)OH, —CH(C≡CR$^z$)OH, —R$^z$, —NR$^z_2$, —OCOR$^y$, —OCO$_2$R$^y$, —SCOR$^y$, —SCO$_2$R$^y$, —NHCOR$^z$, —NHCO$_2$R$^y$, —CH$_2$NHaryl, —(CH$_2$)$_q$—OR$^z$, and —(CH$_2$)$_q$—SR$^z$;

q is an integer 2 or 3;

Each R$^z$ is selected from the group consisting of R$^y$ and —H;

Each R$^y$ is selected from the group consisting of alkyl, aryl, heterocycloalkyl, and aralkyl;

Each R$^x$ is independently selected from the group consisting of —H, and alkyl, or together R$^x$ and R$^x$ form a cycloalkyl group;

Each R$^v$ is selected from the group consisting of —H, lower alkyl, acyloxyalkyl, alkoxycarbonyloxyalkyl, and lower acyl;

with the provisos that:

a) V, Z, W, W' are not all —H; and b) when Z is —R$^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In another aspect, the invention relates to a compound of Formula III:

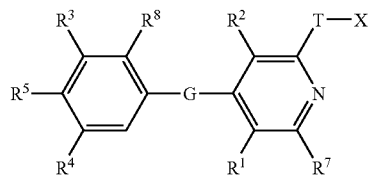

wherein:

G is selected from the group consisting of —O—, —S—, —Se—, —S(=O)—, —S(=O)$_2$—, —CH$_2$—, —CF$_2$—, —CHF—, —C(O)—, —CH(OH)—, —NH—, and —N(C$_1$-C$_4$ alkyl)-, or CH$_2$ linked to any of the preceding groups;

T is selected from the group consisting of —(CR$^a_2$)$_k$—, —CR$^b$=CR$^b$—(CR$^a_2$)$_n$—, —(CR$^a_2$)$_n$—CR$^b$=CR$^b$—, (CR$^a_2$)—CR$^b$=CR$^b$—(CR$^a_2$)$_k$—, —O(CR$^b_2$)(CR$^a_2$)$_n$, —S(CR$^b_2$)(CR$^a_2$)$_n$—, —N(R$^c$)(CR$^b_2$)(CR$^a_2$)$_n$—, —N(R$^b$)C(O)(CR$^a_2$)$_n$—, —(CR$^a_2$)CH(NR$^b$R$^c$)—, —C(O)(CR$^a_2$)$_m$—, —(CR$^a_2$)$_m$C(O)—, —(CR$^a_2$)C(O)(CR$^a_2$)$_n$—, —(CR$^a_2$)$_n$C(O)(CR$^a_2$)—, —C(O)NH(CR$^b_2$)(CR$^a_2$)$_p$—, and —(CH$_2$)$_n$C(O)N(R$^b$)C(R$^a$)$_2$—;

k is an integer from 0-4;

m is an integer from 0-3;

n is an integer from 0-2;

p is an integer from 0-1;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and optionally substituted —C$_1$-C$_4$ alkyl;

Each R$^c$ is independently selected from the group consisting of hydrogen and optionally substituted —C$_1$-C$_4$ alkyl, optionally substituted —C(O)—C$_1$-C$_4$ alkyl, and —C(O)H;

R$^1$ and R$^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano;

R$^8$ is selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a_2$)aryl, C(O)aryl, C(O)alkyl and cyano;

R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_m$aryl, optionally substituted —(CR$^a_2$)$_m$cycloalkyl, optionally substituted —(CR$^a_2$)$_n$heterocycloalkyl, —OR$^d$, —SR$^d$, —S(=O)R$^e$, —S(=O)$_2$R$^e$, —S(=O)$_2$NR$^f$R$^g$, —C(O)NR$^f$R$^g$, —C(O)OR$^h$, —C(O)R$^e$, —N(O)C(O)R$^e$, —N(R$^b$)C(O)NR$^f$R$^g$, —N(R$^b$)S(=O)$_2$R$^e$, —N(R$^b$)S(=O)$_2$NR$^f$R$^g$, and —NR$^f$R$^g$;

Each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, optionally substituted —(CR$^b_2$)$_n$heterocycloalkyl, and —C(O)NR$^f$R$^g$;

Each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_n$aryl, optionally substituted —(CR$^a_2$)$_n$cycloalkyl, and optionally substituted —(CR$^b_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl, or R$^f$ and R$^g$ may together form an optionally substituted heterocyclic ring, which may contain a second heterogroup selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl; or $R^3$ and $R^8$ are taken together along with the carbon atoms to which they are attached to form an optionally substituted ring of 5 to 6 atoms with 0-2 unsaturations, not including the unsaturation on the ring to which $R^3$ and $R^8$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom; or $R^8$ and G are taken together along with the carbon atoms to which they are attached to form an optionally substituted ring comprising —CH=CH—CH=, —N=CH—CH=, —CH=N—CH= or —CH=CH—N=;

$R^5$ is selected from the group consisting of —OH, optionally substituted —$OC_1$-$C_6$ alkyl, —OC(O)$R^e$, —OC(O)O$R^h$, —F, —NHC(O)$R^e$, —NHS(=O)$R^e$, —NHS(=O)$_2R^e$, —NHC(=S)NH($R^h$), and —NHC(O)NH($R^h$); or $R^3$ and $R^5$ are taken together along with the carbons they are attached to form an optionally substituted ring of 5 to 6 atoms with 0-2 unsaturations, not including the unsaturation on the ring to which $R^3$ and $R^5$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom;

$R^7$ is selected from the group consisting of hydrogen, halogen, amino, hydroxyl, —O—$C_1$-$C_4$ alkyl, —SH and —S—$C_1$-$C_4$ alkyl;

X is P(O)Y$R^{11}$Y'$R^{11}$;

Y and Y' are each independently selected from the group consisting of —O—, and —$NR^v$—;

when Y and Y' are both —O—, $R^{11}$ attached to —O— is independently selected from the group consisting of —H, alkyl, optionally substituted aryl, optionally substituted heterocycloalkyl, optionally substituted $CH_2$-heterocycloalkyl wherein the cyclic moiety contains a carbonate or thiocarbonate, optionally substituted -alkylaryl, —C($R^z$)$_2$OC(O)N$R^z_2$, —$NR^z$—C(O)—$R^y$, —C($R^z$)$_2$—OC(O)$R^y$, —C($R^z$)$_2$—O—C(O)O$R^y$, —C($R^z$)$_2$OC(O)S$R^y$, -alkyl-S—C(O)$R^y$, -alkyl-S—S-alkylhydroxy, and -alkyl-S-S-S-alkylhydroxy;

when Y and Y' are both —$NR^v$—, then $R^{11}$ attached to —$NR^v$— is independently selected from the group consisting of —H, —[C($R^z$)$_2$]$_q$—COO$R^y$, —C($R^x$)$_2$COO$R^y$, —[C($R^z$)$_2$]$_q$—C(O)S$R^y$, and -cycloalkylene-COO$R^y$;

when Y is —O— and Y' is $NR^v$, then $R^{11}$ attached to —O— is independently selected from the group consisting of —H, alkyl, optionally substituted aryl, optionally substituted heterocycloalkyl, optionally substituted $CH_2$-heterocycloalkyl wherein the cyclic moiety contains a carbonate or thiocarbonate, optionally substituted -alkylaryl, —C($R^z$)$_2$OC(O)N$R^z_2$, —$NR^z$—C(O)—$R^y$, —C($R^z$)$_2$—OC(O)$R^y$, —C($R^z$)$_2$—O—C(O)O$R^y$, —C($R^z$)$_2$OC(O)S$R^y$, -alkyl-S—C(O)$R^y$, -alkyl-S—S-alkylhydroxy, and -alkyl-S-S-S-alkylhydroxy; and $R^{11}$ attached to —$NR^v$— is independently selected from the group consisting of —H, —[C($R^z$)$_2$]$_q$—COO$R^y$, —C($R^x$)$_2$COO$R^y$, —[C($R^z$)$_2$]$_q$—C(O)S$R^y$, and -cycloalkylene-COO$R^y$;

or when Y and Y' are independently selected from —O— and —$NR^v$—, then $R^{11}$ and $R^{11}$ together form a cyclic group comprising -alkyl-S-S-alkyl-, or together $R^{11}$ and $R^{11}$ are the group:

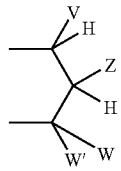

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl; or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon or carbon substituted by hydrogen, and said cyclic group is fused to an aryl group at the beta and gamma position to the Y attached to the phosphorus; or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon or carbon substituted by hydrogen, and V must be aryl, substituted aryl, heteroaryl, or substituted heteroaryl;

Z is selected from the group consisting of —CH$R^z$OH, —CH$R^z$OC(O)$R^y$, —CH$R^z$OC(S)$R^y$, —CH$R^z$OC(S)O$R^y$, —CH$R^z$OC(O)S$R^y$, —CH$R^z$OCO$_2R^y$, —O$R^z$, —S$R^z$, —CH$R^z$N$_3$, —CH$_2$aryl, —CH(aryl)OH, —CH(CH=C$R^z_2$)OH, —CH(C≡C$R^z$)OH, —$R^z$, —$NR^z_2$, —OCO$R^y$, —OCO$_2R^y$, —SCO$R^y$, —SCO$_2R^y$, —NHCO$R^y$, —NHCO$_2R^y$, —CH$_2$NHaryl, —(CH$_2$)$_q$—O$R^z$, and —(CH$_2$)$_q$—S$R^z$;

q is an integer 2 or 3;

Each $R^z$ is selected from the group consisting of $R^y$ and —H;

Each $R^y$ is selected from the group consisting of alkyl, aryl, heterocycloalkyl, and aralkyl;

Each $R^x$ is independently selected from the group consisting of —H, and alkyl, or together $R^x$ and $R^x$ form a cycloalkyl group;

Each $R^v$ is selected from the group consisting of —H, lower alkyl, acyloxyalkyl, alkoxycarbonyloxyalkyl, and lower acyl;

with the provisos that:

a) when G is —O—, T is —NH—CH$_2$—, R$^1$ and R$^2$ are each chloro, R$^3$ is iso-propyl, R$^4$ is hydrogen, R$^7$ is fluoro, and R$^5$ is —OH, then X is not P(O)(OH)$_2$, P(O)(OH)(OCH$_3$) or P(O)(OCH$_3$)$_2$;

b) V, Z, W, W' are not all —H; and c) when Z is —R$^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In a further aspect, the invention relates to a compound of Formula III:

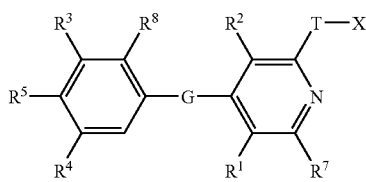

wherein:

G is selected from the group consisting of —O—, —S—, —Se—, —S(=O)—, —S(=O)$_2$—, —CH$_2$—, —CF$_2$—, —CHF—, —C(O)—, —CH(OH)—, —NH—, and —N(C$_1$-C$_4$ alkyl)-, or CH$_2$ linked to any of the preceding groups;

T is selected from the group consisting of —(CR$^a_2$)$_k$—, —CR$^b$=CR$^b$—(CR$^a_2$)$_n$—, —(CR$^a_2$)$_n$—CRb=CR$^b$—, —(CR$^a_2$)—CR$^b$=CR$^b$—(CR$^a_2$)$_k$—, —O(CR$^b_2$)(CR$^a_2$)$_n$—, —S(CR$^b_2$)(CR$^a_2$)$_n$—, —N(R$^c$)(CR$^b_2$)(CR$^a_2$)$_n$—, —N(R$^b$)C(O)(CR$^a_2$)$_n$—, —(CR$^a_2$)$_n$CH(NR$^b$R$^c$)—, —C(O)(CR$^a_2$)$_m$—, —(CR$^a_2$)$_m$C(O)—, —(CR$^a_2$)C(O)(CR$^a_2$)$_n$—, —(CR$^a_2$)$_n$C(O)(CR$^a_2$)—, —C(O)NH(CR$^b_2$)(CR$^a_2$)$_p$—, and —(CH$_2$)$_n$C(O)N(R$^b$)C(R$^a$)$_2$—;

k is an integer from 0-4;
m is an integer from 0-3;
n is an integer from 0-2;
p is an integer from 0-1;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and optionally substituted —C$_1$-C$_4$ alkyl;

Each R$^c$ is independently selected from the group consisting of hydrogen, optionally substituted —C$_1$-C$_4$ alkyl, optionally substituted —C(O)—C$_1$-C$_4$ alkyl, and —C(O)H;

R$^1$ and R$^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano;

1. R$^8$ is selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a_2$)aryl, C(O)aryl, C(O)alkyl and cyano;

R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_m$aryl, optionally substituted —(CR$^a_2$)$_m$cycloalkyl, optionally substituted (CR$^a_2$)$_m$heterocycloalkyl, —OR$^d$, —SR$^d$, —S(=O)R$^e$, —S(=O)$_2$R$^e$, —S(=O)$_2$NR$^f$R$^g$, —C(O)NR$^f$R$^g$, —C(O)OR$^h$, —C(O)R$^e$, —N(R$^b$)C(O)R$^e$, —N(O)C(O)NR$^f$R$^g$, —N(R$^b$)S(=O)$_2$R$^e$, —N(R$^b$)S(=O)$_2$NR$^f$R$^g$, and —NR$^f$R$^g$;

Each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, optionally substituted —(CR$^b_2$)$_n$heterocycloalkyl, and —C(O)NR$^f$R$^g$;

Each R$^e$ is optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_n$aryl, optionally substituted —(CR$^a_2$)$_n$cycloalkyl, and optionally substituted —(CR$^a_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)hd nheterocycloalkyl, or R$^f$ and R$^g$ may together form an optionally substituted heterocyclic ring, which may contain a second heterogroup selected from the group of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl; or R$^3$ and R$^8$ are taken together along with the carbon atoms to which they are attached to form an optionally substituted ring of 5 to 6 atoms with 0-2 unsaturations, not including the unsaturation on the ring to which R$^3$ and R$^8$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom; or R$^8$ and G are taken together along with the carbon atoms to which they are attached to form an optionally substituted ring comprising —CH=CH—CH=, —N=CH—CH=, —CH=N—CH= or —CH=CH—N=;

R$^5$ is selected from the group consisting of —OH, optionally substituted —OC$_1$-C$_6$ alkyl, —OC(O)R$^e$, —OC(O)OR$^h$, —F, —NHC(O)R$^e$, —NHS(=O)R$^e$, —NHS(=O)$_2$R$^e$, —NHC(=S)NH(R$^h$), and —NHC(O)NH(R$^h$); or R$^3$ and R$^5$ are taken together along with the carbons they are attached to form an optionally substituted ring of 5 to 6 atoms with 0-2 unsaturations, not including the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

R⁷ is selected from the group consisting of hydrogen, halogen, amino, hydroxyl, —O—C₁-C₄ alkyl, —SH and —S—C₁-C₄ alkyl;

X is P(O)YR¹¹Y'R¹¹;

Y and Y' are each independently selected from the group consisting of —O—, and —NR$^v$—;

when Y and Y' are both —O—, R¹¹ attached to —O— is independently selected from the group consisting of —H, alkyl, optionally substituted aryl, optionally substituted heterocycloalkyl, optionally substituted CH₂-heterocycloakyl wherein the cyclic moiety contains a carbonate or thiocarbonate, optionally substituted -alkylaryl, —C(R$^z$)₂OC(O)NR$^z$₂, —NR$^z$—C(O)—R$^y$, —C(R$^z$)₂—OC(O)R$^y$, —C(R$^z$)₂—O—C(O)OR$^y$, —C(R$^z$)₂OC(O)SR$^y$, -alkyl-S—C(O)R$^y$, -alkyl-S-S-alkylhydroxy, and -alkyl-S-S-S-alkylhydroxy;

when Y and Y' are both —NR$^v$—, then R¹¹ attached to —NR$^v$— is independently selected from the group consisting of —H, —[C(R$^z$)₂]$_q$—COOR$^y$, —C(R$^x$)₂COOR$^y$, —[C(R$^z$)₂]$_q$—C(O)SR$^y$, and -cycloalkylene-COOR$^y$;

when Y is —O— and Y' is NR$^v$, then R¹¹ attached to —O— is independently selected from the group consisting of —H, alkyl, optionally substituted aryl, optionally substituted heterocycloalkyl, optionally substituted CH₂-heterocycloakyl wherein the cyclic moiety contains a carbonate or thiocarbonate, optionally substituted -alkylaryl, —C(R$^z$)₂OC(O)NR$^z$₂, —NR$^z$—C(O)—R$^y$, —C(R$^z$)₂—OC(O)R$^y$, —C(R$^z$)₂—O—C(O)OR$^y$, —C(R$^z$)₂OC(O)SR$^y$, -alkyl-S—C(O)R$^y$, -alkyl-S-S-alkylhydroxy, and -alkyl-S-S-S-alkylhydroxy; and R¹¹ attached to —NR$^v$— is independently selected from the group consisting of —H, —[C(R$^z$)₂]$_q$—COOR$^y$, —C(R$^x$)₂COOR$^y$, —[C(R$^z$)₂]$_q$—C(O)SR$^y$, and -cycloalkylene-COOR$^y$; or when Y and Y' are independently selected from —O— and —NR$^v$—, then R¹¹ and R¹¹ together form a cyclic group comprising -alkyl-S-S-alkyl-, or together R¹¹ and R¹¹ are the group:

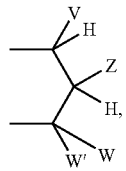

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon or carbon substituted by hydrogen, and said cyclic group is fused to an aryl group at the beta and gamma position to the Y attached to the phosphorus; or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus; or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or together W and W' are connected via an additional 2-5 atoms to form a cyclic group, wherein 0-2 atoms are heteroatoms and the remaining atoms are carbon or carbon substituted by hydrogen, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO₂R$^y$, —OR$^z$, —SR$^z$, —CHR$^z$N₃, —CH₂aryl, —CH(aryl)OH, —CH(CH=CR$^z$₂)OH, —CH(C≡CR$^z$)OH, —R$^z$, —NR$^z$₂, —OCOR$^y$, —OCO₂R$^y$, —SCOR$^y$, —SCO₂R$^y$, —NHCOR$^z$, —NHCO₂R$^y$, —CH₂NHaryl, —(CH₂)$_q$—OR$^z$, and —(CH₂)$_q$—SR$^z$;

q is an integer 2 or 3;

Each R$^z$ is selected from the group consisting of R$^y$ and —H;

Each R$^y$ is selected from the group consisting of alkyl, aryl, heterocycloalkyl, and aralkyl;

Each R$^x$ is independently selected from the group consisting of —H, and alkyl, or together R$^x$ and R$^x$ form a cycloalkyl group;

Each R$^v$ is selected from the group consisting of —H, lower alkyl, acyloxyalkyl, alkoxycarbonyloxyalkyl, and lower acyl;

with the provisos that:

a) when G is selected from the group consisting of —O—, —S—, —S(=O)—, —S(=O)₂—, —CH₂—, —CH(OH)—, —C(O)— and —NR$^b$—; T is -A-B— where A is selected from the group consisting of —NR$^b$—, —O—, —CH₂— and —S— and B is selected from the group consisting of a bond and substituted or unsubstituted C₁-C₃ alkyl; R³ is selected from the group consisting of halogen, trifluoromethyl, substituted or unsubstituted C₁-C₆ alkyl, substituted or unsubstituted aryl, substituted or unsubstituted heteroaryl, aryloxy, substituted amide, sulfone, sulfonamide and C₃-C₇ cycloalkyl, wherein said aryl, heteroaryl or cycloalkyl ring(s) are attached or fused to the aromatic; R⁴ is selected from the group consisting of hydrogen, halogen, substituted or unsubstituted C₁-C₆ alkyl, substituted or unsubstituted aryl, and substituted or unsubstituted heteroaryl; R¹ and R² are each independently selected from the group consisting of halogen, and substituted or unsubstituted C₁-C₄ alkyl; R⁷ is selected from the group consisting of hydrogen, halogen, amino, hydroxyl, —C₁-C₄ alkyl, —O—C₁-C₄ alkyl, —SH and —S—C₁-C₄ alkyl; and R⁵ is selected from the group consisting of hydroxyl, optionally substituted —OC₁-C₆ alkyl, and —OC(O)R$^e$; then X is not —P(O)(OH)₂ or a lower alkyl ester or acyloxyalkyl ester thereof;

b) V, Z, W, W' are not all —H; and c) when Z is —R$^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In another aspect, when G is —O—, T is —NH—CH$_2$—, R$^1$ and R$^2$ are each chloro, R$^3$ is iso-propyl, R$^7$ is fluoro and R$^5$ is —OH, then R$^4$ is not hydrogen. In a further aspect, when G is selected from the group consisting of oxygen, sulfur, sulfoxide, sulfonyl, —CH$_2$—, —C(O)— and —NR$^b$—; T is -A-B— where A is selected from the group consisting of —NR$^b$—, —O—, —CH$_2$— and —S— and B is selected from the group consisting of a bond and substituted or unsubstituted C$_1$-C$_3$ alkyl; R$^3$ is selected from the group consisting of halogen, trifluoromethyl, substituted or unsubstituted C$_1$-C$_6$ alkyl, substituted or unsubstituted aryl, substituted or unsubstituted heteroaryl, aryloxy, substituted amide, sulfone, sulfonamide and C$_3$-C$_7$ cycloalkyl, wherein said aryl, heteroaryl or cycloalkyl ring(s) are attached or fused to the aromatic; R$^4$ is selected from the group consisting of hydrogen, halogen, substituted or unsubstituted C$_1$-C$_6$ alkyl, substituted or unsubstituted aryl, and substituted or unsubstituted heteroaryl; R$^1$ and R$^2$ are each independently selected from the group consisting of halogen, substituted or unsubstituted C$_1$-C$_4$ alkyl, and substituted or unsubstituted C$_3$-C$_5$ cycloalkyl; and R$^7$ is selected from the group consisting of hydrogen, halogen, amino, hydroxyl, —O—C$_1$-C$_4$ alkyl, —SH and —S—C$_1$-C$_4$ alkyl; then R$^5$ is not hydroxyl, optionally substituted —OC$_1$-C$_6$ alkyl, or —OC(O)R$^e$.

In one aspect, G is selected from the group consisting of —O— and —CH$_2$—. In a further aspect, G is —O—. In another aspect, G is —S—. In a further aspect, G is —S(=O)—. In another aspect, G is —S(=O)$_2$—. In a further aspect, G is —CH$_2$—. In another aspect, G is —CF$_2$—. In a further aspect, G is —CHF—. In another aspect, G is —C(O)—. In another aspect, G is —CH(OH)—. In a further aspect, G is —NH—. In another aspect, G is —N(C$_1$-C$_4$ alkyl)-.

In another aspect, T is selected from the group consisting of —O(CR$^b_2$)(CR$^a_2$)$_p$—, —N(R$^c$)(CR$^b_2$)(CR$^a_2$)$_p$—, —S(CR$^b_2$)(CR$^a_2$)$_p$—, and —NR$^b$(CO)—. In a further aspect, T is —(CR$^a_2$)$_k$—. In another aspect, T is —CR$^b$=CR$^b$—(CR$^a_2$)$_n$—. In a further aspect, T is —(CR$^a_2$)$_n$—CR$^b$=CR$^b$—. In another aspect, T is —(CR$^a_2$)—CR$^b$=CR$^b$—(CR$^a_2$)—. In a further aspect, T is —O(CR$^b_2$)(CR$^a_2$)$_n$— or —NH(CR$^b_2$)(CR$^a_2$)$_p$—. In another aspect, T is —S(CR$^b_2$)(CR$^a_2$)$_n$—. In a further aspect, T is —N(R$^c$)(CR$^b_2$)(CR$^a_2$)$_n$—. In another aspect, T is —N(R$^b$)C(O)(CR$^a_2$)$_n$. In a further aspect, T is —(CR$^a_2$)$_n$CH(NR$^b$R$^c$)—. In another aspect, T is —C(O)(CR$^a_2$)$_m$—. In a further aspect, T is —(CR$^a_2$)$_m$C(O)—. In another aspect, T is —(CR$^a_2$)C(O)(CR$^a_2$)$_n$—. In a further aspect, T is —(CR$^a_2$)$_n$C(O)(CR$^a_2$)—. In yet another aspect, T is —C(O)NH(CR$^b_2$)(CR$^a_2$)$_p$—.

In one aspect k is 0. In a further aspect, k is 1. In an additional aspect, k is 2. In a further aspect, k is 3. In yet another aspect, k is 4. In one aspect m is 0. In a further aspect, m is 1. In an additional aspect, m is 2. In a further aspect, m is 3. In one aspect n is 0. In a further aspect, n is 1. In an additional aspect, n is 2. In one aspect, p is 0. In another aspect, p is 1.

In one aspect, each R$^a$ is hydrogen with the proviso that when one R$^a$ is attached to C through an O, S, or N atom, then the other R$^a$ attached to the same C is a hydrogen, or attached via a carbon atom. In another aspect, each R$^a$ is optionally substituted —C$_1$-C$_4$ alkyl with the proviso that when one R$^a$ is attached to C through an O, S, or N atom, then the other R$^a$ attached to the same C is a hydrogen, or attached via a carbon atom. In a further aspect, each R$^a$ is halogen with the proviso that when one R$^a$ is attached to C through an O, S, or N atom, then the other R$^a$ attached to the same C is a hydrogen, or attached via a carbon atom. In another aspect, each R$^a$ is —OH with the proviso that when one R$^a$ is attached to C through an O, S, or N atom, then the other R$^a$ attached to the same C is a hydrogen, or attached via a carbon atom. In a further aspect, each R$^a$ is optionally substituted —O—C$_1$-C$_4$ alkyl with the proviso that when one R$^a$ is attached to C through an O, S, or N atom, then the other R$^a$ attached to the same C is a hydrogen, or attached via a carbon atom. In another aspect, each R$^a$ is —OCF$_3$ with the proviso that when one R$^a$ is attached to C through an O, S, or N atom, then the other R$^a$ attached to the same C is a hydrogen, or attached via a carbon atom. In a further aspect, each R$^a$ is optionally substituted —S—C$_1$-C$_4$ alkyl with the proviso that when one R$^a$ is attached to C through an O, S, or N atom, then the other R$^a$ attached to the same C is a hydrogen, or attached via a carbon atom. In another aspect, each R$^a$ is —NR$^b$R$^c$ with the proviso that when one R$^a$ is attached to C through an O, S, or N atom, then the other R$^a$ attached to the same C is a hydrogen, or attached via a carbon atom. In a further aspect, each R$^a$ is optionally substituted —C$_2$-C$_4$ alkenyl with the proviso that when one R$^a$ is attached to C through an O, S, or N atom, then the other R$^a$ attached to the same C is a hydrogen, or attached via a carbon atom. In another aspect, each R$^a$ is optionally substituted —C$_2$-C$_4$ alkynyl with the proviso that when one R$^a$ is attached to C through an O, S, or N atom, then the other R$^a$ attached to the same C is a hydrogen, or attached via a carbon atom.

In one aspect, R$^b$ is hydrogen. In an additional aspect, R$^b$ is optionally substituted —C$_1$-C$_4$ alkyl.

In one aspect, R$^c$ is hydrogen. In another aspect, R$^c$ is optionally substituted —C$_1$-C$_4$ alkyl. In a further aspect, R$^c$ is optionally substituted —C(O)—C$_1$-C$_4$ alkyl. In yet another aspect, R$^c$ is —C(O)H.

In a further aspect, R$^1$ and R$^2$ are the same and are selected from the group consisting of halogen, —C$_1$-C$_4$ alkyl, —CF$_3$, and cyano. In yet another aspect, R$^1$ and R$^2$ are different and are selected from the group consisting of halogen, —C$_1$-C$_4$ alkyl, —CF$_3$, and cyano. In an additional aspect, R$^1$ and R$^2$ are each halogen. In an additional aspect, R$^1$ and R$^2$ are not both halogen. In another aspect, R$^1$ and R$^2$ are each optionally substituted —C$_1$-C$_4$ alkyl. In a further aspect, R$^1$ and R$^2$ are each optionally substituted —S—C$_1$-C$_3$ alkyl. In another aspect, R$^1$ and R$^2$ are each optionally substituted —C$_2$-C$_4$ alkenyl. In a further aspect, R$^1$ and R$^2$ are each optionally substituted —C$_2$-C$_4$ alkynyl. In another aspect, R$^1$ and R$^2$ are each —CF$_3$. In a further aspect, R$^1$ and R$^2$ are each —OCF$_3$. In another aspect, R$^1$ and R$^2$ are each optionally substituted-O—C$_1$-C$_3$ alkyl. In a further aspect, R$^1$ and R$^2$ are each cyano.

In yet another aspect, R$^3$ and R$^4$ are each hydrogen. In another aspect, R$^3$ and R$^4$ are each halogen. In a further aspect, R$^3$ and R$^4$ are each —CF$_3$. In another aspect, R$^3$ and R$^4$ are each —OCF$_3$. In a further aspect, R$^3$ and R$^4$ are each cyano. In another aspect, R$^3$ and R$^4$ are each optionally substituted —C$_1$-C$_{12}$ alkyl. In a further aspect, R$^3$ and R$^4$ are each optionally substituted —C$_2$-C$_{12}$ alkenyl. In another aspect, R$^3$ and R$^4$ are each optionally substituted —C$_2$-C$_{12}$ alkynyl. In a further aspect, R$^3$ and R$^4$ are each optionally substituted —(CR$^a_2$)$_m$aryl. In another aspect, R$^3$ and R$^4$ are each optionally substituted —(CR$^a_2$)$_m$cycloalkyl. In a further aspect, R$^3$ and R$^4$ are each optionally substituted —(CR$^a_2$)$_m$heterocycloalkyl. In another aspect, R$^3$ and R$^4$ are each —OR$^d$. In another aspect, R$^3$ and R$^4$ are each —SR$^d$. In a further aspect, R$^3$ and R$^4$ are each —S(=O)R$^e$. In another aspect, R$^3$ and R$^4$ are each —S(=O)$_2$R$^e$. In a further aspect, R$^3$ and R$^4$ are each —S(=O)$_2$NR$^f$R$^g$. In another aspect, R$^3$ and R$^4$ are each —C(O)NR$^f$R$^g$. In a further aspect, R$^3$ and R$^4$ are each —C(O)OR$^h$. In another aspect, R$^3$ and R$^4$ are each —C(O)R$^e$. In a further aspect, R$^3$ and R$^4$ are each —N(R$^b$)C(O)R$^e$. In another aspect, R$^3$ and R$^4$ are each —N(R$^b$)C(O)NR$^f$R$^g$. In a further aspect, $R^3$ and $R^4$ are each —N($R^b$)S(=O)$_2R^e$. In another aspect, $R^3$ and $R^4$ are each —N($R^b$)S(=O)$_2$NR$^f$R$^g$. In a further aspect, $R^3$ and $R^4$ are each —NR$^f$R$^g$.

In another aspect, $R^4$ is selected from the group consisting of hydrogen, halogen, —C$_1$-C$_4$ alkyl, cyano and CF$_3$. In another aspect, $R^4$ is hydrogen. In a further aspect, $R^3$ is selected from the group consisting of halogen, optionally substituted —C$_1$-C$_6$ alkyl, —CF$_3$, cyano, —C(O)NR$^f$R$^g$, optionally substituted —(CR$^a_2$)$_n$aryl, —SO$_2$NR$^f$R$^g$, and —SO$_2R^e$. In a further aspect, $R^3$ is isopropyl or 4-fluorobenzyl.

In another aspect, each $R^d$ is optionally substituted —C$_1$-C$_{12}$ alkyl. In a further aspect, each $R^d$ is optionally substituted —C$_2$-C$_{12}$ alkenyl. In another aspect, each $R^d$ is optionally substituted —C$_2$-C$_{12}$ alkynyl. In a further aspect, each $R^d$ is optionally substituted —(CR$^b_2$)$_n$aryl. In another aspect, each $R^d$ is optionally substituted —(CR$^b_2$)$_n$cycloalkyl. In a further aspect, each $R^d$ is optionally substituted —(CR$^b_2$)$_n$heterocycloalkyl. In another aspect, each $R^d$ is —C(O)NR$^f$R$^g$.

In an additional aspect, $R^e$ is optionally substituted —C$_1$-C$_{12}$ alkyl. In another aspect, $R^e$ is optionally substituted —C$_2$-C$_{12}$ alkenyl. In a further aspect, $R^e$ is optionally substituted —C$_2$-C$_{12}$ alkynyl. In another aspect, $R^e$ is optionally substituted —(CR$^a_2$)$_n$aryl. In a further aspect, $R^e$ is optionally substituted —(CR$^a_2$)$_n$cycloalkyl. In another aspect, $R^e$ is optionally substituted —(CR$^a_2$)$_n$heterocycloalkyl.

In one aspect, $R^f$ and $R^g$ are each hydrogen. In an additional aspect, $R^f$ and $R^g$ are each optionally substituted —C$_1$-C$_{12}$ alkyl. In another aspect, $R^f$ and $R^g$ are each optionally substituted —C$_2$-C$_{12}$ alkenyl. In an additional aspect, $R^f$ and $R^g$ are each optionally substituted —C$_2$-C$_{12}$ alkynyl. In a further aspect, $R^f$ and $R^g$ are each optionally substituted —(CR$^b_2$)$_n$aryl. In an additional aspect, $R^f$ and $R^g$ are each optionally substituted —(CR$^b_2$)$_n$cycloalkyl. In another aspect, $R^f$ and $R^g$ are each optionally substituted —(CR$^b_2$)$_n$heterocycloalkyl.

In an additional aspect, $R^f$ and $R^g$ may together form an optionally substituted heterocyclic ring, which may contain a second heterogroup which is O. In another aspect, $R^f$ and $R^g$ may together form an optionally substituted heterocyclic ring, which may contain a second heterogroup which is NR$^c$. In another aspect, $R^f$ and $R^g$ may together form an optionally substituted heterocyclic ring, which may contain a second heterogroup which is S. In one aspect, $R^f$ and $R^g$ may together form an unsubstituted heterocyclic ring, which may contain a second heterogroup. In another aspect, the optionally substituted heterocyclic ring may be substituted with 1 substituent selected from the group consisting of optionally substituted —C$_1$-C$_4$ alkyl, —OR$^b$, oxo, cyano, —CF$_3$, optionally substituted phenyl, and —C(O)OR$^h$. In further aspect, the optionally substituted heterocyclic ring may be substituted with 2 substituents selected from the group consisting of optionally substituted —C$_1$-C$_4$ alkyl, —OR$^b$, oxo, cyano, —CF$_3$, optionally substituted phenyl, and —C(O)OR$^h$. In another aspect, the optionally substituted heterocyclic ring may be substituted with 3 substituents selected from the group consisting of optionally substituted —C$_1$-C$_4$ alkyl, —OR$^b$, oxo, cyano, —CF$_3$, optionally substituted phenyl, and —C(O)OR$^h$. In a further aspect, the optionally substituted heterocyclic ring may be substituted with 4 substituents selected from the group consisting of optionally substituted —C$_1$-C$_4$ alkyl, —OR$^b$, oxo, cyano, —CF$_3$, optionally substituted phenyl, and —C(O)OR$^h$.

In a further aspect, $R^h$ is optionally substituted —C$_1$-C$_{12}$ alkyl. In another aspect, $R^h$ is optionally substituted —C$_2$-C$_{12}$ alkenyl. In a further aspect, $R^h$ is optionally substituted —C$_2$-C$_{12}$ alkynyl. In another aspect, $R^h$ is optionally substituted —(CR$^b_2$)$_n$aryl. In a further aspect, $R^h$ is optionally substituted —(CR$^b_2$)$_n$cycloalkyl. In another aspect, $R^h$ is optionally substituted —(CR$^b_2$)$_n$heterocycloalkyl.

In one aspect, $R^5$ is selected from the group consisting of —OH, —OC(O)R$^e$, —OC(O)OR$^h$, —F, and —NHC(O)R$^e$. In another aspect, $R^5$ is —OH. In an additional aspect, $R^5$ is optionally substituted —OC$_1$-C$_6$ alkyl. In another aspect, $R^5$ is —OC(O)R$^e$. In a further aspect, $R^5$ is —OC(O)OR$^h$. In another aspect, $R^5$ is —F. In another aspect, $R^5$ is —NHC(O)R$^e$. In a further aspect, $R^5$ is —NHS(=O)R$^e$. In another aspect, $R^5$ is —NHS(=O)$_2$R$^e$. In a further aspect, $R^5$ is —NHC(=S)NH(R$^h$). In another aspect, $R^5$ is —NHC(O)NH(R$^h$).

In one aspect, X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][—OR$^{11}$], and —P(O)[—OCH(V)CH$_2$CH$_2$O—], wherein V is selected from the group consisting of optionally substituted aryl, aryl, heteroaryl, and optionally substituted heteroaryl. In another aspect, X is selected from the group consisting of —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][—OR$^{11}$], —P(O)[—OCH(V)CH$_2$CH$_2$O—], —P(O)(OH)(OR$^{11}$), —P(O)(OR$^e$)(OR$^e$), —P(O)[—OCR$^z_2$OC(O)R$^y$](OR$^e$), —P(O)[—OCR$^z_2$OC(O)OR$^y$](OR$^e$), and —P(O)[—N(H)CR$^z_2$C(O)OR$^y$](OR$^e$), wherein V is selected from the group consisting of optionally substituted aryl, aryl, heteroaryl, and optionally substituted heteroaryl. In a further aspect, X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^b_2$C(O)OR$^y$][—OR$^{11}$], —P(O)[—OCH(V)CH$_2$CH$_2$O—], —P(O)(OH)(OR$^e$), —P(O)(OR$^e$)(OR$^e$), —P(O)[—OCR$^z_2$OC(O)R$^y$](OR$^e$), —P(O)[—OCR$^z_2$OC(O)OR$^y$](OR$^e$), —P(O)[—N(H)CR$^z_2$C(O)OR$^y$](OR$^e$), and —P(O)(OH)(NH$_2$), wherein V is selected from the group consisting of optionally substituted aryl, aryl, heteroaryl, and optionally substituted heteroaryl. In a further aspect, wherein X is selected from the group consisting of —PO$_3$H$_2$, —P(O)[—OCH$_2$OC(O)-t-butyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$] [3,4-methylenedioxyphenyl], —P(O)[—N(H)C(CH$_3$)$_2$C(O)OCH$_2$CH$_3$] [3,4-methylenedioxyphenyl], —P(O)[—OCH(3-chlorophenyl)CH$_2$CH$_2$O—], —P(O)[—OCH(pyrid-4-yl)CH$_2$CH$_2$O—], —P(O)(OH)(OCH$_3$), —P(O)(OH)(OCH$_2$CH$_3$), —P(O)[—OCH$_2$OC(O)-t-butyl](OCH$_3$), —P(O)[—OCH$_2$OC(O)O-i-propyl](OCH$_3$), —P(O)[—OCH(CH$_3$)OC(O)-t-butyl](OCH$_3$), —P(O)[—OCH(CH$_3$)OC(O)O-i-propyl](OCH$_3$), —P(O)[—N(H)CH(CH$_3$)C(O)OCH$_2$CH$_3$](OCH$_3$), —P(O)[—N(H)C(CH$_3$)$_2$C(O)OCH$_2$CH$_3$](OCH$_3$), and —P(O)(OH)(NH$_2$).

In another aspect, $R^7$ is selected from the group consisting of hydrogen, fluoro, chloro, amino, hydroxyl, and —O—CH$_3$.

In one aspect, G is selected from the group consisting of —O— and —CH$_2$—; T is selected from the group consisting of —(CR$^a_2$)$_n$—, —O(CR$^b_2$)(CR$^a_2$)$_p$—, —N(R$^c$)(CR$^b_2$)(CR$^{a2}$)$_p$—, —S(CR$^b_2$)(CR$^a_2$)$_p$—, —NR$^b$(CO)—, and —CH$_2$CH(NR$^c$R$^b$)$_p$—; $R^1$ and $R^2$ are each independently selected from the group consisting of halogen, —C$_1$-C$_4$ alkyl, —CF$_3$, and cyano; $R^4$ is selected from the group consisting of hydrogen, halogen, —C$_1$-C$_4$ alkyl, cyano and CF$_3$; $R^5$ is selected from the group consisting of —OH, —OC(O)R$^e$, —OC(O)OR$^h$, —F, and —NHC(O)R$^e$; $R^3$ is selected from the group consisting of halogen, optionally substituted —C$_1$-C$_6$ alkyl, —CF$_3$, cyano, —C(O)NR$^f$R$^g$, optionally substituted —(CR$^a_2$)$_n$aryl, —SO$_2$NR$^f$R$^g$, and —SO$_2$R$^e$; R$^7$ is selected from the group consisting of hydrogen, fluoro, chloro, amino, hydroxyl, and —O—CH$_3$; and X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][—OR$^{11}$] and —P(O)[—OCH(V)CH$_2$CH$_2$O—], wherein V is selected from the group consisting of optionally substituted aryl, aryl, heteroaryl, and optionally substituted heteroaryl.

In a further aspect, when G is —O—, T is —CH$_2$—, R$^1$ and R$^2$ are chloro, R$^3$ is iso-propyl, R$^7$ is fluoro, and R$^5$ is —OH, then R$^4$ is not hydrogen. In another aspect, when G is selected from the group consisting of —O— and —CH$_2$—; T is -A-B— where A is selected from the group consisting of —NR$^b$—, —O—, —CH$_2$— and —S— and B is selected from the group consisting of a bond and substituted or unsubstituted C$_1$-C$_3$ alkyl; R$^3$ is selected from the group consisting of halogen, trifluoromethyl, substituted or unsubstituted C$_1$-C$_6$ alkyl, substituted or unsubstituted aryl, substituted or unsubstituted heteroaryl, aryloxy, substituted amide, sulfone, sulfonamide and C$_3$-C$_7$ cycloalkyl, wherein said aryl, heteroaryl or cycloalkyl ring(s) are attached or fused to the aromatic; R$^4$ is selected from the group consisting of hydrogen, halogen, and substituted or unsubstituted C$_1$-C$_4$ alkyl; R$^1$ and R$^2$ are each independently selected from the group consisting of halogen and substituted or unsubstituted —C$_1$-C$_4$ alkyl; and R$^7$ is selected from the group consisting of hydrogen, fluoro, chloro, amino, hydroxyl, and —O—CH$_3$; then R$^5$ is not hydroxyl, optionally substituted —OC$_1$-C$_6$ alkyl, or —OC(O)R$^e$.

In an additional aspect, T is —N(H)C(O)—; R$^1$ and R$^2$ are each independently selected from the group consisting of iodo, bromo, chloro, methyl, and cyano; R$^4$ is selected from the group consisting of hydrogen and iodo; R$^5$ is selected from the group consisting of —OH and —OC(O)R$^e$; R$^3$ is selected from the group consisting of iodo, bromo, optionally substituted —C$_1$-C$_6$ alkyl, optionally substituted —CH$_2$aryl, optionally substituted —CH(OH)aryl, —C(O)-amido, —S(=O)$_2$-amido, wherein the amido group is selected from the group consisting of phenethylamino, piperidinyl, 4-methypiperizinyl, morpholinyl, cyclohexylamino, anilinyl, and indolinyl, and —SO$_2$R$^e$ wherein R$^e$ is selected from the group consisting of phenyl, 4-chlorophenyl, 4-fluorophenyl, and 4-pyridyl; and R$^7$ is selected from the group consisting of hydrogen and fluoro.

In an additional aspect, T is —N(H)C(O)—; G is —O—; R$^1$ and R$^2$ are each chloro; R$^4$ is hydrogen; R$^5$ is —OH; R$^3$ is -iso-propyl; and R$^7$ is fluoro.

In an additional aspect, T is —N(H)C(O)—; G is —O—; R$^1$ and R$^2$ are each chloro; R$^4$ is hydrogen; R$^5$ is —OH; R$^3$ is -iso-propyl; R$^7$ is fluoro; X is selected from the group consisting of —PO$_3$H$_2$, —P(O)[—OCH$_2$OC(O)-t-butyl]$_2$, —P(O)[—OCH$_2$OC(O)O-i-propyl]2, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$] [3,4-methylenedioxyphenyl], —P(O)[—N(H)C(CH$_3$)$_2$C(O)OCH$_2$CH$_3$] [3,4-methylenedioxyphenyl], and —P(O)[—OCH(3-chlorophenyl)CH$_2$CH$_2$O—].

In another aspect, T is —OCH$_2$—; R$^1$ and R$^2$ are each independently selected from the group consisting of iodo, bromo, chloro, methyl, and cyano; R$^4$ is selected from the group consisting of hydrogen and iodo; R$^5$ is selected from the group consisting of —OH, and —OC(O)R$^e$; R$^3$ is selected from the group consisting of iodo, bromo, optionally substituted C$_1$-C$_6$ alkyl, optionally substituted —CH$_2$aryl, optionally substituted —CH(OH)aryl, —C(O)-amido, —S(=O)$_2$-amido wherein the amido group is selected from the group consisting of phenethylamino, piperidinyl, 4-methylpiperiz-inyl, morpholinyl, cyclohexylamino, anilinyl, and indolinyl, and —SO$_2$R$^e$ wherein R$^e$ is selected from the group consisting of phenyl, 4-chlorophenyl, 4-fluorophenyl, and 4-pyridyl; and R$^7$ is selected from the group consisting of hydrogen and fluoro.

In another aspect, T is —OCH$_2$—; G is —O—; R$^1$ and R$^2$ are each chloro; R$^4$ is hydrogen; R$^5$ is —OH; R$^3$ is iso-propyl; and R$^7$ is fluoro.

In another aspect, T is —OCH$_2$—; G is —O—; R$^1$ and R$^2$ are each chloro; R$^4$ is hydrogen; R$^5$ is —OH; R$^3$ is iso-propyl; R$^7$ is fluoro; and X is selected from the group consisting of —PO$_3$H$_2$, —P(O)[—OCH$_2$OC(O)-t-butyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$] [3,4-methylenedioxyphenyl], —P(O)[—N(H)C(CH$_3$)$_2$C(O)OCH$_2$CH$_3$] [3,4-methylenedioxyphenyl], and —P(O)[—OCH(3-chlorophenyl)CH$_2$CH$_2$O—].

In an additional aspect, T is —CH$_2$—; R$^1$ and R$^2$ are each independently selected from the group consisting of iodo, bromo, chloro, methyl, and cyano; R$^4$ is selected from the group consisting of hydrogen and iodo; R$^5$ is selected from the group consisting of —OH, and —OC(O)R$^e$; R$^3$ is selected from the group consisting of iodo, bromo, optionally substituted C$_1$-C$_6$ alkyl, optionally substituted —CH$_2$aryl, optionally substituted —CH(OH)aryl, —C(O)-amido, —S(=O)$_2$-amido, wherein the amido group is selected from the group consisting of phenethylamino, piperidinyl, 4-methylpiperiz-inyl, morpholinyl, cyclohexylamino, anilinyl, and indolinyl, and —SO$_2$R$^e$ wherein R$^e$ is selected from the group consisting of phenyl, 4-chlorophenyl, 4-fluorophenyl, and 4-pyridyl; and R$^7$ is selected from the group consisting of hydrogen and fluoro.

In an additional aspect, T is —CH$_2$—; G is —O—; R$^1$ and R$^2$ are each chloro; R$^4$ is hydrogen; R$^5$ is —OH; R$^3$ is i-propyl; and R$^7$ is fluoro.

In an additional aspect, T is —CH$_2$—; G is —O—; R$^1$ and R$^2$ are each chloro; R$^4$ is hydrogen; R$^5$ is —OH; R$^3$ is i-propyl; R$^7$ is fluoro; and X is selected from the group consisting of —PO$_3$H$_2$, —P(O)[—OCH$_2$OC(O)-t-butyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$] [3,4-methylenedioxyphenyl], —P(O)[—N(H)C(CH$_3$)$_2$C(O)OCH$_2$CH$_3$] [3,4-methylenedioxyphenyl], and —P(O)[—OCH(3-chlorophenyl)CH$_2$CH$_2$O—].

In a further aspect, T is —CH$_2$CH$_2$—; R$^1$ and R$^2$ are each independently selected from the group consisting of iodo, bromo, chloro, methyl, and cyano; R$^4$ is selected from the group consisting of hydrogen and iodo; R$^5$ is selected from the group consisting of —OH and —OC(O)R$^e$; R$^3$ is selected from the group consisting of iodo, bromo, optionally substituted C$_1$-C$_6$ alkyl, optionally substituted —CH$_2$aryl, optionally substituted —CH(OH)aryl, —C(O)-amido, —S(=O)$_2$-amido, wherein the amido group is selected from the group consisting of phenethylamino, piperidinyl, 4-methylpiperiz-inyl, morpholinyl, cyclohexylamino, anilinyl, and indolinyl, and —SO$_2$R$^e$ wherein R$^e$ is selected from the group consisting of phenyl, 4-chlorophenyl, 4-fluorophenyl, and 4-pyridyl; and R$^7$ is selected from the group consisting of hydrogen and fluoro.

In another aspect, T is —CH$_2$CH$_2$—; G is —O—; R$^1$ and R$^2$ are each chloro; R$^4$ is hydrogen; R$^5$ is —OH; R$^3$ is iso-propyl; and R$^7$ is fluoro.

In another aspect, T is —CH$_2$CH$_2$—; G is —O—; R$^1$ and R$^2$ are each chloro; R$^4$ is hydrogen; R$^5$ is —OH; R$^3$ is iso-propyl; R$^7$ is fluoro; and X is selected from the group consisting of —PO$_3$H$_2$, —P(O)[—OCH$_2$OC(O)-t-butyl]$_2$, —P(O)

[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$] [3,4-methylenedioxyphenyl], —P(O)[—N(H)C(CH$_3$)$_2$C(O)OCH$_2$CH$_3$] [3,4-methylenedioxyphenyl], and —P(O)[—OCH(3-chlorophenyl)CH$_2$CH$_2$O—].

In another aspect, T is —NHCH$_2$—; R$^1$ and R$^2$ are each independently selected from the group consisting of iodo, bromo, chloro, methyl, and cyano; R$^4$ is selected from the group consisting of hydrogen and iodo; R$^5$ is selected from the group consisting of —OH, and —OC(O)R$^e$; R$^3$ is selected from the group consisting of iodo, bromo, optionally substituted C$_1$-C$_6$ alkyl, optionally substituted —CH$_2$aryl, optionally substituted —CH(OH)aryl, —C(O)-amido, —S(=O)$_2$-amido, wherein the amido group is selected from the group consisting of phenethylamino, piperidinyl, 4-methylpiperizinyl, morpholinyl, cyclohexylamino, anilinyl, and indolinyl, and —SO$_2$R$^e$ wherein R$^e$ is selected from the group consisting of phenyl, 4-chlorophenyl, 4-fluorophenyl, and 4-pyridyl; and R$^7$ is selected from the group consisting of hydrogen and fluoro.

In yet another aspect, T is —NHCH$_2$—; G is —O—; R$^1$ and R$^2$ are each chloro; R$^4$ is selected from the group consisting of hydrogen and iodo R$^5$ is —OH; R$^3$ is iso-propyl; and R$^7$ is fluoro.

In another aspect, T is —NHCH$_2$—; G is —O—; R$^1$ and R$^2$ are each bromo; R$^4$ is selected from the group consisting of hydrogen and iodo R$^5$ is —OH; R$^3$ is iso-propyl; and R$^7$ is fluoro.

In another aspect, T is —NHCH$_2$—; G is —O—; R$^1$ and R$^2$ are each bromo; R$^4$ is selected from the group consisting of hydrogen and iodo R$^5$ is —OH; R$^3$ is iso-propyl; R$^7$ is fluoro; and X is selected from the group consisting of —PO$_3$H$_2$, —P(O)[—OCH$_2$OC(O)-t-butyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$] [3,4-methylenedioxyphenyl], —P(O)[—N(H)C(CH$_3$)$_2$C(O)OCH$_2$CH$_3$] [3,4-methylenedioxyphenyl], and —P(O)[—OCH(3-chlorophenyl)CH$_2$CH$_2$O—].

In one aspect, G is —O—; T is —CH$_2$CH(NH$_2$)—; R$^1$ and R$^2$ are each chloro; R$^4$ and R$^8$ are selected from the group consisting of hydrogen and iodo; R$^5$ is —OH; and R$^3$ is iodo. In another aspect, G is —O—; T is —N(H)C(O)—; R$^1$ and R$^2$ are each chloro; R$^4$ and R$^8$ are hydrogen; R$^5$ is —OH; and R$^3$ is —CH$_2$(4-fluorophenyl). In a further aspect, G is —O—; T is —OCH$_2$—; R$^1$ and R$^2$ are each methyl; R$^4$ and R$^8$ are hydrogen; R$^5$ is —OH; and R$^3$ is iso-propyl. In an additional aspect, G is —O—; T is —CH$_2$—; R$^1$ and R$^2$ are each chloro; R$^4$ and R$^8$ are hydrogen; R$^5$ is —OH; and R$^3$ is iso-propyl. In another aspect, G is —O—; T is —CH$_2$CH$_2$—; R$^1$ and R$^2$ are each chloro; R$^4$ and R$^8$ are hydrogen; R$^5$ is —OH; and R$^3$ is iso-propyl.

In another aspect, X is —P(O)YR$^{11}$Y'R$^{11}$ wherein Y and Y' are each independently selected from —O— and —NR$^v$—; together R$^{11}$ and R$^{11}$ are the group:

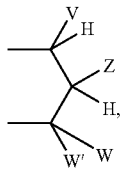

wherein

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkylthiocarbonyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus; or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus; or together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl; or or together W and W' are connected via an additional 2-5 atoms to form a cyclic group, wherein O$_2$ atoms are heteroatoms and the remaining atoms are carbon, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH=CR$^z$$_2$)OH, —CH(C≡CR$^z$)OH, —R$^z$, —NR$^z$$_2$, —OCOR$^y$, —OCO$_2$R$^y$, —SCOR$^y$, —SCO$_2$R$^y$, —NHCOR$^z$, —NHCO$_2$R$^y$, —CH$_2$NHaryl, —(CH$_2$)$_q$—OR$^z$, and —(CH$_2$)$_q$—SR$^z$;

q is an integer 2 or 3;

with the provisos that:
a) V, Z, W, W' are not all —H; and
b) when Z is —R$^z$, then at least one of V, W, and W' is not —H, alkyl, aralkyl, or heterocycloalkyl;

Each R$^z$ is selected from the group consisting of R$^y$ and —H;

Each R$^y$ is selected from the group consisting of alkyl, aryl, heterocycloalkyl, and aralkyl; and Each R$^v$ is selected from the group consisting of —H, lower alkyl, acyloxyalkyl, alkoxycarbonyloxyalkyl, and lower acyl.

In one aspect, V is optionally substituted aryl. In another aspect, V is selected from the group consisting of 3-chlorophenyl, 4-chlorophenyl, 3-bromophenyl, 3-fluorophenyl, pyrid-4-yl, pyrid-3-yl and 3,5-dichlorophenyl.

In one aspect, the relative stereochemistry between the V-group substituent and T on the dioxaphosphonane ring is cis. In another aspect, the cis dioxaphosphonane ring has R stereochemistry at the carbon where V is attached. In another aspect, the cis dioxaphosphonane ring has S stereochemistry at the carbon where V is attached.

In one aspect R$^{11}$ is not hydrogen.

In one aspect, X is —P(O)YR$^{11}$Y'', wherein Y'' is —C$_1$-C$_6$ alkyl. In one aspect, Y'' is selected from the group consisting of methyl, ethyl, propyl, isopropyl, butyl, isobutyl, and tert-butyl. In another aspect, X is PO$_2$H$_2$, P(O)(OH)(R$^z$), —P(O)

[—OCR$^z_2$OC(O)R$^y$](R$^z$), —P(O)[—OCR$^z_2$OC(O)OR$^y$](R$^z$), —P(O)[—N(H)CR$^z_2$C(O)OR$^y$](R$^z$), —P(O)[—N(H)CR$^z_2$C(O)OR$^y$][—OR$^{11}$], or —P(O)(OH)[—N(H)CR$^z_2$C(O)OR$^y$].

In a further aspect, X is —P(O)(OH)(CH$_3$), —P(O)(OH)(CH$_2$CH$_3$), —P(O)(OH)(isopropyl), or —P(O)(OH)(t-butyl).

In a further aspect, X is —PO$_3$H$_2$.

In one aspect, the invention relates to a compound of Formula VIII:

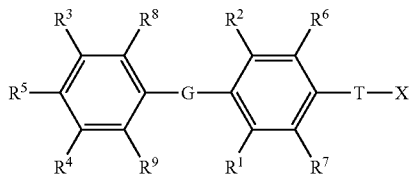

wherein:

G is selected from the group consisting of —O—, —S—, —Se—, —S(=O)—, —S(=O)$_2$—, —Se—, —CH$_2$—, —CF$_2$—, —CHF—, —C(O)—, —CH(OH)—, —CH(C$_1$-C$_4$ alkyl)-, —CH(C$_1$-C$_4$ alkoxy)-, —C(=CH$_2$)—, —NH—, and —N(C$_1$-C$_4$ alkyl)-, or CH$_2$ linked to any of the preceding groups;

T is selected from the group consisting of —(CR$^a_2$)$_k$—, —CR$^b$=CR$^b$—(CR$^a_2$)$_n$—, —(CR$^a_2$)$_n$—, —CR$^b$=CR$^b$—, (CR$^a_2$)—CR$^b$=CR$^b$—(CR$^a_2$)—, —O(CR$^b_2$)(CR$^a_2$)$_n$, —S(CR$^b_2$)(CR$^a_2$)$_n$—, —N(R$^c$)(CR$^b_2$)(CR$^a_2$)$_n$—, —N(R$^b$)C(O)(CR$^a_2$)$_n$—, (CR$^a_2$)$_n$CH(NR$^b$R$^c$)—, —C(O)(CR$^a_2$)$_m$—, —(CR$^a_2$)$_m$C(O)—, —(CR$^a_2$)C(O)(CR$^a_2$)$_n$—, —(CR$^a_2$)$_n$C(O)(CR$^a_2$)—, —C(O)NH(CR$^b_2$)(CR$^a_2$)$_p$—, and —(CH$_2$)$_n$C(O)N(R$^b$)C(R$^a_2$)$_2$—;

k is an integer from 0-4;
m is an integer from 0-3;
n is an integer from 0-2;
p is an integer from 0-1;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and optionally substituted —C$_1$-C$_4$ alkyl;

Each R$^c$ is independently selected from the group consisting of hydrogen and optionally substituted —C$_1$-C$_4$ alkyl, optionally substituted —C(O)—C$_1$-C$_4$ alkyl, and —C(O)H;

R$^1$, R$^2$, R$^6$, and R$^7$ are each independently selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano; with the proviso that at least one of R$^1$ and R$^2$ is not hydrogen;

R$^8$ and R$^9$ are each independently selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a_2$)aryl, C(O)aryl, C(O)alkyl and cyano;

or R$^6$ and T are taken together along with the carbons they are attached to form an optionally substituted ring of 5 to 6 atoms with 0-2 unsaturations, not including the unsaturation on the ring to which R$^3$ and R$^5$ are attached, including 0 to 2 heteroatoms independently selected from —NR$^i$—, —O—, and —S—, with the proviso that when there are 2 heteroatoms in the ring and both heteroatoms are different than nitrogen then both heteroatoms have to be separated by at least one carbon atom; and X is attached to this ring by a direct bond to a ring carbon, or by —(CR$^a_2$)— or —C(O)— bonded to a ring carbon or a ring nitrogen;

R$^i$ is selected from the group consisting of hydrogen, —C(O)C$_1$-C$_4$ alkyl, —C$_1$-C$_4$ alkyl, and —C$_1$-C$_4$-aryl; or R$^1$ and R$^7$ are taken together along with the carbons to which they are attached to form an optionally substituted ring of 5 to 6 atoms with 0-2 unsaturations, not including the unsaturation on the ring to which R$^1$ and R$^7$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_m$aryl, optionally substituted —(CR$^a_2$)$_m$cycloalkyl, optionally substituted —(CR$^a_2$)$_m$heterocycloalkyl, —OR$^d$, —SR$^d$, —S(=O)R$^e$, —S(=O)$_2$R$^e$, —S(=O)$_2$NR$^f$R$^g$, —C(O)NR$^f$R$^g$, —C(O)OR$^h$, —C(O)R$^e$, —N(R$^b$)C(O)R$^e$, —N(R$^b$)C(O)NR$^f$R$^g$, —N(O)S(=O)$_2$R$^e$, —N(O)S(=O)$_2$NR$^f$R$^g$, and —NR$^f$R$^g$;

Each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, optionally substituted —(CR$^b_2$)$_n$heterocycloalkyl, and —C(O)NR$^f$R$^g$;

Each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_n$aryl, optionally substituted —(CR$^a_2$)$_n$cycloalkyl, and optionally substituted —(CR$^a_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl, or R$^f$ and R$^g$ may together form an optionally substituted heterocyclic ring, said heterocyclic ring may contain a second heterogroup within the ring selected from the group consisting of O, NR$^e$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl; or R$^3$ and R$^8$ are taken together along with the carbon atoms to which they are attached to form an optionally substituted ring of 5 to 6 atoms with 0-2 unsaturations, not including the unsaturation on the ring to which R$^3$ and R$^8$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom; or R$^8$ and G are taken together along with the carbon atoms to which they are attached to form an optionally substituted ring comprising —CH=CH—CH=, —N=CH—CH=, —CH=N—CH= or —CH=CH—N=;

R$^5$ is selected from the group consisting of —OH, optionally substituted —OC$_1$-C$_6$ alkyl, —OC(O)R$^e$, —OC(O)OR$^h$, —F, —NHC(O)R$^e$, —NHS(=O)R$^e$, —NHS(=O)$_2$R$^e$, —NHC(=S)NH(R$^h$), and —NHC(O)NH(R$^h$); or R$^3$ and R$^5$ are taken together along with the carbons they are attached to form an optionally substituted ring of 5 to 6 atoms with 0-2 unsaturations, not including the unsaturation on the ring to which R$^3$ and R$^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

X is P(O)YR$^{11}$Y'R$^{11}$;

Y and Y' are each independently selected from the group consisting of —O—, and —NR$^v$—;

when Y and Y' are both —O—, R$^{11}$ attached to —O— is independently selected from the group consisting of —H, alkyl, optionally substituted aryl, optionally substituted heterocycloalkyl, optionally substituted CH$_2$-heterocycloalkyl wherein the cyclic moiety contains a carbonate or thiocarbonate, optionally substituted -alkylaryl, —C(R$^z$)$_2$OC(O)NR$^z$$_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy;

when Y and Y' are both —NR$^v$—, then R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

when Y is —O— and Y' is NR$^v$, then R$^{11}$ attached to —O— is independently selected from the group consisting of —H, alkyl, optionally substituted aryl, optionally substituted heterocycloalkyl, optionally substituted CH$_2$-heterocycloalkyl wherein the cyclic moiety contains a carbonate or thiocarbonate, optionally substituted -alkylaryl, —C(R$^z$)$_2$OC(O)NR$^z$$_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy; and R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

but if both R$^{11}$ are alkyl, at least one is higher alkyl;

and both R$^{11}$ are not —H; or when Y and Y' are independently selected from —O— and —NR$^v$—, then R$^{11}$ and R$^{11}$ together form a cyclic group comprising -alkyl-S-S-alkyl-, or together R$^{11}$ and R$^{11}$ are the group:

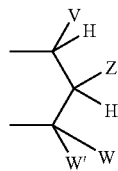

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl; or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon or carbon substituted by hydrogen, and said cyclic group is fused to an aryl group at the beta and gamma position to the Y attached to the phosphorus; or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus; or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or together W and W' are connected via an additional 2-5 atoms to form a cyclic group, wherein 0-2 atoms are heteroatoms and the remaining atoms are carbon or carbon substituted by hydrogen, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CH$^z$OC(S)OR$^y$, —CHR$^z$OC(O)SR$^y$, —CH$^z$OCO$_2$R$^y$, —OR$^z$, —SR$^z$, —CHR$^z$N$_3$, —CH$_2$aryl, —CH(aryl)OH, —CH(CH=CR$^z$$_2$)OH, —CH(C≡CR$^z$)OH, —R$^z$, —NR$^z$$_2$, —OCOR$^y$, —OCO$_2$R$^y$, —SCOR$^y$, —SCO$_2$R$^y$, —NHCOR$^z$, —NHCO$_2$R$^y$, —C H$_2$NHaryl, —(CH$_2$)$_q$—OR$^z$, and —(CH$_2$)$_q$—SR$^z$;

q is an integer 2 or 3;

Each R$^z$ is selected from the group consisting of R$^y$ and —H;

Each R$^y$ is selected from the group consisting of alkyl, aryl, heterocycloalkyl, and aralkyl;

Each R$^x$ is independently selected from the group consisting of —H, and alkyl, or together R$^x$ and R$^x$ form a cycloalkyl group;

Each R$^v$ is selected from the group consisting of —H, lower alkyl, acyloxyalkyl, alkoxycarbonyloxyalkyl, and lower acyl;

with the provisos that:

a) V, Z, W, W' are not all —H; and b) when Z is —R$^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In another aspect, the invention relates to a compound of Formula VIII:

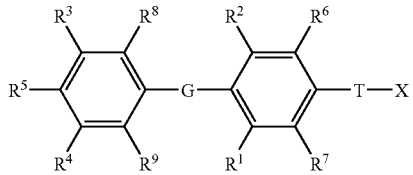

wherein:

G is selected from the group consisting of —O—, —S—, —Se—, —S(=O)—, —S(=O)$_2$—, —Se—, —CH$_2$—, —CF$_2$—, —CHF—, —C(O)—, —CH(OH)—, —CH(C$_1$-C$_4$ alkyl)-, —CH(C$_1$-C$_4$ alkoxy)-, —C(=CH$_2$)—, —NH—, and —N(C$_1$-C$_4$ alkyl)-, or CH$_2$ linked to any of the preceding groups;

T is selected from the group consisting of —(CR$^a_2$)$_k$—, —CR$^b$=CR$^b$—(CR$^a_2$)$_n$—, (CR$^a_2$)$_n$—CR$^b$=CR$^b$—, (CR$^a_2$)—CR$^b$=CR$^b$—(CR$^a_2$)—, —O(CR$^b_2$)(CR$^a_2$)$_n$—, —S(CR$^b_2$)(CR$^a_2$)$_n$—, —N(R$^c$)(CR$^b_2$)(CR$^a_2$)$_n$—, —N(R$^b$)C(O)(CR$^a_2$)$_n$—, —(CR$^a_2$)$_n$CH(NR$^b$R$^c$)—, —C(O)(CR$^a_2$)$_m$—, —(CR$^a_2$)$_m$C(O)—, —(CR$^a_2$)C(O)(CR$^a_2$)$_n$—, —(CR$^a_2$)$_n$C(O)(CR$^a_2$)—, —C(O)NH(CR$^b_2$)(CR$^a_2$)$_p$—, and —(CH$_2$)$_n$C(O)N(R$^b$)C(R$^a$)$_2$—;

k is an integer from 0-4;
m is an integer from 0-3;
n is an integer from 0-2;
p is an integer from 0-1;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and optionally substituted —C$_1$-C$_4$ alkyl;

Each R$^c$ is independently selected from the group consisting of hydrogen and optionally substituted —C$_1$-C$_4$ alkyl, optionally substituted —C(O)—C$_1$-C$_4$ alkyl, and —C(O)H;

R$^1$, R$^2$, R$^6$, and R$^7$ are each independently selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano; with the proviso that at least one of R$^1$ and R$^2$ is not hydrogen;

R$^8$ and R$^9$ are each independently selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a_2$)aryl, C(O)aryl, C(O)alkyl and cyano;

or R$^6$ and T are taken together along with the carbons they are attached to form an optionally substituted ring of 5 to 6 atoms with 0-2 unsaturations, not including the unsaturation on the ring to which R$^3$ and R$^5$ are attached, including 0 to 2 heteroatoms independently selected from —NR$^i$—, —O—, and —S—, with the proviso that when there are 2 heteroatoms in the ring and both heteroatoms are different than nitrogen then both heteroatoms have to be separated by at least one carbon atom; and X is attached to this ring by a direct bond to a ring carbon, or by —(CR$^a_2$)— or —C(O)— bonded to a ring carbon or a ring nitrogen;

R$^i$ is selected from the group consisting of hydrogen, —C(O)C$_1$-C$_4$ alkyl, —C$_1$-C$_4$ alkyl, and —C$_1$-C$_4$-aryl; or R$^1$ and R$^7$ are taken together along with the carbons to which they are attached to form an optionally substituted ring of 5 to 6 atoms with 0-2 unsaturations, not including the unsaturation on the ring to which R$^1$ and R$^7$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_n$aryl, optionally substituted —(CR$^a_2$)$_n$cycloalkyl, optionally substituted —(CR$^a_2$)$_n$heterocycloalkyl, —OR$^d$, —SR$^d$, —S(=O)R$^e$, —S(=O)$_2$R$^e$, —S(=O)$_2$NR$^f$R$^g$, —C(O)NR$^f$R$^g$, —C(O)OR, —C(O)R$^e$, —N(R$^b$)C(O)R$^e$, —N(R$^b$)C(O)NR$^f$R$^g$, —N(R$^b$) S(=O)S(=)$_2$NR$^f$R$^g$, and —NR$^f$R$^g$;

Each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(C$_1$-C$_{12}$)$_n$ cycloalkyl, optionally substituted —(CR$^b_2$)$_n$heterocloalkyl, and —C(O)NR$^f$R$^g$;

Each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_n$aryl, optionally substituted —(CR$^a_2$)$_n$cycloalkyl, and optionally substituted —(CR$^a_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl, or R$^f$ and R$^g$ may together form an optionally substituted heterocyclic ring, said heterocyclic ring may contain a second heterogroup within the ring selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl; or R$^3$ and R$^8$ are taken together along with the carbon atoms to which they are attached to form an optionally substituted ring of 5 to 6 atoms with 0-2 unsaturations, not including the unsaturation on the ring to which R$^3$ and R$^8$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom; or R$^8$ and G are taken together along with the carbon atoms to which they are attached to form an optionally substituted ring comprising —CH=CH—CH=, —N=CH—CH=, —CH=N—CH= or —CH=CH—N=;

$R^5$ is selected from the group consisting of —OH, optionally substituted —$OC_1$-$C_6$ alkyl, —OC(O)$R^e$, —OC(O)$OR^h$, —F, —NHC(O)$R^e$, —NHS(=O)$R^e$, —NHS(=O)$_2R^e$, —NHC(=S)NH($R^h$), and —NHC(O)NH($R^h$); or $R^3$ and $R^5$ are taken together along with the carbons they are attached to form an optionally substituted ring of 5 to 6 atoms with 0-2 unsaturations, not including the unsaturation on the ring to which $R^3$ and $R^5$ are attached, including 0 to 2 heteroatoms independently selected from —$NR^h$—, —O—, and —S—, with the proviso that when there are 2 heteroatoms in the ring and both heteroatoms are different than nitrogen then both heteroatoms have to be separated by at least one carbon atom;

X is P(O)Y$R^{11}$Y'$R^{11}$;

Y and Y' are each independently selected from the group consisting of —O—, and —$NR^v$—;

when Y and Y' are both —O—, $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —C($R^z$)$_2$OC(O)$NR^z_2$, —$NR^z$—C(O)—$R^y$, —C($R^z$)$_2$—OC(O)$R^y$, —C($R^z$)$_2$—O—C(O)$OR^y$, —C($R^z$)$_2$OC(O)$SR^y$, -alkyl-S—C(O)$R^y$, -alkyl-S-S-alkylhydroxy, and -alkyl-S-S-S-alkylhydroxy;

when Y and Y' are both —$NR^v$—, then $R^{11}$ attached to —$NR^v$— is independently selected from the group consisting of —H, —[C($R^z$)$_2$]$_q$—COO$R^y$, —C($R^x$)$_2$COO$R^y$, —[C($R^z$)$_2$]$_q$—C(O)$SR^y$, and -cycloalkylene-COO$R^y$;

when Y is —O— and Y' is $NR^v$, then $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —C($R^z$)$_2$OC(O)$NR^z_2$, —$NR^z$—C(O)—$R^y$, —C($R^z$)$_2$—OC(O)$R^y$, —C($R^z$)$_2$—O—C(O)$OR^y$, —C($R^z$)$_2$OC(O)$SR^y$, -alkyl-S—C(O)$R^y$, -alkyl-S-S-alkylhydroxy, and -alkyl-S-S-S-alkylhydroxy; and $R^{11}$ attached to —$NR^v$— is independently selected from the group consisting of —H, —[C($R^z$)$_2$]$_q$—COO$R^y$, —C($R^x$)$_2$COO$R^y$, —[C($R^z$)$_2$]$_q$—C(O)$SR^y$, and -cycloalkylene-COO$R^y$; or when Y and Y' are independently selected from —O— and —$NR^v$—, then $R^{11}$ and $R^{11}$ together form a cyclic group comprising -alkyl-S-S-alkyl-, or together $R^{11}$ and $R^{11}$ are the group:

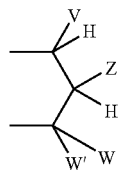

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl; or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon or carbon substituted by hydrogen, and said cyclic group is fused to an aryl group at the beta and gamma position to the Y attached to the phosphorus; or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus; or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or together W and W' are connected via an additional 2-5 atoms to form a cyclic group, wherein 0-2 atoms are heteroatoms and the remaining atoms are carbon or carbon substituted by hydrogen, and V must be aryl, substituted aryl, heteroaryl, or substituted heteroaryl;

Z is selected from the group consisting of —CH$R^z$OH, —CH$R^z$OC(O)$R^y$, —CH$R^z$OC(S)$R^y$, —CH$R^z$OC(S)$OR^y$, —CH$R^z$OC(O)$SR^y$, —CH$R^z$OCO$_2R^y$, —O$R^z$, —S$R^z$, —CH$^z N_3$, —$CH_2$aryl, —CH(aryl)OH, —CH(CH=C$R^z_2$)OH, —CH(C≡C$R^z$)OH, —$R^z$, —$NR^z_2$, —OCO$R^y$, —OCO$_2R^y$, —SCO$R^y$, —SCO$_2R^y$, —NHCO$R^z$, —NHCO$_2R^y$, —$CH_2$NHaryl, —($CH_2$)$_q$—O$R^z$, and —($CH_2$)$_q$—S$R^z$;

q is an integer 2 or 3;

Each $R^z$ is selected from the group consisting of $R^y$ and —H;

Each $R^y$ is selected from the group consisting of alkyl, aryl, heterocycloalkyl, and aralkyl;

Each $R^x$ is independently selected from the group consisting of —H, and alkyl, or together $R^x$ and $R^x$ form a cycloalkyl group;

Each $R^v$ is selected from the group consisting of —H, lower alkyl, acyloxyalkyl, alkoxycarbonyloxyalkyl, and lower acyl;

with the provisos that:

a) when G is —O—, T is —$CH_2$—, $R^1$ and $R^2$ are each chloro, $R^3$ is phenyl, $R^4$ is hydrogen, and $R^5$ is —OH, then X is not P(O)(OH)(OCH$_2$CH$_3$);

b) when G is —O—, T is —$CH_2$—, $R^1$ and $R^2$ are each bromo, $R^3$ is iso-propyl, $R^4$ is hydrogen, and $R^5$ is —OH, then X is not P(O)(OH)$_2$ or P(O)(OCH$_2$CH$_3$)$_2$;

c) V, Z, W, W' are not all —H; and d) when Z is —$R^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In a further aspect, the invention relates to a compound of Formula VIII:

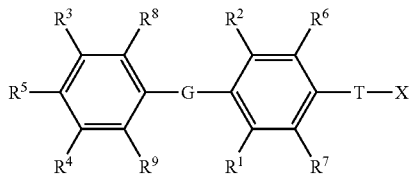

wherein:

G is selected from the group consisting of —O—, —S—, —Se—, —S(=O)—, —S(=O)$_2$—, —Se—, —CH$_2$—, —CF$_2$—, —CHF—, —C(O)—, —CH(OH)—, —CH(C$_1$-C$_4$ alkyl)-, —CH(C$_1$-C$_4$ alkoxy)-, —C(=CH$_2$)—, —NH—, and —N(C$_1$-C$_4$ alkyl)-, or CH$_2$ linked to any of the preceding groups;

T is selected from the group consisting of —(CR$^a_2$)$_k$—, —CR$^b$=CR$^b$—(CR$^a_2$)$_n$—, —(CR$^a_2$)$_n$—CR$^b$=CR$^b$—, —(CR$^a_2$)—CR$^b$=CR$^b$—(CR$^a_2$)—, —O(CR$^b_2$)(CR$^a_2$)$_n$—, —S(CR$^b_2$)(CR$^a_2$)$_n$—, —N(R$^c$)(CR$^b_2$)(CR$^a_2$)$_n$—, —N(R$^b$)C(O)(CR$^a_2$)$_n$—, —(CR$^a_2$)$_n$CH(NR$^b$R$^c$)—, —C(O)(CR$^a_2$)$_m$—, —(CR$^a_2$)$_m$C(O)—, —(CR$^a_2$)C(O)(CR$^a_2$)$_n$—, —(CR$^a_2$)$_n$C(O)(CR$^a_2$)—, —C(O)NH(CR$^b_2$)(CR$^a_2$)$_p$—, and —(CH$_2$)$_n$C(O)N(R$^b$)C(R$^a_2$)$_2$—;

k is an integer from 0-4;
m is an integer from 0-3;
n is an integer from 0-2;
p is an integer from 0-1;

Each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$-C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

Each R$^b$ is independently selected from the group consisting of hydrogen and optionally substituted —C$_1$-C$_4$ alkyl;

Each R$^c$ is independently selected from the group consisting of hydrogen and optionally substituted —C$_1$-C$_4$ alkyl, optionally substituted —C(O)—C$_1$-C$_4$ alkyl, and —C(O)H;

R$^1$, R$^2$, R$^6$, and R$^7$ are each independently selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano; with the proviso that at least one of R$^1$ and R$^2$ is not hydrogen;

R$^8$ and R$^9$ are each independently selected from the group consisting of hydrogen, halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, hydroxy, (CR$^a_2$)aryl, C(O)aryl, C(O)alkyl and cyano;

or R$^6$ and T are taken together along with the carbons they are attached to form an optionally substituted ring of 5 to 6 atoms with 0-2 unsaturations, not including the unsaturation on the ring to which R$^3$ and R$^5$ are attached, including 0 to 2 heteroatoms independently selected from —NR$^i$—, —O—, and —S—, with the proviso that when there are 2 heteroatoms in the ring and both heteroatoms are different than nitrogen then both heteroatoms have to be separated by at least one carbon atom; and X is attached to this ring by a direct bond to a ring carbon, or by —(CR$^a_2$)— or —C(O)— bonded to a ring carbon or a ring nitrogen;

R$^i$ is selected from the group consisting of hydrogen, —C(O)C$_1$-C$_4$ alkyl, —C$_1$-C$_4$ alkyl, and —C$_1$-C$_4$-aryl; or R$^1$ and R$^7$ are taken together along with the carbons to which they are attached to form an optionally substituted ring of 5 to 6 atoms with 0-2 unsaturations, not including the unsaturation on the ring to which R$^1$ and R$^7$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_n$aryl, optionally substituted —(CR$^a_2$)$_n$cycloalkyl, optionally substituted —(CR$^a_2$)$_n$heterocycloalkyl, —OR$^d$, —SR$^d$, —S(=O)R$^e$, —S(=O)$_2$R$^e$, —S(=O)$_2$NR$^f$R$^g$, —C(O)NR$^f$R$^g$, —C(O)OR$^h$, —C(O)R$^e$, —N(R$^b$)C(O)R$^e$, —N(R$^b$)C(O)NR$^f$R$^g$, —N(R$^b$)S(=O)$_2$R$^e$, —N(R$^b$)S(=O)$_2$NR$^f$R$^g$, and —NR$^f$R$^g$;

Each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, optionally substituted —(CR$^b_2$)$_n$heterocycloalkyl, and —C(O)NR$^f$R$^g$;

Each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a_2$)$_n$aryl, optionally substituted —(CR$^a_2$)$_n$cycloalkyl, and optionally substituted —(CR$^a_2$)$_n$heterocycloalkyl;

R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl, or R$^f$ and R$^g$ may together form an optionally substituted heterocyclic ring, said heterocyclic ring may contain a second heterogroup within the ring selected from the group consisting of O, NR$^c$, and S, wherein said optionally substituted heterocyclic ring may be substituted with 0-4 substituents selected from the group consisting of optionally substituted —C$_1$-C$_4$ alkyl, —OR$^b$, oxo, cyano, —CF$_3$, optionally substituted phenyl, and —C(O)OR$^h$;

Each R$^h$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b_2$)$_n$aryl, optionally substituted —(CR$^b_2$)$_n$cycloalkyl, and optionally substituted —(CR$^b_2$)$_n$heterocycloalkyl; or R$^3$ and R$^8$ are taken together along with the carbon atoms to which they are attached to form an optionally substituted ring of 5 to 6 atoms with 0-2 unsaturations, not including the unsaturation on the ring to which R$^3$ and R$^8$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom; or R$^8$ and G are taken together along with the carbon atoms to which they are attached to form an optionally substituted ring comprising —CH═CH—CH═, —N═CH—CH═, —CH═N—CH═ or —CH═CH—N═;

$R^5$ is selected from the group consisting of —OH, optionally substituted —OC$_1$-C$_6$ alkyl, —OC(O)R$^e$, —OC(O)OR$^h$, —F, —NHC(O)R$^e$, —NHS(═O)R$^e$, —NHS(═O)$_2$R$^e$, —NHC(═S)NH(R$^h$), and —NHC(O)NH(R$^h$); or $R^3$ and $R^5$ are taken together along with the carbons they are attached to form an optionally substituted ring of 5 to 6 atoms with 0-2 unsaturations, not including the unsaturation on the ring to which $R^3$ and $R^5$ are attached, including 0 to 2 heteroatoms independently selected from —NR$^h$—, —O—, and —S—, with the proviso that when there are 2 heteroatoms in the ring and both heteroatoms are different than nitrogen then both heteroatoms have to be separated by at least one carbon atom;

X is P(O)YR$^{11}$Y'R$^{11}$;

Y and Y' are each independently selected from the group consisting of —O—, and —NR$^v$—;

when Y and Y' are both —O—, R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR$^z_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy;

when Y and Y' are both —NR$^v$—, then R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;

when Y is —O— and Y' is NR$^v$, then R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR$^z_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S-S-alkylhydroxy, and -alkyl-S-S-S-alkylhydroxy; and R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$; or when Y and Y' are independently selected from —O— and —NR$^v$—, then R$^{11}$ and R$^{11}$ together form a cyclic group comprising -alkyl-S-S-alkyl-, or together R$^{11}$ and R$^{11}$ are the group:

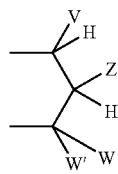

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl; or together V and Z are connected via an additional 3-5 atoms to form a cyclic group containing 5-7 atoms, wherein 0-1 atoms are heteroatoms and the remaining atoms are carbon, substituted with hydrogen, hydroxy, acyloxy, alkylthiocarbonyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon or carbon substituted by hydrogen, and said cyclic group is fused to an aryl group at the beta and gamma position to the Y attached to the phosphorus; or together V and W are connected via an additional 3 carbon atoms to form an optionally substituted cyclic group containing 6 carbon atoms or carbon substituted by hydrogen and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus; or together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or together W and W' are connected via an additional 2-5 atoms to form a cyclic group, wherein 0-2 atoms are heteroatoms and the remaining atoms are carbon or carbon substituted by hydrogen, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CH$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH═CR$^z_2$)OH, —CH(C≡CR$^z$)OH, —R$^z$, —NR$^z_2$, —OCOR$^y$, —OCO$_2$R$^y$, —SCOR$^y$, —SCO$_2$R$^y$, —NHCOR$^z$, —NHCO$_2$R$^y$, —CH$_2$NHaryl, —(CH$_2$)$_q$—OR$^z$, and —(CH$_2$)$_q$—SR$^z$;

q is an integer 2 or 3;

Each R$^z$ is selected from the group consisting of R$^y$ and —H;

Each R$^y$ is selected from the group consisting of alkyl, aryl, heterocycloalkyl, and aralkyl;

Each R$^x$ is independently selected from the group consisting of —H, and alkyl, or together R$^x$ and R$^x$ form a cycloalkyl group;

Each R$^v$ is selected from the group consisting of —H, lower alkyl, acyloxyalkyl, alkoxycarbonyloxyalkyl, and lower acyl;

with the provisos that:

a) when G is —O—, —S—, —Se—, —S(═O)—, —S(═O)$_2$—, —CH$_2$—, —C(O)—, —NH— and, T is —(CH$_2$)$_{0-4}$— or —C(O)NH(CR$^b_2$)—, R$^1$ and R$^2$ are independently chosen from the group consisting of hydrogen, halogen, —C$_1$-C$_4$ alkyl, R$^8$ and R$^9$ are each independently selected from hydrogen, halogen and C$_{1-4}$alkyl, R$^6$ and R$^7$ are each independently selected from hydrogen, halogen O—C$_{1-3}$alkyl, hydroxy, cyano and C$_{1-4}$alkyl, R$^3$ is —C(O)NR$^{25}$R$^{26}$, —CH$_2$—NR$^{25}$R$^{26}$, —NR$^{25}$—C(O)R$^{26}$, —OR$^{27}$, R$^{28}$, or

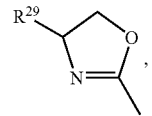

$R^4$ is hydrogen, halogen, cyano or alkyl, and $R^5$ is —OH, $R^{25}$ and $R^{26}$ are each independently selected from the group consisting of hydrogen, aryl, heteroaryl, alkyl, cycloalkyl, aralkyl or heteroaralkyl, $R^{27}$ is aryl, heteroaryl, alkyl, aralkyl, or heteroaralkyl, $R^{28}$ is aryl, heteroaryl, or cycloalkyl, $R^{29}$ is hydrogen, aryl, heteroaryl, alkyl, aralkyl, heteroaralkyl, then X is not —P(O)(OH)$_2$, or —P(O)(O-lower alkyl)$_2$;

b) when G is —O—, —S—, —Se—, —S(=O)—, —S(=O)$_2$—, —CH$_2$—, —CF$_2$—, —C(O)—, —NH— and, T is —C(O)NH(CR$^b{}_2$)—, R$^1$ and R$^2$ are independently halogen, cyano, —C$_1$-C$_4$ alkyl, R$^8$ and R$^9$ are each independently selected from hydrogen, halogen and C$_{1-4}$alkyl, R$^6$ and R$^7$ are each independently selected from hydrogen, halogen O-C$_{1-3}$alkyl, hydroxy, cyano and C$_{1-4}$alkyl, R$^3$ is halogen, —C$_1$-C$_6$ alkyl, —C$_2$-C$_6$ alkynyl, —C$_4$-C$_7$ cycloalkenyl, —C$_3$-C$_7$ cycloalkoxy, —S(=O)$_2$(NR$^{14}$R$^{15}$), —N(R$^{16}$)S(=O)$_2$R$^{17}$, —SR$^{17}$, —S(=O)R$^{17}$, —S(=O)$_2$R$^{17}$, —C(O)R$^{16}$, or —CR$^{18}$(OR$^{16}$)R$^{19}$, R$^4$ is halogen, cyano or alkyl, and R$^5$ is —OH, optionally substituted —OC$_1$-C$_6$ alkyl, aroyl or alkanoyl, R$^{14}$, R$^{15}$, R$^{16}$, R$^{18}$ and R$^{19}$ are independently selected from the group consisting of hydrogen, alkyl, cycloalkyl, aryl, heteroalkyl, arylalkyl, and heteroarylalkyl, R$^{17}$ is selected from the group consisting of alkyl, cycloalkyl, aryl, heteroalkyl, arylalkyl, and heteroarylalkyl, or R$^{14}$ and R$^{15}$ may be joined so as to comprise a chain of 3 to 6 methylene groups to form a ring of 4 to 7-membered in size, then X is not —P(O)(OH)$_2$ or —P(O)(O-lower alkyl)$_2$;

c) when G is O and T is —(CH$_2$)$_k$—, R$^1$ and R$^2$ are independently halogen, alkyl of 1 to 3 carbons, R$^3$ is alkyl of 1 to 4 carbons or cycloalkyl of 3 to 7 carbons, R$^4$ is hydrogen, R$^5$ is OH, R$^6$, R$^7$, R$^8$ and R$^9$ are hydrogen, then X is not phosphonic acid or a lower alkyl ester thereof;

d) when G is O, T is —(CH$_2$)$_{1-3}$— or —(CH$_2$)$_{1-2}$—CH(R$^{aa}$), R$^{aa}$ is —OH, —NH$_2$, —NH(C$_{1-4}$alkyl), —NH(C$_{2-4}$alkenyl), or —NH(C$_{2-4}$alkynyl), R$^4$, R$^6$, R$^7$, R$^8$ and R$^9$ are hydrogen, R$^1$ and R$^2$ are independently selected from halogen, C$_1$ alkyl substituted with 1, 2, or 3 hydrogen, fluorine, or a bioisosteric equivalent, C$_{1-4}$ alkyl and CF$_3$, and R$^3$ and R$^5$ are taken together along with the carbon atoms to which they are attached to form a five member heterocyclic ring of formula -A-C(R$^{bb}$)=B— wherein A, attached where the R$^5$ group is attached, is selected from —O—, —S—, and —NR$^h$—, B is selected from —CH—, and —N—, R$^b$ is selected from C$_{6-10}$aryl, C$_{5-9}$heteroaryl, or C$_{1-4}$alkyl, then X is not phosphonic acid, phosphamic acid, or a lower alkyl ester or acyloxyalkyl ester thereof;

e) when G is O, R$^4$, R$^6$, R$^7$, R$^8$ and R$^9$ are hydrogen, R$^3$ is selected from hydrogen, halogen, cyano, C$_{6-10}$aryl, C$_{5-10}$heteroaryl, C$_{1-10}$alkyl, C$_{3-8}$cycloalkyl, C$_{2-10}$alkenyl, C$_{2-10}$alkynyl, and R$^5$ is —NHC(O)R$^e$, NHS(=O)R$^e$, —NHS(=O)$_2$R$^e$, —NHC(=S)NH(R$^h$) or —NHC(O)NH(R$^h$), then X is not phosphonic acid or phosphamic acid or a lower alkyl ester thereof;

f) when G is —CH$_2$—O—, wherein the oxygen atom is attached to the ring bearing the T group, R6 and R7 are hydrogen, T is —(CH$_2$)$_{1-2}$CH(R$^{cc}$), R$^{cc}$ is —OH, —SH, —NH$_2$, or —NH(C$_{1-4}$), R$^1$ and R$^2$ are each independently selected from chlorine, bromine, C$_{1-4}$ alkyl, C$_{2-4}$ alkenyl, and C$_{2-4}$ alkynyl, then X is not phosphonic acid or phosphamic acid or a lower alkyl ester thereof;

g) when G is O, T is —(CR$^a{}_2$)$_{0-4}$—, R$^4$, R$^6$, R$^7$ and R$^8$ are hydrogen, R$^5$ is hydroxy, methoxy, or —NHC(O)R$^e$, R$^3$ is hydrogen, halogen, C$_{1-4}$alkyl, C$_{3-6}$cycloalkyl, or C$_{5-8}$cycloalkylalkyl, R$^1$ and R$^2$ are each independently selected from hydrogen, halogen, C$_{1-4}$alkyl, or C$_{3-6}$cycloalkyl, and R$^9$ is C$_{1-4}$alkyl, CH$_2$aryl, C(O)aryl, or C(O)alkyl, then X is not phosphonic acid or a lower alkyl ester thereof;

h) V, Z, W, W' are not all —H; and i) when Z is —R$^z$, then at least one of V, W, and W' is not —H, alkyl, aralkyl, or heterocycloalkyl;

and pharmaceutically acceptable salts and prodrugs thereof and pharmaceutically acceptable salts of said prodrugs.

In one aspect, when G is —O—, T is —CH$_2$—, R$^1$ and R$^2$ are each bromo, R$^3$ is iso-propyl, R$^4$ is hydrogen, and R$^5$ is —OH, then X is not P(O)(OH)$_2$ or P(O)(OCH$_2$CH$_3$)$_2$. In another aspect, when G is —O—, T is —(CH$_2$)$_{0-4}$—, R$^1$ and R$^2$ are independently halogen, alkyl of 1 to 3 carbons, and cycloalkyl of 3 to 5 carbons, R$^3$ is alkyl of 1 to 4 carbons or cycloalkyl of 3 to 7 carbons, R$^4$ is hydrogen, and R$^5$ is —OH, then X is not —P(O)(OH)$_2$ or —P(O)(O lower alkyl)$_2$. In a further aspect, when G is —O—, R$^5$ is —NHC(O)R$^e$, —NHS(=O)$_{1-2}$R$^e$, —NHC(S)NH(R$^h$), or —NHC(O)NH(R$^h$), T is —(CH$_2$)$_n$—, —CH=CH—, —O(CH$_2$)$_{1-2}$—, or —NH(CH$_2$)$_{1-2}$—, then X is not —P(O)(OH)$_2$ or —P(O)(OH)NH$_2$.

In one aspect, G is selected from the group consisting of —O— and —CH$_2$—. In a further aspect, G is —O—. In another aspect, G is —S—. In a further aspect, G is —S(=O)—. In another aspect, G is —S(=O)$_2$—. In a further aspect, G is —CH$_2$—. In another aspect, G is —CF$_2$—. In a further aspect, G is —CHF—. In another aspect, G is —C(O)—. In another aspect, G is —CH(OH)—. In a further aspect, G is —NH—. In another aspect, G is —N(C$_1$-C$_4$ alkyl)-. In yet another aspect, G is —Se—. In another aspect, G is —CH(C$_1$-C$_4$ alkyl)-. In another aspect, G is —CH(C$_1$-C$_4$ alkoxy)-. In another aspect, G is —C(=CH$_2$)—, In another aspect, T is selected from the group consisting of —(CR$^a{}_2$)$_n$—, —O(CR$^b{}_2$)(CR$^a{}_2$)$_p$—, —N(R$^c$)(CR$^b{}_2$)(CR$^a{}_2$)$_p$—, —S(CR$^b{}_2$)(CR$^a{}_2$)$_p$—, —NR$^b$(CO)—, and —CH$_2$CH(NR$^c$R$^b$)—. In a further aspect, T is —(CR$^a{}_2$)$_k$—. In another aspect, T is —CR$^b$=CR$^b$—(CR$^a{}_2$)$_n$. In a further aspect, T is —(CR$^a{}_2$)$_n$—CR$^b$=CR$^b$—. In another aspect, T is —(CR$^a{}_2$)—CR$^b$=CR$^b$—(CR$^a{}_2$)—. In a further aspect, T is —O(CR$^b{}_2$)(CR$^a{}_2$)$_n$— or —NH(CR$^b{}_2$)(CR$^a{}_2$)$_p$—. In another aspect, T is —S(CR$^b{}_2$)(CR$^a{}_2$)$_n$—. In a further aspect, T is —N(R$^c$)(CR$^b{}_2$)(CR$^a{}_2$)$_n$—. In another aspect, T is —N(R$^b$)C(O)(CR$^a{}_2$)$_n$—. In a further aspect, T is —(CR$^a{}_2$)$_n$CH(NR$^b$R$^c$)—. In another aspect, T is —C(O)(CR$^a{}_2$)$_m$—. In a further aspect, T is —(CR$^a{}_2$)$_m$C(O)—. In another aspect, T is —(CR$^a{}_2$)C(O)(CR$^a{}_2$)$_n$—. In a further aspect, T is —(CR$^a{}_2$)$_n$C(O)(CR$^a{}_2$)—. In yet another aspect, T is —C(O)NH(CR$^b{}_2$)(CR$^a{}_2$)$_p$—.

In one aspect k is 0. In a further aspect, k is 1. In an additional aspect, k is 2. In a further aspect, k is 3. In yet another aspect, k is 4. In one aspect m is 0. In a further aspect, m is 1. In an additional aspect, m is 2. In a further aspect, m is 3. In one aspect n is 0. In a further aspect, n is 1. In an additional aspect, n is 2. In one aspect, p is 0. In another aspect, p is 1.

In one aspect, each R$^a$ is hydrogen with the proviso that when one R$^a$ is attached to C through an O, S, or N atom, then the other R$^a$ attached to the same C is a hydrogen, or attached via a carbon atom. In another aspect, each R$^a$ is optionally substituted —C$_1$-C$_4$ alkyl with the proviso that when one R$^a$ is attached to C through an O, S, or N atom, then the other R$^a$ attached to the same C is a hydrogen, or attached via a carbon atom. In a further aspect, each R$^a$ is halogen with the proviso that when one R$^a$ is attached to C through an O, S, or N atom, then the other R$^a$ attached to the same C is a hydrogen, or attached via a carbon atom. In another aspect, each $R^a$ is —OH with the proviso that when one $R^a$ is attached to C through an O, S, or N atom, then the other $R^a$ attached to the same C is a hydrogen, or attached via a carbon atom. In a further aspect, each $R^a$ is optionally substituted —O—$C_1$-$C_4$ alkyl with the proviso that when one $R^a$ is attached to C through an O, S, or N atom, then the other $R^a$ attached to the same C is a hydrogen, or attached via a carbon atom. In another aspect, each $R^a$ is —$OCF_3$ with the proviso that when one $R^a$ is attached to C through an O, S, or N atom, then the other $R^a$ attached to the same C is a hydrogen, or attached via a carbon atom. In a further aspect, each $R^a$ is optionally substituted —S—$C_1$-$C_4$ alkyl with the proviso that when one $R^a$ is attached to C through an O, S, or N atom, then the other $R^a$ attached to the same C is a hydrogen, or attached via a carbon atom. In another aspect, each $R^a$ is —$NR^bR^c$ with the proviso that when one $R^a$ is attached to C through an O, S, or N atom, then the other $R^a$ attached to the same C is a hydrogen, or attached via a carbon atom. In a further aspect, each $R^a$ is optionally substituted —$C_2$-$C_4$ alkenyl with the proviso that when one $R^a$ is attached to C through an O, S, or N atom, then the other $R^a$ attached to the same C is a hydrogen, or attached via a carbon atom. In another aspect, each $R^a$ is optionally substituted —$C_2$-$C_4$ alkynyl with the proviso that when one $R^a$ is attached to C through an O, S, or N atom, then the other $R^a$ attached to the same C is a hydrogen, or attached via a carbon atom.

In one aspect, $R^b$ is hydrogen. In an additional aspect, $R^b$ is optionally substituted —$C_1$-$C_4$ alkyl.

In one aspect, $R^c$ is hydrogen. In another aspect, $R^c$ is optionally substituted —$C_1$-$C_4$ alkyl. In a further aspect, $R^c$ is optionally substituted —C(O)—$C_1$-$C_4$ alkyl. In yet another aspect, $R^c$ is —C(O)H.

In a further aspect, $R^1$ and $R^2$ are the same and are selected from the group consisting of halogen, —$C_1$-$C_4$ alkyl, —$CF_3$, and cyano. In yet another aspect, $R^1$ and $R^2$ are different and are selected from the group consisting of halogen, —$C_1$-$C_4$ alkyl, —$CF_3$, and cyano. In an additional aspect, $R^1$ and $R^2$ are each halogen. In an additional aspect, $R^1$ and $R^2$ are not both halogen. In another aspect, $R^1$, $R^2$, $R^6$, $R^7$, $R^8$, and $R^9$ are each optionally substituted —$C_1$-$C_4$ alkyl. In a further aspect, $R^1$, $R^2$, $R^6$, $R^7$, $R^8$, and $R^9$ are each optionally substituted —S—$C_1$-$C_3$ alkyl. In another aspect, $R^1$, $R^2$, $R^6$, $R^7$, $R^8$, and $R^9$ are each optionally substituted —$C_2$-$C_4$ alkenyl. In a further aspect, $R^1$, $R^2$, $R^6$, $R^7$, $R^8$, and $R^9$ are each optionally substituted —$C_2$-$C_4$ alkynyl. In another aspect, $R^1$, $R^2$, $R^6$, $R^7$, $R^8$, and $R^9$ are each —$CF_3$. In a further aspect, $R^1$, $R^2$, $R^6$, $R^7$, $R^8$, and $R^9$ are each —$OCF_3$. In another aspect, $R^1$, $R^2$, $R^6$, $R^7$, $R^8$, and $R^9$ are each optionally substituted-O—$C_1$-$C_3$ alkyl. In a further aspect, $R^1$, $R^2$, $R^6$, $R^7$, $R^8$, and $R^9$ are each cyano. In a further aspect, $R^6$ and $R^7$ are independently hydrogen, halogen, —$C_1$-$C_4$ alkyl, cyano or $CF_3$. In a further aspect, $R^6$ and $R^7$ are independently hydrogen, halogen, or methyl. In another aspect, $R^8$ and $R^9$ are independently hydrogen, halogen, —$C_1$-$C_4$ alkyl, —$C_1$-$C_4$ alkylaryl, C(O)aryl, cyano and $CF_3$. In another aspect, $R^8$ and $R^9$ are independently hydrogen, halogen, —$C_1$-$C_4$ alkyl, —$C_1$-$C_4$ alkylaryl or C(O)aryl. In another aspect, $R^8$ and $R^9$ are independently hydrogen, halogen, methyl, benzyl or benzoate.

In one aspect, $R^6$ and T are taken together along with the carbons they are attached to form an optionally substituted ring of 5 to 6 atoms with 0-2 unsaturations including 0 to 2 heteroatoms independently selected from —$NR^i$—, —O—, and —S—, with the proviso that when there are 2 heteroatoms in the ring and both heteroatoms are different than nitrogen then both heteroatoms have to be separated by at least one carbon atom; and X is attached to this ring to either a carbon or a nitrogen by either —$(CR^a_2)$— or —C(O)— or a bond if X is attached directly to a carbon atom. In one aspect, $R^6$ and T are taken together along with the carbons they are attached to form a ring of 5 to 6 atoms containing 0 unsaturations. In another aspect, $R^6$ and T are taken together along with the carbons they are attached to form a ring of 5 to 6 atoms containing 1 unsaturation. $R^6$ and T are taken together along with the carbons they are attached to form a ring of 5 to 6 atoms containing 2 unsaturations. In one aspect, 0 to 2 heteroatoms are —$NR^i$—. In another aspect, 0 to 2 heteroatoms are —O—. In another aspect, 0 to 2 heteroatoms are —S—.

In one aspect, $R^i$ is hydrogen. In another aspect, $R^i$ is —C(O)$C_1$-$C_4$ alkyl. In another aspect, $R^i$ is —$C_1$-$C_4$ alkyl. In a further aspect, $R^i$ is —$C_1$-$C_4$-aryl.

In yet another aspect, $R^3$ and $R^4$ are each hydrogen. In another aspect, $R^3$ and $R^4$ are each halogen. In a further aspect, $R^3$ and $R^4$ are each —$CF_3$. In another aspect, $R^3$ and $R^4$ are each —$OCF_3$. In a further aspect, $R^3$ and $R^4$ are each cyano. In another aspect, $R^3$ and $R^4$ are each optionally substituted —$C_1$-$C_{12}$ alkyl. In a further aspect, $R^3$ and $R^4$ are each optionally substituted —$C_2$-$C_{12}$ alkenyl. In another aspect, $R^3$ and $R^4$ are each optionally substituted —$C_2$-$C_{12}$ alkynyl. In a further aspect, $R^3$ and $R^4$ are each optionally substituted —$(CR^a_2)_n$aryl. In another aspect, $R^3$ and $R^4$ are each optionally substituted —$(CR^a_2)_n$cycloalkyl. In a further aspect, $R^3$ and $R^4$ are each optionally substituted —$(CR^a_2)_m$heterocycloalkyl. In another aspect, $R^3$ and $R^4$ are each —$OR^d$. In another aspect, $R^3$ and $R^4$ are each —$SR^d$. In a further aspect, $R^3$ and $R^4$ are each —S(=O)$R^e$. In another aspect, $R^3$ and $R^4$ are each —S(=O)$_2R^e$. In a further aspect, $R^3$ and $R^4$ are each —S(=O)$_2NR^fR^g$. In another aspect, $R^3$ and $R^4$ are each —C(O)$NR^fR^g$. In a further aspect, $R^3$ and $R^4$ are each —C(O)$OR^h$. In another aspect, $R^3$ and $R^4$ are each —C(O)$R^e$. In a further aspect, $R^3$ and $R^4$ are each —N($R^b$)C(O)$R^e$. In another aspect, $R^3$ and $R^4$ are each —N($R^b$)C(O)$NR^fR^g$. In a further aspect, $R^3$ and $R^4$ are each —N($R^b$)S(=O)$_2R^e$. In another aspect, $R^3$ and $R^4$ are each —N($R^b$)S(=O)$_2NR^fR^g$. In a further aspect, $R^3$ and $R^4$ are each —$NR^fR^g$.

In another aspect, $R^4$ is selected from the group consisting of hydrogen, halogen, —$C_1$-$C_4$ alkyl, cyano and $CF_3$. In another aspect, $R^4$ is hydrogen. In a further aspect, $R^3$ is selected from the group consisting of halogen, optionally substituted —$C_1$-$C_6$ alkyl, —$CF_3$, cyano, —C(O)$NR^fR^g$, optionally substituted —$(CR^a_2)_n$aryl, —$SO_2NR^fR^g$, and —$SO_2R^e$. In a further aspect, $R^3$ is isopropyl or 4-fluorobenzyl.

In another aspect, each $R^d$ is optionally substituted —$C_1$-$C_{12}$ alkyl. In a further aspect, each $R^d$ is optionally substituted —$C_2$-$C_{12}$ alkenyl. In another aspect, each $R^d$ is optionally substituted —$C_2$-$C_{12}$ alkynyl. In a further aspect, each $R^d$ is optionally substituted —$(CR^b_2)_n$aryl. In another aspect, each $R^d$ is optionally substituted —$(CR^b_2)_n$cycloalkyl. In a further aspect, each $R^d$ is optionally substituted —$(CR^a_2)_n$heterocycloalkyl. In another aspect, each $R^d$ is —C(O)$NR^fR^g$.

In an additional aspect, $R^e$ is optionally substituted —$C_1$-$C_{12}$ alkyl. In another aspect, $R^e$ is optionally substituted —$C_2$-$C_{12}$ alkenyl. In a further aspect, $R^e$ is optionally substituted —$C_2$-$C_{12}$ alkynyl. In another aspect, $R^e$ is optionally substituted —$(CR^a_2)_n$aryl. In a further aspect, $R^e$ is optionally substituted —$(CR^a_2)_n$cycloalkyl. In another aspect, $R^e$ is optionally substituted —$(CR^a_2)_n$heterocycloalkyl.

In one aspect, $R^f$ and $R^g$ are each hydrogen. In an additional aspect, $R^f$ and $R^g$ are each optionally substituted —$C_1$-$C_{12}$ alkyl. In another aspect, $R^f$ and $R^g$ are each optionally substituted —$C_2$-$C_{12}$ alkenyl. In an additional aspect, $R^f$ and $R^g$ are each optionally substituted —$C_2$-$C_{12}$ alkynyl. In a further aspect, $R^f$ and $R^g$ are each optionally substituted —$(CR^b_2)_n$ aryl. In an additional aspect, $R^f$ and $R^g$ are each optionally substituted —$(CR^b{}_2)_n$cycloalkyl. In another aspect, $R^f$ and $R^g$ are each optionally substituted —$(CR^b{}_2)_n$heterocycloalkyl.

In an additional aspect, $R^f$ and $R^g$ may together form an optionally substituted heterocyclic ring, which may contain a second heterogroup which is O. In another aspect, $R^f$ and $R^g$ may together form an optionally substituted heterocyclic ring, which may contain a second heterogroup which is $NR^c$. In another aspect, $R^f$ and $R^g$ may together form an optionally substituted heterocyclic ring, which may contain a second heterogroup which is S. In one aspect, $R^f$ and $R^g$ may together form an unsubstituted heterocyclic ring, which may contain a second heterogroup. In another aspect, the optionally substituted heterocyclic ring may be substituted with 1 substituent selected from the group consisting of optionally substituted —$C_1$-$C_4$ alkyl, —$OR^b$, oxo, cyano, —$CF_3$, optionally substituted phenyl, and —$C(O)OR^h$. In further aspect, the optionally substituted heterocyclic ring may be substituted with 2 substituents selected from the group consisting of optionally substituted —$C_1$-$C_4$ alkyl, —$OR^b$, oxo, cyano, —$CF_3$, optionally substituted phenyl, and —$C(O)OR^h$. In another aspect, the optionally substituted heterocyclic ring may be substituted with 3 substituents selected from the group consisting of optionally substituted —$C_1$-$C_4$ alkyl, —$OR^b$, oxo, cyano, —$CF_3$, optionally substituted phenyl, and —$C(O)OR^h$. In a further aspect, the optionally substituted heterocyclic ring may be substituted with 4 substituents selected from the group consisting of optionally substituted —$C_1$-$C_4$ alkyl, —$OR^b$, oxo, cyano, —$CF_3$, optionally substituted phenyl, and —$C(O)OR^h$.

In a further aspect, $R^h$ is optionally substituted —$C_1$-$C_{12}$ alkyl. In another aspect, $R^h$ is optionally substituted —$C_2$-$C_{12}$ alkenyl. In a further aspect, $R^h$ is optionally substituted —$C_2$-$C_{12}$ alkynyl. In another aspect, $R^h$ is optionally substituted —$(CR^b{}_2)_n$aryl. In a further aspect, $R^h$ is optionally substituted —$(CR^b{}_2)_n$cycloalkyl. In another aspect, $R^h$ is optionally substituted —$(CR^b{}_2)_n$heterocycloalkyl.

In one aspect, $R^5$ is selected from the group consisting of —OH, —$OC(O)R^e$, —$OC(O)OR^h$, —F, and —$NHC(O)R^e$. In another aspect, $R^5$ is —OH. In an additional aspect, $R^5$ is optionally substituted —$OC_1$-$C_6$ alkyl. In another aspect, $R^5$ is —$OC(O)R^e$. In a further aspect, $R^5$ is —$OC(O)OR^h$. In another aspect, $R^5$ is —F. In another aspect, $R^5$ is —$NHC(O)R^e$. In a further aspect, $R^5$ is —$NHS(=O)R^e$. In another aspect, $R^5$ is —$NHS(=O)_2R^e$. In a further aspect, $R^5$ is —$NHC(=S)NH(R^h)$. In another aspect, $R^5$ is —$NHC(O)NH(R^h)$.

In one aspect, G is —O—; T is —$CH_2CH(NH_2)$—; $R^1$ and $R^2$ are each iodo; $R^4$ is selected from the group consisting of hydrogen and iodo; $R^6$, $R^7$, $R^8$ and $R^9$ are hydrogen; $R^5$ is —OH; and $R^3$ is iodo. In another aspect, G is —O—; T is —$N(H)C(O)$—; $R^1$ and $R^2$ are each methyl; $R^4$, $R^6$, $R^7$, $R^8$ and $R^9$ are hydrogen; $R^5$ is —OH; and $R^3$ is —CH(OH)(4-fluorophenyl). In a further aspect, G is —$CH_2$—; T is —$OCH_2$—; $R^1$ and $R^2$ are each methyl; $R^4$, $R^6$, $R^7$, $R^8$ and $R^9$ are hydrogen; $R^5$ is —OH; and $R^3$ is iso-propyl. In an additional aspect, G is —O—; T is —$CH_2$—; $R^1$ and $R^2$ are each chloro; $R^4$, $R^6$, $R^7$, $R^8$ and $R^9$ are hydrogen; $R^5$ is —OH; and $R^3$ is iso-propyl. In a further aspect, G is —O—; T is —$CH_2CH_2$—; $R^1$ and $R^2$ are each chloro; $R^4$, $R^6$, $R^7$, $R^8$ and $R^9$ are hydrogen; $R^5$ is —OH; and $R^3$ is iso-propyl.

In one aspect, X is —$P(O)YR^{11}Y'R^{11}$.

In one aspect, X is selected from the group consisting of —$PO_3H_2$, —$P(O)[—OCR^z{}_2OC(O)R^y]_2$, —$P(O)[—OCR^z{}_2OC(O)OR^y]_2$, —$P(O)[—N(H)CR^z{}_2C(O)OR^y]_2$, —$P(O)[—N(H)CR^z{}_2C(O)OR^y][—OR^{11}]$, and —$P(O)[—OCH(V)CH_2CH_2O—]$, wherein V is selected from the group consisting of optionally substituted aryl, aryl, heteroaryl, and optionally substituted heteroaryl. In another aspect, X is selected from the group consisting of —$PO_3H_2$, —$P(O)[—OCR^z{}_2OC(O)R^y]_2$, —$P(O)[—OCR^z{}_2OC(O)OR^y]_2$, —$P(O)[—OCH_2CH_2SC(O)Me]_2$, —$P(O)[—N(H)CR^z{}_2C(O)OR^y]_2$, —$P(O)[—N(H)CR^z{}_2C(O)OR^y][—OR^{11}]$ and —$P(O)[—OCH(V)CH_2CH_2O—]$, wherein V is selected from the group consisting of optionally substituted aryl, aryl, heteroaryl, and optionally substituted heteroaryl. In another aspect, X is selected from the group consisting of —$PO_3H_2$, —$P(O)[—OCR^z{}_2OC(O)R^y]_2$, —$P(O)[—OCR^z{}_2OC(O)OR^y]_2$, —$P(O)[—Oalk-SC(O)R^y]_2$, —$P(O)[—N(H)CR^z{}_2C(O)OR^y]_2$, —$P(O)[—N(H)CR^z{}_2C(O)OR^y][—OR^{"}]$ and —$P(O)[—OCH(V)CH_2CH_2O—]$, wherein V is selected from the group consisting of optionally substituted aryl, aryl, heteroaryl, and optionally substituted heteroaryl. In one aspect, X is selected from the group consisting of —$P(O)[—OCR^z{}_2OC(O)R^y]_2$, —$P(O)[—OCR^z{}_2OC(O)OR^y]_2$, —$P(O)[—N(H)CR^z{}_2C(O)OR^y]_2$, —$P(O)[—N(H)CR^z{}_2C(O)OR^y][—OR^{11}]$, —$P(O)[—OCH(V)CH_2CH_2O—]$, —$P(O)(OH)(OR^{11})$, —$P(O)(OR^e)(OR^e)$, —$P(O)[—OCR^z{}_2OC(O)R^y](OR^e)$, —$P(O)[—OCR^z{}_2OC(O)OR^y](OR^e)$, and —$P(O)[—N(H)CR^z{}_2C(O)OR^y](OR^e)$, wherein V is selected from the group consisting of optionally substituted aryl, aryl, heteroaryl, and optionally substituted heteroaryl. In another aspect, X is selected from the group consisting of —$PO_3H_2$, —$P(O)[—OCR^z{}_2OC(O)R^y]_2$, —$P(O)[—OCR^z{}_2OC(O)OR^y]_2$, —$P(O)[—N(H)CR^z{}_2C(O)OR^y]_2$, —$P(O)[—N(H)CR^z{}_2C(O)OR^y][—OR^{11}]$, —$P(O)[—OCH(V)CH_2CH_2O—]$, —$P(O)(OH)(OR^e)$, —$P(O)(OR^{11})(OR^e)$, —$P(O)[—OCR^z{}_2OC(O)R^y](OR^e)$, —$P(O)[—OCR^z{}_2OC(O)OR^y](OR^e)$, —$P(O)[—N(H)CR^z{}_2C(O)OR^y](OR^e)$, and —$P(O)(OH)(NH_2)$, wherein V is selected from the group consisting of optionally substituted aryl, aryl, heteroaryl, and optionally substituted heteroaryl.

In one aspect, X is selected from the group consisting of —$PO_3H_2$, —$P(O)[—OCH_2OC(O)$-t-butyl$]_2$, —$P(O)[—OCH_2OC(O)O$-i-propyl$]_2$, —$P(O)[—N(H)CH(CH_3)C(O)OCH_2CH_3]_2$, —$P(O)[—N(H)C(CH_3)_2C(O)OCH_2CH_3]_2$, —$P(O)[—N(H)CH(CH_3)C(O)OCH_2CH_3]$ [3,4-methylenedioxyphenyl], —$P(O)[—N(H)C(CH_3)_2C(O)OCH_2CH_3]$ [3,4-methylenedioxyphenyl], —$P(O)[—O—CH_2CH_2S—C(O)CH_3]_2$, and —$P(O)[—OCH(3$-chlorophenyl$)CH_2CH_2O—]$. In a further aspect, X is selected from the group consisting of —$PO_3H_2$, —$P(O)[—OCH_2OC(O)$-t-butyl$]_2$, —$P(O)[—OCH_2OC(O)O$-i-propyl$]_2$, —$P(O)[—N(H)CH(CH_3)C(O)OCH_2CH_3]_2$, —$P(O)[—N(H)C(CH_3)_2C(O)OCH_2CH_3]_2$, —$P(O)[—N(H)CH(CH_3)C(O)OCH_2CH_3]$[3,4-methylenedioxy-phenyl], —$P(O)[—N(H)C(CH_3)_2C(O)OCH_2CH_3]$ [3,4-methylenedioxyphenyl], and —$P(O)[—OCH(3$-chlorophenyl$)CH_2CH_2O—]$. In another aspect, X is —$PO_3H_2$. In yet another aspect, X is selected from the group consisting of —$P(O)[—OCH_2OC(O)$-t-butyl$]_2$ and —$P(O)[—OCH_2OC(O)$-i-propyl$]_2$. In another aspect, X is selected from the group consisting of —$PO_3H_2$, —$P(O)[—OCH_2OC(O)$-t-butyl$]_2$, —$P(O)[—OCH_2OC(O)O$-i-propyl$]_2$, —$P(O)[—N(H)CH(CH_3)C(O)OCH_2CH_3]_2$, —$P(O)[—N(H)C(CH_3)_2C(O)OCH_2CH_3]_2$, —$P(O)[—N(H)CH(CH_3)C(O)OCH_2CH_3]$ [3,4-methylenedioxyphenyl], —$P(O)[—N(H)C(CH_3)_2C(O)OCH_2CH_3]$ [3,4-methylenedioxyphenyl], —$P(O)[—OCH(3$-chlorophenyl$)CH_2CH_2O—]$, —$P(O)[—OCH(pyrid-4-yl)CH_2CH_2O—]$, —$P(O)(OH)(OCH_3)$, —$P(O)(OH)(OCH_2CH_3)$, —$P(O)[—OCH_2OC(O)$-t-butyl$](OCH_3)$, —$P(O)[—OCH_2OC(O)O$-i-propyl$](OCH_3)$, —$P(O)[—OCH(CH_3)OC(O)$-t-butyl$](OCH_3)$, —$P(O)[—OCH(CH_3)OC(O)O$-i-propyl$](OCH_3)$, —$P(O)[—N(H)CH(CH_3)C(O)OCH_2CH_3](OCH_3)$, —$P(O)[—N(H)C(CH_3)_2C(O)OCH_2CH_3](OCH_3)$, and —$P(O)(OH)(NH_2)$.

In one aspect, X is selected from the group consisting of —P(O)[—OCH$_2$OC(O)O-ethyl]$_2$ and —P(O)[—OCH$_2$OC(O)O-i-propyl]$_2$. In another aspect, X is selected from the group consisting of —P(O)[—N(H)CH(CH$_3$)C(O)OCH$_2$CH$_3$]$_2$ and —P(O)[—N(H)C(CH$_3$)$_2$C(O)OCH$_2$CH$_3$]$_2$. In a further aspect, X is —P(O)[—OCH$_2$CH$_2$SC(O)Me]$_2$. In another aspect, X is selected from the group consisting of —P(O)[—N(H)CH(CH$_3$)C(O)OCH$_2$CH$_3$] [3,4-methylenedioxyphenyl] and —P(O)[—N(H)C(CH$_3$)$_2$C(O)OCH$_2$CH$_3$] [3,4-methylenedioxyphenyl]. In a further aspect, X is selected from the group consisting of —PO$_3$H$_2$, —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][—OR$^{11}$] and —P(O)[—OCH(V)CH$_2$CH$_2$O—], wherein V is selected from the group consisting of optionally substituted aryl, aryl, heteroaryl, and optionally substituted heteroaryl. In another aspect, X is selected from the group consisting of —PO$_3$H$_2$, —P(O)[—OCH$_2$OC(O)-t-butyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$] [3,4-methylenedioxyphenyl], —P(O)[—N(H)C(CH$_3$)$_2$C(O)OCH$_2$CH$_3$] [3,4-methylenedioxyphenyl], and —P(O)[—OCH(3-chlorophenyl)CH$_2$CH$_2$O—].

Each of the individual species of compounds of Formula VIII which can be generated by making all of the above permutations may be specifically set forth as for inclusion or specifically may be excluded from the present invention.

In an additional aspect, this invention relates to Formulas I, II, III, or VIII wherein X is P(O)YR$^{11}$Y'R$^{11}$.

In one aspect, Y and Y' are each independently selected from the group consisting of —O—, and —NR$^v$—. In another aspect, Y and Y' are each independently selected from the group consisting of —O—, and —NR$^v$—; when Y and Y' are both —O—, R$^{11}$ attached to —O— is —H, alkyl. In another aspect, Y and Y' are each independently selected from the group consisting of —O—, and —NR$^v$—; when Y and Y' are both —O—, R$^{11}$ attached to —O— is optionally substituted aryl. In another aspect, Y and Y' are each independently selected from the group consisting of —O—, and —NR$^v$—; when Y and Y' are both —O—, R$^{11}$ attached to —O— is optionally substituted heterocycloalkyl. In a further aspect, Y and Y' are each independently selected from the group consisting of —O—, and —NR$^v$—; when Y and Y' are both —O—, R$^{11}$ attached to —O— is optionally substituted CH$_2$-heterocycloakyl. In one aspect, the cyclic moiety contains a carbonate or thiocarbonate. In another aspect, the cyclic moiety contains optionally substituted -alkylaryl. In another aspect, the cyclic moiety contains a —C(R$^z$)$_2$OC(O)NR$^z_2$. In another aspect, the cyclic moiety contains —NR$^z$—C(O)—R$^y$. In another aspect, the cyclic moiety contains —C(R$^z$)$_2$—OC(O)R$^y$. In another aspect, the cyclic moiety contains —C(R$^z$)$_2$—O—C(O)OR$^y$. In a further aspect, the cyclic moiety contains —C(R$^z$)$_2$OC(O)SR$^y$. In another aspect, the cyclic moiety contains -alkyl-S—C(O)R$^y$. In another aspect, the cyclic moiety contains -alkyl-S-S-alkylhydroxy. In a further aspect, the cyclic moiety contains -alkyl-S-S-S-alkylhydroxy.

In yet another aspect, Y and Y' are both —NR$^v$—. In another aspect, when Y and Y' are both —NR$^v$—, then R$^{11}$ attached to —NR$^v$— is —H. In a further aspect, when Y and Y' are both —NR$^v$—, then R$^{11}$ attached to —NR$^v$— is —[C(R$^z$)$_2$]$_q$—COOR$^y$. In another aspect, when Y and Y' are both —NR$^v$—, then R$^{11}$ attached to —NR$^v$— is —C(R$^x$)$_2$COOR$^y$. In a further aspect, when Y and Y' are both —NR$^v$—, then R$^{11}$ attached to —NR$^v$— is —[C(R$^z$)$_2$]$_q$—C(O)SR$^y$. In another aspect, when Y and Y' are both —NR$^v$—, then R$^{11}$ attached to —NR$^v$— is -cycloalkylene-COOR$^y$.

In one aspect, Y is —O— and Y' is NR$^v$. In another aspect, when Y is —O— and Y' is NR$^v$, then R$^{11}$ attached to —O— is —H. In a further aspect, when Y is —O— and Y' is NR$^v$, then R$^{11}$ attached to —O— is alkyl. In another aspect, when Y is —O— and Y' is NR$^v$, then R$^{11}$ attached to —O— is optionally substituted aryl. In a further aspect, when Y is —O— and Y' is NR$^v$, then R$^{11}$ attached to —O— is optionally substituted heterocycloalkyl. In another aspect, when Y is —O— and Y' is NR$^v$, then R$^{11}$ attached to —O— is optionally substituted CH$_2$-heterocycloakyl. In one aspect, the cyclic moiety contains a carbonate or thiocarbonate. In another aspect, the cyclic moiety contains optionally substituted -alkylaryl. In another aspect, the cyclic moiety contains —C(R$^z$)$_2$OC(O)NR$^z_2$. In another aspect, the cyclic moiety contains —NR$^z$—C(O)—R$^y$. In another aspect, the cyclic moiety contains —C(R$^z$)$_2$—OC(O)R$^y$. In another aspect, the cyclic moiety contains —C(R$^z$)$_2$—O—C(O)OR$^y$. In a further aspect, the cyclic moiety contains —C(R$^z$)$_2$OC(O)SR$^y$. In another aspect, the cyclic moiety contains -alkyl-S—C(O)R$^y$. In another aspect, the cyclic moiety contains -alkyl-S-S-alkylhydroxy. In a further aspect, the cyclic moiety contains -alkyl-S-S-S-alkylhydroxy.

In another aspect, when Y is —O— and Y' is NR$^v$, and R$^{11}$ attached to —NR$^v$— is —H. In a further aspect, when Y is —O— and Y' is NR$^v$, and R$^{11}$ attached to —NR$^v$— is —[C(R$^z$)$_2$]$_q$—COOR$^y$. In another aspect, when Y is —O— and Y' is NR$^v$, and R$^{11}$ attached to —NR$^v$— is —C(RX)$_2$COOR$^y$. In a further aspect, when Y is —O— and Y' is NR$^v$, and R$^{11}$ attached to —NR$^v$— is —[C(R$^z$)$_2$]$_q$—C(O)SR$^y$. In another aspect, when Y is —O— and Y' is NR$^v$, and R$^{11}$ attached to —NR$^v$— is -cycloalkylene-COOR$^y$.

In another aspect, Y and Y' are independently selected from —O— and —NR$^v$—, then R$^{11}$ and R$^{11}$ together form a cyclic group comprising -alkyl-S-S-alkyl-.

In one aspect, Y and Y' are independently selected from —O— and —NR$^v$— and together R$^{11}$ and R$^{11}$ are the group:

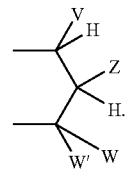

In a further aspect, V is hydrogen. In another aspect, V is optionally substituted alkyl. In a further aspect, V is optionally substituted aralkyl. In another aspect, V is heterocycloalkyl. In another aspect, V is aryl. In a further aspect, V is substituted aryl. In another aspect, V is heteroaryl. In a further aspect, V is substituted heteroaryl. In another aspect, V is optionally substituted 1-alkenyl. In a further aspect, V is optionally substituted 1-alkynyl.

In a further aspect, W is hydrogen. In another aspect, W is optionally substituted alkyl. In a further aspect, W is optionally substituted aralkyl. In another aspect, W is heterocycloalkyl. In another aspect, W is aryl. In a further aspect, W is substituted aryl. In another aspect, W is heteroaryl. In a further aspect, W is substituted heteroaryl. In another aspect, W is optionally substituted 1-alkenyl. In a further aspect, W is optionally substituted 1-alkynyl.

In a further aspect, W' is hydrogen. In another aspect, W' is optionally substituted alkyl. In a further aspect, W' is optionally substituted aralkyl. In another aspect, W' is heterocycloalkyl. In another aspect, W' is aryl. In a further aspect, W' is substituted aryl. In another aspect, W' is heteroaryl. In a further aspect, W' is substituted heteroaryl. In another aspect, W' is optionally substituted 1-alkenyl. In a further aspect, W' is optionally substituted 1-alkynyl.

In one aspect, together V and Z are connected via an additional 3-5 atoms to form a cyclic group containing 5-7 atoms, wherein 0-1 atoms are heteroatoms and the remaining atoms are carbon. In one aspect, the ring is substituted with hydroxyl attached to a carbon atom that is three atoms from both Y groups attached to the phosphorus. In another aspect, the ring is substituted with acyloxy attached to a carbon atom that is three atoms from both Y groups attached to the phosphorus. In a further aspect, the ring is substituted with alkylthiocarbonyloxy attached to a carbon atom that is three atoms from both Y groups attached to the phosphorus. In another aspect, the ring is substituted with alkoxycarbonyloxy attached to a carbon atom that is three atoms from both Y groups attached to the phosphorus. In a further aspect, the ring is substituted with aryloxycarbonyloxy attached to a carbon atom that is three atoms from both Y groups attached to the phosphorus.

In yet another aspect, together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus.

In a further aspect, together V and W are connected via an additional 3 carbon atoms to form an optionally substituted cyclic group containing 6 carbon atoms and substituted with one substituent. In one aspect, the substituent is hydroxyl that is attached to one of said carbon atoms that is three atoms from a Y attached to the phosphorus. In another aspect, the substituent is acyloxy that is attached to one of said carbon atoms that is three atoms from a Y attached to the phosphorus. In another aspect, the substituent is alkoxycarbonyloxy that is attached to one of said carbon atoms that is three atoms from a Y attached to the phosphorus. In another aspect, the substituent is alkylthiocarbonyloxy that is attached to one of said carbon atoms that is three atoms from a Y attached to the phosphorus. In another aspect, the substituent is aryloxycarbonyloxy that is attached to one of said carbon atoms that is three atoms from a Y attached to the phosphorus.

In another aspect, together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl.

In yet another aspect, together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl.

In one aspect, Z is —CHR$^z$OH. In another aspect, Z is —CHR$^z$OC(O)R$^y$. In a further aspect, Z is —CHR$^z$OC(S)R$^y$. In another aspect, Z is —CHR$^z$OC(S)OR$^y$. In a further aspect, Z is —CHR$^z$OC(O)SR$^y$. In another aspect, Z is —CHR$^z$OCO$_2$R$^y$. In a further aspect, Z is —OR$^z$. In another aspect, Z is —SR$^z$. In a further aspect, Z is —CHR$^z$N$_3$. In another aspect, Z is —CH$_2$aryl. In a further aspect, Z is —CH(aryl)OH. In another aspect, Z is —CH(CH=CR$^z_2$)OH. In another aspect, Z is —CH(C≡CR$^z$)OH. In a further aspect, Z is —R$^z$. In another aspect, Z is —NR$^z_2$. In a further aspect, Z is —OCOR$^y$. In another aspect, Z is —OCO$_2$R$^y$. In a further aspect, Z is —SCOR$^y$. In another aspect, Z is —SCO$_2$R$^y$. In a further aspect, Z is —NHCOR$^z$. In another aspect, Z is —NHCO$_2$R$^y$. In a further aspect, Z is —CH$_2$NHaryl. In another aspect, Z is —(CH$_2$)$_q$—OR$^z$. In a further aspect, Z is —(CH$_2$)$_q$—SR$^z$.

In one aspect R$^{11}$ is not hydrogen. In one aspect, q is 2. In a further aspect, q is 3.

In one aspect, R$^y$ is alkyl. In another aspect, R$^y$ is aryl. In a further aspect, R$^y$ is heterocycloalkyl. In another aspect, R$^y$ is aralkyl.

In one aspect, R$^x$ is —H. In another aspect, R$^x$ is alkyl. In yet another aspect, together R$^x$ and R$^x$ form a cycloalkyl group.

In one aspect, R$^v$ is —H. In another aspect, R$^v$ is lower alkyl. In another aspect, R$^v$ is acyloxyalkyl. In another aspect, R$^v$ is alkoxycarbonyloxyalkyl. In another aspect, R$^v$ is lower acyl.

In one aspect, the present invention excludes throughout unsubstituted lower alkyl diesters of X when X is PO$_3$H$_2$, e.g., where X is —P(O)(OCH$_2$CH$_3$)$_2$.

Specific Compounds

In one aspect the following compounds are included in the invention but the compounds are not limited to these illustrative compounds. The compounds are shown without depiction of stereochemistry since the compounds are biologically active as the diastereomeric mixture or as a single stereoisomer. Compounds named in Table 2 are designated by numbers assigned to the variables of formulas V-VII using the following convention: V$^1$.V$^2$.V$^3$.V$^4$.

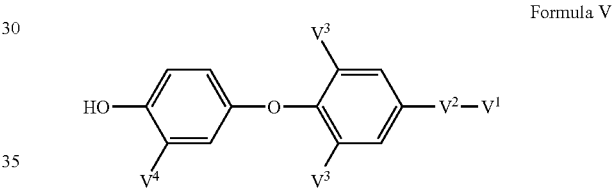

Formula V

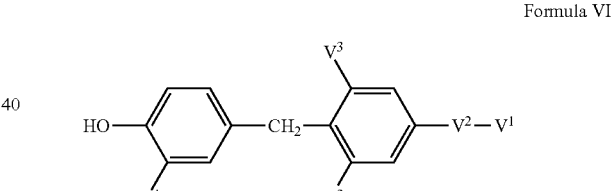

Formula VI

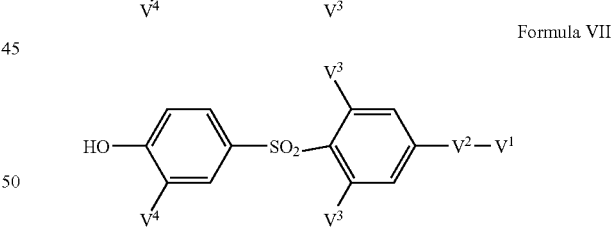

Formula VII

Variable V$^1$:
1) —P(O)(OH)$_2$
2) —P(O)[O—CH$_2$OC(O)C(CH$_3$)$_3$]$_2$
3) —P(O)[O—CH$_2$OC(O)CHO(CH$_3$)$_2$]$_2$
4) —P(O)[O—CH$_2$OC(O)OCH$_2$CH$_3$]$_2$
5) —P(O)[NH—CH(CH$_3$)C(O)OCH$_2$CH$_3$]$_2$
6) —P(O)[NH—C(CH$_3$)$_2$C(O)OCH$_2$CH$_3$]$_2$
7) —P(O)(OC$_6$H$_5$)$_2$
8) —P(O)(O—CH(3-chlorophenyl)CH$_2$CH$_2$—O)
9) —P(O)(O—CH(4-pyridyl)CH$_2$CH$_2$—O)

Variable V$^2$:
1) —CH$_2$—
2) —OCH$_2$—
3) —CH$_2$—CH$_2$—

4) —NHCH$_2$—
5) —NH(CO)—
6) —CH$_2$—CH(NH$_2$)— (R-configuration)
7) —CH$_2$—CH(NH$_2$)— (S-configuration)
8) —CH=CH— (trans)
9) -null Variable V$^3$:
1) —Omethyl
2) iodo
3) bromo
4) chloro
5) fluoro
6) methyl
7) trifluoromethyl
8) cyano
9) —OCF$_3$ Variable V$^4$:
1) iodo
2) CH(CH$_3$)$_2$
3) C$_6$H$_{11}$
4) C$_6$H$_5$
5) —C(O)NHC$_6$H$_{11}$
6) —CH(OH)(4-fluorophenyl)
7) —SO$_2$(4-fluorophenyl)
8) —SO$_2$(N-piperazinyl)
9) bromo In another aspect additional compounds are listed in Table 2 using Formula V, VI or VII. For example, the compound 1.3.6.7 from Formula V represents the compound of Formula V wherein V$^1$ is 1, i.e., of group V$^1$ is 1, i.e., of group —P(O)(OH)$_2$; V$^2$ is 3, i.e., of group —CH$_2$—CH$_2$—; V$^3$ is 6, i.e., of group methyl; and V$^4$ is 7, i.e., of group —SO$_2$(4-fluorophenyl).

TABLE 2

| | | | | | | | | | |
|---|---|---|---|---|---|---|---|---|---|
| 1.1.1.1 | 1.1.1.2 | 1.1.1.3 | 1.1.1.4 | 1.1.1.5 | 1.1.1.6 | 1.1.1.7 | 1.1.1.8 | 1.1.1.9 | 1.1.2.1 |
| 1.1.2.2 | 1.1.2.3 | 1.1.2.4 | 1.1.2.5 | 1.1.2.6 | 1.1.2.7 | 1.1.2.8 | 1.1.2.9 | 1.1.3.1 | 1.1.3.2 |
| 1.1.3.3 | 1.1.3.4 | 1.1.3.5 | 1.1.3.6 | 1.1.3.7 | 1.1.3.8 | 1.1.3.9 | 1.1.4.1 | 1.1.4.2 | 1.1.4.3 |
| 1.1.4.4 | 1.1.4.5 | 1.1.4.6 | 1.1.4.7 | 1.1.4.8 | 1.1.4.9 | 1.1.5.1 | 1.1.5.2 | 1.1.5.3 | 1.1.5.4 |
| 1.1.5.5 | 1.1.5.6 | 1.1.5.7 | 1.1.5.8 | 1.1.5.9 | 1.1.6.1 | 1.1.6.2 | 1.1.6.3 | 1.1.6.4 | 1.1.6.5 |
| 1.1.6.6 | 1.1.6.7 | 1.1.6.8 | 1.1.6.9 | 1.1.7.1 | 1.1.7.2 | 1.1.7.3 | 1.1.7.4 | 1.1.7.5 | 1.1.7.6 |
| 1.1.7.7 | 1.1.7.8 | 1.1.7.9 | 1.1.8.1 | 1.1.8.2 | 1.1.8.3 | 1.1.8.4 | 1.1.8.5 | 1.1.8.6 | 1.1.8.7 |
| 1.1.8.8 | 1.1.8.9 | 1.1.9.1 | 1.1.9.2 | 1.1.9.3 | 1.1.9.4 | 1.1.9.5 | 1.1.9.6 | 1.1.9.7 | 1.1.9.8 |
| 1.1.9.9 | 1.2.1.1 | 1.2.1.2 | 1.2.1.3 | 1.2.1.4 | 1.2.1.5 | 1.2.1.6 | 1.2.1.7 | 1.2.1.8 | 1.2.1.9 |
| 1.2.2.1 | 1.2.2.2 | 1.2.2.3 | 1.2.2.4 | 1.2.2.5 | 1.2.2.6 | 1.2.2.7 | 1.2.2.8 | 1.2.2.9 | 1.2.3.1 |
| 1.2.3.2 | 1.2.3.3 | 1.2.3.4 | 1.2.3.5 | 1.2.3.6 | 1.2.3.7 | 1.2.3.8 | 1.2.3.9 | 1.2.4.1 | 1.2.4.2 |
| 1.2.4.3 | 1.2.4.4 | 1.2.4.5 | 1.2.4.6 | 1.2.4.7 | 1.2.4.8 | 1.2.4.9 | 1.2.5.1 | 1.2.5.2 | 1.2.5.3 |
| 1.2.5.4 | 1.2.5.5 | 1.2.5.6 | 1.2.5.7 | 1.2.5.8 | 1.2.5.9 | 1.2.6.1 | 1.2.6.2 | 1.2.6.3 | 1.2.6.4 |
| 1.2.6.5 | 1.2.6.6 | 1.2.6.7 | 1.2.6.8 | 1.2.6.9 | 1.2.7.1 | 1.2.7.2 | 1.2.7.3 | 1.2.7.4 | 1.2.7.5 |
| 1.2.7.6 | 1.2.7.7 | 1.2.7.8 | 1.2.7.9 | 1.2.8.1 | 1.2.8.2 | 1.2.8.3 | 1.2.8.4 | 1.2.8.5 | 1.2.8.6 |
| 1.2.8.7 | 1.2.8.8 | 1.2.8.9 | 1.2.9.1 | 1.2.9.2 | 1.2.9.3 | 1.2.9.4 | 1.2.9.5 | 1.2.9.6 | 1.2.9.7 |
| 1.2.9.8 | 1.2.9.9 | 1.3.1.1 | 1.3.1.2 | 1.3.1.3 | 1.3.1.4 | 1.3.1.5 | 1.3.1.6 | 1.3.1.7 | 1.3.1.8 |
| 1.3.1.9 | 1.3.2.1 | 1.3.2.2 | 1.3.2.3 | 1.3.2.4 | 1.3.2.5 | 1.3.2.6 | 1.3.2.7 | 1.3.2.8 | 1.3.2.9 |
| 1.3.3.1 | 1.3.3.2 | 1.3.3.3 | 1.3.3.4 | 1.3.3.5 | 1.3.3.6 | 1.3.3.7 | 1.3.3.8 | 1.3.3.9 | 1.3.4.1 |
| 1.3.4.2 | 1.3.4.3 | 1.3.4.4 | 1.3.4.5 | 1.3.4.6 | 1.3.4.7 | 1.3.4.8 | 1.3.4.9 | 1.3.5.1 | 1.3.5.2 |
| 1.3.5.3 | 1.3.5.4 | 1.3.5.5 | 1.3.5.6 | 1.3.5.7 | 1.3.5.8 | 1.3.5.9 | 1.3.6.1 | 1.3.6.2 | 1.3.6.3 |
| 1.3.6.4 | 1.3.6.5 | 1.3.6.6 | 1.3.6.7 | 1.3.6.8 | 1.3.6.9 | 1.3.7.1 | 1.3.7.2 | 1.3.7.3 | 1.3.7.4 |
| 1.3.7.5 | 1.3.7.6 | 1.3.7.7 | 1.3.7.8 | 1.3.7.9 | 1.3.8.1 | 1.3.8.2 | 1.3.8.3 | 1.3.8.4 | 1.3.8.5 |
| 1.3.8.6 | 1.3.8.7 | 1.3.8.8 | 1.3.8.9 | 1.3.9.1 | 1.3.9.2 | 1.3.9.3 | 1.3.9.4 | 1.3.9.5 | 1.3.9.6 |
| 1.3.9.7 | 1.3.9.8 | 1.3.9.9 | 1.4.1.1 | 1.4.1.2 | 1.4.1.3 | 1.4.1.4 | 1.4.1.5 | 1.4.1.6 | 1.4.1.7 |
| 1.4.1.8 | 1.4.1.9 | 1.4.2.1 | 1.4.2.2 | 1.4.2.3 | 1.4.2.4 | 1.4.2.5 | 1.4.2.6 | 1.4.2.7 | 1.4.2.8 |
| 1.4.2.9 | 1.4.3.1 | 1.4.3.2 | 1.4.3.3 | 1.4.3.4 | 1.4.3.5 | 1.4.3.6 | 1.4.3.7 | 1.4.3.8 | 1.4.3.9 |
| 1.4.4.1 | 1.4.4.2 | 1.4.4.3 | 1.4.4.4 | 1.4.4.5 | 1.4.4.6 | 1.4.4.7 | 1.4.4.8 | 1.4.4.9 | 1.4.5.1 |
| 1.4.5.2 | 1.4.5.3 | 1.4.5.4 | 1.4.5.5 | 1.4.5.6 | 1.4.5.7 | 1.4.5.8 | 1.4.5.9 | 1.4.6.1 | 1.4.6.2 |
| 1.4.6.3 | 1.4.6.4 | 1.4.6.5 | 1.4.6.6 | 1.4.6.7 | 1.4.6.8 | 1.4.6.9 | 1.4.7.1 | 1.4.7.2 | 1.4.7.3 |
| 1.4.7.4 | 1.4.7.5 | 1.4.7.6 | 1.4.7.7 | 1.4.7.8 | 1.4.7.9 | 1.4.8.1 | 1.4.8.2 | 1.4.8.3 | 1.4.8.4 |
| 1.4.8.5 | 1.4.8.6 | 1.4.8.7 | 1.4.8.8 | 1.4.8.9 | 1.4.9.1 | 1.4.9.2 | 1.4.9.3 | 1.4.9.4 | 1.4.9.5 |
| 1.4.9.6 | 1.4.9.7 | 1.4.9.8 | 1.4.9.9 | 1.5.1.1 | 1.5.1.2 | 1.5.1.3 | 1.5.1.4 | 1.5.1.5 | 1.5.1.6 |
| 1.5.1.7 | 1.5.1.8 | 1.5.1.9 | 1.5.2.1 | 1.5.2.2 | 1.5.2.3 | 1.5.2.4 | 1.5.2.5 | 1.5.2.6 | 1.5.2.7 |
| 1.5.2.8 | 1.5.2.9 | 1.5.3.1 | 1.5.3.2 | 1.5.3.3 | 1.5.3.4 | 1.5.3.5 | 1.5.3.6 | 1.5.3.7 | 1.5.3.8 |
| 1.5.3.9 | 1.5.4.1 | 1.5.4.2 | 1.5.4.3 | 1.5.4.4 | 1.5.4.5 | 1.5.4.6 | 1.5.4.7 | 1.5.4.8 | 1.5.4.9 |
| 1.5.5.1 | 1.5.5.2 | 1.5.5.3 | 1.5.5.4 | 1.5.5.5 | 1.5.5.6 | 1.5.5.7 | 1.5.5.8 | 1.5.5.9 | 1.5.6.1 |
| 1.5.6.2 | 1.5.6.3 | 1.5.6.4 | 1.5.6.5 | 1.5.6.6 | 1.5.6.7 | 1.5.6.8 | 1.5.6.9 | 1.5.7.1 | 1.5.7.2 |
| 1.5.7.3 | 1.5.7.4 | 1.5.7.5 | 1.5.7.6 | 1.5.7.7 | 1.5.7.8 | 1.5.7.9 | 1.5.8.1 | 1.5.8.2 | 1.5.8.3 |
| 1.5.8.4 | 1.5.8.5 | 1.5.8.6 | 1.5.8.7 | 1.5.8.8 | 1.5.8.9 | 1.5.9.1 | 1.5.9.2 | 1.5.9.3 | 1.5.9.4 |
| 1.5.9.5 | 1.5.9.6 | 1.5.9.7 | 1.5.9.8 | 1.5.9.9 | 1.6.1.1 | 1.6.1.2 | 1.6.1.3 | 1.6.1.4 | 1.6.1.5 |
| 1.6.1.6 | 1.6.1.7 | 1.6.1.8 | 1.6.1.9 | 1.6.2.1 | 1.6.2.2 | 1.6.2.3 | 1.6.2.4 | 1.6.2.5 | 1.6.2.6 |
| 1.6.2.7 | 1.6.2.8 | 1.6.2.9 | 1.6.3.1 | 1.6.3.2 | 1.6.3.3 | 1.6.3.4 | 1.6.3.5 | 1.6.3.6 | 1.6.3.7 |
| 1.6.3.8 | 1.6.3.9 | 1.6.4.1 | 1.6.4.2 | 1.6.4.3 | 1.6.4.4 | 1.6.4.5 | 1.6.4.6 | 1.6.4.7 | 1.6.4.8 |
| 1.6.4.9 | 1.6.5.1 | 1.6.5.2 | 1.6.5.3 | 1.6.5.4 | 1.6.5.5 | 1.6.5.6 | 1.6.5.7 | 1.6.5.8 | 1.6.5.9 |
| 1.6.6.1 | 1.6.6.2 | 1.6.6.3 | 1.6.6.4 | 1.6.6.5 | 1.6.6.6 | 1.6.6.7 | 1.6.6.8 | 1.6.6.9 | 1.6.7.1 |
| 1.6.7.2 | 1.6.7.3 | 1.6.7.4 | 1.6.7.5 | 1.6.7.6 | 1.6.7.7 | 1.6.7.8 | 1.6.7.9 | 1.6.8.1 | 1.6.8.2 |
| 1.6.8.3 | 1.6.8.4 | 1.6.8.5 | 1.6.8.6 | 1.6.8.7 | 1.6.8.8 | 1.6.8.9 | 1.6.9.1 | 1.6.9.2 | 1.6.9.3 |
| 1.6.9.4 | 1.6.9.5 | 1.6.9.6 | 1.6.9.7 | 1.6.9.8 | 1.6.9.9 | 1.7.1.1 | 1.7.1.2 | 1.7.1.3 | 1.7.1.4 |
| 1.7.1.5 | 1.7.1.6 | 1.7.1.7 | 1.7.1.8 | 1.7.1.9 | 1.7.2.1 | 1.7.2.2 | 1.7.2.3 | 1.7.2.4 | 1.7.2.5 |
| 1.7.2.6 | 1.7.2.7 | 1.7.2.8 | 1.7.2.9 | 1.7.3.1 | 1.7.3.2 | 1.7.3.3 | 1.7.3.4 | 1.7.3.5 | 1.7.3.6 |
| 1.7.3.7 | 1.7.3.8 | 1.7.3.9 | 1.7.4.1 | 1.7.4.2 | 1.7.4.3 | 1.7.4.4 | 1.7.4.5 | 1.7.4.6 | 1.7.4.7 |
| 1.7.4.8 | 1.7.4.9 | 1.7.5.1 | 1.7.5.2 | 1.7.5.3 | 1.7.5.4 | 1.7.5.5 | 1.7.5.6 | 1.7.5.7 | 1.7.5.8 |
| 1.7.5.9 | 1.7.6.1 | 1.7.6.2 | 1.7.6.3 | 1.7.6.4 | 1.7.6.5 | 1.7.6.6 | 1.7.6.7 | 1.7.6.8 | 1.7.6.9 |
| 1.7.7.1 | 1.7.7.2 | 1.7.7.3 | 1.7.7.4 | 1.7.7.5 | 1.7.7.6 | 1.7.7.7 | 1.7.7.8 | 1.7.7.9 | 1.7.8.1 |
| 1.7.8.2 | 1.7.8.3 | 1.7.8.4 | 1.7.8.5 | 1.7.8.6 | 1.7.8.7 | 1.7.8.8 | 1.7.8.9 | 1.7.9.1 | 1.7.9.2 |
| 1.7.9.3 | 1.7.9.4 | 1.7.9.5 | 1.7.9.6 | 1.7.9.7 | 1.7.9.8 | 1.7.9.9 | 1.8.1.1 | 1.8.1.2 | 1.8.1.3 |

TABLE 2-continued

| | | | | | | | | | |
|---|---|---|---|---|---|---|---|---|---|
| 1.8.1.4 | 1.8.1.5 | 1.8.1.6 | 1.8.1.7 | 1.8.1.8 | 1.8.1.9 | 1.8.2.1 | 1.8.2.2 | 1.8.2.3 | 1.8.2.4 |
| 1.8.2.5 | 1.8.2.6 | 1.8.2.7 | 1.8.2.8 | 1.8.2.9 | 1.8.3.1 | 1.8.3.2 | 1.8.3.3 | 1.8.3.4 | 1.8.3.5 |
| 1.8.3.6 | 1.8.3.7 | 1.8.3.8 | 1.8.3.9 | 1.8.4.1 | 1.8.4.2 | 1.8.4.3 | 1.8.4.4 | 1.8.4.5 | 1.8.4.6 |
| 1.8.4.7 | 1.8.4.8 | 1.8.4.9 | 1.8.5.1 | 1.8.5.2 | 1.8.5.3 | 1.8.5.4 | 1.8.5.5 | 1.8.5.6 | 1.8.5.7 |
| 1.8.5.8 | 1.8.5.9 | 1.8.6.1 | 1.8.6.2 | 1.8.6.3 | 1.8.6.4 | 1.8.6.5 | 1.8.6.6 | 1.8.6.7 | 1.8.6.8 |
| 1.8.6.9 | 1.8.7.1 | 1.8.7.2 | 1.8.7.3 | 1.8.7.4 | 1.8.7.5 | 1.8.7.6 | 1.8.7.7 | 1.8.7.8 | 1.8.7.9 |
| 1.8.8.1 | 1.8.8.2 | 1.8.8.3 | 1.8.8.4 | 1.8.8.5 | 1.8.8.6 | 1.8.8.7 | 1.8.8.8 | 1.8.8.9 | 1.8.9.1 |
| 1.8.9.2 | 1.8.9.3 | 1.8.9.4 | 1.8.9.5 | 1.8.9.6 | 1.8.9.7 | 1.8.9.8 | 1.8.9.9 | 1.9.1.1 | 1.9.1.2 |
| 1.9.1.3 | 1.9.1.4 | 1.9.1.5 | 1.9.1.6 | 1.9.1.7 | 1.9.1.8 | 1.9.1.9 | 1.9.2.1 | 1.9.2.2 | 1.9.2.3 |
| 1.9.2.4 | 1.9.2.5 | 1.9.2.6 | 1.9.2.7 | 1.9.2.8 | 1.9.2.9 | 1.9.3.1 | 1.9.3.2 | 1.9.3.3 | 1.9.3.4 |
| 1.9.3.5 | 1.9.3.6 | 1.9.3.7 | 1.9.3.8 | 1.9.3.9 | 1.9.4.1 | 1.9.4.2 | 1.9.4.3 | 1.9.4.4 | 1.9.4.5 |
| 1.9.4.6 | 1.9.4.7 | 1.9.4.8 | 1.9.4.9 | 1.9.5.1 | 1.9.5.2 | 1.9.5.3 | 1.9.5.4 | 1.9.5.5 | 1.9.5.6 |
| 1.9.5.7 | 1.9.5.8 | 1.9.5.9 | 1.9.6.1 | 1.9.6.2 | 1.9.6.3 | 1.9.6.4 | 1.9.6.5 | 1.9.6.6 | 1.9.6.7 |
| 1.9.6.8 | 1.9.6.9 | 1.9.7.1 | 1.9.7.2 | 1.9.7.3 | 1.9.7.4 | 1.9.7.5 | 1.9.7.6 | 1.9.7.7 | 1.9.7.8 |
| 1.9.7.9 | 1.9.8.1 | 1.9.8.2 | 1.9.8.3 | 1.9.8.4 | 1.9.8.5 | 1.9.8.6 | 1.9.8.7 | 1.9.8.8 | 1.9.8.9 |
| 1.9.9.1 | 1.9.9.2 | 1.9.9.3 | 1.9.9.4 | 1.9.9.5 | 1.9.9.6 | 1.9.9.7 | 1.9.9.8 | 1.9.9.9 | 2.1.1.1 |
| 2.1.1.2 | 2.1.1.3 | 2.1.1.4 | 2.1.1.5 | 2.1.1.6 | 2.1.1.7 | 2.1.1.8 | 2.1.1.9 | 2.1.2.1 | 2.1.2.2 |
| 2.1.2.3 | 2.1.2.4 | 2.1.2.5 | 2.1.2.6 | 2.1.2.7 | 2.1.2.8 | 2.1.2.9 | 2.1.3.1 | 2.1.3.2 | 2.1.3.3 |
| 2.1.3.4 | 2.1.3.5 | 2.1.3.6 | 2.1.3.7 | 2.1.3.8 | 2.1.3.9 | 2.1.4.1 | 2.1.4.2 | 2.1.4.3 | 2.1.4.4 |
| 2.1.4.5 | 2.1.4.6 | 2.1.4.7 | 2.1.4.8 | 2.1.4.9 | 2.1.5.1 | 2.1.5.2 | 2.1.5.3 | 2.1.5.4 | 2.1.5.5 |
| 2.1.5.6 | 2.1.5.7 | 2.1.5.8 | 2.1.5.9 | 2.1.6.1 | 2.1.6.2 | 2.1.6.3 | 2.1.6.4 | 2.1.6.5 | 2.1.6.6 |
| 2.1.6.7 | 2.1.6.8 | 2.1.6.9 | 2.1.7.1 | 2.1.7.2 | 2.1.7.3 | 2.1.7.4 | 2.1.7.5 | 2.1.7.6 | 2.1.7.7 |
| 2.1.7.8 | 2.1.7.9 | 2.1.8.1 | 2.1.8.2 | 2.1.8.3 | 2.1.8.4 | 2.1.8.5 | 2.1.8.6 | 2.1.8.7 | 2.1.8.8 |
| 2.1.8.9 | 2.1.9.1 | 2.1.9.2 | 2.1.9.3 | 2.1.9.4 | 2.1.9.5 | 2.1.9.6 | 2.1.9.7 | 2.1.9.8 | 2.1.9.9 |
| 2.2.1.1 | 2.2.1.2 | 2.2.1.3 | 2.2.1.4 | 2.2.1.5 | 2.2.1.6 | 2.2.1.7 | 2.2.1.8 | 2.2.1.9 | 2.2.2.1 |
| 2.2.2.2 | 2.2.2.3 | 2.2.2.4 | 2.2.2.5 | 2.2.2.6 | 2.2.2.7 | 2.2.2.8 | 2.2.2.9 | 2.2.3.1 | 2.2.3.2 |
| 2.2.3.3 | 2.2.3.4 | 2.2.3.5 | 2.2.3.6 | 2.2.3.7 | 2.2.3.8 | 2.2.3.9 | 2.2.4.1 | 2.2.4.2 | 2.2.4.3 |
| 2.2.4.4 | 2.2.4.5 | 2.2.4.6 | 2.2.4.7 | 2.2.4.8 | 2.2.4.9 | 2.2.5.1 | 2.2.5.2 | 2.2.5.3 | 2.2.5.4 |
| 2.2.5.5 | 2.2.5.6 | 2.2.5.7 | 2.2.5.8 | 2.2.5.9 | 2.2.6.1 | 2.2.6.2 | 2.2.6.3 | 2.2.6.4 | 2.2.6.5 |
| 2.2.6.6 | 2.2.6.7 | 2.2.6.8 | 2.2.6.9 | 2.2.7.1 | 2.2.7.2 | 2.2.7.3 | 2.2.7.4 | 2.2.7.5 | 2.2.7.6 |
| 2.2.7.7 | 2.2.7.8 | 2.2.7.9 | 2.2.8.1 | 2.2.8.2 | 2.2.8.3 | 2.2.8.4 | 2.2.8.5 | 2.2.8.6 | 2.2.8.7 |
| 2.2.8.8 | 2.2.8.9 | 2.2.9.1 | 2.2.9.2 | 2.2.9.3 | 2.2.9.4 | 2.2.9.5 | 2.2.9.6 | 2.2.9.7 | 2.2.9.8 |
| 2.2.9.9 | 2.3.1.1 | 2.3.1.2 | 2.3.1.3 | 2.3.1.4 | 2.3.1.5 | 2.3.1.6 | 2.3.1.7 | 2.3.1.8 | 2.3.1.9 |
| 2.3.2.1 | 2.3.2.2 | 2.3.2.3 | 2.3.2.4 | 2.3.2.5 | 2.3.2.6 | 2.3.2.7 | 2.3.2.8 | 2.3.2.9 | 2.3.3.1 |
| 2.3.3.2 | 2.3.3.3 | 2.3.3.4 | 2.3.3.5 | 2.3.3.6 | 2.3.3.7 | 2.3.3.8 | 2.3.3.9 | 2.3.4.1 | 2.3.4.2 |
| 2.3.4.3 | 2.3.4.4 | 2.3.4.5 | 2.3.4.6 | 2.3.4.7 | 2.3.4.8 | 2.3.4.9 | 2.3.5.1 | 2.3.5.2 | 2.3.5.3 |
| 2.3.5.4 | 2.3.5.5 | 2.3.5.6 | 2.3.5.7 | 2.3.5.8 | 2.3.5.9 | 2.3.6.1 | 2.3.6.2 | 2.3.6.3 | 2.3.6.4 |
| 2.3.6.5 | 2.3.6.6 | 2.3.6.7 | 2.3.6.8 | 2.3.6.9 | 2.3.7.1 | 2.3.7.2 | 2.3.7.3 | 2.3.7.4 | 2.3.7.5 |
| 2.3.7.6 | 2.3.7.7 | 2.3.7.8 | 2.3.7.9 | 2.3.8.1 | 2.3.8.2 | 2.3.8.3 | 2.3.8.4 | 2.3.8.5 | 2.3.8.6 |
| 2.3.8.7 | 2.3.8.8 | 2.3.8.9 | 2.3.9.1 | 2.3.9.2 | 2.3.9.3 | 2.3.9.4 | 2.3.9.5 | 2.3.9.6 | 2.3.9.7 |
| 2.3.9.8 | 2.3.9.9 | 2.4.1.1 | 2.4.1.2 | 2.4.1.3 | 2.4.1.4 | 2.4.1.5 | 2.4.1.6 | 2.4.1.7 | 2.4.1.8 |
| 2.4.1.9 | 2.4.2.1 | 2.4.2.2 | 2.4.2.3 | 2.4.2.4 | 2.4.2.5 | 2.4.2.6 | 2.4.2.7 | 2.4.2.8 | 2.4.2.9 |
| 2.4.3.1 | 2.4.3.2 | 2.4.3.3 | 2.4.3.4 | 2.4.3.5 | 2.4.3.6 | 2.4.3.7 | 2.4.3.8 | 2.4.3.9 | 2.4.4.1 |
| 2.4.4.2 | 2.4.4.3 | 2.4.4.4 | 2.4.4.5 | 2.4.4.6 | 2.4.4.7 | 2.4.4.8 | 2.4.4.9 | 2.4.5.1 | 2.4.5.2 |
| 2.4.5.3 | 2.4.5.4 | 2.4.5.5 | 2.4.5.6 | 2.4.5.7 | 2.4.5.8 | 2.4.5.9 | 2.4.6.1 | 2.4.6.2 | 2.4.6.3 |
| 2.4.6.4 | 2.4.6.5 | 2.4.6.6 | 2.4.6.7 | 2.4.6.8 | 2.4.6.9 | 2.4.7.1 | 2.4.7.2 | 2.4.7.3 | 2.4.7.4 |
| 2.4.7.5 | 2.4.7.6 | 2.4.7.7 | 2.4.7.8 | 2.4.7.9 | 2.4.8.1 | 2.4.8.2 | 2.4.8.3 | 2.4.8.4 | 2.4.8.5 |
| 2.4.8.6 | 2.4.8.7 | 2.4.8.8 | 2.4.8.9 | 2.4.9.1 | 2.4.9.2 | 2.4.9.3 | 2.4.9.4 | 2.4.9.5 | 2.4.9.6 |
| 2.4.9.7 | 2.4.9.8 | 2.4.9.9 | 2.5.1.1 | 2.5.1.2 | 2.5.1.3 | 2.5.1.4 | 2.5.1.5 | 2.5.1.6 | 2.5.1.7 |
| 2.5.1.8 | 2.5.1.9 | 2.5.2.1 | 2.5.2.2 | 2.5.2.3 | 2.5.2.4 | 2.5.2.5 | 2.5.2.6 | 2.5.2.7 | 2.5.2.8 |
| 2.5.2.9 | 2.5.3.1 | 2.5.3.2 | 2.5.3.3 | 2.5.3.4 | 2.5.3.5 | 2.5.3.6 | 2.5.3.7 | 2.5.3.8 | 2.5.3.9 |
| 2.5.4.1 | 2.5.4.2 | 2.5.4.3 | 2.5.4.4 | 2.5.4.5 | 2.5.4.6 | 2.5.4.7 | 2.5.4.8 | 2.5.4.9 | 2.5.5.1 |
| 2.5.5.2 | 2.5.5.3 | 2.5.5.4 | 2.5.5.5 | 2.5.5.6 | 2.5.5.7 | 2.5.5.8 | 2.5.5.9 | 2.5.6.1 | 2.5.6.2 |
| 2.5.6.3 | 2.5.6.4 | 2.5.6.5 | 2.5.6.6 | 2.5.6.7 | 2.5.6.8 | 2.5.6.9 | 2.5.7.1 | 2.5.7.2 | 2.5.7.3 |
| 2.5.7.4 | 2.5.7.5 | 2.5.7.6 | 2.5.7.7 | 2.5.7.8 | 2.5.7.9 | 2.5.8.1 | 2.5.8.2 | 2.5.8.3 | 2.5.8.4 |
| 2.5.8.5 | 2.5.8.6 | 2.5.8.7 | 2.5.8.8 | 2.5.8.9 | 2.5.9.1 | 2.5.9.2 | 2.5.9.3 | 2.5.9.4 | 2.5.9.5 |
| 2.5.9.6 | 2.5.9.7 | 2.5.9.8 | 2.5.9.9 | 2.6.1.1 | 2.6.1.2 | 2.6.1.3 | 2.6.1.4 | 2.6.1.5 | 2.6.1.6 |
| 2.6.1.7 | 2.6.1.8 | 2.6.1.9 | 2.6.2.1 | 2.6.2.2 | 2.6.2.3 | 2.6.2.4 | 2.6.2.5 | 2.6.2.6 | 2.6.2.7 |
| 2.6.2.8 | 2.6.2.9 | 2.6.3.1 | 2.6.3.2 | 2.6.3.3 | 2.6.3.4 | 2.6.3.5 | 2.6.3.6 | 2.6.3.7 | 2.6.3.8 |
| 2.6.3.9 | 2.6.4.1 | 2.6.4.2 | 2.6.4.3 | 2.6.4.4 | 2.6.4.5 | 2.6.4.6 | 2.6.4.7 | 2.6.4.8 | 2.6.4.9 |
| 2.6.5.1 | 2.6.5.2 | 2.6.5.3 | 2.6.5.4 | 2.6.5.5 | 2.6.5.6 | 2.6.5.7 | 2.6.5.8 | 2.6.5.9 | 2.6.6.1 |
| 2.6.6.2 | 2.6.6.3 | 2.6.6.4 | 2.6.6.5 | 2.6.6.6 | 2.6.6.7 | 2.6.6.8 | 2.6.6.9 | 2.6.7.1 | 2.6.7.2 |
| 2.6.7.3 | 2.6.7.4 | 2.6.7.5 | 2.6.7.6 | 2.6.7.7 | 2.6.7.8 | 2.6.7.9 | 2.6.8.1 | 2.6.8.2 | 2.6.8.3 |
| 2.6.8.4 | 2.6.8.5 | 2.6.8.6 | 2.6.8.7 | 2.6.8.8 | 2.6.8.9 | 2.6.9.1 | 2.6.9.2 | 2.6.9.3 | 2.6.9.4 |
| 2.6.9.5 | 2.6.9.6 | 2.6.9.7 | 2.6.9.8 | 2.6.9.9 | 2.7.1.1 | 2.7.1.2 | 2.7.1.3 | 2.7.1.4 | 2.7.1.5 |
| 2.7.1.6 | 2.7.1.7 | 2.7.1.8 | 2.7.1.9 | 2.7.2.1 | 2.7.2.2 | 2.7.2.3 | 2.7.2.4 | 2.7.2.5 | 2.7.2.6 |
| 2.7.2.7 | 2.7.2.8 | 2.7.2.9 | 2.7.3.1 | 2.7.3.2 | 2.7.3.3 | 2.7.3.4 | 2.7.3.5 | 2.7.3.6 | 2.7.3.7 |
| 2.7.3.8 | 2.7.3.9 | 2.7.4.1 | 2.7.4.2 | 2.7.4.3 | 2.7.4.4 | 2.7.4.5 | 2.7.4.6 | 2.7.4.7 | 2.7.4.8 |
| 2.7.4.9 | 2.7.5.1 | 2.7.5.2 | 2.7.5.3 | 2.7.5.4 | 2.7.5.5 | 2.7.5.6 | 2.7.5.7 | 2.7.5.8 | 2.7.5.9 |
| 2.7.6.1 | 2.7.6.2 | 2.7.6.3 | 2.7.6.4 | 2.7.6.5 | 2.7.6.6 | 2.7.6.7 | 2.7.6.8 | 2.7.6.9 | 2.7.7.1 |
| 2.7.7.2 | 2.7.7.3 | 2.7.7.4 | 2.7.7.5 | 2.7.7.6 | 2.7.7.7 | 2.7.7.8 | 2.7.7.9 | 2.7.8.1 | 2.7.8.2 |
| 2.7.8.3 | 2.7.8.4 | 2.7.8.5 | 2.7.8.6 | 2.7.8.7 | 2.7.8.8 | 2.7.8.9 | 2.7.9.1 | 2.7.9.2 | 2.7.9.3 |
| 2.7.9.4 | 2.7.9.5 | 2.7.9.6 | 2.7.9.7 | 2.7.9.8 | 2.7.9.9 | 2.8.1.1 | 2.8.1.2 | 2.8.1.3 | 2.8.1.4 |
| 2.8.1.5 | 2.8.1.6 | 2.8.1.7 | 2.8.1.8 | 2.8.1.9 | 2.8.2.1 | 2.8.2.2 | 2.8.2.3 | 2.8.2.4 | 2.8.2.5 |
| 2.8.2.6 | 2.8.2.7 | 2.8.2.8 | 2.8.2.9 | 2.8.3.1 | 2.8.3.2 | 2.8.3.3 | 2.8.3.4 | 2.8.3.5 | 2.8.3.6 |
| 2.8.3.7 | 2.8.3.8 | 2.8.3.9 | 2.8.4.1 | 2.8.4.2 | 2.8.4.3 | 2.8.4.4 | 2.8.4.5 | 2.8.4.6 | 2.8.4.7 |
| 2.8.4.8 | 2.8.4.9 | 2.8.5.1 | 2.8.5.2 | 2.8.5.3 | 2.8.5.4 | 2.8.5.5 | 2.8.5.6 | 2.8.5.7 | 2.8.5.8 |
| 2.8.5.9 | 2.8.6.1 | 2.8.6.2 | 2.8.6.3 | 2.8.6.4 | 2.8.6.5 | 2.8.6.6 | 2.8.6.7 | 2.8.6.8 | 2.8.6.9 |
| 2.8.7.1 | 2.8.7.2 | 2.8.7.3 | 2.8.7.4 | 2.8.7.5 | 2.8.7.6 | 2.8.7.7 | 2.8.7.8 | 2.8.7.9 | 2.8.8.1 |

TABLE 2-continued

| | | | | | | | | | |
|---|---|---|---|---|---|---|---|---|---|
| 2.8.8.2 | 2.8.8.3 | 2.8.8.4 | 2.8.8.5 | 2.8.8.6 | 2.8.8.7 | 2.8.8.8 | 2.8.8.9 | 2.8.9.1 | 2.8.9.2 |
| 2.8.9.3 | 2.8.9.4 | 2.8.9.5 | 2.8.9.6 | 2.8.9.7 | 2.8.9.8 | 2.8.9.9 | 2.9.1.1 | 2.9.1.2 | 2.9.1.3 |
| 2.9.1.4 | 2.9.1.5 | 2.9.1.6 | 2.9.1.7 | 2.9.1.8 | 2.9.1.9 | 2.9.2.1 | 2.9.2.2 | 2.9.2.3 | 2.9.2.4 |
| 2.9.2.5 | 2.9.2.6 | 2.9.2.7 | 2.9.2.8 | 2.9.2.9 | 2.9.3.1 | 2.9.3.2 | 2.9.3.3 | 2.9.3.4 | 2.9.3.5 |
| 2.9.3.6 | 2.9.3.7 | 2.9.3.8 | 2.9.3.9 | 2.9.4.1 | 2.9.4.2 | 2.9.4.3 | 2.9.4.4 | 2.9.4.5 | 2.9.4.6 |
| 2.9.4.7 | 2.9.4.8 | 2.9.4.9 | 2.9.5.1 | 2.9.5.2 | 2.9.5.3 | 2.9.5.4 | 2.9.5.5 | 2.9.5.6 | 2.9.5.7 |
| 2.9.5.8 | 2.9.5.9 | 2.9.6.1 | 2.9.6.2 | 2.9.6.3 | 2.9.6.4 | 2.9.6.5 | 2.9.6.6 | 2.9.6.7 | 2.9.6.8 |
| 2.9.6.9 | 2.9.7.1 | 2.9.7.2 | 2.9.7.3 | 2.9.7.4 | 2.9.7.5 | 2.9.7.6 | 2.9.7.7 | 2.9.7.8 | 2.9.7.9 |
| 2.9.8.1 | 2.9.8.2 | 2.9.8.3 | 2.9.8.4 | 2.9.8.5 | 2.9.8.6 | 2.9.8.7 | 2.9.8.8 | 2.9.8.9 | 2.9.9.1 |
| 2.9.9.2 | 2.9.9.3 | 2.9.9.4 | 2.9.9.5 | 2.9.9.6 | 2.9.9.7 | 2.9.9.8 | 2.9.9.9 | 3.1.1.1 | 3.1.1.2 |
| 3.1.1.3 | 3.1.1.4 | 3.1.1.5 | 3.1.1.6 | 3.1.1.7 | 3.1.1.8 | 3.1.1.9 | 3.1.2.1 | 3.1.2.2 | 3.1.2.3 |
| 3.1.2.4 | 3.1.2.5 | 3.1.2.6 | 3.1.2.7 | 3.1.2.8 | 3.1.2.9 | 3.1.3.1 | 3.1.3.2 | 3.1.3.3 | 3.1.3.4 |
| 3.1.3.5 | 3.1.3.6 | 3.1.3.7 | 3.1.3.8 | 3.1.3.9 | 3.1.4.1 | 3.1.4.2 | 3.1.4.3 | 3.1.4.4 | 3.1.4.5 |
| 3.1.4.6 | 3.1.4.7 | 3.1.4.8 | 3.1.4.9 | 3.1.5.1 | 3.1.5.2 | 3.1.5.3 | 3.1.5.4 | 3.1.5.5 | 3.1.5.6 |
| 3.1.5.7 | 3.1.5.8 | 3.1.5.9 | 3.1.6.1 | 3.1.6.2 | 3.1.6.3 | 3.1.6.4 | 3.1.6.5 | 3.1.6.6 | 3.1.6.7 |
| 3.1.6.8 | 3.1.6.9 | 3.1.7.1 | 3.1.7.2 | 3.1.7.3 | 3.1.7.4 | 3.1.7.5 | 3.1.7.6 | 3.1.7.7 | 3.1.7.8 |
| 3.1.7.9 | 3.1.8.1 | 3.1.8.2 | 3.1.8.3 | 3.1.8.4 | 3.1.8.5 | 3.1.8.6 | 3.1.8.7 | 3.1.8.8 | 3.1.8.9 |
| 3.1.9.1 | 3.1.9.2 | 3.1.9.3 | 3.1.9.4 | 3.1.9.5 | 3.1.9.6 | 3.1.9.7 | 3.1.9.8 | 3.1.9.9 | 3.2.1.1 |
| 3.2.1.2 | 3.2.1.3 | 3.2.1.4 | 3.2.1.5 | 3.2.1.6 | 3.2.1.7 | 3.2.1.8 | 3.2.1.9 | 3.2.2.1 | 3.2.2.2 |
| 3.2.2.3 | 3.2.2.4 | 3.2.2.5 | 3.2.2.6 | 3.2.2.7 | 3.2.2.8 | 3.2.2.9 | 3.2.3.1 | 3.2.3.2 | 3.2.3.3 |
| 3.2.3.4 | 3.2.3.5 | 3.2.3.6 | 3.2.3.7 | 3.2.3.8 | 3.2.3.9 | 3.2.4.1 | 3.2.4.2 | 3.2.4.3 | 3.2.4.4 |
| 3.2.4.5 | 3.2.4.6 | 3.2.4.7 | 3.2.4.8 | 3.2.4.9 | 3.2.5.1 | 3.2.5.2 | 3.2.5.3 | 3.2.5.4 | 3.2.5.5 |
| 3.2.5.6 | 3.2.5.7 | 3.2.5.8 | 3.2.5.9 | 3.2.6.1 | 3.2.6.2 | 3.2.6.3 | 3.2.6.4 | 3.2.6.5 | 3.2.6.6 |
| 3.2.6.7 | 3.2.6.8 | 3.2.6.9 | 3.2.7.1 | 3.2.7.2 | 3.2.7.3 | 3.2.7.4 | 3.2.7.5 | 3.2.7.6 | 3.2.7.7 |
| 3.2.7.8 | 3.2.7.9 | 3.2.8.1 | 3.2.8.2 | 3.2.8.3 | 3.2.8.4 | 3.2.8.5 | 3.2.8.6 | 3.2.8.7 | 3.2.8.8 |
| 3.2.8.9 | 3.2.9.1 | 3.2.9.2 | 3.2.9.3 | 3.2.9.4 | 3.2.9.5 | 3.2.9.6 | 3.2.9.7 | 3.2.9.8 | 3.2.9.9 |
| 3.3.1.1 | 3.3.1.2 | 3.3.1.3 | 3.3.1.4 | 3.3.1.5 | 3.3.1.6 | 3.3.1.7 | 3.3.1.8 | 3.3.1.9 | 3.3.2.1 |
| 3.3.2.2 | 3.3.2.3 | 3.3.2.4 | 3.3.2.5 | 3.3.2.6 | 3.3.2.7 | 3.3.2.8 | 3.3.2.9 | 3.3.3.1 | 3.3.3.2 |
| 3.3.3.3 | 3.3.3.4 | 3.3.3.5 | 3.3.3.6 | 3.3.3.7 | 3.3.3.8 | 3.3.3.9 | 3.3.4.1 | 3.3.4.2 | 3.3.4.3 |
| 3.3.4.4 | 3.3.4.5 | 3.3.4.6 | 3.3.4.7 | 3.3.4.8 | 3.3.4.9 | 3.3.5.1 | 3.3.5.2 | 3.3.5.3 | 3.3.5.4 |
| 3.3.5.5 | 3.3.5.6 | 3.3.5.7 | 3.3.5.8 | 3.3.5.9 | 3.3.6.1 | 3.3.6.2 | 3.3.6.3 | 3.3.6.4 | 3.3.6.5 |
| 3.3.6.6 | 3.3.6.7 | 3.3.6.8 | 3.3.6.9 | 3.3.7.1 | 3.3.7.2 | 3.3.7.3 | 3.3.7.4 | 3.3.7.5 | 3.3.7.6 |
| 3.3.7.7 | 3.3.7.8 | 3.3.7.9 | 3.3.8.1 | 3.3.8.2 | 3.3.8.3 | 3.3.8.4 | 3.3.8.5 | 3.3.8.6 | 3.3.8.7 |
| 3.3.8.8 | 3.3.8.9 | 3.3.9.1 | 3.3.9.2 | 3.3.9.3 | 3.3.9.4 | 3.3.9.5 | 3.3.9.6 | 3.3.9.7 | 3.3.9.8 |
| 3.3.9.9 | 3.4.1.1 | 3.4.1.2 | 3.4.1.3 | 3.4.1.4 | 3.4.1.5 | 3.4.1.6 | 3.4.1.7 | 3.4.1.8 | 3.4.1.9 |
| 3.4.2.1 | 3.4.2.2 | 3.4.2.3 | 3.4.2.4 | 3.4.2.5 | 3.4.2.6 | 3.4.2.7 | 3.4.2.8 | 3.4.2.9 | 3.4.3.1 |
| 3.4.3.2 | 3.4.3.3 | 3.4.3.4 | 3.4.3.5 | 3.4.3.6 | 3.4.3.7 | 3.4.3.8 | 3.4.3.9 | 3.4.4.1 | 3.4.4.2 |
| 3.4.4.3 | 3.4.4.4 | 3.4.4.5 | 3.4.4.6 | 3.4.4.7 | 3.4.4.8 | 3.4.4.9 | 3.4.5.1 | 3.4.5.2 | 3.4.5.3 |
| 3.4.5.4 | 3.4.5.5 | 3.4.5.6 | 3.4.5.7 | 3.4.5.8 | 3.4.5.9 | 3.4.6.1 | 3.4.6.2 | 3.4.6.3 | 3.4.6.4 |
| 3.4.6.5 | 3.4.6.6 | 3.4.6.7 | 3.4.6.8 | 3.4.6.9 | 3.4.7.1 | 3.4.7.2 | 3.4.7.3 | 3.4.7.4 | 3.4.7.5 |
| 3.4.7.6 | 3.4.7.7 | 3.4.7.8 | 3.4.7.9 | 3.4.8.1 | 3.4.8.2 | 3.4.8.3 | 3.4.8.4 | 3.4.8.5 | 3.4.8.6 |
| 3.4.8.7 | 3.4.8.8 | 3.4.8.9 | 3.4.9.1 | 3.4.9.2 | 3.4.9.3 | 3.4.9.4 | 3.4.9.5 | 3.4.9.6 | 3.4.9.7 |
| 3.4.9.8 | 3.4.9.9 | 3.5.1.1 | 3.5.1.2 | 3.5.1.3 | 3.5.1.4 | 3.5.1.5 | 3.5.1.6 | 3.5.1.7 | 3.5.1.8 |
| 3.5.1.9 | 3.5.2.1 | 3.5.2.2 | 3.5.2.3 | 3.5.2.4 | 3.5.2.5 | 3.5.2.6 | 3.5.2.7 | 3.5.2.8 | 3.5.2.9 |
| 3.5.3.1 | 3.5.3.2 | 3.5.3.3 | 3.5.3.4 | 3.5.3.5 | 3.5.3.6 | 3.5.3.7 | 3.5.3.8 | 3.5.3.9 | 3.5.4.1 |
| 3.5.4.2 | 3.5.4.3 | 3.5.4.4 | 3.5.4.5 | 3.5.4.6 | 3.5.4.7 | 3.5.4.8 | 3.5.4.9 | 3.5.5.1 | 3.5.5.2 |
| 3.5.5.3 | 3.5.5.4 | 3.5.5.5 | 3.5.5.6 | 3.5.5.7 | 3.5.5.8 | 3.5.5.9 | 3.5.6.1 | 3.5.6.2 | 3.5.6.3 |
| 3.5.6.4 | 3.5.6.5 | 3.5.6.6 | 3.5.6.7 | 3.5.6.8 | 3.5.6.9 | 3.5.7.1 | 3.5.7.2 | 3.5.7.3 | 3.5.7.4 |
| 3.5.7.5 | 3.5.7.6 | 3.5.7.7 | 3.5.7.8 | 3.5.7.9 | 3.5.8.1 | 3.5.8.2 | 3.5.8.3 | 3.5.8.4 | 3.5.8.5 |
| 3.5.8.6 | 3.5.8.7 | 3.5.8.8 | 3.5.8.9 | 3.5.9.1 | 3.5.9.2 | 3.5.9.3 | 3.5.9.4 | 3.5.9.5 | 3.5.9.6 |
| 3.5.9.7 | 3.5.9.8 | 3.5.9.9 | 3.6.1.1 | 3.6.1.2 | 3.6.1.3 | 3.6.1.4 | 3.6.1.5 | 3.6.1.6 | 3.6.1.7 |
| 3.6.1.8 | 3.6.1.9 | 3.6.2.1 | 3.6.2.2 | 3.6.2.3 | 3.6.2.4 | 3.6.2.5 | 3.6.2.6 | 3.6.2.7 | 3.6.2.8 |
| 3.6.2.9 | 3.6.3.1 | 3.6.3.2 | 3.6.3.3 | 3.6.3.4 | 3.6.3.5 | 3.6.3.6 | 3.6.3.7 | 3.6.3.8 | 3.6.3.9 |
| 3.6.4.1 | 3.6.4.2 | 3.6.4.3 | 3.6.4.4 | 3.6.4.5 | 3.6.4.6 | 3.6.4.7 | 3.6.4.8 | 3.6.4.9 | 3.6.5.1 |
| 3.6.5.2 | 3.6.5.3 | 3.6.5.4 | 3.6.5.5 | 3.6.5.6 | 3.6.5.7 | 3.6.5.8 | 3.6.5.9 | 3.6.6.1 | 3.6.6.2 |
| 3.6.6.3 | 3.6.6.4 | 3.6.6.5 | 3.6.6.6 | 3.6.6.7 | 3.6.6.8 | 3.6.6.9 | 3.6.7.1 | 3.6.7.2 | 3.6.7.3 |
| 3.6.7.4 | 3.6.7.5 | 3.6.7.6 | 3.6.7.7 | 3.6.7.8 | 3.6.7.9 | 3.6.8.1 | 3.6.8.2 | 3.6.8.3 | 3.6.8.4 |
| 3.6.8.5 | 3.6.8.6 | 3.6.8.7 | 3.6.8.8 | 3.6.8.9 | 3.6.9.1 | 3.6.9.2 | 3.6.9.3 | 3.6.9.4 | 3.6.9.5 |
| 3.6.9.6 | 3.6.9.7 | 3.6.9.8 | 3.6.9.9 | 3.7.1.1 | 3.7.1.2 | 3.7.1.3 | 3.7.1.4 | 3.7.1.5 | 3.7.1.6 |
| 3.7.1.7 | 3.7.1.8 | 3.7.1.9 | 3.7.2.1 | 3.7.2.2 | 3.7.2.3 | 3.7.2.4 | 3.7.2.5 | 3.7.2.6 | 3.7.2.7 |
| 3.7.2.8 | 3.7.2.9 | 3.7.3.1 | 3.7.3.2 | 3.7.3.3 | 3.7.3.4 | 3.7.3.5 | 3.7.3.6 | 3.7.3.7 | 3.7.3.8 |
| 3.7.3.9 | 3.7.4.1 | 3.7.4.2 | 3.7.4.3 | 3.7.4.4 | 3.7.4.5 | 3.7.4.6 | 3.7.4.7 | 3.7.4.8 | 3.7.4.9 |
| 3.7.5.1 | 3.7.5.2 | 3.7.5.3 | 3.7.5.4 | 3.7.5.5 | 3.7.5.6 | 3.7.5.7 | 3.7.5.8 | 3.7.5.9 | 3.7.6.1 |
| 3.7.6.2 | 3.7.6.3 | 3.7.6.4 | 3.7.6.5 | 3.7.6.6 | 3.7.6.7 | 3.7.6.8 | 3.7.6.9 | 3.7.7.1 | 3.7.7.2 |
| 3.7.7.3 | 3.7.7.4 | 3.7.7.5 | 3.7.7.6 | 3.7.7.7 | 3.7.7.8 | 3.7.7.9 | 3.7.8.1 | 3.7.8.2 | 3.7.8.3 |
| 3.7.8.4 | 3.7.8.5 | 3.7.8.6 | 3.7.8.7 | 3.7.8.8 | 3.7.8.9 | 3.7.9.1 | 3.7.9.2 | 3.7.9.3 | 3.7.9.4 |
| 3.7.9.5 | 3.7.9.6 | 3.7.9.7 | 3.7.9.8 | 3.7.9.9 | 3.8.1.1 | 3.8.1.2 | 3.8.1.3 | 3.8.1.4 | 3.8.1.5 |
| 3.8.1.6 | 3.8.1.7 | 3.8.1.8 | 3.8.1.9 | 3.8.2.1 | 3.8.2.2 | 3.8.2.3 | 3.8.2.4 | 3.8.2.5 | 3.8.2.6 |
| 3.8.2.7 | 3.8.2.8 | 3.8.2.9 | 3.8.3.1 | 3.8.3.2 | 3.8.3.3 | 3.8.3.4 | 3.8.3.5 | 3.8.3.6 | 3.8.3.7 |
| 3.8.3.8 | 3.8.3.9 | 3.8.4.1 | 3.8.4.2 | 3.8.4.3 | 3.8.4.4 | 3.8.4.5 | 3.8.4.6 | 3.8.4.7 | 3.8.4.8 |
| 3.8.4.9 | 3.8.5.1 | 3.8.5.2 | 3.8.5.3 | 3.8.5.4 | 3.8.5.5 | 3.8.5.6 | 3.8.5.7 | 3.8.5.8 | 3.8.5.9 |
| 3.8.6.1 | 3.8.6.2 | 3.8.6.3 | 3.8.6.4 | 3.8.6.5 | 3.8.6.6 | 3.8.6.7 | 3.8.6.8 | 3.8.6.9 | 3.8.7.1 |
| 3.8.7.2 | 3.8.7.3 | 3.8.7.4 | 3.8.7.5 | 3.8.7.6 | 3.8.7.7 | 3.8.7.8 | 3.8.7.9 | 3.8.8.1 | 3.8.8.2 |
| 3.8.8.3 | 3.8.8.4 | 3.8.8.5 | 3.8.8.6 | 3.8.8.7 | 3.8.8.8 | 3.8.8.9 | 3.8.9.1 | 3.8.9.2 | 3.8.9.3 |
| 3.8.9.4 | 3.8.9.5 | 3.8.9.6 | 3.8.9.7 | 3.8.9.8 | 3.8.9.9 | 3.9.1.1 | 3.9.1.2 | 3.9.1.3 | 3.9.1.4 |
| 3.9.1.5 | 3.9.1.6 | 3.9.1.7 | 3.9.1.8 | 3.9.1.9 | 3.9.2.1 | 3.9.2.2 | 3.9.2.3 | 3.9.2.4 | 3.9.2.5 |
| 3.9.2.6 | 3.9.2.7 | 3.9.2.8 | 3.9.2.9 | 3.9.3.1 | 3.9.3.2 | 3.9.3.3 | 3.9.3.4 | 3.9.3.5 | 3.9.3.6 |
| 3.9.3.7 | 3.9.3.8 | 3.9.3.9 | 3.9.4.1 | 3.9.4.2 | 3.9.4.3 | 3.9.4.4 | 3.9.4.5 | 3.9.4.6 | 3.9.4.7 |
| 3.9.4.8 | 3.9.4.9 | 3.9.5.1 | 3.9.5.2 | 3.9.5.3 | 3.9.5.4 | 3.9.5.5 | 3.9.5.6 | 3.9.5.7 | 3.9.5.8 |

TABLE 2-continued

| | | | | | | | | |
|---|---|---|---|---|---|---|---|---|
| 3.9.5.9 | 3.9.6.1 | 3.9.6.2 | 3.9.6.3 | 3.9.6.4 | 3.9.6.5 | 3.9.6.6 | 3.9.6.7 | 3.9.6.8 | 3.9.6.9 |
| 3.9.7.1 | 3.9.7.2 | 3.9.7.3 | 3.9.7.4 | 3.9.7.5 | 3.9.7.6 | 3.9.7.7 | 3.9.7.8 | 3.9.7.9 | 3.9.8.1 |
| 3.9.8.2 | 3.9.8.3 | 3.9.8.4 | 3.9.8.5 | 3.9.8.6 | 3.9.8.7 | 3.9.8.8 | 3.9.8.9 | 3.9.9.1 | 3.9.9.2 |
| 3.9.9.3 | 3.9.9.4 | 3.9.9.5 | 3.9.9.6 | 3.9.9.7 | 3.9.9.8 | 3.9.9.9 | 4.1.1.1 | 4.1.1.2 | 4.1.1.3 |
| 4.1.1.4 | 4.1.1.5 | 4.1.1.6 | 4.1.1.7 | 4.1.1.8 | 4.1.1.9 | 4.1.2.1 | 4.1.2.2 | 4.1.2.3 | 4.1.2.4 |
| 4.1.2.5 | 4.1.2.6 | 4.1.2.7 | 4.1.2.8 | 4.1.2.9 | 4.1.3.1 | 4.1.3.2 | 4.1.3.3 | 4.1.3.4 | 4.1.3.5 |
| 4.1.3.6 | 4.1.3.7 | 4.1.3.8 | 4.1.3.9 | 4.1.4.1 | 4.1.4.2 | 4.1.4.3 | 4.1.4.4 | 4.1.4.5 | 4.1.4.6 |
| 4.1.4.7 | 4.1.4.8 | 4.1.4.9 | 4.1.5.1 | 4.1.5.2 | 4.1.5.3 | 4.1.5.4 | 4.1.5.5 | 4.1.5.6 | 4.1.5.7 |
| 4.1.5.8 | 4.1.5.9 | 4.1.6.1 | 4.1.6.2 | 4.1.6.3 | 4.1.6.4 | 4.1.6.5 | 4.1.6.6 | 4.1.6.7 | 4.1.6.8 |
| 4.1.6.9 | 4.1.7.1 | 4.1.7.2 | 4.1.7.3 | 4.1.7.4 | 4.1.7.5 | 4.1.7.6 | 4.1.7.7 | 4.1.7.8 | 4.1.7.9 |
| 4.1.8.1 | 4.1.8.2 | 4.1.8.3 | 4.1.8.4 | 4.1.8.5 | 4.1.8.6 | 4.1.8.7 | 4.1.8.8 | 4.1.8.9 | 4.1.9.1 |
| 4.1.9.2 | 4.1.9.3 | 4.1.9.4 | 4.1.9.5 | 4.1.9.6 | 4.1.9.7 | 4.1.9.8 | 4.1.9.9 | 4.2.1.1 | 4.2.1.2 |
| 4.2.1.3 | 4.2.1.4 | 4.2.1.5 | 4.2.1.6 | 4.2.1.7 | 4.2.1.8 | 4.2.1.9 | 4.2.2.1 | 4.2.2.2 | 4.2.2.3 |
| 4.2.2.4 | 4.2.2.5 | 4.2.2.6 | 4.2.2.7 | 4.2.2.8 | 4.2.2.9 | 4.2.3.1 | 4.2.3.2 | 4.2.3.3 | 4.2.3.4 |
| 4.2.3.5 | 4.2.3.6 | 4.2.3.7 | 4.2.3.8 | 4.2.3.9 | 4.2.4.1 | 4.2.4.2 | 4.2.4.3 | 4.2.4.4 | 4.2.4.5 |
| 4.2.4.6 | 4.2.4.7 | 4.2.4.8 | 4.2.4.9 | 4.2.5.1 | 4.2.5.2 | 4.2.5.3 | 4.2.5.4 | 4.2.5.5 | 4.2.5.6 |
| 4.2.5.7 | 4.2.5.8 | 4.2.5.9 | 4.2.6.1 | 4.2.6.2 | 4.2.6.3 | 4.2.6.4 | 4.2.6.5 | 4.2.6.6 | 4.2.6.7 |
| 4.2.6.8 | 4.2.6.9 | 4.2.7.1 | 4.2.7.2 | 4.2.7.3 | 4.2.7.4 | 4.2.7.5 | 4.2.7.6 | 4.2.7.7 | 4.2.7.8 |
| 4.2.7.9 | 4.2.8.1 | 4.2.8.2 | 4.2.8.3 | 4.2.8.4 | 4.2.8.5 | 4.2.8.6 | 4.2.8.7 | 4.2.8.8 | 4.2.8.9 |
| 4.2.9.1 | 4.2.9.2 | 4.2.9.3 | 4.2.9.4 | 4.2.9.5 | 4.2.9.6 | 4.2.9.7 | 4.2.9.8 | 4.2.9.9 | 4.3.1.1 |
| 4.3.1.2 | 4.3.1.3 | 4.3.1.4 | 4.3.1.5 | 4.3.1.6 | 4.3.1.7 | 4.3.1.8 | 4.3.1.9 | 4.3.2.1 | 4.3.2.2 |
| 4.3.2.3 | 4.3.2.4 | 4.3.2.5 | 4.3.2.6 | 4.3.2.7 | 4.3.2.8 | 4.3.2.9 | 4.3.3.1 | 4.3.3.2 | 4.3.3.3 |
| 4.3.3.4 | 4.3.3.5 | 4.3.3.6 | 4.3.3.7 | 4.3.3.8 | 4.3.3.9 | 4.3.4.1 | 4.3.4.2 | 4.3.4.3 | 4.3.4.4 |
| 4.3.4.5 | 4.3.4.6 | 4.3.4.7 | 4.3.4.8 | 4.3.4.9 | 4.3.5.1 | 4.3.5.2 | 4.3.5.3 | 4.3.5.4 | 4.3.5.5 |
| 4.3.5.6 | 4.3.5.7 | 4.3.5.8 | 4.3.5.9 | 4.3.6.1 | 4.3.6.2 | 4.3.6.3 | 4.3.6.4 | 4.3.6.5 | 4.3.6.6 |
| 4.3.6.7 | 4.3.6.8 | 4.3.6.9 | 4.3.7.1 | 4.3.7.2 | 4.3.7.3 | 4.3.7.4 | 4.3.7.5 | 4.3.7.6 | 4.3.7.7 |
| 4.3.7.8 | 4.3.7.9 | 4.3.8.1 | 4.3.8.2 | 4.3.8.3 | 4.3.8.4 | 4.3.8.5 | 4.3.8.6 | 4.3.8.7 | 4.3.8.8 |
| 4.3.8.9 | 4.3.9.1 | 4.3.9.2 | 4.3.9.3 | 4.3.9.4 | 4.3.9.5 | 4.3.9.6 | 4.3.9.7 | 4.3.9.8 | 4.3.9.9 |
| 4.4.1.1 | 4.4.1.2 | 4.4.1.3 | 4.4.1.4 | 4.4.1.5 | 4.4.1.6 | 4.4.1.7 | 4.4.1.8 | 4.4.1.9 | 4.4.2.1 |
| 4.4.2.2 | 4.4.2.3 | 4.4.2.4 | 4.4.2.5 | 4.4.2.6 | 4.4.2.7 | 4.4.2.8 | 4.4.2.9 | 4.4.3.1 | 4.4.3.2 |
| 4.4.3.3 | 4.4.3.4 | 4.4.3.5 | 4.4.3.6 | 4.4.3.7 | 4.4.3.8 | 4.4.3.9 | 4.4.4.1 | 4.4.4.2 | 4.4.4.3 |
| 4.4.4.4 | 4.4.4.5 | 4.4.4.6 | 4.4.4.7 | 4.4.4.8 | 4.4.4.9 | 4.4.5.1 | 4.4.5.2 | 4.4.5.3 | 4.4.5.4 |
| 4.4.5.5 | 4.4.5.6 | 4.4.5.7 | 4.4.5.8 | 4.4.5.9 | 4.4.6.1 | 4.4.6.2 | 4.4.6.3 | 4.4.6.4 | 4.4.6.5 |
| 4.4.6.6 | 4.4.6.7 | 4.4.6.8 | 4.4.6.9 | 4.4.7.1 | 4.4.7.2 | 4.4.7.3 | 4.4.7.4 | 4.4.7.5 | 4.4.7.6 |
| 4.4.7.7 | 4.4.7.8 | 4.4.7.9 | 4.4.8.1 | 4.4.8.2 | 4.4.8.3 | 4.4.8.4 | 4.4.8.5 | 4.4.8.6 | 4.4.8.7 |
| 4.4.8.8 | 4.4.8.9 | 4.4.9.1 | 4.4.9.2 | 4.4.9.3 | 4.4.9.4 | 4.4.9.5 | 4.4.9.6 | 4.4.9.7 | 4.4.9.8 |
| 4.4.9.9 | 4.5.1.1 | 4.5.1.2 | 4.5.1.3 | 4.5.1.4 | 4.5.1.5 | 4.5.1.6 | 4.5.1.7 | 4.5.1.8 | 4.5.1.9 |
| 4.5.2.1 | 4.5.2.2 | 4.5.2.3 | 4.5.2.4 | 4.5.2.5 | 4.5.2.6 | 4.5.2.7 | 4.5.2.8 | 4.5.2.9 | 4.5.3.1 |
| 4.5.3.2 | 4.5.3.3 | 4.5.3.4 | 4.5.3.5 | 4.5.3.6 | 4.5.3.7 | 4.5.3.8 | 4.5.3.9 | 4.5.4.1 | 4.5.4.2 |
| 4.5.4.3 | 4.5.4.4 | 4.5.4.5 | 4.5.4.6 | 4.5.4.7 | 4.5.4.8 | 4.5.4.9 | 4.5.5.1 | 4.5.5.2 | 4.5.5.3 |
| 4.5.5.4 | 4.5.5.5 | 4.5.5.6 | 4.5.5.7 | 4.5.5.8 | 4.5.5.9 | 4.5.6.1 | 4.5.6.2 | 4.5.6.3 | 4.5.6.4 |
| 4.5.6.5 | 4.5.6.6 | 4.5.6.7 | 4.5.6.8 | 4.5.6.9 | 4.5.7.1 | 4.5.7.2 | 4.5.7.3 | 4.5.7.4 | 4.5.7.5 |
| 4.5.7.6 | 4.5.7.7 | 4.5.7.8 | 4.5.7.9 | 4.5.8.1 | 4.5.8.2 | 4.5.8.3 | 4.5.8.4 | 4.5.8.5 | 4.5.8.6 |
| 4.5.8.7 | 4.5.8.8 | 4.5.8.9 | 4.5.9.1 | 4.5.9.2 | 4.5.9.3 | 4.5.9.4 | 4.5.9.5 | 4.5.9.6 | 4.5.9.7 |
| 4.5.9.8 | 4.5.9.9 | 4.6.1.1 | 4.6.1.2 | 4.6.1.3 | 4.6.1.4 | 4.6.1.5 | 4.6.1.6 | 4.6.1.7 | 4.6.1.8 |
| 4.6.1.9 | 4.6.2.1 | 4.6.2.2 | 4.6.2.3 | 4.6.2.4 | 4.6.2.5 | 4.6.2.6 | 4.6.2.7 | 4.6.2.8 | 4.6.2.9 |
| 4.6.3.1 | 4.6.3.2 | 4.6.3.3 | 4.6.3.4 | 4.6.3.5 | 4.6.3.6 | 4.6.3.7 | 4.6.3.8 | 4.6.3.9 | 4.6.4.1 |
| 4.6.4.2 | 4.6.4.3 | 4.6.4.4 | 4.6.4.5 | 4.6.4.6 | 4.6.4.7 | 4.6.4.8 | 4.6.4.9 | 4.6.5.1 | 4.6.5.2 |
| 4.6.5.3 | 4.6.5.4 | 4.6.5.5 | 4.6.5.6 | 4.6.5.7 | 4.6.5.8 | 4.6.5.9 | 4.6.6.1 | 4.6.6.2 | 4.6.6.3 |
| 4.6.6.4 | 4.6.6.5 | 4.6.6.6 | 4.6.6.7 | 4.6.6.8 | 4.6.6.9 | 4.6.7.1 | 4.6.7.2 | 4.6.7.3 | 4.6.7.4 |
| 4.6.7.5 | 4.6.7.6 | 4.6.7.7 | 4.6.7.8 | 4.6.7.9 | 4.6.8.1 | 4.6.8.2 | 4.6.8.3 | 4.6.8.4 | 4.6.8.5 |
| 4.6.8.6 | 4.6.8.7 | 4.6.8.8 | 4.6.8.9 | 4.6.9.1 | 4.6.9.2 | 4.6.9.3 | 4.6.9.4 | 4.6.9.5 | 4.6.9.6 |
| 4.6.9.7 | 4.6.9.8 | 4.6.9.9 | 4.7.1.1 | 4.7.1.2 | 4.7.1.3 | 4.7.1.4 | 4.7.1.5 | 4.7.1.6 | 4.7.1.7 |
| 4.7.1.8 | 4.7.1.9 | 4.7.2.1 | 4.7.2.2 | 4.7.2.3 | 4.7.2.4 | 4.7.2.5 | 4.7.2.6 | 4.7.2.7 | 4.7.2.8 |
| 4.7.2.9 | 4.7.3.1 | 4.7.3.2 | 4.7.3.3 | 4.7.3.4 | 4.7.3.5 | 4.7.3.6 | 4.7.3.7 | 4.7.3.8 | 4.7.3.9 |
| 4.7.4.1 | 4.7.4.2 | 4.7.4.3 | 4.7.4.4 | 4.7.4.5 | 4.7.4.6 | 4.7.4.7 | 4.7.4.8 | 4.7.4.9 | 4.7.5.1 |
| 4.7.5.2 | 4.7.5.3 | 4.7.5.4 | 4.7.5.5 | 4.7.5.6 | 4.7.5.7 | 4.7.5.8 | 4.7.5.9 | 4.7.6.1 | 4.7.6.2 |
| 4.7.6.3 | 4.7.6.4 | 4.7.6.5 | 4.7.6.6 | 4.7.6.7 | 4.7.6.8 | 4.7.6.9 | 4.7.7.1 | 4.7.7.2 | 4.7.7.3 |
| 4.7.7.4 | 4.7.7.5 | 4.7.7.6 | 4.7.7.7 | 4.7.7.8 | 4.7.7.9 | 4.7.8.1 | 4.7.8.2 | 4.7.8.3 | 4.7.8.4 |
| 4.7.8.5 | 4.7.8.6 | 4.7.8.7 | 4.7.8.8 | 4.7.8.9 | 4.7.9.1 | 4.7.9.2 | 4.7.9.3 | 4.7.9.4 | 4.7.9.5 |
| 4.7.9.6 | 4.7.9.7 | 4.7.9.8 | 4.7.9.9 | 4.8.1.1 | 4.8.1.2 | 4.8.1.3 | 4.8.1.4 | 4.8.1.5 | 4.8.1.6 |
| 4.8.1.7 | 4.8.1.8 | 4.8.1.9 | 4.8.2.1 | 4.8.2.2 | 4.8.2.3 | 4.8.2.4 | 4.8.2.5 | 4.8.2.6 | 4.8.2.7 |
| 4.8.2.8 | 4.8.2.9 | 4.8.3.1 | 4.8.3.2 | 4.8.3.3 | 4.8.3.4 | 4.8.3.5 | 4.8.3.6 | 4.8.3.7 | 4.8.3.8 |
| 4.8.3.9 | 4.8.4.1 | 4.8.4.2 | 4.8.4.3 | 4.8.4.4 | 4.8.4.5 | 4.8.4.6 | 4.8.4.7 | 4.8.4.8 | 4.8.4.9 |
| 4.8.5.1 | 4.8.5.2 | 4.8.5.3 | 4.8.5.4 | 4.8.5.5 | 4.8.5.6 | 4.8.5.7 | 4.8.5.8 | 4.8.5.9 | 4.8.6.1 |
| 4.8.6.2 | 4.8.6.3 | 4.8.6.4 | 4.8.6.5 | 4.8.6.6 | 4.8.6.7 | 4.8.6.8 | 4.8.6.9 | 4.8.7.1 | 4.8.7.2 |
| 4.8.7.3 | 4.8.7.4 | 4.8.7.5 | 4.8.7.6 | 4.8.7.7 | 4.8.7.8 | 4.8.7.9 | 4.8.8.1 | 4.8.8.2 | 4.8.8.3 |
| 4.8.8.4 | 4.8.8.5 | 4.8.8.6 | 4.8.8.7 | 4.8.8.8 | 4.8.8.9 | 4.8.9.1 | 4.8.9.2 | 4.8.9.3 | 4.8.9.4 |
| 4.8.9.5 | 4.8.9.6 | 4.8.9.7 | 4.8.9.8 | 4.8.9.9 | 4.9.1.1 | 4.9.1.2 | 4.9.1.3 | 4.9.1.4 | 4.9.1.5 |
| 4.9.1.6 | 4.9.1.7 | 4.9.1.8 | 4.9.1.9 | 4.9.2.1 | 4.9.2.2 | 4.9.2.3 | 4.9.2.4 | 4.9.2.5 | 4.9.2.6 |
| 4.9.2.7 | 4.9.2.8 | 4.9.2.9 | 4.9.3.1 | 4.9.3.2 | 4.9.3.3 | 4.9.3.4 | 4.9.3.5 | 4.9.3.6 | 4.9.3.7 |
| 4.9.3.8 | 4.9.3.9 | 4.9.4.1 | 4.9.4.2 | 4.9.4.3 | 4.9.4.4 | 4.9.4.5 | 4.9.4.6 | 4.9.4.7 | 4.9.4.8 |
| 4.9.4.9 | 4.9.5.1 | 4.9.5.2 | 4.9.5.3 | 4.9.5.4 | 4.9.5.5 | 4.9.5.6 | 4.9.5.7 | 4.9.5.8 | 4.9.5.9 |
| 4.9.6.1 | 4.9.6.2 | 4.9.6.3 | 4.9.6.4 | 4.9.6.5 | 4.9.6.6 | 4.9.6.7 | 4.9.6.8 | 4.9.6.9 | 4.9.7.1 |
| 4.9.7.2 | 4.9.7.3 | 4.9.7.4 | 4.9.7.5 | 4.9.7.6 | 4.9.7.7 | 4.9.7.8 | 4.9.7.9 | 4.9.8.1 | 4.9.8.2 |
| 4.9.8.3 | 4.9.8.4 | 4.9.8.5 | 4.9.8.6 | 4.9.8.7 | 4.9.8.8 | 4.9.8.9 | 4.9.9.1 | 4.9.9.2 | 4.9.9.3 |
| 4.9.9.4 | 4.9.9.5 | 4.9.9.6 | 4.9.9.7 | 4.9.9.8 | 4.9.9.9 | 5.1.1.1 | 5.1.1.2 | 5.1.1.3 | 5.1.1.4 |
| 5.1.1.5 | 5.1.1.6 | 5.1.1.7 | 5.1.1.8 | 5.1.1.9 | 5.1.2.1 | 5.1.2.2 | 5.1.2.3 | 5.1.2.4 | 5.1.2.5 |
| 5.1.2.6 | 5.1.2.7 | 5.1.2.8 | 5.1.2.9 | 5.1.3.1 | 5.1.3.2 | 5.1.3.3 | 5.1.3.4 | 5.1.3.5 | 5.1.3.6 |

TABLE 2-continued

| | | | | | | | | |
|---|---|---|---|---|---|---|---|---|
| 5.1.3.7 | 5.1.3.8 | 5.1.3.9 | 5.1.4.1 | 5.1.4.2 | 5.1.4.3 | 5.1.4.4 | 5.1.4.5 | 5.1.4.6 | 5.1.4.7 |
| 5.1.4.8 | 5.1.4.9 | 5.1.5.1 | 5.1.5.2 | 5.1.5.3 | 5.1.5.4 | 5.1.5.5 | 5.1.5.6 | 5.1.5.7 | 5.1.5.8 |
| 5.1.5.9 | 5.1.6.1 | 5.1.6.2 | 5.1.6.3 | 5.1.6.4 | 5.1.6.5 | 5.1.6.6 | 5.1.6.7 | 5.1.6.8 | 5.1.6.9 |
| 5.1.7.1 | 5.1.7.2 | 5.1.7.3 | 5.1.7.4 | 5.1.7.5 | 5.1.7.6 | 5.1.7.7 | 5.1.7.8 | 5.1.7.9 | 5.1.8.1 |
| 5.1.8.2 | 5.1.8.3 | 5.1.8.4 | 5.1.8.5 | 5.1.8.6 | 5.1.8.7 | 5.1.8.8 | 5.1.8.9 | 5.1.9.1 | 5.1.9.2 |
| 5.1.9.3 | 5.1.9.4 | 5.1.9.5 | 5.1.9.6 | 5.1.9.7 | 5.1.9.8 | 5.1.9.9 | 5.2.1.1 | 5.2.1.2 | 5.2.1.3 |
| 5.2.1.4 | 5.2.1.5 | 5.2.1.6 | 5.2.1.7 | 5.2.1.8 | 5.2.1.9 | 5.2.2.1 | 5.2.2.2 | 5.2.2.3 | 5.2.2.4 |
| 5.2.2.5 | 5.2.2.6 | 5.2.2.7 | 5.2.2.8 | 5.2.2.9 | 5.2.3.1 | 5.2.3.2 | 5.2.3.3 | 5.2.3.4 | 5.2.3.5 |
| 5.2.3.6 | 5.2.3.7 | 5.2.3.8 | 5.2.3.9 | 5.2.4.1 | 5.2.4.2 | 5.2.4.3 | 5.2.4.4 | 5.2.4.5 | 5.2.4.6 |
| 5.2.4.7 | 5.2.4.8 | 5.2.4.9 | 5.2.5.1 | 5.2.5.2 | 5.2.5.3 | 5.2.5.4 | 5.2.5.5 | 5.2.5.6 | 5.2.5.7 |
| 5.2.5.8 | 5.2.5.9 | 5.2.6.1 | 5.2.6.2 | 5.2.6.3 | 5.2.6.4 | 5.2.6.5 | 5.2.6.6 | 5.2.6.7 | 5.2.6.8 |
| 5.2.6.9 | 5.2.7.1 | 5.2.7.2 | 5.2.7.3 | 5.2.7.4 | 5.2.7.5 | 5.2.7.6 | 5.2.7.7 | 5.2.7.8 | 5.2.7.9 |
| 5.2.8.1 | 5.2.8.2 | 5.2.8.3 | 5.2.8.4 | 5.2.8.5 | 5.2.8.6 | 5.2.8.7 | 5.2.8.8 | 5.2.8.9 | 5.2.9.1 |
| 5.2.9.2 | 5.2.9.3 | 5.2.9.4 | 5.2.9.5 | 5.2.9.6 | 5.2.9.7 | 5.2.9.8 | 5.2.9.9 | 5.3.1.1 | 5.3.1.2 |
| 5.3.1.3 | 5.3.1.4 | 5.3.1.5 | 5.3.1.6 | 5.3.1.7 | 5.3.1.8 | 5.3.1.9 | 5.3.2.1 | 5.3.2.2 | 5.3.2.3 |
| 5.3.2.4 | 5.3.2.5 | 5.3.2.6 | 5.3.2.7 | 5.3.2.8 | 5.3.2.9 | 5.3.3.1 | 5.3.3.2 | 5.3.3.3 | 5.3.3.4 |
| 5.3.3.5 | 5.3.3.6 | 5.3.3.7 | 5.3.3.8 | 5.3.3.9 | 5.3.4.1 | 5.3.4.2 | 5.3.4.3 | 5.3.4.4 | 5.3.4.5 |
| 5.3.4.6 | 5.3.4.7 | 5.3.4.8 | 5.3.4.9 | 5.3.5.1 | 5.3.5.2 | 5.3.5.3 | 5.3.5.4 | 5.3.5.5 | 5.3.5.6 |
| 5.3.5.7 | 5.3.5.8 | 5.3.5.9 | 5.3.6.1 | 5.3.6.2 | 5.3.6.3 | 5.3.6.4 | 5.3.6.5 | 5.3.6.6 | 5.3.6.7 |
| 5.3.6.8 | 5.3.6.9 | 5.3.7.1 | 5.3.7.2 | 5.3.7.3 | 5.3.7.4 | 5.3.7.5 | 5.3.7.6 | 5.3.7.7 | 5.3.7.8 |
| 5.3.7.9 | 5.3.8.1 | 5.3.8.2 | 5.3.8.3 | 5.3.8.4 | 5.3.8.5 | 5.3.8.6 | 5.3.8.7 | 5.3.8.8 | 5.3.8.9 |
| 5.3.9.1 | 5.3.9.2 | 5.3.9.3 | 5.3.9.4 | 5.3.9.5 | 5.3.9.6 | 5.3.9.7 | 5.3.9.8 | 5.3.9.9 | 5.4.1.1 |
| 5.4.1.2 | 5.4.1.3 | 5.4.1.4 | 5.4.1.5 | 5.4.1.6 | 5.4.1.7 | 5.4.1.8 | 5.4.1.9 | 5.4.2.1 | 5.4.2.2 |
| 5.4.2.3 | 5.4.2.4 | 5.4.2.5 | 5.4.2.6 | 5.4.2.7 | 5.4.2.8 | 5.4.2.9 | 5.4.3.1 | 5.4.3.2 | 5.4.3.3 |
| 5.4.3.4 | 5.4.3.5 | 5.4.3.6 | 5.4.3.7 | 5.4.3.8 | 5.4.3.9 | 5.4.4.1 | 5.4.4.2 | 5.4.4.3 | 5.4.4.4 |
| 5.4.4.5 | 5.4.4.6 | 5.4.4.7 | 5.4.4.8 | 5.4.4.9 | 5.4.5.1 | 5.4.5.2 | 5.4.5.3 | 5.4.5.4 | 5.4.5.5 |
| 5.4.5.6 | 5.4.5.7 | 5.4.5.8 | 5.4.5.9 | 5.4.6.1 | 5.4.6.2 | 5.4.6.3 | 5.4.6.4 | 5.4.6.5 | 5.4.6.6 |
| 5.4.6.7 | 5.4.6.8 | 5.4.6.9 | 5.4.7.1 | 5.4.7.2 | 5.4.7.3 | 5.4.7.4 | 5.4.7.5 | 5.4.7.6 | 5.4.7.7 |
| 5.4.7.8 | 5.4.7.9 | 5.4.8.1 | 5.4.8.2 | 5.4.8.3 | 5.4.8.4 | 5.4.8.5 | 5.4.8.6 | 5.4.8.7 | 5.4.8.8 |
| 5.4.8.9 | 5.4.9.1 | 5.4.9.2 | 5.4.9.3 | 5.4.9.4 | 5.4.9.5 | 5.4.9.6 | 5.4.9.7 | 5.4.9.8 | 5.4.9.9 |
| 5.5.1.1 | 5.5.1.2 | 5.5.1.3 | 5.5.1.4 | 5.5.1.5 | 5.5.1.6 | 5.5.1.7 | 5.5.1.8 | 5.5.1.9 | 5.5.2.1 |
| 5.5.2.2 | 5.5.2.3 | 5.5.2.4 | 5.5.2.5 | 5.5.2.6 | 5.5.2.7 | 5.5.2.8 | 5.5.2.9 | 5.5.3.1 | 5.5.3.2 |
| 5.5.3.3 | 5.5.3.4 | 5.5.3.5 | 5.5.3.6 | 5.5.3.7 | 5.5.3.8 | 5.5.3.9 | 5.5.4.1 | 5.5.4.2 | 5.5.4.3 |
| 5.5.4.4 | 5.5.4.5 | 5.5.4.6 | 5.5.4.7 | 5.5.4.8 | 5.5.4.9 | 5.5.5.1 | 5.5.5.2 | 5.5.5.3 | 5.5.5.4 |
| 5.5.5.5 | 5.5.5.6 | 5.5.5.7 | 5.5.5.8 | 5.5.5.9 | 5.5.6.1 | 5.5.6.2 | 5.5.6.3 | 5.5.6.4 | 5.5.6.5 |
| 5.5.6.6 | 5.5.6.7 | 5.5.6.8 | 5.5.6.9 | 5.5.7.1 | 5.5.7.2 | 5.5.7.3 | 5.5.7.4 | 5.5.7.5 | 5.5.7.6 |
| 5.5.7.7 | 5.5.7.8 | 5.5.7.9 | 5.5.8.1 | 5.5.8.2 | 5.5.8.3 | 5.5.8.4 | 5.5.8.5 | 5.5.8.6 | 5.5.8.7 |
| 5.5.8.8 | 5.5.8.9 | 5.5.9.1 | 5.5.9.2 | 5.5.9.3 | 5.5.9.4 | 5.5.9.5 | 5.5.9.6 | 5.5.9.7 | 5.5.9.8 |
| 5.5.9.9 | 5.6.1.1 | 5.6.1.2 | 5.6.1.3 | 5.6.1.4 | 5.6.1.5 | 5.6.1.6 | 5.6.1.7 | 5.6.1.8 | 5.6.1.9 |
| 5.6.2.1 | 5.6.2.2 | 5.6.2.3 | 5.6.2.4 | 5.6.2.5 | 5.6.2.6 | 5.6.2.7 | 5.6.2.8 | 5.6.2.9 | 5.6.3.1 |
| 5.6.3.2 | 5.6.3.3 | 5.6.3.4 | 5.6.3.5 | 5.6.3.6 | 5.6.3.7 | 5.6.3.8 | 5.6.3.9 | 5.6.4.1 | 5.6.4.2 |
| 5.6.4.3 | 5.6.4.4 | 5.6.4.5 | 5.6.4.6 | 5.6.4.7 | 5.6.4.8 | 5.6.4.9 | 5.6.5.1 | 5.6.5.2 | 5.6.5.3 |
| 5.6.5.4 | 5.6.5.5 | 5.6.5.6 | 5.6.5.7 | 5.6.5.8 | 5.6.5.9 | 5.6.6.1 | 5.6.6.2 | 5.6.6.3 | 5.6.6.4 |
| 5.6.6.5 | 5.6.6.6 | 5.6.6.7 | 5.6.6.8 | 5.6.6.9 | 5.6.7.1 | 5.6.7.2 | 5.6.7.3 | 5.6.7.4 | 5.6.7.5 |
| 5.6.7.6 | 5.6.7.7 | 5.6.7.8 | 5.6.7.9 | 5.6.8.1 | 5.6.8.2 | 5.6.8.3 | 5.6.8.4 | 5.6.8.5 | 5.6.8.6 |
| 5.6.8.7 | 5.6.8.8 | 5.6.8.9 | 5.6.9.1 | 5.6.9.2 | 5.6.9.3 | 5.6.9.4 | 5.6.9.5 | 5.6.9.6 | 5.6.9.7 |
| 5.6.9.8 | 5.6.9.9 | 5.7.1.1 | 5.7.1.2 | 5.7.1.3 | 5.7.1.4 | 5.7.1.5 | 5.7.1.6 | 5.7.1.7 | 5.7.1.8 |
| 5.7.1.9 | 5.7.2.1 | 5.7.2.2 | 5.7.2.3 | 5.7.2.4 | 5.7.2.5 | 5.7.2.6 | 5.7.2.7 | 5.7.2.8 | 5.7.2.9 |
| 5.7.3.1 | 5.7.3.2 | 5.7.3.3 | 5.7.3.4 | 5.7.3.5 | 5.7.3.6 | 5.7.3.7 | 5.7.3.8 | 5.7.3.9 | 5.7.4.1 |
| 5.7.4.2 | 5.7.4.3 | 5.7.4.4 | 5.7.4.5 | 5.7.4.6 | 5.7.4.7 | 5.7.4.8 | 5.7.4.9 | 5.7.5.1 | 5.7.5.2 |
| 5.7.5.3 | 5.7.5.4 | 5.7.5.5 | 5.7.5.6 | 5.7.5.7 | 5.7.5.8 | 5.7.5.9 | 5.7.6.1 | 5.7.6.2 | 5.7.6.3 |
| 5.7.6.4 | 5.7.6.5 | 5.7.6.6 | 5.7.6.7 | 5.7.6.8 | 5.7.6.9 | 5.7.7.1 | 5.7.7.2 | 5.7.7.3 | 5.7.7.4 |
| 5.7.7.5 | 5.7.7.6 | 5.7.7.7 | 5.7.7.8 | 5.7.7.9 | 5.7.8.1 | 5.7.8.2 | 5.7.8.3 | 5.7.8.4 | 5.7.8.5 |
| 5.7.8.6 | 5.7.8.7 | 5.7.8.8 | 5.7.8.9 | 5.7.9.1 | 5.7.9.2 | 5.7.9.3 | 5.7.9.4 | 5.7.9.5 | 5.7.9.6 |
| 5.7.9.7 | 5.7.9.8 | 5.7.9.9 | 5.8.1.1 | 5.8.1.2 | 5.8.1.3 | 5.8.1.4 | 5.8.1.5 | 5.8.1.6 | 5.8.1.7 |
| 5.8.1.8 | 5.8.1.9 | 5.8.2.1 | 5.8.2.2 | 5.8.2.3 | 5.8.2.4 | 5.8.2.5 | 5.8.2.6 | 5.8.2.7 | 5.8.2.8 |
| 5.8.2.9 | 5.8.3.1 | 5.8.3.2 | 5.8.3.3 | 5.8.3.4 | 5.8.3.5 | 5.8.3.6 | 5.8.3.7 | 5.8.3.8 | 5.8.3.9 |
| 5.8.4.1 | 5.8.4.2 | 5.8.4.3 | 5.8.4.4 | 5.8.4.5 | 5.8.4.6 | 5.8.4.7 | 5.8.4.8 | 5.8.4.9 | 5.8.5.1 |
| 5.8.5.2 | 5.8.5.3 | 5.8.5.4 | 5.8.5.5 | 5.8.5.6 | 5.8.5.7 | 5.8.5.8 | 5.8.5.9 | 5.8.6.1 | 5.8.6.2 |
| 5.8.6.3 | 5.8.6.4 | 5.8.6.5 | 5.8.6.6 | 5.8.6.7 | 5.8.6.8 | 5.8.6.9 | 5.8.7.1 | 5.8.7.2 | 5.8.7.3 |
| 5.8.7.4 | 5.8.7.5 | 5.8.7.6 | 5.8.7.7 | 5.8.7.8 | 5.8.7.9 | 5.8.8.1 | 5.8.8.2 | 5.8.8.3 | 5.8.8.4 |
| 5.8.8.5 | 5.8.8.6 | 5.8.8.7 | 5.8.8.8 | 5.8.8.9 | 5.8.9.1 | 5.8.9.2 | 5.8.9.3 | 5.8.9.4 | 5.8.9.5 |
| 5.8.9.6 | 5.8.9.7 | 5.8.9.8 | 5.8.9.9 | 5.9.1.1 | 5.9.1.2 | 5.9.1.3 | 5.9.1.4 | 5.9.1.5 | 5.9.1.6 |
| 5.9.1.7 | 5.9.1.8 | 5.9.1.9 | 5.9.2.1 | 5.9.2.2 | 5.9.2.3 | 5.9.2.4 | 5.9.2.5 | 5.9.2.6 | 5.9.2.7 |
| 5.9.2.8 | 5.9.2.9 | 5.9.3.1 | 5.9.3.2 | 5.9.3.3 | 5.9.3.4 | 5.9.3.5 | 5.9.3.6 | 5.9.3.7 | 5.9.3.8 |
| 5.9.3.9 | 5.9.4.1 | 5.9.4.2 | 5.9.4.3 | 5.9.4.4 | 5.9.4.5 | 5.9.4.6 | 5.9.4.7 | 5.9.4.8 | 5.9.4.9 |
| 5.9.5.1 | 5.9.5.2 | 5.9.5.3 | 5.9.5.4 | 5.9.5.5 | 5.9.5.6 | 5.9.5.7 | 5.9.5.8 | 5.9.5.9 | 5.9.6.1 |
| 5.9.6.2 | 5.9.6.3 | 5.9.6.4 | 5.9.6.5 | 5.9.6.6 | 5.9.6.7 | 5.9.6.8 | 5.9.6.9 | 5.9.7.1 | 5.9.7.2 |
| 5.9.7.3 | 5.9.7.4 | 5.9.7.5 | 5.9.7.6 | 5.9.7.7 | 5.9.7.8 | 5.9.7.9 | 5.9.8.1 | 5.9.8.2 | 5.9.8.3 |
| 5.9.8.4 | 5.9.8.5 | 5.9.8.6 | 5.9.8.7 | 5.9.8.8 | 5.9.8.9 | 5.9.9.1 | 5.9.9.2 | 5.9.9.3 | 5.9.9.4 |
| 5.9.9.5 | 5.9.9.6 | 5.9.9.7 | 5.9.9.8 | 5.9.9.9 | 6.1.1.1 | 6.1.1.2 | 6.1.1.3 | 6.1.1.4 | 6.1.1.5 |
| 6.1.1.6 | 6.1.1.7 | 6.1.1.8 | 6.1.1.9 | 6.1.2.1 | 6.1.2.2 | 6.1.2.3 | 6.1.2.4 | 6.1.2.5 | 6.1.2.6 |
| 6.1.2.7 | 6.1.2.8 | 6.1.2.9 | 6.1.3.1 | 6.1.3.2 | 6.1.3.3 | 6.1.3.4 | 6.1.3.5 | 6.1.3.6 | 6.1.3.7 |
| 6.1.3.8 | 6.1.3.9 | 6.1.4.1 | 6.1.4.2 | 6.1.4.3 | 6.1.4.4 | 6.1.4.5 | 6.1.4.6 | 6.1.4.7 | 6.1.4.8 |
| 6.1.4.9 | 6.1.5.1 | 6.1.5.2 | 6.1.5.3 | 6.1.5.4 | 6.1.5.5 | 6.1.5.6 | 6.1.5.7 | 6.1.5.8 | 6.1.5.9 |
| 6.1.6.1 | 6.1.6.2 | 6.1.6.3 | 6.1.6.4 | 6.1.6.5 | 6.1.6.6 | 6.1.6.7 | 6.1.6.8 | 6.1.6.9 | 6.1.7.1 |
| 6.1.7.2 | 6.1.7.3 | 6.1.7.4 | 6.1.7.5 | 6.1.7.6 | 6.1.7.7 | 6.1.7.8 | 6.1.7.9 | 6.1.8.1 | 6.1.8.2 |
| 6.1.8.3 | 6.1.8.4 | 6.1.8.5 | 6.1.8.6 | 6.1.8.7 | 6.1.8.8 | 6.1.8.9 | 6.1.9.1 | 6.1.9.2 | 6.1.9.3 |
| 6.1.9.4 | 6.1.9.5 | 6.1.9.6 | 6.1.9.7 | 6.1.9.8 | 6.1.9.9 | 6.2.1.1 | 6.2.1.2 | 6.2.1.3 | 6.2.1.4 |

TABLE 2-continued

| | | | | | | | | | |
|---|---|---|---|---|---|---|---|---|---|
| 6.2.1.5 | 6.2.1.6 | 6.2.1.7 | 6.2.1.8 | 6.2.1.9 | 6.2.2.1 | 6.2.2.2 | 6.2.2.3 | 6.2.2.4 | 6.2.2.5 |
| 6.2.2.6 | 6.2.2.7 | 6.2.2.8 | 6.2.2.9 | 6.2.3.1 | 6.2.3.2 | 6.2.3.3 | 6.2.3.4 | 6.2.3.5 | 6.2.3.6 |
| 6.2.3.7 | 6.2.3.8 | 6.2.3.9 | 6.2.4.1 | 6.2.4.2 | 6.2.4.3 | 6.2.4.4 | 6.2.4.5 | 6.2.4.6 | 6.2.4.7 |
| 6.2.4.8 | 6.2.4.9 | 6.2.5.1 | 6.2.5.2 | 6.2.5.3 | 6.2.5.4 | 6.2.5.5 | 6.2.5.6 | 6.2.5.7 | 6.2.5.8 |
| 6.2.5.9 | 6.2.6.1 | 6.2.6.2 | 6.2.6.3 | 6.2.6.4 | 6.2.6.5 | 6.2.6.6 | 6.2.6.7 | 6.2.6.8 | 6.2.6.9 |
| 6.2.7.1 | 6.2.7.2 | 6.2.7.3 | 6.2.7.4 | 6.2.7.5 | 6.2.7.6 | 6.2.7.7 | 6.2.7.8 | 6.2.7.9 | 6.2.8.1 |
| 6.2.8.2 | 6.2.8.3 | 6.2.8.4 | 6.2.8.5 | 6.2.8.6 | 6.2.8.7 | 6.2.8.8 | 6.2.8.9 | 6.2.9.1 | 6.2.9.2 |
| 6.2.9.3 | 6.2.9.4 | 6.2.9.5 | 6.2.9.6 | 6.2.9.7 | 6.2.9.8 | 6.2.9.9 | 6.3.1.1 | 6.3.1.2 | 6.3.1.3 |
| 6.3.1.4 | 6.3.1.5 | 6.3.1.6 | 6.3.1.7 | 6.3.1.8 | 6.3.1.9 | 6.3.2.1 | 6.3.2.2 | 6.3.2.3 | 6.3.2.4 |
| 6.3.2.5 | 6.3.2.6 | 6.3.2.7 | 6.3.2.8 | 6.3.2.9 | 6.3.3.1 | 6.3.3.2 | 6.3.3.3 | 6.3.3.4 | 6.3.3.5 |
| 6.3.3.6 | 6.3.3.7 | 6.3.3.8 | 6.3.3.9 | 6.3.4.1 | 6.3.4.2 | 6.3.4.3 | 6.3.4.4 | 6.3.4.5 | 6.3.4.6 |
| 6.3.4.7 | 6.3.4.8 | 6.3.4.9 | 6.3.5.1 | 6.3.5.2 | 6.3.5.3 | 6.3.5.4 | 6.3.5.5 | 6.3.5.6 | 6.3.5.7 |
| 6.3.5.8 | 6.3.5.9 | 6.3.6.1 | 6.3.6.2 | 6.3.6.3 | 6.3.6.4 | 6.3.6.5 | 6.3.6.6 | 6.3.6.7 | 6.3.6.8 |
| 6.3.6.9 | 6.3.7.1 | 6.3.7.2 | 6.3.7.3 | 6.3.7.4 | 6.3.7.5 | 6.3.7.6 | 6.3.7.7 | 6.3.7.8 | 6.3.7.9 |
| 6.3.8.1 | 6.3.8.2 | 6.3.8.3 | 6.3.8.4 | 6.3.8.5 | 6.3.8.6 | 6.3.8.7 | 6.3.8.8 | 6.3.8.9 | 6.3.9.1 |
| 6.3.9.2 | 6.3.9.3 | 6.3.9.4 | 6.3.9.5 | 6.3.9.6 | 6.3.9.7 | 6.3.9.8 | 6.3.9.9 | 6.4.1.1 | 6.4.1.2 |
| 6.4.1.3 | 6.4.1.4 | 6.4.1.5 | 6.4.1.6 | 6.4.1.7 | 6.4.1.8 | 6.4.1.9 | 6.4.2.1 | 6.4.2.2 | 6.4.2.3 |
| 6.4.2.4 | 6.4.2.5 | 6.4.2.6 | 6.4.2.7 | 6.4.2.8 | 6.4.2.9 | 6.4.3.1 | 6.4.3.2 | 6.4.3.3 | 6.4.3.4 |
| 6.4.3.5 | 6.4.3.6 | 6.4.3.7 | 6.4.3.8 | 6.4.3.9 | 6.4.4.1 | 6.4.4.2 | 6.4.4.3 | 6.4.4.4 | 6.4.4.5 |
| 6.4.4.6 | 6.4.4.7 | 6.4.4.8 | 6.4.4.9 | 6.4.5.1 | 6.4.5.2 | 6.4.5.3 | 6.4.5.4 | 6.4.5.5 | 6.4.5.6 |
| 6.4.5.7 | 6.4.5.8 | 6.4.5.9 | 6.4.6.1 | 6.4.6.2 | 6.4.6.3 | 6.4.6.4 | 6.4.6.5 | 6.4.6.6 | 6.4.6.7 |
| 6.4.6.8 | 6.4.6.9 | 6.4.7.1 | 6.4.7.2 | 6.4.7.3 | 6.4.7.4 | 6.4.7.5 | 6.4.7.6 | 6.4.7.7 | 6.4.7.8 |
| 6.4.7.9 | 6.4.8.1 | 6.4.8.2 | 6.4.8.3 | 6.4.8.4 | 6.4.8.5 | 6.4.8.6 | 6.4.8.7 | 6.4.8.8 | 6.4.8.9 |
| 6.4.9.1 | 6.4.9.2 | 6.4.9.3 | 6.4.9.4 | 6.4.9.5 | 6.4.9.6 | 6.4.9.7 | 6.4.9.8 | 6.4.9.9 | 6.5.1.1 |
| 6.5.1.2 | 6.5.1.3 | 6.5.1.4 | 6.5.1.5 | 6.5.1.6 | 6.5.1.7 | 6.5.1.8 | 6.5.1.9 | 6.5.2.1 | 6.5.2.2 |
| 6.5.2.3 | 6.5.2.4 | 6.5.2.5 | 6.5.2.6 | 6.5.2.7 | 6.5.2.8 | 6.5.2.9 | 6.5.3.1 | 6.5.3.2 | 6.5.3.3 |
| 6.5.3.4 | 6.5.3.5 | 6.5.3.6 | 6.5.3.7 | 6.5.3.8 | 6.5.3.9 | 6.5.4.1 | 6.5.4.2 | 6.5.4.3 | 6.5.4.4 |
| 6.5.4.5 | 6.5.4.6 | 6.5.4.7 | 6.5.4.8 | 6.5.4.9 | 6.5.5.1 | 6.5.5.2 | 6.5.5.3 | 6.5.5.4 | 6.5.5.5 |
| 6.5.5.6 | 6.5.5.7 | 6.5.5.8 | 6.5.5.9 | 6.5.6.1 | 6.5.6.2 | 6.5.6.3 | 6.5.6.4 | 6.5.6.5 | 6.5.6.6 |
| 6.5.6.7 | 6.5.6.8 | 6.5.6.9 | 6.5.7.1 | 6.5.7.2 | 6.5.7.3 | 6.5.7.4 | 6.5.7.5 | 6.5.7.6 | 6.5.7.7 |
| 6.5.7.8 | 6.5.7.9 | 6.5.8.1 | 6.5.8.2 | 6.5.8.3 | 6.5.8.4 | 6.5.8.5 | 6.5.8.6 | 6.5.8.7 | 6.5.8.8 |
| 6.5.8.9 | 6.5.9.1 | 6.5.9.2 | 6.5.9.3 | 6.5.9.4 | 6.5.9.5 | 6.5.9.6 | 6.5.9.7 | 6.5.9.8 | 6.5.9.9 |
| 6.6.1.1 | 6.6.1.2 | 6.6.1.3 | 6.6.1.4 | 6.6.1.5 | 6.6.1.6 | 6.6.1.7 | 6.6.1.8 | 6.6.1.9 | 6.6.2.1 |
| 6.6.2.2 | 6.6.2.3 | 6.6.2.4 | 6.6.2.5 | 6.6.2.6 | 6.6.2.7 | 6.6.2.8 | 6.6.2.9 | 6.6.3.1 | 6.6.3.2 |
| 6.6.3.3 | 6.6.3.4 | 6.6.3.5 | 6.6.3.6 | 6.6.3.7 | 6.6.3.8 | 6.6.3.9 | 6.6.4.1 | 6.6.4.2 | 6.6.4.3 |
| 6.6.4.4 | 6.6.4.5 | 6.6.4.6 | 6.6.4.7 | 6.6.4.8 | 6.6.4.9 | 6.6.5.1 | 6.6.5.2 | 6.6.5.3 | 6.6.5.4 |
| 6.6.5.5 | 6.6.5.6 | 6.6.5.7 | 6.6.5.8 | 6.6.5.9 | 6.6.6.1 | 6.6.6.2 | 6.6.6.3 | 6.6.6.4 | 6.6.6.5 |
| 6.6.6.6 | 6.6.6.7 | 6.6.6.8 | 6.6.6.9 | 6.6.7.1 | 6.6.7.2 | 6.6.7.3 | 6.6.7.4 | 6.6.7.5 | 6.6.7.6 |
| 6.6.7.7 | 6.6.7.8 | 6.6.7.9 | 6.6.8.1 | 6.6.8.2 | 6.6.8.3 | 6.6.8.4 | 6.6.8.5 | 6.6.8.6 | 6.6.8.7 |
| 6.6.8.8 | 6.6.8.9 | 6.6.9.1 | 6.6.9.2 | 6.6.9.3 | 6.6.9.4 | 6.6.9.5 | 6.6.9.6 | 6.6.9.7 | 6.6.9.8 |
| 6.6.9.9 | 6.7.1.1 | 6.7.1.2 | 6.7.1.3 | 6.7.1.4 | 6.7.1.5 | 6.7.1.6 | 6.7.1.7 | 6.7.1.8 | 6.7.1.9 |
| 6.7.2.1 | 6.7.2.2 | 6.7.2.3 | 6.7.2.4 | 6.7.2.5 | 6.7.2.6 | 6.7.2.7 | 6.7.2.8 | 6.7.2.9 | 6.7.3.1 |
| 6.7.3.2 | 6.7.3.3 | 6.7.3.4 | 6.7.3.5 | 6.7.3.6 | 6.7.3.7 | 6.7.3.8 | 6.7.3.9 | 6.7.4.1 | 6.7.4.2 |
| 6.7.4.3 | 6.7.4.4 | 6.7.4.5 | 6.7.4.6 | 6.7.4.7 | 6.7.4.8 | 6.7.4.9 | 6.7.5.1 | 6.7.5.2 | 6.7.5.3 |
| 6.7.5.4 | 6.7.5.5 | 6.7.5.6 | 6.7.5.7 | 6.7.5.8 | 6.7.5.9 | 6.7.6.1 | 6.7.6.2 | 6.7.6.3 | 6.7.6.4 |
| 6.7.6.5 | 6.7.6.6 | 6.7.6.7 | 6.7.6.8 | 6.7.6.9 | 6.7.7.1 | 6.7.7.2 | 6.7.7.3 | 6.7.7.4 | 6.7.7.5 |
| 6.7.7.6 | 6.7.7.7 | 6.7.7.8 | 6.7.7.9 | 6.7.8.1 | 6.7.8.2 | 6.7.8.3 | 6.7.8.4 | 6.7.8.5 | 6.7.8.6 |
| 6.7.8.7 | 6.7.8.8 | 6.7.8.9 | 6.7.9.1 | 6.7.9.2 | 6.7.9.3 | 6.7.9.4 | 6.7.9.5 | 6.7.9.6 | 6.7.9.7 |
| 6.7.9.8 | 6.7.9.9 | 6.8.1.1 | 6.8.1.2 | 6.8.1.3 | 6.8.1.4 | 6.8.1.5 | 6.8.1.6 | 6.8.1.7 | 6.8.1.8 |
| 6.8.1.9 | 6.8.2.1 | 6.8.2.2 | 6.8.2.3 | 6.8.2.4 | 6.8.2.5 | 6.8.2.6 | 6.8.2.7 | 6.8.2.8 | 6.8.2.9 |
| 6.8.3.1 | 6.8.3.2 | 6.8.3.3 | 6.8.3.4 | 6.8.3.5 | 6.8.3.6 | 6.8.3.7 | 6.8.3.8 | 6.8.3.9 | 6.8.4.1 |
| 6.8.4.2 | 6.8.4.3 | 6.8.4.4 | 6.8.4.5 | 6.8.4.6 | 6.8.4.7 | 6.8.4.8 | 6.8.4.9 | 6.8.5.1 | 6.8.5.2 |
| 6.8.5.3 | 6.8.5.4 | 6.8.5.5 | 6.8.5.6 | 6.8.5.7 | 6.8.5.8 | 6.8.5.9 | 6.8.6.1 | 6.8.6.2 | 6.8.6.3 |
| 6.8.6.4 | 6.8.6.5 | 6.8.6.6 | 6.8.6.7 | 6.8.6.8 | 6.8.6.9 | 6.8.7.1 | 6.8.7.2 | 6.8.7.3 | 6.8.7.4 |
| 6.8.7.5 | 6.8.7.6 | 6.8.7.7 | 6.8.7.8 | 6.8.7.9 | 6.8.8.1 | 6.8.8.2 | 6.8.8.3 | 6.8.8.4 | 6.8.8.5 |
| 6.8.8.6 | 6.8.8.7 | 6.8.8.8 | 6.8.8.9 | 6.8.9.1 | 6.8.9.2 | 6.8.9.3 | 6.8.9.4 | 6.8.9.5 | 6.8.9.6 |
| 6.8.9.7 | 6.8.9.8 | 6.8.9.9 | 6.9.1.1 | 6.9.1.2 | 6.9.1.3 | 6.9.1.4 | 6.9.1.5 | 6.9.1.6 | 6.9.1.7 |
| 6.9.1.8 | 6.9.1.9 | 6.9.2.1 | 6.9.2.2 | 6.9.2.3 | 6.9.2.4 | 6.9.2.5 | 6.9.2.6 | 6.9.2.7 | 6.9.2.8 |
| 6.9.2.9 | 6.9.3.1 | 6.9.3.2 | 6.9.3.3 | 6.9.3.4 | 6.9.3.5 | 6.9.3.6 | 6.9.3.7 | 6.9.3.8 | 6.9.3.9 |
| 6.9.4.1 | 6.9.4.2 | 6.9.4.3 | 6.9.4.4 | 6.9.4.5 | 6.9.4.6 | 6.9.4.7 | 6.9.4.8 | 6.9.4.9 | 6.9.5.1 |
| 6.9.5.2 | 6.9.5.3 | 6.9.5.4 | 6.9.5.5 | 6.9.5.6 | 6.9.5.7 | 6.9.5.8 | 6.9.5.9 | 6.9.6.1 | 6.9.6.2 |
| 6.9.6.3 | 6.9.6.4 | 6.9.6.5 | 6.9.6.6 | 6.9.6.7 | 6.9.6.8 | 6.9.6.9 | 6.9.7.1 | 6.9.7.2 | 6.9.7.3 |
| 6.9.7.4 | 6.9.7.5 | 6.9.7.6 | 6.9.7.7 | 6.9.7.8 | 6.9.7.9 | 6.9.8.1 | 6.9.8.2 | 6.9.8.3 | 6.9.8.4 |
| 6.9.8.5 | 6.9.8.6 | 6.9.8.7 | 6.9.8.8 | 6.9.8.9 | 6.9.9.1 | 6.9.9.2 | 6.9.9.3 | 6.9.9.4 | 6.9.9.5 |
| 6.9.9.6 | 6.9.9.7 | 6.9.9.8 | 6.9.9.9 | 7.1.1.1 | 7.1.1.2 | 7.1.1.3 | 7.1.1.4 | 7.1.1.5 | 7.1.1.6 |
| 7.1.1.7 | 7.1.1.8 | 7.1.1.9 | 7.1.2.1 | 7.1.2.2 | 7.1.2.3 | 7.1.2.4 | 7.1.2.5 | 7.1.2.6 | 7.1.2.7 |
| 7.1.2.8 | 7.1.2.9 | 7.1.3.1 | 7.1.3.2 | 7.1.3.3 | 7.1.3.4 | 7.1.3.5 | 7.1.3.6 | 7.1.3.7 | 7.1.3.8 |
| 7.1.3.9 | 7.1.4.1 | 7.1.4.2 | 7.1.4.3 | 7.1.4.4 | 7.1.4.5 | 7.1.4.6 | 7.1.4.7 | 7.1.4.8 | 7.1.4.9 |
| 7.1.5.1 | 7.1.5.2 | 7.1.5.3 | 7.1.5.4 | 7.1.5.5 | 7.1.5.6 | 7.1.5.7 | 7.1.5.8 | 7.1.5.9 | 7.1.6.1 |
| 7.1.6.2 | 7.1.6.3 | 7.1.6.4 | 7.1.6.5 | 7.1.6.6 | 7.1.6.7 | 7.1.6.8 | 7.1.6.9 | 7.1.7.1 | 7.1.7.2 |
| 7.1.7.3 | 7.1.7.4 | 7.1.7.5 | 7.1.7.6 | 7.1.7.7 | 7.1.7.8 | 7.1.7.9 | 7.1.8.1 | 7.1.8.2 | 7.1.8.3 |
| 7.1.8.4 | 7.1.8.5 | 7.1.8.6 | 7.1.8.7 | 7.1.8.8 | 7.1.8.9 | 7.1.9.1 | 7.1.9.2 | 7.1.9.3 | 7.1.9.4 |
| 7.1.9.5 | 7.1.9.6 | 7.1.9.7 | 7.1.9.8 | 7.1.9.9 | 7.2.1.1 | 7.2.1.2 | 7.2.1.3 | 7.2.1.4 | 7.2.1.5 |
| 7.2.1.6 | 7.2.1.7 | 7.2.1.8 | 7.2.1.9 | 7.2.2.1 | 7.2.2.2 | 7.2.2.3 | 7.2.2.4 | 7.2.2.5 | 7.2.2.6 |
| 7.2.2.7 | 7.2.2.8 | 7.2.2.9 | 7.2.3.1 | 7.2.3.2 | 7.2.3.3 | 7.2.3.4 | 7.2.3.5 | 7.2.3.6 | 7.2.3.7 |
| 7.2.3.8 | 7.2.3.9 | 7.2.4.1 | 7.2.4.2 | 7.2.4.3 | 7.2.4.4 | 7.2.4.5 | 7.2.4.6 | 7.2.4.7 | 7.2.4.8 |
| 7.2.4.9 | 7.2.5.1 | 7.2.5.2 | 7.2.5.3 | 7.2.5.4 | 7.2.5.5 | 7.2.5.6 | 7.2.5.7 | 7.2.5.8 | 7.2.5.9 |
| 7.2.6.1 | 7.2.6.2 | 7.2.6.3 | 7.2.6.4 | 7.2.6.5 | 7.2.6.6 | 7.2.6.7 | 7.2.6.8 | 7.2.6.9 | 7.2.7.1 |
| 7.2.7.2 | 7.2.7.3 | 7.2.7.4 | 7.2.7.5 | 7.2.7.6 | 7.2.7.7 | 7.2.7.8 | 7.2.7.9 | 7.2.8.1 | 7.2.8.2 |

TABLE 2-continued

| | | | | | | | | | |
|---|---|---|---|---|---|---|---|---|---|
| 7.2.8.3 | 7.2.8.4 | 7.2.8.5 | 7.2.8.6 | 7.2.8.7 | 7.2.8.8 | 7.2.8.9 | 7.2.9.1 | 7.2.9.2 | 7.2.9.3 |
| 7.2.9.4 | 7.2.9.5 | 7.2.9.6 | 7.2.9.7 | 7.2.9.8 | 7.2.9.9 | 7.3.1.1 | 7.3.1.2 | 7.3.1.3 | 7.3.1.4 |
| 7.3.1.5 | 7.3.1.6 | 7.3.1.7 | 7.3.1.8 | 7.3.1.9 | 7.3.2.1 | 7.3.2.2 | 7.3.2.3 | 7.3.2.4 | 7.3.2.5 |
| 7.3.2.6 | 7.3.2.7 | 7.3.2.8 | 7.3.2.9 | 7.3.3.1 | 7.3.3.2 | 7.3.3.3 | 7.3.3.4 | 7.3.3.5 | 7.3.3.6 |
| 7.3.3.7 | 7.3.3.8 | 7.3.3.9 | 7.3.4.1 | 7.3.4.2 | 7.3.4.3 | 7.3.4.4 | 7.3.4.5 | 7.3.4.6 | 7.3.4.7 |
| 7.3.4.8 | 7.3.4.9 | 7.3.5.1 | 7.3.5.2 | 7.3.5.3 | 7.3.5.4 | 7.3.5.5 | 7.3.5.6 | 7.3.5.7 | 7.3.5.8 |
| 7.3.5.9 | 7.3.6.1 | 7.3.6.2 | 7.3.6.3 | 7.3.6.4 | 7.3.6.5 | 7.3.6.6 | 7.3.6.7 | 7.3.6.8 | 7.3.6.9 |
| 7.3.7.1 | 7.3.7.2 | 7.3.7.3 | 7.3.7.4 | 7.3.7.5 | 7.3.7.6 | 7.3.7.7 | 7.3.7.8 | 7.3.7.9 | 7.3.8.1 |
| 7.3.8.2 | 7.3.8.3 | 7.3.8.4 | 7.3.8.5 | 7.3.8.6 | 7.3.8.7 | 7.3.8.8 | 7.3.8.9 | 7.3.9.1 | 7.3.9.2 |
| 7.3.9.3 | 7.3.9.4 | 7.3.9.5 | 7.3.9.6 | 7.3.9.7 | 7.3.9.8 | 7.3.9.9 | 7.4.1.1 | 7.4.1.2 | 7.4.1.3 |
| 7.4.1.4 | 7.4.1.5 | 7.4.1.6 | 7.4.1.7 | 7.4.1.8 | 7.4.1.9 | 7.4.2.1 | 7.4.2.2 | 7.4.2.3 | 7.4.2.4 |
| 7.4.2.5 | 7.4.2.6 | 7.4.2.7 | 7.4.2.8 | 7.4.2.9 | 7.4.3.1 | 7.4.3.2 | 7.4.3.3 | 7.4.3.4 | 7.4.3.5 |
| 7.4.3.6 | 7.4.3.7 | 7.4.3.8 | 7.4.3.9 | 7.4.4.1 | 7.4.4.2 | 7.4.4.3 | 7.4.4.4 | 7.4.4.5 | 7.4.4.6 |
| 7.4.4.7 | 7.4.4.8 | 7.4.4.9 | 7.4.5.1 | 7.4.5.2 | 7.4.5.3 | 7.4.5.4 | 7.4.5.5 | 7.4.5.6 | 7.4.5.7 |
| 7.4.5.8 | 7.4.5.9 | 7.4.6.1 | 7.4.6.2 | 7.4.6.3 | 7.4.6.4 | 7.4.6.5 | 7.4.6.6 | 7.4.6.7 | 7.4.6.8 |
| 7.4.6.9 | 7.4.7.1 | 7.4.7.2 | 7.4.7.3 | 7.4.7.4 | 7.4.7.5 | 7.4.7.6 | 7.4.7.7 | 7.4.7.8 | 7.4.7.9 |
| 7.4.8.1 | 7.4.8.2 | 7.4.8.3 | 7.4.8.4 | 7.4.8.5 | 7.4.8.6 | 7.4.8.7 | 7.4.8.8 | 7.4.8.9 | 7.4.9.1 |
| 7.4.9.2 | 7.4.9.3 | 7.4.9.4 | 7.4.9.5 | 7.4.9.6 | 7.4.9.7 | 7.4.9.8 | 7.4.9.9 | 7.5.1.1 | 7.5.1.2 |
| 7.5.1.3 | 7.5.1.4 | 7.5.1.5 | 7.5.1.6 | 7.5.1.7 | 7.5.1.8 | 7.5.1.9 | 7.5.2.1 | 7.5.2.2 | 7.5.2.3 |
| 7.5.2.4 | 7.5.2.5 | 7.5.2.6 | 7.5.2.7 | 7.5.2.8 | 7.5.2.9 | 7.5.3.1 | 7.5.3.2 | 7.5.3.3 | 7.5.3.4 |
| 7.5.3.5 | 7.5.3.6 | 7.5.3.7 | 7.5.3.8 | 7.5.3.9 | 7.5.4.1 | 7.5.4.2 | 7.5.4.3 | 7.5.4.4 | 7.5.4.5 |
| 7.5.4.6 | 7.5.4.7 | 7.5.4.8 | 7.5.4.9 | 7.5.5.1 | 7.5.5.2 | 7.5.5.3 | 7.5.5.4 | 7.5.5.5 | 7.5.5.6 |
| 7.5.5.7 | 7.5.5.8 | 7.5.5.9 | 7.5.6.1 | 7.5.6.2 | 7.5.6.3 | 7.5.6.4 | 7.5.6.5 | 7.5.6.6 | 7.5.6.7 |
| 7.5.6.8 | 7.5.6.9 | 7.5.7.1 | 7.5.7.2 | 7.5.7.3 | 7.5.7.4 | 7.5.7.5 | 7.5.7.6 | 7.5.7.7 | 7.5.7.8 |
| 7.5.7.9 | 7.5.8.1 | 7.5.8.2 | 7.5.8.3 | 7.5.8.4 | 7.5.8.5 | 7.5.8.6 | 7.5.8.7 | 7.5.8.8 | 7.5.8.9 |
| 7.5.9.1 | 7.5.9.2 | 7.5.9.3 | 7.5.9.4 | 7.5.9.5 | 7.5.9.6 | 7.5.9.7 | 7.5.9.8 | 7.5.9.9 | 7.6.1.1 |
| 7.6.1.2 | 7.6.1.3 | 7.6.1.4 | 7.6.1.5 | 7.6.1.6 | 7.6.1.7 | 7.6.1.8 | 7.6.1.9 | 7.6.2.1 | 7.6.2.2 |
| 7.6.2.3 | 7.6.2.4 | 7.6.2.5 | 7.6.2.6 | 7.6.2.7 | 7.6.2.8 | 7.6.2.9 | 7.6.3.1 | 7.6.3.2 | 7.6.3.3 |
| 7.6.3.4 | 7.6.3.5 | 7.6.3.6 | 7.6.3.7 | 7.6.3.8 | 7.6.3.9 | 7.6.4.1 | 7.6.4.2 | 7.6.4.3 | 7.6.4.4 |
| 7.6.4.5 | 7.6.4.6 | 7.6.4.7 | 7.6.4.8 | 7.6.4.9 | 7.6.5.1 | 7.6.5.2 | 7.6.5.3 | 7.6.5.4 | 7.6.5.5 |
| 7.6.5.6 | 7.6.5.7 | 7.6.5.8 | 7.6.5.9 | 7.6.6.1 | 7.6.6.2 | 7.6.6.3 | 7.6.6.4 | 7.6.6.5 | 7.6.6.6 |
| 7.6.6.7 | 7.6.6.8 | 7.6.6.9 | 7.6.7.1 | 7.6.7.2 | 7.6.7.3 | 7.6.7.4 | 7.6.7.5 | 7.6.7.6 | 7.6.7.7 |
| 7.6.7.8 | 7.6.7.9 | 7.6.8.1 | 7.6.8.2 | 7.6.8.3 | 7.6.8.4 | 7.6.8.5 | 7.6.8.6 | 7.6.8.7 | 7.6.8.8 |
| 7.6.8.9 | 7.6.9.1 | 7.6.9.2 | 7.6.9.3 | 7.6.9.4 | 7.6.9.5 | 7.6.9.6 | 7.6.9.7 | 7.6.9.8 | 7.6.9.9 |
| 7.7.1.1 | 7.7.1.2 | 7.7.1.3 | 7.7.1.4 | 7.7.1.5 | 7.7.1.6 | 7.7.1.7 | 7.7.1.8 | 7.7.1.9 | 7.7.2.1 |
| 7.7.2.2 | 7.7.2.3 | 7.7.2.4 | 7.7.2.5 | 7.7.2.6 | 7.7.2.7 | 7.7.2.8 | 7.7.2.9 | 7.7.3.1 | 7.7.3.2 |
| 7.7.3.3 | 7.7.3.4 | 7.7.3.5 | 7.7.3.6 | 7.7.3.7 | 7.7.3.8 | 7.7.3.9 | 7.7.4.1 | 7.7.4.2 | 7.7.4.3 |
| 7.7.4.4 | 7.7.4.5 | 7.7.4.6 | 7.7.4.7 | 7.7.4.8 | 7.7.4.9 | 7.7.5.1 | 7.7.5.2 | 7.7.5.3 | 7.7.5.4 |
| 7.7.5.5 | 7.7.5.6 | 7.7.5.7 | 7.7.5.8 | 7.7.5.9 | 7.7.6.1 | 7.7.6.2 | 7.7.6.3 | 7.7.6.4 | 7.7.6.5 |
| 7.7.6.6 | 7.7.6.7 | 7.7.6.8 | 7.7.6.9 | 7.7.7.1 | 7.7.7.2 | 7.7.7.3 | 7.7.7.4 | 7.7.7.5 | 7.7.7.6 |
| 7.7.7.7 | 7.7.7.8 | 7.7.7.9 | 7.7.8.1 | 7.7.8.2 | 7.7.8.3 | 7.7.8.4 | 7.7.8.5 | 7.7.8.6 | 7.7.8.7 |
| 7.7.8.8 | 7.7.8.9 | 7.7.9.1 | 7.7.9.2 | 7.7.9.3 | 7.7.9.4 | 7.7.9.5 | 7.7.9.6 | 7.7.9.7 | 7.7.9.8 |
| 7.7.9.9 | 7.8.1.1 | 7.8.1.2 | 7.8.1.3 | 7.8.1.4 | 7.8.1.5 | 7.8.1.6 | 7.8.1.7 | 7.8.1.8 | 7.8.1.9 |
| 7.8.2.1 | 7.8.2.2 | 7.8.2.3 | 7.8.2.4 | 7.8.2.5 | 7.8.2.6 | 7.8.2.7 | 7.8.2.8 | 7.8.2.9 | 7.8.3.1 |
| 7.8.3.2 | 7.8.3.3 | 7.8.3.4 | 7.8.3.5 | 7.8.3.6 | 7.8.3.7 | 7.8.3.8 | 7.8.3.9 | 7.8.4.1 | 7.8.4.2 |
| 7.8.4.3 | 7.8.4.4 | 7.8.4.5 | 7.8.4.6 | 7.8.4.7 | 7.8.4.8 | 7.8.4.9 | 7.8.5.1 | 7.8.5.2 | 7.8.5.3 |
| 7.8.5.4 | 7.8.5.5 | 7.8.5.6 | 7.8.5.7 | 7.8.5.8 | 7.8.5.9 | 7.8.6.1 | 7.8.6.2 | 7.8.6.3 | 7.8.6.4 |
| 7.8.6.5 | 7.8.6.6 | 7.8.6.7 | 7.8.6.8 | 7.8.6.9 | 7.8.7.1 | 7.8.7.2 | 7.8.7.3 | 7.8.7.4 | 7.8.7.5 |
| 7.8.7.6 | 7.8.7.7 | 7.8.7.8 | 7.8.7.9 | 7.8.8.1 | 7.8.8.2 | 7.8.8.3 | 7.8.8.4 | 7.8.8.5 | 7.8.8.6 |
| 7.8.8.7 | 7.8.8.8 | 7.8.8.9 | 7.8.9.1 | 7.8.9.2 | 7.8.9.3 | 7.8.9.4 | 7.8.9.5 | 7.8.9.6 | 7.8.9.7 |
| 7.8.9.8 | 7.8.9.9 | 7.9.1.1 | 7.9.1.2 | 7.9.1.3 | 7.9.1.4 | 7.9.1.5 | 7.9.1.6 | 7.9.1.7 | 7.9.1.8 |
| 7.9.1.9 | 7.9.2.1 | 7.9.2.2 | 7.9.2.3 | 7.9.2.4 | 7.9.2.5 | 7.9.2.6 | 7.9.2.7 | 7.9.2.8 | 7.9.2.9 |
| 7.9.3.1 | 7.9.3.2 | 7.9.3.3 | 7.9.3.4 | 7.9.3.5 | 7.9.3.6 | 7.9.3.7 | 7.9.3.8 | 7.9.3.9 | 7.9.4.1 |
| 7.9.4.2 | 7.9.4.3 | 7.9.4.4 | 7.9.4.5 | 7.9.4.6 | 7.9.4.7 | 7.9.4.8 | 7.9.4.9 | 7.9.5.1 | 7.9.5.2 |
| 7.9.5.3 | 7.9.5.4 | 7.9.5.5 | 7.9.5.6 | 7.9.5.7 | 7.9.5.8 | 7.9.5.9 | 7.9.6.1 | 7.9.6.2 | 7.9.6.3 |
| 7.9.6.4 | 7.9.6.5 | 7.9.6.6 | 7.9.6.7 | 7.9.6.8 | 7.9.6.9 | 7.9.7.1 | 7.9.7.2 | 7.9.7.3 | 7.9.7.4 |
| 7.9.7.5 | 7.9.7.6 | 7.9.7.7 | 7.9.7.8 | 7.9.7.9 | 7.9.8.1 | 7.9.8.2 | 7.9.8.3 | 7.9.8.4 | 7.9.8.5 |
| 7.9.8.6 | 7.9.8.7 | 7.9.8.8 | 7.9.8.9 | 7.9.9.1 | 7.9.9.2 | 7.9.9.3 | 7.9.9.4 | 7.9.9.5 | 7.9.9.6 |
| 7.9.9.7 | 7.9.9.8 | 7.9.9.9 | 8.1.1.1 | 8.1.1.2 | 8.1.1.3 | 8.1.1.4 | 8.1.1.5 | 8.1.1.6 | 8.1.1.7 |
| 8.1.1.8 | 8.1.1.9 | 8.1.2.1 | 8.1.2.2 | 8.1.2.3 | 8.1.2.4 | 8.1.2.5 | 8.1.2.6 | 8.1.2.7 | 8.1.2.8 |
| 8.1.2.9 | 8.1.3.1 | 8.1.3.2 | 8.1.3.3 | 8.1.3.4 | 8.1.3.5 | 8.1.3.6 | 8.1.3.7 | 8.1.3.8 | 8.1.3.9 |
| 8.1.4.1 | 8.1.4.2 | 8.1.4.3 | 8.1.4.4 | 8.1.4.5 | 8.1.4.6 | 8.1.4.7 | 8.1.4.8 | 8.1.4.9 | 8.1.5.1 |
| 8.1.5.2 | 8.1.5.3 | 8.1.5.4 | 8.1.5.5 | 8.1.5.6 | 8.1.5.7 | 8.1.5.8 | 8.1.5.9 | 8.1.6.1 | 8.1.6.2 |
| 8.1.6.3 | 8.1.6.4 | 8.1.6.5 | 8.1.6.6 | 8.1.6.7 | 8.1.6.8 | 8.1.6.9 | 8.1.7.1 | 8.1.7.2 | 8.1.7.3 |
| 8.1.7.4 | 8.1.7.5 | 8.1.7.6 | 8.1.7.7 | 8.1.7.8 | 8.1.7.9 | 8.1.8.1 | 8.1.8.2 | 8.1.8.3 | 8.1.8.4 |
| 8.1.8.5 | 8.1.8.6 | 8.1.8.7 | 8.1.8.8 | 8.1.8.9 | 8.1.9.1 | 8.1.9.2 | 8.1.9.3 | 8.1.9.4 | 8.1.9.5 |
| 8.1.9.6 | 8.1.9.7 | 8.1.9.8 | 8.1.9.9 | 8.2.1.1 | 8.2.1.2 | 8.2.1.3 | 8.2.1.4 | 8.2.1.5 | 8.2.1.6 |
| 8.2.1.7 | 8.2.1.8 | 8.2.1.9 | 8.2.2.1 | 8.2.2.2 | 8.2.2.3 | 8.2.2.4 | 8.2.2.5 | 8.2.2.6 | 8.2.2.7 |
| 8.2.2.8 | 8.2.2.9 | 8.2.3.1 | 8.2.3.2 | 8.2.3.3 | 8.2.3.4 | 8.2.3.5 | 8.2.3.6 | 8.2.3.7 | 8.2.3.8 |
| 8.2.3.9 | 8.2.4.1 | 8.2.4.2 | 8.2.4.3 | 8.2.4.4 | 8.2.4.5 | 8.2.4.6 | 8.2.4.7 | 8.2.4.8 | 8.2.4.9 |
| 8.2.5.1 | 8.2.5.2 | 8.2.5.3 | 8.2.5.4 | 8.2.5.5 | 8.2.5.6 | 8.2.5.7 | 8.2.5.8 | 8.2.5.9 | 8.2.6.1 |
| 8.2.6.2 | 8.2.6.3 | 8.2.6.4 | 8.2.6.5 | 8.2.6.6 | 8.2.6.7 | 8.2.6.8 | 8.2.6.9 | 8.2.7.1 | 8.2.7.2 |
| 8.2.7.3 | 8.2.7.4 | 8.2.7.5 | 8.2.7.6 | 8.2.7.7 | 8.2.7.8 | 8.2.7.9 | 8.2.8.1 | 8.2.8.2 | 8.2.8.3 |
| 8.2.8.4 | 8.2.8.5 | 8.2.8.6 | 8.2.8.7 | 8.2.8.8 | 8.2.8.9 | 8.2.9.1 | 8.2.9.2 | 8.2.9.3 | 8.2.9.4 |
| 8.2.9.5 | 8.2.9.6 | 8.2.9.7 | 8.2.9.8 | 8.2.9.9 | 8.3.1.1 | 8.3.1.2 | 8.3.1.3 | 8.3.1.4 | 8.3.1.5 |
| 8.3.1.6 | 8.3.1.7 | 8.3.1.8 | 8.3.1.9 | 8.3.2.1 | 8.3.2.2 | 8.3.2.3 | 8.3.2.4 | 8.3.2.5 | 8.3.2.6 |
| 8.3.2.7 | 8.3.2.8 | 8.3.2.9 | 8.3.3.1 | 8.3.3.2 | 8.3.3.3 | 8.3.3.4 | 8.3.3.5 | 8.3.3.6 | 8.3.3.7 |
| 8.3.3.8 | 8.3.3.9 | 8.3.4.1 | 8.3.4.2 | 8.3.4.3 | 8.3.4.4 | 8.3.4.5 | 8.3.4.6 | 8.3.4.7 | 8.3.4.8 |
| 8.3.4.9 | 8.3.5.1 | 8.3.5.2 | 8.3.5.3 | 8.3.5.4 | 8.3.5.5 | 8.3.5.6 | 8.3.5.7 | 8.3.5.8 | 8.3.5.9 |

TABLE 2-continued

| | | | | | | | | |
|---|---|---|---|---|---|---|---|---|
| 8.3.6.1 | 8.3.6.2 | 8.3.6.3 | 8.3.6.4 | 8.3.6.5 | 8.3.6.6 | 8.3.6.7 | 8.3.6.8 | 8.3.6.9 | 8.3.7.1 |
| 8.3.7.2 | 8.3.7.3 | 8.3.7.4 | 8.3.7.5 | 8.3.7.6 | 8.3.7.7 | 8.3.7.8 | 8.3.7.9 | 8.3.8.1 | 8.3.8.2 |
| 8.3.8.3 | 8.3.8.4 | 8.3.8.5 | 8.3.8.6 | 8.3.8.7 | 8.3.8.8 | 8.3.8.9 | 8.3.9.1 | 8.3.9.2 | 8.3.9.3 |
| 8.3.9.4 | 8.3.9.5 | 8.3.9.6 | 8.3.9.7 | 8.3.9.8 | 8.3.9.9 | 8.4.1.1 | 8.4.1.2 | 8.4.1.3 | 8.4.1.4 |
| 8.4.1.5 | 8.4.1.6 | 8.4.1.7 | 8.4.1.8 | 8.4.1.9 | 8.4.2.1 | 8.4.2.2 | 8.4.2.3 | 8.4.2.4 | 8.4.2.5 |
| 8.4.2.6 | 8.4.2.7 | 8.4.2.8 | 8.4.2.9 | 8.4.3.1 | 8.4.3.2 | 8.4.3.3 | 8.4.3.4 | 8.4.3.5 | 8.4.3.6 |
| 8.4.3.7 | 8.4.3.8 | 8.4.3.9 | 8.4.4.1 | 8.4.4.2 | 8.4.4.3 | 8.4.4.4 | 8.4.4.5 | 8.4.4.6 | 8.4.4.7 |
| 8.4.4.8 | 8.4.4.9 | 8.4.5.1 | 8.4.5.2 | 8.4.5.3 | 8.4.5.4 | 8.4.5.5 | 8.4.5.6 | 8.4.5.7 | 8.4.5.8 |
| 8.4.5.9 | 8.4.6.1 | 8.4.6.2 | 8.4.6.3 | 8.4.6.4 | 8.4.6.5 | 8.4.6.6 | 8.4.6.7 | 8.4.6.8 | 8.4.6.9 |
| 8.4.7.1 | 8.4.7.2 | 8.4.7.3 | 8.4.7.4 | 8.4.7.5 | 8.4.7.6 | 8.4.7.7 | 8.4.7.8 | 8.4.7.9 | 8.4.8.1 |
| 8.4.8.2 | 8.4.8.3 | 8.4.8.4 | 8.4.8.5 | 8.4.8.6 | 8.4.8.7 | 8.4.8.8 | 8.4.8.9 | 8.4.9.1 | 8.4.9.2 |
| 8.4.9.3 | 8.4.9.4 | 8.4.9.5 | 8.4.9.6 | 8.4.9.7 | 8.4.9.8 | 8.4.9.9 | 8.5.1.1 | 8.5.1.2 | 8.5.1.3 |
| 8.5.1.4 | 8.5.1.5 | 8.5.1.6 | 8.5.1.7 | 8.5.1.8 | 8.5.1.9 | 8.5.2.1 | 8.5.2.2 | 8.5.2.3 | 8.5.2.4 |
| 8.5.2.5 | 8.5.2.6 | 8.5.2.7 | 8.5.2.8 | 8.5.2.9 | 8.5.3.1 | 8.5.3.2 | 8.5.3.3 | 8.5.3.4 | 8.5.3.5 |
| 8.5.3.6 | 8.5.3.7 | 8.5.3.8 | 8.5.3.9 | 8.5.4.1 | 8.5.4.2 | 8.5.4.3 | 8.5.4.4 | 8.5.4.5 | 8.5.4.6 |
| 8.5.4.7 | 8.5.4.8 | 8.5.4.9 | 8.5.5.1 | 8.5.5.2 | 8.5.5.3 | 8.5.5.4 | 8.5.5.5 | 8.5.5.6 | 8.5.5.7 |
| 8.5.5.8 | 8.5.5.9 | 8.5.6.1 | 8.5.6.2 | 8.5.6.3 | 8.5.6.4 | 8.5.6.5 | 8.5.6.6 | 8.5.6.7 | 8.5.6.8 |
| 8.5.6.9 | 8.5.7.1 | 8.5.7.2 | 8.5.7.3 | 8.5.7.4 | 8.5.7.5 | 8.5.7.6 | 8.5.7.7 | 8.5.7.8 | 8.5.7.9 |
| 8.5.8.1 | 8.5.8.2 | 8.5.8.3 | 8.5.8.4 | 8.5.8.5 | 8.5.8.6 | 8.5.8.7 | 8.5.8.8 | 8.5.8.9 | 8.5.9.1 |
| 8.5.9.2 | 8.5.9.3 | 8.5.9.4 | 8.5.9.5 | 8.5.9.6 | 8.5.9.7 | 8.5.9.8 | 8.5.9.9 | 8.6.1.1 | 8.6.1.2 |
| 8.6.1.3 | 8.6.1.4 | 8.6.1.5 | 8.6.1.6 | 8.6.1.7 | 8.6.1.8 | 8.6.1.9 | 8.6.2.1 | 8.6.2.2 | 8.6.2.3 |
| 8.6.2.4 | 8.6.2.5 | 8.6.2.6 | 8.6.2.7 | 8.6.2.8 | 8.6.2.9 | 8.6.3.1 | 8.6.3.2 | 8.6.3.3 | 8.6.3.4 |
| 8.6.3.5 | 8.6.3.6 | 8.6.3.7 | 8.6.3.8 | 8.6.3.9 | 8.6.4.1 | 8.6.4.2 | 8.6.4.3 | 8.6.4.4 | 8.6.4.5 |
| 8.6.4.6 | 8.6.4.7 | 8.6.4.8 | 8.6.4.9 | 8.6.5.1 | 8.6.5.2 | 8.6.5.3 | 8.6.5.4 | 8.6.5.5 | 8.6.5.6 |
| 8.6.5.7 | 8.6.5.8 | 8.6.5.9 | 8.6.6.1 | 8.6.6.2 | 8.6.6.3 | 8.6.6.4 | 8.6.6.5 | 8.6.6.6 | 8.6.6.7 |
| 8.6.6.8 | 8.6.6.9 | 8.6.7.1 | 8.6.7.2 | 8.6.7.3 | 8.6.7.4 | 8.6.7.5 | 8.6.7.6 | 8.6.7.7 | 8.6.7.8 |
| 8.6.7.9 | 8.6.8.1 | 8.6.8.2 | 8.6.8.3 | 8.6.8.4 | 8.6.8.5 | 8.6.8.6 | 8.6.8.7 | 8.6.8.8 | 8.6.8.9 |
| 8.6.9.1 | 8.6.9.2 | 8.6.9.3 | 8.6.9.4 | 8.6.9.5 | 8.6.9.6 | 8.6.9.7 | 8.6.9.8 | 8.6.9.9 | 8.7.1.1 |
| 8.7.1.2 | 8.7.1.3 | 8.7.1.4 | 8.7.1.5 | 8.7.1.6 | 8.7.1.7 | 8.7.1.8 | 8.7.1.9 | 8.7.2.1 | 8.7.2.2 |
| 8.7.2.3 | 8.7.2.4 | 8.7.2.5 | 8.7.2.6 | 8.7.2.7 | 8.7.2.8 | 8.7.2.9 | 8.7.3.1 | 8.7.3.2 | 8.7.3.3 |
| 8.7.3.4 | 8.7.3.5 | 8.7.3.6 | 8.7.3.7 | 8.7.3.8 | 8.7.3.9 | 8.7.4.1 | 8.7.4.2 | 8.7.4.3 | 8.7.4.4 |
| 8.7.4.5 | 8.7.4.6 | 8.7.4.7 | 8.7.4.8 | 8.7.4.9 | 8.7.5.1 | 8.7.5.2 | 8.7.5.3 | 8.7.5.4 | 8.7.5.5 |
| 8.7.5.6 | 8.7.5.7 | 8.7.5.8 | 8.7.5.9 | 8.7.6.1 | 8.7.6.2 | 8.7.6.3 | 8.7.6.4 | 8.7.6.5 | 8.7.6.6 |
| 8.7.6.7 | 8.7.6.8 | 8.7.6.9 | 8.7.7.1 | 8.7.7.2 | 8.7.7.3 | 8.7.7.4 | 8.7.7.5 | 8.7.7.6 | 8.7.7.7 |
| 8.7.7.8 | 8.7.7.9 | 8.7.8.1 | 8.7.8.2 | 8.7.8.3 | 8.7.8.4 | 8.7.8.5 | 8.7.8.6 | 8.7.8.7 | 8.7.8.8 |
| 8.7.8.9 | 8.7.9.1 | 8.7.9.2 | 8.7.9.3 | 8.7.9.4 | 8.7.9.5 | 8.7.9.6 | 8.7.9.7 | 8.7.9.8 | 8.7.9.9 |
| 8.8.1.1 | 8.8.1.2 | 8.8.1.3 | 8.8.1.4 | 8.8.1.5 | 8.8.1.6 | 8.8.1.7 | 8.8.1.8 | 8.8.1.9 | 8.8.2.1 |
| 8.8.2.2 | 8.8.2.3 | 8.8.2.4 | 8.8.2.5 | 8.8.2.6 | 8.8.2.7 | 8.8.2.8 | 8.8.2.9 | 8.8.3.1 | 8.8.3.2 |
| 8.8.3.3 | 8.8.3.4 | 8.8.3.5 | 8.8.3.6 | 8.8.3.7 | 8.8.3.8 | 8.8.3.9 | 8.8.4.1 | 8.8.4.2 | 8.8.4.3 |
| 8.8.4.4 | 8.8.4.5 | 8.8.4.6 | 8.8.4.7 | 8.8.4.8 | 8.8.4.9 | 8.8.5.1 | 8.8.5.2 | 8.8.5.3 | 8.8.5.4 |
| 8.8.5.5 | 8.8.5.6 | 8.8.5.7 | 8.8.5.8 | 8.8.5.9 | 8.8.6.1 | 8.8.6.2 | 8.8.6.3 | 8.8.6.4 | 8.8.6.5 |
| 8.8.6.6 | 8.8.6.7 | 8.8.6.8 | 8.8.6.9 | 8.8.7.1 | 8.8.7.2 | 8.8.7.3 | 8.8.7.4 | 8.8.7.5 | 8.8.7.6 |
| 8.8.7.7 | 8.8.7.8 | 8.8.7.9 | 8.8.8.1 | 8.8.8.2 | 8.8.8.3 | 8.8.8.4 | 8.8.8.5 | 8.8.8.6 | 8.8.8.7 |
| 8.8.8.8 | 8.8.8.9 | 8.8.9.1 | 8.8.9.2 | 8.8.9.3 | 8.8.9.4 | 8.8.9.5 | 8.8.9.6 | 8.8.9.7 | 8.8.9.8 |
| 8.8.9.9 | 8.9.1.1 | 8.9.1.2 | 8.9.1.3 | 8.9.1.4 | 8.9.1.5 | 8.9.1.6 | 8.9.1.7 | 8.9.1.8 | 8.9.1.9 |
| 8.9.2.1 | 8.9.2.2 | 8.9.2.3 | 8.9.2.4 | 8.9.2.5 | 8.9.2.6 | 8.9.2.7 | 8.9.2.8 | 8.9.2.9 | 8.9.3.1 |
| 8.9.3.2 | 8.9.3.3 | 8.9.3.4 | 8.9.3.5 | 8.9.3.6 | 8.9.3.7 | 8.9.3.8 | 8.9.3.9 | 8.9.4.1 | 8.9.4.2 |
| 8.9.4.3 | 8.9.4.4 | 8.9.4.5 | 8.9.4.6 | 8.9.4.7 | 8.9.4.8 | 8.9.4.9 | 8.9.5.1 | 8.9.5.2 | 8.9.5.3 |
| 8.9.5.4 | 8.9.5.5 | 8.9.5.6 | 8.9.5.7 | 8.9.5.8 | 8.9.5.9 | 8.9.6.1 | 8.9.6.2 | 8.9.6.3 | 8.9.6.4 |
| 8.9.6.5 | 8.9.6.6 | 8.9.6.7 | 8.9.6.8 | 8.9.6.9 | 8.9.7.1 | 8.9.7.2 | 8.9.7.3 | 8.9.7.4 | 8.9.7.5 |
| 8.9.7.6 | 8.9.7.7 | 8.9.7.8 | 8.9.7.9 | 8.9.8.1 | 8.9.8.2 | 8.9.8.3 | 8.9.8.4 | 8.9.8.5 | 8.9.8.6 |
| 8.9.8.7 | 8.9.8.8 | 8.9.8.9 | 8.9.9.1 | 8.9.9.2 | 8.9.9.3 | 8.9.9.4 | 8.9.9.5 | 8.9.9.6 | 8.9.9.7 |
| 8.9.9.8 | 8.9.9.9 | 9.1.1.1 | 9.1.1.2 | 9.1.1.3 | 9.1.1.4 | 9.1.1.5 | 9.1.1.6 | 9.1.1.7 | 9.1.1.8 |
| 9.1.1.9 | 9.1.2.1 | 9.1.2.2 | 9.1.2.3 | 9.1.2.4 | 9.1.2.5 | 9.1.2.6 | 9.1.2.7 | 9.1.2.8 | 9.1.2.9 |
| 9.1.3.1 | 9.1.3.2 | 9.1.3.3 | 9.1.3.4 | 9.1.3.5 | 9.1.3.6 | 9.1.3.7 | 9.1.3.8 | 9.1.3.9 | 9.1.4.1 |
| 9.1.4.2 | 9.1.4.3 | 9.1.4.4 | 9.1.4.5 | 9.1.4.6 | 9.1.4.7 | 9.1.4.8 | 9.1.4.9 | 9.1.5.1 | 9.1.5.2 |
| 9.1.5.3 | 9.1.5.4 | 9.1.5.5 | 9.1.5.6 | 9.1.5.7 | 9.1.5.8 | 9.1.5.9 | 9.1.6.1 | 9.1.6.2 | 9.1.6.3 |
| 9.1.6.4 | 9.1.6.5 | 9.1.6.6 | 9.1.6.7 | 9.1.6.8 | 9.1.6.9 | 9.1.7.1 | 9.1.7.2 | 9.1.7.3 | 9.1.7.4 |
| 9.1.7.5 | 9.1.7.6 | 9.1.7.7 | 9.1.7.8 | 9.1.7.9 | 9.1.8.1 | 9.1.8.2 | 9.1.8.3 | 9.1.8.4 | 9.1.8.5 |
| 9.1.8.6 | 9.1.8.7 | 9.1.8.8 | 9.1.8.9 | 9.1.9.1 | 9.1.9.2 | 9.1.9.3 | 9.1.9.4 | 9.1.9.5 | 9.1.9.6 |
| 9.1.9.7 | 9.1.9.8 | 9.1.9.9 | 9.2.1.1 | 9.2.1.2 | 9.2.1.3 | 9.2.1.4 | 9.2.1.5 | 9.2.1.6 | 9.2.1.7 |
| 9.2.1.8 | 9.2.1.9 | 9.2.2.1 | 9.2.2.2 | 9.2.2.3 | 9.2.2.4 | 9.2.2.5 | 9.2.2.6 | 9.2.2.7 | 9.2.2.8 |
| 9.2.2.9 | 9.2.3.1 | 9.2.3.2 | 9.2.3.3 | 9.2.3.4 | 9.2.3.5 | 9.2.3.6 | 9.2.3.7 | 9.2.3.8 | 9.2.3.9 |
| 9.2.4.1 | 9.2.4.2 | 9.2.4.3 | 9.2.4.4 | 9.2.4.5 | 9.2.4.6 | 9.2.4.7 | 9.2.4.8 | 9.2.4.9 | 9.2.5.1 |
| 9.2.5.2 | 9.2.5.3 | 9.2.5.4 | 9.2.5.5 | 9.2.5.6 | 9.2.5.7 | 9.2.5.8 | 9.2.5.9 | 9.2.6.1 | 9.2.6.2 |
| 9.2.6.3 | 9.2.6.4 | 9.2.6.5 | 9.2.6.6 | 9.2.6.7 | 9.2.6.8 | 9.2.6.9 | 9.2.7.1 | 9.2.7.2 | 9.2.7.3 |
| 9.2.7.4 | 9.2.7.5 | 9.2.7.6 | 9.2.7.7 | 9.2.7.8 | 9.2.7.9 | 9.2.8.1 | 9.2.8.2 | 9.2.8.3 | 9.2.8.4 |
| 9.2.8.5 | 9.2.8.6 | 9.2.8.7 | 9.2.8.8 | 9.2.8.9 | 9.2.9.1 | 9.2.9.2 | 9.2.9.3 | 9.2.9.4 | 9.2.9.5 |
| 9.2.9.6 | 9.2.9.7 | 9.2.9.8 | 9.2.9.9 | 9.3.1.1 | 9.3.1.2 | 9.3.1.3 | 9.3.1.4 | 9.3.1.5 | 9.3.1.6 |
| 9.3.1.7 | 9.3.1.8 | 9.3.1.9 | 9.3.2.1 | 9.3.2.2 | 9.3.2.3 | 9.3.2.4 | 9.3.2.5 | 9.3.2.6 | 9.3.2.7 |
| 9.3.2.8 | 9.3.2.9 | 9.3.3.1 | 9.3.3.2 | 9.3.3.3 | 9.3.3.4 | 9.3.3.5 | 9.3.3.6 | 9.3.3.7 | 9.3.3.8 |
| 9.3.3.9 | 9.3.4.1 | 9.3.4.2 | 9.3.4.3 | 9.3.4.4 | 9.3.4.5 | 9.3.4.6 | 9.3.4.7 | 9.3.4.8 | 9.3.4.9 |
| 9.3.5.1 | 9.3.5.2 | 9.3.5.3 | 9.3.5.4 | 9.3.5.5 | 9.3.5.6 | 9.3.5.7 | 9.3.5.8 | 9.3.5.9 | 9.3.6.1 |
| 9.3.6.2 | 9.3.6.3 | 9.3.6.4 | 9.3.6.5 | 9.3.6.6 | 9.3.6.7 | 9.3.6.8 | 9.3.6.9 | 9.3.7.1 | 9.3.7.2 |
| 9.3.7.3 | 9.3.7.4 | 9.3.7.5 | 9.3.7.6 | 9.3.7.7 | 9.3.7.8 | 9.3.7.9 | 9.3.8.1 | 9.3.8.2 | 9.3.8.3 |
| 9.3.8.4 | 9.3.8.5 | 9.3.8.6 | 9.3.8.7 | 9.3.8.8 | 9.3.8.9 | 9.3.9.1 | 9.3.9.2 | 9.3.9.3 | 9.3.9.4 |
| 9.3.9.5 | 9.3.9.6 | 9.3.9.7 | 9.3.9.8 | 9.3.9.9 | 9.4.1.1 | 9.4.1.2 | 9.4.1.3 | 9.4.1.4 | 9.4.1.5 |
| 9.4.1.6 | 9.4.1.7 | 9.4.1.8 | 9.4.1.9 | 9.4.2.1 | 9.4.2.2 | 9.4.2.3 | 9.4.2.4 | 9.4.2.5 | 9.4.2.6 |
| 9.4.2.7 | 9.4.2.8 | 9.4.2.9 | 9.4.3.1 | 9.4.3.2 | 9.4.3.3 | 9.4.3.4 | 9.4.3.5 | 9.4.3.6 | 9.4.3.7 |

TABLE 2-continued

| | | | | | | | | | |
|---|---|---|---|---|---|---|---|---|---|
| 9.4.3.8 | 9.4.3.9 | 9.4.4.1 | 9.4.4.2 | 9.4.4.3 | 9.4.4.4 | 9.4.4.5 | 9.4.4.6 | 9.4.4.7 | 9.4.4.8 |
| 9.4.4.9 | 9.4.5.1 | 9.4.5.2 | 9.4.5.3 | 9.4.5.4 | 9.4.5.5 | 9.4.5.6 | 9.4.5.7 | 9.4.5.8 | 9.4.5.9 |
| 9.4.6.1 | 9.4.6.2 | 9.4.6.3 | 9.4.6.4 | 9.4.6.5 | 9.4.6.6 | 9.4.6.7 | 9.4.6.8 | 9.4.6.9 | 9.4.7.1 |
| 9.4.7.2 | 9.4.7.3 | 9.4.7.4 | 9.4.7.5 | 9.4.7.6 | 9.4.7.7 | 9.4.7.8 | 9.4.7.9 | 9.4.8.1 | 9.4.8.2 |
| 9.4.8.3 | 9.4.8.4 | 9.4.8.5 | 9.4.8.6 | 9.4.8.7 | 9.4.8.8 | 9.4.8.9 | 9.4.9.1 | 9.4.9.2 | 9.4.9.3 |
| 9.4.9.4 | 9.4.9.5 | 9.4.9.6 | 9.4.9.7 | 9.4.9.8 | 9.4.9.9 | 9.5.1.1 | 9.5.1.2 | 9.5.1.3 | 9.5.1.4 |
| 9.5.1.5 | 9.5.1.6 | 9.5.1.7 | 9.5.1.8 | 9.5.1.9 | 9.5.2.1 | 9.5.2.2 | 9.5.2.3 | 9.5.2.4 | 9.5.2.5 |
| 9.5.2.6 | 9.5.2.7 | 9.5.2.8 | 9.5.2.9 | 9.5.3.1 | 9.5.3.2 | 9.5.3.3 | 9.5.3.4 | 9.5.3.5 | 9.5.3.6 |
| 9.5.3.7 | 9.5.3.8 | 9.5.3.9 | 9.5.4.1 | 9.5.4.2 | 9.5.4.3 | 9.5.4.4 | 9.5.4.5 | 9.5.4.6 | 9.5.4.7 |
| 9.5.4.8 | 9.5.4.9 | 9.5.5.1 | 9.5.5.2 | 9.5.5.3 | 9.5.5.4 | 9.5.5.5 | 9.5.5.6 | 9.5.5.7 | 9.5.5.8 |
| 9.5.5.9 | 9.5.6.1 | 9.5.6.2 | 9.5.6.3 | 9.5.6.4 | 9.5.6.5 | 9.5.6.6 | 9.5.6.7 | 9.5.6.8 | 9.5.6.9 |
| 9.5.7.1 | 9.5.7.2 | 9.5.7.3 | 9.5.7.4 | 9.5.7.5 | 9.5.7.6 | 9.5.7.7 | 9.5.7.8 | 9.5.7.9 | 9.5.8.1 |
| 9.5.8.2 | 9.5.8.3 | 9.5.8.4 | 9.5.8.5 | 9.5.8.6 | 9.5.8.7 | 9.5.8.8 | 9.5.8.9 | 9.5.9.1 | 9.5.9.2 |
| 9.5.9.3 | 9.5.9.4 | 9.5.9.5 | 9.5.9.6 | 9.5.9.7 | 9.5.9.8 | 9.5.9.9 | 9.6.1.1 | 9.6.1.2 | 9.6.1.3 |
| 9.6.1.4 | 9.6.1.5 | 9.6.1.6 | 9.6.1.7 | 9.6.1.8 | 9.6.1.9 | 9.6.2.1 | 9.6.2.2 | 9.6.2.3 | 9.6.2.4 |
| 9.6.2.5 | 9.6.2.6 | 9.6.2.7 | 9.6.2.8 | 9.6.2.9 | 9.6.3.1 | 9.6.3.2 | 9.6.3.3 | 9.6.3.4 | 9.6.3.5 |
| 9.6.3.6 | 9.6.3.7 | 9.6.3.8 | 9.6.3.9 | 9.6.4.1 | 9.6.4.2 | 9.6.4.3 | 9.6.4.4 | 9.6.4.5 | 9.6.4.6 |
| 9.6.4.7 | 9.6.4.8 | 9.6.4.9 | 9.6.5.1 | 9.6.5.2 | 9.6.5.3 | 9.6.5.4 | 9.6.5.5 | 9.6.5.6 | 9.6.5.7 |
| 9.6.5.8 | 9.6.5.9 | 9.6.6.1 | 9.6.6.2 | 9.6.6.3 | 9.6.6.4 | 9.6.6.5 | 9.6.6.6 | 9.6.6.7 | 9.6.6.8 |
| 9.6.6.9 | 9.6.7.1 | 9.6.7.2 | 9.6.7.3 | 9.6.7.4 | 9.6.7.5 | 9.6.7.6 | 9.6.7.7 | 9.6.7.8 | 9.6.7.9 |
| 9.6.8.1 | 9.6.8.2 | 9.6.8.3 | 9.6.8.4 | 9.6.8.5 | 9.6.8.6 | 9.6.8.7 | 9.6.8.8 | 9.6.8.9 | 9.6.9.1 |
| 9.6.9.2 | 9.6.9.3 | 9.6.9.4 | 9.6.9.5 | 9.6.9.6 | 9.6.9.7 | 9.6.9.8 | 9.6.9.9 | 9.7.1.1 | 9.7.1.2 |
| 9.7.1.3 | 9.7.1.4 | 9.7.1.5 | 9.7.1.6 | 9.7.1.7 | 9.7.1.8 | 9.7.1.9 | 9.7.2.1 | 9.7.2.2 | 9.7.2.3 |
| 9.7.2.4 | 9.7.2.5 | 9.7.2.6 | 9.7.2.7 | 9.7.2.8 | 9.7.2.9 | 9.7.3.1 | 9.7.3.2 | 9.7.3.3 | 9.7.3.4 |
| 9.7.3.5 | 9.7.3.6 | 9.7.3.7 | 9.7.3.8 | 9.7.3.9 | 9.7.4.1 | 9.7.4.2 | 9.7.4.3 | 9.7.4.4 | 9.7.4.5 |
| 9.7.4.6 | 9.7.4.7 | 9.7.4.8 | 9.7.4.9 | 9.7.5.1 | 9.7.5.2 | 9.7.5.3 | 9.7.5.4 | 9.7.5.5 | 9.7.5.6 |
| 9.7.5.7 | 9.7.5.8 | 9.7.5.9 | 9.7.6.1 | 9.7.6.2 | 9.7.6.3 | 9.7.6.4 | 9.7.6.5 | 9.7.6.6 | 9.7.6.7 |
| 9.7.6.8 | 9.7.6.9 | 9.7.7.1 | 9.7.7.2 | 9.7.7.3 | 9.7.7.4 | 9.7.7.5 | 9.7.7.6 | 9.7.7.7 | 9.7.7.8 |
| 9.7.7.9 | 9.7.8.1 | 9.7.8.2 | 9.7.8.3 | 9.7.8.4 | 9.7.8.5 | 9.7.8.6 | 9.7.8.7 | 9.7.8.8 | 9.7.8.9 |
| 9.7.9.1 | 9.7.9.2 | 9.7.9.3 | 9.7.9.4 | 9.7.9.5 | 9.7.9.6 | 9.7.9.7 | 9.7.9.8 | 9.7.9.9 | 9.8.1.1 |
| 9.8.1.2 | 9.8.1.3 | 9.8.1.4 | 9.8.1.5 | 9.8.1.6 | 9.8.1.7 | 9.8.1.8 | 9.8.1.9 | 9.8.2.1 | 9.8.2.2 |
| 9.8.2.3 | 9.8.2.4 | 9.8.2.5 | 9.8.2.6 | 9.8.2.7 | 9.8.2.8 | 9.8.2.9 | 9.8.3.1 | 9.8.3.2 | 9.8.3.3 |
| 9.8.3.4 | 9.8.3.5 | 9.8.3.6 | 9.8.3.7 | 9.8.3.8 | 9.8.3.9 | 9.8.4.1 | 9.8.4.2 | 9.8.4.3 | 9.8.4.4 |
| 9.8.4.5 | 9.8.4.6 | 9.8.4.7 | 9.8.4.8 | 9.8.4.9 | 9.8.5.1 | 9.8.5.2 | 9.8.5.3 | 9.8.5.4 | 9.8.5.5 |
| 9.8.5.6 | 9.8.5.7 | 9.8.5.8 | 9.8.5.9 | 9.8.6.1 | 9.8.6.2 | 9.8.6.3 | 9.8.6.4 | 9.8.6.5 | 9.8.6.6 |
| 9.8.6.7 | 9.8.6.8 | 9.8.6.9 | 9.8.7.1 | 9.8.7.2 | 9.8.7.3 | 9.8.7.4 | 9.8.7.5 | 9.8.7.6 | 9.8.7.7 |
| 9.8.7.8 | 9.8.7.9 | 9.8.8.1 | 9.8.8.2 | 9.8.8.3 | 9.8.8.4 | 9.8.8.5 | 9.8.8.6 | 9.8.8.7 | 9.8.8.8 |
| 9.8.8.9 | 9.8.9.1 | 9.8.9.2 | 9.8.9.3 | 9.8.9.4 | 9.8.9.5 | 9.8.9.6 | 9.8.9.7 | 9.8.9.8 | 9.8.9.9 |
| 9.9.1.1 | 9.9.1.2 | 9.9.1.3 | 9.9.1.4 | 9.9.1.5 | 9.9.1.6 | 9.9.1.7 | 9.9.1.8 | 9.9.1.9 | 9.9.2.1 |
| 9.9.2.2 | 9.9.2.3 | 9.9.2.4 | 9.9.2.5 | 9.9.2.6 | 9.9.2.7 | 9.9.2.8 | 9.9.2.9 | 9.9.3.1 | 9.9.3.2 |
| 9.9.3.3 | 9.9.3.4 | 9.9.3.5 | 9.9.3.6 | 9.9.3.7 | 9.9.3.8 | 9.9.3.9 | 9.9.4.1 | 9.9.4.2 | 9.9.4.3 |
| 9.9.4.4 | 9.9.4.5 | 9.9.4.6 | 9.9.4.7 | 9.9.4.8 | 9.9.4.9 | 9.9.5.1 | 9.9.5.2 | 9.9.5.3 | 9.9.5.4 |
| 9.9.5.5 | 9.9.5.6 | 9.9.5.7 | 9.9.5.8 | 9.9.5.9 | 9.9.6.1 | 9.9.6.2 | 9.9.6.3 | 9.9.6.4 | 9.9.6.5 |
| 9.9.6.6 | 9.9.6.7 | 9.9.6.8 | 9.9.6.9 | 9.9.7.1 | 9.9.7.2 | 9.9.7.3 | 9.9.7.4 | 9.9.7.5 | 9.9.7.6 |
| 9.9.7.7 | 9.9.7.8 | 9.9.7.9 | 9.9.8.1 | 9.9.8.2 | 9.9.8.3 | 9.9.8.4 | 9.9.8.5 | 9.9.8.6 | 9.9.8.7 |
| 9.9.8.8 | 9.9.8.9 | 9.9.9.1 | 9.9.9.2 | 9.9.9.3 | 9.9.9.4 | 9.9.9.5 | 9.9.9.6 | 9.9.9.7 | 9.9.9.8 |
| 9.9.9.9 | | | | | | | | | |

In another aspect, phosphonic acid monoester compounds are included in the invention having alternative variable $V1'$ and variables V2, V3, and V4 as disclosed above. Compounds named in Table 2 are designated by numbers assigned to the variables of formulas V-VII using the following convention: $V^{1'}.V^2.V^3.V^4$.

Variable $V^{1'}$:
1) —P(O)(OH)(OCH$_3$)
2) —P(O)(OH)(OCH$_2$CH$_3$)
3) —P(O)(OH)(O-i-propyl)
4) —P(O)[—OCH$_2$OC(O)-t-butyl](OCH$_3$)
5) —P(O)[—OCH$_2$OC(O)O-i-propyl](OCH$_3$)
6) —P(O)[—N(H)CH(CH$_3$)C(O)OCH$_2$CH$_3$](OCH$_3$)
7) —P(O)[—N(H)C(CH$_3$)$_2$C(O)OCH$_2$CH$_3$](OCH$_3$)
8) —P(O)[—OCH(CH$_3$)OC(O)-t-butyl](OCH$_3$)
9) —P(O)[—OCH(CH$_3$)OC(O)O-i-propyl](OCH$_3$)

In another aspect, the following compounds are included in the invention but the compounds are not limited to these illustrative compounds. The compounds are shown without depiction of stereochemistry since the compounds are biologically active as the diastereomeric mixture or as a single stereoisomer. Compounds included are designated by numbers assigned to the variables of formulas XI-XVI using the following convention: V1.V2.V3.V4.V5.V6. Each individual compound from 1.1.1.1.1.1 to 9.9.9.9.9.9 (e.g., 2.3.4.5.6.7. or 8.7.3.5.2.1) is included in the present invention as an individual species and may be specifically set forth as such for inclusion or may be specifically excluded from the present invention. As the understanding as to what is included is clear from the description thus, a Table is not included so as to not unduly lengthen the specification.

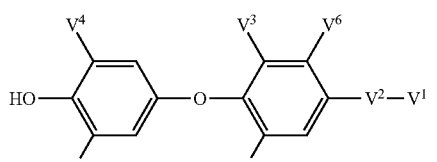

Formula XI

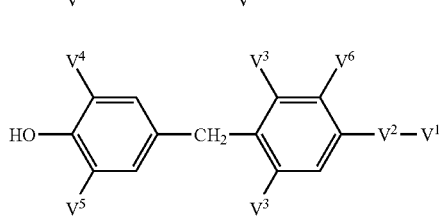

Formula XII

Formula XIII

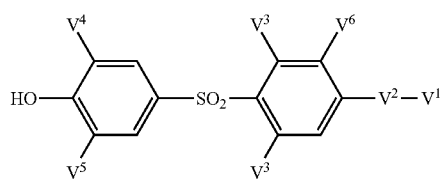

Formula XIV

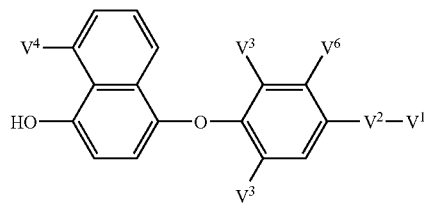

Formula XV

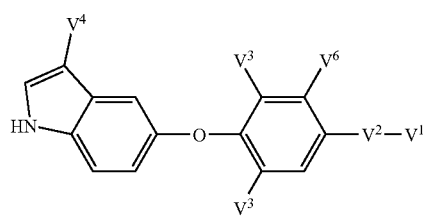

Formula XVI

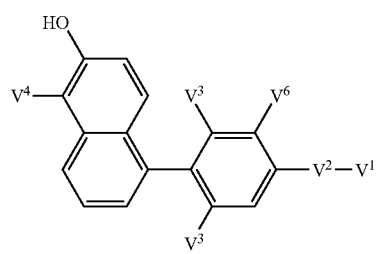

Variable $V^1$:
1) —P(O)(OH)$_2$
2) —P(O)[O—CH$_2$OC(O)C(CH$_3$)$_3$]$_2$
3) —P(O)[O—CH$_2$OC(O)CH(CH$_3$)$_2$]$_2$
4) —P(O)[O—CH$_2$OC(O)OCH$_2$CH$_3$]$_2$
5) —P(O)[NH—CH(CH$_3$)C(O)OCH$_2$CH$_3$]$_2$
6) —P(O)[NH—C(CH$_3$)$_2$C(O)OCH$_2$CH$_3$]$_2$
7) —P(O)(OC$_6$H$_5$)$_2$
8) —P(O)(O—CH(3-chlorophenyl)CH$_2$CH$_2$—O)
9) —P(O)(O—CH(4-pyridyl)CH$_2$CH$_2$—O)

Variable $V^2$:
1) —CH$_2$—
2) —OCH$_2$—
3) —CH$_2$—CH$_2$—
4) —NHCH$_2$—
5) —NH(CO)—
6) —CH$_2$—CH(NH$_2$)— (R-configuration)
7) —CH$_2$—CH(NH$_2$)— (S-configuration)
8) —CH=CH— (trans)
9) -null Variable $V^3$:
1) —OCH$_3$
2) iodo
3) bromo
4) chloro
5) fluoro
6) methyl
7) trifluoromethyl
8) cyano
9) —OCF$_3$ Variable $V^4$:
1) iodo
2) CH(CH$_3$)$_2$
3) -(3-trifluoromethylphenoxy)
4) -(3-ethylphenyl)
5) —C(O)NH—CH$_2$—CH$_2$-phenyl
6) —CH(OH)(4-fluorophenyl)
7) —SO$_2$(4-fluorophenyl)
8) -(4-fluorobenzyl)
9) -1-ethyl-propyl Variable $V^5$ and $V^6$
1) hydrogen
2) iodo
3) bromo
4) chloro
5) fluoro
6) methyl
7) trifluoromethyl
8) cyano
9) —OCH$_3$ In another aspect, phosphonic acid monoester compounds are included in the invention having alternative variable $V^{1'}$ and variables $V^2$, $V^3$, $V^4$, $V^5$, and $V^6$ as disclosed above. Compounds are designated by numbers assigned to the variables of formulas XI-XVI using the following convention: $V^1.V^2.V^3.V^4V^5.V^6$.

Variable $V^{1'}$:
1) —P(O)(OH)(OCH$_3$)
2) —P(O)(OH)(OCH$_2$CH$_3$)
3) —P(O)(OH)(O-i-propyl)
4) —P(O)[—OCH$_2$OC(O)-t-butyl](OCH$_3$)
5) —P(O)[—OCH$_2$OC(O)O-i-propyl](OCH$_3$)
6) —P(O)[—N(H)CH(CH$_3$)C(O)OCH$_2$CH$_3$](OCH$_3$)
7) —P(O)[—N(H)C(CH$_3$)$_2$C(O)OCH$_2$CH$_3$](OCH$_3$)
8) —P(O)[—OCH(CH$_3$)OC(O)-t-butyl](OCH$_3$)
9) —P(O)[—OCH(CH$_3$)OC(O)O-i-propyl](OCH$_3$)

In another aspect the following compounds are included in the invention but the compounds are not limited to these illustrative compounds. The compounds are shown without depiction of stereochemistry since the compounds are biologically active as the diastereomeric mixture or as a single stereoisomer. Compounds included are designated by numbers assigned to the variables of formulas XVII and XVIII using the following convention: $V^1.V^2.V^3.V^4.V^5.V^6.V^7$ Each individual compound from 1.1.1.1.1.1.1 to 9.9.9.9.9.9.2 (e.g., 2.3.4.5.6.7.1 or 8.7.3.5.2.1.1) is included in the present invention as an individual species and may be specifically set forth as such for inclusion or may be specifically excluded from the present invention. As the understanding is to what is included is clear from the description thus, a Table is not included so as to not unduly lengthen the specification.

Formula XVII

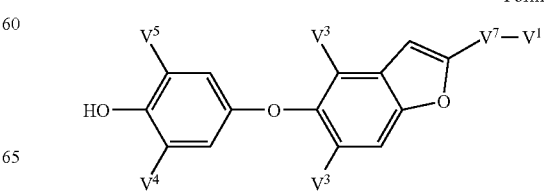

-continued

Formula XVIII

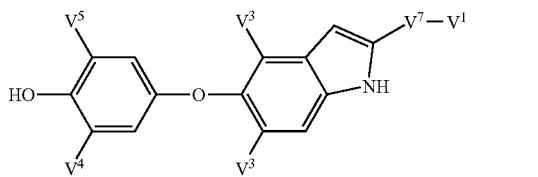

Variable $V^7$:
1) —$CH_2$—
2) -null

In another aspect, phosphonic acid monoester compounds are included in the invention having alternative variable $V^{1'}$ and variables $V^2$, $V^3$, $V^4$, $V^5$, $V^6$, and $V^7$ as disclosed above. The compounds are designated by numbers assigned to the variables of formulas XVII-XVIII using the following convention: $V^{1'}.V^2.V^3.V^4.V^5.V^6.V^7$.

Variable $V^{1'}$:
1) —P(O)(OH)(OCH$_3$)
2) —P(O)(OH)(OCH$_2$CH$_3$)
3) —P(O)(OH)(O-i-propyl)
4) —P(O)[—OCH$_2$OC(O)-t-butyl](OCH$_3$)
5) —P(O)[—OCH$_2$OC(O)O-i-propyl](OCH$_3$)
6) —P(O)[—N(H)CH(CH$_3$)C(O)OCH$_2$CH$_3$](OCH$_3$)
7) —P(O)[—N(H)C(CH$_3$)$_2$C(O)OCH$_2$CH$_3$](OCH$_3$)
8) —P(O)[—OCH(CH$_3$)OC(O)-t-butyl](OCH$_3$)
9) —P(O)[—OCH(CH$_3$)OC(O)O-i-propyl](OCH$_3$)

The present invention provides for compounds of Formula I including but not limited to wherein:

Phosphonic Acids

G is —O—, T is —CH$_2$CH(NH$_2$)—, R$^1$ is —I, R$^2$ is —I, R$^3$ is —I, R$^4$ is —H, R$^5$ is —OH, X is —PO$_3$H$_2$;

G is —O—, T is —CH$_2$CH(NH$_2$)—, R$^1$ is —I, R$^2$ is —I, R$^3$ is —I, R$^4$ is —I, R$^5$ is —OH, X is —PO$_3$H$_2$;

G is —O—, T is —CH$_2$—, R$^1$ is —I, R$^2$ is —I, R$^3$ is —I, R$^4$ is —H, R$^5$ is —OH, X is —PO$_3$H$_2$;

G is —O—, T is —N(H)C(O)—, R$^1$ is —CH$_3$, R$^2$ is —CH$_3$, R$^3$ is CH(OH)(4-fluorophenyl), R$^4$ is —H, R$^5$ is —OH, X is —PO$_3$H$_2$;

G is —CH$_2$—, T is —OCH$_2$—, R$^1$ is —CH$_3$, R$^2$ is —CH$_3$, R$^3$ is i-propyl, R$^4$ is —H, R$^5$ is —OH, X is —PO$_3$H$_2$;

G is —O—, T is —CH$_2$—, R$^1$ is —C$^1$, R$^2$ is —C$^1$, R$^3$ is i-propyl, R$^4$ is —H, R$^5$ is —OH, X is —PO$_3$H$_2$;

G is —O—, T is —OCH$_2$—, R$^1$ is —I, R$^2$ is —I, R$^3$ is i-propyl, R$^4$ is —H, R$^5$ is —OH, X is PO$_3$H$_2$;

BisPOM

G is —O—, T is —CH$_2$CH(NH$_2$)—, R$^1$ is —I, R$^2$ is —I, R$^3$ is —I, R$^4$ is —H, R$^5$ is —OH, X is —P(O)[—OCH$_2$OC(O)C(CH$_3$)$_3$]$_2$;

G is —O—, T is —CH$_2$CH(NH$_2$)—, R$^1$ is —I, R$^2$ is —I, R$^3$ is —I, R$^4$ is —I, R$^5$ is —OH, X is —P(O)[—OCH$_2$OC(O)C(CH$_3$)$_3$]$_2$;

G is —O—, T is —CH$_2$—, R$^1$ is —I, R$^2$ is —I, R$^3$ is —I, R$^4$ is —H, R$^5$ is —OH, X is —P(O)[—OCH$_2$OC(O)C(CH$_3$)$_3$]$_2$;

G is —O—, T is —N(H)C(O)—, R$^1$ is —CH$_3$, R$^2$ is —CH$_3$, R$^3$ is CH(OH)(4-fluorophenyl), R$^4$ is —H, R$^5$ is —OH, X is —P(O)[—OCH$_2$OC(O)C(CH$_3$)$_3$]$_2$;

G is —CH$_2$—, T is —OCH$_2$—, R$^1$ is —CH$_3$, R$^2$ is —CH$_3$, R$^3$ is i-propyl, R$^4$ is —H, R$^5$ is —OH, X is —P(O)[—OCH$_2$OC(O)C(CH$_3$)$_3$]$_2$;

G is —O—, T is —CH$_2$—, R$^1$ is —Cl, R$^2$ is —Cl, R$^3$ is i-propyl, R$^4$ is —H, R$^5$ is —OH, X is —P(O)[—OCH$_2$OC(O)C(CH$_3$)$_3$]$_2$;

G is —O—, T is —OCH$_2$—, R$^1$ is —I, R$^2$ is —I, R$^3$ is i-propyl, R$^4$ is —H, R$^5$ is —OH, X is —P(O)[—OCH$_2$OC(O)C(CH$_3$)$_3$]$_2$;

Carbonates

G is —O—, T is —CH$_2$CH(NH$_2$)—, R$^1$ is —I, R$^2$ is —I, R$^3$ is —I, R$^4$ is —H, R$^5$ is —OH, X is —P(O)[—OCH$_2$OC(O)OCH(CH$_3$)$_2$]$_2$;

G is —O—, T is —CH$_2$CH(NH$_2$)—, R$^1$ is —I, R$^2$ is —I, R$^3$ is —I, R$^4$ is —I, R$^5$ is —OH, X is —P(O)[—OCH$_2$OC(O)OCH(CH$_3$)$_2$]$_2$;

G is —O—, T is —CH$_2$—, R$^1$ is —I, R$^2$ is —I, R$^3$ is —I, R$^4$ is —H, R$^5$ is —OH, X is —P(O)[—OCH$_2$OC(O)OCH(CH$_3$)$_2$]$_2$;

G is —O—, T is —N(H)C(O)—, R$^1$ is —CH$_3$, R$^2$ is —CH$_3$, R$^3$ is CH(OH)(4-fluorophenyl), R$^4$ is —H, R$^5$ is —OH, X is —P(O)[—OCH$_2$OC(O)OCH(CH$_3$)$_2$]$_2$;

G is —CH$_2$—, T is —OCH$_2$—, R$^1$ is —CH$_3$, R$^2$ is —CH$_3$, R$^3$ is i-propyl, R$^4$ is —H, R$^5$ is —OH, X is —P(O)[—OCH$_2$OC(O)OCH(CH$_3$)$_2$]$_2$;

G is —O—, T is —CH$_2$—, R$^1$ is —C$^1$, R$^2$ is —C$^1$, R$^3$ is i-propyl, R$^4$ is —H, R$^5$ is —OH, X is —P(O)[—OCH$_2$OC(O)OCH(CH$_3$)$_2$]$_2$;

G is —O—, T is —OCH$_2$—, R$^1$ is —I, R$^2$ is —I, R$^3$ is i-propyl, R$^4$ is —H, R$^5$ is —OH, X is —P(O)[—OCH$_2$OC(O)OCH(CH$_3$)$_2$]$_2$;

Bisamidates

G is —O—, T is —CH$_2$CH(NH$_2$)—, R$^1$ is —I, R$^2$ is —I, R$^3$ is —I, R$^4$ is —H, R$^5$ is —OH, X is —P(O)[N(H)CH(CH$_3$)C(O)OCH$_2$CH$_3$]$_2$;

G is —O—, T is —CH$_2$CH(NH$_2$)—, R$^1$ is —I, R$^2$ is —I, R$^3$ is —I, R$^4$ is —I, R$^5$ is —OH, X is —P(O)[N(H)CH(CH$_3$)C(O)OCH$_2$CH$_3$]$_2$;

G is —O—, T is —CH$_2$—, R$^1$ is —I, R$^2$ is —I, R$^3$ is —I, R$^4$ is —H, R$^5$ is —OH, X is —P(O)[N(H)CH(CH$_3$)C(O)OCH$_2$CH$_3$]$_2$;

G is —O—, T is —N(H)C(O)—, R$^1$ is —CH$_3$, R$^2$ is —CH$_3$, R$^3$ is CH(OH)(4-fluorophenyl), R$^4$ is —H, R$^5$ is —OH, X is —P(O)[N(H)CH(CH$_3$)C(O)OCH$_2$CH$_3$]$_2$;

G is —CH$_2$—, T is —OCH$_2$—, R$^1$ is —CH$_3$, R$^2$ is —CH$_3$, R$^3$ is i-propyl, R$^4$ is —H, R$^5$ is —OH, X is —P(O)[N(H)CH(CH$_3$)C(O)OCH$_2$CH$_3$]$_2$;

G is —O—, T is —CH$_2$—, R$^1$ is —C$^1$, R$^2$ is —C$^1$, R$^3$ is i-propyl, R$^4$ is —H, R$^5$ is —OH, X is —P(O)[N(H)CH(CH$_3$)C(O)OCH$_2$CH$_3$]$_2$;

G is —O—, T is —OCH$_2$—, R$^1$ is —I, R$^2$ is —I, R$^3$ is i-propyl, R$^4$ is —H, R$^5$ is —OH, X is —P(O)[N(H)CH(CH$_3$)C(O)OCH$_2$CH$_3$]$_2$;

Bisamidates #2

G is —O—, T is —CH$_2$CH(NH$_2$)—, R$^1$ is —I, R$^2$ is —I, R$^3$ is —I, R$^4$ is —H, R$^5$ is —OH, X is —P(O)[N(H)C(CH$_3$)$_2$C(O)OCH$_2$CH$_3$]$_2$;

G is —O—, T is —CH$_2$CH(NH$_2$)—, R$^1$ is —I, R$^2$ is —I, R$^3$ is —I, R$^4$ is —I, R$^5$ is —OH, X is —P(O)[N(H)C(CH$_3$)$_2$C(O)OCH$_2$CH$_3$]$_2$;

G is —O—, T is —CH$_2$—, R$^1$ is —I, R$^2$ is —I, R$^3$ is —I, R$^4$ is —H, R$^5$ is —OH, X is —P(O)[N(H)C(CH$_3$)$_2$C(O)OCH$_2$CH$_3$]$_2$;

G is —O—, T is —N(H)C(O)—, R$^1$ is —CH$_3$, R$^2$ is —CH$_3$, R$^3$ is CH(OH)(4-fluorophenyl), R$^4$ is —H, R$^5$ is —OH, X is —P(O)[N(H)C(CH$_3$)$_2$C(O)OCH$_2$CH$_3$]$_2$;

G is —CH$_2$—, T is —OCH$_2$—, R$^1$ is —CH$_3$, R$^2$ is —CH$_3$, R$^3$ is i-propyl, R$^4$ is —H, R$^5$ is —OH, X is —P(O)[N(H)C(CH$_3$)$_2$C(O)OCH$_2$CH$_3$]$_2$;

G is —O—, T is —CH$_2$—, R$^1$ is —C$^1$, R$^2$ is —C$^1$, R$^3$ is i-propyl, R$^4$ is —H, R$^5$ is —OH, X is —P(O)[N(H)C(CH$_3$)$_2$C(O)OCH$_2$CH$_3$]$_2$;

G is —O—, T is —OCH$_2$—, R$^1$ is —I, R$^2$ is —I, R$^3$ is i-propyl, R$^4$ is —H, R$^5$ is —OH, X is —P(O)[N(H)C(CH$_3$)$_2$C(O)OCH$_2$CH$_3$]$_2$;

4-aryl-2-oxo-2-λ$^5$-1,3,2-dioxaphosphonanes

G is —O—, T is —CH$_2$CH(NH$_2$)—, R$^1$ is —I, R$^2$ is —I, R$^3$ is —I, R$^4$ is —H, R$^5$ is —OH, X is —P(O)[—OCH(3-chlorophenyl)CH$_2$CH$_2$O—];

G is —O—, T is —CH$_2$CH(NH$_2$)—, R$^1$ is —I, R$^2$ is —I, R$^3$ is —I, R$^4$ is —I, R$^5$ is —OH, X is —P(O)[—OCH(3-chlorophenyl)CH$_2$CH$_2$O—];

G is —O—, T is —CH$_2$—, R$^1$ is —I, R$^2$ is —I, R$^3$ is —I, R$^4$ is —H, R$^5$ is —OH, X is —P(O)[—OCH(3-chlorophenyl)CH$_2$CH$_2$O—];

G is —O—, T is —N(H)C(O)—, R$^1$ is —CH$_3$, R$^2$ is —CH$_3$, R$^3$ is CH(OH)(4-fluorophenyl), R$^4$ is —H, R$^5$ is —OH, X is —P(O)[—OCH(3-chlorophenyl)CH$_2$CH$_2$O—];

G is —CH$_2$—, T is —OCH$_2$—, R$^1$ is —CH$_3$, R$^2$ is —CH$_3$, R$^3$ is i-propyl, R$^4$ is —H, R$^5$ is —OH, X is —P(O)[—OCH(3-chlorophenyl)CH$_2$CH$_2$O—];

G is —O—, T is —CH$_2$—, R$^1$ is —Cl, R$^2$ is —Cl, R$^3$ is i-propyl, R$^4$ is —H, R$^5$ is —OH, X is —P(O)[—OCH(3-chlorophenyl)CH$_2$CH$_2$O—];

G is —O—, T is —OCH$_2$—, R$^1$ is —I, R$^2$ is —I, R$^3$ is i-propyl, R$^4$ is —H, R$^5$ is —OH, X is —P(O)[—OCH(3-chlorophenyl)CH$_2$CH$_2$O—].

The present invention further provides for monoester compounds of Formula I including but not limited to wherein:

Phosphonic Acids

G is —O—, T is —CH$_2$CH(NH$_2$)—, R$^1$ is —I, R$^2$ is —I, R$^3$ is —I, R$^4$ is —H, R$^5$ is —OH, X is —P(O(OH)(OCH$_3$));

G is —O—, T is —CH$_2$CH(NH$_2$)—, R$^1$ is —I, R$^2$ is —I, R$^3$ is —I, R$^4$ is —I, R$^5$ is —OH, X is —P(O(OH)(OCH$_3$));

G is —O—, T is —CH$_2$—, R$^1$ is —I, R$^2$ is —I, R$^3$ is —I, R$^4$ is —H, R$^5$ is —OH, X is —P(O(OH)(OCH$_3$));

G is —O—, T is —N(H)C(O)—, R$^1$ is —CH$_3$, R$^2$ is —CH$_3$, R$^3$ is CH(OH)(4-fluorophenyl), R$^4$ is —H, R$^5$ is —OH, X is —P(O(OH)(OCH$_3$));

G is —CH$_2$—, T is —OCH$_2$—, R$^1$ is —CH$_3$, R$^2$ is —CH$_3$, R$^3$ is i-propyl, R$^4$ is —H, R$^5$ is —OH, X is —P(O(OH)(OCH$_3$));

G is —O—, T is —CH$_2$—, R$^1$ is —C$^1$, R$^2$ is —C$^1$, R$^3$ is i-propyl, R$^4$ is —H, R$^5$ is —OH, X is —P(O(OH)(OCH$_3$));

G is —O—, T is —OCH$_2$—, R$^1$ is —I, R$^2$ is —I, R$^3$ is i-propyl, R$^4$ is —H, R$^5$ is —OH, X is —P(O(OH)(OCH$_3$));

POM Esters

G is —O—, T is —CH$_2$CH(NH$_2$)—, R$^1$ is —I, R$^2$ is —I, R$^3$ is —I, R$^4$ is —H, R$^5$ is —OH, X is —P(O)[—OCH$_2$OC(O)C(CH$_3$)$_3$](OCH$_3$);

G is —O—, T is —CH$_2$CH(NH$_2$)—, R$^1$ is —I, R$^2$ is —I, R$^3$ is —I, R$^4$ is —I, R$^5$ is —OH, X is —P(O)[—OCH$_2$OC(O)C(CH$_3$)$_3$](OCH$_3$);

G is —O—, T is —CH$_2$—, R$^1$ is —I, R$^2$ is —I, R$^3$ is —I, R$^4$ is —H, R$^5$ is —OH, X is —P(O)[—OCH$_2$OC(O)C(CH$_3$)$_3$](OCH$_3$);

G is —O—, T is —N(H)C(O)—, R$^1$ is —CH$_3$, R$^2$ is —CH$_3$, R$^3$ is CH(OH)(4-fluorophenyl), R$^4$ is —H, R$^5$ is —OH, X is —P(O)[—OCH$_2$OC(O)C(CH$_3$)$_3$](OCH$_3$);

G is —CH$_2$—, T is —OCH$_2$—, R$^1$ is —CH$_3$, R$^2$ is —CH$_3$, R$^3$ is i-propyl, R$^4$ is —H, R$^5$ is —OH, X is —P(O)[—OCH$_2$OC(O)C(CH$_3$)$_3$](OCH$_3$);

G is —O—, T is —CH$_2$—, R$^1$ is —C$^1$, R$^2$ is —C$^1$, R$^3$ is i-propyl, R$^4$ is —H, R$^5$ is —OH, X is —P(O)[—OCH$_2$OC(O)C(CH$_3$)$_3$](OCH$_3$);

G is —O—, T is —OCH$_2$—, R$^1$ is —I, R$^2$ is —I, R$^3$ is i-propyl, R$^4$ is —H, R$^5$ is —OH, X is —P(O)[—OCH$_2$OC(O)C(CH$_3$)$_3$](OCH$_3$);

Carbonates

G is —O—, T is —CH$_2$CH(NH$_2$)—, R$^1$ is —I, R$^2$ is —I, R$^3$ is —I, R$^4$ is —H, R$^5$ is —OH, X is —P(O)[—OCH$_2$OC(O)OCH(CH$_3$)$_2$](OCH$_3$);

G is —O—, T is —CH$_2$CH(NH$_2$)—, R$^1$ is —I, R$^2$ is —I, R$^3$ is —I, R$^4$ is —I, R$^5$ is —OH, X is —P(O)[—OCH$_2$OC(O)OCH(CH$_3$)$_2$](OCH$_3$);

G is —O—, T is —CH$_2$—, R$^1$ is —I, R$^2$ is —I, R$^3$ is —I, R$^4$ is —H, R$^5$ is —OH, X is —P(O)[—OCH$_2$OC(O)OCH(CH$_3$)$_2$](OCH$_3$);

G is —O—, T is —N(H)C(O)—, R$^1$ is —CH$_3$, R$^2$ is —CH$_3$, R$^3$ is CH(OH)(4-fluorophenyl), R$^4$ is —H, R$^5$ is —OH, X is —P(O)[—OCH$_2$OC(O)OCH(CH$_3$)$_2$](OCH$_3$);

G is —CH$_2$—, T is —OCH$_2$—, R$^1$ is —CH$_3$, R$^2$ is —CH$_3$, R$^3$ is i-propyl, R$^4$ is —H, R$^5$ is —OH, X is —P(O)[—OCH$_2$OC(O)OCH(CH$_3$)$_2$](OCH$_3$);

G is —O—, T is —CH$_2$—, R$^1$ is —C$^1$, R$^2$ is —C$^1$, R$^3$ is i-propyl, R$^4$ is —H, R$^5$ is —OH, X is —P(O)[—OCH$_2$OC(O)OCH(CH$_3$)$_2$](OCH$_3$);

G is —O—, T is —OCH$_2$—, R$^1$ is —I, R$^2$ is —I, R$^3$ is i-propyl, R$^4$ is —H, R$^5$ is —OH, X is —P(O)[—OCH$_2$OC(O)OCH(CH$_3$)$_2$](OCH$_3$);

Amidates

G is —O—, T is —CH$_2$CH(NH$_2$)—, R$^1$ is —I, R$^2$ is —I, R$^3$ is —I, R$^4$ is —H, R$^5$ is —OH, X is —P(O)[N(H)CH(CH$_3$)C(O)OCH$_2$CH$_3$](OCH$_3$);

G is —O—, T is —CH$_2$CH(NH$_2$)—, R$^1$ is —I, R$^2$ is —I, R$^3$ is —I, R$^4$ is —I, R$^5$ is —OH, X is —P(O)[N(H)CH(CH$_3$)C(O)OCH$_2$CH$_3$](OCH$_3$);

G is —O—, T is —CH$_2$—, R$^1$ is —I, R$^2$ is —I, R$^3$ is —I, R$^4$ is —H, R$^5$ is —OH, X is —P(O)[N(H)CH(CH$_3$)C(O)OCH$_2$CH$_3$](OCH$_3$);

G is —O—, T is —N(H)C(O)—, R$^1$ is —CH$_3$, R$^2$ is —CH$_3$, R$^3$ is CH(OH)(4-fluorophenyl), R$^4$ is —H, R$^5$ is —OH, X is —P(O)[N(H)CH(CH$_3$)C(O)OCH$_2$CH$_3$](OCH$_3$);

G is —CH$_2$—, T is —OCH$_2$—, R$^1$ is —CH$_3$, R$^2$ is —CH$_3$, R$^3$ is i-propyl, R$^4$ is —H, R$^5$ is —OH, X is —P(O)[N(H)CH(CH$_3$)C(O)OCH$_2$CH$_3$](OCH$_3$);

G is —O—, T is —CH$_2$—, R$^1$ is —C$^1$, R$^2$ is —C$^1$, R$^3$ is i-propyl, R$^4$ is —H, R$^5$ is —OH, X is —P(O)[N(H)CH(CH$_3$)C(O)OCH$_2$CH$_3$](OCH$_3$);

G is —O—, T is —OCH$_2$—, R$^1$ is —I, R$^2$ is —I, R$^3$ is i-propyl, R$^4$ is —H, R$^5$ is —OH, X is —P(O)[N(H)CH(CH$_3$)C(O)OCH$_2$CH$_3$](OCH$_3$);

Amidates #2

G is —O—, T is —CH$_2$CH(NH$_2$)—, R$^1$ is —I, R$^2$ is —I, R$^3$ is —I, R$^4$ is —H, R$^5$ is —OH, X is —P(O)[N(H)C(CH$_3$)$_2$C(O)OCH$_2$CH$_3$](OCH$_3$);

G is —O—, T is —CH$_2$CH(NH$_2$)—, R$^1$ is —I, R$^2$ is —I, R$^3$ is —I, R$^4$ is —I, R$^5$ is —OH, X is —P(O)[N(H)C(CH$_3$)$_2$C(O)OCH$_2$CH$_3$](OCH$_3$);

G is —O—, T is —CH$_2$—, R$^1$ is —I, R$^2$ is —I, R$^3$ is —I, R$^4$ is —H, R$^5$ is —OH, X is —P(O)[N(H)C(CH$_3$)$_2$C(O)OCH$_2$CH$_3$](OCH$_3$);

G is —O—, T is —N(H)C(O)—, R$^1$ is —CH$_3$, R$^2$ is —CH$_3$, R$^3$ is CH(OH)(4-fluorophenyl), R$^4$ is —H, R$^5$ is —OH, X is —P(O)[N(H)C(CH$_3$)$_2$C(O)OCH$_2$CH$_3$](OCH$_3$);

G is —CH$_2$—, T is —OCH$_2$—, R$^1$ is —CH$_3$, R$^2$ is —CH$_3$, R$^3$ is i-propyl, R$^4$ is —H, R$^5$ is —OH, X is —P(O)[N(H)C(CH$_3$)$_2$C(O)OCH$_2$CH$_3$](OCH$_3$);

G is —O—, T is —CH$_2$—, R$^1$ is —Cl, R$^2$ is —Cl, R$^3$ is i-propyl, R$^4$ is —H, R$^5$ is —OH, X is —P(O)[N(H)C(CH$_3$)$_2$C(O)OCH$_2$CH$_3$](OCH$_3$);

G is —O—, T is —OCH$_2$—, R$^1$ is —I, R$^2$ is —I, R$^3$ is i-propyl, R$^4$ is —H, R$^5$ is —OH, X is —P(O)[N(H)C(CH$_3$)$_2$C(O)OCH$_2$CH$_3$](OCH$_3$).

In one aspect, the invention relates to compounds selected from the group consisting of:

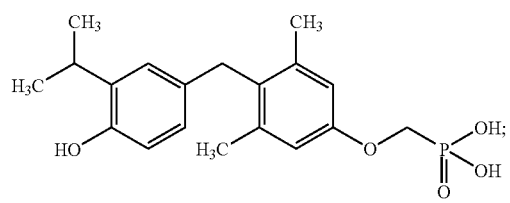

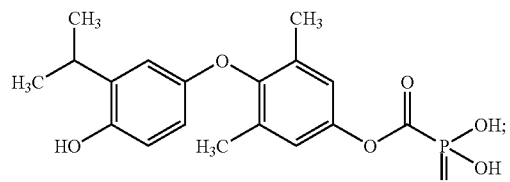

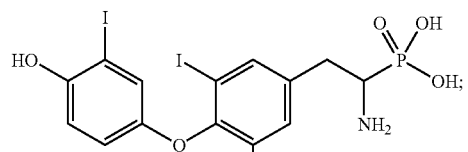

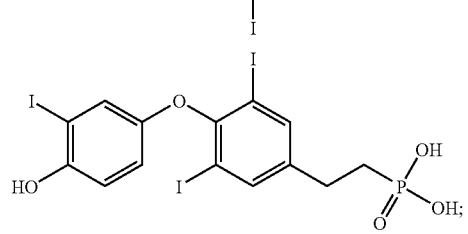

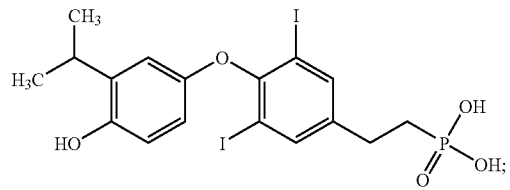

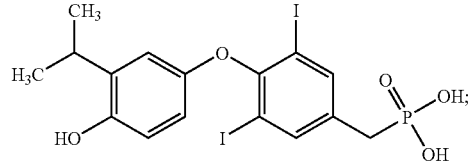

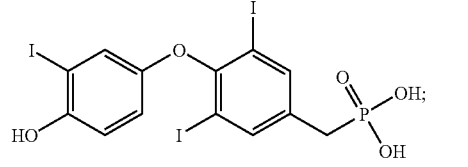

-continued

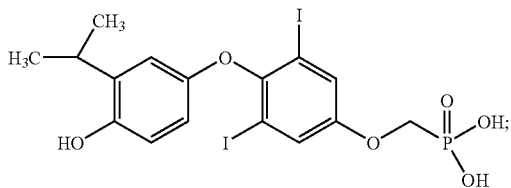

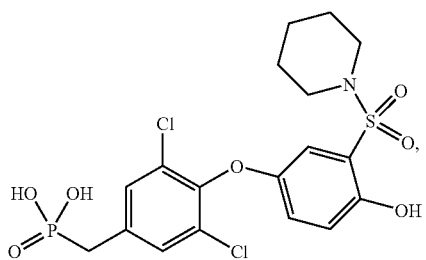

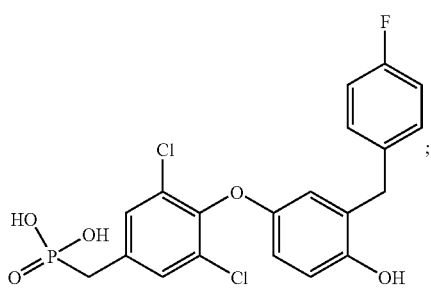

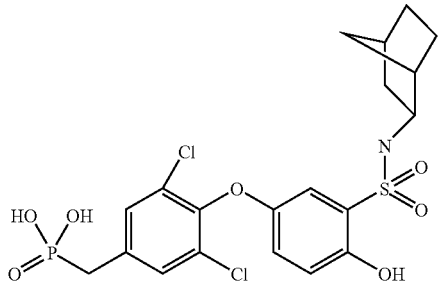

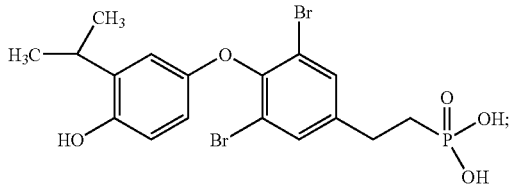

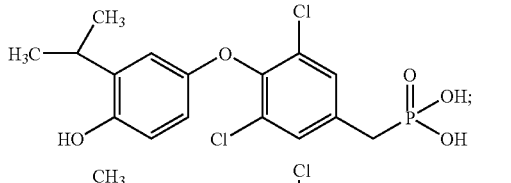

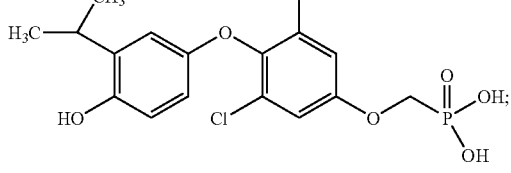

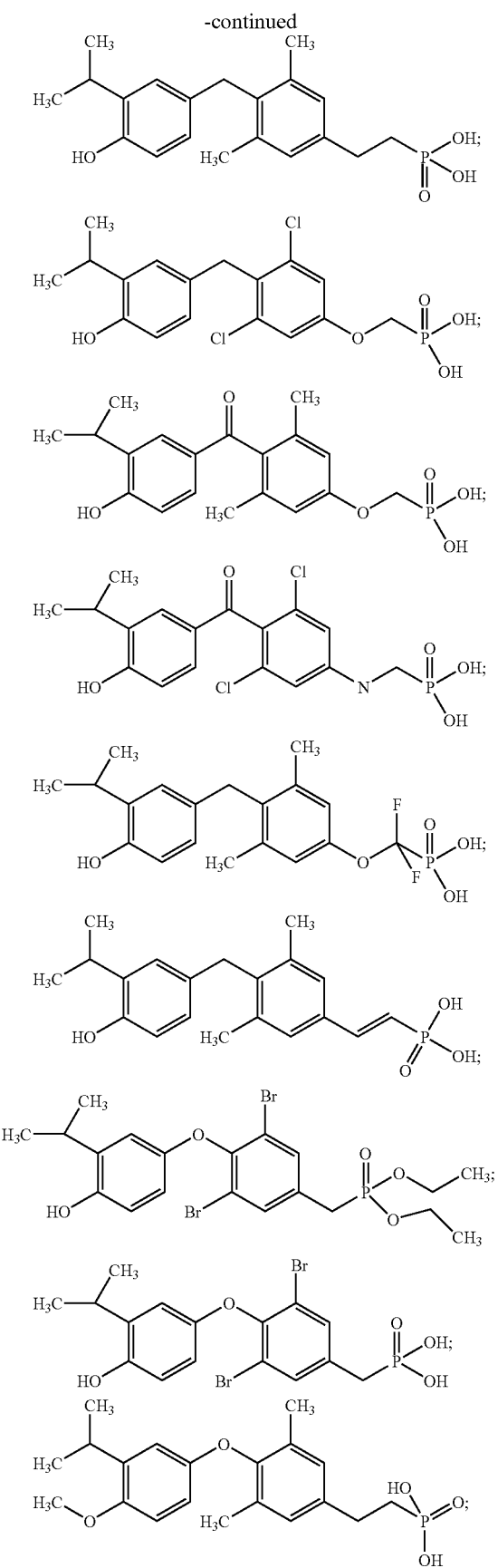
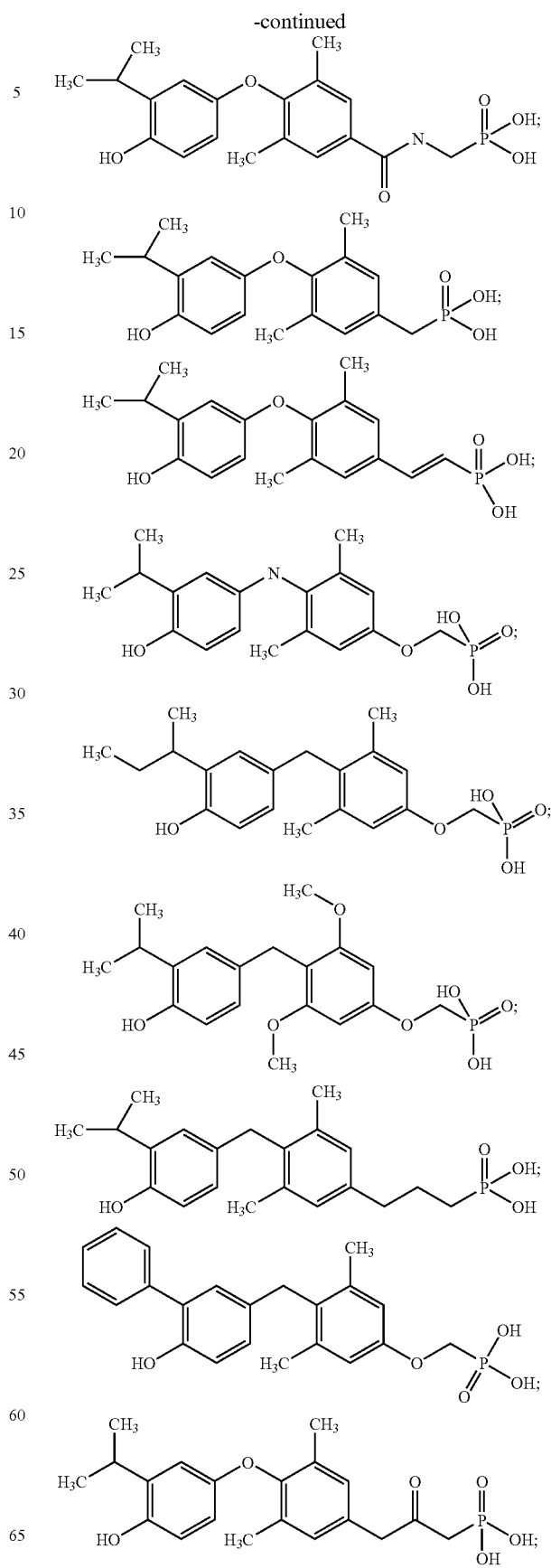

-continued
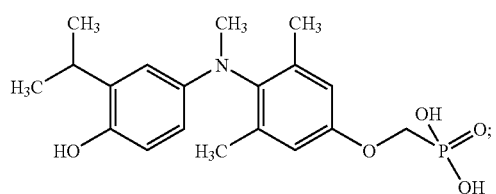
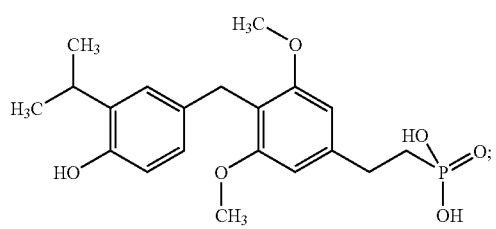
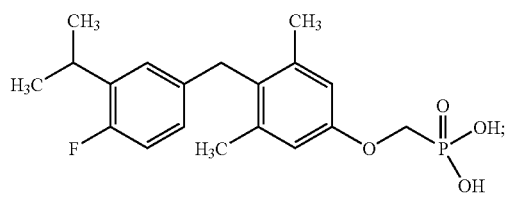
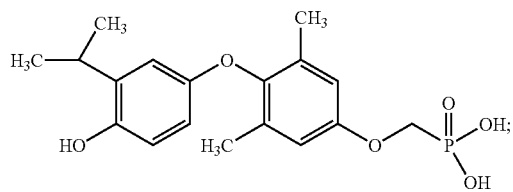
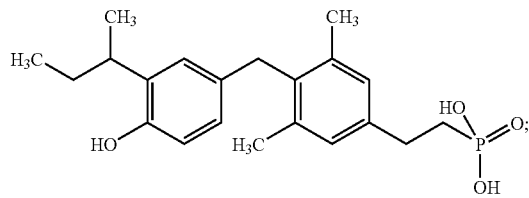
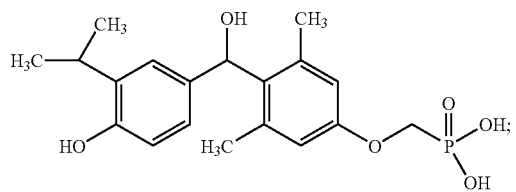
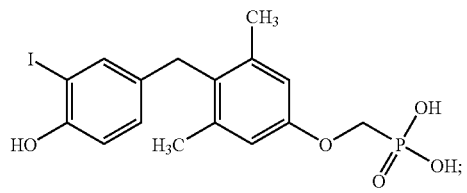
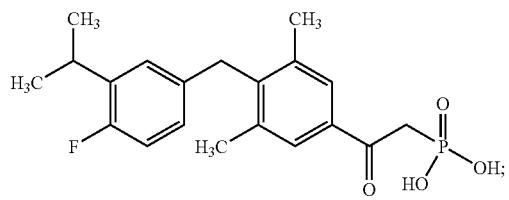
-continued
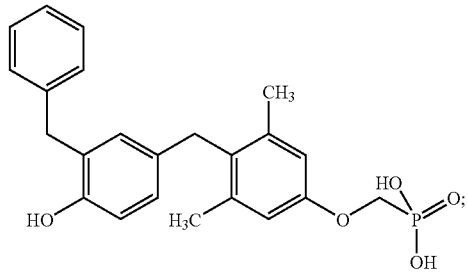
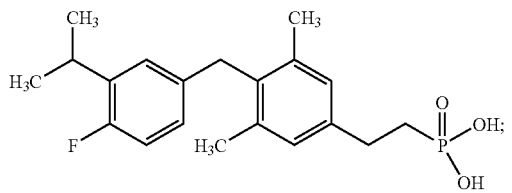
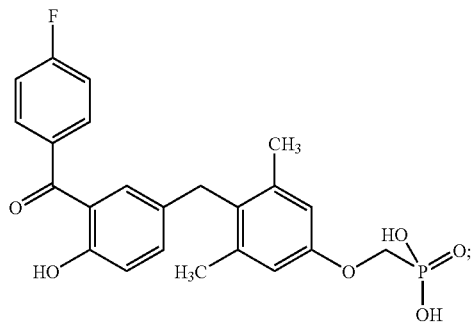
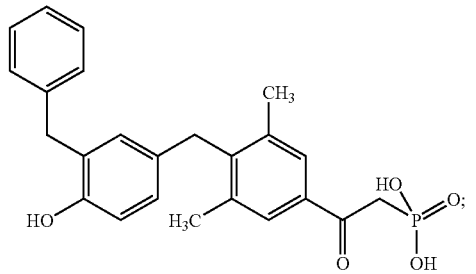
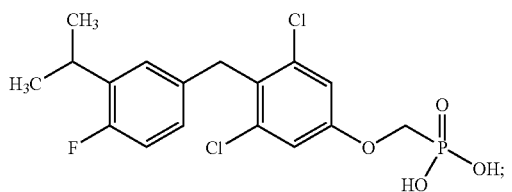
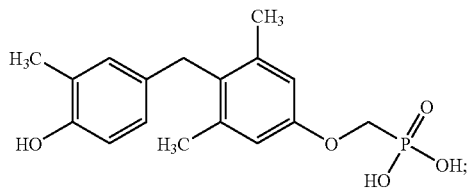
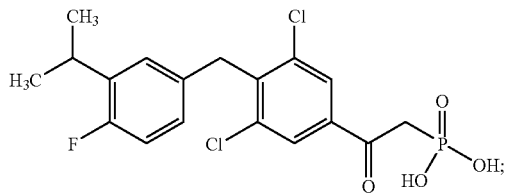

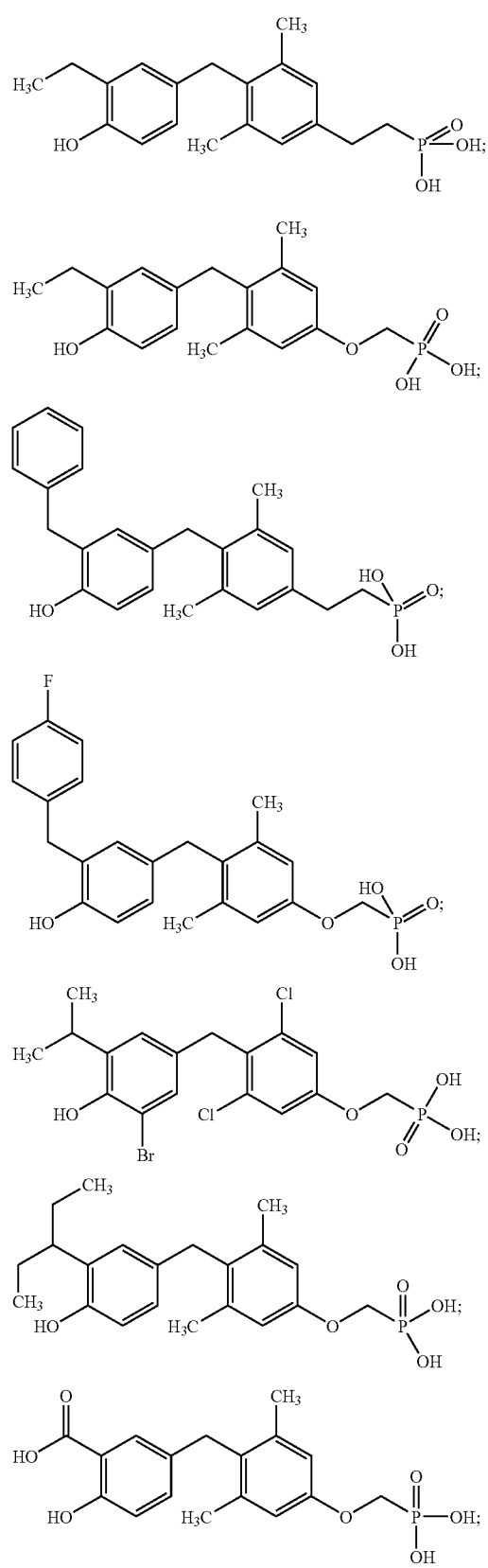
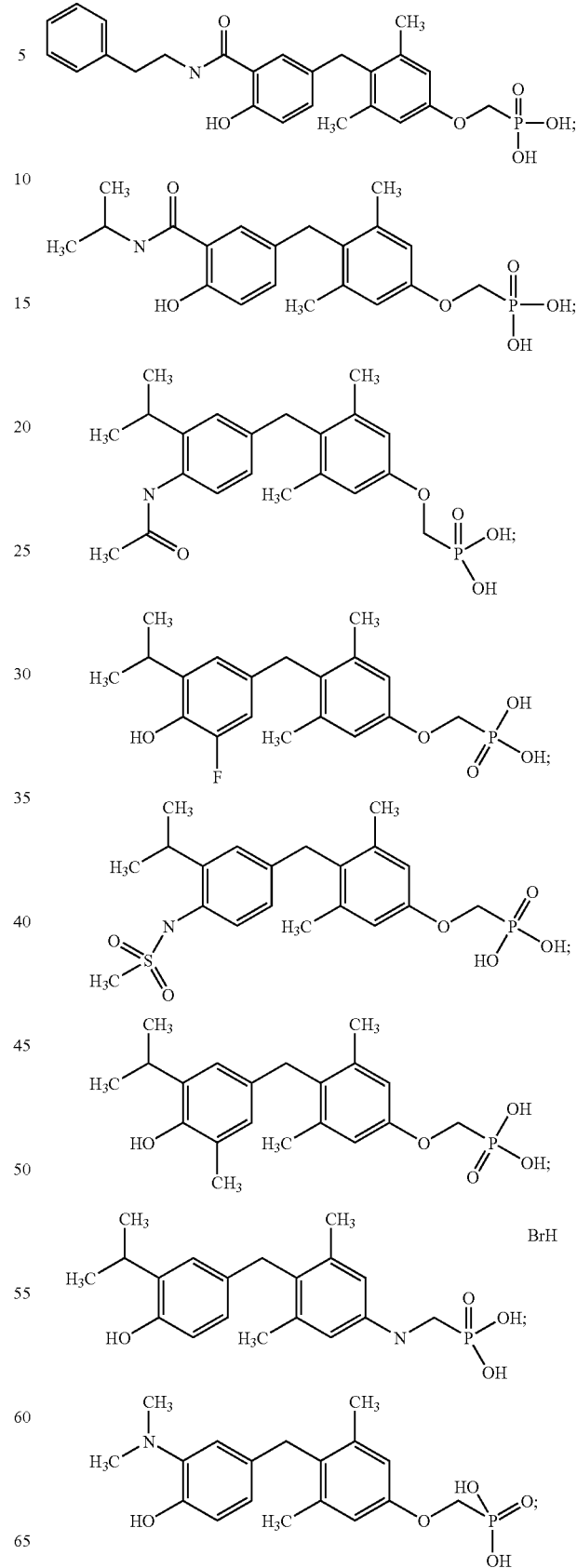

159
-continued
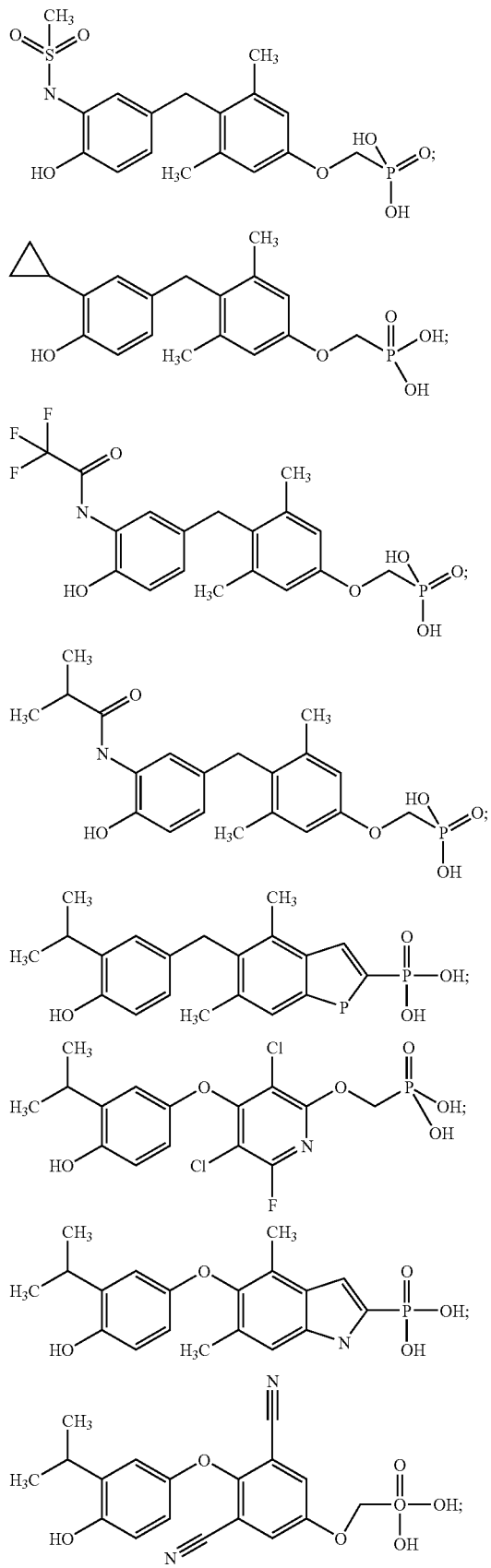
160
-continued
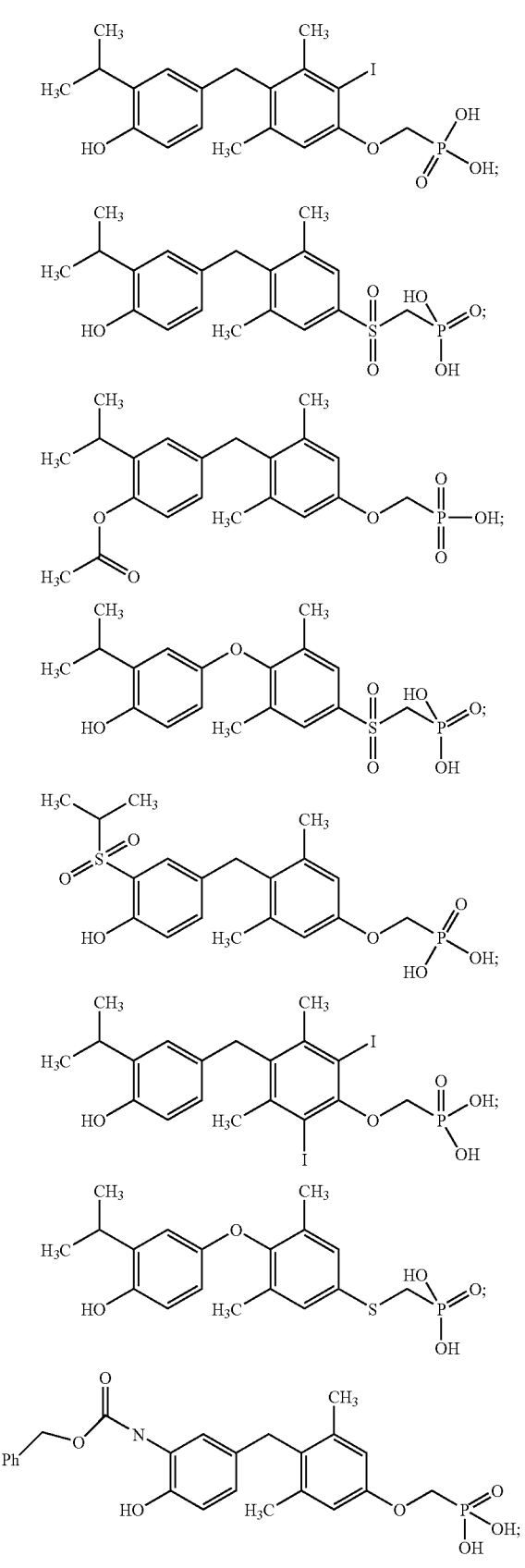

-continued
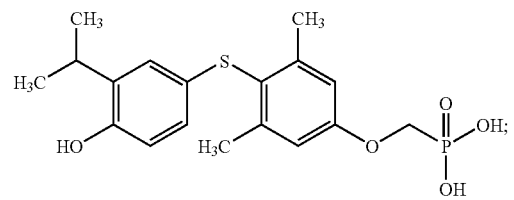
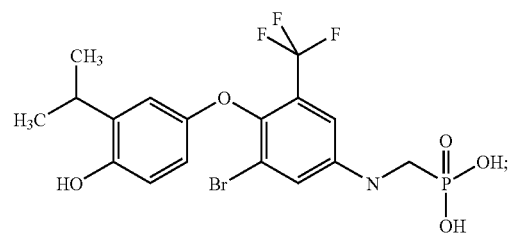
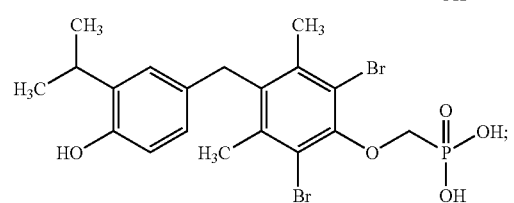
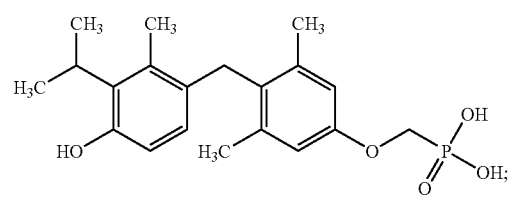
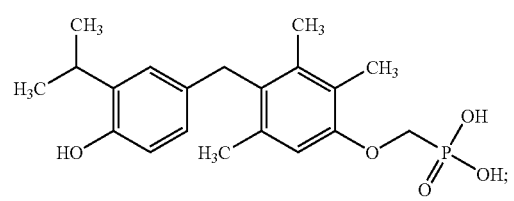
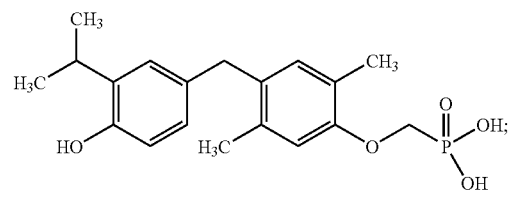
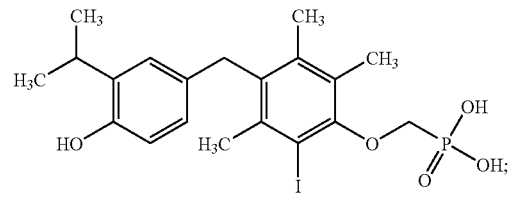
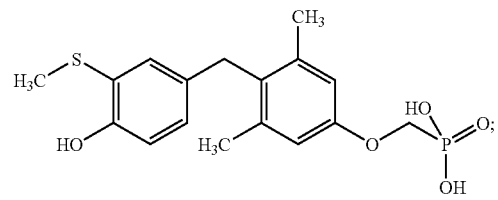
-continued
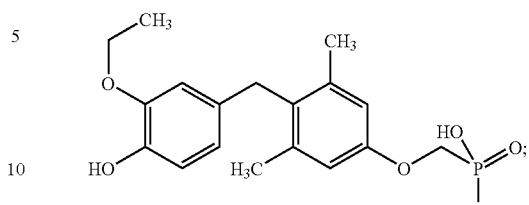
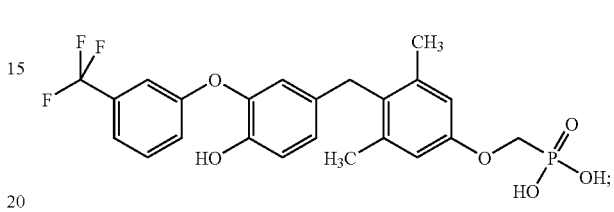
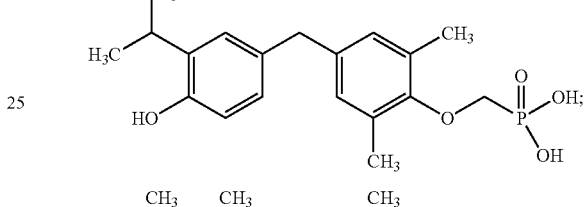
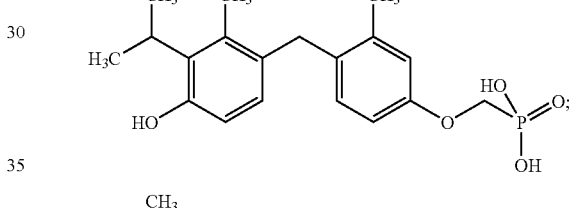
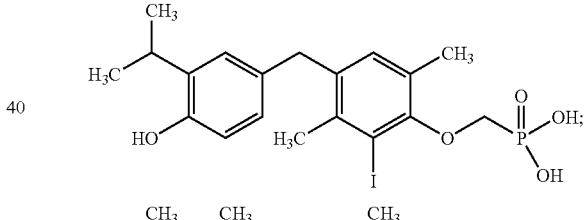
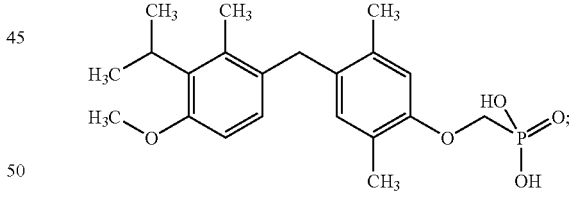
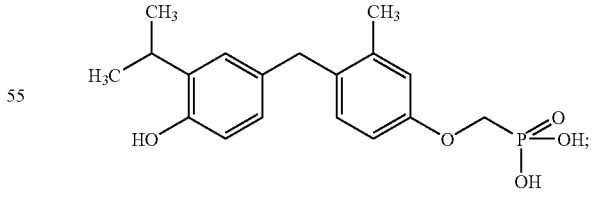
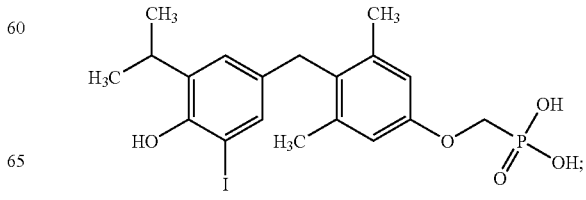

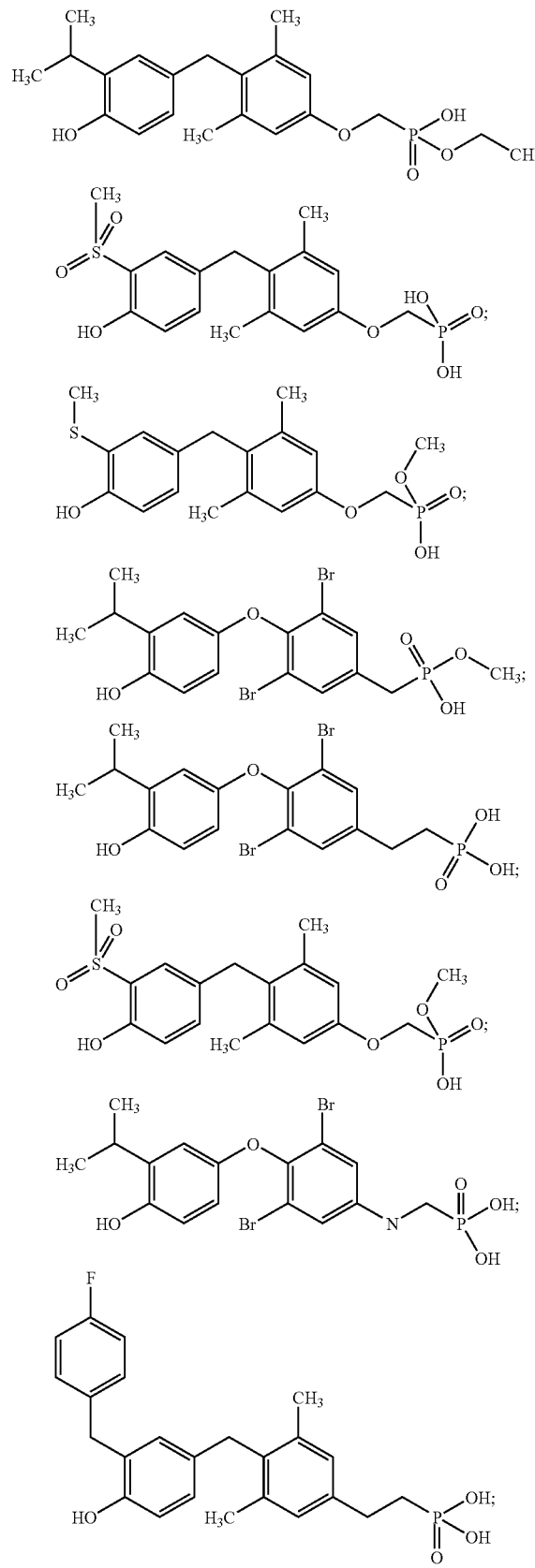
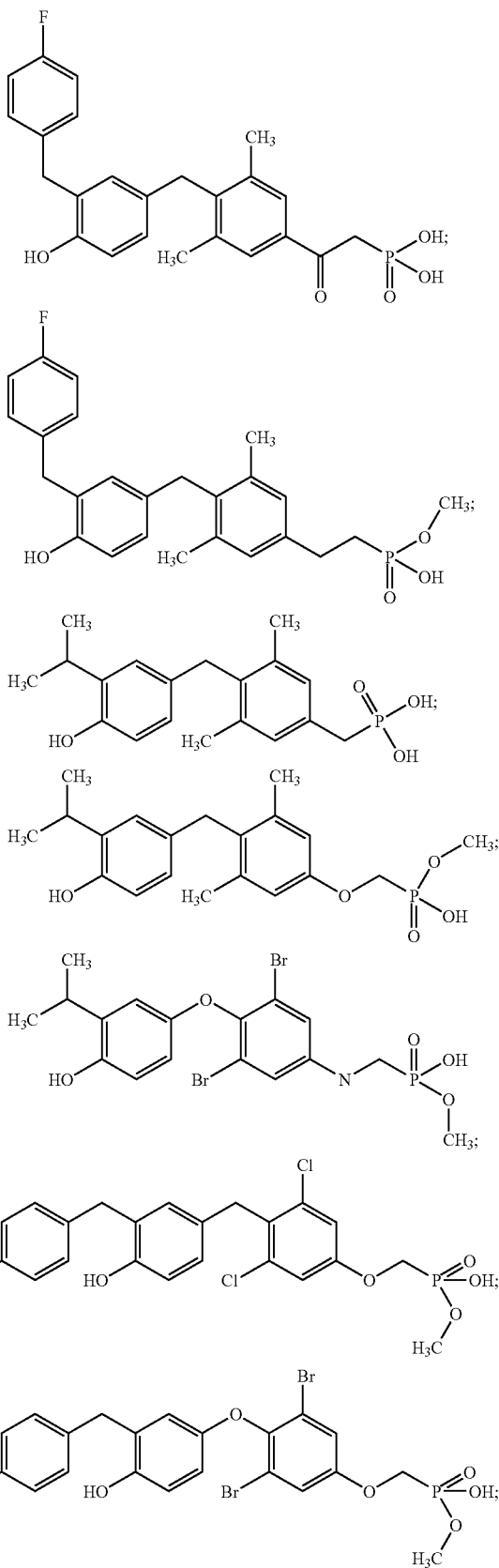

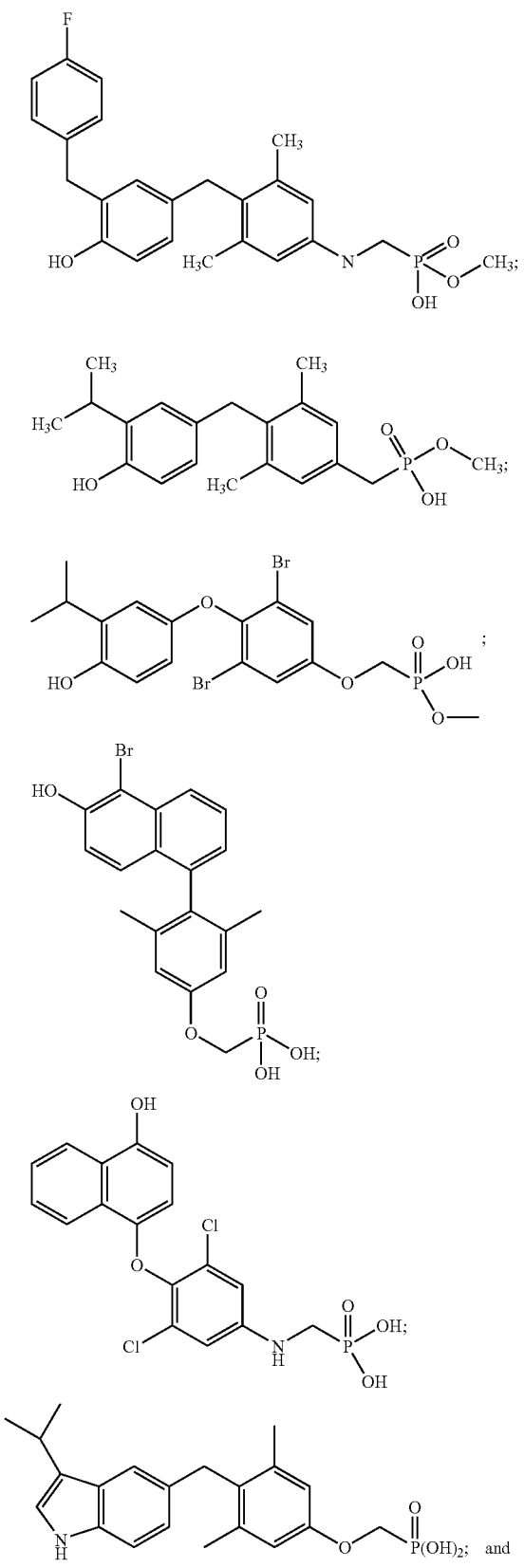

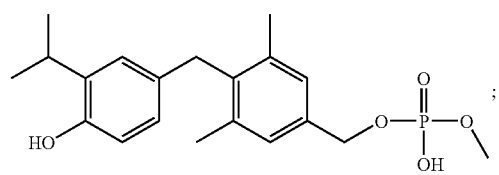

and monoesters thereof, and prodrugs of the compounds or the monoesters of the compounds, and pharmaceutically acceptable salts thereof. In one embodiment, the prodrugs are bis-POM, carbonate, bisamidate, or 4-aryl-2-oxo-2-$\lambda^5$-,3,2-dioxaphosphonane prodrugs of the compounds or bis-POM, carbonate, or bisamidate prodrugs of the monoesters of the compounds.

In another aspect, the invention relates to prodrug compounds selected from the group consisting of:

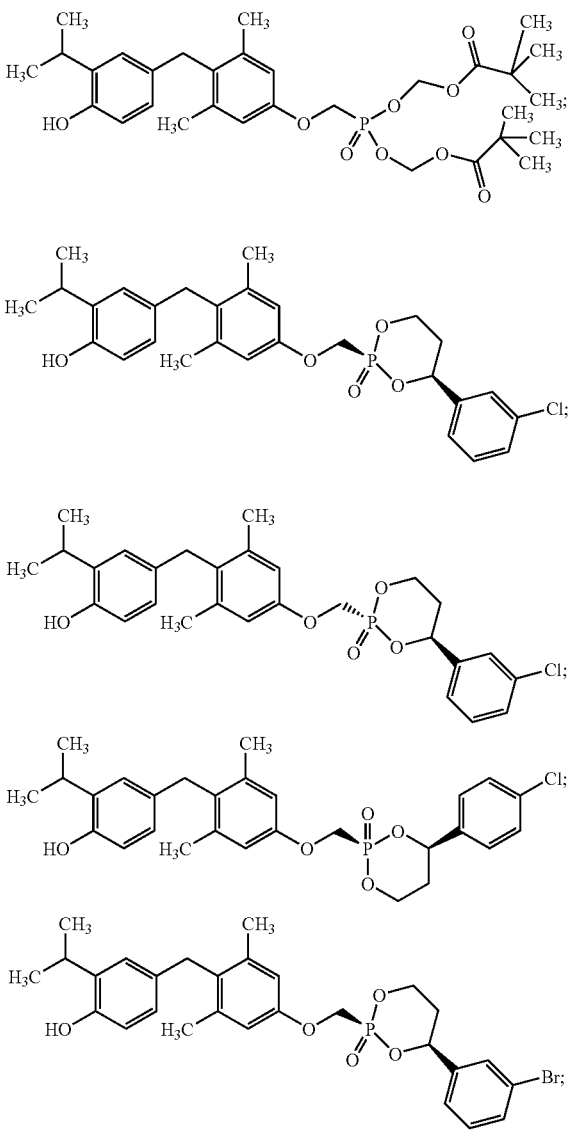

167
-continued
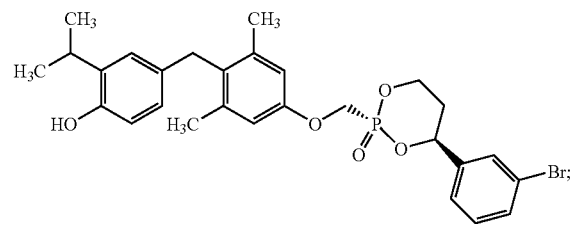
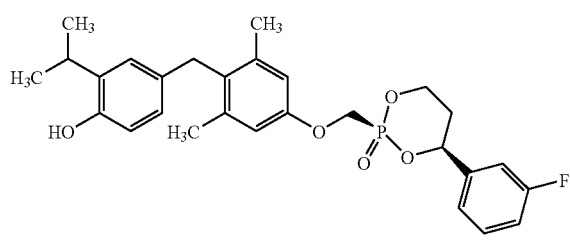
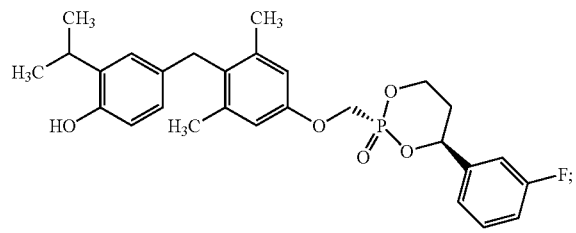
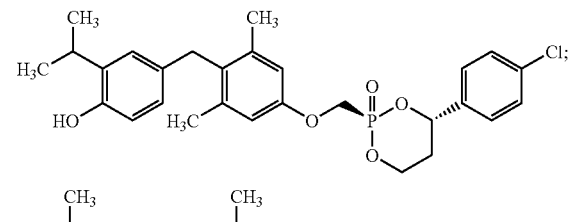
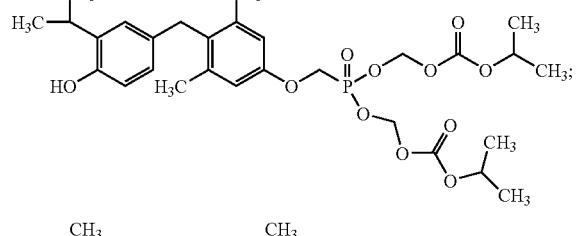
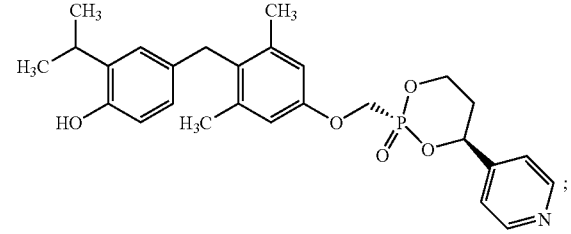
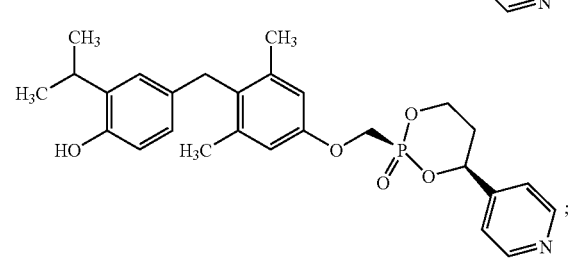
168
-continued
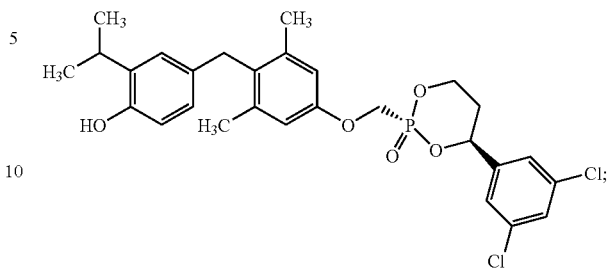
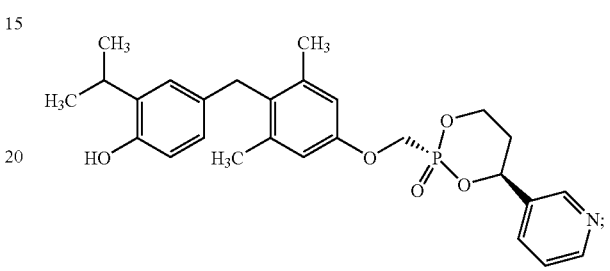
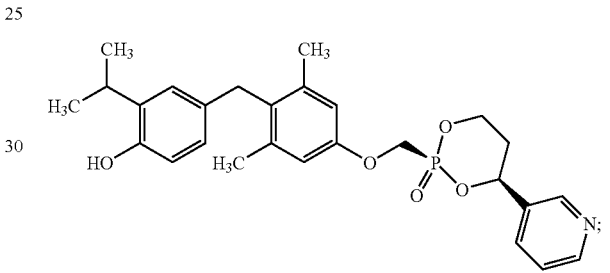
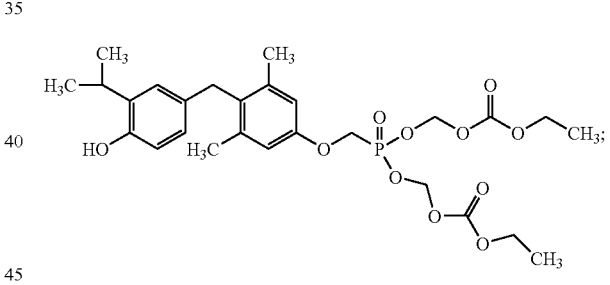
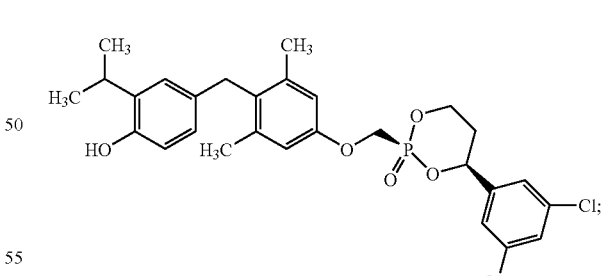
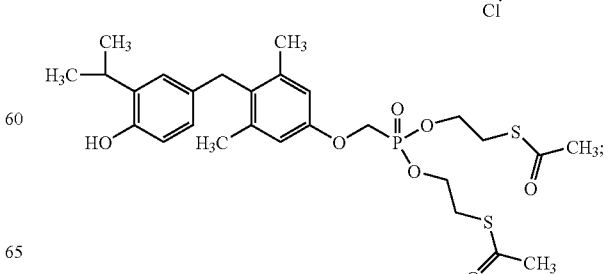

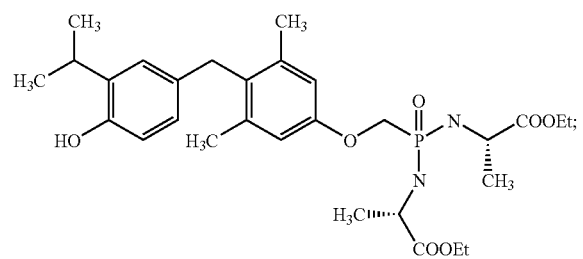
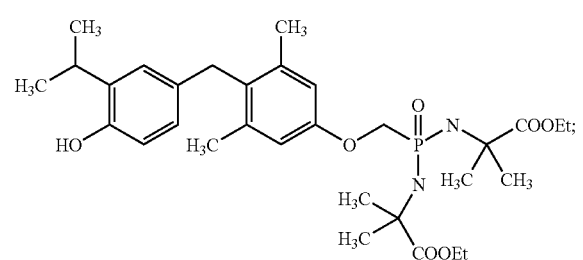
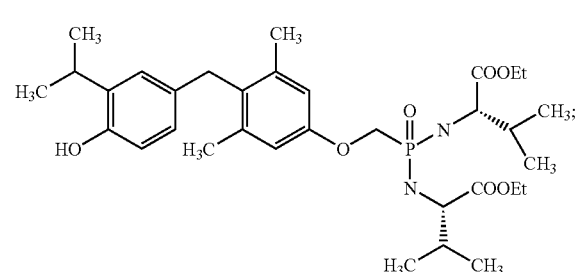
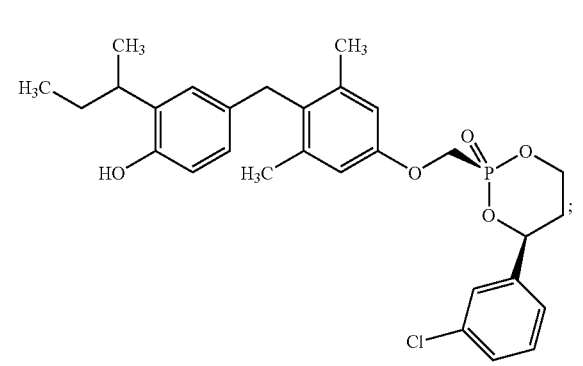
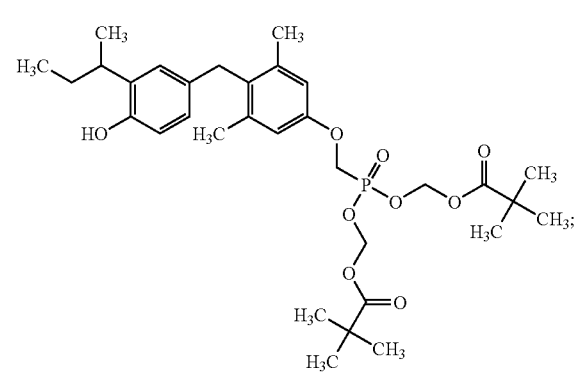
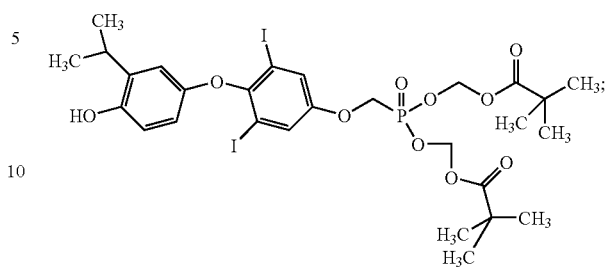
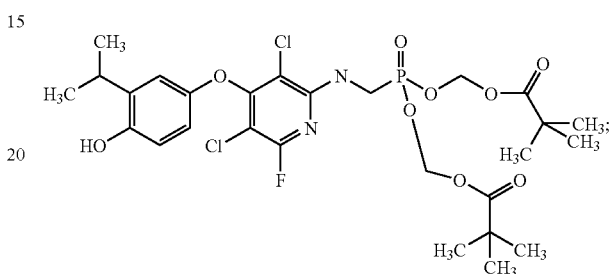
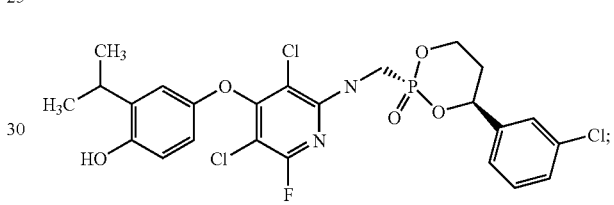
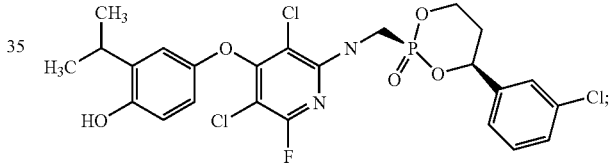
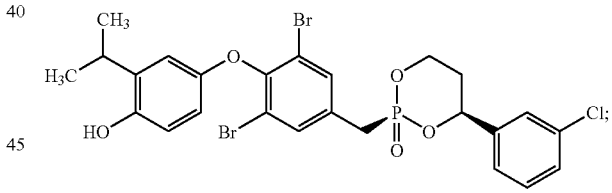
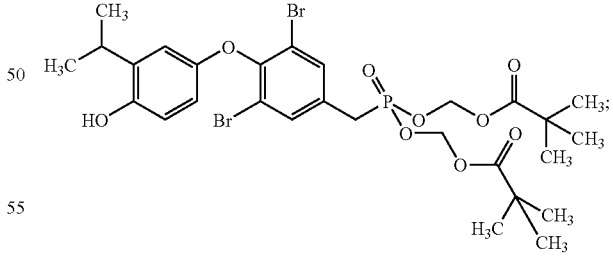
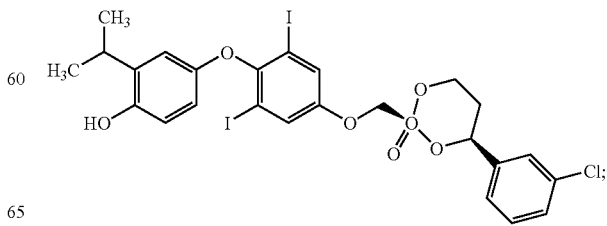

-continued
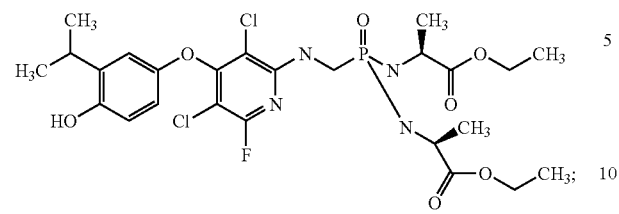
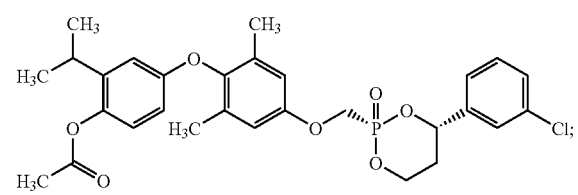
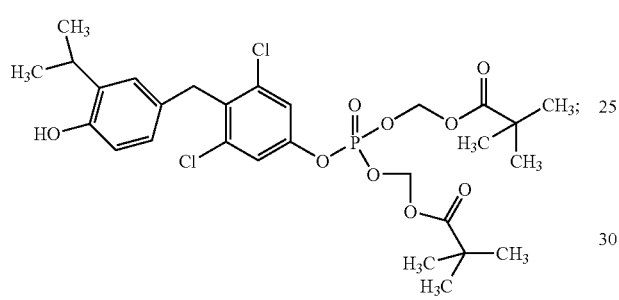
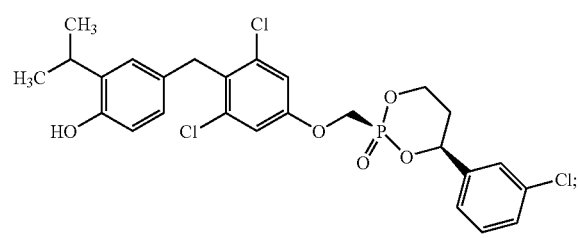
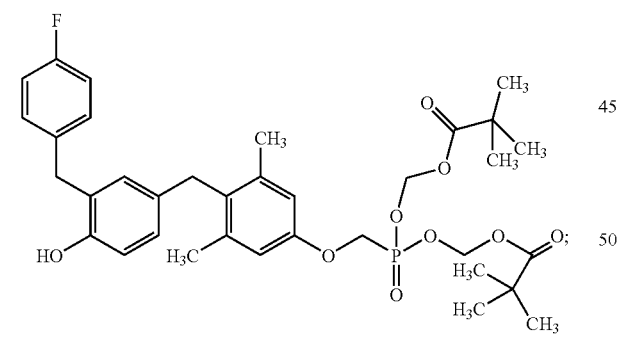
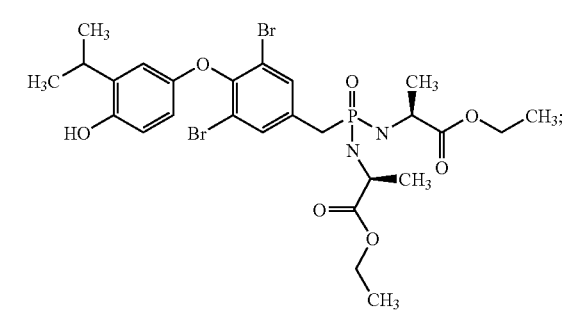
-continued
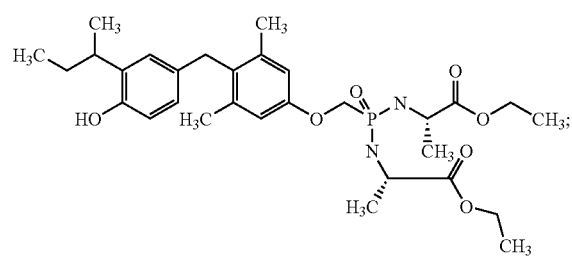
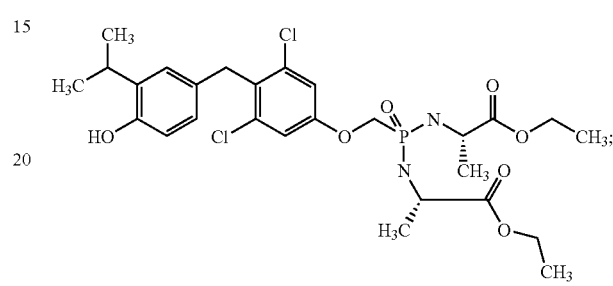
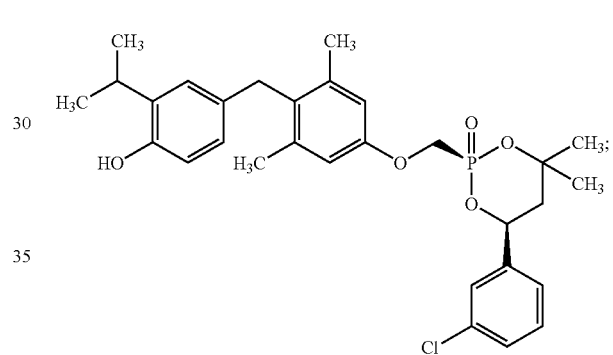
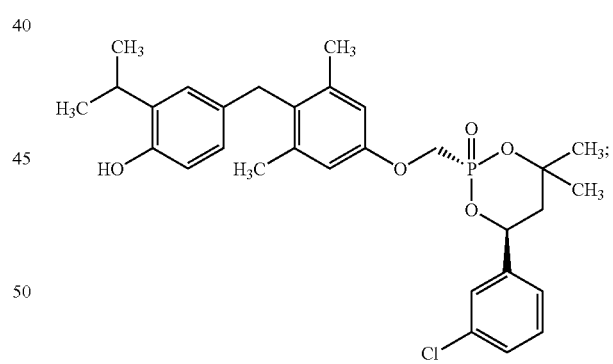
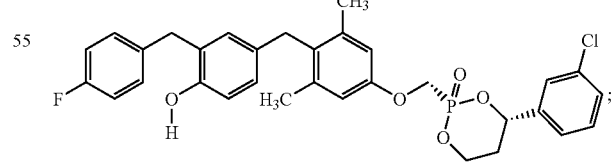
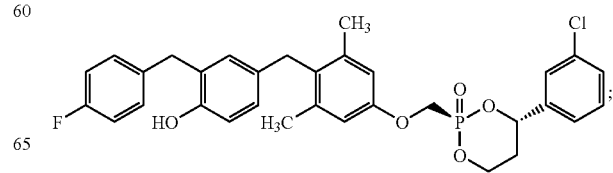

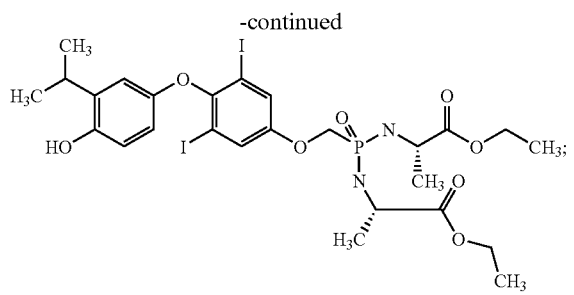
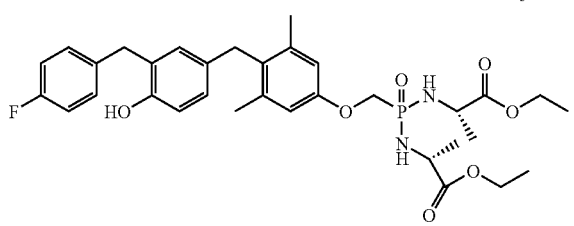
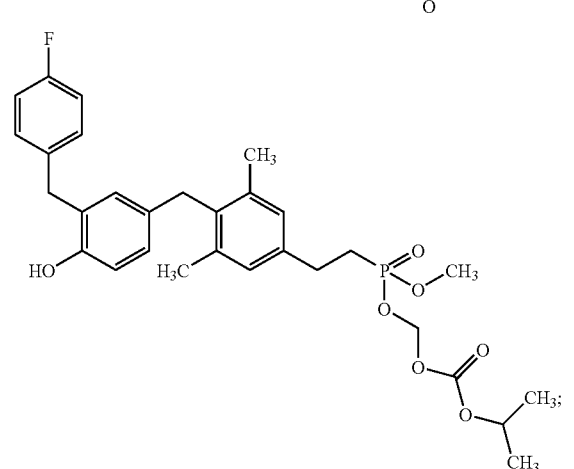
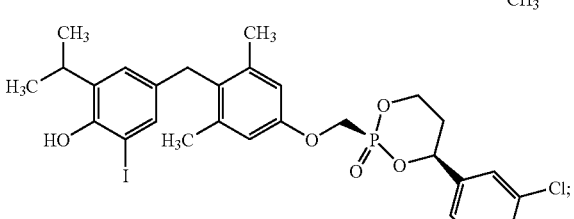
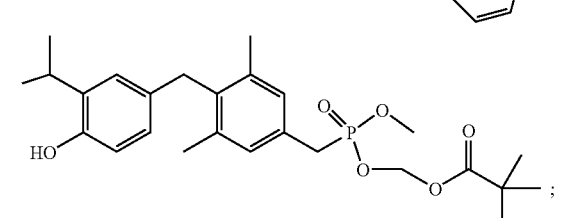
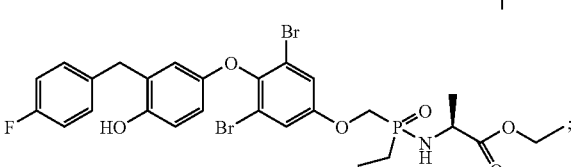
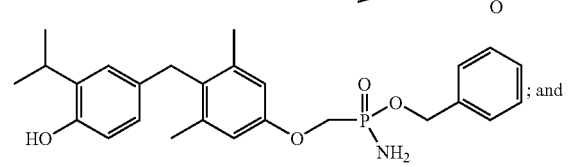

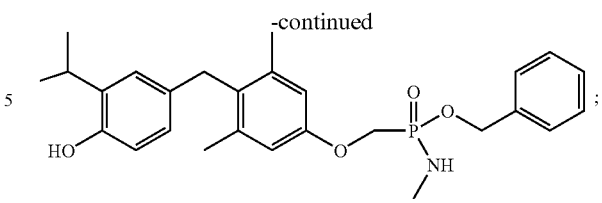

and pharmaceutically acceptable salts thereof.

In one aspect, the invention relates to lower alkyl monoesters (e.g., methyl, ethyl, propyl, isopropyl, butyl, tert-butyl, pentyl, hexyl) of each of the exemplified phosphonic acid-containing compounds in Examples 1-96. In another aspect, the invention relates to prodrugs of each of the exemplified phosphonic acid-containing compounds in Examples 1-96 or prodrugs of monoesters of the exemplified phosphonic acid-containing compounds in Examples 1-96. In one embodiment, the prodrugs of the exemplified phosphonic acid-containing compounds in Examples 1-96 or monoesters of the exemplified phosphonic acid-containing compounds in Examples 1-96 comprise the prodrug moieties disclosed above under the definition of phosphonate prodrugs.

Moreover, the compounds of the present invention can be administered in combination with other pharmaceutical agents that are used to lower serum cholesterol such as a cholesterol biosynthesis inhibitor or a cholesterol absorption inhibitor, especially a HMG-CoA reductase inhibitor, or a HMG-CoA synthase inhibitor, or a HMG-CoA reductase or synthase gene expression inhibitor, a cholesteryl ester transfer protein (CETP) inhibitor (e.g., torcetrapib), a bile acid sequesterant (e.g., cholestyramine (Questran®), colesevelam and colestipol (Colestid®)), or a bile acid reabsorption inhibitor (see, for example, U.S. Pat. No. 6,245,744, U.S. Pat. No. 6,221,897, U.S. Pat. No. 6,277,831, EP 0683 773, EP 0683 774), a cholesterol absorption inhibitor as described (e.g., ezetimibe, tiqueside, pamaqueside or see, e.g., in WO 0250027), a PPARalpha agonist, a mixed PPAR alpha/gamma agonist such as, for example, AZ 242 (Tesaglitazar, (S)-3-(4-[2-(4-methanesulfonyloxyphenyl)ethoxy]phenyl)-2-ethoxypropionic acid), BMS 298585 (N-[(4-methoxyphenoxy)carbonyl]-N-[[4-[2-(5-methyl-2-phenyl-4-oxazolyl) ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876, a MTP inhibitor such as, for example, implitapide, a fibrate, an ACAT inhibitor (e.g., avasimibe), an angiotensin II receptor antagonist, a squalene synthetase inhibitor, a squalene epoxidase inhibitor, a squalene cyclase inhibitor, combined squalene epoxidase/squalene cyclase inhibitor, a lipoprotein lipase inhibitor, an ATP citrate lyase inhibitor, lipoprotein(a) antagonist, an antioxidant or niacin (e.g., slow release niacin). The compounds of the present invention may also be administered in combination with a naturally occurring compound that act to lower plasma cholesterol levels. Such naturally occurring compounds are commonly called nutraceuticals and include, for example, garlic extract and niacin.

In one aspect, the HMG-CoA reductase inhibitor is from a class of therapeutics commonly called statins. Examples of HMG-CoA reductase inhibitors that may be used include but are not limited to lovastatin (MEVACOR; see U.S. Pat. Nos. 4,231,938; 4,294,926; 4,319,039), simvastatin (ZOCOR; see U.S. Pat. Nos. 4,444,784; 4,450,171; 4,820,850; 4,916,239), pravastatin (PRAVACHOL; see U.S. Pat. Nos. 4,346,227; 4,537,859; 4,410,629; 5,030,447 and 5,180,589), lactones of pravastatin (see U.S. Pat. No. 4,448,979), fluvastatin (LESCOL; see U.S. Pat. Nos. 5,354,772; 4,911,165; 4,739,073; 4,929,437; 5,189,164; 5,118,853; 5,290,946; 5,356,896), lactones of fluvastatin, atorvastatin (LIPITOR; see U.S. Pat. Nos. 5,273,995; 4,681,893; 5,489,691; 5,342,952), lactones of atorvastatin, cerivastatin (also known as rivastatin and BAYCHOL; see U.S. Pat. No. 5,177,080, and European Application No. EP-491226A), lactones of cerivastatin, rosuvastatin (CRESTOR; see U.S. Pat. No. 5,260,440 and RE37314, and European Patent No. EP521471), lactones of rosuvastatin, itavastatin, nisvastatin, visastatin, atavastatin, bervastatin, compactin, dihydrocompactin, dalvastatin, fluindostatin, pitivastatin, mevastatin (see U.S. Pat. No. 3,983, 140), and velostatin (also referred to as synvinolin). Other examples of HMG-CoA reductase inhibitors are described in U.S. Pat. Nos. 5,217,992; 5,196,440; 5,189,180; 5,166,364; 5,157,134; 5,110,940; 5,106,992; 5,099,035; 5,081,136; 5,049,696; 5,049,577; 5,025,017; 5,011,947; 5,010,105; 4,970,221; 4,940,800; 4,866,058; 4,686,237; 4,647,576; European Application Nos. 0142146A2 and 0221025A1; and PCT Application Nos. WO 86/03488 and WO 86/07054. Also included are pharmaceutically acceptable forms of the above. All of the above references are incorporated herein by reference.

Non-limiting examples of suitable bile acid sequestrants include cholestyramine (a styrene-divinylbenzene copolymer containing quaternary ammonium cationic groups capable of binding bile acids, such as QUESTRAN or QUESTRAN LIGHT cholestyramine which are available from Bristol-Myers Squibb), colestipol (a copolymer of diethylenetriamine and 1-chloro-2,3-epoxypropane, such as COLESTID tablets which are available from Pharmacia), colesevelam hydrochloride (such as WelChol Tablets (poly(allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl)alkylamines and poliglusam, insoluble quaternized polystyrenes, saponins and mixtures thereof. Other useful bile acid sequestrants are disclosed in PCT Patent Applications Nos. WO 97/11345 and WO 98/57652, and U.S. Pat. Nos. 3,692,895 and 5,703,188 which are incorporated herein by reference. Suitable inorganic cholesterol sequestrants include bismuth salicylate plus montmorillonite clay, aluminum hydroxide and calcium carbonate antacids.

In the above description, a fibrate base compound is a medicament for inhibiting synthesis and secretion of triglycerides in the liver and activating lipoprotein lipase, thereby lowering the triglyceride level in the blood. Examples include bezafibrate, beclobrate, binifibrate, ciprofibrate, clinofibrate, clofibrate, clofibric acid, ethofibrate, fenofibrate, gemfibrozil, nicofibrate, pirifibrate, ronifibrate, simfibrate and theofibrate. Such an ACAT inhibitor includes, for example: a compound having the general formula (I) disclosed in WO 92/09561 [preferably FR-129169, of which the chemical name is N-(1, 2-diphenylethyl)-2-(2-octyloxyphenyl)acetamide]; a compound having the general formula (I) including a pharmacologically acceptable salt/co-crystal, ester or prodrug thereof disclosed in the Japanese Patent Publication (Kohyo) Hei 8-510256 (WO 94/26702, U.S. Pat. No. 5,491,172) {preferably CI-1011, of which the chemical name is 2,6-diisopropylphenyl-N-[(2,4,6-triisopropylphenyl)acetyl]sulfamate, and in the present invention CI-1011 including a pharmacologically acceptable salt/co-crystal, ester or prodrug thereof; a compound having the general formula (I) including a pharmacologically acceptable salt/co-crystal, ester or prodrug thereof disclosed in EP 421441 (U.S. Pat. No. 5,120,738) {preferably F-1394, of which the chemical name is (1S,2S)-2-[3-(2,2-dimethylpropyl)-3-nonylureido]cyclohexan-1-yl 3-[(4R)-N-(2,2,5,5-tetramethyl-1,-3-dioxane-4-carbonyl) amino]propionate, and in the present invention F-1394 including a pharmacologically acceptable salt/co-crystal, ester or prodrug thereof}; a compound including a pharmacologically acceptable salt/co-crystal, ester or prodrug thereof disclosed in the Japanese Patent Publication (Kohyo) 2000-500771 (WO 97/19918, U.S. Pat. No. 5,990,173) [preferably F-12511, of which the chemical name is (S)-2',3',5'-trimethyl-4'-hydroxy-α-dodecylthio-.alpha.-phenylacetanilide, and in the present invention F-12511 including a pharmacologically acceptable salt/co-crystal, ester or prodrug thereof]; a compound having the general formula (I) including a pharmacologically acceptable salt/co-crystal, ester or prodrug thereof disclosed in the Japanese Patent Publication (Kokai) Hei 10-195037 (EP 790240, U.S. Pat. No. 5,849,732) [preferably T-2591, of which the chemical name is 1-(3-t-butyl-2-hydroxy-5-methoxyphenyl)-3-(2-cyclohexylethyl)-3-(4-dimethylaminophenyl)urea, and in the present invention T-2591 including a pharmacologically acceptable salt/co-crystal, ester or prodrug thereof]; a compound having the general formula (I) including a pharmacologically acceptable salt/co-crystal, ester or prodrug thereof disclosed in WO 96/26948 {preferably FCE-28654, of which the chemical name is 1-(2,6-diisopropylphenyl)-3-[(4R,5R)-4,5-dimethyl-2-(4-phosphonophenyl)-1,3-dioxolan-2-ylmethyl]urea, including a pharmacologically acceptable salt/co-crystal, ester or prodrug thereof}; a compound having the general formula (I) or a pharmacologically acceptable salt thereof disclosed in the specification of WO 98/54153 (EP 987254) {preferably K-10085, of which the chemical name is N-[2,4-bis(methylthio)-6-methyl-3-pyridyl]-2-[4-[2-(oxazolo[4,5-b]pyridine-2-ylthio)ethyl]piperazin-1-yl]acetamide, including a pharmacologically acceptable salt/co-crystal, ester or prodrug thereof}; a compound having the general formula (I) disclosed in WO 92/09572 (EP 559898, U.S. Pat. No. 5,475,130) [preferably HL-004, of which the chemical name is N-(2,6-diisopropylphenyl)-2-tetradecylthioacetamide]; a compound having the general formula (I) including a pharmacologically acceptable salt/co-crystal, ester or prodrug thereof disclosed in the Japanese Patent Publication (Kokai) Hei 7-82232 (EP 718281) {preferably NTE-122, of which the chemical name is trans-1,4-bis[1-cyclohexyl-3-(4-dimethylaminophenyl)ureidomethyl]cyclohexane, and in the present invention NTE-122 includes pharmacologically acceptable salts of NTE-122}; a compound including a pharmacologically acceptable salt/co-crystal, ester or prodrug thereof disclosed in the Japanese Patent Publication (Kohyo) Hei 10-510512 (WO 96/10559) {preferably FR-186054, of which the chemical name is 1-benzyl-1-[3-(pyrazol-3-yl) benzyl]-3-[2,4-bis(methylthio)-6-methylpyridin-3-yl]urea, and in the present invention FR-186054 including a pharmacologically acceptable salt/co-crystal, ester or prodrug thereof}; a compound having the general formula (I) including a pharmacologically acceptable salt/co-crystal, ester or prodrug thereof disclosed in WO 96/09287 (EP 0782986, U.S. Pat. No. 5,990,150) [preferably N-(1-pentyl-4,6-dimethylindolin-7-yl)-2,2-dimethylpropaneamide, and in the present invention including a pharmacologically acceptable salt/co-crystal, ester or prodrug thereof]; and a compound having the general formula (I) including a pharmacologically acceptable salt/co-crystal, ester or prodrug thereof disclosed in WO 97/12860 (EP 0866059, U.S. Pat. No. 6,063,806) [preferably N-(1-octyl-5-carboxymethyl-4,6-dimethylindolin-7-yl)-2,2-dimethylpropaneamide, including a pharmacologically acceptable salt/co-crystal, ester or prodrug thereof].

The ACAT inhibitor preferably is a compound selected from the group consisting of FR-129169, CI-1011, F-1394, F-12511, T-2591, FCE-28654, K-10085, HL-004, NTE-122, FR-186054, N-(1-octyl-5-carboxymethyl-4,6-dimethylindolin-7-yl)-2,2-dimethylpropaneamide (hereinafter referred as compound A), and N-(1-pentyl-4,6-dimethylindolin-7-yl)-2,2-dimethylpropaneamide (hereinafter referred as compound B), including a pharmacologically acceptable salt/co-crystal, ester or prodrug thereof. The ACAT inhibitor more preferably is a compound selected from the group consisting of CI-1011, F-12511, N-(1-octyl-5-carboxymethyl-4,6-dimethylindolin-7-yl)-2,2-dimethylpropaneamide (compound A), and N-(1-pentyl-4,6-dimethylindolin-7-yl)-2,2-dimethylpropaneamide (compound B), including a pharmacologically acceptable salt/co-crystal, ester or prodrug thereof; most preferred is N-(1-octyl-5-carboxymethyl-4,6-dimethylindolin-7-yl)-2,2-dimethylpropaneamide (compound A).

An angiotensin II receptor antagonist includes, for example, a biphenyl tetrazole compound or biphenylcarboxylic acid derivative such as: a compound having the general formula (I) including a pharmacologically acceptable salt/co-crystal, ester or prodrug thereof disclosed in the Japanese Patent Publication (Kokai) Sho 63-23868 (U.S. Pat. No. 5,138,069) {preferably losartan, of which the chemical name is 2-butyl-4-chloro-1-[2'-(1H-tetrazol-5-yl)biphenyl-4-ylmethyl]-1H-imidazol-5-methanol, and in the present invention losartan including a pharmacologically acceptable salt/co-crystal, ester or prodrug thereof}; a compound having the general formula (I) including a pharmacologically acceptable salt/co-crystal, ester or prodrug thereof disclosed in the Japanese Patent Publication (Kohyo) Hei 4-506222 (WO 91/14679) {preferably irbesartan, of which the chemical name is 2-N-butyl-4-spirocyclopentane-1-[2'-(1H-tetrazol-5-yl)biphenyl-4-ylmethyl]-2-imidazoline-5-one, and in the present invention irbesartan including a pharmacologically acceptable salt/co-crystal, ester or prodrug thereof}; a compound having the general formula (I), an ester thereof, including a pharmacologically acceptable salt/co-crystal, ester or prodrug thereof disclosed in the Japanese Patent Publication (Kokai) Hei 4-235149 (EP 433983) {preferably valsartan, of which the chemical name is (S)-N-valeryl-N-[2'-(1H-tetrazol-5-yl)biphenyl-4-ylmethyl]valine, and in the present invention valsartan including a pharmacologically acceptable salt/co-crystal, ester or prodrug thereof}; a carboxylic acid derivative having the general formula (I), including a pharmacologically acceptable salt/co-crystal, ester or prodrug thereof disclosed in the Japanese Patent Publication (Kokai) Hei 4-364171 (U.S. Pat. No. 5,196,444) {preferably candesartan, of which the chemical name is 1-(cyclohexyloxycarbonyloxy)ethyl 2-ethoxy-1-[2'-(1H-tetrazol-5-yl)biphenyl-4-ylmethyl]-1H-benzimidazole-7-carboxylate, and in the present invention candesartan including a pharmacologically acceptable salt/co-crystal, ester or prodrug thereof (TCV-116 or the like), including a pharmacologically acceptable salt/co-crystal, ester or prodrug thereof}; a carboxylic acid derivative having the general formula (I), including a pharmacologically acceptable salt/co-crystal, ester or prodrug thereof disclosed in the Japanese Patent Publication (Kokai) Hei 5-78328 (U.S. Pat. No. 5,616,599) {preferably olmesartan, of which the chemical name is (5-methyl-2-oxo-1,3-dioxolen-4-yl)methyl 4-(1-hydroxy-1-methylethyl)-2-propyl-1-[2'-(1H-tetrazol-5-yl)biphenyl-4-ylmethyl]imidazole-5-carboxylate, and in the present invention olmesartan includes carboxylic acid derivatives thereof, pharmacologically acceptable esters of the carboxylic acid derivatives (CS-866 or the like), including a pharmacologically acceptable salt/co-crystal, ester or prodrug thereof}; and a compound having the general formula (I), including a pharmacologically acceptable salt/co-crystal, ester or prodrug thereof disclosed in the Japanese Patent Publication (Kokai) Hei 4-346978 (U.S. Pat. No. 5,591,762, EP 502,314) {preferably telmisartan, of which the chemical name is 4'-[[2-n-propyl-4-methyl-6-(1-methylbenzimidazol-2-yl)-benzimidazol-1-yl]-methyl] biphenyl-2-carboxylate, including a pharmacologically acceptable salt/co-crystal, ester or prodrug thereof}. The angiotensin II receptor antagonist preferably is losartan, irbesartan, valsartan, candesartan, olmesartan, or telmisartan; more preferred is losartan or olmesartan; and most preferred is olmesartan.

In addition to being useful in treating or preventing certain diseases and disorders, combination therapy with compounds of this invention maybe useful in reducing the dosage of the second drug or agent (e.g., atorvastatin).

In addition, the compounds of the present invention can be used in combination with an apolipoprotein B secretion inhibitor and/or microsomal triglyceride transfer protein (MTP) inhibitor. Some apolipoprotein B secretion inhibitors and/or MTP inhibitors are disclosed in U.S. Pat. No. 5,919, 795.

Any HMG-CoA reductase inhibitor may be employed as an additional compound in the combination therapy aspect of the present invention. The term HMG-CoA reductase inhibitor refers to a compound that inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., *Methods of Enzymology*, 71: 455-509 (1981); and the references cited therein). A variety of these compounds are described and referenced below. U.S. Pat. No. 4,231,938 discloses certain compounds isolated after cultivation of a microorganism belonging to the genus *Aspergillus*, such as lovastatin. Also U.S. Pat. No. 4,444,784 discloses synthetic derivatives of the aforementioned compounds, such as simvastatin. Additionally, U.S. Pat. No. 4,739,073 discloses certain substituted indoles, such as fluvastatin. Further, U.S. Pat. No. 4,346,227 discloses ML-236B derivatives, such as pravastatin. In addition, EP 491,226 teaches certain pyridyldihydroxyheptenoic acids, such as rivastatin. Also, U.S. Pat. No. 4,647,576 discloses certain 6-[2-(substituted-pyrrol-1-yl)-alkyl]-pyran-2-ones such as atorvastatin. Other HMG-CoA reductase inhibitors will be known to those skilled in the art. Examples of currently or previously marketed products containing HMG-CoA reductase inhibitors include cerivastatin Na, rosuvastatin Ca, fluvastatin, atorvastatin, lovastatin, pravastatin Na and simvastatin.

Any HMG-CoA synthase inhibitor may be used as an additional compound in the combination therapy aspect of this invention. The term HMG-CoA synthase inhibitor refers to a compound that inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., *Methods of Enzymology* 35: 155-160 (1975); and *Methods of Enzymology*, 110: 19-26 (1985); and the references cited therein). A variety of these compounds are described and referenced below. U.S. Pat. No. 5,120,729 discloses certain beta-lactam derivatives. U.S. Pat. No. 5,064,856 discloses certain spiro-lactone derivatives prepared by culturing the microorganism MF5253. U.S. Pat. No. 4,847,271 discloses certain oxetane compounds such as 11-(3-hydroxymethyl-4-oxo-2-oxetayl)-3,5,7-trimethyl-2,4-undecadienoic acid derivatives. Other HMG-CoA synthase inhibitors useful in the methods, compositions and kits of the present invention will be known to those skilled in the art.

Any compound that decreases HMG-CoA reductase gene expression may be used as an additional compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (*Methods of Enzymology*, 110: 9-19 (1985)). Several such compounds are described and referenced below; however, other inhibitors of HMG-CoA reductase gene expression will be known to those skilled in the art, for example, U.S. Pat. No. 5,041,432 discloses certain 15-substituted lanosterol derivatives that are inhibitors of HMG-CoA reductase gene expression. Other oxygenated sterols that suppress the biosynthesis of HMG-CoA reductase are discussed by E. I. Mercer (*Prog. Lip. Res.*, 32:357-416 (1993)).

Any compound having activity as a CETP inhibitor can serve as the second compound in the combination therapy aspect of the instant invention. The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below; however, other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815-816 (1996), and *Bioorg. Med. Chem. Lett.*, 6:1951-1954 (1996), respectively.

Any ACAT inhibitor can serve as an additional compound in the combination therapy aspect of this invention. The term ACAT inhibitor refers to a compound that inhibits the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research*, 24:1127 (1983). A variety of these compounds are described and referenced below; however, other ACAT inhibitors will be known to those skilled in the art. U.S. Pat. No. 5,510,379 discloses certain carboxysulfonates, while WO 96/26948 and WO 96/10559 both disclose urea derivatives having ACAT inhibitory activity.

Any compound having activity as a squalene synthetase inhibitor can serve as an additional compound in the combination therapy aspect of the instant invention. The term squalene synthetase inhibitor refers to compounds that inhibit the condensation of two molecules of famesylpyrophosphate to form squalene, a reaction that is catalyzed by the enzyme squalene synthetase. Such inhibition is readily determined by those skilled in the art according to standard methodology (*Methods of Enzymology* 15:393-454 (1969); and *Methods of Enzymology* 110: 359-373 (1985); and references cited therein). A summary of squalene synthetase inhibitors has been complied in *Curr. Op. Ther Patents*, 861-4, (1993). EP 0 567 026 A1 discloses certain 4,1-benzoxazepine derivatives as squalene synthetase inhibitors and their use in the treatment of hypercholesterolemia and as fungicides. EP 0 645 378 A1 discloses certain seven- or eight-membered heterocycles as squalene synthetase inhibitors and their use in the treatment and prevention hypercholesterolemia and fungal infections. EP 0 645 377 A1 discloses certain benzoxazepine derivatives as squalene synthetase inhibitors useful for the treatment of hypercholesterolemia or coronary sclerosis. EP 0 611 749 A1 discloses certain substituted amic acid derivatives useful for the treatment of arteriosclerosis. EP 0 705 607 A2 discloses certain condensed seven- or eight-membered heterocyclic compounds useful as antihypertriglyceridemic agents. WO 96/09827 discloses certain combinations of cholesterol absorption inhibitors and cholesterol biosynthesis inhibitors including benzoxazepine derivatives and benzothiazepine derivatives. EP 0 701 725 A1 discloses a process for preparing certain optically-active compounds, including benzoxazepine derivatives, having plasma cholesterol and triglyceride lowering activities.

Other compounds that are currently or previously marketed for hyperlipidemia, including hypercholesterolemia, and which are intended to help prevent or treat atherosclerosis, include bile acid sequestrants, such as colestipol HCl and cholestyramine; and fibric acid derivatives, such as clofibrate, fenofibrate, and gemfibrozil. These compounds can also be used in combination with a compound of the present invention.

It is also contemplated that the compounds of the present invention be administered with a lipase inhibitor and/or a glucosidase inhibitor, which are typically used in the treatment of conditions resulting from the presence of excess triglycerides, free fatty acids, cholesterol, cholesterol esters or glucose including, inter alia, obesity, hyperlipidemia, hyperlipoproteinemia, Syndrome X, and the like.

In a combination with a compound of the present invention, any lipase inhibitor or glucosidase inhibitor may be employed. In one aspect lipase inhibitors comprise gastric or pancreatic lipase inhibitors. In a further aspect glucosidase inhibitors comprise amylase inhibitors. Examples of glucosidase inhibitors are those inhibitors selected from the group consisting of acarbose, adiposine, voglibose, miglitol, emiglitate, camiglibose, tendamistate, trestatin, pradimicin-Q and salbostatin. Examples of amylase inhibitors include tendamistat and the various cyclic peptides related thereto disclosed in U.S. Pat. No. 4,451,455, AI-3688 and the various cyclic polypeptides related thereto disclosed in U.S. Pat. No. 4,623,714, and trestatin, consisting of a mixture of trestatin A, trestatin B and trestatin C and the various trehalose-containing aminosugars related thereto disclosed in U.S. Pat. No. 4,273,765.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid phospholipid micelles, which are subsequently absorbed at the level of the brush border of the small intestine. The micelles eventually enter the peripheral circulation as chylomicrons. Accordingly, compounds, including lipase inhibitors that selectively limit or inhibit the absorption of ingested fat precursors are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology* 92: 125 (1987).

A variety of lipase inhibitors are known to one of ordinary skill in the art. However, in the practice of the methods, pharmaceutical compositions, and kits of the instant invention, generally lipase inhibitors are those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267.

The pancreatic lipase inhibitors lipstatin, 2S,3S,SS,7Z,1OZ)-5-[(S)-2-formamido-4-methyl-valeryloxy]-2-hexyl-3-hydroxy-7,1(t-hexadecanoic acid lactone, and tetrahydrolipostatin (orlistat), 2S,3S,55)-5-[(S)-2-formamido-4-methyl-valeryloxy]-2-hexyl-3-hydroxy-hexadecanoic acid lactone, and the variously substituted N-formylleucine derivatives and stereoisomers thereof, are disclosed in U.S. Pat. No. 4,598,089.

The pancreatic lipase inhibitor FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813.

The pancreatic lipase inhibitor WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151.

The lipase inhibitor Bay-N-3176, N-3-trifluoromethylphenyl-N'-3-chloro-4-trifluoromethylphenylurea, and the various urea derivatives related thereto, are disclosed in U.S. Pat. No. 4,405,644.

The pancreatic lipase inhibitor valilactone, and a process for the preparation thereof by the microbial cultivation of *Aetinomycetes* strain MG147-CF2, are disclosed in Kitahara, et al., *J. Antibiotics*, 40(11): 1647-50 (1987).

The lipase inhibitor esteracin, and certain processes for the preparation thereof by the microbial cultivation of *Streptomyces* strain ATCC 31336, are disclosed in U.S. Pat. Nos. 4,189,438 and 4,242,453.

The pancreatic lipase inhibitors ebelactone A and ebelactone B, and a process for the preparation thereof by the microbial cultivation of *Actinomycetes* strain MG7-G1, are disclosed in Umezawa, et al., *J. Antibiotics*, 33, 1594-1596 (1980). The use of ebelactones A and B in the suppression of monoglyceride formation is disclosed in Japanese Kokai 08-143457, published Jun. 4, 1996.

The lipase inhibitor RHC 80267, cyclo-O,O'-[(1,6-hexanediyl)-bis-(iminocarbonyl)]dioxime, and the various bis (iminocarbonyl)dioximes related thereto may be prepared as described in Petersen et al., *Liebig's Annalen*, 562: 205-29 (1949).

The ability of RHC 80267 to inhibit the activity of myocardial lipoprotein lipase is disclosed in Carroll et al., *Lipids*, 27 305-7 (1992) and Chuang et al., *J. Mol. Cell Cardiol.*, 22: 1009-16 (1990).

In another aspect of the present invention, the compounds of Formula I can be used in combination with an additional anti-obesity agent. The additional anti-obesity agent in one aspect is selected from the group consisting of a $\beta_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a lipase inhibitor, a bombesin agonist, a neuropeptide-Y antagonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, and a ciliary neurotrophic factor.

In an additional aspect the anti-obesity agents comprise those compounds selected from the group consisting of sibutramine, fenfluramine, dexfenfluramine, bromocriptine, phentermine, ephedrine, leptin, phenylpropanolamine pseudoephedrine, {4-[2-(2-[6-aminopyridin-3-yl]-2(R)-hydroxyethylamino)ethoxy]phenyl} acetic acid, {4{2-(2-[6-aminopyridin-3-yl]-2(R)-hydroxyethylamino)ethoxy] phenyl}benzoic acid, {4-[2-(2 {6-aminopyridin-3-yl]-2(R)-hydroxyethylamino)ethoxy]phenyl}propionic acid, and {4-[2-(2-[6-aminopyridin-3-yl]-2(R)-hydroxyethylamino)ethoxy]phenoxy} acetic acid.

In one aspect, the present invention concerns the prevention or treatment of diabetes, including impaired glucose tolerance, insulin resistance, insulin dependent diabetes mellitus (Type I) and non-insulin dependent diabetes mellitus (NIDDM or Type II). Also included in the prevention or treatment of diabetes are the diabetic complications, such as neuropathy, nephropathy, retinopathy or cataracts.

In one aspect the type of diabetes to be treated by the compounds of the present invention is non-insulin dependent diabetes mellitus, also known as Type II diabetes or NIDDM.

Diabetes can be treated by administering to a patient having diabetes (Type I or Type II), insulin resistance, impaired glucose tolerance, or any of the diabetic complications such as neuropathy, nephropathy, retinopathy or cataracts, a therapeutically effective amount of a compound of the present invention. It is also contemplated that diabetes be treated by administering a compound of the present invention along with other agents that can be used to prevent or treat diabetes.

Representative agents that can be used to treat diabetes in combination with a compound of the present invention include insulin and insulin analogs (e.g., LysPro insulin); GLP-1 (7-37) (insulinotropin) and GLP-1 (7-36)—$NH_2$. Agents that enhance insulin secretion, e.g., eblorpropamide, glibenclamide, tolbutamide, tolazamide, acetohexamide, glypizide, glimepiride, repaglinide, nateglinide, meglitinide; biguanides: metformin, phenformin, buformin; A2-antagonists and imidazolines: midaglizole, isaglidole, deriglidole, idazoxan, efaroxan, fluparoxan; other insulin secretagogues linogliride, A-4166; glitazones: ciglitazone, pioglitazone, englitazone, troglitazone, darglitazone, BRL49653; fatty acid oxidation inhibitors: clomoxir, etomoxir; a-glucosidase inhibitors: acarbose, miglitol, emiglitate, voglibose, MDL25, 637, camiglibose, MDL-73,945; ~3-agonists: BRL 35135, BRL 37344, RO 16-8714, ICI D7114, CL 316,243; phosphodiesterase inhibitors: -386,398; lipid-lowering agents benfluorex; antiobesity agents: fenfluramine; vanadate and vanadium complexes (e.g., bis(cysteinamide N-octyl) oxovanadium) and peroxovanadium complexes; amylin antagonists; glucagon antagonists; gluconeogenesis inhibitors; somatostatin analogs; antilipolytic agents: nicotinic acid, acipimox, WAG 994. Also contemplated to be used in combination with a compound of the present invention are pramlintide (symlin™), AC 2993 and nateglinide. Any agent or combination of agents can be administered as described above.

In addition, the compounds of the present invention can be used in combination with one or more aldose reductase inhibitors, DPPIV inhibitor, glycogen phosphorylase inhibitors, sorbitol dehydrogenase inhibitors, NHE-1 inhibitors and/or glucocorticoid receptor antagonists.

Any compound having activity as a fructose -1,6-bisphosphatase (FBPase) inhibitor can serve as the second compound in the combination therapy aspect of the instant invention (e.g., 2-Amino-5-isobutyl-4-{2-[5-(N,N'-bis((S)-1-ethoxycarbonyl)ethyl)phosphonamido]furanyl}thiazoles). FBPase is a key regulatory enzyme in gluconeogenesis, the metabolic pathway by which the liver synthesizes glucose from 3-carbon precursors. The term FBPase inhibitor refers to compounds that inhibit FBPase enzyme activity and thereby block the conversion of fructose -1,6-bisphosphate, the substrate of the enzyme, to fructose 6-phosphate. FBPase inhibition can be determined directly at the enzyme level by those skilled in the art according to standard methodology (e.g., Gidh-Jain M, Zhang Y, van Poelje P D et al., *J Biol. Chem.* 1994, 269(44): 27732-8). Alternatively, FBPase inhibition can be assessed according to standard methodology by measuring the inhibition of glucose production by isolated hepatocytes or in a perfused liver, or by measuring blood glucose lowering in normal or diabetic animals (e.g., Vincent M F, Erion M D, Gruber H E, Van den Berghe, *Diabetologia.* 1996, 39(10): 1148-55.; Vincent M F, Marangos P J, Gruber H E, Van den Berghe G, *Diabetes* 1991 40(10):1259-66). In some cases, in vivo metabolic activation of a compound may be required to generate the FBPase inhibitor. This class of compounds may be inactive in the enzyme inhibition screen, may or may not be active in hepatocytes, but is active in vivo as evidenced by glucose lowering in the normal, fasted rat and/or in animal models of diabetes.

A variety of FBPase inhibitors are described and referenced below; however, other FBPase inhibitors will be known to those skilled in the art. Gruber et al. U.S. Pat. No. 5,658,889 described the use of inhibitors of the AMP site of FBPase to treat diabetes; WO 98/39344 and U.S. Pat. No. 6,284,748 describe purine inhibitors; WO 98/39343 and U.S. Pat. No. 6,110,903 describe benzothiazole inhibitors to treat diabetes; WO 98/39342 and U.S. Pat. No. 6,054,587 describe indole inhibitors to treat diabetes; and WO 00/14095 and U.S. Pat. No. 6,489,476 describe heteroaromatic phosphonate inhibitors to treat diabetes. Other FBPase inhibitors are described in Wright S W, Carlo A A, Carty M D et al., *J Med. Chem.* 2002 45(18):3865-77 and WO 99/47549.

The compounds of the present invention can also be used in combination with sulfonylureas such as amaryl, alyburide, glucotrol, chlorpropamide, diabinese, tolazamide, tolinase, acetohexamide, glipizide, tolbutamide, orinase, glimepiride, DiaBeta, micronase, glibenclamide, and gliclazide.

The compounds of the present invention can also be used in combination with antihypertensive agents. Any anti-hypertensive agent can be used as the second agent in such combinations. Examples of presently marketed products containing antihypertensive agents include calcium channel blockers, such as Cardizem, Adalat, Calan, Cardene, Covera, Dilacor, DynaCirc, Procardia XL, Sular, Tiazac, Vascor, Verelan, Isoptin, Nimotop, Norvasc, and Plendil; angiotensin converting enzyme (ACE) inhibitors, such as Accupril, Altace, Capropril, Lotensin, Mavik, Monopril, Prinivil, Univasc, Vasotec and Zestril.

Examples of compounds that may be used in combination with the compounds of the present invention to prevent or treat osteoporosis include: anti-resorptive agents including progestins, polyphosphonates, bisphosphonate(s), estrogen agonists/antagonists, estrogen, estrogen/progestin combinations, Premarin, estrone, estriol or 17α- or 17β-ethynyl estradiol); progestins including algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol; and bone resorption inhibiting polyphosphonates including polyphosphonates such as of the type disclosed in U.S. Pat. No. 3,683,080, the disclosure of which is incorporated herein by reference. Examples of polyphosphonates include geminal diphosphonates (also referred to as bis-phosphonates), tiludronate disodium, ibandronic acid, alendronate, resindronate zoledronic acid, 6-amino-1-hydroxy-hexylidene-bisphosphonic acid and 1-hydroxy-3(methylpentylamino)-propylidene-bisphosphonic acid. Salts, co-crystals and esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl) amino methane diphosphonic acid, butane-4-amino-1-hydroxy-1,1-diphosphonic acid, pentane-5-amino-1-hydroxy-1,1-diphosphonic acid, and hexane-6-amino-1-hydroxy-1,1-diphosphonic acid.

Estrogen agonist/antagonist include 3-(4-(1,2-diphenyl-but-1-enyl)-phenyl)-acrylic acid, tamoxifen: (ethanamine, 2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516, the disclosure of which is incorporated herein by reference, 4-hydroxy tamoxifen, which is disclosed in U.S. Pat. No. 4,623,660, the disclosure of which is incorporated herein by reference, raloxifene: (methanone, (6-hydroxy-2-(4-hydroxyphenyl)benzo[b]thien-3-yl)(4-(2-(1-piperidinyl)eth-oxy) phenyl)-hydrochloride) which is disclosed in U.S. Pat. No. 4,418,068, the disclosure of which is incorporated herein by reference, toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225, the disclosure of which is incorporated herein by reference, centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822, 287, the disclosure of which is incorporated herein by reference, levormeloxifene, idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155, the disclosure of which is incorporated herein by reference, 2-(4-methoxy-phenyl)-3-[4-(2-piperidin-1-yl-ethoxy)-phenoxy]-benzo[b]thiophen-6-ol which is disclosed in U.S. Pat. No. 5,488,058, the disclosure of which is incorporated herein by reference, 6-(4-hydroxy-phenyl)-5-(4-(2-piperidin-1-yl-ethoxy)-benzyl)-naphthalen-2-ol, which is disclosed in U.S. Pat. No. 5,484,795, the disclosure of which is incorporated herein by reference, (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone which is disclosed, along with methods of preparation, in PCT publication no. WO 95/10513 assigned to Pfizer Inc, TSE-424 (Wyeth-Ayerst Laboratories) and arazoxifene, cis-6-(4-fluoro-phenyl)-5-(4-(2-piperidin-1-yl-ethoxy)-phenyl)-5,6,7,8-tetrahydro-naphthalene-2-ol; (−)-cis-6-phenyl-5-(4-(2-pyrrolidin-1-yl-ethoxy)-phenyl)-5,6,7,8-te-trahydro-naphthalene-2-ol (also known as lasofoxifene); cis-6-phenyl-5-(4-(2-pyrrolidin-1-yl-ethoxy)-phenyl)-5,6,7,8-tetrahydro-naphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-(4-(2-piperidin-1-yl-ethoxy)-phenyl)-5,6,7,8-tetrahydro-naphthalene-2-ol; 1-(4'-pyrrolidinolethoxyphenyl)-2-phenyl-6-hydroxy-1,2,3,4-tetrahydroisoquinoline, 2-phenyl-3-aroyl-benzothiophene and 2-phenyl-3-aroylbenzothiophene-1-oxide.

Other anti-osteoporosis agents, which can be used as the second agent in combination with a compound of the present invention, include, for example, the following: parathyroid hormone (PTH) (a bone anabolic agent); parathyroid hormone (PTH) secretagogues (see, e.g., U.S. Pat. No. 6,132,774), particularly calcium receptor antagonists; calcitonin; and vitamin D and vitamin D analogs. Further anti-osteoporosis agents includes a selective androgen receptor modulator (SARM). Examples of suitable SARMs include compounds such as cyproterone acetate, chlormadinone, flutamide, hydroxyflutamide, bicalutamide, nilutamide, spironolactone, 4-(trifluoromethyl)-2(1H)-pyrrolidino[3,2-g]quinoline derivatives, 1,2-dihydropyridino[5,6-g]quinoline derivatives and piperidino[3,2-g]quinolinone derivatives. Other examples include cypterone, also known as (1b,2b)-6-chloro-1,2-dihydro-17-hydroxy-3'-H-cyclopropa[1,2]pregna-1,4,6-triene-3,20-dione is disclosed in U.S. Pat. No. 3,234,093. Chlormadinone, also known as 17-(acetyloxy)-6-chloropregna-4,6-diene-3,20-dione, in its acetate form, acts as an anti-androgen and is disclosed in U.S. Pat. No. 3,485,852. Nilutamide, also known as 5,5-dimethyl-3-[4-nito-3-(trifluoromethyl)phenyl]-2,4-imidazolidinedione and by the trade name Nilandron® is disclosed in U.S. Pat. No. 4,097,578. Flutamide, also known as 2-methyl-N-[4-nitro-3-(trifluoromethyl)phenyl]propanamide and the trade name Eulexin® is disclosed in U.S. Pat. No. 3,847,988. Bicalutamide, also known as 4'-cyano-a',a',a'-trifluoro-3-(4-fluorophenylsulfonyl)-2-hydroxy-2-methylpropiono-m-toluidide and the trade name Casodex® is disclosed in EP-100172. The enantiomers of biclutamide are discussed by Tucker and Chesterton, J. Med. Chem. 1988, 31, 885-887. Hydroxyflutamide, a known androgen receptor antagonist in most tissues, has been suggested to function as a SARM for effects on IL-6 production by osteoblasts as disclosed in Hofbauer et al. J. Bone Miner. Res. 1999, 14, 1330-1337. Additional SARMs have been disclosed in U.S. Pat. No. 6,017,924; WO 01/16108, WO 01/16133, WO 01/16139, WO 02/00617, WO 02/16310, U.S. Patent Application Publication No. U.S. 2002/0099096, U.S. Patent Application Publication No. U.S. 2003/0022868, WO 03/011302 and WO 03/011824. All of the above references are hereby incorporated by reference herein.

Formulations

Unit dose amounts and dose scheduling for the pharmaceutical compositions of the present invention can be determined using methods well known in the art. In one aspect, the compounds of the invention are administered orally in a total daily dose of about 0.375 µg/kg/day to about 3.75 mg/kg/day. In another aspect the total daily dose is from about 3.75 µg/kg/day to about 0.375 mg/kg/day. In another aspect the total daily dose is from about 3.75 µg/kg/day to about 37.5 µg/kg/day. In another aspect the total daily dose is from about 3.75 µg/kg/day to about 60 µg/kg/day. In a further aspect the dose range is from 30 µg/kg/day to 3.0 mg/kg/day. In one aspect, the compounds of the invention are administered orally in a unit dose of about 0.375 µg/kg to about 3.75 mg/kg. In another aspect the unit dose is from about 3.75 µg/kg to about 0.375 mg/kg. In another aspect the unit dose is from about 3.75 µg/kg to about 37.5 µg/kg. In another aspect the unit dose is from about 3.75 µg/kg to about 60 µg/kg. In one aspect, the compounds of the invention are administered orally in a unit dose of about 0.188 µg/kg to about 1.88 mg/kg. In another aspect the unit dose is from about 1.88 µg/kg to about 0.188 mg/kg. In another aspect the unit dose is from about 1.88 µg/kg to about 18.8 µg/kg. In another aspect the unit dose is from about 1.88 µg/kg to about 30 µg/kg. In one aspect, the compounds of the invention are administered orally in a unit dose of about 0.125 µg/kg to about 1.25 mg/kg. In another aspect the unit dose is from about 1.25 µg/kg to about 0.125 mg/kg. In another aspect the unit dose is from about 1.25 µg/kg to about 12.5 µg/kg. In another aspect the unit dose is from about 1.25 µg/kg to about 20 µg/kg. In one embodiment the unit dose is administered once a day. In another embodiment the unit dose is administered twice a day. In another embodiment the unit dose is administered three times a day. In another embodiment the unit dose is administered four times a day.

Dose refers to the equivalent of the free acid. The use of controlled-release preparations to control the rate of release of the active ingredient may be preferred. The daily dose may be administered in multiple divided doses over the period of a day. Doses and dosing schedules may be adjusted to the form of the drug or form of delivery used. For example, different dosages and scheduling of doses may be used when the form of the drug is in a controlled release form or intravenous delivery is used with a liquid form.

Compounds of this invention when used in combination with other compounds or agents may be administered as a daily dose or an appropriate fraction of the daily dose (e.g., bid). Administration of compounds of this invention may occur at or near the time in which the other compound or agent is administered or at a different time. When compounds of this invention are used in combination with other compounds or agents, the other compound or agent (e.g., atorvastatin) may be administered at the approved dose or a lower dose.

For the purposes of this invention, the compounds may be administered by a variety of means including orally, parenterally, by inhalation including but not limited to nasal spray, topically, implantables or rectally in formulations containing pharmaceutically acceptable carriers, adjuvants and vehicles. The term parenteral as used here includes subcutaneous, intravenous, intramuscular, and intra-arterial injections with a variety of infusion techniques. Intra-arterial and intravenous injection as used herein includes administration through catheters. Oral administration is generally preferred.

Pharmaceutical compositions containing the active ingredient may be in any form suitable for the intended method of administration. When used for oral use for example, tablets, pellets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets and pellets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets and pellets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders, pellets, and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

In another aspect the pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 0.2 to 2000 µmol (approximately 0.1 to 1000 mg) of active material compounded with an appropriate and convenient amount of carrier material which may vary from about 5 to about 99.9% of the total compositions. It is preferred that the pharmaceutical composition be prepared which provides easily measurable amounts for administration. For example, an aqueous solution intended for intravenous infusion should contain from about 0.05 to about 500 µmol (approximately 0.025 to 250 mg) of the active ingredient per milliliter of solution in order that infusion of a suitable volume at a rate of about 30 mL/h can occur.

As noted above, formulations suitable for oral administration may be presented as discrete units such as capsules, cachets, pellets, or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. Tablets may optionally be provided with an enteric coating, to provide release in parts of the gut other than the stomach. This is particularly advantageous with the compounds of the present invention when such compounds are susceptible to acid hydrolysis.

Pharmaceutical compositions comprising the compounds of the present invention can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to treat or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the compositions of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized forms of compositions of the invention and thus effect controlled delivery of the drug. Examples of specific anion exchangers include, but are not limited to, DUOLITE A568 and DUOLITE AP143 (Rohm & Haas, Spring House, Pa. USA).

One embodiment of the invention encompasses a unit dosage form which comprises a compound of the present invention or a pharmaceutically acceptable salt, or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS (Alza Corporation, Mountain View, Calif. USA). This technology can readily be adapted for the delivery of compounds and compositions of the invention. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS that can be used to administer compounds and compositions of the invention include, but are not limited to, the OROS Push-Pull, Delayed Push-Pull, Multi-Layer Push-Pull, and Push-Stick Systems, all of which are well known. Additional OROS systems that can be used for the controlled oral delivery of compounds and compositions of the invention include OROS-CT and L-OROS. Id.; see also, Delivery Times, vol. II, issue II (Alza Corporation).

Conventional OROS oral dosage forms are made by compressing a drug powder (e.g., a T3 mimetic composition of the present invention) into a hard tablet, coating the tablet with cellulose derivatives to form a semi-permeable membrane, and then drilling an orifice in the coating (e.g., with a laser). (Kim, Cherng-ju, Controlled Release Dosage Form Design, 231-238 Technomic Publishing, Lancaster, Pa. 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS drug delivery systems cannot be used to effectively deliver drugs with low water solubility.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer comprises a compound of the present invention, including a polymorph, solvate, hydrate, dehydrate, co-crystal, anhydrous, or amorphous form thereof. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a compound of the present invention, including a polymorph, solvate, hydrate, dehydrate, co-crystal, anhydrous, or amorphous form thereof. See U.S. Pat. No. 6,342,249, the entirety of which is incorporated herein by reference.

Transdermal Delivery System: The controlled release formulations of the present invention may be formulated as a transdermal delivery system, such as transdermal patches. In certain embodiments of the present invention, a transdermal patch comprises a compound of the present invention contained in a reservoir or a matrix, and an adhesive which allows the transdermal device to adhere to the skin, allowing the passage of the active agent from the transdermal device through the skin of the patient. Once the compound has penetrated the skin layer, the drug is absorbed into the blood stream where it exerts desired pharmaceutical effects. The transdermal patch releases the compound of the present invention in a controlled-release manner, such that the blood levels of the a compound of the present invention is maintained at a therapeutically effective level through out the dosing period, and the blood levels of the a compound of the present invention is maintained at a concentration that is sufficient to reduce side effects associated with immediate release dosage forms but not sufficient to negate the therapeutic effectiveness of the compound.

Transdermal refers to the delivery of a compound by passage through the skin or mucosal tissue and into the blood stream. There are four main types of transdermal patches listed below.

Single-layer Drug-in-Adhesive: The adhesive layer of this system also contains the drug. In this type of patch the adhesive layer not only serves to adhere the various layers together, along with the entire system to the skin, but is also responsible for the releasing of the drug. The adhesive layer is surrounded by a temporary liner and a backing.

Multi-layer Drug-in-Adhesive: The multi-layer drug-in adhesive patch is similar to the single-layer system in that both adhesive layers are also responsible for the releasing of the drug. The multi-layer system is different however that it adds another layer of drug-in-adhesive, usually separated by a membrane (but not in all cases). This patch also has a temporary liner-layer and a permanent backing.

Reservoir: Unlike the Single-layer and Multi-layer Drug-in-adhesive systems the reservoir transdermal system has a separate drug layer. The drug layer is a liquid compartment containing a drug solution or suspension separated by the adhesive layer. This patch is also backed by the backing layer.

Matrix: The Matrix system has a drug layer of a semisolid matrix containing a drug solution or suspension. The adhesive layer in this patch surrounds the drug layer partially overlaying it.

Other modes of transdermal delivery are known in the art and are included in the present invention.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

In one aspect the unit dosage formulations are those containing a daily dose or unit, daily sub-dose, or an appropriate fraction thereof, of a drug.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Synthesis of Compounds of Formula I

The compounds in this invention may be prepared by the processes described in the following Schemes, as well as relevant published literature procedures that are used by those skilled in the art. It should be understood that the following schemes are provided solely for the purpose of illustration and do not limit the invention which is defined by the claims. Typically the synthesis of a compound of Formula I includes the following general steps: (1) Preparation of a phosphonate prodrug; (2) Deprotection of a phosphonate ester; (3) Introduction of a phosphonate group; (4) Construction of the diaryl ring system; and (5) Preparation of key precursors. The order of introduction of a phosphonate group and the construction of the diaryl backbone in the synthesis of compounds of Formula I can be freely decided by those skilled in the art based on the structure of the substrate. In all applicable structures contained in the Schemes described in this invention, PG refers to a protecting group and FG refers to a functional group that can be transformed into T. Protection and deprotection in the Schemes may be carried out according to the procedures generally known in the art (e.g., "Protecting Groups in Organic Synthesis", 3rd Edition, Wiley, 1999).

All stereoisomers of the compounds of the instant invention are contemplated, either in admixture or in pure or substantially pure form. The compounds of the present invention can have stereogenic centers at the phosphorus atom and at any of the carbons including any of the R substituents. Consequently, compounds of Formula I can exist in enantiomeric or diastereomeric forms or in mixture thereof. The processes for preparation can utilize racemates, enantiomers or diastereomers as starting materials. When enantiomeric or diastereomeric products are prepared, they can be separated by conventional methods for example, chromatographic or fractional crystallization.

Preparation of a Phosphonate Prodrug

Prodrugs can be introduced at different stages of the synthesis. Most often these prodrugs are made from the phosphonic acids of Formula I because of their lability.

Phosphonic acids of Formula I can be alkylated with electrophiles such as alkyl halides and alkyl sulfonates under nucleophilic substitution conditions to give phosphonate esters. For example, compounds of Formula I-VII wherein $YR^{11}$ is an acyloxyalkyl group can be prepared by direct alkylation of compounds of Formula I-VII with an appropriate acyloxyalkyl halide (e.g., Cl, Br, I; *Phosphorus Sulfur* 54:143 (1990); *Synthesis* 62 (1988)) in the presence of a suitable base (e.g., pyridine, TEA, diisopropylethylamine) in suitable solvents such as DMF (*J. Med. Chem.* 37:1875 (1994)). The carboxylate component of these acyloxyalkyl halides includes but is not limited to acetate, propionate, isobutyrate, pivalate, benzoate, carbonate and other carboxylates.

Dimethylformamide dialkyl acetals can also be used for the alkylation of phosphonic acids (*Collect. Czech Chem. Commu.* 59:1853 (1994)). Compounds of Formula I wherein $YR^{11}$ is a cyclic carbonate, a lactone or a phthalidyl group can also be synthesized by direct alkylation of the free phosphonic acids with appropriate halides in the presence of a suitable base such as NaH or diisopropylethylamine (*J. Med. Chem.* 38:1372 (1995); *J. Med. Chem.* 37:1857 (1994); *J. Pharm. Sci.* 76:180 (1987)).

Alternatively, these phosphonate prodrugs can be synthesized by the reactions of the corresponding dichlorophosphonates and an alcohol (*Collect Czech Chem. Commun.* 59:1853 (1994)). For example, a dichlorophosphonate is reacted with substituted phenols and arylalkyl alcohols in the presence of a base such as pyridine or TEA to give the compounds of Formula I-VII wherein $YR^{11}$ is an aryl group (*J. Med. Chem.* 39:4109 (1996); *J. Med. Chem.* 38:1372 (1995); *J. Med. Chem.* 37:498 (1994)) or an arylalkyl group (*J. Chem. Soc. Perkin Trans.* 1 38:2345 (1992)). The disulfide-containing prodrugs (*Antiviral Res.* 22:155 (1993)) can be prepared from a dichlorophosphonate and 2-hydroxyethyldisulfide under standard conditions. Dichlorophosphonates are also useful for the preparation of various phosphonamides as prodrugs. For example, treatment of a dichlorophosphonate with ammonia gives both a monophosphonamide and a diphosphonamide; treatment of a dichlorophosphonate with 1-amino-3-propanol gives a cyclic 1,3-propylphosphonamide; treatment of a chlorophosphonate monophenyl ester with an amino acid ester in the presence of a suitable base gives a substituted monophenyl monophosphonamidate.

Such reactive dichlorophosphonates can be generated from the corresponding phosphonic acids with a chlorinating agent (e.g., thionyl chloride, *J. Med. Chem.* 1857 (1994); oxalyl chloride, *Tetrahedron Lett.* 31:3261 (1990); phosphorous pentachloride, *Synthesis* 490 (1974)). Alternatively, a dichlorophosphonate can be generated from its corresponding disilyl phosphonate esters (*Synth. Commu.* 17:1071 (1987)) or dialkyl phosphonate esters (*Tetrahedron Lett.* 24:4405 (1983); *Bull. Soc. Chim.* 130:485 (1993)).

It is envisioned that compounds of Formula I can be mixed phosphonate ester (e.g., phenyl and benzyl esters, or phenyl and acyloxyalkyl esters) including the chemically combined mixed esters such as phenyl and benzyl combined prodrugs reported in *Bioorg. Med. Chem. Lett.* 7:99 (1997).

Dichlorophosphonates are also useful for the preparation of various phosphonamides as prodrugs. For example, treatment of a dichlorophosphonate with an amine (e.g. an amino acid alkyl ester such as L-alanine ethyl ester) in the presence of a suitable base (e.g. triethylamine, pyridine, etc.) gives the corresponding bisphosphonamide; treatment of a dichlorophosphonate with 1-amino-3-propanol gives a cyclic 1,3-propylphosphonamide; treatment of a chlorophosphonate monophenyl ester with an amino acid ester in the presence of a suitable base gives a substituted monophenyl monophosphonamidate. Direct couplings of a phosphonic acid with an amine (e.g. an amino acid alkyl ester such as L-alanine ethyl ester) are also reported to give the corresponding bisamidates under Mukaiyama conditions (*J. Am. Chem. Soc.*, 94:8528 (1972)).

The SATE (S-acetyl thioethyl) prodrugs can be synthesized by the coupling reaction of the phosphonic acids of Formula I and S-acyl-2-thioethanol in the presence of DCC, EDCI or PyBOP (*J. Med. Chem.* 39:1981 (1996)).

Cyclic phosphonate esters of substituted 1,3-propane diols can be synthesized by either reactions of the corresponding dichlorophosphonate with a substituted 1,3-propanediol or coupling reactions using suitable coupling reagents (e.g., DCC, EDCI, PyBOP; *Synthesis* 62 (1988)). The reactive dichlorophosphonate intermediates can be prepared from the corresponding acids and chlorinating agents such as thionyl chloride (*J. Med. Chem.* 1857 (1994)), oxalyl chloride (*Tetrahedron Lett.* 31:3261 (1990)) and phosphorus pentachloride (*Synthesis* 490 (1974)). Alternatively, these dichlorophosphonates can also be generated from disilyl esters (*Synth. Commun.* 17:1071 (1987)) and dialkyl esters (*Tetrahedron Lett.* 24:4405 (1983); *Bull. Soc. Chim. Fr.,* 130:485 (1993)).

Alternatively, these cyclic phosphonate esters of substituted 1,3-propane diols are prepared from phosphonic acids by coupling with diols under Mitsunobu reaction conditions (*Synthesis* 1 (1981); *J. Org. Chem.* 52:6331 (1992)), and other acid coupling reagents including, but not limited to, carbodiimides (*Collect. Czech. Chem. Commun.* 59:1853 (1994); *Bioorg. Med. Chem. Lett.* 2:145 (1992); *Tetrahedron Lett.* 29:1189 (1988)), and benzotriazolyloxytris-(dimethylamino) phosphonium salts (*Tetrahedron Lett.* 34:6743 (1993)).

Phosphonic acids also undergo cyclic prodrug formation with cyclic acetals or cyclic ortho esters of substituted propane-1,3-diols to provide prodrugs as in the case of carboxylic acid esters (*Helv. Chim. Acta.* 48:1746 (1965)). Alternatively, more reactive cyclic sulfites or sulfates are also suitable coupling precursors to react with phosphonic acid salts. These precursors can be made from the corresponding diols as described in the literature.

Alternatively, cyclic phosphonate esters of substituted 1,3-propane diols can be synthesized by trans esterification reaction with substituted 1,3-propane diol under suitable conditions. Mixed anhydrides of parent phosphonic acids generated in situ under appropriate conditions react with diols to give prodrugs as in the case of carboxylic acid esters (*Bull. Chem. Soc. Jpn.* 52:1989 (1979)). Aryl esters of phosphonates are also known to undergo transesterification with alkoxy intermediates (*Tetrahedron Lett.* 38:2597 (1997); *Synthesis* 968 (1993)).

One aspect of the present invention provides methods to synthesize and isolate single isomers of prodrugs of phosphonic acids of Formula I. Because phosphorus is a stereogenic atom, formation of a prodrug with a substituted-1,3-propanediol will produce a mixture of isomers. For example, formation of a prodrug with a racemic 1-(V)-substituted-1,3-propane diol gives a racemic mixture of cis-prodrugs and a racemic mixture of trans-prodrugs. In an other aspect, the use of the enantioenriched substituted-1,3-propane diol with the R-configuration gives enantioenriched R-cis- and R-trans-prodrugs. These compounds can be separated by a combination of column chromatography and/or fractional crystallization.

A. Deprotection of A Phosphonate Ester

Compounds of Formula I wherein X is —$PO_3H_2$ may be prepared from phosphonate esters using the known cleavage methods. Silyl halides are generally used to cleave various phosphonate esters and give the desired phosphonic acid upon mild hydrolysis of the resulting silyl phosphonate esters. When needed, acid scavengers (for example, HMDS) can be used for the acid sensitive compounds. Such silyl halides include TMSCl (*J. Org. Chem.* 28:2975 (1963)), TMSBr (*Tetrahedron Lett.* 155 (1977)) and TMSI (*J. Chem. Soc., Chem. Commu.* 870 (1978)). Alternatively, phosphonate esters can be cleaved under strong acid conditions (*Tetrahedron Lett.* 33:4137 (1992); *Synthesis-Stuttgart* 10:955 (1993)). Those phosphonate esters can also be cleaved via dichlorophosphonates prepared by treating the phosphonate esters with halogenating agents such as $PCl_5$, $SOCl_2$ and $BF_3$ (*J. Chem. Soc.* 238 (1961)) followed by aqueous hydrolysis to give the phosphonic acids. Aryl and benzyl phosphonate esters can be cleaved under hydrogenolysis conditions (*Synthesis* 412 (1982); *J. Med. Chem.* 281208 (1985)) or metal reduction conditions (*J. Chem. Soc.* 99:5118 (1977)). Electrochemical (*J. Org. Chem.* 44:4508 (1979)) and pyrolysis (*Synth. Commu.* 10:299 (1980)) conditions have been used to cleave various phosphonate esters.

Introduction of A Phosphonate Group

The introduction of a phosphonate group can generally be accomplished according to known methods. Compounds of Formula I wherein T is —$O(CR^b_2)(CR^a_2)_n$—, —$S(CR^b_2)$ $(CR^a_2)_n$ or —$N(R^c)(CR^b_2)(CR^a_2)_n$— may be prepared by coupling a phenol, thiophenol, or aniline with a phosphonate ester component such as $I(CR^b_2)(CR^a_2)_nP(O)(OEt)_2$, $TsO(CR^b_2)(CR^a_2)_nP(O)(OEt)_2$, or $TfO(CR^b_2)(CR^a_2)_nP(O)(OEt)_2$ in the presence of a base such as NaH, $K_2CO_3$, KO-t-Bu or TEA (*Tetrahedron Lett.* 27:1477 (1986); *J. Chem. Soc. Perkin Tran* 1 1987 (1994)) as described in Scheme 1. Following the procedures described as above, deprotection of the phosphonate ester 2 gives the desired phosphonic acid 3.

Compounds of Formula I wherein T is —$N(R^b)C(O)$ $(CR^a_2)_n$— can be prepared by coupling an aniline 1 (M=NH) with a carboxylic acid containing a phosphonate moiety $(EtO)_2P(O)(CR^a_2)_{1-2}CO_2H$ in the presence of DCC or EDC according to the known methods (for example, *J. Org. Chem.* 42:2019 (1977)) or converting an aniline 1 (M=NH) to an isocyanate with diphosgene followed by reacting with $P(OEt)_3$ (*J. Org. Chem.* 1661 (1956); *Tetrahedron Lett.* 37:5861 (1996)). Deprotection of the phosphonate ester 2 as described above leads to the phosphonic acid 3.

For compounds of Formula I wherein T is —$(CR^a_2)_k$—, the phosphonate group can be introduced by a number of known methods. For example, the coupling reaction of a phenyl bromide (*J. Org. Chem.* 64:120 (1999)), iodide (*Phosphorus Sulfur* 130:59 (1997)) or triflate (*J. Org. Chem.* 66:348 (2001)) with diethyl phosphonate in the presence of a Pd catalyst is widely used within the art (when k is 0). Other methods such as Michaelis-Arbuzov reaction (*Chem. Rev.* 81:415 (1981)) can also be an efficient way to introduce the phosphonate group by coupling a benzyl or arylalkyl halide with triethyl phosphonate (when m is 1-3).

For compounds of Formula I wherein T is —$(CR^a_2)_n$—$CR^b$=$CR^b$—, the phosphonate group can be introduced by coupling an aldehyde and tetraethyl methylenediphosphonate in the presence of a base such as NaH, NaOH or KO-t-Bu (*Tetrahedron Lett.* 29:3007 (1988)). For compounds of Formula I, II, III, V, VI, and VII wherein T is —$CR^b$=$CR^b$—$(CR^a_2)_n$— or —$(CR^a_2)$—$CR^b$=$CR^b$—$(CR^a_2)$—, the phosphonate group can be introduced by Michaelis-Arbuzov reaction of the corresponding olefinic halide with triethyl phosphite.

For compounds of Formula I wherein T is —$(CR^a_2)_m$ (CO)—, the phosphonate group can be introduced by reacting diethyl phosphite with an acid chloride (*J. Org. Chem.* 29:3862 (1964); *Tetrahedron* 54:12233 (1998)) or an aldehyde followed by oxidation (*Tetrahedron* 52:9963 (1996)). Also, this type of compounds can be transformed into the compounds of Formula I, II, III, V, VI, and VII wherein T is —$(CR^a_2)_n$CH($NR^bR^c$)— according to known procedures (*Tetrahedron Lett.* 37:407 (1996)).

For compounds of Formula I wherein T is —(CO) $(CR^a_2)_m$—, the phosphonate group can be introduced by a number of known methods such as reacting a substituted benzoyl chloride with diethylphosphonoacetic acid (*Synthetic Commu.* 30:609 (2000)) or a phosphonate copper reagent (*Tetrahedron Lett.* 31:1833 (1990)). Alternatively, coupling of triethyl phosphonate with a silyl enol ether (*Synthetic Commu.* 24:629 (1994)) or a α-bromobenzophenone (*Phosphorus Sulfur* 90:47 (1994)) can also introduce the phosphonate group.

For compounds of Formula I wherein T is —C(O)NH $(CR^b_2)(CR^a_2)_p$—, the phosphonate group can be introduced by coupling reaction of a substituted benzoic acid and an aminophosphonate according to the standard amide bond formation methods (*Tetrahedron Lett.* 31:7119 (1990); *Tetrahedron Lett.* 30:6917 (1989); *J. Org. Chem.* 58:618 (1993)).

For compounds of Formula I wherein T is —$(CR^a_2)C(O)$ $(CR^a_2)_n$— or $(CR^a_2)_nC(O)(CR^a_2)$, the phosphonate group can be introduced by reacting a benzyl bromide with a functionalized phosphonate (*Tetrahedron Lett.* 30:4787 (1989)). Alternatively, a coupling reaction of a substituted phenylacetate and methylphosphonate also yields the desired product (*J. Am. Chem. Soc.* 121:1990 (1999)).

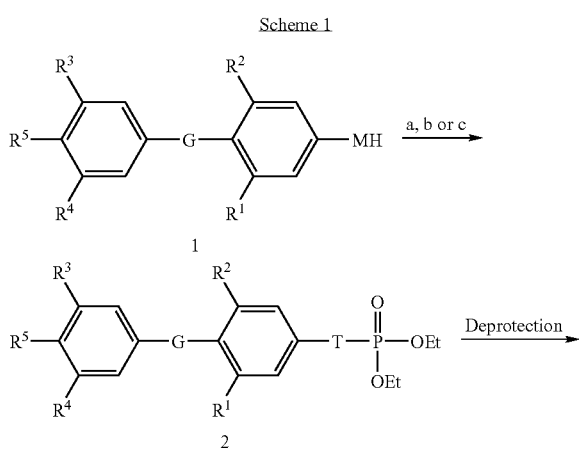

Scheme 1

-continued

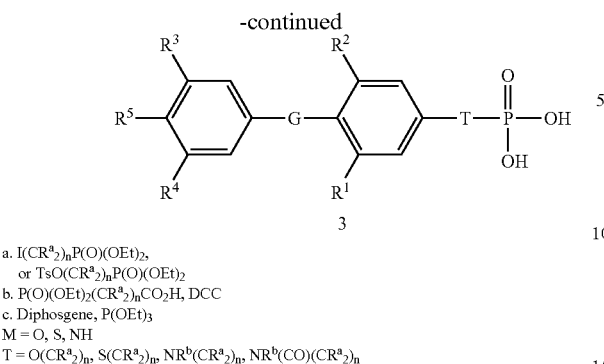

a. I(CR$^a_2$)$_n$P(O)(OEt)$_2$,
   or TsO(CR$^a_2$)$_n$P(O)(OEt)$_2$
b. P(O)(OEt)$_2$(CR$^a_2$)$_n$CO$_2$H, DCC
c. Diphosgene, P(OEt)$_3$
M = O, S, NH
T = O(CR$^a_2$)$_n$, S(CR$^a_2$)$_n$, NR$^b$(CR$^a_2$)$_n$, NR$^b$(CO)(CR$^a_2$)$_n$ Construction of The Diaryl Ring Compounds of Formula I wherein G is —O— can be prepared according to known methods. As described in Scheme 2, 2a is reacted with 2b at room temperature in the presence of Cu powder and a suitable base such as TEA, diisopropylamine or pyridine to provide the coupling product 4 (*J. Med. Chem.* 38:695 (1995)). Deprotection of the methoxy group with suitable reagents such as boron tribromide, boron trichloride or boron trifluoride in CH$_2$Cl$_2$ gives the intermediate 5. Introduction of the phosphonate group followed by deprotection of the phosphonate ester as described in Scheme 1 leads to the desired phosphonic acid 6. Those skilled in the art can use other known methods such as coupling of an arylboronic acid and a phenol in the presence of Cu(OAc)$_2$ (*Tetrahedron Lett.* 39:2937 (1998)), nucleophilic substitution of a fluorobenzene (*Synthesis-Stuttgart* 1:63 (1991)) or iodobenzene (*J. Am. Chem. Soc.* 119:10539 (1997)) with a phenol and coupling of a bromobenzene with a phenol in the presence of Pd$_2$(dba)$_3$ (*Tetrahedron Lett.* 38:8005 (1997)) to form the diaryl ether system.

Scheme 2

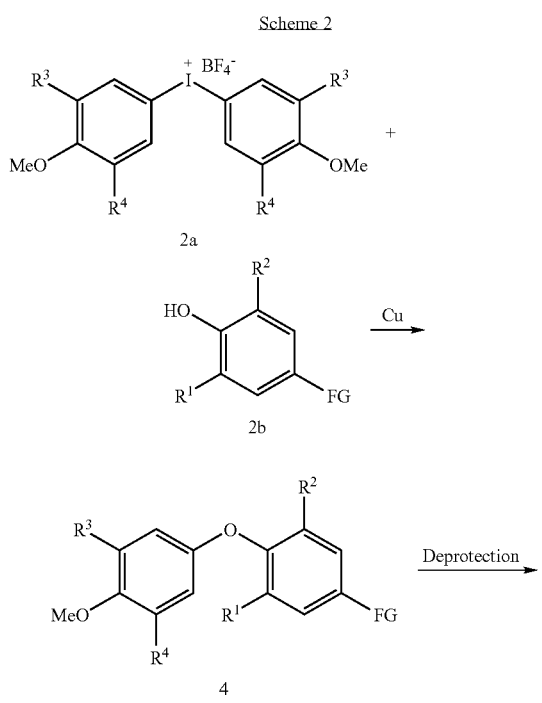

-continued

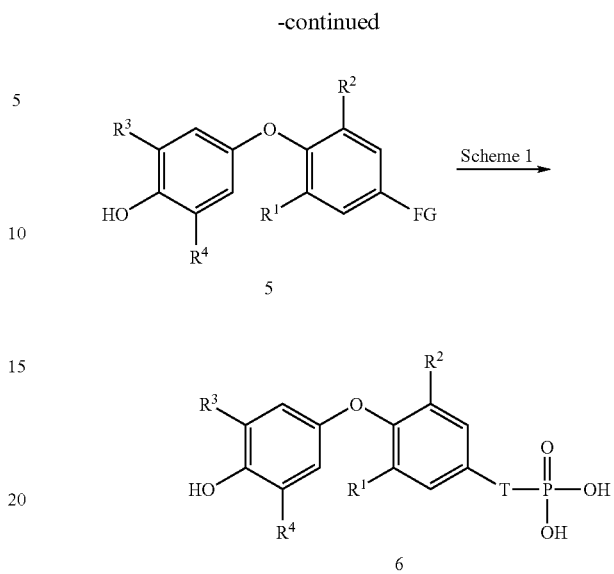

FG = functional group that can be transformed into T

For compounds of Formula I wherein G is —CH$_2$—, the installation of the diaryl ring can be accomplished by a number of known methods. For example, as described in Scheme 3, benzyl alcohol 7 is formed by treatment of 3a with n-BuLi at −78° C. in THF followed by reacting with 3b (*Bioorg. Med. Chem. Lett.* 10:2607 (2000)). Hydrogenolysis with Pd—C or dehydroxylation of benzyl alcohol 7 by NaBH$_4$ (*Synthetic Commu.* 17:1001 (1987)) and (i-Bu)$_3$Al (*Synthesis* 736 (1987)) followed by removal of the protecting group gives the diaryl intermediate 8. Phosphonic acid 9 is formed from 8 according to the same procedures as described in Scheme 1. Alternatively, coupling of benzyl bromide with an aryl Grignard reagent (*Tetrahedron Lett.* 22:2715 (1981)), an arylboronic acid (*Tetrahedron, Lett.* 40:7599 (1999)) or a zinc reagent (*Chem. Lett.* 11:1241 (1999)) and reduction of a diaryl ketone (*J. Org. Chem.* 51:3038 (1986)) are all widely used methods for the construction of the diaryl ring.

Scheme 3

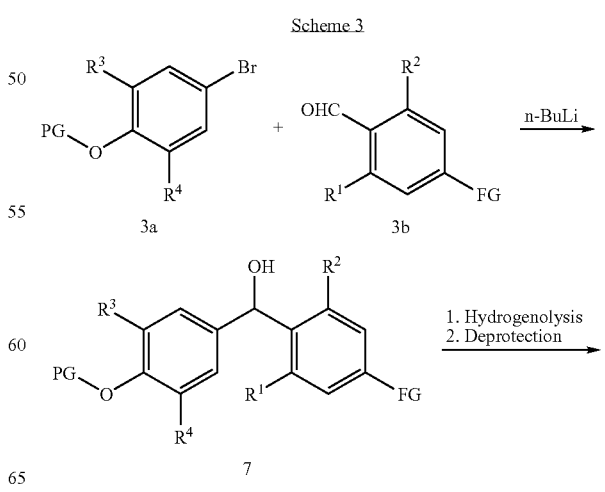

-continued

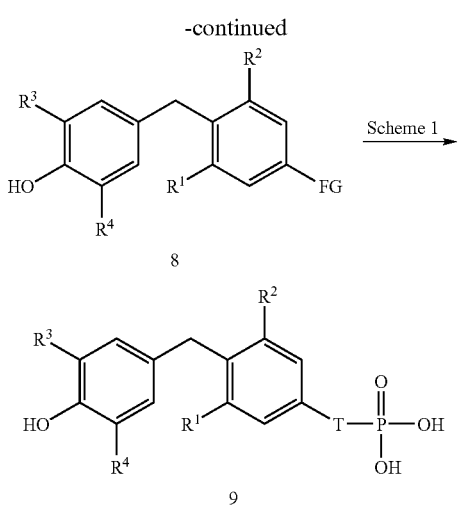

PG = protecting group
FG = functional group that can be transformed into T

For compounds of Formula I wherein G is —S—, —S(=O)— or —S(=O$_2$)—, the formation of the diaryl ring can be achieved according to known methods. As illustrated in Scheme 4, 3a can be reacted with 4a in the presence of a catalyst such as Pd$_2$(dba)$_3$ or CuBr to provide the diaryl sulfide 10 (*Tetrahedron* 57:3069 (2001); *Tetrahedron Lett.* 41:1283 (2000)). Phosphonic acid 12 is formed from 10 after removal of the protecting groups followed by the same procedures as described in Scheme 1. The diaryl sulfide 10 can also be converted to the sulfoxide 13 according to known methods (*Synthetic Commu.* 16:1207 (1986); *J. Org. Chem.* 62:4253 (1997); *Tetrahedron Lett.* 31:4533 (1990)), which leads to the phosphonic acid 15 following the same procedures as described in Scheme 1. Also, the biaryl sulfide 10 can be converted to the sulfone (*Tetrahedron Lett.* 32:7353 (1991); *J. Prakt. Chem.* 160 (1942)) which leads to the phosphonic acid (G is —S(=O$_2$)—) following the same procedures as described above. In addition, nucleophilic substitution of chlorobenzene and bromobenzene with a thiol is also an efficient way to install the diaryl sulfide ring (*J. Med. Chem.* 31:254 (1988); *J. Org. Chem.* 63:6338 (1998)).

Scheme 4

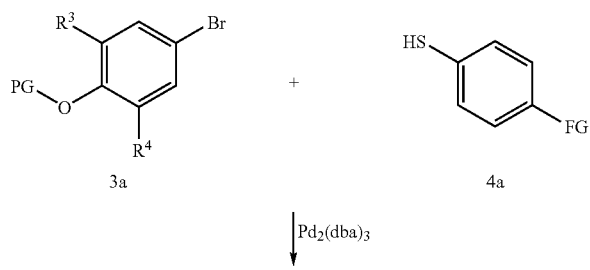

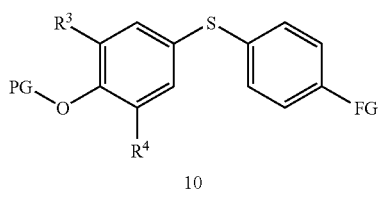

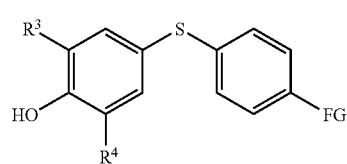

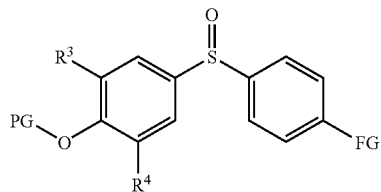

PG = protection group
FG = functional group that can be transformed into T

For compounds of Formula I wherein G is —NH— or —N(C$_1$-C$_4$ alkyl)-, the diarylamine backbone can be formed by a number of known methods. Among those conditions, one widely used by those skilled in the art is the coupling reaction of an aniline with an aryl bromide (*J. Org. Chem.* 64:5575 (1999); *J. Org. Chem.* 62:6066 (1997); *Tetrahedron Lett.* 37:6993 (1996); *Org. Lett.* 1:2057 (1999)) or an aryl tosylate (*J. Org. Chem.* 62:1268 (1997)) in the presence of a catalyst such as PdCl$_2$ or Pd$_2$(dba)$_3$. As illustrated in Scheme 5, the diarylamine intermediate 16 can be prepared by coupling of bromide 3a and aniline 5a in the presence of Pd$_2$(dba)$_3$. After removal of the protecting group, the diarylamine 17 is converted to the phosphonic acid 18 following the same procedures as described in Scheme 1. Alternatively, coupling of an aniline and aryl halide using other catalysts such as copper-bronze (*Org. Synth.* 2:446 (1943); *J. Org. Chem.* 20 (1955)) and Cu(OAc)$_2$ (*J. Med. Chem.* 4:470 (1986); *Synthetic Commu.* 26:3877 (1996)) to construct the diarylamine backbone is also a feasible approach.

R = H, C$_1$-C$_4$ alkyl
PG = Protecting Group
FG = Functional group that can be transformed into T For compounds of Formula I wherein G is —CHF— or —CF$_2$—, the diaryl backbone can be established from the benzyl alcohol 7. Accordingly, as described in Scheme 6, benzyl alcohol 7 can be converted to the benzyl fluoride 19 by reacting with DAST in CH$_2$Cl$_2$ according to known procedures (*J. Chem. Soc., Chem. Commu.* 11:511 (1981); *Tetrahedron Lett.* 36:6271 (1995); *Tetrahedron* 14:2875 (1988)).

Also, the benzyl alcohol 7 can be easily oxidized to the benzophenone 22 according to known methods such as MnO$_2$ oxidation, PCC oxidation, Swern oxidation and Dess-Martin oxidation, which is subsequently converted to the benzyl difluoride 23 by treatment with DAST (*J. Fluorine* 61:117 (1993)) or other known reagents (*J. Org. Chem.* 51:3508 (1986); *Tetrahedron* 55:1881 (1999)). After removal of the protecting groups, the benzyl fluoride 20 and difluoride 24 are converted to the desired phosphonic acids following the same procedures as described in Scheme 1.

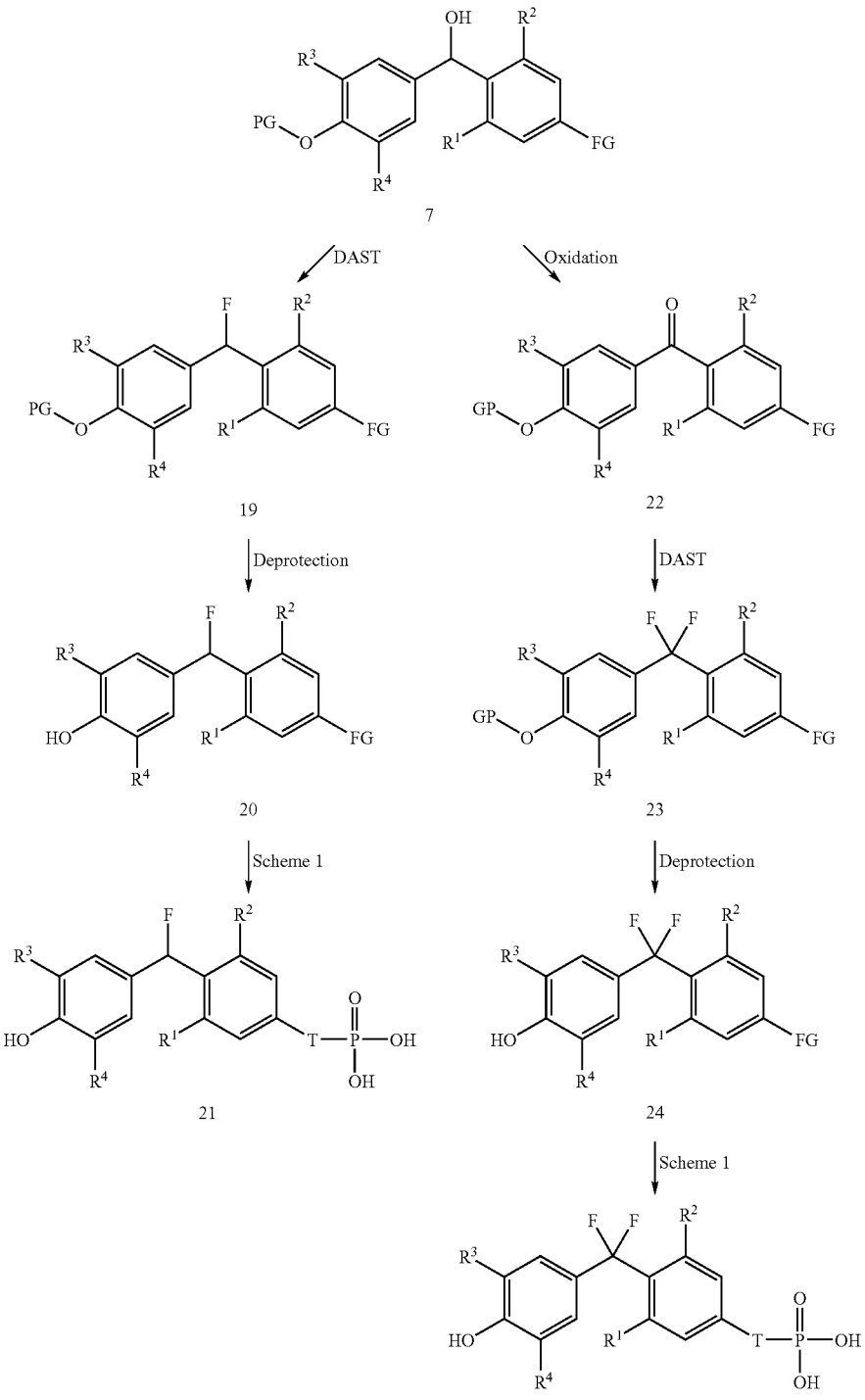

PG = Protection Group
FG = Functional group that can be transformed into T

Compounds of Formula I wherein G is —CH(OH)— or —C(O)— can be prepared from the intermediates 7 and 22. Removal of the protecting groups of 7 and 22 followed by introduction of the phosphate and deprotection as described in Scheme 1 provides the desired phosphonic acids of Formula I.

Compounds of Formula VIII can be synthesized using the same methods described above for the synthesis of compounds of Formula I.

Synthesis of Compounds of Formula II

The synthesis of compounds of Formula II where A is —NH— and B is —CH— or —C-alkyl- can be accomplished from the corresponding amino diaryl precursor 1 using the well-known, to those skilled in the art, Fisher indole synthesis (Scheme 6a) (*Phosphorus and Sulfur* 37:41-63 (1988)). Alternatively, the aryl-indole scaffold is constructed using the procedures previously described and the phosphonic acid moiety is introduced by making the anion next to the nitrogen of the indole derivative, protected at the nitrogen, with a base such as BuLi and quenching the anion with diethyl chlorophosphate. Further protecting group and functional group manipulations of intermediates 2 provide compounds of Formula II.

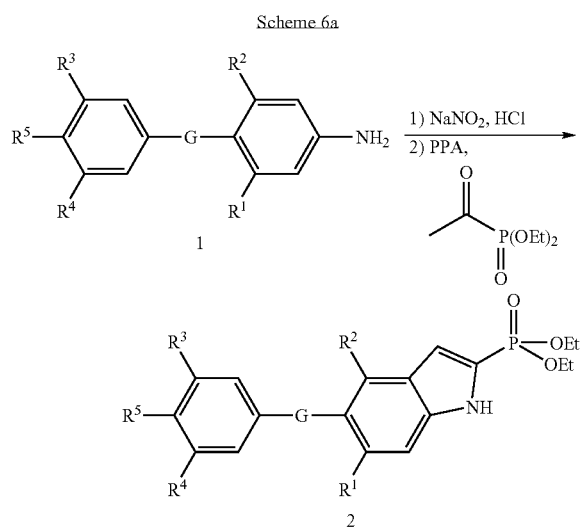

Scheme 6a

Compounds of Formula II where A is —O— and B is —CH— are synthesized from the corresponding diaryl phenol precursor 3 and ring cyclization with the dimethylacetal of bromoacetaldehyde to give benzofuran 4 (Scheme 6b) (*J. Chem. Soc., Perkin Trans.* 1, 4:729 (1984)). The phosphonic acid moiety can then be introduced by making the anion next to the oxygen of the benzofuran with a base such as BuLi and quenching the anion with diethyl chlorophosphate to provide phosphonate 5. Further protecting group and functional group manipulations of intermediate 5 provides compounds of Formula II.

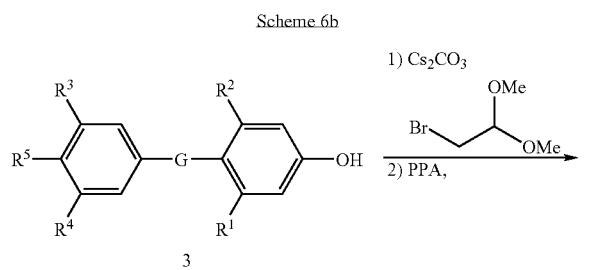

Scheme 6b

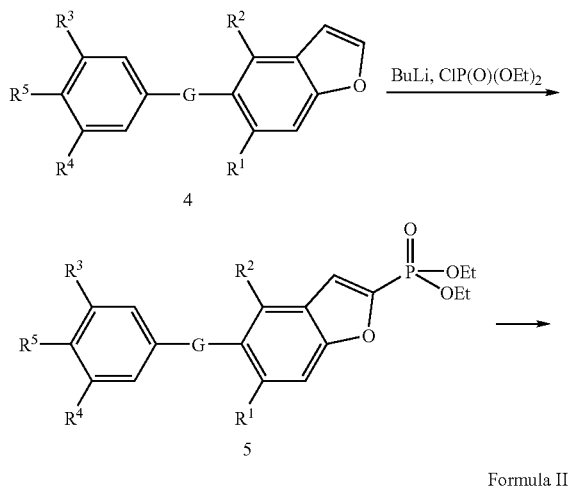

Formula II

Compounds of Formula II where A is —NH—, —O— or —S— and B is —N— can be made from condensation of the corresponding diaryl precursor 6 with an orthoformate such as triethyl orthoformate in presence of acid to give heterocycle 7 (*Org. Prep. Proced. Int.,* 22(5):613-618 (1990)). The phosphonic acid moiety can then be introduced by making the anion at the 2-position of the heterocycle 7 with a base such as BuLi and quenching the anion with diethyl chlorophosphate to give phosphonate 8. Further protecting group and functional group manipulations of intermediates 8 provide compounds of Formula II.

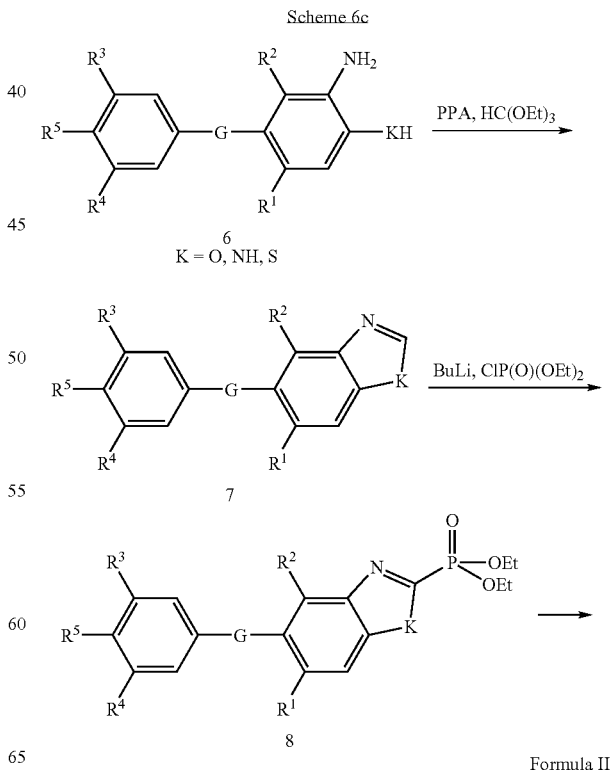

Scheme 6c

Formula II

Synthesis of Compounds of Formula III

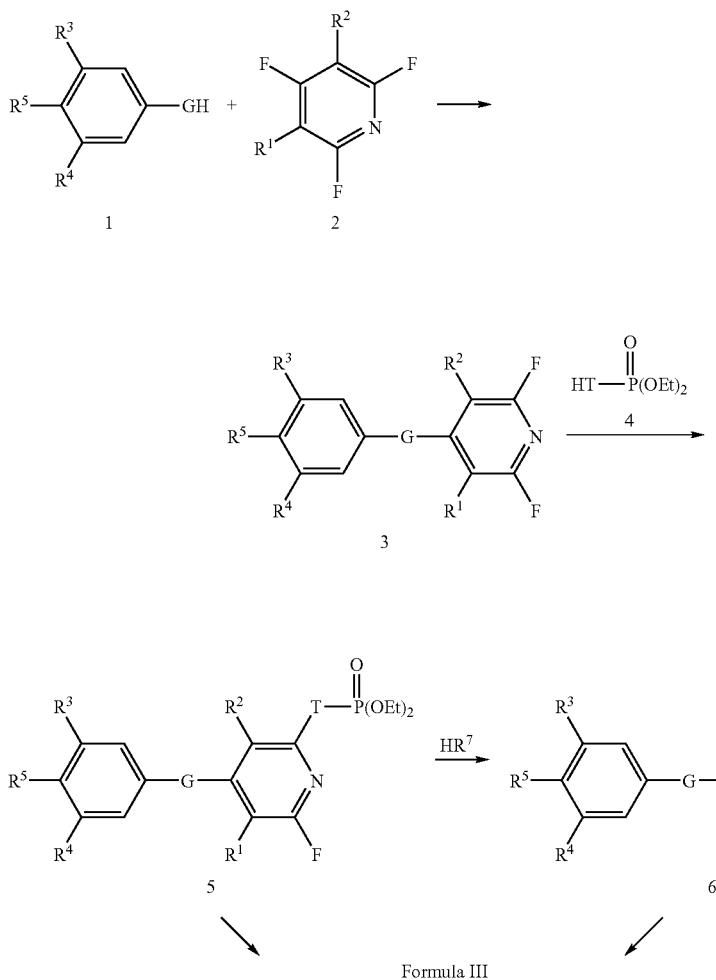

Scheme 6d

The general synthesis of compounds of Formula III wherein G is —O—, —S— or —NH— utilizes the displacement of an appropriately substituted phenol, thiophenol or aniline 1 with a pentasubstituted pyridine such as 3,5-dichloro-2,4,6-trifluoro-pyridine 2 to provide intermediate 3 (Scheme 6d) (*Org. Prep. Proced. Int.* 32(5):502-504 (2000)). Subsequent displacement of the 2-fluoro and 6-fluoro substituents on the pyridine ring with nucleophiles 4 and $HR^7$ sequentially provide intermediates 5 and 6. Examples of suitable nucleophiles, include but are not limited to, diethyl hydroxymethyl-phosphonate and diethyl aminomethyl-phosphonate. Example of reactants $HR^7$, include but are not limited to, alkylthiol, sodium alkoxide, alkylamine or benzylamine. Compounds of Formula III where G is —S(=O)— and —S(=O)$_2$— can be derived from intermediates 5 and 6 when G is —S— via oxidation with an oxidizing agent such as mCPBA. Further protecting group and functional group manipulations of intermediates 5 and 6 will provide compounds of Formula III.

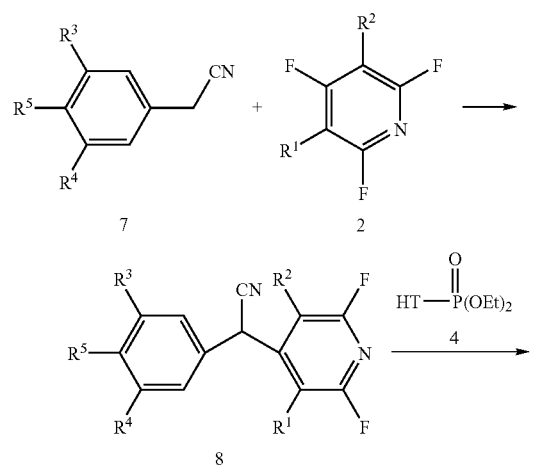

Scheme 6e

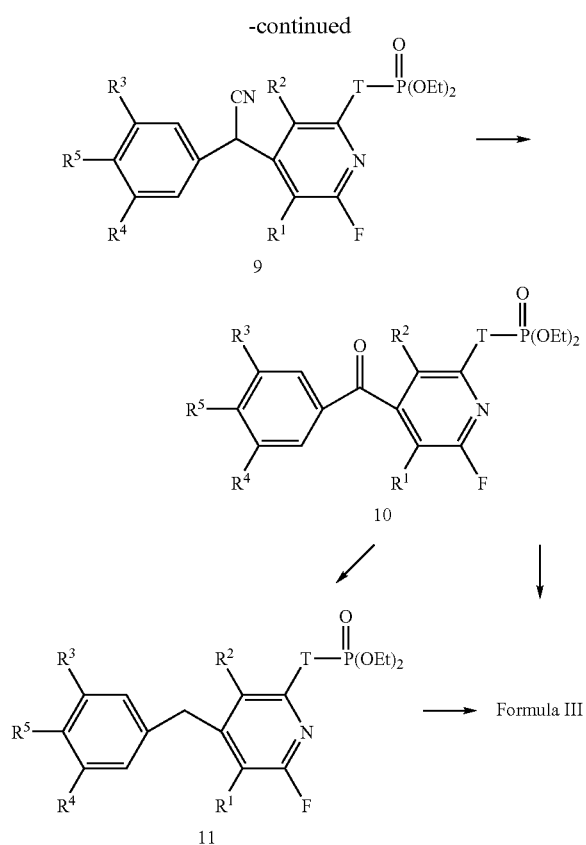

Compounds of Formula III wherein G is —CH$_2$— or —C(O)— are synthesized according to scheme 6e. Condensation of benzyl cyanide 7 with pentasubstituted pyridine 2 provide intermediate 8. Displacement of 2-fluoro with reagent 4 gives intermediate 9. Oxidation of benzyl cyanide 9 provides keto derivative 10 which after deprotection and functional group manipulation gives a compound of Formula III. Alternatively, reductive deoxygenation of keto intermediate followed by deprotection and functional group manipulation gives a compound of Formula III.

Synthesis of Phosphonic Acid Monoesters

Compound of the invention where the acidic group is a phosphonic acid monoester may be prepared from the diester intermediate, used for the synthesis of phosphonic acid thyromimetic, by monohydrolysis. Synthesis of phosphonic acid monoester may be accomplished by treatment of phosphonate diesters with aqueous alkaline solution such as NaOH, KOH or LiOH at rt or while heating. Sodium azide can also be used in DMF (*Bioorg. Med. Chem. Lett.* 14(13), 3559-62 (2004)) to accomplish the hydrolysis. Alternatively, organic bases such as morpholine or N-methyl-piperazine can be used for the hydrolysis of one of the phosphonate ester groups (*Synth. Comm.* 34(2):331-344 (2004)).

Synthesis of Cyclic Phosphonic Acids

Cyclic phosphonates can be synthesized by condensing a di-benzylic alcohol with trimethylphosphite (*Bull. Acad. Sci. USSR Div. Chem. Sci.* 37:1810-14 (1988)) to get the cyclic phosphite which is then converted to the cyclic phosphonate by a photo-Arbuzov rearrangement (*J. Organomet. Chem.* 646:239-46 (2002)). Alternatively, the cyclic phosphite can be obtained by condensing a di-benzylic alcohol with HMPT (*J. Org. Chem.* 57(10):2812-18 (1992)) or diethylphosphoramidous dichloride to get a cyclic phosphoramidous diester which is then converted to the cyclic phosphite by reaction with an alcohol, such as methanol or phenol, in the presence of an activating agent such as tetrazole or methylthio-tetrazole (*J. Org. Chem.* 61:7996-97 (1996)). The phosphonic acid is then obtained by selective monosaponification.

Synthesis of Prodrugs of Phosphonate Monoesters

Prodrugs can be introduced at different stages of the synthesis. Most often these prodrugs are made from the phosphonic acid monoesters because of their lability.

Phosphonic acid monoesters can be alkylated with electrophiles such as alkyl halides and alkyl sulfonates under nucleophilic substitution conditions to give phosphonate esters. For example, compounds of Formula I wherein YR$^{11}$ is an acyloxyalkyl group can be prepared by direct alkylation of compounds of Formula I with an appropriate acyloxyalkyl halide (e.g., Cl, Br, I; *Phosphorus Sulfur* 54:143 (1990); *Synthesis* 62 (1988)) in the presence of a suitable base (e.g., pyridine, TEA, diisopropylethylamine) in suitable solvents such as DMF (*J. Med. Chem.* 37:1875 (1994)). The carboxylate component of these acyloxyalkyl halides includes but is not limited to acetate, propionate, isobutyrate, pivalate, benzoate, carbonate and other carboxylates.

Dimethylformamide dialkyl acetals can also be used for the alkylation of phosphonic acid monoesters (*Collect. Czech Chem. Commu.* 59:1853 (1994)). Compounds of Formula I wherein YR$^{11}$ is a cyclic carbonate, a lactone or a phthalidyl group can also be synthesized by direct alkylation of the free phosphonic acids with appropriate halides in the presence of a suitable base such as NaH or diisopropylethylamine (*J. Med. Chem.* 38:1372 (1995); *J. Med. Chem.* 37:1857 (1994); *J. Pharm. Sci.* 76:180 (1987)).

Alternatively, these monoester phosphonate prodrugs can be synthesized by the reactions of the corresponding chlorophosphonate and an alcohol (*Collect Czech Chem. Commun.* 59:1853 (1994)). For example, a chlorophosphonate is reacted with substituted phenols and arylalkyl alcohols in the presence of a base such as pyridine or TEA to give the compounds of Formula I wherein YR$^{11}$ is an aryl group (*J. Med. Chem.* 39:4109 (1996); *J. Med. Chem.* 38:1372 (1995); *J. Med. Chem.* 37:498 (1994)) or an arylalkyl group (*J. Chem. Soc. Perkin Trans.* 1 38:2345 (1992)). The disulfide-containing prodrugs (*Antiviral Res.* 22:155 (1993)) can be prepared from a chlorophosphonate and 2-hydroxyethyldisulfide under standard conditions. Chlorophosphonates are also useful for the preparation of various phosphonamides as prodrugs. For example, treatment of a chlorophosphonate with ammonia gives the phosphonamide.

Such reactive dichlorophosphonates can be generated from the corresponding phosphonic acid monoesters with a chlorinating agent (e.g., thionyl chloride, *J. Med. Chem.* 1857 (1994); oxalyl chloride, *Tetrahedron Lett.* 31:3261 (1990); phosphorous pentachloride, *Synthesis* 490 (1974)). Alternatively, a dichlorophosphonate can be generated from its corresponding silyl phosphonic acid monester (*Synth. Commu.* 17:1071 (1987)).

Chlorophosphonates are also useful for the preparation of various phosphonamides as prodrugs. For example, treatment of a chlorophosphonate with an amine (e.g. an amino acid alkyl ester such as L-alanine ethyl ester) in the presence of a suitable base (e.g. triethylamine, pyridine, etc.) gives the corresponding phosphonamide. Direct couplings of phosphonic acid monoesters with an amine (e.g. an amino acid alkyl ester such as L-alanine ethyl ester) are also reported to give the corresponding amidate under Mukaiyama conditions (*J. Am. Chem. Soc.* 94:8528 (1972)).

The SATE (S-acetyl thioethyl) prodrugs can be synthesized by the coupling reaction of the phosphonic acid monoesters of Formula I and S-acyl-2-thioethanol in the presence of DCC, EDCI or PyBOP (*J. Med. Chem.* 39:1981 (1996)).

Preparation of Key Precursors

A. Preparation of Compounds with Substituents on the Ring

Starting material and key intermediates required for the synthesis of the compounds in this invention are either commercially available or prepared using an existing method in the literature or a modification of a known method. Syntheses of some of those compounds are described herein.

Precursor 2a is prepared by reacting an anisole with iodine trifluoroacetate according to the reference procedures (*J. Med. Chem.* 38:695 (1995)). Anisoles with different $R^3$ and $R^4$ groups are either commercially available or can be prepared according to the literature procedures (e.g., *J. Med. Chem.* 32:320 (1989)).

Starting material 2b is either commercially available or prepared according to known procedures. For example, compounds of 2b wherein FG is $NH_2$-derived group can be prepared by reacting 3a with benzophenone imine in the presence of a Pd catalyst such as $Pd_2(dba)_3$ or $Pd(OAc)_2$ (*Tetrahedron Lett.* 38:6367 (1997); *J. Am. Chem. Soc.* 120:827 (1998)). Compounds of 2b wherein FG is S-derived group can be prepared by reacting a feasible 4-aminoanisole with $NaNO_2$ and potassium ethyl xanthate (*J. Am. Chem. Soc.* 68 (1946); *Heterocycles* 26:973 (1987)).

The useful precursor 3a can either be commercially available reagents or prepared according to the existing methods. As described in Scheme 7, a simple protection of commercially available 4-bromophenol 7b with different $R^3$ and $R^4$ groups according to the procedures known in the art leads to 3a. Compound 3a can also be prepared by bromination of protected phenol 7d (*J. Org. Chem.* 53:5545 (1988); *J. Org. Chem.* 59:4473 (1994); *Synthesis-Stuttgart* 10:868 (1986)). Introduction of various $R^3$ and $R^4$ groups to 4-bromophenol 7a can be carried out to give 7b which leads to 7a after protection (*Tetrahedron Lett.* 36:8453 (1995); *J. Heterocyclic Chem.* 28:1395 (1991); *J. Fluorine Chem.* 40.23 (1988); *Synthesis-Stuttgart* 11:1878 (1999); *Synthetic Commu.* 16:681 (1986)). 7b can also be prepared by the bromination of phenol 7c (*J. Comb. Chem.* 2:434 (2000); *Chem. Soc. Jpn.* 61:2681 (1988); *Synthesis-Stuttgart* 5:467 (1992); *Org. Synth.* 72:95 (1993)).

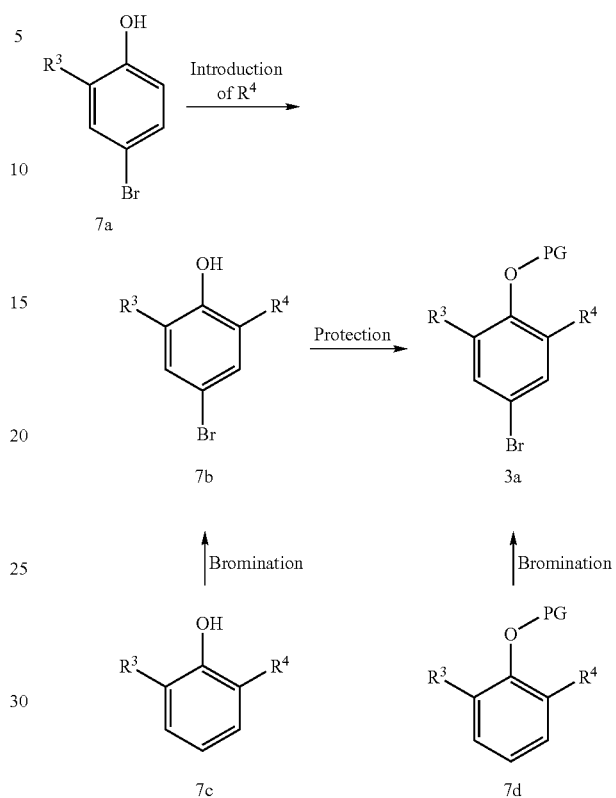

A number of methods are available for the preparation of the benzaldehyde 3b. As illustrated in Scheme 8, bromobenzene 8a can be converted to benzaldehyde 3b by reacting with DMF (*Aust. J. Chem.* 51:177 (1998); *Bioorg. Med. Chem. Lett.* 10:2607 (2000)) or carbon monoxide in the presence of a palladium catalyst (*Bull. Chem. Soc. Jpn* 67:2329 (1994)). 3b may be formed by oxidation of benzyl alcohol 8c using common methods such as $MnO_2$ oxidation, PCC oxidation, Swern oxidation and Dess-Martin oxidation. Reduction of benzonitrile 8b and benzoyl chloride 8d also produces benzaldehyde 3b (*Org. Synth.* 3:551 (1995); *J. Org. Chem.* 46:602 (1981)).

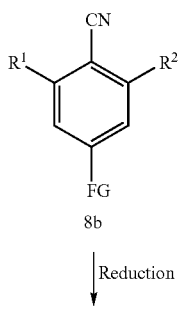

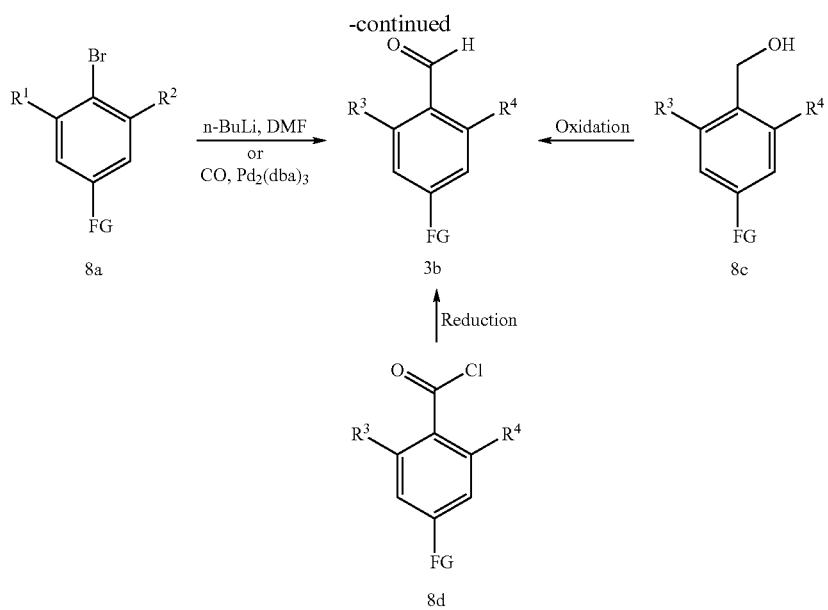

For some of the compounds of Formula II-V, the $R^3$ and $R^4$ groups can be introduced after the biaryl ring backbone is installed. As illustrated in Scheme 9, the intermediate 4 ($R^3$, $R^4$=H) is converted to the benzylaldehyde 26 upon treatment with $SnCl_4$ and methoxymethyl dichloride. Various alkyl groups ($C_1$-$C_{12}$) are introduced by reacting the benzylaldehyde 26 with a Wittig reagent followed by the reduction of the resulting alkene with $Et_3SiH$ to afford the intermediate 27 (*J. Med. Chem.* 31:37 (1988)). Also, benzylaldehyde 31 can be oxidized by $NaOCl_2$ to give the benzoic acid 29 (*Bioorg. Med. Chem. Lett.* 13:379 (2003)) which can be reacted with an alcohol or amine under standard conditions to give the ester or amide 30. Intermediates 27 and 30 can be converted to the corresponding phosphonic acids 28 and 33 following the same procedures as described in Scheme 2. In addition, deprotection of intermediate 4 provides the phenol 32 which can be converted to a variety of sulfonamides 33 upon treatment with $ClSO_3H$ and an amine. Phosphonic acids ($R^3$=S$(=O)_2NR^fR^8$) can be formed following the same procedures as described in Scheme 1.

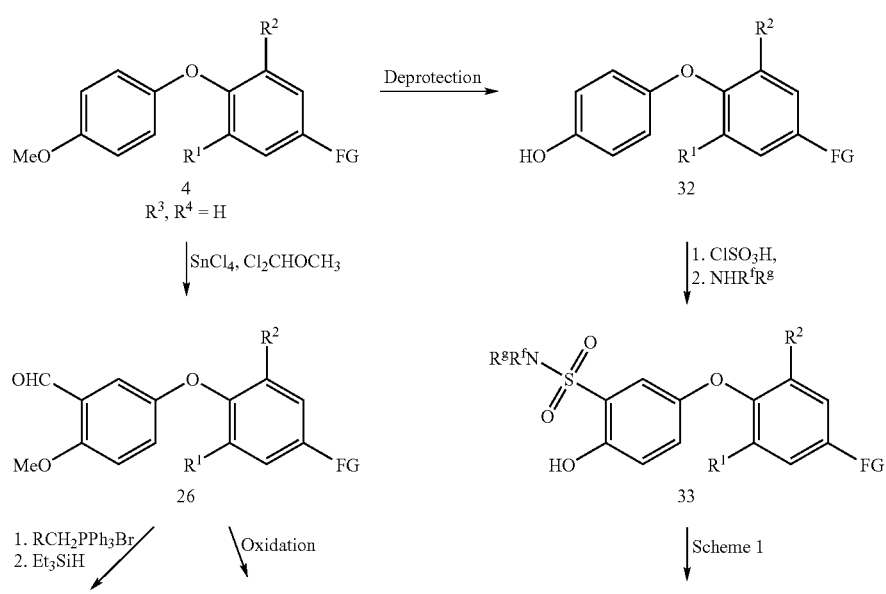

Scheme 9

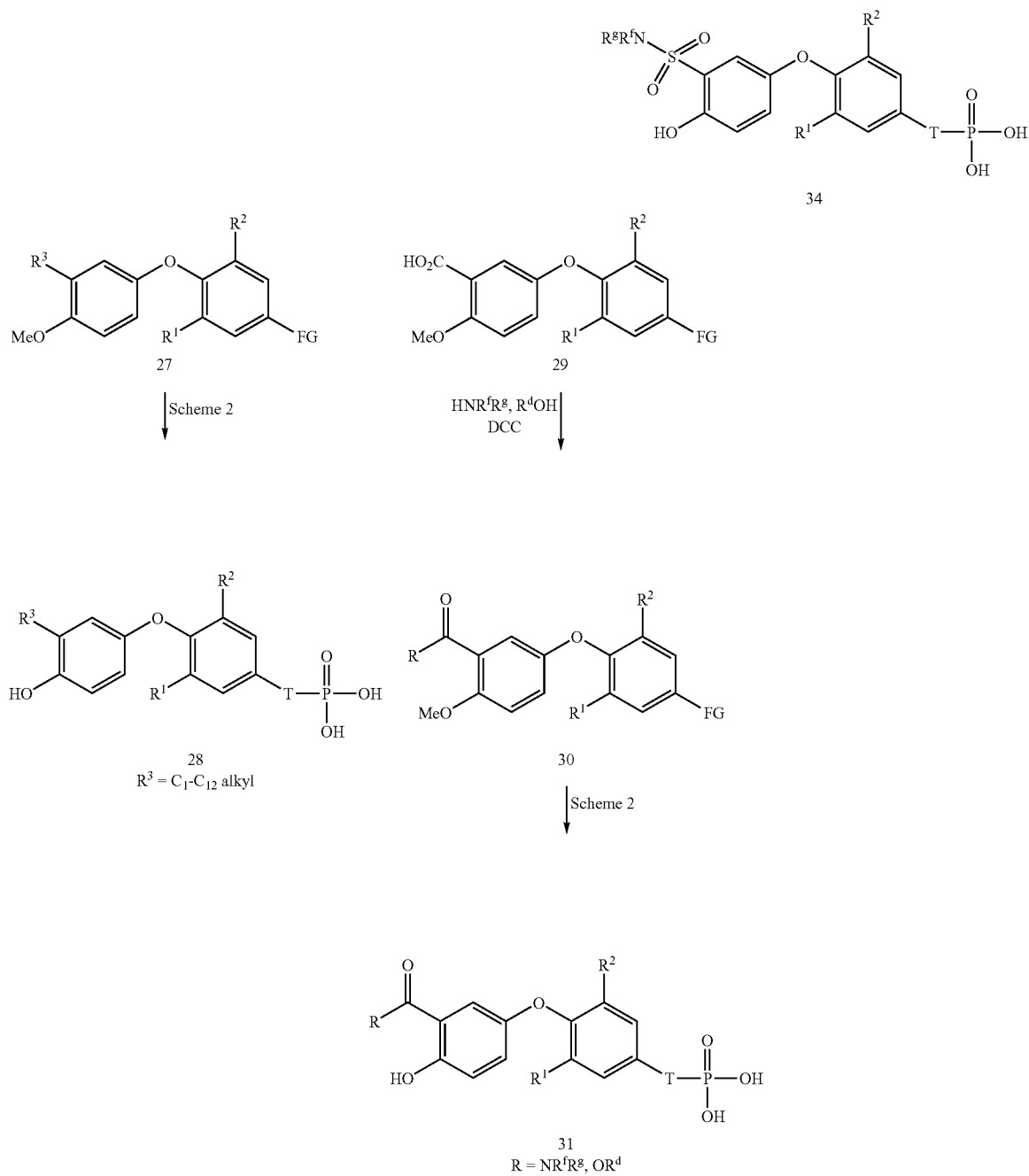

B. Preparation of 1,3-Diols

Various methods can be used to prepare 1,3-propanediols such as 1-substituted, 2-substituted, 1,2- or 1,3-annulated 1,3-propanediols.

1. 1-Substituted 1,3-Propanediols 1,3-Propanediols useful in the synthesis of compounds in the present invention can be prepared using various synthetic methods. As described in Scheme 10, additions of an aryl Grignard to a 1-hydroxy-propan-3-al give 1-aryl-substituted 1,3-propanediols (path a). This method is suitable for the conversion of various aryl halides to 1-arylsubstituted-1,3-propanediols (*J. Org. Chem.* 53:911 (1988)). Conversions of aryl halides to 1-substituted 1,3-propanediols can also be achieved using Heck reactions (e.g., couplings with a 1,3-diox-4-ene) followed by reductions and subsequent hydrolysis reactions (*Tetrahedron Lett.* 33:6845 (1992)). Various aromatic aldehydes can also be converted to 1-substituted-1,3-propanediols using alkenyl Grignard addition reactions followed by hydroboration-oxidation reactions (path b).

Scheme 10

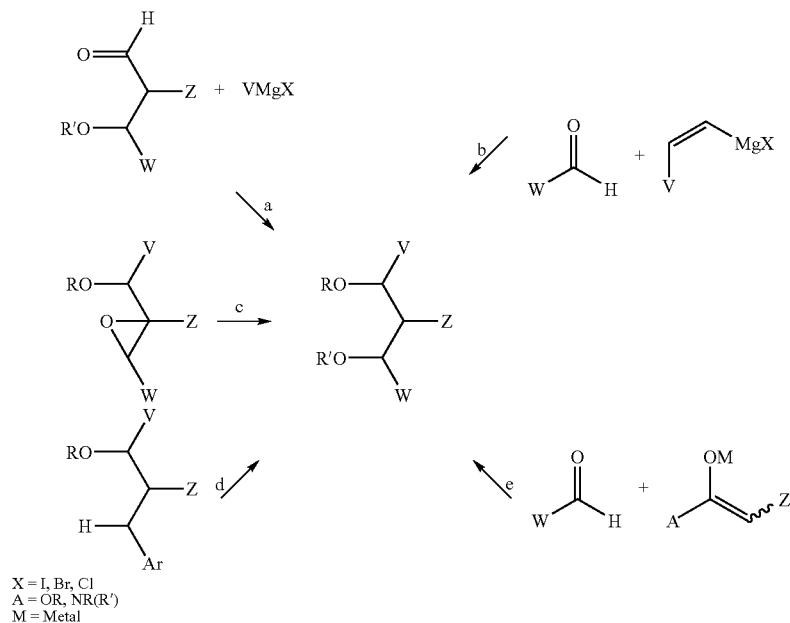

X = I, Br, Cl
A = OR, NR(R')
M = Metal

Aldol reactions between an enolate (e.g., lithium, boron, tin enolates) of a carboxylic acid derivative (e.g., tert-butyl acetate) and an aldehyde (e.g., the Evans's aldol reactions) are especially useful for the asymmetric synthesis of enantioenriched 1,3-propanediols. For example, reaction of a metal enolate of t-butyl acetate with an aromatic aldehyde followed by reduction of the ester (path e) gives a 1,3-propanediol (*J. Org. Chem.* 55:4744 (1990)). Alternatively, epoxidation of cinnamyl alcohols using known methods (e.g., Sharpless epoxidations and other asymmetric epoxidation reactions) followed by reduction reactions (e.g., using Red-Al) give various 1,3-propanediols (path c). Enantioenriched 1,3-propanediols can be obtained via asymmetric reduction reactions (e.g., enantioselective borane reductions) of 3-hydroxy-ketones (*Tetrahedron Lett.* 38:761 (1997)). Alternatively, resolution of racemic 1,3-propanediols using various methods (e.g., enzymatic or chemical methods) can also give enantioenriched 1,3-propanediol. Propan-3-ols with a 1-heteroaryl substituent (e.g., a pyridyl, a quinolinyl or an isoquinolinyl) can be oxygenated to give 1-substituted 1,3-propanediols using N-oxide formation reactions followed by a rearrangement reaction in acetic anhydride conditions (path d) (*Tetrahedron* 37:1871 (1981)).

2. 2-Substituted 1,3-Propanediols

A variety of 2-substituted 1,3-propanediols useful for the synthesis of compounds of Formula I-VII can be prepared from various other 1,3-propanediols (e.g., 2-(hydroxymethyl)-1,3-propanediols) using conventional chemistry (*Comprehensive Organic Transformations*, VCH, New York, 1989). For example, as described in Scheme 11, reductions of a trialkoxycarbonylmethane under known conditions give a triol via complete reduction (path a) or a bis(hydroxymethyl) acetic acid via selective hydrolysis of one of the ester groups followed by reduction of the remaining two other ester groups. Nitrotriols are also known to give triols via reductive elimination (path b) (*Synthesis* 8:742 (1987)). Furthermore, a 2-(hydroxymethyl)-1,3-propanediol can be converted to a mono acylated derivative (e.g., acetyl, methoxycarbonyl) using an acyl chloride or an alkyl chloroformate (e.g., acetyl chloride or methyl chloroformate) (path d) using known chemistry (*Protective Groups In Organic Synthesis*; Wiley, New York, 1990). Other functional group manipulations can also be used to prepare 1,3-propanediols such as oxidation of one the hydroxymethyl groups in a 2-(hydroxymethyl)-1,3-propanediol to an aldehyde followed by addition reactions with an aryl Grignard (path c). Aldehydes can also be converted to alkyl amines via reductive amination reactions (path e).

Scheme 11

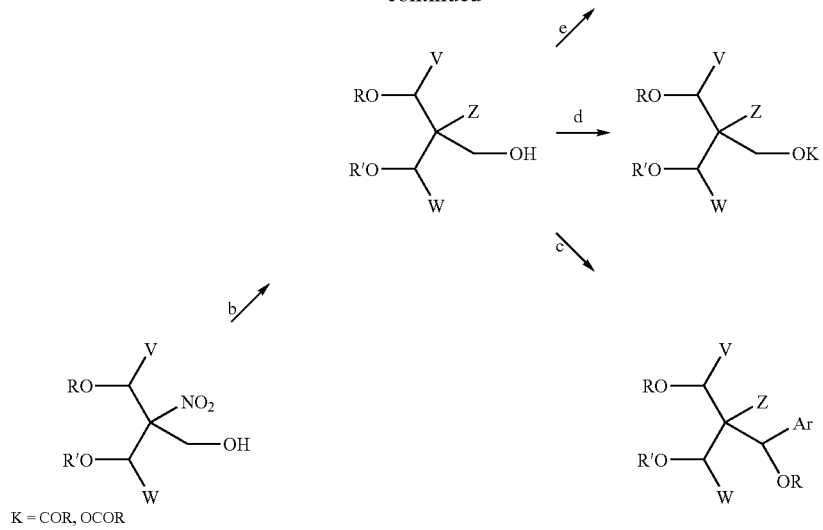

3. Annulated 1,3-Propane Diols

Compounds of Formula I-VII wherein V and Z or V and W are connected by four carbons to form a ring can be prepared from a 1,3-cyclohexanediol. For example, cis, cis-1,3,5-cyclohexanetriol can be modified to give various other 1,3,5-cyclohexanetriols which are useful for the preparations of compounds of Formula I wherein $R^{11}$ and $R^{11}$ together are

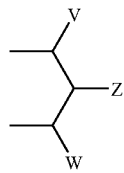

wherein together V and W are connected via 3 atoms to form a cyclic group containing 6 carbon atoms substituted with a hydroxy group. It is envisioned that these modifications can be performed either before or after formation of a cyclic phosphonate 1,3-propanediol ester. Various 1,3-cyclohexanediols can also be prepared using Diels-Alder reactions (e.g., using a pyrone as the diene: Tetrahedron Lett. 32:5295 (1991)). 2-Hydroxymethylcyclohexanols and 2-hydroxymethylcyclopentanols are useful for the preparations of compounds of Formula I wherein $R^{11}$ and $R^{11}$ together are

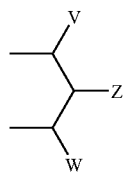

wherein together V and Z are connected via 2 or 3 atoms to form a cyclic group containing 5 or 6 carbon atoms. 1,3-Cyclohexanediol derivatives are also prepared via other cycloaddition reaction methodologies. For example, cycloadducts from the cycloadditon reactions of a nitrile oxide and an olefin can be converted to a 2-ketoethanol derivative which can be further converted to a 1,3-propanediol (including 1,3-cyclohexanediol, 2-hydroxymethylcyclohexanol and 2-hydroxymethylcyclopentanol) using known chemistry (J. Am. Chem. Soc. 107:6023 (1985)). Alternatively, precursors to 1,3-cyclohexanediol can be made from quinic acid (Tetrahedron Lett. 32:547 (1991)).

EXPERIMENTAL

Example 1

Compound 1: N-[3,5-dimethyl-4-(3'-iso-propyl-4'-hydroxyphenoxy)]-carbamoylphosphonic acid Step a:

A mixture of 3,5-dimethyl-4-(3'-iso-propyl-4'-methoxyphenoxy)aniline (J. Med. Chem. 38:695 (1995), 0.1 g, 0.35 mmol) and diphosgene (0.04 g, 0.19 mmol) in dioxane (3.0 mL) was heated at 60° C. for 3 h. The reaction mixture was cooled to room temperature and the solvent was removed under reduced pressure. To the residue was added a solution of diethyl phosphite (0.06 g, 0.42 mmol) in hexanes (1.0 mL with 3 drops of triethylamine) and the reaction mixture was heated under reflux for 3 h. The reaction mixture was cooled to room temperature and the solvent was removed under reduced pressure. The crude product was purified by column chromatography on silica gel, eluting with ethyl acetate-hexanes (1:3) to afford the diethyl phosphonate as an oil (0.1 g, 64%): $^1$H NMR (300 MHz, CDCl$_3$): δ 8.44 (s, 1H), 7.17 (s, 2H), 6.10-6.60 (m, 3H), 4.10 (m, 4H), 3.58 (s, 3H), 3.07 (m, 1H), 1.92 (s, 3H), 1.93 (s, 3H), 1.22 (m, 6H), 0.99 (m, 6H); TLC conditions: Uniplate silica gel, 250 microns; Mobile phase=hexanes-ethyl acetate (3:1); $R_f$=0.3.

Step b:

To a solution of diethyl N-[3,5-dimethyl-4-(3'-iso-propyl-4'-methoxy-phenoxy)] carbamoylphosphonate (0.1 g, 0.22 mmol) in CH$_2$Cl$_2$ (1.5 mL) at −78° C. was added bromotrimethylsilane (0.30 mL, 2.2 mmol). The reaction mixture was stirred at room temperature for 16 h and the solvent was removed under reduced pressure. The residue was dissolved in CH$_2$Cl$_2$ (2.0 mL) and the solution was cooled to −78° C. Boron tribromide (1.3 mL, 1.3 mmol, 1.0 M in CH$_2$Cl$_2$) was added and the reaction mixture was stirred at room temperature for 16 h. The reaction mixture was poured into ice and extracted with ethyl acetate (20 mL). The organic layer was dried over MgSO$_4$, filtered and concentrated under reduced pressure. The crude product was purified by preparative LC-MS to afford the title compound as a yellow solid (0.035 g, 42%): mp 67-70° C.; Anal. Calcd for (C$_{18}$H$_{22}$NO$_6$P+0.2H$_2$O+0.3 CH$_3$OH): C, 55.99; H, 6.06; N, 3.57. Found: C, 55.79; H, 6.21; N, 3.39.

Example 2

Compound 2: 1-amino-2-[3,5-diiodo-4-(4'-hydroxy-3'-iodophenoxy)-phenyl]ethylphosphonic acid Step a:

To a solution of 4-benzyloxyphenylacetyl chloride (4.0 g, 16.2 mmol) in THF (10.0 mL) at room temperature was slowly added triethyl phosphite (3.33 mL, 19.5 mmol). The reaction mixture was stirred at room temperature for 16 h and the solvent was removed under reduced pressure. The residue was treated with hexanes (20 mL) and the mixture was filtered. White solid was collected and air-dried. The solid was dissolved in pyridine (25.0 mL) and hydroxylamine hydrochloride (1.96 g, 28 mmol) was added. The reaction mixture was stirred at room temperature for 72 h and the solvent was removed under reduced pressure. The crude product was purified by column chromatography on silica gel, eluting with ethyl acetate-hexanes (7:3) to afford diethyl 2-(4-benzyloxyphenyl)-1-(hydroxyimino)ethylphosphonate as a colorless oil (5.2 g, 85%): $^1$H NMR (300 MHz, CDCl$_3$): δ 7.18-7.38 (m, 7H), 6.80 (d, J=6.2 Hz, 2H), 4.94 (s, 2H), 3.80-4.10 (m, 4H), 3.80 (s, 1H), 3.76 (s, 1H), 1.16 (t, J=6.0 Hz, 6H); TLC conditions: Uniplate silica gel, 250 microns; Mobile phase=hexanes-ethyl acetate (2:3); R$_f$=0.55.

Step b:

To a mixture of diethyl 2-(4-benzyloxyphenyl)-1-hydroxyiminoethylphosphonate (2.0 g, 5.3 mmol) and NiCl$_2$ (2.53 g, 10.6 mmol) in CH$_3$OH (40.0 mL) at room temperature was slowly added NaBH$_4$ (1.0 g, 26.4 mmol). The reaction mixture was stirred at room temperature for 16 h and the solvent was removed under reduced pressure. The residue was treated with 10% aqueous KOH (100 mL) and the mixture was extracted with ethyl ether (2×100 mL). The organic layers were dried over MgSO$_4$, filtered and concentrated under reduced pressure. The residue was dissolved in THF (14.0 mL) and (BOC)$_2$O (0.74 g, 3.4 mmol) was added. The reaction mixture was heated under reflux for 4 h and cooled to room temperature. The solvent was removed under reduced pressure and the residue was purified by column chromatography on silica gel, eluting with 4% CH$_3$OH in CH$_2$Cl$_2$ to afford diethyl 2-(4-benzyloxyphenyl)-1-(tert-butoxycarbonylamino)ethylphosphonate as an oil (1.12 g, 46%): $^1$H NMR (300 MHz, CD$_3$OD): δ 7.38 (m, 5H), 7.13 (d, J=8.4 Hz, 2H), 6.88 (d, J=8.4 Hz, 2H), 4.88 (s, 2H), 4.12 (m, 5H), 3.08 (m, 1H), 2.70 (m, 1H), 1.34 (m, 6H); TLC conditions: Uniplate silica gel, 250 microns; Mobile phase=CH$_3$OH—CH$_2$Cl$_2$ (5:95); R$_f$=0.45.

Step c:

A mixture of diethyl 2-(4-benzyloxyphenyl)-1-(tert-butoxycarbonylamino)ethylphosphonate (1.1 g, 2.4 mmol) and Pd—C (0.23 g, 10%) in CH$_3$OH (10 mL) was stirred under a H$_2$ atmosphere for 16 h and filtered through a Celite plug. The solvent was removed under reduced pressure and the residue was dissolved in CHCl$_3$ (15.0 mL). To the solution was added bis(pyridine)iodonium tetrafluoroborate (1.90 g, 5.1 mmol). The reaction mixture was stirred at room temperature for 1 h and the solvent was removed under reduced pressure. The crude product was purified by column chromatography on silica gel, eluting with acetone-hexanes (1:1) to afford diethyl 1-(tert-butoxycarbonylamino)-2-(3,5-diiodo-4-hydroxyphenyl)ethylphosphonate as a yellow solid (1.30 g, 88%): $^1$H NMR (300 MHz, CD$_3$OD): δ 7.67 (s, 2H), 7.13 (d, J=8.4 Hz, 1H), 4.00-4.25 (m, 5H), 3.00 (m, 1H), 2.64 (m, 1H), 1.38 (m, 6H); TLC conditions: Uniplate silica gel, 250 microns; Mobile phase=CH$_3$OH—CH$_2$Cl$_2$ (5:95); R$_f$=0.70.

Step d:

To a mixture of diethyl 1-(tert-butoxycarbonylamino)-2-(3,5-diiodo-4-hydroxyphenyl)ethylphosphonate (0.6 g, 0.96 mmol), 4-(tert-butyldimethylsilyloxy) phenylboronic acid (0.73 g, 2.89 mmol), copper acetate (0.21 g, 1.16 mmol) and 4A molecular sieves (1.20 g) in CH$_2$Cl$_2$ (8.0 mL) was added a solution of pyridine (0.4 mL, 4.8 mmol) and TEA (0.7 mL, 4.8 mmol). The reaction mixture was stirred at room temperature for 48 h, filtered through a Celite plug and concentrated under reduced pressure. The residue was purified by column chromatography on silica gel, eluting with acetone-hexanes (1:3) to afford diethyl 1-(tert-butoxycarbonylamino)-2-[4-(4'-(tert-butyldimethylsilyloxy)phenoxy)-3,5-diiodophenyl]ethylphosphonate as a white solid (0.48 g, 60%): $^1$H NMR (300 MHz, CD$_3$OD): δ 7.64 (s, 2H), 7.18 (d, J=8.4 Hz, 1H), 6.64 (d, J=8.4 Hz, 1H), 6.53 (d, J=8.4 Hz, 1H), 6.38 (d, J=8.4 Hz, 1H), 4.00 (m, 5H), 2.90 (m, 1H), 2.58 (m, 1H), 1.20 (m, 6H), 0.90 (m, 9H), 0.03 (s, 3H), 0.02 (s, 3 H); TLC conditions: Uniplate silica gel, 250 microns; Mobile phase=acetone-hexanes (3:7); R$_f$=0.60.

Step e:

To a mixture of diethyl 1-(tert-butoxycarbonylamino)-2-[4-(4-(tert-butyldimethylsilanyloxy)phenoxy)-3,5-diiodophenyl]ethylphosphonate (0.45 g, 0.54 mmol) in THF (6.0 mL) at 0° C. was added TBAF (0.81 mL, 0.81 mmol, 1.0 M in THF). The reaction mixture was stirred at room temperature for 20 min and the solvent was removed under reduced pressure. The crude product was purified by column chromatography on silica gel, eluting with acetone-hexanes (1:1) to afford diethyl 1-(tert-butoxycarbonylamino)-2-[3,5-diiodo-4-(4'-hydroxyphenoxy)phenyl] ethylphosphonate as a white solid (0.24 g, 62%): $^1$H NMR (300 MHz, CD$_3$OD): δ 7.74 (s, 2H), 6.58 (d, J=8.4 Hz, 2H), 6.45 (d, J=8.4 Hz, 2H), 4.12 (m, 5H), 3.08 (m, 1H), 2.64 (m, 1H), 1.32 (m, 6H); TLC conditions: Uniplate silica gel, 250 microns; Mobile phase=acetone-hexanes (1:1); R$_f$=0.40.

Step f:

A mixture of diethyl 1-(tert-butoxycarbonylamino)-2-[3,5-diiodo-4-(4'-hydroxyphenoxy) phenyl]ethylphosphonate (0.14 g, 0.20 mmol) in 70% aqueous TFA (5.0 mL) was stirred at room temperature for 1 h and the solvent was removed under reduced pressure. The residue was dissolved in C$_2$H$_5$OH (4.0 mL) and cooled to 0° C. To the solution was added 40% aqueous methylamine (0.80 mL) followed by a solution of potassium iodide (0.16 g, 0.96 mmol) and iodine (0.06 g, 0.23 mmol) in H$_2$O (0.6 mL). The reaction mixture was stirred at 0° C. for 1 h, quenched with water and extracted with ethyl acetate (2×10 mL). The organic layers were dried over MgSO$_4$, filtered and concentrated under reduced pressure. The crude product was purified by column chromatography on silica gel, eluting with 4% CH$_3$OH in CH$_2$Cl$_2$ to afford diethyl 1-amino-2-[3,5-diiodo-4-(4'-hydroxy-3'-iodophenoxy)phenyl]ethylphosphonate as a yellow solid (0.10 g, 69%): $^1$H NMR (300 MHz, CD$_3$OD): δ 7.85 (s, 2H), 7.00 (d, J=5.2 Hz, 1H), 6.74 (d, J=8.4 Hz, 1H), 6.64 (dd, J=3.2, 8.4 Hz, 1H), 4.18 (m, 5H), 3.08 (m, 1H), 2.78 (m, 1H), 1.36 (m, 6H);

TLC conditions: Uniplate silica gel, 250 microns; Mobile phase=CH$_3$OH—CH$_2$Cl$_2$ (5:95): R$_f$=0.55.

Step g:

To a mixture of diethyl 1-amino-2-[3,5-diiodo-4-(4'-hydroxy-3'-iodo-phenoxy)phenyl]ethylphosphonate (0.05 g, 0.07 mmol) in CH$_2$Cl$_2$ (2.0 mL) at −78° C. was added bromotrimethylsilane (0.18 mL, 1.34 mmol). The reaction mixture was stirred at room temperature for 24 h and the solvent was removed under reduced pressure. The crude product was treated with CH$_3$CN—H$_2$O (5.0 mL, 9:1) and the solvent was removed under reduced pressure to afford 1-amino-2-[3,5-diiodo-4-(4'-hydroxy-3'-iodophenoxy) phenyl]ethylphosphonic acid as a yellow solid (0.044 g, 95%): mp 140° C., dec; LC-MS m/z=688 [C$_{14}$H$_{13}$I$_3$NO$_5$P+H]$^+$; Anal. Calcd for (C$_{14}$H$_{13}$I$_3$NO$_5$P+1.0H$_2$O+0.3 HBr): C, 23.06; H, 2.11; N, 1.92. Found: C, 22.74; H, 2.16; N, 1.67.

Example 3

Compound 3: 2-[3,5-diiodo-4-(4'-hydroxy-3'-iodophenoxy)phenyl]ethylphosphonic acid Step a:

To a solution of tetraethyl methylenediphosphonate (1.6 g, 5.6 mmol) in THF (16.0 mL) at 0° C. was slowly added sodium hydride (0.14 g, 5.6 mmol). The reaction mixture was stirred at 0° C. for 30 min and a solution of 4-benzyloxybenzaldehyde (1.0 g, 4.7 mmol) in THF (4.0 mL) was added. The reaction mixture was stirred at 0° C. for 30 min, quenched with H$_2$O (30 mL) and extracted with ethyl acetate (30 mL). The organic layer was dried over MgSO$_4$, filtered and concentrated under reduced pressure. The crude product was purified by column chromatography on silica gel, eluting with ethyl acetate-hexanes (1:1) to afford the phosphonate as white solid (1.5 g). The solid was dissolved in CH$_3$OH (15.0 mL) and Pd—C (0.40 g) was added. The reaction mixture was stirred under a H$_2$ atmosphere for 16 h, filtered through a Celite plug and concentrated under reduced pressure to afford diethyl 2-(4-hydroxyphenyl)ethylphosphonate as an oil (1.10 g, 91%): $^1$H NMR (300 MHz, CD$_3$OD): δ 7.03 (d, J=8.4 Hz, 2H), 6.69 (d, J=8.4 Hz, 2H), 4.05 (m, 4H), 2.77 (m, 2H), 2.05 (m, 2H), 1.30 (t, J=6.9 Hz, 6H); TLC conditions: Uniplate silica gel, 250 microns; Mobile phase=hexanes-ethyl acetate (1:1); R$_f$=0.5.

Step b:

To a solution of diethyl 2-(4-hydroxyphenyl)ethylphosphonate (0.5 g, 1.9 mmol) in CH$_2$Cl$_2$ (12.0 mL) at room temperature was added bis(pyridine)iodonium tetrafluoroborate (1.6 g, 4.3 mmol). The reaction mixture was stirred at room temperature for 1 h and the solvent was removed under reduced pressure. The crude product was purified by column chromatography on silica gel, eluting with acetone-hexanes (1:1) to afford diethyl 2-(3,5-diiodo-4-hydroxyphenyl)ethylphosphonate as a white solid (0.92 g, 90%): $^1$H NMR (300 MHz, CD$_3$OD): δ 7.62 (s, 2H), 4.05 (m, 4H), 2.77 (m, 2H), 2.05 (m, 2H), 1.29 (t, J=6.9 Hz, 6H); TLC conditions: Uniplate silica gel, 250 microns; Mobile phase=acetone-hexanes (1:1); R$_f$=0.57.

Step c:

Diethyl 2-[3,5-diiodo-4-(4'-hydroxyphenoxy)phenyl]ethylphosphonate was synthesized from diethyl 2-(3,5-diiodo-4-hydroxyphenyl)ethylphosphonate (0.5 g, 0.98 mmol) by following the procedure described in example 2, step d followed by example 2, step e: white solid (0.15 g, 25%) $^1$H NMR (300 MHz, CD$_3$OD): δ 7.81 (s, 2H), 6.68 (d, J=8.4 Hz, 2H), 6.53 (d, J=8.4 Hz, 2H), 4.07 (m, 4H), 2.84 (m, 2H), 2.16 (m, 2H), 1.32 (t, J=6.9 Hz, 6H); TLC conditions: Uniplate silica gel, 250 microns; Mobile phase=acetone-hexanes (1:1); phenol: R$_f$=0.35.

Step d:

To a solution of diethyl 2-[3,5-diiodo-4-(4'-hydroxyphenoxy)phenyl] ethylphosphonate (0.15 g, 0.25 mmol) in ethanol (5.0 mL) at 0° C. was slowly added a solution of potassium iodide (0.19 g, 0.75 mmol) and iodine (0.07 g, 0.3 mmol) in H$_2$O (0.5 mL). The reaction mixture was stirred at 0° C. for 1 h, quenched with H$_2$O (10.0 mL) and extracted with ethyl acetate (15.0 mL). The organic layer was dried over MgSO$_4$, filtered and concentrated under reduced pressure. The crude product was purified by column chromatography on silica gel, eluting with 2% CH$_3$OH in CH$_2$Cl$_2$ to afford diethyl 2-[3,5-diiodo-4-(4'-hydroxy-3'-iodophenoxy)phenyl]ethylphosphonate as a white solid (0.10 g, 56%): $^1$H NMR (300 MHz, CD$_3$OD): δ 7.83 (s, 2H), 6.96 (d, J=5.4 Hz, 1H), 6.73 (d, J=8.4 Hz, 2H), 6.62 (dd, J=4.2, 8.4 Hz, 1H), 4.08 (m, 4H), 2.88 (m, 2H), 2.18 (m, 2H), 1.32 (t, J=6.9 Hz, 6H); TLC conditions: Uniplate silica gel, 250 microns; Mobile phase =CH$_3$OH—CH$_2$Cl$_2$ (5:95); R$_f$=0.50.

Step e:

To a solution of diethyl 2-[3,5-diiodo-4-(4'-hydroxy-3'-iodophenoxy)phenyl] ethylphosphonate (0.06 g, 0.08 mmol) in CH$_2$Cl$_2$ (1.5 mL) at 0° C. was slowly added bromotrimethylsilane (0.11 mL, 0.80 mmol). The reaction mixture was stirred at room temperature for 16 h and the solvent was removed under reduced pressure. The residue was treated with CH$_3$CN—H$_2$O (1:1, 5.0 mL) and the solvent was removed under reduced pressure to afford 2-[3,5-diiodo-4-(4'-hydroxy-3'-iodophenoxy)phenyl]ethylphosphonic acid as an off-white solid (0.05 g, 96%): mp 188° C., dec; LC-MS m/z=673 [C$_{14}$H$_{12}$I$_3$O$_5$P+H]$^+$; Anal. Calcd for (C$_{14}$H$_{12}$I$_3$O$_5$P+1.0 CH$_3$OH+0.3 HBr): C, 24.45; H, 2.02; I, 53.45. Found: C, 24.79; H, 1.87; I, 53.36.

Example 4

Compound 4: 2-[3,5-diiodo-4-(4'-hydroxy-3'-isopropylphenoxy)-phenyl]ethylphosphonic acid Step a:

To a mixture of bis(4-methoxy-3-iso-propylphenyl)iodonium tetrafluoroborate (0.30 g, 0.59 mmol, Yokoyama et al. *J. Med. Chem.* 38:695 (1995)) and copper (0.05 g, 0.78 mmol) in CH$_2$Cl$_2$ (1.5 mL) at 0° C. was slowly added a solution of diethyl 2-(3,5-diiodo-4-hydroxyphenyl)ethylphosphonate (0.2 g, 0.39 mmol) and TEA (0.10 mL, 0.66 mmol) in CH$_2$Cl$_2$ (0.6 mL). The reaction mixture was stirred at room temperature for 96 h, filtered through a Celite plug and concentrated under reduced pressure. The crude product was purified by column chromatography on silica gel, eluting with acetone-hexanes (2:3) to afford diethyl 2-[3,5-diiodo-4-(4'-methoxy-3'-iso-propylphenoxy)phenyl]ethylphosphonate as an off-white solid (0.25 g, 97%): $^1$H NMR (300 MHz, CD$_3$OD): δ 7.82 (s, 2H), 6.78 (d, J=9.0 Hz, 1H), 6.68 (d, J=3.0 Hz, 1H), 4.07 (m, 4H), 3.30 (m, 1H), 2.85 (m, 2H), 2.18 (m, 2H), 1.30 (t, J=6.9 Hz, 6H), 1.15 (d, J=7.2 Hz, 6H); TLC conditions: Uniplate silica gel, 250 microns; Mobile phase=acetone-hexanes (3:7); R$_f$=0.64.

Step b:

To a solution of diethyl 2-[3,5-diiodo-4-(4'-methoxy-3'-iso-propylphenoxy) phenyl]ethylphosphonate (0.25 g, 0.38 mmol) in CH$_2$Cl$_2$ (3.0 mL) at 0° C. was slowly added bromotrimethylsilane (0.60 mL, 3.8 mmol). The reaction mixture was stirred at room temperature for 16 h and the solvent was removed under reduced pressure. The residue was dissolved in CH$_2$Cl$_2$ (3.0 mL) and cooled to −78° C. Boron tribromide (1.80 mL, 1.80 mmol, 1.0 M CH$_2$Cl$_2$) was slowly added and the reaction mixture was stirred at room temperature for 16 h. The reaction mixture was poured into ice (50 g) and extracted with ethyl acetate (20 mL). The organic layer was dried over MgSO$_4$, filtered and concentrated to afford 2-[3,5-diiodo-4-(4'-hydroxy-3'-iso-propylphenoxy)phenyl]ethylphosphonic acid as an off-white solid (0.20 g, 91%): mp 184-186° C.; LC-MS m/z=589 [C$_{17}$H$_{19}$I$_2$O$_5$P+H]$^+$; Anal. Calcd for C$_{17}$H$_{19}$I$_2$O$_5$P: C, 34.72; H, 3.26. Found: C, 34.75; H, 3.12.

Example 5

Compound 5: 3,5-diiodo-4-(4'-hydroxy-3'-iso-propylphenoxy)-benzylphosphonic acid Step a:

A mixture of 4-benzyloxybenzyl bromide (Chow et al., *J. Org. Chem.* 62:5116-27 (1997)) (1.0 g, 4.4 mmol) and triethyl phosphite (1.0 mL, 5.8 mmol) in DMF (2.8 mL) was heated at 155° C. for 4 h. The reaction mixture was cooled to room temperature, quenched with H$_2$O (10 mL) and extracted with ethyl acetate (20 mL). The organic layer was dried over MgSO$_4$, filtered and concentrated under reduced pressure. The crude product was purified by column chromatography on silica gel, eluting with acetone-hexanes (2:3) to afford the phosphonate as an oil (1.3 g). The phosphonate was dissolved in CH$_3$OH (12.0 mL) and Pd—C (10%, 0.33 g) was added. The reaction mixture was stirred under a H$_2$ atmosphere for 16 h, filtered through a Celite plug and concentrated under reduced pressure to afford diethyl 4-hydroxybenzylphosphonate as an oil (0.9 g, 84%): $^1$H NMR (300 MHz, CD$_3$OD): δ 7.12 (d, J=8.4 Hz, 2H), 6.73 (d, J=8.4 Hz, 2H), 4.05 (m, 4H), 3.16 (s, 1H), 3.09 (s, 1H), 1.26 (t, J=6.9 Hz, 6H); TLC conditions: Uniplate silica gel, 250 microns; Mobile phase=acetone-hexanes (1:1); R$_f$=0.5.

Step b:

Diethyl 3,5-diiodo-4-hydroxybenzylphosphonate (0.85 g, 85%) was synthesized from diethyl 4-hydroxybenzylphosphonate (0.5 g, 2.1 mmol) by following the procedure described in example 3, step b: $^1$H NMR (300 MHz, CD$_3$OD): δ 7.67 (d, J=2.7 Hz, 2H), 4.08 (m, 4H), 3.15 (s, 1H), 3.08 (s, 1H), 1.28 (t, J=6.9 Hz, 6H); TLC conditions: Uniplate silica gel, 250 microns; Mobile phase=acetone-hexanes (2:3); R$_f$=0.6.

Step c:

Diethyl 3,5-diiodo-4-(4'-methoxy-3'-iso-propylphenoxy)benzylphosphonate (0.22 g, 88%) was synthesized from diethyl 3,5-diiodo-4-hydroxybenzylphosphonate (0.2 g, 0.4 mmol) by following the procedure described in example 4, step a: $^1$H NMR (300 MHz, CD$_3$OD): δ 7.87 (d, J=2.7 Hz, 2H), 6.80 (d, J=8.7 Hz, 1H), 6.62 (d, J=2.0 Hz, 1H) 6.42 (dd, J=3.3, 8.7 Hz, 1H), 4.08 (m, 4H), 3.78 (s, 3H), 3.25 (m, 3H), 1.32 (t, J=6.9 Hz, 6H), 1.14 (d, J=6.9 Hz, 6H); TLC conditions: Uniplate silica gel, 250 microns; Mobile phase=acetone-hexanes (2:3); R$_f$=0.6.

Step d:

3,5-Diiodo-4-(4'-hydroxy-3'-iso-propylphenoxy)benzylphosphonic acid (0.18 g, 92%) was synthesized from diethyl 3,5-diiodo-4-(3'-iso-propyl-4'-methoxyphenoxy)benzylphosphonate (0.22 g, 0.34 mmol) by following the procedure described in example 4, step b: mp>220° C.; LC-MS m/z=575 [C$_{16}$H$_{17}$I$_2$O$_4$P+H]$^+$; Anal. Calcd for (C$_{16}$H$_{17}$I$_2$O$_5$P+0.3H$_2$O+0.5CH$_3$OH): C, 33.28; H, 3.32; I, 42.62. Found: C, 33.49; H, 3.23; I, 42.51.

Example 6

Compound 6: 3,5-diiodo-4-(4'-hydroxy-3'-iodophenoxy)benzylphosphonic acid

Step a:

Diethyl 3,5-diiodo-4-(4'-hydroxyphenoxy)benzylphosphonate (0.11 g, 17%) was obtained from diethyl 3,5-diiodo-4-hydroxybenzylphosphonate (0.55 g, 1.1 mmol) by following the procedure described in example 3, step c: $^1$H NMR (300 MHz, CD$_3$OD): δ 7.87 (d, J=2.7 Hz, 2H), 6.70 (d, J=8.7 Hz, 2H), 6.54 (d, J=2.0 Hz, 2H) 4.10 (m, 4H), 3.30 (s, 1H), 3.22 (s, 1H), 1.31 (m, 6H); TLC conditions: Uniplate silica gel, 250 microns; Mobile phase=acetone-hexanes (1:1); R$_f$=0.4.

Step b:

Diethyl 3,5-diiodo-4-(4'-hydroxy-3'-iodophenoxy)benzylphosphonate (0.08 g, 63%) was obtained from diethyl 3,5-diiodo-4-(4'-hydroxyphenoxy)benzylphosphonate (0.1 g, 0.1 mmol) by following the procedure described in example 3, step d: $^1$H NMR (300 MHz, CD$_3$OD): δ 7.87 (d, J=2.4 Hz, 2H), 6.92 (d, J=6.4 Hz, 1H), 6.74 (d, J=8.7 Hz, 1H), 6.62 (dd, J=2.4, 8.7 Hz, 1H), 4.10 (m, 4H), 3.30 (s, 1H), 3.22 (s, 1H), 1.31 (t, J=6.9 Hz, 6H); TLC conditions: Uniplate silica gel, 250 microns; Mobile phase=CH$_3$OH—CH$_2$Cl$_2$ (2:98); R$_f$=0.6.

Step c:

3,5-Diiodo-4-(4'-hydroxy-3'-iodophenoxy)benzylphosphonic acid (0.06 g, 90%) was obtained from diethyl 4-(4'-hydroxy-3'-iodophenoxy)-3,5-diiodobenzylphosphonate (0.08 g, 0.1 mmol) by following the procedure described in example 3, step e: mp 168° C., dec; LC-MS m/z=659 [C$_{13}$H$_{10}$I$_3$O$_5$P+H]$^+$; Anal. Calcd for (C$_{13}$H$_{10}$I$_3$O$_5$P+1.6H$_2$O+0.5CH$_3$OH): C, 23.07; H, 2.18; I, 54.17. Found: C, 22.71; H, 1.80; I, 53.82.

Example 7

Compound 7: [3,5-dimethyl-4-(4'-hydroxy-3'-iso-propylbenzyl)phenoxy]-methylphosphonic acid Step a:

To a stirring solution of NaH (0.855 g, 21.4 mmol) in DMF (40.0 mL) at 0° C. was added a solution of 3,5-dimethyl-4-(4'-methoxymethoxy-3'-iso-propylbenzyl)phenol (5.60 g, 17.8 mmol), (Chiellini et al., *Bioorg. Med. Chem. Lett.* 10:2607 (2000)) in DMF (7.0 mL). The reaction mixture was stirred at room temperature for 1 h and cooled to 0° C. A solution of diethyl tosyloxymethylphosphonate (6.89 g, 21.4 mmol) in DMF (7.0 mL) was added. The reaction mixture was stirred at room temperature for 16 h, quenched with CH$_3$OH followed by dilution with water (100 mL) and extracted with ether (100 mL×2). The combined organic layers were dried over MgSO$_4$, filtered and concentrated under reduced pressure. The crude product was purified by column chromatography on silica gel, eluting with acetone-hexanes (1:3) to afford diethyl [3,5-dimethyl-4-(4'-methoxymethoxy-3'-iso-propylbenzyl)phenoxy]methylphosphonate as a colorless oil (5.32 g, 64%): $^1$H NMR (300 MHz, DMSO-d$_6$): δ 6.94 (d, J=3.0 Hz, 1H), 6.87 (d, J=9.0 Hz, 1H), 6.73 (s, 2H), 6.58 (m, 1H), 5.14 (s, 2H), 4.36 (d, J=9.0 Hz, 2H), 4.10 (m, 4H), 3.85 (s, 2H), 3.36 (s, 3H), 3.21 (m, 1H), 2.17 (d, J=6.0 Hz, 6H), 1.25 (m, 6H), 1.12-1.10 (d, J=6.0 Hz, 6H); TLC conditions: Uniplate silica gel, 250 microns; Mobile phase=hexanes-acetone (1:1); R$_f$=0.62.

Step b:

To a solution of diethyl 3,5-dimethyl-4-(4'-methoxymethoxy-3'-iso-propyl-benzyl)phenoxymethylphosphonate (5.32 g, 11.45 mmol) in dichloromethane (60.0 mL) at 0° C. was added bromotrimethylsilane (22.67 mL, 171.7 mmol). The reaction mixture was stirred at room temperature for 16 h and the solvent was removed under reduced pressure. The residue was treated with acetonitrile-water (1:1, 50 mL) and the solvent was removed under reduced pressure. The residue was treated with toluene and sonicated for 10 min. The mixture was filtered and washed with hexanes to afford [3,5-dimethyl-4-(4'-hydroxy-3'-iso-propylbenzyl)phenoxy]methylphosphonic acid as a pink solid (4.00 g, 95%): mp 55-58° C.; LC-MS m/z=365 $[C_{19}H_{25}O_5P+H]^+$; Anal. Calcd for $(C_{19}H_{25}O_5P+0.5H_2O+0.2\ CH_3OH)$: C, 60.72; H, 7.11. Found: C, 60.72, H, 7.18.

Using the appropriate starting material, compounds 7-1 to 7-21 were prepared in an analogous manner to that described for the synthesis of compound 7.

Compound 7-1: [3,5-dimethyl-4-(4'-hydroxy-3'-phenylbenzyl)phenoxy]-methylphosphonic acid Intermediate 3,5-dimethyl-4-(4'-methoxymethoxy-3'-phenylbenzyl) phenol was prepared from 2-phenylphenol according to the procedure described in Chiellini et al., *Bioorg. Med. Chem. Lett.* 10:2607 (2000) and transformed into the title compound by the procedure used for the synthesis of compound 7. $^1$H NMR (300 MHz, DMSO-$d_6$): δ 9.29 (s, 1H), 6.60-7.60 (m, 8H), 4.02 (d, J=15 Hz, 2H), 2.18 (s, 2H); LC-MS m/z=399 $[C_{29}H_{41}O_{11}P+H]^+$; Anal. Calcd for $(C_{29}H_{41}O_{11}P+1.7H_2O+0.4\ CH_3OH)$: C, 60.89; H, 6.39. Found: C, 60.53; H, 6.19.

Compound 7-2: [3,5-dimethoxy-4-(4'-hydroxy-3'-iso-propylbenzyl)-phenoxy]methylphosphonic acid Intermediate 3,5-dimethoxy-4-(3'-iso-propyl-4'-methoxymethoxy-benzyl)phenol was prepared from 2,6-dimethoxy-4-hydroxybenzaldehyde according to the procedure described in Chiellini et al., *Bioorg. Med. Chem. Lett.* 10:2607 (2000) and transformed into the title compound by the procedure used for the synthesis of compound 7. $^1$H NMR (300 MHz, DMSO-$d_6$): δ 8.86 (s, 1H), 6.96 (d, J=1.8 Hz, 1H), 6.64 (dd, J=1.8 Hz, J=8.4 Hz, 1H), 6.54 (d, J=8.4 Hz, 1H), 6.27 (s, 2H), 4.07 (d, J=10.2 Hz, 2H), 3.74 (s, 6H), 3.64 (s, 2H), 3.08 (m, 1H), 1.08 (d, J=6.9 Hz, 6H); LC-MS m/z=397 $[C_{19}H_{25}O_7P+H]^+$; Anal Calcd for $(C_{19}H_{25}O_7P+0.4\ CH_3CO_2C_2H_5+0.9H_2O)$: C, 55.25; H, 6.75. Found: C, 55.22; H, 7.13.

Compound 7-3: [3,5-dimethyl-4-(3'-sec-butyl-4'-hydroxybenzyl)phenoxy]-methylphosphonic acid Intermediate 3,5-dimethyl-4-(3'-sec-butyl-4'-methoxymethoxybenzyl) phenol was prepared from commercially available 2-sec-butylphenol according to the procedure described in Chiellini et al., *Bioorg. Med. Chem. Lett.* 10:2607 (2000) and transformed into the title compound by the procedure used for the synthesis of compound 7. $^1$H NMR (200 MHz, DMSO-$d_6$): δ 8.92 (s, 1H), 6.77 (s, 1H), 6.68 (s, 2H), 6.61 (d, J=8.6 Hz, 1H), 6.47 (d, J=8.6 Hz, 1H), 4.02 (d, J=10.2 Hz, 2H), 3.78 (s, 2H), 2.90 (m, 1H), 1.45 (q, J=6.6 Hz, 2H), 1.05 (d, J=7.0 Hz, 3H), 0.74 (t, J=7.0 Hz, 3H); LC-MS m/z=379 $[C_{20}H_{27}O_5P+H]^+$; Anal Calcd for $(C_{20}H_{27}O_5P+0.7H_2O)$: C, 61.43; H, 7.32. Found: C, 61.22; H, 7.55.

Compound 7-4: [3,5-dimethyl-4-(3'-iso-propyl-4'-methoxybenzyl)phenoxy]-methylphosphonic acid Intermediate 3,5-dimethyl-4-(3'-iso-propyl-4'-methoxybenzyl)phenol was prepared from 2-iso-propylanisole according to the procedure described in Chiellini et al., *Bioorg. Med. Chem. Lett.* 10:2607 (2000) and transformed into the title compound by the procedure used for the synthesis of compound 7. $^1$H NMR (300 MHz, DMSO-$d_6$): δ 6.99 (d, J=2.1 Hz, 1H), 6.88 (d, J=8.4 Hz, 1H), 6.76 (s, 2H), 6.66 (m, 1H), 4.09 (d, J=10.2 Hz, 2H), 3.91 (s, 2H), 3.78 (s, 3H), 3.23 (m, 1H), 2.29 (s, 6H), 1.16 (d, J=7.2 Hz, 6H); LC-MS m/z=378 $[C_{20}H_{27}O_5P+H]^-$; Anal. Calcd for $(C_{20}H_{27}O_5P+0.3H_2O)$: C, 62.59; H, 7.25. Found: C, 62.37; H, 7.40.

Compound 7-5: [3,5-dichloro-4-(4'-hydroxy-3'-iso-propylbenzyl)phenoxy] methylphosphonic acid Intermediate 3,5-dichloro-4-(3'-sec-butyl-4'-methoxymethoxy-benzyl)phenol was prepared from 2,6-dichloro-4-benzyloxybenzaldehyde (*Organic Letters* 4:2833 (2000)) according to the procedure described in Chiellini et al., *Bioorg. Med. Chem. Lett.* 10:2607 (2000) and transformed into the title compound by the procedure used for the synthesis of compound 7. m.p.: 118-120° C.; $^1$H NMR (300 MHz, CD$_3$OD): δ 7.01 (s, 2H), 6.87 (d, J=1.8 Hz, 1H), 6.60 (dd, J=3.0, 8.4 Hz, 1H), 6.47 (d, J=8.4 Hz, 1H), 4.12 (d, J=9.9 Hz, 2H), 4.02 (s, 2H), 3.20-3.10 (m, 1H), 1.03 (d, J=6.9 Hz, 6H); LC-MS m/z=405 $[C_{17}H_{19}Cl_2O_5P]^+$; Anal Calcd for: $(C_{17}H_{19}Cl_2O_5P)$: C, 50.39, H, 4.73 Cl: 17.60. Found: C, 50.33, H, 5.03; Cl, 16.09.

Compound 7-6: difluoro-[3,5-dimethyl-4-(4'-hydroxy-3'-iso-propylbenzyl)-phenoxy]methylphosphonic acid Intermediate 3,5-dimethyl-4-(3'-iso-propyl-4'-methoxymethoxy-benzyl)phenol was prepared from 2-iso-propylphenol according to the procedure described in Chiellini et al., *Bioorg. Med. Chem. Lett.* 10:2607 (2000) and transformed into the title compound by the procedure used for the synthesis of compound 7 using diethyl bromodifluoromethylphosphonate. $^1$H NMR (300 MHz, DMSO-$d_6$): δ 9.02 (s, 1H), 6.88 (m, 3H), 6.65 (m, 1H), 4.46 (m, 1H), 3.84 (s, 3H), 3.12 (s, 2H), 3.12 (m, 1H), 2.19 (s, 6H), 1.12 (d, J=6.0 Hz, 6H); HPLC conditions: Column=3 Chromolith SpeedRODs RP-18e, 100×4.6 mm; Mobile phase=Solvent A (Acetonitrile)=HPLC grade acetonitrile; Solvent B (buffer)=20 mM ammonium phosphate buffer (pH 6.1, 0.018 M NH$_4$H$_2$PO$_4$/0.002 M (NH$_4$)$_2$HPO$_4$) with 5% acetonitrile. Flow rate=4 mL/min; UV@ 255 nm. Retention time in minutes (rt=5.68, 95% purity).

Compound 7-7: [3,5-dimethyl-4-[4'-hydroxy-3'-methylbenzyl]phenoxy]-methylphosphonic acid Intermediate 3,5-dimethyl-4-[3'-methyl-4'-methoxymethoxy-benzyl]phenol was prepared from 4-bromo-2-methyl-phenol according to the procedure described in Chiellini et al., *Bioorg. Med. Chem. Lett.* 10:2607 (2000) and transformed into the title compound by the procedure used for the synthesis of compound 7. mp>230° C.; $^1$H NMR (300 MHz, DMSO-$d_6$): δ 8.99(s, 1H), 6.68-6.525(m, 5H), 6.71(s, 2H), 4.03(d, 2H, J=7.5 Hz), 3.77(s, 2H), 2.15(s, 6H), 2.02(s, 3H); LC-MS m/z=335 $[C_{17}H_{21}O_5P-H]$; TLC conditions: Uniplate silica gel, 250 microns; Mobile phase=isopropyl alcohol/water/ammonium hydroxide [7:2:1]; $R_f$=0.23; Anal. Calcd for ($C_{17}H_{21}O_5P$+0.6$H_2O$): C, 58.82; H, 6.45; Found: C, 58.73, H, 6.73.

Compound 7-8: [3,5-dimethyl-4-[3'-ethyl-4'-hydroxybenzyl]phenoxy]-methylphosphonic acid Intermediate 3,5-dimethyl-4-[3'-ethyl-4'-methoxymethoxy-benzyl]phenol was prepared from 4-bromo-2-ethyl-phenol according to the procedure described in Chiellini et al., *Bioorg. Med. Chem. Lett.* 10:2607 (2000) and transformed into the title compound by the procedure used for the synthesis of compound 7. $^1$H NMR (300 MHz, DMSO-$d_6$): δ 8.96(s, 1H), 6.72-6.49(m, 5H), 4.03(d, 2H, J=10.2 Hz), 3.78(s, 2H), 2.48(q, 2H, J=8.1 Hz), 2.16(s, 6H), 1.06(t, 3H, J=7.5 Hz); LC-MS m/z=349 [$C_{18}H_{23}O_5P$-H]; TLC conditions: Uniplate silica gel, 250 microns; Mobile phase=Isopropyl alcohol/ammonium hydroxide/water [7:2:1]; $R_f$=0.20; Anal. Calcd for ($C_{17}H_{21}O_5P$+1.3$H_2O$+0.3 $CH_2Cl_2$): C, 55.30; H, 6.59; Found: C, 55.36, H, 6.66.

Compound 7-9: [3,5-dimethyl-4-[3'-(1-ethylpropyl)-4'-hydroxybenzyl]-phenoxy]methylphosphonic acid Intermediate 3,5-dimethyl-4-[3'-(1-ethylpropyl)-4'-methoxymethoxy-benzyl]phenol was prepared from 2-(1-ethylpropyl)phenol (*J. Chem. Soc. Perkins Trans.* 2: 165 (1985)) according to the procedure described in Chiellini et al., *Bioorg. Med. Chem. Lett.* 10:2607 (2000) and transformed into the title compound by the procedure used for the synthesis of compound 7. m.p. 60-64° C.; $^1$H NMR (300 MHz, DMSO-$d_6$): δ 8.84 (s, 1H), 6.72 (s, 1H), 6.67 (s, 2H), 6.60 (m, 1H), 6.46 (m, 1H), 4.04 (d, J=9.0 Hz, 2H), 3.78 (s, 2H), 2.74 (m, 1H), 2.15 (s, 6H), 1.49 (m, 4H), 0.68 (m, 6H); LC-MS m/z=393 [$C_{21}H_{29}O_5P$+H]$^+$; Anal. Calcd for ($C_{21}H_{29}O_5P$+0.5$H_2O$+0.2 $CH_3CO_2CH_2CH_3$): C, 62.48; H, 7.60. Found: C, 62.22; H, 7.83.

Compound 7-10: [3,5-dimethyl-4-(4'-hydroxy-3'-iso-propyl-5'-methyl-benzyl)phenoxy]methylphosphonic Acid Intermediate 3,5-dimethyl-4-(3'-iso-propyl-5'-methyl-4'-methoxymethoxy-benzyl)phenol was prepared from 2-iso-propyl-6-methylphenol (*J. Med. Chem.* 12:1350 (1980)) according to the procedure described in Chiellini et al., *Bioorg. Med. Chem. Lett.* 10:2607 (2000) and transformed into the title compound by the procedure used for the synthesis of compound 7. mp: 65-68° C.; $^1$H NMR (300 MHz, CD$_3$OD): δ 6.75 (s, 2H), 6.69 (d, J=2.1 Hz, 1H), 6.49 (d, J=2.1 Hz, 1H), 4.22 (d, J=10.2 Hz, 2H), 3.89 (s, 2H), 3.27 (m, 1H), 2.23 (s, 6H), 2.14 (s, 3H), 1.15 (d, J=7.2 Hz, 6H); LC-MS m/z=377 [$C_{20}H_{27}O_5P$-H]$^+$; Anal. Calcd for ($C_{20}H_{27}O_5P$+1.0$H_2O$): C, 60.60; H, 6.37. Found: C, 60.70; H, 7.75.

Compound 7-11: [3,5-dimethyl-4-(5'-fluoro-4'-hydroxy-3'-iso-propylbenzyl)-phenoxy]methylphosphonic acid Step a:
To a mixture of 4-bromo-2-fluoroanisole (2.0 g, 9.70 mmol) and 2-propanol (1.2 g, 19.4 mmol) at room temperature was added 80% $H_2SO_4$ (10.0 mL). The reaction mixture was heated at 80° C. for 12 h, cooled to room temperature, quenched with ice (50 g) and extracted with ether (20 mL×2). The combined organic extracts were dried over MgSO$_4$, filtered and concentrated under reduced pressure. The crude product was purified by column chromatography on silica gel, eluting with 5% ethyl acetate in hexanes to afford 4-bromo-6-fluoro-2-iso-propylanisole (0.92 g, 38%): $^1$H NMR (300 MHz, CD$_3$OD): δ 7.36 (d, J=10.5 Hz, 1H), 7.22 (d, J=10.5 Hz, 1H), 3.91 (s, 3H), 3.24 (m, 1H), 1.26 (d, J=6.6 Hz, 6H); TLC conditions: Uniplate silica gel, 250 microns; Mobile phase=ethyl acetate-hexanes (5:95); $R_f$=0.50.

Step b:
To a solution of 4-bromo-6-fluoro-2-iso-propylanisole (0.92 g, 3.70 mmol) in CH$_2$Cl$_2$ (10.0 mL) at −78° C. was added BBr$_3$ (5.5 mL, 5.5 mmol, 1.0 M in CH$_2$Cl$_2$). After 5 min, the reaction mixture was stirred at room temperature for 16 h, poured into ice (50 g) and extracted with ethyl acetate (20.0 mL). The organic layer was separated, dried over MgSO$_4$ and filtered. The solvent was removed under reduced pressure to afford 4-bromo-6-fluoro-2-iso-propylphenol (0.90 g, 100%) as a dark oil, which was used for the next step without further purification: $^1$H NMR (300 MHz, CD$_3$OD): δ 7.26 (d, J=10.5 Hz, 1H), 6.92 (d, J=10.5 Hz, 1H), 3.30 (m, 1H), 1.23 (d, J=6.6 Hz, 6H); TLC conditions: Uniplate silica gel, 250 microns; Mobile phase=ethyl acetate-hexanes (1:9); $R_f$=0.40.

Intermediate 3,5-dimethyl-4-(5'-fluoro-3'-iso-propyl-4'-methoxy-methoxybenzyl)phenol was prepared from 4-bromo-6-fluoro-2-iso-propylphenol according to the procedure described in Chiellini et al., *Bioorg. Med. Chem. Lett.* 10:2607 (2000) and transformed into the title compound by the procedure used for the synthesis of compound 7. mp: 166-168° C.; $^1$H NMR (300 MHz, CD$_3$OD): δ 6.89 (d, J=9.0 Hz, 1H), 6.80 (s, 2H), 6.03 (d, J=9.0 Hz, 1H), 4.25 (d, J=8.4 Hz, 2H), 3.91 (s, 2H), 3.34 (m, 1H), 2.18 (s, 6H), 1.30 (d, J=6.9 Hz, 6H); LC-MS m/z=383 [$C_{19}H_{24}FO_5P$+H]$^+$; Anal Calcd for ($C_{19}H_{24}FO_5P$+0.6$H_2O$): C, 58.04; H, 6.46. Found: C, 57.88; H, 6.46.

Compound 7-12: [4-(4'-acetylamino-3'-iso-propyl-benzyl)-3,5-dimethyl-phenoxy]methylphosphonic acid Step a:
To a cooled solution of 2-iso-propyl aniline (714 mg, 5.28 mmol) in dichloromethane (20 mL) at −50° C. in a dry ice/acetone bath was added a solution of bromine (269 μl, 5.28 mmol) in dichloromethane (5 mL) over 20 min. After completion of the addition, the reaction mixture was stirred for an additional hour. Purification by column chromatography (silica gel, hexane/ethyl acetate) gave 4-bromo-2-iso-propyl-phenylamine as a brown oil (1.53 g, 57%); $^1$H NMR (300 MHz, DMSO-$d_6$): δ 7.01(m, 2H), 6.55(d, 1H, J=13 Hz), 5.05(bs, 2H), 2.92(m, 1H), 1.11 (d, 6H, J=7 Hz); TLC conditions: Uniplate silica gel, 250 microns; Mobile phase=Hexane/ethyl acetate [10:1]; $R_f$=0.11

Step b:
A solution of 4-bromo-2-iso-propyl-phenylamine (780 mg, 3.64 mmol) in acetic anhydride (4 mL) was stirred at room temperature over night. The reaction was poured into water and the resulting white precipitate was filtered off and dried under vacuum to give N-(4-bromo-2-iso-propyl-phenyl)-acetamide as a light pink solid (0.770 g, 83%); $^1$H NMR (300 MHz, DMSO-$d_6$): δ 9.39(s, 1H), 7.43(d, 1H, J=2.4 Hz), 3.16(m, 1H), 2.04(s, 3H), 1.13(d, 6H, J=7 Hz); TLC conditions: Uniplate silica gel, 250 microns; Mobile phase=dichloromethane; $R_f$=0.21

Intermediate 3,5-dimethyl-4-(5'-fluoro-3'-iso-propyl-4'-methoxy-methoxybenzyl)phenol was prepared from N-(4-bromo-2-iso-propyl-phenyl)-acetamide according to the procedure described in Chiellini et al., *Bioorg. Med. Chem. Lett.*

10:2607 (2000) and transformed into the title compound by the procedure used for the synthesis of compound 7: mp>230° C.; LC-MS m/z=404 [$C_{21}H_{28}NO_5P-H$]; 1H NMR (300 MHz, DMSO-$d_6$): δ 9.23(s, 1H), 7.03(m, 2H), 6.71(s, 2H), 6.60(d, 1H, J=9.3 Hz), 4.04(d, 2H, J=9.3 Hz), 3.91(s, 2H), 2.17(s, 6H), 2.00(s, 3H), 1.06(d, 6H, J=6.9 Hz); TLC conditions: Uniplate silica gel, 250 microns; Mobile phase=isopropyl alcohol/water/ammonium hydroxide [7:2:1]; Rf=0.26; Anal. Calcd for ($C_{21}H_{28}NO_5P+0.4H_2O$): C, 61.13; H, 7.03; N, 3.39 Found: C, 61.36, H, 7.22, N, 3.03.

Compound 7-13: [4-(3'-iso-propyl-4'-methanesulfonylaminobenzyl)-3,5-dimethyl phenoxy]methylphosphonic acid Step a:
Intermediate N-[4-(4'-hydroxy-2',6'-dimethyl-benzyl)-2-iso-propyl-phenyl]-acetamide from the synthesis of compound 7-12 (320 mg, 0.68 mmol) was combined with HCl (10 mL) and water (2 mL) in a round bottom flask and heated at reflux over night. The solvent was removed under reduced pressure and the resulting solid was dissolved in a mixture of ethyl acetate (50 mL) and water (2 mL). The organic layer was removed and dried over sodium sulfate, filtered and concentrated under reduced pressure to give 4-(4'-amino-3'-iso-propylbenzyl)-3,5-dimethylphenol as a white powder (0.179 g, 98%): $^1$H NMR (300 MHz, DMSO-$d_6$): δ 8.934(s, 1H), 6.73 (d, 1H, J=1.8 Hz), 6.43(m, 5H), 4.58(bs, 2H), 3.69(s, 2H), 2.92(m, 1H), 2.10(s, 6H), 1.07(d, 6H, J=6.6 Hz); TLC conditions: Uniplate silica gel, 250 microns; Mobile phase=Ethyl acetate; Rf=0.69.

Step b:
To a solution of 4-(4'-amino-3'-iso-propylbenzyl)-3,5-dimethylphenol (80 mg, 0.30 mmol) in DMF (3 mL) was added sodium hydride (8.5 mg, 0.36 mmol) and the reaction was stirred for 10 min. at room temperature. Trifluoromethanesulfonic acid diethoxyphosphorylmethyl ester was added and the reaction was stirred over night. An aqueous saturated solution of ammonium chloride (3 mL) was added and the resulting mixture was added to ethyl acetate (50 mL) and water (10 mL). The aqueous layer was removed and the ethyl acetate layer was washed 5× with 10 mL water and 1× with 10 mL brine. The ethyl acetate was dried over sodium sulfate, filtered and concentrated. The residue was purified by prep plate TLC using a 2000 µm silica gel plate eluted with ethyl acetate/dichloromethane [3:1] to give diethyl [4-(4'-amino-3'-iso-propylbenzyl)-3,5-dimethylphenoxy]methylphosphonate (0.061 g, 49%): $^1$H NMR (300 MHz, DMSO-$d_6$): δ 6.74(d, 1H, J=1.8 Hz), 6.72(s, 2H), 6.45(d, 1H, J=14.4 Hz), 6.36(dd, 1H, J=2 Hz, J=7.5 Hz), 4.60(s, 2H), 4.35(d, 2H, J=9.6 Hz), 4.11(m, 4H), 3.75(s, 2H), 2.90(m, 1H), 2.17(s, 6H), 1.25(t, 6H, J=7 Hz), 1.07(d, 6H, J=7.2 Hz); TLC conditions: Uniplate silica gel, 250 microns; Mobile phase=Ethyl acetate/Dichloromethane [1:1]; Rf=0.54.

Step c:
To a solution consisting of diethyl [4-(4'-amino-3'-iso-propylbenzyl)-3,5-dimethylphenoxy]methylphosphonate (43.6 mg, 0.104 mmol), in dichloromethane (2 mL) was added methane sulfonyl chloride (1 eq, 8 µl), and pyridine (1 eq, 8.4 µl). The reaction was stirred overnight at room temperature under an $N_2$ atmosphere (balloon). The solvent was removed under reduced pressure and the resulting residue was dissolved in ethyl acetate (25 mL) and washed 2× with water (10 mL), 1× with 1N HCl (10 mL), and 1 x with brine (10 mL). The ethyl acetate was dried over sodium sulfate filtered and concentrated under reduced pressure giving pure diethyl [4-(3'-iso-propyl-4'-methanesulfonylaminobenzyl)-3,5-dimethylphenoxy]methylphosphonate (0.047 g, 97%): $^1$H NMR (300 MHz, DMSO-$d_6$): δ 8.94(s, 1H), 7.08(m, 2H), 6.76(s, 2H), 6.68(dd, 1H, J=2.1 Hz, J=8.7 Hz), 4.36(d, 2H, J=10.2 Hz), 4.11(m, 4H), 3.39(m, 1H), 2.94(s, 3H), 2.23(s, 6H), 1.25(m, 6H), 1.08(d, 6H, J=7 Hz); TLC conditions: Uniplate silica gel, 250 microns; Mobile phase=Ethyl acetate/Dichloromethane [1:1]; Rf=0.36.

Step d:
To a solution consisting of diethyl [4-(3'-iso-propyl-4'-methanesulfonylaminobenzyl)-3,5-dimethylphenoxy]methylphosphonate (43.8 mg, 0.09 mmol) and dichloromethane (2 mL) was added HMDS (191 µl, 0.9 mmol) and TMSBr (191 µl, 0.9 mmol). The reaction was stirred over night at room temperature. The solvent was removed under reduced pressure and the resulting residue was co-evaporated 3× with 2 mL dichloromethane. The resulting residue was taken up in 1N NaOH (2 mL) and washed 2× with dichloromethane. The residual dichloromethane was removed under reduced pressure and the resulting aqueous layer was acidified with concentrated HCl. The resulting precipitate was filtered off and dried under vacuum to give the title compound as a light brown powder (0.022 g, 55%): $^1$H NMR (300 MHz, DMSO-$d_6$): δ 8.93 (s, 1H), 7.10 (m, 2H), 6.67 (m, 3H), 4.02 (d, 2H, J=10 Hz), 3.91(s, 2H), 2.93(s, 3H), 2.16(s, 6H), 1.08(d, 6H, J=7 Hz); TLC conditions: Uniplate silica gel, 250 microns; Mobile phase=Isopropyl alcohol/water/ammonium hydroxide [7:2:1]; $R_f$=0.36; Anal. Calcd for ($C_{20}H_{28}O_6PS+0.9H_2O$): C, 52.48; H, 3.56; N, 3.06. Found: C, 52.49, H, 6.56, N, 3.23.

Compound 7-14: [3,5-dichloro-4-(5'-bromo-4'-hydroxy-3'-iso-propylbenzyl)phenoxy]methylphosphonic acid Step a:
To a mixture of diethyl [3,5-dichloro-4-(3'-iso-propyl-4'-methoxymethoxybenzyl)phenoxy]methylphosphonate (0.25 g, 0.49 mmol, intermediate for the synthesis of compound 7-5) in methanol (3.0 mL) at 0° C. was added 2 N HCl (1.0 mL). The reaction mixture was stirred at room temperature for 24 h, quenched with water (10.0 mL) and extracted with ethyl acetate (10.0 mL). The organic layer was dried over $MgSO_4$, filtered and concentrated under reduced pressure. The crude product was purified by column chromatography on silica gel, eluting with 30% acetone in hexanes to afford diethyl [3,5-dichloro-4-(4'-hydroxy-3'-iso-propylbenzyl)phenoxy]-methylphosphonate (0.17 g, 74%) as a colorless oil: $^1$H NMR (300 MHz, $CD_3OD$): δ 7.18 (s, 2H), 7.00 (d, J=2.4 Hz, 1H), 6.75 (dd, J=8.1, 2.4 Hz, 1H), 6.62 (d, J=8.1 Hz, 1H), 4.48 (d, J=10.5 Hz, 2H), 4.25 (m, 4H), 4.17 (s, 2H), 3.25 (m, 1H), 1.38 (t, J=7.2 Hz, 6H), 1.18 (d, J=6.6 Hz, 6H); TLC conditions: Uniplate silica gel, 250 microns; Mobile phase=acetone-hexanes (2:3); $R_f$=0.70.

Step b:
To a mixture of diethyl [3,5-dichloro-4-(4'-hydroxy-3'-iso-propylbenzyl)phenoxy]methylphosphonate (0.16 g, 0.35 mmol) in $CH_2Cl_2$ (3.0 mL) at 0° C. was added tetrabutylammonium tribromide (0.18 g, 0.38 mmol). The reaction mixture was stirred at room temperature for 4 h and the solvent was removed under reduced pressure. The crude product was purified by column chromatography on silica gel, eluting with 30% acetone in hexanes to afford diethyl [3,5-dichloro-4-(5'-bromo-4'-hydroxy-3'-iso-propylbenzyl)-phenoxy]methylphosphonate (0.12 g, 64%) as yellow oil: $^1$H NMR (300 MHz, $CD_3OD$): δ 7.18 (s, 2H), 7.02 (s, 2H), 4.50 (d, J=10.5 Hz, 2H), 4.25 (m, 4H), 4.18 (s, 2H), 3.25 (m, 1H), 1.38 (t, J=7.2 Hz, 6H), 1.18 (d, J=6.6 Hz, 6H); TLC conditions: Uniplate silica gel, 250 microns; Mobile phase=acetone-hexanes (2:3); $R_f$=0.80.

The title compound was prepared by the procedure described for the synthesis of compound 7, step b: mp: 188-190° C.; $^1$H NMR (300 MHz, CD$_3$OD): δ 7.18 (s, 2H), 7.03 (s, 2H), 4.32 (d, J=10.2 Hz, 1H), 4.18 (s, 2H), 3.20-3.40 (m, 1H), 1.19 (d, J=7.2 Hz, 6H); LC-MS m/z=483 [C$_{20}$H$_{27}$O$_5$P–H]$^+$; Anal. Calcd for (C$_{17}$H$_{18}$BrCl$_2$O$_5$P+0.4H$_2$O): C, 41.56; H, 3.86. Found: C, 41.44; H, 4.15.

Compound 7-15: [3,5-Dimethyl-4-[3'-ethoxy-4'-hydroxybenzyl]phenoxy]-methylphosphonic acid Intermediate 3,5-dimethyl-4-[3'-ethoxy-4'-methoxymethoxybenzyl]-phenol was prepared from 4-bromo-2-ethoxy-phenol according to the procedure described in Chiellini et al., *Bioorg. Med. Chem. Lett.* 10:2607 (2000) and transformed into the title compound by the procedure used for the synthesis of compound 7: $^1$H NMR (300 MHz, DMSO-d$_6$): δ 8.62 (s, 1H), 6.71 (s, 2H), 6.65 (d, J=8.1 Hz, 1H), 6.59 (d, J=1.5 Hz, 1H), 6.27 (dd, J=1.5, 8.1 Hz, 1H), 4.04 (d, J=10.2 Hz, 2H), 3.93 (q, J=6.9 Hz, 2H), 3.82 (s, 2H), 2.16 (s, 6H), 1.29 (t, J=6.9 Hz, 3H); mp: shrinks at 145° C.; LC-MS m/z=367 [C$_{18}$H$_{23}$O6P+H]$^+$; Anal Calcd for (C$_{18}$H$_{23}$O$_6$P+0.2MeOH+0.4H$_2$O): C, 57.53; H, 6.53. Found: C, 57.39; H, 6.23.

Compound 7-16: [3,5-Dimethyl-4-(4'-hydroxy-3'-iso-propyl-2'-methyl-benzyl)phenoxy]methylphosphonic Acid Step a:

To a solution of ethyl 2-methoxy-6-methylbenzoate (1.0 g, 5.1 mmol) in THF (15.0 mL) at –78° C. was added methylmagnesium bromide (3.78 mL, 11.32 mmol). After 5 min, the reaction mixture was allowed to warm to room temperature and stirred for 4 h. The mixture was cooled to 0° C., quenched with 1.0 M HCl and extracted with ether. The organic layer was dried over MgSO$_4$, filtered and concentrated under reduced pressure. The crude product was purified by column chromatography on silica gel, eluting with 10% ethyl acetate in hexanes to afford 2-(2-methoxy-6-methylphenyl)-2-propanol (0.60 g, 65%) as colorless oil: $^1$H NMR (300 MHz, DMSO-d$_6$): δ 6.80 (dd, J=12.0 Hz, 11.7 Hz, 1H), 6.60 (d, J=12.0 Hz, 1H), 6.45 (d, J=11.7 Hz, 1H), 4.47 (s, 1H), 3.52 (s, 3H), 2.33 (s, 3H), 1.33 (s, 6H); TLC conditions: Uniplate silica gel, 250 microns; Mobile phase=ethyl acetate-hexanes (1:5); $R_f$=0.54.

Step b:

A solution of 2-(2-methoxy-6-methylphenyl)-2-propanol (0.50 g, 2.77 mmol) in ethyl acetate-acetic acid (9:1, 10.0 mL) at room temperature was stirred under a H$_2$ atmosphere for 16 h. The mixture was filtered through a Celite plug and the solvent was removed under reduced pressure. The residue was dissolved in hexanes and washed with water. The organic layer was dried MgSO$_4$, filtered and concentrated under reduced pressure to afford 2-iso-propyl-3-methylanisole (0.45 g, 100%) as colorless oil, which was used for the next step without further purification: $^1$H NMR (300 MHz, DMSO-d$_6$): δ 7.01 (dd, J=12.0 Hz, 11.7 Hz, 1H), 6.78 (d, J=12.0 Hz, 1H), 6.70 (d, J=11.7 Hz, 1H), 3.74 (s, 3H), 3.28 (m, 1H), 2.26 (s, 3H), 1.24 (d, J=10.8 Hz, 6H); TLC conditions: Uniplate silica gel, 250 microns; Mobile phase=ethyl acetate-hexanes (1:9); $R_f$=0.80.

Step c:

To a solution of 2-iso-propyl-3-methylanisole (0.44 g, 2.7 mmol) in CH$_2$Cl$_2$ at room temperature was added a solution of tetrabutylammonium tribromide (1.42 g, 2.94 mmol) in CH$_2$Cl$_2$. The reaction mixture was stirred for 2 h and the solvent was removed under reduced pressure. The crude product was purified by column chromatography on silica gel, eluting with 5% ethyl acetate in hexanes to afford 4-bromo-2-iso-propyl-3-methylanisole as yellowish oil (0.60 g, 92%): $^1$H NMR (300 MHz, DMSO-d$_6$): δ 7.37 (d, J=13.2 Hz, 1H), 6.78 (d, J=13.2 Hz, 1H), 3.74 (s, 3H), 3.38 (m, 1H), 2.38 (s, 3H), 1.25 (d, J=10.8 Hz, 6H); TLC conditions: Uniplate silica gel, 250 microns; Mobile phase=ethyl acetate-hexanes (5:95); $R_f$=0.80.

The title compound was prepared from 4-bromo-2-iso-propyl-3-methylanisole according to the procedure described for the synthesis of compound 7-11: mp: 180-183° C.; $^1$H NMR (300 MHz, CD$_3$OD): δ 6.76 (s, 2H), 6.34 (d, J=8.4 Hz, 1H), 6.03 (d, J=8.4 Hz, 1H), 4.22 (d, J=10.5 Hz, 1H), 3.81 (s, 2H), 3.50 (m, 1H), 2.37 (s, 3H), 2.16 (s, 3H), 1.39 (d, J=6.9 Hz, 6H); LC-MS m/z=379 [C$_{20}$H$_{27}$O$_5$P+H]$^+$; Anal. Calcd for (C$_{20}$H$_{27}$O$_5$P+0.5H$_2$O): C, 62.01; H, 7.28. Found: C, 61.98; H, 7.26.

Compound 7-17: [2,5-Dimethyl-4-(4'-hydroxy-3'-iso-propylbenzyl)-phenoxy]methylphosphonic acid Step a:

To a stirred suspension of 2,5-dimethyl phenol (5.0 g, 40.9 mmol) in H$_2$O (150 mL), at room temperature was added tetrabutylammonium tribromide (19.9 g, 41.39 mmol) in CHCl$_3$ (150 mL). The reaction mixture was stirred for 2 h at rt, the organic layer was separated and dried over Na$_2$SO$_4$, filtered and concentrated. The residue was purified by column chromatography on silica gel eluting with hexane-ethyl acetate (1:5) to afford 2,5-dimethyl-4-bromophenol as a brown solid (6.2 g, 76%); $^1$H NMR (300 MHz, DMSO-d$_6$): δ 9.47 (s, 1H), 7.24 (s, 1H), 6.74 (s, 1H), 2.21 (s, 3H), 2.07 (s, 3H); TLC conditions: Uniplate silica gel, 250 microns; Mobile phase=hexanes-ethyl acetate (9:1); $R_f$=0.52.

Step b:

Intermediate 2,5-dimethyl-4-(3'-iso-propyl-4'-methoxymethoxy-benzyl)phenol was prepared from 2,5-dimethyl-4-bromo-t-butyldimethylsilyloxyphenol, and 3-iso-propyl-4-methoxymethoxy-benzaldehyde according to the procedure described in (Chiellini et al., *Bioorg. Med. Chem. Lett.* 10:2607 (2000)) and transformed into the title compound by the procedure used for the synthesis of compound 7-13, step b followed by example 7, step b, (0.14 g, 90%); $^1$H NMR (300 MHz, CD$_3$OD): δ 6.88 (d, J=8.7 Hz, 2H), 6.79 (s, 1H), 6.64-6.72 (m, 2H), 4.20 (d, J=10.2 Hz, 2H), 3.80 (s, 2H), 3.10-3.15 (m, 1H), 2.22 (s, 3H), 2.20 (s, 3H), 1.17 (d, J=6.9 Hz, 6H); LC-MS m/z=365 [C$_{20}$H$_{25}$O$_6$P+H]$^+$; HPLC conditions: ODSAQ AQ-303-5 column; mobile phase=CH$_3$OH: 0.05% TFA (7:3) flow rate=1.0 mL/min; detection=LUV @ 254 nm retention time in min: 10.96; Anal Calcd for (C$_{20}$H$_{25}$O$_6$P+0.3H$_2$O): C, 61.84; H, 6.92. Found: C, 61.60; H, 6.72.

Compound 7-18: [2,5-Dimethyl-6-iodo-4-(4'-hydroxy-3'-iso-propylbenzyl)phenoxy]methylphosphonic acid Step a:

To a stirred solution of 2,5-dimethyl-4-(4'-methoxymethoxy-3'-iso-propylbenzyl)phenol (intermediate for the synthesis of compound 7-17; 0.35 g, 1.11 mmol) in EtOH (5.0 mL) and CH$_3$NH$_2$ 40% in water (2.5 mL) was added iodine (0.34 g, 1.33 mmol) and KI (0.27 g 1.66 mmol) in $H_2O$ (3 mL) at 0° C. The reaction mixture was stirred at 0° C. for 2 h, quenched with brine (50 mL) and extracted with ethyl acetate (100 mL×2). The combined organic layers were dried over $Na_2SO_4$, filtered and concentrated under reduced pressure. The crude product was purified by column chromatography on silica gel, eluting with ethyl acetate-hexanes (1:3) to afford 2,5-dimethyl-6-iodo-4-(4'-methoxymethoxy-3'-iso-propylbenzyl)phenol as a colorless oil (0.32 g, 64%): $^1H$ NMR (300 MHz, $CDCl_3$): δ 7.02 (d, J=2.4 Hz, 1H), 6.95 (d, J=8.7 Hz, 1H), 6.88 (s, 1H), 6.75 (dd, J=2.4, 8.4 Hz, 1H), 5.20 (s, 2H), 3.95 (s, 2H), 3.51 (s, 3H), 3.35-3.30 (m, 1H), 2.39 (s, 3H), 2.30 (s, 3H), 1.22 (d, J=6.9 Hz, 6H); TLC conditions: Uniplate silica gel, 250 microns; Mobile phase=hexanes-ethylacetate (9:1); $R_f$=0.6.

Step b:

The title compound was prepared from 6-iodo-3,5-dim-ethyl-4-(4'-methoxymethoxy-3'-iso-propylbenzyl)phenol according to the procedure described for the synthesis of example 7-17, step b as white solid (0.15 g, 75%) mp 190° C.; $^1H$ NMR (300 MHz, $CD_3OD$): δ 6.99 (s, 1H), 6.92 (s, 1H), 6.65 (s, 2H), 4.16 (d, J=10.5 Hz, 2H), 3.94 (s, 2H), 3.30-3.18 (m, 1H), 2.38 (s, 6H), 1.18 (d, J=6.9 Hz, 6H); LC-MS m/z=490 $[C_{19}H_{23}I_2O_5P+H]^+$; Anal Calcd for ($C_{20}H_{25}O_6P$+ 1.2$H_2O$+1.0 $CHCl_3$): C, 38.05; H, 4.37. Found: C, 38.04; H, 4.33.

Compound 7-19: [2,6-dimethyl-4-(4'-hydroxy-3'-iso-propylbenzyl)-phenoxymethyl]phosphonic acid Intermediate 2,6-dimethyl-4-(4'-methoxymethoxy-3'-iso-propyl-benzyl)phenol was prepared from 3,5-dimethyl-4-hy-droxy benzaldehyde and bromo-4-methoxymethoxy-3-iso-propylbenzene according to the procedure described in Chiellini et al., *Bioorg. Med. Chem. Lett.* 10:2607 (2000) and transformed into the title compound according to the procedure described for the synthesis of compound 7-17, step b; (0.12 g, 85%); $^1H$ NMR (300 MHz, $CD_3OD$): δ 6.97 (s, 1H), 6.83 (s, 2H), 6.77 (d, J=7.5 Hz, 1H), 6.65 (d, J=7.5 Hz, 1H), 4.0 (d, J=9.9 Hz, 2H), 3.75 (s, 2H), 3.20-3.29 (m, 1H), 2.28 (s, 6H), 1.19 (d, J=6.6 Hz, 6H); LC-MS m/z=363 $[C_{20}H_{25}O_6P-H]^+$; (94%) HPLC conditions: ODSAQ AQ-303-5 column; mobile phase=$CH_3OH$: 0.05% TFA/$H_2O$ (7:3) flow rate=1.0 mL/min; detection=UV @ 254 nm retention time in min: 10.92; Anal Calcd for ($C_{20}H_{25}O_6P$+1.2$H_2O$): C, 59.12; H, 7.15. Found: C, 58.96; H, 6.77.

Compound 7-20: [4-(4'-hydroxy-3'-iso-propylben-zyl)-3-methyl-phenoxy]methylphosphonic Acid Intermediate 4-(4'-methoxymethoxy-3'-iso-propylben-zyl)-3-methyl-phenol was prepared from 4-bromo-3-methyl-phenol (*J. Med. Chem.* 12:1350 (1980)) and 4-meth-oxymethoxy-3-iso-propylbenzaldehyde according to the procedure described in Chiellini et al., *Bioorg. Med. Chem. Lett.* 10:2607 (2000) and transformed into the title compound by the procedure used for the synthesis of compound 7. $^1H$ NMR (300 MHz, DMSO-$d_6$): δ 9.04 (s, 1H), 7.02-6.99 (d, J=8.7 Hz, 1H), 6.92 (s, 1H), 6.81-6.76 (m, 2H), 6.67 (s, 2H), 4.03 (d, J=10.5 Hz, 2H), 3.76 (s, 2H), 3.16-3.14 (m, 1H), 2.19 (s, 3H), 1.14-1.12 (d, J=6.9 Hz, 6H); TLC conditions: Uniplate silica gel, 250 microns; Mobile phase=ethyl acetate; $R_f$=0.11;

Compound 7-21: [2,5-Dimethyl-4-(4'-methoxy-2'-methyl-3'-iso-propylbenzyl)phenoxy]methylphos-phonic acid Step a:

First step: To a stirring solution of 2,5-dimethyl-4-meth-oxybenzaldehyde (0.82 g, 5.0 mmol) at −20° C. in $CH_2Cl_2$ (10 mL) was added $BBr_3$ (10 mL, 1M in $CH_2Cl_2$). The reaction mixture was stirred at room temperature for 16 hrs. It was added ice and diluted with $CH_2Cl_2$. The organic layer was dried over $Na_2SO_4$, filtered and concentrated under reduced pressure. The crude product was purified by column chromatography on silica gel, eluting with ethyl acetate/hexanes (1:1) to afford 2,5-dimethyl-4-hydroxy-benzaldehyde as a yellow solid (0.43 g, 57%): $^1H$ NMR (300 MHz, DMSO-$d_6$): δ 10.41 (s, 1H), 9.99 (s, 1H), 7.56 (s, 1H), 6.69 (s, 1H), 2.51 (s, 3H), 2.14 (s, 3H); TLC conditions: Uniplate silica gel, 250 microns; Mobile phase=20% ethyl acetate in hexanes; $R_f$=0.48.

Step b:

To a stirring solution of 2,5-dimethyl-4-hydroxy-benzal-dehyde (0.43 g, 2.86 mmol) in DMF (8 mL) at room temperature was added imidazole (0.43 g, 6.29 mmol) and chloro-triisopropyl-silane (0.74 mL, 3.43 mmol). The mixture was stirred at room temperature for 16 hrs. The solvent was removed under reduced pressure and the residue was partitioned between ethyl acetate and water. The organic layer was dried over $Na_2SO_4$, filtered and concentrated under reduced pressure. The crude product was purified by column chromatography on silica gel, eluting with ethyl acetate-hexanes (15:75) to afford 2,5-dimethyl-4-triisopropylsilanyloxy-ben-zaldehyde as a colorless oil (0.7 g, 80%): $^1H$ NMR (300 MHz, DMSO-$d_6$): δ 10.07 (s, 1H), 7.65 (s, 1H), 6.69 (s, 1H), 2.55 (s, 3H), 2.21 (s, 3H), 1.35 (m, 3H), 1.10 (d, J=6.9 Hz, 18H); TLC conditions: Uniplate silica gel, 250 microns; Mobile phase=5% ethyl acetate in hexanes; $R_f$=0.68.

Intermediate 2,5-dimethyl-4-(4'-methoxy-2'-methyl-3'-iso-propyl-benzyl) phenol was prepared from 2,5-dimethyl-4-triisopropylsilanyloxy-benzaldehyde and 1-bromo-4-methoxy-2-methyl-3-iso-propylbenzene according to the procedure described in Chiellini et al., *Bioorg. Med. Chem. Lett.* 10:2607 (2000) and transformed into the title compound by the procedure described for the synthesis of compound 7: $^1H$ NMR (300 MHz, DMSO-$d_6$): δ 6.93 (s, 1H), 6.75 (d, J=8.4 Hz, 1H), 6.65 (d, J=8.4 Hz, 1H), 6.64 (s, 1H), 4.09 (d, J=9.9 Hz, 2H), 3.79 (s, 2H), 3.77 (s, 3H), 3.34 (m, 1H), 2.22 (s, 3H), 2.20 (s, 3H), 2.10 (s, 3H), 1.31 (d, J=7.2 Hz, 6H); LC-MS m/z=391 $[C21H29O5P-H]^-$.

Alternative Method for the Preparation of Compound 7

Step a:

A 3 neck 2 liter flask fitted with mechanical stirring, nitrogen bubbler, sodium hydroxide trap, and a cool water bath was charged with 2-iso-propyl phenol (157.8 g, 1.1 mol) and dichloromethane (1000 ml). While maintaining the internal temperature at 15° C. to 20° C., bromine (179.4 g, 1.1 mol) was added dropwise over 45 min. (The rate of addition is controlled so that the bromine color dissipates almost immediately). The reaction was complete by TLC (silica gel plates, 20% EtOAC/hexanes, $R_f$ S.M.=0.7, $R_f$ product=0.8). The flask was purged with nitrogen to remove most of the hydrogen bromide. The reaction mixture was then concentrated to an oil (252.0 g, 100%) which is pure enough to use in the next step. NMR: See Berthelot et al., *Can J. Chem.* 67:2061 (1989).

Step b:

A 3 liter 3 neck round bottom flask equipped with mechanical stirring, temperature probe, cooling bath, and addition funnel with nitrogen inlet was charged with 4-bromo-2-isopropylphenol (160 g, 0.75 mol) and methylene chloride (750 ml). While maintaining the temperature between 15° C. and 20° C., a solution of diisopropylethylamine (146 g, 1.13 mol) and chloromethyl methyl ether (66.4 g, 0.83 mol) in methylene chloride (100 ml) was added over 15 minutes. The solution was heated to reflux for 16 hours. The reaction was complete by TLC (silica gel plates, 10% EtOAC/hexanes, $R_f$ S.M.=0.5, $R_f$ product=0.9). After cooling to room temperature, the reaction was quenched by the addition of water (800 ml). After separation of layers, the aqueous phase was extracted with methylene chloride (500 ml). The combined organic layers were dried over MgSO$_4$, and then concentrated to an oil (204 g). The oil was purified by column chromatography (1.8 kg silica gel, 2.5% EtOAc/hexanes) to yield a clear oil (154 g, 79%). NMR See Chiellini et al., *Biorg. Med. Chem. Lett.* 10:2607 (2000).

Alternative Step b

A 5 liter 4 neck indented round bottom flask equipped with a mechanical multi-paddle stirrer, and an addition funnel with nitrogen inlet was charged with 4-bromo-2-iso-propylphenol (100 g, 0.47 mol) and methylene chloride (2000 ml). Under high agitation, half of the P$_2$O$_5$ (75 g, 1.1 mol) was added. The reaction was stirred for one hour during which time dough balls formed. Additional P$_2$O$_5$ (75 g, 1.1 mol) was added and stirred for one hour. The reaction was complete by TLC (silica gel plates, 10% EtOAC/hexanes, $R_f$ S.M.=0.5, $R_f$ product=0.9). The reaction was carefully quenched by the addition of 10% K$_2$CO$_3$ (2000 ml). After separation of layers, the aqueous phase was extracted with methylene chloride (1000 ml). The combined organic layers were dried over MgSO$_4$, and then concentrated to an oil (116 g). The oil was purified by column chromatography (1.5 kg silica gel, 2.5% EtOAc/hexanes) to yield a clear oil (99.9 g, 83%).

Step c:

A 2 liter 3 neck round bottom flask equipped with mechanical stirring, cooling bath, temperature probe, and addition funnel with nitrogen inlet was charged with 4-bromo-3,5-dimethylphenol (90.0 g, 448 mmol), imidazole (90 g, 1.32 mol), and methylene chloride (900 ml). The solution was cooled to 10° C. Triisopropylsilyl chloride (95.0 g, 493 mmol) was added over 10 minutes. The temperature rose to 20° C. The solution became turbid, and a white precipitate formed. The reaction mixture was stirred at room temperature for 2.5 hours. The reaction was complete by TLC (silica gel plates, 10% EtOAc/hexane, $R_f$ S.M.=0.3, $R_f$ product=0.9). Water (600 ml) was added and stirred for 20 minutes. After separation of layers, the organic phase was dried over MgSO$_4$ and concentrated to an oil (178 g) which is acceptable for use in the next step. The oil was purified by column chromatography (1.8 kg silica gel, 5% EtOAc/hexane) to yield an oil (153 g, 96%). NMR See Chiellini et al., *Bioorg. Med. Chem. Lett.* 10:2607 (2000).

Step d:

A 3 liter 3 neck round bottom flask equipped with mechanical stirring, thermometer, cooling bath and 250 ml addition funnel was charged with 4-bromo-3,5-dimethylphenoxytriisopropylsilane (150 g, 420 mmol) and THF (1125 ml). The solution was cooled to −73° C. While maintaining the temperature at less than or equal to −70° C., 2.5 M n-butyllithium (252 ml, 630 mmol) was added over 1.5 hours. The solution was stirred at −73° C. for an additional 2.5 hours. While maintaining the temperature at less than or equal to −70° C., a solution of dimethylformamide (61.3 g, 840 mmol) in THF (60 ml) was added over 35 minutes. After stirring for 30 minutes at −73° C., TLC indicated that the reaction was complete (silica gel plates, 10% EtOAc/hexane, $R_f$ S.M.=0.9, $R_f$ product=0.7). The reaction was warmed to room temperature, and then quenched by the addition of saturated ammonium chloride in water (1000 ml). After separation of layers, the aqueous phase was extracted with MTBE (250 ml). The combined organic layers were dried over MgSO$_4$, and concentrated to an oil (125 g). The oil was purified by column chromatography (1.5 kg silica gel, 5% EtOAc/hexanes) to yield an oil (113 g, 87%). NMR See Chiellini et al., *Bioorg. Med. Chem. Lett.* 10:2607 (2000).

Step e:

A 5 liter 3 neck round bottom flask equipped with a cooling bath, mechanical stirring, temperature probe, and addition funnel with nitrogen inlet was charged with bromo-4-methoxymethoxy-3-iso-propyl (136 g, 525 mmol) and THF (1300 ml). The solution was cooled to −75° C. While maintaining the temperature at less than or equal to −70° C., n-butyllithium solution (310 ml, 775 mmol) was added over 45 minutes. The solution was stirred at −75° C. for 1 hour. While maintaining the temperature at less than or equal to −70° C., a solution of 2,6-dimethyl-4-triisopropylsilyloxybenzaldehyde (134 g, 438 mmol) in THF (200 ml) was added over 2 hours. The solution was stirred at −75° C. for 1 hour. TLC indicated that the reaction was complete (silica gel plates, 10% EtOAc/hexane, $R_f$ Bromide=0.9, $R_f$ Aldehyde=0.7, $R_f$ product=0.2). After warming to room temperature, the reaction was quenched with saturated ammonium chloride in water (200 ml). After separation of layers, the aqueous phase was extracted with ethyl acetate (800 ml). The combined organic layers were washed with brine (700 ml), dried over MgSO$_4$, and concentrated to an oil (262 g). The oil was split into halves, and each half was purified by column chromatography (1.8 kg silica gel, 5 to 10% EtOAc/hexane) to yield the product as a clear oil containing some EtOAc (148 g of product, 69%). The fractions containing the product and an impurity were combined to give a clear oil (19.3 g). This was purified by column chromatography (400 g silica gel, 5 to 10% EtOAc/hexanes) to give additional product as a clear oil (16.9 g, 7%). NMR See Chiellini et al., *Bioorg. Med. Chem. Lett.* 10:2607 (2000).

Step f:

A 2 liter round bottom flask equipped with magnetic stirring and a 3 way adapter was charged with (4-methoxymethoxy-3-iso-propylphenyl)-(2,6-dimethyl-4-triisopropylsilyloxy)-methanol (72.1 g, 139 mmol), ethyl acetate (665 ml), acetic acid (35 ml), and 10% Pd on Carbon (5.22 g). The flask was purged 3 times with nitrogen, and then a hydrogen balloon was attached to the adapter. After purging 3 times with hydrogen, the mixture was stirred at room temperature for 3 hours. The reaction was complete by TLC (silica gel plates, 10% EtOAc/hexane, $R_f$ S.M.=0.2, $R_f$ product=0.9). After purging with nitrogen, the mixture was filtered through a small pad of Celite; rinsed with EtOAc (70 ml). The filtrate was washed with water (2×100 ml), and then by saturated NaHCO$_3$ in water until the wash was basic (4×100 ml). The organic layer was dried over MgSO$_4$ and then concentrated to an oil (62.5 g, 96%). NMR See Chiellini et al., *Bioorg. Med. Chem. Lett.* 10:2607 (2000).

Step g:

A 1 liter 1 neck round bottom flask equipped with magnetic stirring was charged with the 2,6-dimethyl-(4'-methoxymethoxy-3'-iso-propylbenzyl)-4-triisopropylsilyloxybenzene (62.5 g, 133 mmol) and THF (600 ml). Tetraethylammonium fluoride hydrate (25.9 g, 174 mmol) was slightly ground in a beaker and then charged to the flask. The slurry was stirred at room temperature for 1 hour until TLC indicated that the reaction was complete (silica gel plates, 20% EtOAc/hexane, $R_f$ S.M.=0.9, $R_f$ product=0.4). Water (300 ml) was added and stirred for 15 minutes. The mixture was diluted with MTBE (600 ml), and the layers were separated. The aqueous phase was extracted with MTBE (600 ml). The combined organic layers were washed with water (100 ml) followed by brine (200 ml). After drying over MgSO$_4$, the organic layer was concentrated to an oil (65 g). This was purified by column chromatography (1300 g silica gel, 10 to 20% EtOAc/hexanes) to give the product as a clear oil (57.0 g, 95%). NMR See Chiellini et al., *Bioorg. Med. Chem. Lett.* 10:2607 (2000).

Step h:

A 5 liter 3 neck round bottom flask equipped with a cooling bath, mechanical stirring, temperature probe, and addition funnel with nitrogen inlet was charged with 60% sodium hydride in mineral oil (10.62 g, 266 mmol). The sodium hydride was washed with hexanes (150 ml). Dimethylformamide (250 ml) was added, and the mixture cooled to 5° C. While maintaining the temperature <10° C. a solution of 3,5-dimethyl-4-(4'-methoxymethoxy-3'-iso-propylbenzyl)-phenol (55.53 g, 117 mmol) in DMF (150 ml) was added over 30 minutes. The solution was stirred at room temperature for 1 hour, and then cooled back to 5° C. While maintaining the temperature at less than or equal to 10° C., a solution of the diethyl p-toluenesulfonyloxymethyl-phosphonate (86.93 g, 269 mmol) in DMF (150 ml) was added over 15 minutes. The solution was stirred at room temperature for 16 hours. The reaction was concentrated to a paste. The paste was treated with water (330 ml) and extracted with ethyl acetate (330 ml, 2×250 ml). The combined organic layers were washed with brine (150 ml), dried over MgSO$_4$, and concentrated to an oil (116 g). The oil was purified by column chromatography (1.5 kg silica gel, 10 to 50% EtOAc/hexane) to yield the product as a clear oil containing some EtOAc (54.76 g of product, 66%). The fractions containing the product and diethyl p-toluenesulfonyloxmethyl were combined to give a clear oil (6.03 g). This was purified by column chromatography (120 g silica gel, 30 to 40% EtOAc/hexanes) to give the product as a clear oil (3.74 g, 4%). NMR see compound 7, step a.

Step i:

A 500 ml 3 neck round bottom flask equipped with magnetic stirring, temperature probe, addition funnel with a nitrogen inlet, and a cooling bath was charged with the diethyl [3,5-dimethyl-4-(4'-methoxymethoxy-3'-iso-propylbenzyl) phenoxy]methylphosphonate (19.61 g, 42.2 mmol) and dichloromethane (200 ml). The solution was cooled to −30° C. Trimethylsilyl bromide (64.96 g, 424 mmol) was added over 15 min. The bath was removed, and the solution stirred at room temperature for 16 hours. The reaction was concentrated on the rotary evaporator at 50° C. The oil was then put on the vacuum pump for 30 minutes. The oil was dissolved in acetonitrile/water (110 ml/1 10 ml) and stirred at 50° C. for 30 min. The solution was concentrated to an oil. Acetonitrile (110 ml) was added, and the solution was concentrated to an oil. Methanol/toluene (30/190 ml) was added and the solution was concentrated to an oil. Methanol/toluene (30/190 ml) was added and the solution was concentrated to a foam. Toluene (220 ml) was added and the solution was concentrated to a solid. Toluene/hexane (190 ml/30 ml) was added, and the mixture was sonicated for 5 minutes. The solids were scraped down the sides of the flask, and the mixture was stirred at room temperature for 2 hours. The solids were collected by vacuum filtration and washed with hexane/toluene (2 ml/8 ml). The solids were dried overnight in the vacuum oven at 45 to 50° C. to yield MB7344 as an off-white solid (14.36 g). NMR see compound 7, step b.

Preparation of Diethyl p-toluenesulfonyloxymethylphosphonate

A 12 L, 3-neck round bottom flask was equipped with a mechanical stirrer, condenser, thermometer and heating mantle. The flask was flushed with nitrogen and charged with diethyl phosphite (554 g, 3.77 mol), paraformaldehyde (142 g, 4.72 mol), toluene (2 L) and triethylamine (53 mL, 5.76 mol). The mixture was stirred at 85-90° for 2 h, then at reflux for 1 h. The resulting yellow solution was cooled to 4° C. (ice bath) and p-toluenesulfonyl chloride (718 g, 3.77 mol) was added. The condenser was replaced with an addition funnel and triethylamine (750 mL) was added slowly with stirring, maintaining the temperature <10° C. After the addition was complete (45 min.), the resulting mixture was stirred at ambient temperature for 14 h. The mixture was filtered and the filtercake was washed with toluene (2×250 mL). The combined filtrate and washings were washed with water (2×1 L, dried (MgSO$_4$, 200 g), filtered through Celite 521, and concentrated under reduced pressure to provide 1004 g of a cloudy yellow oil (77.6%). $^1$H NMR (CDCl$_3$): NMR (DMSO): 7.82 (d, J=8.2 Hz, 2H), 7.48 (d, J=8.2 Hz, 2H), 4.36 (d, J=9.6 Hz, 2H), 4.00 (m, 4H), 2.41 (s, 3H), 1.16 (m, 6H); TLC conditions: Uniplate silica gel, 250 microns; Mobile phase=40% EtOAc/hexanes, Rf=0.24.

Example 8

Compound 8: [3,5-diiodo-4-(4'-hydroxy-3'-iso-propylphenoxy)-phenoxy]methylphosphonic acid Step a:

To a solution of 4-benzoyloxyphenol (0.2 g, 0.93 mmol) in dichloromethane (9.3 mL) at 0° C. was added bis(pyridine) iodonium tetrafluoroborate (0.76 g, 2.06 mmol). The reaction mixture was stirred at room temperature for 1 h. The solvent was removed under reduced pressure and the residue was purified by column chromatography on silica gel, eluting with acetone-hexanes (1:9) to afford 4-benzoyloxy-3,5-diiodophenol as an off-white solid (0.22 g, 50%): $^1$H NMR (300 MHz, DMSO-d$_6$): δ 9.60 (s, 1H), 8.06 (m, 2H), 7.72 (s, 2H), 7.59 (m, 3H); TLC conditions: Uniplate silica gel, 250 microns; Mobile phase=hexanes-acetone (4:1); $R_f$=0.45.

Step b:

To a mixture of bis(4-methoxy-3-iso-propylphenyl)iodonium tetrafluoroborate (0.77 g, 1.51 mmol) and copper powder (0.13 g, 2.01 mmol) in CH$_2$Cl$_2$ (4.4 mL) at 0° C. was added a solution of TEA (0.15 mL, 1.10 mmol) and 4-benzoyloxy-3,5-diiodophenol (0.47 g, 1.00 mmol) in dichloromethane (4.0 mL). The reaction mixture was stirred at room temperature for 24 h and filtered through a Celite plug. The solvent was removed under reduced pressure and the residue was purified by column chromatography on silica gel, eluting with acetone-hexanes (1:9) to afford 3,5-diiodo-4-(4'-methoxy-3'-iso-propylphenoxy)phenyl benzoate as an off-white solid (0.61 g, 98%): $^1$H NMR (300 MHz, DMSO-d$_6$): δ 8.10 (m, 2H), 7.96 (s, 2H), 7.73 (m, 1H), 7.60 (m, 2H), 6.85 (d, J=9.0 Hz, 1H), 6.73 (d, J=3.0 Hz, 1H), 6.35 (m, 1H), 3.74 (s, 3H), 3.21 (m, 1H), 1.13 (d, J=6.0 Hz, 6H); TLC conditions: Uniplate silica gel, 250 microns; Mobile phase=hexanes-acetone (1:9); $R_f$=0.42.

Step c:

A mixture of 3,5-diiodo-4-(4'-methoxy-3'-iso-propylphenoxy)phenyl benzoate (0.10 g, 0.16 mmol) and 1 N NaOH (0.81 mL, 0.81 mmol) in methanol (1.63 mL) was at room temperature for 24 h. The reaction mixture was neutralized with 2 N HCl, diluted with $H_2O$ and extracted with $CH_2Cl_2$ (10 mL×2). The organic layers were concentrated under reduced pressure and the crude product was purified preparatory TLC with acetone-hexanes (1:4) as mobile phase to afford 3,5-diiodo-4-(4'-methoxy-3'-iso-propylphenoxy)phenol as an off-white solid (0.079 g, 95%): $^1$H NMR (300 MHz, DMSO-$d_6$): δ 9.99 (s, 1H), 7.28 (s, 2H), 6.81 (d, J=12.0 Hz, 1H), 6.67 (d, J=3.0 Hz, 1H), 6.30 (m, 1H), 3.72 (s, 3H), 3.18 (m, 1H), 1.11 (d, J=6.9 Hz, 6H); TLC conditions: Uniplate silica gel, 250 microns; Mobile phase=hexanes-acetone (7:3); $R_f$=0.42.

Step d:

To a stirred solution of 3,5-diiodo-4-(4'-methoxy-3'-iso-propylphenoxy)phenol (0.28 g, 0.55 mmol) in dichloromethane (17.0 mL) at −78° C. was added $BBr_3$ (13.1 mL, 13.1 mmol, 1.0 M solution in $CH_2Cl_2$). The reaction mixture was stirred at −78° C. for 10 min, allowed to warm to room temperature and stirred for 16 h. The reaction mixture was poured into ice and extracted with $CH_2Cl_2$ (20 mL×2). The organic layers were dried over $MgSO_4$, filtered and concentrated under reduced pressure. The crude product was purified by column chromatography on silica gel, eluting with acetone-hexanes (3:7) to afford 3,5-diiodo-4-(4'-hydroxy-3'-iso-propylphenoxy)phenol as an off-white solid (0.18 g, 66%): $^1$H NMR (300 MHz, DMSO-$d_6$): δ 9.95 (s, 1H), 8.91 (s, 1H), 7.27 (s, 2H), 6.62 (d, J=9.0 Hz, 1H), 6.56 (d, J=3.0 Hz, 1H), 6.18 (m, 1H), 3.72 (s, 3H), 3.14 (m, 1H), 1.10 (d, J=6.0 Hz, 6H); TLC conditions: Uniplate silica gel, 250 microns; Mobile phase=hexanes-acetone (7:3); $R_f$=0.28.

Step e:

To a mixture of 3,5-diiodo-4-(4'-hydroxy-3'-iso-propylphenoxy)phenol (0.067 g, 0.14 mmol) and $Cs_2CO_3$ (0.220 g, 0.675 mmol) in DMF (1.35 mL) at 0° C. was added trifluoromethanesulfonic acid diethoxyphosphorylmethyl ester (0.040 g, 0.14 mmol). The reaction mixture was stirred at room temperature for 5 h, quenched with 1 N HCl and extracted with EtOAc (10 mL×2). The organic layers were dried over $MgSO_4$, filtered and concentrated under reduced pressure. The residue was purified by preparatory TLC with acetone-hexane (2:3) as mobile phase to afford diethyl [3,5-diiodo-4-(4'-hydroxy-3'-iso-propylphenoxy)phenoxy]methylphosphonate as an off-white solid (0.048 g, 55%): $^1$H NMR (300 MHz, DMSO-$d_6$): δ 8.95 (s, 1H), 7.57 (s, 2H), 6.63 (d, J=9.0 Hz, 1H), 6.56 (d, J=3.0 Hz, 1H), 6.19 (m, 1H), 4.51 (d, J=9.0 Hz, 2H), 4.08 (m, 4H), 3.14 (m, 1H), 1.25 (m, 6H), 1.10 (d, J=6.0 Hz, 6H); TLC conditions: Uniplate silica gel, 250 microns; Mobile phase=hexanes-acetone (3:2); $R_f$=0.29.

Step f:

To a solution of diethyl [3,5-diiodo-4-(4'-hydroxy-3'-iso-propylphenoxy) phenoxy]methylphosphonate (0.14 g, 0.22 mmol) in $CH_2Cl_2$ (2.5 mL) at 0° C. was added bromotrimethylsilane (0.28 mL, 2.20 mmol). The reaction mixture was stirred at room temperature 16 h and the solvent was removed under reduced pressure. The residue was treated with acetonitrile-water (1:1, 5.0 mL) and solvent was removed under reduced pressure. The crude product was treated methanol (10 mL) and the solvent was removed under reduced pressure to afford [3,5-diiodo-4-(4'-hydroxy-3'-iso-propylphenoxy) phenoxy]methylphosphonic acid as an off-white solid (0.080 g, 63%): mp 180° C., dec; LC-MS m/z=589 $[C_{16}H_{17}I_2O_6P-H]^-$; HPLC conditions: Column=3 Chromolith SpeedRODs RP-18e, 100×4.6 mm; Mobile phase=Solvent A (Acetonitrile)=HPLC grade acetonitrile; Solvent B (buffer)=20 mM ammonium phosphate buffer (pH 6.1, 0.018 M $NH_4H_2PO_4$/ 0.002 M $(NH_4)_2HPO_4$) with 5% acetonitrile. Flow rate=4 mL/min; UV@ 255 nm. Retention time in minutes. (rt=6.46, 97% purity).

Using the appropriate starting material, compounds 8-1 and 8-2 were prepared in an analogous manner to that described for the synthesis of compound 8.

Compound 8-1: [3,5-dibromo-4-(3'-iso-propyl-4'-hydroxyphenoxy)-phenoxy]methylphosphonic acid Prepared from 4-benzoyloxy-3,5-dibromophenol according to the procedure described in compound 8: mp: 77-80° C.; LC-MS m/z=495,497 $[C_{16}H_{17}Br_2O_6P-H]^-$; $^1$H NMR (300 MHz, DMSO-$d_6$): δ 8.99 (s, 1H), 7.42 (s, 2H), 6.63 (m, 2H), 6.22 (m, 1H), 4.21 (d, J=9.0 Hz, 2H), 3.11 (m, 1H), 1.10 (d, J=6.0 Hz, 6H); Anal. Calcd for ($C_{16}H_{17}Br_2O_6P$+0.2 $C_6H_{14}$): C, 40.06; H, 3.78. Found: C, 40.25, H, 3.89.

Compound 8-2: [3,5-dichloro-4-(3'-iso-propyl-4'-hydroxyphenoxy)-phenoxy]methylphosphonic acid Prepared from 2,6-dichloro-4-(2-methoxyethoxy)phenol (*Synth. Commu.* 27:107 (1997)) according to the procedure described in compound 8: m.p. 73-76° C.; LC-MS m/z=407 $[C_{16}H_{17}Cl_2O_6P-H]^-$; $^1$H NMR (300 MHz, DMSO-$d_6$): δ 9.10 (s, 1H), 7.34 (s, 2H), 6.72 (m, 2H), 6.32 (m, 1H), 4.28 (d, J=9.0 Hz, 2H), 3.22 (m, 1H), 1.17 (d, J=6.0 Hz, 6H); Anal. Calcd for ($C_{16}H_{17}Cl_2O_6P$+0.2 $C_4H_8O_2$+0.4$H_2O$): C, 46.71; H, 4.53. Found: C, 46.95, H, 4.50.

Example 9

Compound 9: 3,5-dichloro-4-[4'-hydroxy-3'-(N-piperidinylsulfonamido)-phenoxy]benzylphosphonic acid Step a:

To a stirred solution of bis(4-methoxyphenyl)iodonium tetrafluoroborate (5.2 g, 13.5 mmol, Yokoyama et al., *J. Med. Chem.* 38:695 (1995)) and copper powder (1.14 g, 18.1 mmol) in $CH_2Cl_2$ (30 mL) at 0° C. was added a solution of methyl 3,5-dichloro-4-hydroxybenzoate (39, 2.0 g, 9.0 mmol) and $Et_3N$ (1.1 g, 1.5 mL, 12.0 mmol) in $CH_2Cl_2$ (10 mL). The reaction mixture was stirred at room temperature for 24 h and filtered through a Celite plug. The filtrate was washed with 2 N HCl (20 mL) and extracted with ethyl acetate (2×100 mL). The combined organic layers were washed with brine and water, dried over $MgSO_4$, filtered and concentrated under reduced pressure. The crude product was purified by column chromatography on silica gel, eluting with ethyl acetate-hexanes (1:9) to afford methyl 3,5-dichloro-4-(4'-methoxyphenoxy)benzoate as a white solid (1.59 g, 55%): mp 82-85° C.; $^1$H NMR (300 MHz, CDCl$_3$): δ 8.04 (s, 2H), 6.85 (dd, J=2.7, 4.8 Hz, 1H), 6.80 (dd, J=1.8, 4.5 Hz, 1H), 6.78 (t, J=3.3 Hz, 1H), 6.74 (d, J=2.4 Hz, 1H), 3.94 (s, 3H), 3.76 (s, 3H); TLC conditions: Uniplate silica gel, 250 microns; Mobile phase=ethyl acetate-hexanes (1:4); $R_f$=0.7.

Step b:

To a stirred solution of methyl 3,5-dichloro-4-(4'-methoxyphenoxy)benzoate (1.5 g, 4.5 mmol) in $CH_2Cl_2$ (50 mL) at −78° C. was added $BBr_3$ (11.4 mL, 11.4 mmol, 1 M solution in $CH_2Cl_2$). The reaction mixture was stirred at room temperature for 14 h, poured into ice water (100 mL) and stirred for 1 h. The reaction mixture was extracted with ethyl acetate (2×100 mL). The combined organic layers were washed with water and brine, dried over $MgSO_4$, filtered and concentrated under reduced pressure. The crude product was recrystallized from CH$_2$Cl$_2$, filtered and dried under reduced pressure to afford 3,5-dichloro-4-(4'-hydroxyphenoxy)benzoic acid as a brown solid (1.02 g, 75%): mp 163-165° C.; $^1$H NMR (300 MHz, DMSO-d$_6$): δ 9.02 (bs, 1H), 8.0 (s, 2H), 6.67 (m, 4H); TLC conditions: Uniplate silica gel, 250 microns; Mobile phase=ethyl acetate-hexanes (2:3); R$_f$=0.3.

Step c:

To a stirred cold solution of CH$_3$OH (35 mL) and acetyl chloride (7 mL, 86.0 mmol) at 0° C. was added dropwise a solution of 3,5-dichloro-(4'-hydroxyphenoxy)benzoic acid (1.3 g, 4.3 mmol) in CH$_3$OH (5 mL). The reaction mixture was heated under reflux for 5 h and cooled to room temperature. The solvent was removed under reduced pressure and the residue was dissolved in ethyl acetate (100 mL). The resulting solution was washed with water and brine, dried over MgSO$_4$, filtered and concentrated under reduced pressure. The crude product was triturated with hexane-ether (8:2), filtered and dried under reduced pressure to afford methyl 3,5-dichloro-4-(4'-hydroxyphenoxy) benzoate as a brown solid (1.22 g, 90%): mp 152-155° C.; $^1$H NMR (300 MHz, DMSO-d$_6$): δ 9.22 (s, 1H), 8.08 (s, 2H), 6.77 (t, J=3.0 Hz, 1H), 6.74 (t, J=2.7 Hz, 1H), 6.72 (t, J=2.7 Hz, 1H), 6.68 (d, J=2.7 Hz, 1H), 3.87 (s, 3H); TLC conditions: Uniplate silica gel, 250 microns; Mobile phase=ethyl acetate-hexanes (2:3); R$_f$=0.5.

Step d:

To a stirred solution of methyl 3,5-dichloro-4-(4'-hydroxyphenoxy)benzoate (1.2 g, 3.8 mmol) in CHCl$_3$ (10 mL) at 0° C. was added chlorosulfonic acid (3.9 mL, 38.3 mmol). The reaction mixture was stirred at 0° C. for 1 h and allowed to warm to room temperature. The reaction mixture was stirred for 2 h, poured into ice water and extracted with ethyl acetate (3×100 mL). The combined organic layers were washed with water, dried over MgSO$_4$ and concentrated under reduced pressure to afford the crude product, which was used in the next step without purification. The crude product (1.1 g, 2.6 mmol) was dissolved in THF (10 mL) and to it was added a solution of piperidine (0.68 g, 1 mL) in THF (5 mL). The reaction mixture was stirred at room temperature for 16 h and the solvent was removed under reduced pressure. The residue was dissolved in ethyl acetate (50 mL) and washed with water and brine. The organic layer was dried over Na$_2$SO$_4$, filtered and concentrated under reduced pressure. The crude product was purified by column chromatography on silica gel, eluting with ethyl acetate-hexanes (3:7) to afford desired methyl 3,5-dichloro-4-[4'-hydroxy-3'-(N-piperidinylsulfonamido) phenoxy]benzoate as a white solid (0.78 g, 60%): mp 122-125° C.; $^1$H NMR (300 MHz, CDCl$_3$): δ 8.58 (s, 1H), 7.04-7.10 (m, 2H), 6.85 (d, J=2.7 Hz, 2H), 3.96 (s, 3H), 3.02 (t, J=5.1 Hz, 4H), 1.63-1.59 (m, 4H), 1.50-1.40 (m, 2H); TLC conditions: Uniplate silica gel, 250 microns; Mobile phase=ethyl acetate-hexanes (3:7); R$_f$=0.35.

Step e:

To a stirred solution of methyl 3,5-dichloro-4-[4'-hydroxy-3'-(N-piperidinylsulfonamido)phenoxy]benzoate (0.95 g, 2.0 mmol) in CH$_2$Cl$_2$ (15 mL) at −78° C. was added DIBAL-H (6.1 mL, 6.1 mmol, 1 M solution in CH$_2$Cl$_2$). The reaction mixture was stirred at room temperature for 5 h, cooled to 0° C., quenched with saturated aqueous NaF solution (20 mL) and stirred at room temperature for 1 h. The reaction mixture was filtered and the filtrate was extracted with ethyl acetate (2×100 mL). The combined organic layers were washed with brine, dried over Na$_2$SO$_4$ and concentrated under reduced pressure. The crude product was purified by column chromatography on silica gel, eluting with ethyl acetate-hexanes (1:4) to afford 3,5-dichloro-4-[4'-hydroxy-3'-(N-piperidinylsulfonamido)phenoxy]benzyl alcohol as a white solid (0.66 g, 75%): mp 142-145° C.; $^1$H NMR (300 MHz, DMSO-d$_6$): δ 8.54 (s, 1H), 7.40 (s, 2H), 7.09 (dd, J=3.0, 9.3 Hz, 1H), 6.98 (dd, J=3.0, 9.3 Hz, 1H), 6.84 (d, J=2.4 Hz, 1H), 4.70 (d, J=3.9 Hz, 2H), 3.02 (t, J=2.4 Hz, 4H), 1.70-1.50 (m, 4H), 1.47-1.50 (m, 2H); TLC conditions: Uniplate silica gel, 250 microns; Mobile phase=ethyl acetate-hexanes (2:3); R$_f$=0.4.

Step f:

To a stirred solution of 3,5-dichloro-4-[4'-hydroxy-3'-(N-piperidinylsulfonamido)phenoxy]benzyl alcohol (0.40 g, 0.92 mmol) in ethyl ether-DME (9:1, 10 mL) at 0° C. was added phosphorous tribromide (1.2 g, 0.5 mL, 4.64 mmol). The reaction mixture was stirred at 0° C. for 5 h, quenched with ice (10 g) and stirred at 0° C. for 30 min. The reaction mixture was extracted with ether (100 mL) and washed with brine. The organic layer was dried over Na$_2$SO$_4$, filtered and concentrated under reduced pressure. The crude product was purified by column chromatography on silica gel, eluting with ethyl acetate-hexanes (1:4) to afford 3,5-dichloro-4-[4'-hydroxy-3'-(N-piperidinylsulfonamido)phenoxy]benzyl bromide as a colorless oil (0.34 g, 75%): $^1$H NMR (300 MHz, CDCl$_3$): δ 8.57 (s, 1H), 7.42 (s, 2H), 7.0 (dd, J=3.0, 9.3 Hz, 1H), 6.97 (d, J=9.3 Hz, 1H), 6.86 (d, J=2.7 Hz, 1H), 4.41 (s, 2H), 3.02 (t, J=5.1 Hz, 4H), 1.65-1.55 (m, 4H), 1.50-1.45 (m, 2H); TLC conditions: Uniplate silica gel, 250 microns; Mobile phase=ethyl acetate-hexanes (3:7); R$_f$=0.75.

Step g:

To a stirred a solution of 3,5-dichloro-4-[4'-hydroxy-3'-(N-piperidinylsulfonamido)phenoxy]benzyl bromide (0.12 g, 0.25 mmol) in toluene (5 mL) at room temperature was added triethylphosphite (0.42 g, 2.5 mmol). The reaction mixture was heated at 130° C. for 8 h and cooled to room temperature. The solvent was removed under reduced pressure and the residue was purified by column chromatography on silica gel, eluting with ethyl acetate-hexanes (1:1) to afford diethyl 3,5-dichloro-4-[4'-hydroxy-3'-(N-piperidinylsulfonamido)phenoxy]benzylphosphonate as a white solid (0.12 g, 90%): mp 132-135° C.; $^1$H NMR (300 MHz, CDCl$_3$): δ 8.55 (s, 1H), 7.33 (d, J=2.7 Hz, 2H), 7.05 (dd, J=3.0, 9.3 Hz, 1H), 6.97 (d, J=9.3 Hz, 1 H), 6.83 (d, J=3.3 Hz, 1H), 4.09 (q, J=6.9 Hz, 4H), 3.07 (d, J=21.6, 2H), 3.02 (t, J=6.0 Hz, 4H), 1.67-1.57 (m, 4H), 1.50-1.42 (m, 2H), 1.30 (t, J=9.0 Hz, 6H); TLC conditions: Uniplate silica gel, 250 microns; Mobile phase=ethyl acetate-hexanes (1:1); R$_f$=0.4.

Step h:

To a stirred solution of diethyl 3,5-dichloro-4-[4'-hydroxy-3'-(N-piperidinylsulfonamido)phenoxy]benzylphosphonate (0.1 g, 0.18 mmol) in CH$_2$Cl$_2$ (5 mL) at 0° C. was added TMSBr (0.27 g, 0.3 mL, 1.8 mmol). The reaction mixture was stirred at 0° C. for 30 min, allowed to warm to room temperature and stirred for 16 h. The solvent was removed under reduced pressure and the residue was dissolved in CH$_3$OH (3 mL). The solvent was removed under reduced pressure. The residue was triturated with water (3 mL). The mixture was filtered and dried under reduced pressure to afford 3,5-dichloro-4-[4'-hydroxy-3'-(N-piperidinylsulfonamido)phenoxy)]-benzylphosphonic acid as a white solid (0.07 g, 78%): mp 68-72° C.; LC-MS m/z=496 [C$_{18}$H$_{20}$Cl$_2$NO$_7$PS+H]$^+$; Anal Calcd for (C$_{20}$H$_{16}$Cl$_2$FO$_5$P+0.5CH$_2$Cl$_2$): C, 41.28; H, 3.93; N, 2.60; S, 5.96. Found: C, 41.27; H, 3.86; N, 2.84; S, 5.84.

Example 10

Compound 10: 3,5-dichloro-4-[4'-hydroxy-3'-(N-exo-2-norbornyl-sulfonamido)phenoxy]benzylphosphonic acid Step a:
Methyl 3,5-dichloro-4-[4'-hydroxy-3'-(N-exo-2-norbornyl-sulfonamido)phenoxy]benzoate was synthesized as a white solid (0.89 g, 55%) from methyl-3,5-dichloro-4-(4'-hydroxy)phenoxybenzoate (1.3 g, 3.1 mmol) by following the procedure described in example 9, step d: mp 142-145° C.; $^1$H NMR (300 MHz, CDCl$_3$): δ 8.43 (s, 1H), 8.05 (s, 2H), 7.06 (dd, J=3.0, 8.7 Hz, 1H), 6.98 (d, J=9.3 Hz, 1H), 6.92 (d, J=3.0 Hz, 1H), 4.53 (d, J=7.5 Hz, 1H), 3.95 (s, 3H), 3.12 (m, 1H), 2.20 (bs, 1H), 2.04 (bs, 1H), 1.66-1.58 (m, 2H), 1.46-1.40 (m, 2H), 1.28-1.24 (m, 2H), 1.20-1.16 (m, 1H), 1.02 (dd, J=1.8, 7.8 Hz, 2H); TLC conditions: Uniplate silica gel, 250 microns; Mobile phase=ethyl acetate-hexanes (2:3); R$_f$=0.3.

Step b:
3,5-Dichloro-4-[4'-hydroxy-3'-(N-exo-2-norbornylsulfonamido)-phenoxy]benzyl alcohol was prepared as a white solid (0.46 g, 85%) from methyl 3,5-dichloro-4-[4'-hydroxy-3'-(N-exo-2-norbornylsulfonamido)-phenoxy]benzoate (0.5 g, 0.97 mmol) by following the procedure described in example 9, step e: mp 130-132° C.; $^1$H NMR (300 MHz, DMSO-d$_6$): δ 7.51 (s, 2H), 7.03 (dd, J=3.3, 9.0 Hz, 1H), 6.89 (d, J=8.7 Hz, 1H), 6.81 (d, J=3.0 Hz, 1H), 4.51 (s, 2H), 2.90 (dd, J=4.2, 8.1 Hz, 1H), 2.06 (bs, 1H), 1.86 (bs, 1H), 1.37 (dd, J=10.2, 24.3 Hz, 2H), 1.30-1.22 (m, 2H), 0.98-0.90 (m, 2H), 0.85-0.79 (m, 2H); TLC conditions: Uniplate silica gel, 250 microns; Mobile phase=ethyl acetate-hexanes (2:3); R$_f$=0.3.

Step c:
3,5-Dichloro-4-[4'-hydroxy-3'-(N-exo-2-norbornylsulfonamido)-phenoxy]benzyl bromide was prepared as a colorless oil (0.08 g, 75%) from 3,5-dichloro-4-[4'-hydroxy-3-(N-exo-2-norbornylsulfonamido)phenoxy]-benzyl alcohol (0.1 g, 0.20 mmol) by following the procedure described in example 9, step f: $^1$H NMR (300 MHz, CDCl$_3$): δ 8.33 (s, 1H), 7.34 (s, 2H), 7.0 (dd, J=3.0, 8.7 Hz, 1H), 6.90 (d, J=9.0 Hz, 1H), 6.85 (d, J=3.0 Hz, 1H), 4.33 (s, 2H), 3.05 (m, 1H), 2.14 (bs, 1H), 1.97 (bs, 1H), 1.59-1.49 (m, 2H), 1.38-1.32 (m, 2H), 1.21-1.16 (m, 2H), 1.12-1.06 (m, 1H), 0.95 (dd, J=1.8, 8.1 Hz, 1H); TLC conditions: Uniplate silica gel, 250 microns; Mobile phase=ethyl acetate-hexanes (2:3); R$_f$=0.75.

Step d:
Diethyl 3,5-dichloro-4-[4'-hydroxy-3'-(N-exo-2-norbornylsulfonamido)phenoxy]-benzylphosphonate was prepared as a colorless oil (0.2 g, 83%) from 3,5-dichloro-4-[4'-hydroxy-3-(N-exo-2-norbornylsulfonamido)phenoxy] benzyl bromide (0.22 g, 0.40 mmol) by following the procedure described in example 9, step g: $^1$H NMR (300 MHz, CDCl$_3$): δ 8.47 (s, 1H), 7.33 (d, J=2.7 Hz, 2H), 7.09 (dd, J=2.7, 8.7 Hz, 1H), 6.97 (dd, J=2.7, 9.0 Hz, 1H), 6.88 (d, J=3.0 Hz, 1H), 4.75 (d, J=7.2 Hz, 1H), 4.09 (q, J=6.9 Hz, 2H), 3.49 (s, 1H), 3.14 (d, J=21.6 Hz, 2H), 3.11-3.05 (m, 1H), 2.2 (bs, 1H), 2.05 (d, J=3.3 Hz, 1H), 1.44-1.22 (m, 6H), 1.20-1.15 (m, 1H), 1.14-1.02 (m, 1H); TLC conditions: Uniplate silica gel, 250 microns; Mobile phase=ethyl acetate-hexanes (2:3); R$_f$=0.3.

Step e:
3,5-Dichloro-4-[3'-(N-exo-2-norbornylsulfonamido)-4'-hydroxy-phenoxy]benzylphosphonic acid was prepared as a white solid (50 mg, 75%) from diethyl 3,5-dichloro-4-[3'-(N-exo-2-norbornylsulfonamido)-4'-hydroxyphenoxy]benzylphosphonate (0.075 g, 0.40 mmol) by following the procedure described in example 9, step h: mp 210-212° C.; LC-MS m/z=522 [C$_{20}$H$_{22}$Cl$_2$NO$_7$PS]$^+$; Anal Calcd for (C$_{20}$H$_{22}$Cl$_2$NO$_7$PS+0.7 CH$_2$Cl$_2$): C, 42.78; H, 4.06; N, 2.41. Found: C, 42.77; H, 4.17; N, 2.62.

Example 11

Compound 11: 3,5-dichloro-4-[3'-(4-fluorobenzyl)-4'-hydroxyphenoxy]-benzylphosphonic acid Step a:
To a stirred solution of methyl 3,5-dichloro-(4'-hydroxyphenoxy)benzoate (0.5 g, 1.52 mmol) and p-fluorobenzoyl chloride (0.69 g, 0.45 mL 3.8 mmol) in CH$_2$Cl$_2$ (50 mL) at room temperature was added TiCl$_4$ (7.6 mL, 7.6 mmol, 1 M solution in CH$_2$Cl$_2$). The reaction mixture was stirred at room temperature for 8 days, quenched with saturated aqueous NH$_4$Cl (25 mL) and stirred for 2 h. The reaction mixture was extracted with CH$_2$Cl$_2$ (2×100 mL). The combined organic layers were washed with brine, dried over Na$_2$SO$_4$, filtered and concentrated under reduced pressure. The crude product was triturated with hexanes-ethyl ether (8:2), filtered and dried under reduced pressure to afford methyl 3,5-dichloro-4-[3-(4-fluorobenzoyl)-4-methoxyphenoxy]benzoate as a yellow solid. (0.39 g, 62%): mp 112-115° C.; $^1$H NMR (300 MHz, CDCl$_3$): δ 8.04 (s, 2H), 7.81 (dd, J=5.7, 9.0 Hz, 2H), 7.09 (t, J=8.4 Hz, 2H), 6.93 (d, J=2.7 Hz, 1H), 6.92 (s, 1H), 6.81 (d, J=3.0 Hz, 1H), 3.94 (s, 3H), 3.69 (s, 3H); TLC conditions: Uniplate silica gel, 250 microns; Mobile phase=ethyl acetate-hexanes (1:4); R$_f$=0.75.

Step b:
To a stirred solution of methyl 3,5-dichloro-4-[3'-(4-fluorobenzoyl)-4'-methoxyphenoxy]benzoate (350 mg, 0.78 mmol) and TFA (2 mL) in CH$_2$Cl$_2$ (50 mL) at room temperature was added triethylsilane (0.5 mL, 3.1 mmol). The reaction mixture was stirred at room temperature for 16 h, quenched with water (25 mL) and extracted with ether (100 mL). The organic layer was dried over Na$_2$SO$_4$, filtered and concentrated under reduced pressure. The crude product was triturated with hexanes, filtered and dried under reduced pressure to afford methyl 3,5-dichloro-4-[3'-(4-fluorobenzyl)-4'-methoxyphenoxy]benzoate as a brown solid (0.31 g, 92%): mp 108-110° C.; $^1$H NMR (300 MHz, CDCl$_3$): δ 7.98 (s, 2H), 7.06 (dd, J=6.0, 9.0 Hz, 2H), 6.88 (t, J=8.7 Hz, 2H), 6.70 (d, J=9.0 Hz, 1H), 6.58 (d, J=3.0 Hz, 1H), 6.48 (dd, J=3.3, 9.0 Hz, 1H), 3.89 (s, 3H), 3.83 (s, 2H), 3.71 (s, 3H); TLC conditions: Uniplate silica gel, 250 microns; Mobile phase=ethyl acetate-hexanes (2:8); R$_f$=0.8.

Step c:
To a stirred suspension of LiAlH$_4$ (0.26 g, 6.95 mmol) in THF (40 mL) at 0° C. was slowly added a solution of methyl 3,5-dichloro-4-[3'-(4-fluorobenzyl)-4'-methoxyphenoxy] benzoate (1.2 g, 2.76 mmol) in THF (10 mL). The reaction mixture was stirred at room temperature for 20 h and cooled to 0° C. The reaction mixture was quenched with 15% aqueous NaOH (1.5 mL), diluted with H$_2$O (3.0 mL) and stirred for 1 h. The reaction mixture was filtered through a Celite plug and the filtrate was extracted with ethyl acetate (100 mL). The combined organic layers were washed with brine, dried over Na$_2$SO$_4$ and concentrated under reduced pressure. The crude product was purified by column chromatography on silica gel, eluting with ethyl acetate-hexanes (1:1) to afford 3,5-dichloro-4-[3'-(4-fluorobenzyl)-4'-methoxyphenoxy] benzyl alcohol as an oil (0.78 g, 70%): $^1$H NMR (300 MHz, CDCl$_3$): δ 7.47 (s, 2H), 7.16 (dd, J=6.0, 8.7 Hz, 2H), 7.04 (t, J=8.7 Hz, 2H), 6.84 (d, J=9.0 Hz, 1H), 6.67 (d, J=3.0 Hz, 1H), 6.45 (dd, J=5.4, 9.3 Hz, 1H), 5.45 (t, J=5.7 Hz, 1H), 4.48 (d, J=5.7 Hz, 2H), 3.82 (s, 2H), 3.69 (s, 3H); TLC conditions: Uniplate silica gel, 250 microns; Mobile phase=ethyl acetate-hexanes (2:3); $R_f$=0.45.

Step d:

To a stirred solution of 3,5-dichloro-4-[3'-(4-fluorobenzyl)-4'-methoxyphenoxy] benzyl alcohol (0.53 g, 1.29 mmol) in $CH_2Cl_2$ (20 mL) at −78° C. was added $BBr_3$ (0.82 g, 3.2 mmol). The reaction mixture was stirred at room temperature for 16 h, poured into ice water (100 mL) and extracted with $CH_2Cl_2$ (200 mL). The organic layer was washed with brine, dried over $Na_2SO_4$, filtered and concentrated under reduced pressure. The crude product was purified by column chromatography on silica gel, eluted with ethyl acetate-hexanes (1:4) to afford 3,5-dichloro-4-[3'-(4-fluorobenzyl)-4'-hydroxyphenoxy] benzyl bromide as a colorless oil (0.4 g, 67%): $^1$H NMR (300 MHz, $CDCl_3$): δ 7.39 (s, 2H), 7.14 (dd, J=5.4, 8.7 Hz, 2H), 6.95 (t, J=8.7 Hz, 2H), 6.66 (d, J=9.0 Hz, 1H), 6.62 (d, J=2.7 Hz, 1H), 6.53 (dd, J=3.0, 8.7 Hz, 1H), 4.04 (s, 2H), 3.90 (s, 2H); TLC conditions: Uniplate silica gel, 250 microns; Mobile phase=ethyl acetate-hexanes (1:4); $R_f$=0.8.

Step e:

To a stirred solution of 3,5-dichloro-4-[3'-(4-fluorobenzyl)-4-hydroxyphenoxy] benzyl bromide (0.25 g, 0.55 mmol) in toluene (5 mL) at room temperature was added triethylphosphite (0.91 g, 5.5 mmol). The reaction mixture was heated at 120° C. for 8 h and cooled to room temperature. The solvent was removed under reduced pressure and the crude product was purified by column chromatography on silica gel, eluting with ethyl acetate-hexanes (1:1) to afford diethyl 3,5-dichloro-4-[3'-(4-fluorobenzyl)-4'-hydroxyphenoxy] benzylphosphonate as a colorless oil (0.2 g, 68%): $^1$H NMR (300 MHz, $CDCl_3$): δ 7.29 (d, J=2.7 Hz, 2H), 7.15 (dd, J=5.4, 9.0 Hz, 2H), 6.95 (t, J=8.7 Hz, 2H), 6.66 (d, J=4.8 Hz, 1H), 6.65 (s, 1H), 6.46 (dd, J=3.0, 8.7 Hz, 1H), 4.07 (q, J=7.2 Hz, 4H), 3.89 (s, 2H), 3.04 (d, J=21.3 Hz, 2H), 1.27 (t, J=7.2 Hz, 3H); TLC conditions: Uniplate silica gel, 250 microns; Mobile phase=ethyl acetate-hexanes (1:1); $R_f$=0.3.

Step f:

To a stirred solution of diethyl 3,5-dichloro-4-[3'-(4-fluorobenzyl)-4'-hydroxyphenoxy]benzyl phosphonate (0.09 g, 0.18 mmol) in $CH_2Cl_2$ (5 mL) at 0° C. was added TMSBr (0.28 g, 0.3 mL). The reaction mixture was stirred at 0° C. for 30 min, allowed to warm to room temperature. The reaction mixture was stirred at room temperature for 16 h and the solvent was removed under reduced pressure. The residue was dissolved in $CH_3OH$ (5 mL) and the solvent was removed under reduced pressure. The residue was triturated with water (3 mL), filtered and dried under reduced pressure to afford 3,5-dichloro-4-[3'-(4-fluorobenzyl)-4'-hydroxyphenoxy] benzylphosphonic acid as a white solid (0.075 g, 94%): mp 207-210° C.; LC-MS m/z=457 $[C_{20}H_{16}Cl_2FO_5P+H]^+$; Anal Calcd for ($C_{20}H_{16}Cl_2FO_5P$+0.8 $CH_2Cl_2$): C, 47.78; H, 3.39. Found: C, 47.78; H, 3.39.

Example 12

Compound 12-1: di(pivaloyloxymethyl) [3,5-Dimethyl-4-(4'-hydroxy-3'-iso-propylbenzyl)phenoxy] methylphosphonate To a mixture of [3,5-dimethyl-4-(4'-hydroxy-3'-iso-propylbenzyl)-phenoxy] methylphosphonic acid (0.2 g, 0.5 mmol) and N,N-diisopropylethylamine (0.57 mL, 3.0 mmol) in $CH_3CN$ (5.0 mL) at 0° C. was added pivaloyloxymethyl iodide (0.6 mL, 3.0 mmol). The reaction mixture was stirred at room temperature for 16 h and the solvent was removed under reduced pressure. The crude product was purified by column chromatography on silica gel, eluting with acetone-hexanes (1:3) to afford the title compound as a white solid (0.22 g, 76%): $^1$H NMR (300 MHz, $CD_3OD$): δ 6.79 (d, J=3.0 Hz, 1H), 6.68 (s, 2H), 6.45-6.60 (m, 2H), 5.75 (m, 4H), 4.44 (d, J=9.9 Hz, 2H), 3.88 (s, 2H), 3.20 (m, 1H), 2.20 (s, 6H), 1.20 (s, 18H), 1.12 (d, J=7.2 Hz, 6H); LC-MS m/z=593 $[C_{31}H_{45}O_9P+H]^+$; Anal. Calcd for ($C_{31}H_{45}O_9P$+0.3$H_2O$): C, 62.26; H, 7.69. Found: C, 62.15; H, 7.77.

Using the appropriate starting material, compounds 12-2 and 12-9 were prepared in an analogous manner to that described for the synthesis of compound 12-1.

Compound 12-2: di(ethoxycarbonyloxymethyl)[3,5-dimethyl-4-(4'-hydroxy-3'-iso-propylbenzyl)phenoxy] methylphosphonate $^1$H NMR (300 MHz, DMSO-$d_6$): δ 9.01 (s, 1H), 6.86 (s, 1H), 6.73 (s, 2H), 6.63-6.61 (m, 1H), 6.47-6.45 (m, 1H), 5.72 (s, 2H), 5.68 (s, 2H), 4.51-4.48 (d, J=7.5 Hz, 2H), 4.17-4.12 (m, 4H), 3.82 (s, 2H), 3.13 (m, 1H), 2.18-2.16 (m, 6H), 1.23-1.18 (m, 6H), 1.12-1.10 (d, J=6.0 Hz, 6H); LC-MS m/z=569 $[C_{27}H_{37}O_{11}P+H]^+$; Anal. Calcd for ($C_{27}H_{37}O_{11}P$): C, 57.04; H, 6.56. Found: C, 56.60, H, 6.14.

Compound 12-3: di(isopropoxycarbonyloxymethyl) [3,5-dimethyl-4-(4'-hydroxy-3'-iso-propylbenzyl) phenoxy]methylphosphonate $^1$H NMR (300 MHz, DMSO-$d_6$): 88.97 (s, 1H), 6.81 (s, 1H), 6.69 (s, 2H), 6.59-6.56 (m, 1H), 6.43-6.40 (m, 1H), 5.68 (s, 2H), 5.63 (s, 2H), 4.81-4.73 (m, 2H), 4.46-4.43 (d, J=7.5 Hz, 2H), 3.78 (s, 2H), 3.12-3.07 (m, 1H), 2.14 (s, 6H), 1.21-1.16 (m, 12H), 1.08-1.06 (d, J=6.0 Hz, 6H); LC-MS m/z=597 $[C_{29}H_4{_1}O_{11}P+H]^+$; Anal. Calcd for ($C_{29}H_{41}O_{11}P$): C, 58.38; H, 6.93. Found: C, 58.10, H, 7.54.

Compound 124: Di-(pivaloyloxymethyl)[3,5-dimethyl-4-(4'-hydroxy-3'-sec-butylbenzyl)phenoxy] methylphosphonate $^1$H NMR (300 MHz, DMSO-$d_6$): δ 8.95 (s, 1H), 6.76 (s, 1H), 6.72 (s, 2H), 6.64-6.61 (d, 1H), 6.65-6.47 (d, 1H), 5.73 (s, 2H), 5.68 (s, 2H), 4.48-4.45 (d, 2H), 3.81 (s, 2H), 2.93-2.90 (q, 1H), 2.17 (s, 6H), 1.52-1.44 (m, 2H), 1.17-1.11 (m, 18H), 1.08-1.06 (d, 3H), 0.78-0.73 (t, 3H); LC-MS m/z=607.2 $[C_{32}H_{47}O_9P+H]^+$; TLC conditions: Uniplate silica gel, 250 microns; Mobile phase=acetone-hexanes (3:7); $R_f$=0.56; Anal. Calcd for ($C_{32}H_{47}O_9P$+0.25 $C_3H_6O$): C, 63.32; H, 7.87. Found: C, 63.72; H, 8.19.

Compound 12-5: Di-(pivaloyloxymethyl)[3,5-dibromo-4-(4'-hydroxy-3'-iso-propylphenoxy)benzyl] phosphonate mp: 90-91° C.; $^1$H NMR (300 MHz, DMSO-$d_6$): δ 9.07 (s, 1H), 7.66 (s, 1H), 6.68-6.66 (m, 2H), 6.26-6.22 (d, 1H), 5.67-5.58 (q, 4H), 3.56-3.48 (d, 2H), 3.19-3.14 (m, 1H), 1.19-1.11 (m, 24H); LC-MS m/z=709.4 $[C_{28}H_{37}Br_2O_9P+H]^+$; TLC conditions: Uniplate silica gel, 250 microns; Mobile phase=acetone-hexanes (3:7); $R_f$=0.50; Anal. Calcd for ($C_{28}H_{37}Br_2O_9P$): C, 47.48; H, 5.26. Found: C, 47.09; H, 4.87.

Compound 12-6: Di-(pivaloyloxymethyl)[3,5-dimethyl-4-(3'-(4-fluorobenzyl)-4'-hydroxy-benzyl)phenoxy]methylphosphonate $^1$H NMR (300 MHz, DMSO-d$_6$): δ 9.17(1H, s), 7.18-7.02 (m, 3H), 6.71-6.64 (m, 4H), 6.54 (m, 1H), 4.45 (d, 2H, J=10 Hz), 3.76 (s, 4H), 2.12 (s, 6H), 1.13 (s, 18H); LC-MS m/z=633 [C$_{33}$H$_{44}$O$_9$P+H]$^+$; TLC conditions: Uniplate silica gel, 250 microns; Mobile phase=ethyl acetate 50% in hexane; R$_f$=0.48; Anal. Calcd for (C$_{33}$H$_{44}$FO$_9$P+0.5H$_2$O): C, 62.99; H, 6.90. Found: C, 62.99; H, 6.90.

Compound 12-7: Di(pivaloyloxymethyl)[3,5-diiodo-4-(4'-hydroxy-3'-iso-propylphenoxy)phenoxy]methylphosphonate mp: 144-147° C.; $^1$H NMR (300 MHz, DMSO-d$_6$): δ 8.99 (s, 1H), 7.59 (s, 2H), 6.68 (m, 1H), 6.56 (m, 1H), 6.25 (m, 1H), 5.73 (d, J=12.0 Hz, 2H), 4.64 (d, J=10.5 Hz, 2H), 3.16 (m, 1H), 1.17 (m, 18H), 1.12 (d, J=6.0 Hz, 6H); LC-MS m/z=819 [C$_{28}$H$_{37}$O$_{10}$I$_2$P+H]$^+$; HPLC conditions: Column=Agilent Zorbax SB-Aq RP-18 filter, 150×3.0; Mobile phase=Solvent A (Acetonitrile)=HPLC grade acetonitrile; Solvent B (buffer)=20 mM ammonium phosphate buffer (pH 6.1, 0.018 M NH$_4$H$_2$PO$_4$/0.002 M (NH$_4$)$_2$HPO$_4$). Flow rate=1.0 mL/min; UV@ 255 nm. Retention time in minutes. (rt=14.66/25.00, 93% purity); TLC conditions: Uniplate silica gel, 250 microns; Mobile phase=ethyl acetate-hexanes (1:1); R$_f$=0.39.

Compound 12-8: Di(pivaloyloxymethyl)[3,5-dichloro-4-(4'-hydroxy-3'-iso-propylbenzyl)phenoxy]methylphosphonate $^1$H NMR (200 MHz, DMSO-d$_6$): δ 9.09 (s, 1H), 7.21 (s, 2H), 6.94 (s, 1H), 6.64 (s, 2H), 5.72 (d, J=21.0 Hz, 2H), 4.64 (d, J=15 Hz, 2H), 4.00 (s, 2H), 3.15 (m, 1H), 1.25 (m, 18H), 1.11 (d, J=4.5 Hz, 6H); LC-MS m/z=633 [C$_{29}$H$_{39}$O$_9$Cl$_2$P+H]$^+$; TLC conditions: Uniplate silica gel, 250 microns; Mobile phase=ethyl acetate-hexanes (3:2); R$_f$=0.62. Anal. Calcd for (C$_{29}$H$_{39}$O$_9$Cl$_2$P+0.3H$_2$O+0.2 CH$_3$CO$_2$CH$_2$CH$_3$): C, 54.49; H, 6.32. Found: C, 54.52, H, 6.33.

Compound 12-9: Di(pivaloyloxymethyl[4,6-dichloro-3-fluoro-5-(4'-hydroxy-3'-iso-propylphenoxy)-pyrid-2-ylamino]methylphosphonate The title compound was prepared according to the procedure described for the synthesis of example 12 using [4,6-dichloro-3-fluoro-5-(4'-hydroxy-3'-iso-propylphenoxy)-pyrid-2-ylamino]methylphosphonic (U.S. Pat. No. 6,747,048 B2):

$^1$H NMR (200 MHz, DMSO-d$_6$): δ 9.20 (s, 1H), 7.54 (t, J=6.0 Hz, 1H), 6.80 (d, J=3.4 Hz, 1H), 6.68 (d, J=8.8 Hz, 1H), 6.44 (dd, J=3.4, 8.8 Hz, 1H), 5.62 (d, J=12.4 Hz, 4H), 3.97 (m, 2H), 3.22 (m, 1H), 1.07-1.17 (m, 24H); TLC conditions: Uniplate silica gel, 250 microns; Mobile phase=ethyl acetate-hexanes (3:2); R$_f$=0.51; LC-MS m/z=654 [C27H36Cl2FN2O9P+H]$^+$; Anal Calcd for (C27H36Cl2FN2O9P+0.2Et$_2$OAc): C, 49.76; H, 5.65; N, 4.17. Found: C, 50.02; H, 6.02; N, 4.07.

Compound 12-10: Isopropyloxycarbonyloxymethyl [3,5-dibromo-4-(4'-hydroxy-3'-isopropylphenoxy)benzyl]methylphosphinite mp: 58-61° C.; $^1$H NMR (200 MHz, DMSO-d$_6$): δ 9.05 (s, 1H), 7.65 (d, J=2.4 Hz, 2H), 6.67 (m, 2H), 6.23 (dd, J=2.8, 10.2 Hz, 1H), 5.56 (d, J=11.0 Hz, 2H), 4.80 (m, 1H), 3.36 (d, J=10.2 Hz, 3H), 3.14 (m, 1H), 1.48 (d, J=10.2 Hz, 3H), 1.25 (d, J=6.8 Hz, 6H), 1.11 (d, J=7.0 Hz, 6H); LC-MS m/z=595 [C$_{22}$H$_{27}$Br$_2$O$_7$P+H]$^+$; Anal. Calcd for (C$_{17}$H$_{19}$Br$_2$O$_4$P): C, 44.47; H, 4.58. Found: C, 44.19; H, 4.80.

Compound 12-11: 2-[3,5-dimethyl-4-(3'-(4'-fluorobenzyl)-4'-hydroxybenzyl)phenyl]ethylphosphonic acid isopropoxycarbonyloxymethyl ester methyl ester $^1$H NMR (300 MHz, DMSO-d$_6$): δ 9.17 (s, 1H), 6.88-7.22 (m, 4H), 6.88 (s, 2H), 6.71 (d, J=2.1 Hz, 1H), 6.65 (d, J=8.1 Hz, 1H), 6.55 (dd, J=2.1, 8.1 Hz, 1H), 5.55 (d, J=12.9 Hz, 2H), 4.83 (m, 1H), 3.79 (s, 2H), 3.76 (s, 2H), 3.63 (d, J=11.1 Hz, 3H), 2.65 (m, 2H), 2.12 (s, 6H), 2.05 (m, 2H), 1.22 (m, 6H); TLC conditions: Uniplate silica gel, 250 microns; Mobile phase=ethyl acetate-hexanes (9:1); R$_f$=0.42; LC-MS m/z=559 [C30H36FO7P+H]$^+$; Anal Calcd for (C30H36FO7P): C, 64.51; H, 6.50. Found: C, 64.54; H, 6.26.

Compound 12-12: Pivaloxymethyl methyl 3,5-Dimethyl-4-(4'-hydroxy-3'-isopropylbenzyl)benzylphosphonate $^1$H NMR (300 MHz, CD$_3$OD): δ 7.03 (d, J=2.1 Hz, 2H), 6.83 (d, J=2.1 Hz, 1H), 6.54 (m, 2H), 5.96 (m, 2H), 3.96 (s, 2H), 3.74 (d, J=10.8 Hz, 3H), 3.25 (d, J=21.0 Hz, 2H), 3.21 (m, 1H), 2.25 (s, 6H), 1.25 (s, 9H), 1.13 (d, J=7.0 Hz, 6H); LC-MS m/z=477 [C$_{26}$H$_{37}$O$_6$P+H]$^+$.

Compound 12-13: Pivaloyloxymethyl [3,5-dibromo-4-(4'-hydroxy-3'-iso-propylphenoxy)phenoxymethyl]methylphosphonate $^1$H NMR (300 MHz, DMSO-d$_6$): δ 9.04 (s, 1H), 7.50 (s, 2H), 6.66 (m, 2H), 6.30 (m, 1H), 5.69 (d, J=13.5 Hz, 2H), 4.51 (d, J=7.5 Hz, 3H), 3.17 (m, 1H), 1.68 (d, J=15.0 Hz, 3H); 1.14 (m, 15H); LC-MS m/z=608 [C$_{23}$H$_{29}$Br$_2$O$_7$P+H]$^+$.

Example 13

Cis and Trans (S)-2-[(3,5-dimethyl-4-(4'-hydroxy-3'-iso-propylbenzyl)-phenoxy)methyl]-4-(3-chlorophenyl)-2-oxo-2×5-[1,3,2]-dioxaphosphonane To a mixture of [4-(4'-hydroxy-3'-iso-propylbenzyl)-3,5-dimethyl-phenoxy] methylphosphonic acid (0.2 g, 0.55 mmol), 1-(3-chlorophenyl)-1,3-propane diol (0.31 g, 1.6 mmol) and pyridine (1 mL) in DMF (5 mL) at room temperature was added 1,3-dicyclohexylcarbodiimide (0.34 g, 1.6 mmol). The reaction mixture was heated at 70° C. for 4 h, cooled to room temperature and filtered through a Celite plug. The solvent was removed under reduced pressure and the crude product was purified by column chromatography on silica gel, eluting with 4% methanol in CH$_2$Cl$_2$ to afford Cis (0.06 g, 15%) and Trans (S)-2-[3,5-dimethyl-4-(4'-hydroxy-3'-iso-propylbenzyl) phenoxy]methyl-4-(3-chlorophenyl)-2-oxo-1,3,2-dioxaphosphonane (0.05 g, 12%) as white solids.

Compound 13-1-cis mp 77-82° C.; LC-MS m/z=516 [C$_{28}$H$_{32}$ClO$_5$P+H]$^+$; Anal. Calcd for (C$_{28}$H$_{32}$ClO$_5$P+0.2H$_2$O): C, 64.85; H, 6.30. Found: C, 64.93; H, 6.65. M.P.: 77-82.0° C.

Alternative improved method for the preparation of compound: Compound 13-1-cis: Cis (S)-2-[(3,5-Dimethyl-4-(4'- hydroxy-3'-iso-propylbenzyl)phenoxy)methyl]-4-(3-Chlorophenyl)-2-oxo-2λ$^5$-[1,3,2]-dioxaphosphinane:

A solution of cis (S)-2-[(4-(4'-acetoxy-3'-iso-propylbenzyl)-3,5-dimethylphenoxy)methyl]-4-(3-chlorophenyl)-2-oxo-2λ$^5$-[1,3,2]-dioxaphosphonane (compound 59-cis, 2.5 g, 4.49 mmol) and 4.0 M HCl in dioxane (2.5 mL, 10.0 mmol) in methanol (25 mL) was stirred at 20° C. for 3.5 hrs. The solvent was removed under reduced pressure. The crude product was purified by column chromatography on silica gel, eluting with acetone-dichloromethane (1:4) to afford cis (S)-2-[(3,5-dimethyl-4-(4'-hydroxy-3'-iso-propylbenzyl) phenoxy)methyl]-4-(3-Chlorophenyl)-2-oxo-2×5-[1,3,2]-dioxaphosphinane (1.9 g, 83%): $^1$H NMR (300 MHz, DMSO-d$_6$): δ 8.97 (s, 1H), 7.47 (m, 1H), 7.38-7.31 (m, 3H), 6.82 (d, J=2.1 Hz, 1H), 6.73 (s, 2H), 6.59 (d, J=8.1 Hz, 1H), 6.43 (dd, J=8.1 and 2.0 Hz, 1H), 5.76-5.71 (m, 1H), 4.61-4.36 (m, 4H), 3.78 (s, 2H), 3.15-3.05 (m, 1H), 2.24-2.17 (m, 2H), 2.14 (s, 6H), 1.07 (d, J=6.9 Hz, 6H). TLC conditions: Uniplate silica gel, 250 microns; Mobile phase=dichloromethane-acetone (9:1); R$_f$=0.28; Anal Calcd for (C$_{28}$H$_{32}$ClO$_5$P+0.2H$_2$O): C, 64.85; H, 6.30. Found: C, 64.64; H, 6.36. Water by KF titration=0.66%.

Compound 13-1-trans mp 88-93° C.; LC-MS m/z=516 [C$_{28}$H$_{32}$ClO$_5$P+H]$^+$; Anal. Calcd for (C$_{28}$H$_{32}$ClO$_5$P+0.2H$_2$O): C, 64.85; H, 6.30. Found: C, 64.93; H, 6.65. M.P.: 88-93.0° C.

Using the appropriate starting material, compounds 13-2 to 13-14 were prepared in an analogous manner to that described for the synthesis of compound 13-1.

Cis and Trans 2-[(3,5-dimethyl-4-(4'-hydroxy-3'-iso-propylbenzyl)phenoxy)methyl]-4-(3-bromophenyl)-2-oxo-2λ$^5$-[1,3,2]-dioxaphosphonane:

Compound 13-2-cis mp 70-75° C.; LC-MS m/z=559,561 [C$_{28}$H$_{32}$BrO$_5$P+H]$^+$; Anal. Calcd for (C$_{28}$H$_{32}$BrO$_5$P): C, 60.12; H, 5.77. Found: C, 60.03, H, 5.76; TLC conditions: Uniplate silica gel, 250 microns; mobile phase=3:2 hexanes-acetone; rf=0.31.

Compound 13-2-trans mp 80-85° C.; LC-MS m/z=559,561 [C$_{28}$H$_{32}$BrO$_5$P+H]$^+$; Anal. Calcd for (C$_{28}$H$_{32}$BrO$_5$P): C, 60.12; H, 5.77. Found: C, 59.76, H, 5.72; TLC conditions: Uniplate silica gel, 250 microns; mobile phase=3:2 hexanes-acetone; rf=0.49.

Cis and Trans 2-[(3,5-dimethyl-4-(4'-hydroxy-3'-iso-propylbenzyl)phenoxy)methyl]-4-(3-fluorophenyl)-2-oxo-2λ$^5$-[1,3,2]-dioxaphosphonane:

Compound 13-3-cis mp 75-80° C.; LC-MS m/z=499 [C$_{28}$H$_{32}$FO$_5$P+H]$^+$; Anal. Calcd for (C$_{28}$H$_{32}$FO$_5$P+0.2 EtOAc): C, 67.02; H, 6.56. Found: C, 67.01, H, 6.58; TLC conditions: Uniplate silica gel, 250 microns; mobile phase=3:2 acetone-hexanes; rf=0.19.

Compound 13-3-trans mp 80-85° C.; LC-MS m/z=499 [C$_{28}$H$_{32}$FO$_5$P+H]$^+$; Anal. Calcd for (C$_{28}$H$_{32}$FO$_5$P+0.2 EtOAc): C, 67.02; H, 6.56. Found: C, 66.93, H, 6.61; TLC conditions: Uniplate silica gel, 250 microns; mobile phase=3:2 acetone-hexanes; rf=0.52.

Cis and Trans 2-[(3,5-dimethyl-4-(4'-hydroxy-3'-iso-propylbenzyl)phenoxy) methyl]-4-(pyrid-3-yl)-2-oxo-25-[1,3,2]-dioxaphosphonane:

Compound 13-4-trans mp 75-78° C.: LC-MS m/z=482 [C$_{27}$H$_{32}$NO$_5$P+H]$^+$; Anal Calcd for C$_{27}$H$_{32}$NO$_5$P: C, 67.35; H, 6.70; N, 2.91. Found: C, 67.17; H, 6.89; N, 2.62; TLC conditions: Uniplate silica gel, 250 microns; mobile phase=CH$_2$Cl$_2$-MeOH (2%); R$_f$=0.3.

Compound 13-4-cis (108 mg, 50%): mp 75-78° C.; LC-MS m/z=482 [C$_{27}$H$_{32}$NO$_5$P+H]$^+$; Anal Calcd for C$_{27}$H$_{32}$NO$_5$P: C, 67.35; H, 6.70, N, 2.91. Found: C, 67.78; H, 6.76; N, 2.63; TLC conditions: Uniplate silica gel, 250 microns; mobile phase=CH$_2$Cl$_2$-MeOH (2%); R$_f$=0.27.

cis and Trans 2-[(3,5-dimethyl-4-(4'-hydroxy-3'-iso-propylbenzyl)phenoxy)methyl]-4-(pyrid-4-yl)-2-oxo-2λ$^5$-[1,3,2]-dioxaphosphonane:

Compound 13-5-trans (52%), mp 75-77° C.; LC-MS m/z=482 [C$_{27}$H$_{32}$NO$_5$P+H]$^+$; Anal Calcd for (C$_{27}$H$_{32}$NO$_5$P+0.4H$_2$O): C, 66.35; H, 6.76; N, 2.87. Found: C, 66.08; H, 6.55; N, 2.74; TLC conditions: Uniplate silica gel, 250 microns; mobile phase=CH$_2$Cl$_2$-MeOH (2%); R$_f$=0.3.

Compound 13-5-cis (20%), mp 75-77° C.; LC-MS m/z=482 [C$_{27}$H$_{32}$NO$_5$P+H]$^+$; Anal Calcd: (MF:C$_{27}$H$_{32}$NO$_5$P) Calcd: C, 67.35; H, 6.70; N, 2.91; Found: C, 67.02; H, 6.78; N, 2.81; TLC conditions: Uniplate silica gel, 250 microns; mobile phase=CH$_2$Cl$_2$-MeOH (2%); R$_f$=0.25.

Cis and Trans 2-[(3,5-dimethyl-4-(4'-hydroxy-3'-iso-propylbenzyl)phenoxy)methyl]-4-(4-chlorophenyl)-2-oxo-2λ$^5$-[1,3,2]-dioxaphosphonane:

Compound 13-6-trans mp 77-80° C.; LC-MS m/z=515 [C$_{28}$H$_{32}$ClO$_5$P]+; Anal Calcd: (MF:C$_{28}$H$_{32}$ClO$_5$P+0.1H$_2$O+0.4 EtOAc) Calcd: C, 64.34; H, 6.48; Found: C, 64.56; H, 6.91; TLC conditions: Uniplate silica gel, 250 microns; mobile phase=ethyl acetate/hexanes (3:2); R$_f$=0.6.

Compound 13-6-cis yellow solid, mp 77-80° C.; LC-MS m/z=515 [C$_{28}$H$_{32}$ClO$_5$P+H]$^+$; Anal Calcd: (MF:C$_{28}$H$_{32}$ClO$_5$P+0.1H$_2$O+0.1 CH$_2$Cl$_2$) Calcd: C, 64.65; H, 6.25; Found: C, 64.61; H, 6.66; TLC conditions: Uniplate silica gel, 250 microns; mobile phase=ethyl acetate/hexanes (3:2); R$_f$=0.5.

Cis and Trans 2-[(3,5-dimethyl-4-(4'-hydroxy-3'-iso-propylbenzyl)phenoxy)methyl]-4-(3,5-dichlorophenyl)-2-oxo-2λ$^5$-[1,3,2]-dioxaphosphonane:

Compound 13-7-trans mp 79-81° C.; LC-MS m/z=549 [C$_{27}$H$_{32}$Cl$_2$O$_5$P+H]$^+$; Anal Calcd for (C$_{28}$H$_{31}$Cl$_2$O$_5$P+0.35H$_2$O): C, 60.45; H, 5.74; Cl, 12.87. Found: C, 60.15; H, 5.67, Cl, 11.97; TLC conditions: Uniplate silica gel, 250 microns; mobile phase=ethyl acetate/hexanes (3:2); R$_f$=0.6.

Compound 13-7-cis (50%) mp 79-81° C.; LC-MS m/z=549 $[C_{28}H_{31}Cl_2O_5P]^+$; Anal Calcd for $(C_{28}H_{31}Cl_2O_5P+0.1H_2O)$: C, 60.94; H, 5.70; Cl, 12.97. Found: C, 60.77; H, 6.18; Cl, 11.56; TLC conditions: Uniplate silica gel, 250 microns; mobile phase=ethyl acetate-hexanes (3:2); $R_f$=0.5.

Compound 13-8: Cis-(S)-2-[(3,5-dimethyl-4-(4'-hydroxy-3'-sec-butylbenzyl)phenoxy)methyl]-4-(3-chlorophenyl)-2-oxo-2λ$^5$-[1,3,2]-dioxaphosphonane mp: 66-70° C.; $^1$H NMR (300 MHz, DMSO-d$_6$): δ 8.91 (s, 1H), 7.39-7.36 (m, 3H), 6.76 (s, 1H), 6.75 (s, 2H), 6.60-5.57 (d, 1H), 6.47-6.44 (d, 1H), 5.75-5.71 (m, 1H), 4.61-4.53 (m, 2H), 4.47-4.36 (m, 2H), 3.78 (s, 2H), 2.92-2.85 (q, 1H), 2.25-2.20 (m, 2H), 2.14 (s, 6H), 1.51-1.36 (m, 2H), 1.05-1.03 (d, 3H), 0.74-0.70 (t, 3H); LC-MS m/z=529.0 $[C_{29}H_{34}ClO_5P+H]^+$; TLC conditions: Uniplate silica gel, 250 microns; Mobile phase=hexanes-ethyl acetate (1:1); $R_f$=0.17; Anal. Calcd for $(C_{29}H_{34}ClO_5P+0.3\ CH_3CO_2CH_2CH_3+0.4H_2O)$: C, 64.47; H, 6.66. Found: C, 64.64; H, 6.82.

Compound 13-9: Cis-(S)-2-[3,5-dibromo-4-(4'-hydroxy-3'-iso-propylphenoxy)benzyl]-4-(3-chlorophenyl)-2-oxo2λ$^5$-[1,3,2]-dioxaphosphonane mp: 83-85° C.; $^1$H NMR (300 MHz, DMSO-d$_6$): δ 9.06 (s, 1H), 7.75 (s, 2H), 7.44-7.42 (m, 3H), 7.32-7.28 (m, 1H), 6.68-6.65(d, 1H), 6.58 (s, 1H), 6.31-6.27 (d, 1H), 5.69-5.65 (d, 1H), 4.59-4.51 (t, 1H), 4.37-4.28 (t, 1H), 3.61-3.53 (d, 2H), 3.18-3.07 (m, 1H), 2.29-2.17 (m, 1H), 1.84-1.77 (m, 1H), 1.07-1.03 (d, 6H); LC-MS m/z=630.8 $[C_{25}H_{24}Br_2ClO_5P+H]^+$; TLC conditions: Uniplate silica gel, 250 microns; Mobile phase=hexanes-ethyl acetate (1:1); $R_f$=0.56; Anal. Calcd for $(C_{25}H_{24}Br_2ClO_5P)$: C, 47.61; H, 3.84. Found: C, 47.88; H, 4.23.

Compound 13-10: Cis (S)-2-[(3,5-diiodo-4-(4'-hydroxy-3'-iso-propylphenoxy)phenoxy)methyl]-4-(3-chlorophenyl)-2-oxo-2λ$^5$-[1,3,2]-dioxaphosphonane mp: 82-86° C.; $^1$H NMR (300 MHz, DMSO-d$_6$): $^1$H NMR (300 MHz, DMSO-d$_6$): δ 8.99 (s, 1H), 7.62 (s, 1H), 7.51 (m, 1H), 7.44 (s, 2H), 7.38 (m, 3H), 6.68 (m, 1H), 6.60 (s, 1H), 6.25 (m, 1H), 5.80 (m, 1H), 4.65 (m, 3H), 4.45 (m, 1H), 3.16 (m, 1H), 2.26 (m, 1H), 1.13 (d, J=6.0 Hz, 6H); LC-MS m/z=741 $[C_{25}H_{24}ClI_2O_6P+H]^+$; TLC conditions: Uniplate silica gel, 250 microns; Mobile phase=ethyl acetate-hexanes (4:1); $R_f$=0.17. Anal. Calcd for $(C_{25}H_{24}ClI_2O_6P+0.2\ CH_3CO_2CH_2CH_3)$: C, 40.86; H, 3.40. Found: C, 41.02, H, 3.49.

Compound 13-11: Cis (S)-2-[(3,5-dichloro-4-(4'-hydroxy-3'-iso-propylbenzyl)phenoxy)methyl]-4-(3-chlorophenyl)-2-oxo-2λ$^5$-[1,3,2]-dioxaphosphonane $^1$H NMR (300 MHz, DMSO-d$_6$): δ 9.10 (s, 1H), 7.43 (s, 1H), 7.38-7.31 (m, 4H), 7.24 (m, 1H), 6.97 (s, 1H), 6.64 (s, 2H), 5.75 (m,1H), 4.69-4.61 (m, 2H), 4.50-4.41 (m, 2H), 4.05 (s, 2H), 3.12 (m, 1H), 2.21 (s, 2H), 1.11 (d, J=9.0 Hz, 6H); LC-MS m/z=554 $[C_{26}H_{26}Cl_3O_5P+H]^+$; TLC conditions: Uniplate silica gel, 250 microns; Mobile phase=ethyl acetate-hexanes (4:1); $R_f$=0.24. Anal. Calcd for $(C_{26}H_{26}Cl_3O_5P+0.5H_2O+0.2\ CH_3CO_2CH_2CH_3)$: C, 55.27; H, 4.95. Found: C, 55.21, H, 4.96.

Cis and Trans 2-[4,6-dichloro-3-fluoro-5-(4'-hydroxy-3'-iso-propylphenoxy)-pyrid-2-ylaminomethyl]-4-(3-chlorophenyl)-2-oxo-2λ$^5$-[1,3,2]-dioxaphosphonane To a stirring solution of [4,6-dichloro-3-fluoro-5-(4'-hydroxy-3'-iso-propylphenoxy)-pyrid-2-ylamino]methylphosphonic (0.2 g, 0.47 mmol, U.S. Pat. No. 6,747,048 B2) and (S)-1-(3-chlorophenyl)-1,3-propanediol (0.18 g, 0.94 mmol) in DMF (6 mL) at room temperature was add pyridine (0.46 mL, 5.64 mmol) and EDCI (0.27 g, 1.41 mmol). The reaction mixture was stirred at 68° C. for 16 hrs. The solvent was removed under reduced pressure, and the residue was partitioned between EtOAc and water. The organic layer was dried over Na$_2$SO$_4$, filtered and concentrated under reduced pressure. The crude product was purified by column chromatography on silica gel, eluting with ethyl acetate to afford:

Compound 13-12-trans (60 mg, 22%): $^1$H NMR (300 MHz, DMSO-d$_6$): δ 9.20 (s, 1H), 7.67 (t, J=6.0 Hz, 1H), 7.36-7.48 (m, 4H), 6.81 (d, J=3.0 Hz, 1H), 6.69 (d, J=9.0 Hz, 1H), 6.44 (dd, J=3.0, 9.0 Hz, 1H), 5.78 (t, J=7.5 Hz, 1H), 4.71 (m, 1H), 4.45 (m, 1H), 4.11 (m, 2H), 3.17 (m, 1H), 2.19 (s, 1H), 1.14 (d, J=6.9 Hz, 6H); TLC conditions: Uniplate silica gel, 250 microns; Mobile phase=ethyl acetate-hexanes (2:1); $R_f$=0.44; LC-MS m/z=576 $[C_{24}H_{23}Cl_3FN_2O_5P+H]^+$; Anal Calcd for $(C_{24}H_{23}Cl_3FN_2O_5P+0.2CH_2Cl_2+0.3H_2O)$: C, 48.58; H, 4.04; N, 4.68. Found: C, 48.64; H, 3.66; N, 4.83.

Compound 13-12-cis (90 mg, 33%): $^1$H NMR (200 MHz, DMSO-d$_6$): δ 9.20 (s, 1H), 7.67 (t, J=6.0 Hz, 1H), 7.21-7.37 (m, 4H), 6.71 (d, J=3.0 Hz, 1H), 6.63 (d, J=9.0 Hz, 1H), 6.34 (dd, J=3.0, 9.0 Hz, 1H), 5.65 (d, J=10.4 Hz, 1H), 4.21-4.61 (m, 2H), 4.11 (m, 1H), 3.80 (m, 1H), 3.07 (m, 1H), 2.11 (m, 1H), 1.88 (m, 1H), 1.04 (m, 6H); TLC conditions: Uniplate silica gel, 250 microns; Mobile phase=ethyl acetate; $R_f$=0.53; LC-MS m/z=576 $[C_{24}H_{23}Cl_3FN_2O_5P+H]^+$; Anal Calcd for $(C_{24}H_{23}Cl_3FN_2O_5P+0.1CH_2Cl_2+0.4H_2O)$: C, 48.94; H, 4.09; N, 4.74. Found: C, 48.57; H, 3.69; N, 4.92.

Step a:

To a solution of diisopropyl amine (12.4 mL, 88.2 mmol) in THF (50 mL) at −78° C. was added n-butyllithium (35.3 mL, 88.2 mmol). The reaction mixture was stirred at −78° C. for 30 min, at which time ethyl acetate was added (16.1 mL, 163.2 mmol). After 1 h, 3-chlorobenzaldehyde was added and the reaction mixture was allowed to warm to room temperature over 2 h. The reaction mixture was quenched with aqueous saturated NH$_4$Cl (20 mL) and extracted with ethyl acetate (2×20 mL). The organic layer was rinsed with water (20 mL) and brine (20 mL), dried over Na$_2$SO$_4$, filtered and concentrated under reduced pressure to afford yellow oil. The crude product was purified by column chromatography on silica gel, eluted with ethyl acetate-hexanes (1:4) to afford ethyl 3-(3-chloro-phenyl)-3-hydroxy-propionate as a yellow oil (10.0 g, 99.0%). $^1$H NMR (400 MHz, d-DMSO): δ 7.43-7.30 (m, 4H), 5.66 (d, 1H), 5.01-4.95 (q, 1H), 4.14-4.04 (m, 2H), 2.71-2.58 (m, 2H), 1.24-1.17 (t, 3H); TLC conditions: Uniplate silica gel, 250 microns; Mobile phase=ethyl acetate-hexanes (1:3); $R_f$=0.50.

Step b:

To a solution of ethyl 3-(3-chloro-phenyl)-3-hydroxy-propionate (10.0 g, 44.1 mmol) in THF (100 mL) and diethyl ether (100 mL) at −78° C. was added methyl magnesium bromide (61.7 mL of a 3.0M solution in diethyl ether, 185.1 mmol). The reaction mixture was allowed to warm to room temperature and stir for 16 h. The reaction mixture was cooled to −50° C. and quenched with aqueous saturated NH$_4$Cl (20 mL), and extracted with diethyl ether (2×20 mL). The organic layer was rinsed with water (20 mL) and brine (20 mL), dried over Na$_2$SO$_4$, filtered and concentrated under reduced pressure. The crude product was purified by column chromatography on silica gel, eluted with ethyl acetate-hexanes (1:3) to afford 1-(3-Chloro-phenyl)-3-methyl-butane-1,3-diol as a yellow oil (5.65 g, 59.7%). $^1$H NMR (400 MHz, d-DMSO): δ 7.40-7.26 (m, 4H), 5.46 (d, 1H), 4.90-4.85 (q, 1H), 4.70 (s, 1H), 1.75-1.62 (m, 2H), 1.23-1.22 (d, 3H), 1.19-1.18 (d, 3H); TLC conditions: Uniplate silica gel, 250 microns; Mobile phase=ethyl acetate-hexanes (1:3); R$_f$=0.32.

Compound 13-13-cis: Cis 2-[(3,5-dimethyl-4-(4'-hydroxy-3'-iso-propylbenzyl)phenoxy)methyl]-4,4-dimethyl-6-(3-chlorophenyl)-2-oxo-2λ$^5$-[1,3,2]-dioxaphosphonane $^1$H NMR (400 MHz, d-DMSO): δ 9.05 (s, 1H), 7.59 (s, 1H), 7.47-7.43 (m, 3H), 6.91 (s, 1H), 6.81 (s, 2H), 6.68-6.65 (d, 1H), 6.53-6.50 (d, 1H), 5.92-5.87 (t, 1H), 4.54-4.40 (m, 2H), 3.87 (s, 2H), 3.23-3.14 (q, 1H), 2.55-2.23 (m, 8H), 1.69 (s, 3H), 1.44 (s, 3H), 1.17-1.14 (d, 6H); LC-MS m/z=544.8 [C$_{30}$H$_{36}$ClO$_5$P+H]$^+$; TLC conditions: Uniplate silica gel, 250 microns; Mobile phase=hexanes-ethyl acetate (1:1); R$_f$=0.16; Anal. Calcd for (C$_{30}$H$_{36}$ClO$_5$P+1.0 CH$_3$CO$_2$CH$_2$CH$_3$): C, 64.70; H, 7.03; Found: C, 64.50; H, 7.32.

Compound 13-13-trans: Trans 2-[(3,5-dimethyl-4-(4'-hydroxy-3'-iso-propylbenzyl)phenoxy)methyl]-4,4-dimethyl-6-(3-chlorophenyl)-2-oxo-2λ$^5$-[1,3,2]-dioxaphosphonane LC-MS m/z=544.8 [C$_{30}$H$_{36}$ClO$_5$P+H]$^+$; $^1$H NMR (400 MHz, d-DMSO): δ 9.00 (s, 1H), 7.54 (s, 1H), 7.49-7.44 (m, 3H), 6.86 (s, 1H), 6.79 (s, 2H), 6.63-6.60 (d, 1H), 6.46-6.43 (d, 1H), 5.85-5.82 (t, 1H), 4.46-4.43 (d, 2H), 3.82 (s, 2H), 3.16-3.11 (q, 1H), 2.28-2.25 (d, 2H), 2.18 (s, 6H), 1.62 (s, 3H), 1.47 (s, 3H), 1.12-1.10 (d, 6H); TLC conditions: Uniplate silica gel, 250 microns; Mobile phase=hexanes-ethyl acetate (1:1); R$_f$=0.27; Anal. Calcd for (C$_{30}$H$_{36}$ClO$_5$P+1.4 CH$_3$CO$_2$CH$_2$CH$_3$): C, 64.17; H, 7.14; Found: C, 64.06; H, 6.98.

Compound 13-14-cis: Cis (S) 2-[(3,5-dimethyl-4-(3'-(4-fluorobenzyl)-4'-hydroxybenzyl)phenoxy)methyl]-4-(3-chlorophenyl)-2-oxo-2-2λ$^5$-[1,3,2]-dioxaphosphonane (0.041 g, 14%); $^1$H NMR (300 MHz, CD$_3$OD): δ 7.46(s, 1H), 7.28(m, 3H), 7.11-6.91(m, 4H), 6.63(m, 5H), 5.72(d, 1H, J=11.4 Hz), 4.71(m, 1H), 4.51(m, 3H), 3.84(m, 4H), 2.44(m, 1H), 2.22(m, 1H), 2.15(s, 6H); TLC conditions: Uniplate silica gel, 250 microns; Mobile phase=hexane 25% in ethyl acetate; Rf=0.21; LC-MS m/z=582 [C$_{32}$H$_{41}$ClFO$_5$P+H]$^+$; Anal Calcd for (C$_{32}$H$_{41}$ClFO$_5$P+0.5H$_2$O): C, 65.14; H, 5.47. Found: C, 65.31; H, 5.67.

Compound 13-14-trans: Trans (S) 2-[(3,5-dimethyl-4-(3'-(4-fluorobenzyl)-4'-hydroxybenzyl)phenoxy)methyl]-4-(3-chlorophenyl)-2-oxo-2λ$^5$-[1,3,2]-dioxaphosphonane (0.030 g, 10%); $^1$H NMR (300 MHz, CD$_3$OD): δ 7.46(s, 1H), 7.28(m, 3H), 7.11-6.91(m, 4H), 6.63(m, 5H), 5.86(d, 1H, J=11.4 Hz), 4.57(m, 4H), 3.84(m, 4H), 2.34(m, 1H), 2.25(m, 1H), 2.15(s, 6H); TLC conditions: Uniplate silica gel, 250 microns; Mobile phase=hexane 25% in ethyl acetate; Rf=0.41; LC-MS m/z=582 [C$_{32}$H$_{41}$ClFO$_5$P+H]$^+$; Anal Calcd for (C$_{32}$H$_{41}$ClFO$_5$P+0.5H$_2$O): C, 65.14; H, 5.47. Found: C, 65.24; H, 5.77.

Compound 13-15-cis: Cis (S)-2-[(3,5-Dimethyl-4-(5'-iodo-4'-hydroxy-3'-iso-propylbenzyl)phenoxy)methyl]-4-(3-chlorophenyl)-2-oxo-2λ$^5$-[1,3,2]-dioxaphosphinane To a solution of cis (S)-2-[(3,5-dimethyl-4-(4'-hydroxy-3'-iso-propylbenzyl)phenoxy)methyl]-4-(3-chlorophenyl)-2-oxo-2λ$^5$-[1,3,2]-dioxaphosphinane (compound 13-1-cis, 0.20 g, 0.39 mmol) in CH$_2$Cl$_2$ (3.0 mL) at 0° C. was added bis(pyridine)iodonium tetrafluoroborate (0.16 g, 0.43 mmol). The reaction mixture was stirred at 0° C. for 1 h and the solvent was removed under reduced pressure. The crude product was purified by column chromatography on silica gel, eluting with 50% acetone in hexanes to afford the title compound (0.20 g, 80%) as a yellow solid: mp: 73-76° C.; $^1$H NMR (300 MHz, CD$_3$OD): δ 7.50 (s, 1H), 7.35 (m, 3H), 7.08 (d, J=2.4 Hz, 1H), 6.90 (d, J=2.4 Hz, 1H), 6.79 (s, 2H), 5.78 (m, 1H), 4.53-4.80 (m, 2H), 4.54 (d, J=11.2 Hz, 1H), 3.94 (s, 2H), 3.28 2.45 (m, 2H), 2.24 (s, 6H), 1.17 (d, J=7.0 Hz, 6H); LC-MS m/z=641 [C$_{28}$H$_{31}$ClIO$_5$P+H]$^+$; Anal. Calcd for (C$_{28}$H$_{31}$ClIO$_5$P): C, 52.48; H, 4.88. Found: C, 52.13; H, 4.52.

Example 14

Compound 14: di(S-acetyl-2-thioethyl) [3,5-dimethyl-4-(4'-hydroxy-3'-iso-propylbenzyl)]phenoxy] methylphosphonate A mixture of S-acetyl-2-thioethanol (0.12 g, 0.96 mmol), [3,5-dimethyl-4-(4'-hydroxy-3'-iso-propylbenzyl)phenoxy] methylphosphonic acid (0.10 g, 0.25 mmol), pyridine (1.0 mL) and dicyclohexylcarbodiimide (0.14 g, 0.69 mmol) in DMF (2.5 mL) was heated at 70° C. for 16 h. The reaction mixture was cooled to room temperature and concentrated under reduced pressure. The crude product was purified by column chromatography on silica gel, eluting with ethyl acetate-hexanes (1:1) to afford di(S-acyl-2-thioethyl) [3,5-dimethyl-4-(4'-hydroxy-3'-iso-propylbenzyl)phenoxy]methylphosphonate as an oil (0.09 g, 56%): LC-MS m/z=569 [C$_{27}$H$_{37}$O$_7$PS$_2$+H]$^+$; Anal. Calcd for (C$_{27}$H$_{37}$O$_7$PS$_2$): C, 57.03; H, 6.56. Found: C, 57.02, H, 7.03; TLC conditions: Uniplate silica gel, 250 microns; mobile phase=2/3 hexanes/EtOAc; phosphonic acid rf=0.00, rf=0.35.

Example 15

Compound 15-1: di-N-(1-1-ethoxycarbonylethylamino) [3,5-dimethyl-4-(4'-hydroxy-3'-iso-propylbenzyl)]phenoxy]methylphosphonamide To a stirred solution of [3,5-dimethyl-4-(4'-hydroxy-3'-iso-propylbenzyl)]phenoxymethyl) phosphonic acid (1, 0.3 g, 0.8 mmol) and DMF(0.1 mL, 0.08 mmol) in 1,2 dichloroethane (10 mL) at room temperature was added oxalylchloride (0.55 g, 2.8 mmol). The reaction mixture was heated at 50° C. for 3 h, cooled to room temperature and concentrated under reduced pressure. To the residue at 0° C. was added a solution of alanine ethylester (0.57 g, 4.3 mmol) and N,N-diisopropylethylamine (0.6 mL, 4.3 mmol) in CH$_2$Cl$_2$. The reaction mixture was stirred for 14 h at room temperature and concentrated under reduced pressure. The residue was partitioned between EtOAc (50 mL) and aqueous NaHCO$_3$ solution (100 mL). The organic layer was separated, washed with brine, dried over Na$_2$SO$_4$, filtered and concentrated under reduced pressure. The crude product was purified by column chromatography on silica gel, eluting with CH$_2$Cl$_2$-MeOH (95:5) to afford Di(ethoxycarbonyl-1-ethylamino) [3,5-Dimethyl-4-(4'-hydroxy-3'-iso-propylbenzyl)]phenoxy]methylphosphonamide as a yellow solid (175 mg, 52%): mp 48-50° C.; LC-MS m/z=563 [C$_{29}$H$_{43}$N$_2$O$_7$P+H]$^+$; Anal Calcd for: (C$_{29}$H$_{43}$N$_2$O$_7$P+0.2 CH$_2$Cl$_2$): C, 60.24; H, 7.52; N, 4.80. Found: C, 59.86; H, 8.01; N, 5.12.

Using the appropriate starting material, compounds 15-2 to 15-9 were prepared in an analogous manner to that described for the synthesis of compound 15-1.

Compound 15-2: di-N-(1-ethoxycarbonyl-1-methylethylamino)[3,5-dimethyl-4-(4'-hydroxy-3'-iso-propylbenzyl)]phenoxy]methylphosphonamide LC-MS m/z=591 [C$_{29}$H$_{43}$N$_2$O$_7$P+H]$^+$; Anal Calcd for (C$_{29}$H$_{43}$N$_2$O$_7$P+0.2 CH$_2$Cl$_2$): C, 60.24; H, 7.52; N, 4.80. Found: C, 59.86; H, 8.01; N, 5.12; TLC conditions: Uniplate silica gel, 250 microns; mobile phase=ethyl acetate/hexanes (4:1); R$_f$=0.4.

Using the appropriate starting material, compound 15-3 was prepared in an analogous manner to that described for the synthesis of compound 15-1.

Compound 15-3: di-N-(1-ethoxycarbonyl-2-methylpropylamino)[3,5-dimethyl-4-(3'-iso-propyl-4'-hydroxybenzyl)phenoxy]methylphosphonamide mp: 52-55° C.; TLC conditions: Uniplate silica gel, 250 microns; Mobile phase=ethyl acetate-hexanes (3:1); R$_f$=0.4; $^1$H NMR (300 MHz, CDCl$_3$): δ 6.84 (d, J=2.1 Hz, 1H), 6.52 (d, J=7.2 Hz, 1H), 6.42 (dd, J=1.8, 4.5 Hz, 1H), 4.02-4.20 (m, 6H), 3.70-3.95 (m, 2H), 3.80 (s, 2H), 3.05-3.35 (m, 3H), 2.13 (s, 6H), 1.09-1.20 (m, 9H), 0.95 (t, J=6.9 Hz, 3H), 0.81 (dd, J=2.1, 6.9 Hz, 6H); LC-MS m/z=619 [C$_{33}$H$_{51}$N$_2$O$_7$P+H]$^+$; Anal Calcd for: (C$_{33}$H$_{51}$N$_2$O$_7$P+0.75H$_2$O): C, 62.29; H, 8.37; N, 4.43. Found: C, 62.48; H, 8.89; N, 4.37.

Compound 15-4: di-N-(L-1-ethoxycarbonylethylamino)[3,5-dimethyl-4-(4'-hydroxy-3'-sec-butylbenzyl)phenoxy]methylphosphonamide $^1$H NMR (300 MHz, DMSO-d$_6$): δ 8.94 (s, 1H), 6.77 (s, 1H), 6.64-6.61 (m, 3H), 6.51-6.48 (d, 1H), 4.87-4.75 (q, 2H), 4.09-3.99 (m, 4H), 3.81 (s, 2H), 2.95-2.88 (q, 1H), 2.17 (s, 6H), 1.57-1.37 (m, 2H), 1.31-1.29 (d, 6H), 1.26-1.16 (m, 4H), 1.08-1.06 (d, 3H), 0.78-0.73 (t, 3H); LC-MS m/z=577.6 [C$_{30}$H$_{45}$N$_2$O$_7$P+H]$^+$; TLC conditions: Uniplate silica gel, 250 microns; Mobile phase=hexanes-ethyl acetate (1:1); R$_f$=0.58; Anal. Calcd for (C$_{30}$H$_{45}$N$_2$O$_7$P+1.1H$_2$O): C, 60.41; H, 7.98; N, 4.70. Found: C, 60.12; H, 7.58; N, 4.49.

Compound 15-5: di-N-(L-1-ethoxycarbonylethylamino)[3,5-dibromo-4-(4'-hydroxy-3'-iso-propylphenoxy)benzyl]phosphonamide $^1$H NMR (300 MHz, DMSO-d$_6$): δ 9.08 (s, 1H), 7.68 (s, 2H), 6.69-6.66 (d, 1H), 6.63 (s, 1H), 6.31-6.28 (d, 1H), 4.76-4.61 (q, 2H), 4.09-4.01 (m, 8H), 3.17-3.08 (q, 1H), 1.27-1.10 (m, 18H); LC-MS m/z=679.4 [C$_{26}$H$_{35}$Br$_2$N$_2$O$_7$P+H]$^+$; TLC conditions: Uniplate silica gel, 250 microns; Mobile phase=dichloromethane-ethyl acetate (1:1); R$_f$=0.34; Anal. Calcd for (C$_{26}$H$_{35}$Br$_2$N$_2$O$_7$P+0.6 CF$_3$CO$_2$H): C, 43.92; H, 4.84; N, 3.78. Found: C, 43.51; H, 4.78; N, 4.26.

Compound 15-6: di-N-(L-1-ethoxycarbonylethylamino)[4,6-dichloro-3-fluoro-5-(4'-hydroxy-3'-iso-propylphenoxy)-pyrid-2-ylamino]methyl phosphonamide To a stirring suspension of [4,6-dichloro-3-fluoro-5-(4'-hydroxy-3'-iso-propylphenoxy)-pyrid-2-ylamino]methylphosphonic (0.11 g, 0.26 mmol, U.S. Pat. No. 6,747,048 B2) and L-alanine (0.16 g, 10.4 mmol) at room temperature in pyridine (2 mL) was added TEA (0.14 mL, 1.04 mmol), followed by a fresh prepared a solution of aldrithio-2 (0.25 g, 1.12 mmol) and PPh$_3$ (0.29 g, 1.12 mmol) in pyridine (2 mL). The reaction mixture was stirred at 85° C. for 16 hrs. The solvent was removed under reduced pressure. The crude product was purified by column chromatography on silica gel, eluting with ethyl acetate to afford the title compound as a yellow foam (40 mg, 25%): $^1$H NMR (300 MHz, DMSO-d$_6$): δ 9.20 (s, 1H), 6.99 (t, J=6.0 Hz, 1H), 6.78 (d, J=3.0 Hz, 1H), 6.68 (d, J=9.0 Hz, 1H), 6.46 (dd, J=3.0, 9.0 Hz, 1H), 4.86 (m, 1H), 4.66 (m, 1H), 4.07 (m, 4H), 3.83 (m, 2H), 3.44 (m, 2H), 3.16 (m, 1H), 1.11-1.27 (m, 18H); TLC conditions: Uniplate silica gel, 250 microns; Mobile phase=ethyl acetate; R$_f$=0.54; LC-MS m/z=624 [C$_{25}$H$_{34}$Cl$_2$FN$_4$O$_7$P+H]$^+$; Anal Calcd for (C$_{25}$H$_{34}$Cl$_2$FN$_4$O$_7$P): C, 48.16; H, 5.50; N, 8.99. Found: C, 47.99; H, 5.26; N, 8.77.

Compound 15-7: Di-N-(1-1-ethoxycarbonylethylamino)[3,5-dichloro-4-(4'-hydroxy-3'-iso-propylbenzyl)]phenoxy]methylphosphonamide $^1$H NMR (300 MHz, DMSO-d$_6$): δ 9.11 (s, 1H), 7.12 (s, 2H), 6.97 (m, 1H), 6.66 (m, 2H), 4.89 (m, 2H), 4.22 (m, 2H), 4.05-3.93 (m, 8H), 3.14 (m, 1H), 1.28 (m, 6H), 1.16 (m, 12H); LC-MS m/z=603 [C$_{27}$H$_{33}$Cl$_2$N$_2$O$_7$P+H]$^+$; Anal. Calcd for (C$_{27}$H$_{33}$Cl$_2$N$_2$O$_7$P+0.5H$_2$O): C, 52.95; H, 6.25; N, 4.57. Found: C, 52.97; H, 6.32; N, 4.71; TLC conditions: Uniplate silica gel, 250 microns; Mobile phase=ethyl acetate-hexanes (4:1); R$_f$=0.26.

Compound 15-8: Di-N-(l-1-ethoxycarbonylethylamino)[3,5-diiodo-4-(4'-hydroxy-3'-iso-propylphenoxy)]phenoxy]methylphosphonamide $^1$H NMR (300 MHz, DMSO-d$_6$): δ 8.99 (s, 1H), 7.50 (s, 2H), 6.68 (m, 1H), 6.56 (m, 1H), 6.25 (m, 1H), 4.87 (m, 2H), 4.18 (m, 2H), 4.06-3.95 (m, 6H), 3.17 (m, 1H), 1.32 (m, 6H), 1.21-1.11 (m, 12H); LC-MS m/z=789 [C$_{26}$H$_{35}$I$_2$N$_2$O$_8$P+H]$^+$; Anal. Calcd for (C$_{26}$H$_{35}$I$_2$N$_2$O$_8$P+0.1H$_2$O): C, 39.52; H, 4.49; N, 3.55. Found: C, 39.49; H, 4.50; N, 3.46; TLC conditions: Uniplate silica gel, 250 microns; Mobile phase=acetone-hexanes (1:1); R$_f$=0.13.

Compound 15-9: Di-N-(l-1-ethoxycarbonylethylamino)[3,5-dimethyl-4-(3'-(4-fluorobenzyl)-4'-hydroxybenzyl)]phenoxy]methylphosphonamide $^1$H NMR (300 MHz, CD$_3$OD): δ 7.12(m, 2H), 7.89(m, 2H), 6.61(m, 5H), 4.19(dd, 2H, J=2.4 Hz and J=14 Hz), 4.08(m, 5H), 3.84(s, 2H), 3.81(s, 2H), 2.15(s, 6H), 2.25(m, 1H), 2.15(s, 6H), 1.40(d, 6H, J=7.5 Hz), 1.21(m, 6H); TLC conditions: Uniplate silica gel, 250 microns; Mobile phase=ethyl acetate; Rf=0.18; LC-MS m/z=629 [C$_{33}$H$_{42}$FN$_2$O$_7$P+H]$^+$, Anal Calcd for (C$_{33}$H$_{42}$FN$_2$O$_7$P+1.1H$_2$O): C, 61.12; H, 6.87, N, 4.32. Found: C, 60.85; H, 6.78, N, 4.72.

Compound 15-10: N-(1-1-ethoxycarbonylethylamino)[3,5-dichloro-4-(3'-(4-fluorobenzyl)-4'-hydroxybenzyl)phenoxymethyl]methylphosphinamide $^1$H NMR (300 MHz, CD$_3$OD): δ 7.11(m, 4H), 6.92(t, 2H), J=8.7 Hz), 6.76(m, 2H), 6.63(d, 1H), J=8 Hz), 4.26(d, 2H), J=7.8 Hz), 4.12(m, 3H), 3.98(m, 2H), 3.83(s, 2H), 1.58(m, 3H), 1.38(m, 3H); TLC conditions: Uniplate silica gel, 250 microns; ethyl acetate-methanol [20:1]; R$_f$=0.2; LC-MS m/z 568 [C$_{27}$H$_{29}$Cl$_2$NFO$_5$P+H]$^+$; Anal Calcd for (C$_{27}$H$_{29}$Cl$_2$FNO$_5$P): C, 56.27;H, 5.34; N, 2.40 Found: C, 56.17; H, 5.71; N, 2.62.

Compound 15-11: Methyl N-(1-1-ethoxycarbonyl-ethylamino) [3,5-dibromo-4-(3'-(4-fluorobenzyl)-4'-hydroxyphenoxy]methylphosphonamide $^1$H NMR (200 MHz, CD$_3$OD): δ 7.12 (s, 2H), 7.18 (m, 2H), 7.94 (t, J=8 Hz, 2H), 6.70 (d, J=8.8 Hz, 1H), 4.33 (m, 2H), 4.08 (m, 1H), 3.83 (s, 2H), 3.77(m, 3H), 1.41(m, 3H), 1.27 (m, 3H); TLC conditions: Uniplate silica gel, 250 microns; ethyl acetate; R$_f$=0.30; LC-MS m/z 676 [C$_{26}$H$_{27}$Br$_2$FO$_7$P+H]$^+$;

Example 16

Compound 16: 3,5-dichloro-4-(4'-hydroxy-3'-isopropylphenoxy)-benzylphosphonic acid Step a:
To a solution of 3,5-dichloro-4-(4'-hydroxy-3'-iso-propylphenoxy)benzyl alcohol in CH$_2$Cl$_2$ (5.0 mL) at −78° C. is added BBr$_3$. The reaction mixture is stirred at room temperature for 16 h, poured into ice water and extracted with ethyl acetate. The organic layer is dried over MgSO$_4$, filtered and concentrated under reduced pressure. The crude product is purified by column chromatography on silica gel, eluting with acetone-hexanes to afford 3,5-dichloro-4-(4'-hydroxy-3'-iso-propyl-phenoxy)benzyl bromide.

Step b:
Diethyl 3,5-dichloro-4-(4'-hydroxy-3'-iso-propylphenoxy)benzyl phosphonate is prepared from 3,5-dichloro-4-(4'-hydroxy-3'-iso-propylphenoxy)benzyl bromide by following the procedure described in example 9, step g.

Step c:
3,5-Dichloro-4-(4'-hydroxy-3'-iso-propylphenoxy)benzylphosphonic acid is prepared from diethyl 3,5-dichloro-4-(4'-hydroxy-3'-iso-propylphenoxy)benzylphosphonate by following the procedure described in example 9, step h.

Example 17

Compound 17: [3,5-dimethyl-4-(4'-hydroxy-3'-isopropylbenzyl)-phenoxy]acetic acid Compound 17 was synthesized by a literature method (Chiellini et al., *Bioorg. Med. Chem. Lett.* 10:2607 (2000))

Example 18

Compound 18: 3,5-dichloro-4-[4'-hydroxy-3'-isopropylphenoxy]-benzeneacetic acid

Example 19

Compound 19: [3,5-dichloro-4-(4'-hydroxy-3'-isopropylphenoxy)]-benzylphosphonic acid Step a:
To a mixture of bis(4-methoxy-3-iso-propylphenyl)iodonium tetrafluoroborate (4.55 g, 8.88 mmol) and copper powder (0.88 g, 13.80 mmol) in CH$_2$Cl$_2$ (40.0 mL) at 0° C. was added a solution of TEA (1.06 mL, 3.71 mmol) and methyl 3,5-dichloro-4-hydroxybenzoate (1.65 g, 6.90 mmol) in dichloromethane (20.0 mL). The reaction mixture was stirred at room temperature for 3 d and filtered through a Celite plug. The solvent was removed under reduced pressure and the residue was purified by column chromatography on silica gel, eluting with acetone-hexanes (1:19) to afford methyl 3,5-dichloro-4-(3'-iso-propyl-4'-methoxyphenoxy)benzoate as an orange oil (2.02 g, 80%): $^1$H NMR (300 MHz, DMSO-d$_6$): δ 8.10 (m, 1H), 6.85 (m, 2H), 6.50 (m, 1H), 3.90 (s, 3H), 3.76 (s, 3H), 3.21 (m, 1H), 1.14 (d, J=6.0 Hz, 6H); TLC conditions: Uniplate silica gel, 250 microns; Mobile phase=hexanes-acetone (17:3); R$_f$=0.51.

Step b:
To a mixture of methyl 3,5-dichloro-4-(3'-iso-propyl-4'-methoxyphenoxy)-benzoate (1.40 g, 3.37 mmol) in THF (10.0 mL) at 0° C. was added a solution of DIBAL-H (8.12 mL, 8.12 mmol, 1.0 M solution in THF). The reaction mixture was stirred at room temperature for 16 h, quenched with cold 1 N HCl and diluted with ethyl acetate. The organic layer was washed with 1 N HCl and brine, dried over MgSO$_4$, filtered and concentrated under reduced pressure to afford 4-(3'-iso-propyl-4'-methoxyphenoxy)-3,5-dichlorobenzyl alcohol as an off-white solid (0.94 g, 100%): $^1$H NMR (300 MHz, DMSO-d$_6$): δ 7.54 (s, 2H), 6.81 (m, 2H), 6.40 (m, 1H), 5.51 (m, 1H), 4.54 (d, J=6.0 Hz, 2H), 3.75 (s, 3H), 3.21 (m, 1H), 1.13 (d, J=6.0 Hz, 6H); TLC conditions: Uniplate silica gel, 250 microns; Mobile phase=hexanes-acetone (17:3); R$_f$=0.27.

Step c:
To a stirred solution of triphenylphosphine (0.42 g, 1.61 mmol) and CBr$_4$ (0.534 g, 1.61 mmol) in diethyl ether (15.0 mL) at room temperature was added 4-(3'-iso-propyl-4'-methoxyphenoxy)-3,5-dichlorobenzyl alcohol (0.50 g, 1.46 mmol). The reaction mixture was stirred at room temperature for 16 h, filtered and concentrated under reduced pressure. The crude product was purified by column chromatography on silica gel, eluting with acetone-hexanes (1:9) to afford 3,5-dichloro-4-(3'-iso-propyl-4'-methoxyphenoxy)benzyl-bromide (0.320 g, 54%): $^1$H NMR (300 MHz, DMSO-d$_6$): δ 7.77 (s, 2H), 6.82 (m, 2H), 6.38 (m, 1H), 4.75 (s, 2H), 3.75 (s, 3H), 3.22 (m, 1H), 1.13 (d, J=6.0 Hz, 6H); TLC conditions: Uniplate silica gel, 250 microns; Mobile phase=hexanes-acetone (1:4); R$_f$=0.46.

Step d:
A mixture of 3,5-dichloro-4-(3'-iso-propyl-4'-methoxyphenoxy)benzyl bromide (0.61 g, 1.51 mmol) and triethylphosphite (0.61 g, 3.56 mmol) in DMF (2.0 mL) was heated under reflux for 4 h. The reaction mixture was cooled to room temperature, diluted with ethyl acetate, and washed with water and brine. The organic layer was concentrated under reduced pressure and the residue was purified by column chromatography on silica gel, eluting with acetone-hexanes (3:7) to afford diethyl 3,5-dichloro-4-(3'-iso-propyl-4'-methoxyphenoxy)benzylphosphonate as an oil (0.59 g, 85%): $^1$H NMR (300 MHz, DMSO-d$_6$): δ 7.55 (s, 2H), 6.88 (d, J=9.0 Hz, 1H), 6.75 (d, J=3.0 Hz, 1H), 6.43 (m, 1H), 4.01 (m, 4H), 3.75 (s, 3H), 3.41 (m, 2H), 3.22 (m, 1H), 1.20 (m, 6H), 1.12 (d, J=6.0 Hz, 6H); TLC conditions: Uniplate silica gel, 250 microns; Mobile phase=hexanes-ethyl acetate (4:1); $R_f$=0.22.

Step e:

To a solution of diethyl 3,5-dichloro-4-(3'-iso-propyl-4'-methoxyphenoxy)benzylphosphonate (0.59 g, 1.28 mmol) in $CH_2Cl_2$ (10.0 mL) at −30° C. was added bromotrimethylsilane (2.53 mL, 19.2 mmol). The reaction mixture was stirred at room temperature for 16 h and the solvent was removed under reduced pressure. The residue was dissolved in dichloromethane (25.0 mL), cooled to −78° C. and to it was added $BBr_3$ (19.0 mL, 19.0 mmol, 1.0 M solution in $CH_2Cl_2$). The reaction mixture was stirred at −78° C. for 10 min, allowed to warm to room temperature and stirred for 16 h. The reaction mixture was poured into ice, concentrated and extracted with ethyl acetate. The organic layer was washed with water (20 mL×2), dried over $MgSO_4$ and filtered. The solvent was removed under reduced pressure to afford 3,5-dichloro-4-(3'-iso-propyl-4'-hydroxyphenoxy)benzylphosphonic acid as a brown solid (0.20 g, 40%): mp: 178-181° C.; LC-MS m/z=391 $[C_{16}H_{17}Cl_2O_5P-H]^-$; $^1$H NMR (300 MHz, DMSO-$d_6$): δ 9.08 (s, 1H), 7.48 (s, 2H), 6.72 (m, 2H), 6.25 (m, 1H), 3.18 (m, 1H), 3.00 (d, J=21.0 Hz, 2H), 3.11 (m, 1H), 1.14 (d, J=6.0 Hz, 6H); Anal. Calcd for $(C_{16}H_{17}Cl_2O_5P+0.2 C_4H_8O_2+0.5H_2O)$: C, 48.30; H, 4.73. Found: C, 48.69, H, 5.16.

Using the appropriate starting material, compounds 19-1 to 19-3 was prepared in an analogous manner to that described for the synthesis of compound 19.

Compound 19-1: diethyl [3,5-dibromo-4-(4'-hydroxy-3'-iso-propyl-phenoxy)]benzylphosphonate Prepared from methyl 3,5-dibromo-4-hydroxybenzoate (*J. Med. Chem.* 46:1580 (2003)) according to the procedure described for the synthesis of compound 19. mp: 145° C.; LC-MS m/z=536 $[C_{20}H_{25}Br_2O_5P+H]^+$; $^1$H NMR (300 MHz, $CD_3OD$): δ 7.53 (s, 2H), 6.50 (m, 2H), 6.23 (m, 1H), 3.98 (m, 4H), 3.11 (m, 1H), 1.21 (m, 6H), 1.02 (d, J=6.0 Hz, 6H); Anal. Calcd for $(C_{20}H_{25}Br_2O_5P)$: C, 44.80; H, 4.70. Found: C, 45.19, H, 4.80.

Compound 19-2: [3,5-dibromo-4-(4'-hydroxy-3'-iso-propylphenoxy)]-benzylphosphonic Acid Prepared from compound 19-1 according to the procedure described for the synthesis of compound 19 step e. mp: 76-79° C.; LC-MS m/z=480 $[C_{16}H_{17}Br_2O_5P+H]^+$; $^1$H NMR (300 MHz, $CD_3OD$): δ 7.52 (s, 2H), 6.55 (m, 2H), 6.20 (m, 1H), 3.14 (m, 1H), 3.00 (d, J=21.0 Hz, 2H), 1.06 (d, J=6.0 Hz, 6H); HPLC conditions: Column =3 Chromolith SpeedRODs RP-18e, 100×4.6 mm; Mobile phase=Solvent A (Acetonitrile)=HPLC grade acetonitrile; Solvent B (buffer)=20 mM ammonium phosphate buffer (pH 6.1, 0.018 M $NH_4H_2PO_4$/ 0.002 M $(NH_4)_2HPO_4$) with 5% acetonitrile. Flow rate=4 mL/min; UV@ 255 nm. Retention time in minutes. (rt=5.80, 96% purity).

Compound 19-3: [3,5-dimethyl-4-(4'-hydroxy-3'-iso-propylphenoxy)]-benzylphosphonic acid Prepared from methyl 3,5-dimethyl-4-hydroxybenzoate according to the procedure described for the synthesis of compound 19. mp: 79-82° C.; LC-MS m/z=351 $[C_{18}H_{23}O_5P+H]^+$; $^1$H NMR (300 MHz, $CD_3OD$): δ 6.93 (s, 2H), 6.51 (m, 2H), 6.13 (m, 1H), 3.13 (m, 1H), 2.98 (d, J=21.0 Hz, 2H), 1.96 (s, 6H), 1.04 (d, J=6.0 Hz, 6H); Anal. Calcd for $(C_{18}H_{23}O_5P+1.2H_2O)$: C, 58.12; H, 6.88. Found: C, 58.01; H, 7.00.

Example 20

Compound 20 [3,5-dimethyl-4-N-(4'-hydroxy-3-iso-propylphenylamino)-phenoxy]methylphosphonic acid Step a:

A solution of 4-amino-3,5-dimethylphenol (5.0 g, 36.46 mmol, Fieser, L. F. *Organic Syntheses*, Collect Vol II, 1943, 39), imidazole (6.21 g, 77.37 mmol) and triisopropylsilyl chloride (7.70 g, 40.1 mmol) in $CH_2Cl_2$ (80 mL) was stirred at room temperature for 1 h. The reaction mixture was diluted with $CH_2Cl_2$ (100.0 mL) and washed with water and brine. The organic layer was dried over $MgSO_4$, filtered and concentrated under reduced pressure. The crude product was purified by column chromatography on silica gel, eluting with ethyl acetate-hexanes (1:19) to afford 2,6-dimethyl-4-triisopropylsilanyloxyphenylamine (8.46 g, 79%): $^1$H NMR (300 MHz, $CDCl_3$): δ 6.57 (s, 2H), 2.19 (s, 6H), 1.23 (m, 3H), 1.12 (m, 18H). TLC conditions: Uniplate silica gel, 250 microns; Mobile phase=ethyl acetate-hexanes (1:9); $R_f$=0.51.

Step b:

A mixture of $Pd_2(dba)_3$ (800 mg, 0.87 mmol) and BINAP (1.09 g, 1.75 mmol) in toluene (70 mL) at 100° C. in a sealed tube was heated for 30 min. The reaction mixture was cooled to room temperature and to it was added 2,6-dimethyl-4-triisopropylsilanyloxyphenylamine (6.15 g, 20.98 mmol) followed by 4-bromo-2-iso-propyl-1-methoxymethoxybenzene (4.0 g, 17.48 mmol) and potassium tert-butoxide (2.18 g, 22.72 mmol). The reaction mixture was heated at 110° C. in the sealed tube for 16 h, cooled to room temperature and filtered through a plug of Celite. The solvent was removed under reduced pressure and the crude product was purified by column chromatography on silica gel, eluting with ethyl acetate-hexanes (1:9) to afford N,N-(2,6-dimethyl-4-triisopropylsilanyloxyphenyl)-(3-iso-propyl-4-methoxymethoxy phenyl)amine as a yellow solid (4.8 g, 58%): $^1$H NMR (300 MHz, $CDCl_3$): δ 6.88 (d, J=8.7 Hz, 1H), 6.67 (s, 1H), 6.41 (d, J=2.7 Hz, 1H), 6.22 (m, 1H), 5.11 (s, 2H), 3.52 (s, 3H), 3.28 (m, 1H), 2.17 (s, 6H), 1.28 (m, 3H), 1.15 (m, 24H). TLC conditions: Uniplate silica gel, 250 microns; Mobile phase=ethyl acetate-hexanes (1:9); $R_f$=0.70.

Step c:

To a solution of N,N-(2,6-dimethyl-4-triisopropylsilanyloxyphenyl)-(3-iso-propyl-4-methoxymethoxyphenyl) amine (800 mg, 1.70 mmol) in THF (10.0 mL) at 0° C. was added TBAF (2.55 mmol, 1.0 M in THF). The reaction mixture was stirred at room temperature for 16 h, diluted with ethyl acetate (10.0 mL) and quenched with $H_2O$ (10.0 mL). The aqueous layer was extracted with ethyl acetate (10.0 mL) and the combined organic layers were dried over $MgSO_4$. The solvent was removed under reduced pressure and the crude product was purified by column chromatography on silica gel, eluting with ethyl acetate-hexanes (1:4) to afford 3,5-dimethyl-4-N-(3-iso-propyl-4'-methoxymethoxyphenylamino)phenol (280 mg, 52%): $^1$H NMR (300 MHz, $CDCl_3$): δ 6.88 (d, J=8.1 Hz, 1H), 6.63 (s, 2H), 6.47 (m, 1H), 6.21(m, 1H), 5.12 (s, 2H), 3.52 (s, 3H), 3.30 (m, 1H), 2.19 (s, 6H), 1.2 (d, 6H). TLC conditions: Uniplate silica gel, 250 microns; Mobile phase=ethyl acetate-hexanes (1:9); $R_f$=0.45.

Step d:

To a solution of sodium hydride (22 mg, 0.86 mmol) in DMF at 0° C. was added a solution of 3,5-dimethyl-4-N-(3- iso-propyl-4'-methoxymethoxyphenylamino)phenol (270 mg, 0.86 mmol) in DMF (2.0 mL). The reaction mixture was stirred at room temperature for 1 h and to it was added a solution of diethyl tosyloxymethylphosphonate (0.34 g, 1.03 mmol) in DMF (1.0 mL). The reaction mixture was stirred at room temperature for 16 h and the solvent was removed under reduced pressure. The residue was partitioned between ethyl acetate (10.0 mL) and saturated aqueous $NaHCO_3$ (10.0 mL). The organic layer was separated and the aqueous layer was extracted with ethyl acetate (10.0 mL). The combined organic layers were dried over $MgSO_4$, filtrated and concentrated under reduced pressure. The crude product was purified by column chromatography on silica gel, eluting with ethyl acetate-hexanes (1:1) to afford diethyl [3,5-dimethyl-4-N-(3-iso-propyl-4'-methoxymethoxyphenylamino)phenoxy]methylphosphonate (160 mg, 52%): $^1$H NMR (300 MHz, $CDCl_3$): δ 6.88 (d, J=8.4 Hz, 1H), 6.75 (s, 2H), 6.46 (m, 1H), 6.20 (m, 1H), 5.12 (s, 2H), 4.25 (m, 6H), 3.52 (s, 3H), 3.28 (m, 1H), 2.21 (s, 6H), 1.40 (m, 6H), 1.20 (d, J=6.9 Hz, 6H). TLC conditions: Uniplate silica gel, 250 microns; Mobile phase=ethyl acetate-hexanes (1:9); $R_f$=0.29.

Step e:

To a solution of diethyl [3,5-dimethyl-4-N-(3-iso-propyl-4'-methoxymethoxyphenylamino)phenoxy]methylphosphonate (150 mg, 0.32 mmol) in $CH_2Cl_2$ (10 mL) at room temperature was added TMSBr (0.51 mL, 3.88 mmol). The reaction mixture was stirred at room temperature for 16 h and the solvent was removed under reduced pressure. The residue was treated with water (5.0 mL), stirred for 2 h and extracted with ethyl acetate (10.0 mL×2). The combined organic layers were dried over $MgSO_4$, filtrated and concentrated under reduced pressure. The crude product was purified by preparatory LC-MS to afford [3,5-dimethyl-4-N-(4'-hydroxy-3-iso-propylphenylamino)phenoxy]methylphosphonic acid as a blue solid (40 mg, 33.9%): $^1$H NMR (300 MHz, $CDCl_3$): δ 8.3 (s, 1H), 6.74 (s, 2H), 6.49 (d, J=8.4 Hz, 1H), 6.36 (d, J=2.4 Hz, 1H), 5.92 (m, 1H), 4.05 (d, J=10.5 Hz, 2H), 3.11 (m, 1H), 2.10 (s, 6H), 1.10 (d, J=6.9 Hz, 6H). mp>200° C.; LC-MS m/z=366 $[C_{18}H_{24}NO_5P+H]^+$; Anal. Calcd for ($C_{18}H_{24}NO_5P$+0.5$H_2O$+0.2 HCl): C, 56.65; H, 6.66; N, 3.67. Found: C, 56.45; H, 6.73; N, 3.71.

Using the appropriate starting material, compound 20-1 was prepared in an analogous manner to that described for the synthesis of compound 20.

Compound 20-1 [3,5-dimethyl-4-(4'-hydroxy-3-iso-propylphenyl-methylamino)phenoxy]methylphosphonic acid Prepared by standard reductive amination (*J. Org. Chem.* 37:1673 (1972)) of N,N-(2,6-dimethyl-4-triisopropylsilanyloxyphenyl)-(3-iso-propyl-4-methoxymethoxyphenyl) amine with formaldehyde followed by the same procedure described for the synthesis compound 20. $^1$H NMR (300 MHz, $CDCl_3$): δ 8.28 (s, 1H), 6.76 (s, 2H), 6.54 (d, J=8.8 Hz, 1H), 6.15 (m, 1H), 5.94 (m, 1H), 4.05 (d, J=10.2 Hz, 2H), 3.13 (m, 1H), 3.02 (s, 3H), 1.97 (s, 6H), 1.06 (d, J=7.0 Hz, 6H). mp>200° C. LC-MS m/z=379 $[C_{19}H_{26}NO_5P+H]^-$; Anal. Calcd for ($C_{19}H_{26}NO_5P$+0.3 HBr +0.1 $CH_2Cl_2$): C, 55.41; H, 6.46; N, 3.38. Found: C, 55.35; H, 6.55; N, 3.43.

Example 21

Compound 21: 2-[3,5-dichloro-4-(4'-hydroxy-3'-iso-propylphenoxy)phenyl]-2-oxoethylphosphonic acid Step a:

To a stirred solution of diethyl methylphosphonate (0.4 g, 2.6 mmol) in anhydrous THF (15 mL) at −78° C. was added n-BuLi (1.95 mL, 1.95 mmol, 1 M solution in hexanes). The reaction mixture was stirred at −78° C. for 1 h and to it was added a solution of methyl 3,5-dichloro-4-(3'-iso-propyl-4'-methoxyphenoxy)benzoate (0.24 g, 0.65 mmol, step a, example 19) in THF (5 mL). The reaction mixture was stirred at −78° C. for 1 h, quenched with 10% AcOH (10 mL) and $H_2O$ (50 mL) and extracted with ethyl acetate (50 mL×2). The combined organic layers were washed with water and brine, dried over $Na_2SO_4$, and concentrated under reduced pressure. The crude product was purified by column chromatography on silica gel, eluting with ethyl acetate-hexanes (1:1) to afford diethyl 2-[3,5-dichloro-4-(3'-iso-propyl-4'-methoxyphenoxy)]-2-oxoethylphosphonate as a colorless oil (0.28 g, 63%): $^1$H NMR (300 MHz, $CDCl_3$): δ 8.05 (s, 2H), 6.85 (d, J=3.3 Hz, 1H), 6.71 (d, J=9.0 Hz, 1H), 6.40 (dd, J=3.3, 9.0 Hz, 1H), 4.08 (q, J=6.3 Hz, 1H), 3.81 (s, 3H), 3.60 (d, J=23.1 Hz, 2H), 3.35-3.25 (m, 1H), 1.32 (t, J=6.9 Hz, 6H), 1.19 (d, J=6.9 Hz, 6H); TLC conditions: Uniplate silica gel, 250 microns; mobile phase=ethyl acetate-hexanes (2:3); $R_f$=0.2.

Step b:

To a stirred solution of diethyl 2-[3,5-dichloro-4-(3'-iso-propyl-4'-methoxyphenoxy)]-2-oxoethylphosphonate (0.26 g, 0.54 mmol) in $CH_2Cl_2$ (7 mL) at 0° C. was added TMSBr (0.83 g, 0.8 mL, 5.4 mmol). The reaction mixture was stirred at 0° C. for 30 min, allowed to warm to room temperature and stirred for 16 h. The solvent was removed under reduced pressure and the residue was dissolved in $CH_3OH$ (3 mL). The solvent was removed under reduced pressure to afford 2-[3,5-dichloro-4-(3'-iso-propyl-4'-methoxyphenoxy)phenyl]-2-oxoethylphosphonic acid as a white solid (0.2 g, 83%): $^1$H NMR (300 MHz, $CD_3OD$): δ 8.09 (s, 2H), 6.83 (d, J=3.3 Hz, 1H), 6.71 (d, J=9.0 Hz, 1H), 6.40 (dd, J=3.3, 9.0 Hz, 1H), 3.81 (s, 3H), 3.60 (d, J=22.1 Hz, 2H), 3.35-3.25 (m, 1H), 1.19 (d, J=6.9 Hz, 6H).

Step c:

To a stirred solution of 2-[3,5-dichloro-4-(3'-iso-propyl-4'-methoxyphenoxy)phenyl]-2-oxoethylphosphonic acid (0.17 g, 0.40 mmol) in $CH_2Cl_2$ (5 mL) at −78° C. was added $BBr_3$ (1.0 mL, 1.0 mmol, 1.0 M in $CH_2Cl_2$). The reaction mixture was stirred at room temperature for 14 h, poured into ice water (25 mL) and stirred for 1 h. The reaction mixture was extracted with ethyl acetate (50 mL×2). The combined organic layers were washed with water and brine, dried over $Na_2SO_4$, filtered and concentrated under reduced pressure. The crude product was recrystallized from $CH_2Cl_2$, filtered and dried to afford 2-[3,5-dichloro-4-(4'-hydroxy-3'-iso-propylphenoxy) phenyl]-2-oxoethylphosphonic acid as a yellow solid (0.14 g, 92%, m.p.: 83-85° C., 98% pure): $^1$H NMR (300 MHz, $CD_3OD$): δ 8.18 (s, 2H), 6.71 (d, J=3.0 Hz, 1H), 6.65 (d, J=8.7 Hz, 1H) 6.37 (dd, J=3.0, 8.7 Hz, 1H), 3.65 (d, J=37.8 Hz, 2H) 3.30-3.20 (m, 1H), 1.18 (d, J=6.9 Hz, 6H); LC-MS m/z=420 $[C_{17}H_{17}Cl_2O_6P+H]^+$; HPLC conditions: ODSAQ AQ-303-5 column; mobile phase=$CH_3OH$:TFA (7:3) flow rate=1.0 ml/min; detection=UV @ 254 nm retention time in min: 13.26; Anal Calcd: ($C_{17}H_{17}Cl_2O_6P$) Calcd: C, 48.09; H, 4.18. Found: C, 47.97; H, 4.39.

Example 22

Compound 22: [3,5-dichloro-4-(4'-hydroxy-3'-iso-propylphenoxy)-phenylamino]methylphosphonic acid Step a:

To a solution of 4-amino-2,6-dichlorophenol (4.0 g, 22.5 mmol) in THF (25 mL) was added t-BOC anhydride (5.88 g, 27.0 mmol). The reaction mixture was heated under reflux for 2.5 h and the solvent was removed under reduced pressure. The crude product was purified by column chromatography on silica gel, eluting with acetone-hexanes (1:9) to afford 3,5-dichloro-4-hydroxyphenylcarbamic acid t-butyl ester as an off-white solid (5.80 g, 93%): $^1$H NMR (300 MHz, DMSO-$d_6$): δ 9.70 (s, 1H), 9.44 (s, 1H), 7.46 (s, 2H), 1.48 (s, 9H); TLC conditions: Uniplate silica gel, 250 microns; Mobile phase=acetone-hexanes (3:7); $R_f$=0.39.

Step b:

To a mixture of bis(4-methoxy-3-iso-propylphenyl)iodonium tetrafluoroborate (2.76 g, 5.39 mmol) and copper powder (0.46 g, 7.18 mmol) in $CH_2Cl_2$ (20.0 mL) at 0° C. was added a solution of TEA (0.55 mL, 3.95 mmol) and 3,5-dichloro-4-hydroxyphenylcarbamic acid tert-butyl ester (1.00 g, 3.59 mmol) in dichloromethane (10.0 mL). The reaction mixture was stirred at room temperature for 14 h and filtered through a Celite plug. The solvent was removed under reduced pressure and the residue was purified by column chromatography on silica gel, eluting with acetone-hexanes (1:19) to afford 3,5-dichloro-4-(3'-iso-propyl-4'-methoxyphenoxy)phenylcarbamic acid tert-butyl ester as an off-white solid (1.45 g, 95%): $^1$H NMR (300 MHz, DMSO-$d_6$): δ 9.81 (s, 1H), 7.68 (m, 2H), 6.79 (m, 2H), 6.42 (m, 1H), 3.75 (s, 3H), 3.20 (m, 1H), 1.51 (s, 9H), 1.33 (d, J=6.0 Hz, 6H); TLC conditions: Uniplate silica gel, 250 microns; Mobile phase=acetone-hexanes (3:7); $R_f$=0.64.

Step c:

To a mixture of 3,5-dichloro-4-(3'-iso-propyl-4'-methoxyphenoxy)phenylcarbamic acid tert-butyl ester (0.400 g, 0.94 mmol) in THF (12.0 mL) at 0° C. was added sodium hydride (0.064 g, 1.22 mmol, 60% dispersion in oil). The reaction mixture was stirred at room temperature for 1 h and cooled to 0° C. To the stirring mixture was added diethyl trifluoromethanesulfonyloxymethylphosphonate (0.18 g, 0.94 mmol). The reaction mixture was stirred at room temperature for 2 h, quenched with water and diluted with ethyl acetate. The organic layer was washed with water and brine and concentrated under reduced pressure. The crude product was purified by column chromatography on silica gel, eluting with ethyl acetate-hexanes (2:3) to afford diethyl N-tert-butoxycarbonyl-[3,5-dichloro-4-(3-iso-propyl-4'-methoxyphenoxy)phenylamino]methylphosphonate as an oil (0.34 g, 63%): $^1$H NMR (300 MHz, DMSO-$d_6$): δ 7.64 (s, 2H), 6.90 (m, 1H), 6.76 (s, 1H), 6.45 (m, 1H), 4.95 (d, J=9.0 Hz, 2H); 4.01 (m, 4H); 3.76 (s, 3H), 3.21 (m, 1H), 1.43 (s, 9H), 1.20 (m, 6H), 1.13 (d, J=6.0 Hz, 6H); TLC conditions: Uniplate silica gel, 250 microns; Mobile phase=ethyl acetate-hexanes (2:3); $R_f$=0.15

Step d:

To a solution of diethyl N-tert-butoxycarbonyl-[3,5-dichloro-4-(3-iso-propyl-4'-methoxy-phenoxy)phenylamino]methyl)phosphonate (0.25 g, 0.43 mmol) in $CH_2Cl_2$ (6.0 mL) at 0° C. was added bromotrimethylsilane (0.86 mL, 6.50 mmol). The reaction mixture was stirred at room temperature 16 h and the solvent was removed under reduced pressure. The residue was dissolved in dichloromethane (5.0 mL), cooled to −78° C. and to it was added $BBr_3$ (2.84 mL, 2.84 mmol, 1.0 M solution in $CH_2Cl_2$). The reaction mixture was stirred at −78° C. for 10 min, allowed to warm to room temperature and stirred for 16 h. The reaction mixture was poured into ice, diluted with ethyl acetate and washed with water. The organic layer was dried over $MgSO_4$ and concentrated under reduced pressure to afford [3,5-dichloro-4-(4'-hydroxy-3-iso-propylphenoxy)phenylamino]methylphosphonic acid as an off-white solid (0.15 g, 85% over two steps): mp: 97-100° C.; LC-MS m/z=405,407 $[C_{16}H_{18}Cl_2NO_5P+H]^+$; $^1$H NMR (300 MHz, DMSO-$d_6$): δ 9.02 (s, 2H), 6.90 (m, 2H), 6.71 (m, 2H), 6.32 (m, 2H), 3.36 (m, 2H), 3.21 (m, 1H), 1.17 (d, J=6.0 Hz, 6H); Anal. Calcd for ($C_{16}H_{15}Cl_2NO_5P$+0.1 $C_4H_8O_2$+0.3$H_2O$): C, 46.85; H, 4.65; N, 3.33. Found: C, 47.09; H, 4.94; N, 3.50. Compound 22-1: [3,5-dibromo-4-(4'-hydroxy-3'-iso-propylphenoxy)-phenylamino]methylphosphonic acid The title compound was prepared from 4-amino-2,6-dibromophenol according to the procedure described for the synthesis of Example 22, steps a-d; $^1$H NMR (200 MHz, DMSO-$d_6$): δ 8.95 (m, 1H), 7.02 (s, 2H), 6.63 (m, 2H), 6.23 (m, 1H), 3.31 (d, J=12.0 Hz, 2H), 3.14 (m, 1H), 1.12 (d, J=6.0 Hz, 6H); LC-MS m/z=496 $[C_{16}H_{18}Br_2NO_5P+H]^+$; HPLC conditions: Column=Agilent zorbax RP18, 150×3.0 mm; Mobile phase=Solvent B (Acetonitrile)=HPLC grade acetonitrile; Solvent A (buffer)=20 mM potassium phosphate buffer (pH 4.7). Flow rate=0.75 mL/min; UV@ 254 nm. Retention time in minutes. (rt=8.70/20 min, 92% purity).

Example 23

Compound 23: N-[3,5-dimethyl-4-(4'-hydroxy-3'-iso-propylphenoxy)-benzamido]methyl phosphonic acid Step a:

To a solution of methyl 3,5-dimethyl-4-(3'-iso-propyl-4'-methoxyphenoxy)benzoate (8.53 g, 16.7 mmol, intermediate for the synthesis of Example 19-3) in methanol (60.0 mL) at 0° C. was added a solution of 1 N NaOH (28.15 mL, 28.15 mmol). The reaction mixture was stirred at room temperature for 16 h and acidified with cold concentrated HCl. The reaction mixture was extracted with ethyl acetate (10.0 mL) and the organic layer was dried over $MgSO_4$. The solvent was removed under reduced pressure to afford 4-(3'-iso-propyl-4'-methoxyphenoxy)-3,5-dimethylbenzoic acid as a pink solid (1.38 g, 78%): $^1$H NMR (300 MHz, DMSO-$d_6$): δ 12.88 (s, 1H), 7.76 (s, 2H), 6.85 (m, 1H), 6.75 (m, 1H), 6.34 (m, 1H), 3.73 (s, 3H), 3.20 (m, 1H), 2.11 (s, 6H), 1.12 (d, J=6.0 Hz, 6H); TLC conditions: Uniplate silica gel, 250 microns; Mobile phase=hexanes-acetone (17:3); $R_f$=0.00.

Step b:

To a mixture of 4-(3'-iso-propyl-4'-methoxyphenoxy)-3,5-dimethylbenzoic acid (0.20 g, 0.63 mmol), diethyl aminomethylphosphonate (0.19 g, 0.76 mmol) and triethylamine in $CH_2Cl_2$ (10.0 mL) at 0° C. was added EDCI (0.18 g, 0.763 mmol) followed by 1-hydroxy-7-azabenzotriazole (0.09 mg, 0.63 mmol). The reaction mixture was stirred at room temperature for 16 h, concentrated and diluted with ethyl acetate (10.0 mL). The organic layer was washed with water (10 mL×3) and brine, dried over $MgSO_4$ and concentrated under reduced pressure. The crude product was purified by preparatory TLC to afford diethyl N-[3,5-dimethyl-4-(3'-iso-propyl-4'-methoxyphenoxy)-benzamido]methylphosphonate as an oil (0.20 g, 68%): $^1$H NMR (300 MHz, DMSO-$d_6$): δ 8.77 (m, 1H), 7.69 (s, 2H), 6.84 (d, J=9.0 Hz, 1H), 6.75 (m, 1H), 6.36 (m, 1H), 4.05 (m, 4H), 3.76 (m, 5H), 3.21 (m, 1H), 2.11

(s, 6H), 1.21 (m, 6H), 1.13 (d, J=6.0 Hz, 6H); TLC conditions: Uniplate silica gel, 250 microns; Mobile phase=hexanes-acetone (1:1); $R_f$=0.28.

Step c:

To a solution of diethyl N-[4-(3'-iso-propyl-4'-methoxyphenoxy)-3,5-dimethylbenzamido]methyl]phosphonate (0.20 g, 0.43 mmol) in $CH_2Cl_2$ (4.3 mL) at −30° C. was added bromotrimethylsilane (0.56 mL, 4.31 mmol). The reaction mixture was stirred at room temperature for 16 h and the solvent was removed under reduced pressure. The residue was dissolved in dichloromethane (5.0 mL), cooled to −78° C., and to it was added $BBr_3$ (1.29 mL, 1.29 mmol, 1.0 M solution in $CH_2Cl_2$). The reaction mixture was stirred at −78° C. for 3 h, allowed to warm to room temperature and stirred for 16 h. The reaction mixture was poured into ice, extracted with ethyl acetate (10.0 mL) and washed with 2% HCl (20 mL×2) and water (20 mL×2). The organic layer was dried over $MgSO_4$, filtered and concentrated under reduced pressure to afford N-[3,5-dimethyl-4-(4'-hydroxy-3'-iso-propylphenoxy) benzamido]methylphosphonic acid as an pink solid (0.08 g, 47% over two steps): mp: 163-166° C.; LC-MS m/z=394 $[C_{19}H_{24}NO_6P+H]^+$; $^1$H NMR (300 MHz, $CD_3OD$): δ 7.52 (s, 2H), 6.51 (m, 2H), 6.19 (m, 1H), 3.70 (d, J=12.0 Hz, 2H), 3.14 (m, 1H), 2.04 (s, 6H), 1.01 (d, J=6.0 Hz, 6H); Anal. Calcd for ($C_{19}H_{24}NO_6P+1.0H_2O$): C, 55.47; H, 6.37; N, 3.40. Found: C, 55.30; H, 6.32; N, 3.12.

Example 24

Compound 24: 2-[3,5-dimethoxy-4-(4'-hydroxy-3'-isopropylbenzyl)phenyl]-ethylphosphonic acid Step a:

To a solution of 3,5-dimethoxy-4-(3'-iso-propyl-4'-methoxymethoxybenzyl)phenol (0.6 g, 1.73 mmol, intermediate for the synthesis of Example 7-2) and DMAP (0.85 g, 6.92 mmol) in $CH_2Cl_2$ (20 mL) at 0° C. was slowly added trifluoromethanesulfonic anhydride (0.44 mL, 2.6 mmol). The reaction mixture was stirred at 0° C. for 2 h and quenched by water (10.0 mL). The organic layer was dried over $Na_2SO_4$, filtered and concentrated under reduced pressure. The crude product was purified by column chromatography on silica gel, eluting with ethyl acetate-hexanes (1:9) to afford 3,5-dimethoxy-4-(3'-iso-propyl-4'-methoxymethoxybenzyl)-1-trifluromethanesulfonyloxyphenyl as a light yellow oil (0.83 g, 100%): $^1$H NMR (300 MHz, DMSO-$d_6$): δ 7.09 (s, 1H), 6.87 (s, 2H), 6.80 (s, 2H), 5.15 (s, 2H), 3.84 (s, 6H), 3.81 (s, 2H), 3.36 (s, 3H), 3.20 (m, 1H), 1.14 (d, J=6.6 Hz, 6H); TLC conditions: Uniplate silica gel, 250 microns; Mobile phase=ethyl acetate-hexanes (1:9); $R_f$=0.73.

Step b:

A mixture of 3,5-dimethoxy-4-(3'-iso-propyl-4'-methoxymethoxybenzyl)-1-trifluromethanesulfonyloxyphenyl (0.83 g, 1.73 mmol), triethylamine (0.96 mL, 6.92 mmol), $Pd(PPh_3)_2Cl_2$ (0.12 g, 0.17 mmol) and diethyl vinylphosphonate (0.37 mL, 2.43 mmol) in DMF (8 mL) was heated at 80° C. for 16 h. The solvent was removed under reduced pressure and the residue was partitioned between EtOAc and saturated aqueous $NaHCO_3$. The organic layer was separated, dried over $Na_2SO_4$, filtered and concentrated under reduced pressure. The crude product was purified by column chromatography on silica gel, eluting with ethyl acetate-$CH_2Cl_2$ (1:1) to afford diethyl 2-[4-(3'-iso-propyl-4'-methoxymethoxybenzyl)-3,5-dimethoxy-phenyl]vinylphosphonate as a light yellow oil (0.1 g, 12%): $^1$H NMR (300 MHz, $CDCl_3$): δ 7.50 (d, J=17.4 Hz, 1H), 7.29 (s, 1H), 7.11 (m, 2H), 6.72 (s, 2H), 6.22 (t, J=17.1 Hz, 1H), 5.17 (s, 2H), 4.21 (m, 4H), 3.96 (s, 2H), 3.87 (s, 6H), 3.49 (s, 3H), 3.31 (m, 1H), 1.40 (t, J=6.9 Hz, 6H), 1.23 (d, J=6.6 Hz, 6H); TLC conditions: Uniplate silica gel, 250 microns; Mobile phase=ethyl acetate-$CH_2Cl_2$ (1:3); $R_f$=0.4.

Step c:

A mixture of diethyl 2-[3,5-dimethoxy-4-(3'-iso-propyl-4'-methoxymethoxybenzyl)phenyl]vinylphosphonate (0.1 g, 0.2 mmol) and Pd/C (20 mg, 10%) in MeOH (20 mL) was stirred under one atmosphere of hydrogen at room temperature for 16 h. The mixture was filtered through a Celite plug. The solvent was removed under reduced pressure and the residue (90 mg) was dissolved in $CH_2Cl_2$ (5 mL). Deprotection with TMSBr as described for the synthesis of Compound 7, step b afforded 2-[3,5-dimethoxy-4-(4'-hydroxy-3'-isopropylbenzyl)phenyl]ethylphosphonic acid as light pink foam (73 mg, 91%). $^1$H NMR (200 MHz, DMSO-$d_6$): δ 8.88 (s, 1H), 7.01 (d, J=1.8 Hz, 1H), 6.71 (dd, J=1.8 Hz, J=8.0 Hz, 1H), 6.55 (d, J=8.4 Hz, 1H), 6.5 (s, 2H), 3.76 (s, 6H), 3.69 (s, 2H), 3.08 (m, 1H), 2.72 (m, 2H), 1.82 (m, 2H), 1.08 (d, J=7.0 Hz, 6H), LC-MS m/z=395 $[C_{20}H_{27}O_6P+H]^+$; Anal Calcd for ($C_{20}H_{27}O_6P+1.3H_2O$): C, 57.49; H, 7.14. Found: C, 57.24; H, 7.24.

Using the appropriate starting material, compounds 24-1 to 24-4 were prepared in an analogous manner to that described for the synthesis of compound 24.

Compound 24-1: 2-[3,5-dimethyl-4-(4'-hydroxy-3'-iso-propylbenzyl)-phenyl]ethylphosphonic acid Prepared from 3,5-dimethyl-4-(3'-iso-propyl-4'-methoxymethoxy-benzyl)phenol (Chiellini et al., *Bioorg. Med. Chem. Lett.* 10:2607 (2000)). mp: 65-68° C.; $^1$H NMR (300 MHz, $CD_3OD$): δ 6.93 (s, 2H), 6.86 (d, J=1.8 Hz, 1H), 6.60 (d, J=8.4 Hz, 1H), 6.54 (dd, J=1.8 Hz, J=8.0 Hz, 1H), 3.94 (s, 2H), 3.24 (m, 1H), 2.82 (m, 2H), 2.23 (s, 6H), 2.01 (m, 2H), 1.15 (d, J=7.0 Hz, 6H), LC-MS m/z=363 $[C_{20}H_{27}O_4P]^+$; Anal Calcd for ($C_{20}H_{27}O_4P+0.6H_2O+0.4CH_3OH$): C, 63.47; H, 7.78. Found: C, 63.39; H, 8.06.

Compound 24-2: trans-2-[3,5-dimethyl-4-(4'-hydroxy-3'-iso-propylbenzyl)-phenyl]vinylphosphonic acid Prepared from 3,5-dimethyl-4-(3'-iso-propyl-4'-methoxymethoxy-benzyl)phenol (Chiellini et al., *Bioorg. Med. Chem. Lett.* 10:2607 (2000)). mp: 82-84° C.; $^1$H NMR (300 MHz, $CD_3OD$): δ 7.38 (m, 1H), 7.27 (s, 2H), 6.84 (d, J=1.8 Hz, 1H), 6.62 (d, J=8.4 Hz, 1H), 6.54 (dd, J=1.8 Hz, J=8.0 Hz, 1H), 6.42 (m, 1H), 4.00 (s, 2H), 3.24 (m, 1H), 2.28 (s, 6H), 1.15 (d, J=7.0 Hz, 6H), LC-MS m/z=361 $[C_{20}H_{25}O_4P+H]^+$; Anal Calcd for ($C_{20}H_{25}O_4P+0.3H_2O$): C, 65.67; H, 7.05. Found: C, 65.43; H, 7.13.

Compound 24-3: 2-[4-(3'-sec-butyl-4'-hydroxy-benzyl)-3,5-dimethyl-phenyl]-ethylphosphonic acid The title compound was prepared from intermediate 4-(3'-sec-butyl-4'-methoxymethoxy-benzyl)-3,5-dimethyl-phenol, prepared from 4-bromo-2-methyl-phenol according to the procedure described in Chiellini et al., *Bioorg. Med. Chem. Lett.* 10:2607 (2000), and transformed into the title compound by the procedure used for the synthesis of compound 24 as a light yellow foam; $^1$H NMR (200 MHz, DMSO-$d_6$): δ 8.88 (s, 1H), 6.86 (s, 2H), 6.80 (s, 1H), 6.61 (d, J=8.0 Hz, 1H), 6.46 (d, J=8.0 Hz, 1H), 3.81 (s, 2H), 2.88 (m, 1H), 2.65 (m, 2H), 2.15 (s, 6H), 1.75 (m, 2H), 1.46 (m, 2H), 1.06 (d, J=7.0 Hz, 3H), 0.74 (t, J=7.4 Hz, 3H), LC-MS m/z=377 [C$_{21}$H$_{29}$O4P+H]$^+$; Anal Calcd for (C$_{21}$H$_{29}$O$_4$P+ 1.6H$_2$O): C, 62.24; H, 8.01. Found: C, 61.87; H, 7.82.

Compound 24-4: 2-[3,5-dimethyl-4-(3'-Ethyl-4'-hydroxy-benzyl)phenyl]-ethylphosphonic acid Intermediate 4-(3'-ethyl-4'-methoxybenzyl)-3,5-dimethylphenol, prepared according to the procedure described in Chiellini et al., *Bioorg. Med. Chem. Lett.* 10:2607 (2000), was transformed into the title compound by the procedure used for the synthesis of compound 24 as a foam (94 mg, 19%); LC-MS m/z=347 [C$_{18}$H$_{23}$O$_5$P−H]; $^1$H NMR (300 MHz, DMSO-d$_6$): δ 8.98(s, 1H), 6.86(d, 1H, J=3 Hz), 6.72(d, 1H, J=1.8 Hz), 6.60(s, 2H), 6.49(dd, 1H, J=2.8 Hz, J=8.4 Hz), 3.82(s, 2H), 2.71(m, 2H), 2.26(s, 3H), 2.09(s, 3H), 1.66(m, 2H), 1.06(t, 3H, J=9 Hz); Uniplate silica gel, 250 microns; Mobile phase=isopropyl alcohol/ammonium hydroxide/water [7:2:1]; Rf=0.22; Anal. Calcd for (C$_{19}$H$_{25}$O$_4$P+1.1H$_2$O): C, 61.98; H, 7.45; Found: C, 61.88, H, 7.19.

Example 25

Compound 25: [3,5-dimethyl-4-(3'-iso-propyl-4'-hydroxybenzoyl)phenoxy]-methylphosphonic acid Step a:

To a stirring solution of (2,6-dimethyl-4-triisopropylsilanyloxyphenyl)-(3'-iso-propyl-4'-methoxymethoxyphenyl)methanol (0.620 g, 1.27 mmol), (Chiellini et al., *Bioorg. Med. Chem. Lett.* 10:2607 (2000)) in THF (10.0 mL) at 0° C. was added tetrabutylammonium fluoride (1.91 mL, 1.91 mmol, 1.0 M solution in THF). The reaction mixture was stirred at room temperature for 20 min, diluted with diethyl ether and washed with water (20 mL×2) and brine. The solvent was removed under reduced pressure and the residue was purified by column chromatography on silica gel, eluting with ethyl acetate-hexanes (1:4) to afford 3,5-dimethyl-4-(3'-iso-propyl-4'-methoxymethoxy-benzylhydroxy)phenol as an oil (0.370 g, 88%): $^1$H NMR (300 MHz, DMSO-d$_6$): δ 9.07 (s, 1H), 7.20 (m, 1H), 6.90 (m, 1H), 6.78 (m, 1H), 6.39 (s, 2H), 5.98 (d, J=3.0 Hz, 1H), 5.52 (d, J=3.0 Hz, 1H) 5.18 (s, 2H), 3.38 (s, 3H), 3.25 (m, 1H), 2.12 (s, 6H), 1.16 (m, 6H); TLC conditions: Uniplate silica gel, 250 microns; Mobile phase=hexanes-ethyl acetate (4:1); R$_f$=0.15.

Step b:

To a mixture of 3,5-dimethyl-4-(3'-iso-propyl-4'-methoxymethoxy-benzylhydroxy)phenol (0.380 g, 1.15 mmol) in DMF (10.0 mL) at 0° C. was added Cs$_2$CO$_3$ (1.87 g, 5.75 mmol). After 5 min, diethyl trifluoromethane-sulfonyloxymethyl phosphonate (0.24 g, 1.15 mmol) was added. The reaction mixture was stirred at 0° C. for 5 h, allowed to warm to room temperature and stirred for 16 h. The reaction mixture was quenched with 1 N HCl, diluted with ethyl acetate, and washed with water (10 mL×4) and brine. The organic layer was concentrated under reduced pressure and the crude product was purified by column chromatography on silica gel, eluting with acetone-hexanes (1:4) as mobile phase to afford diethyl [3,5-dimethyl-4-(3'-iso-propyl-4'-methoxymethoxy-benzylhydroxy)phenoxy]methylphosphonate as an oil (0.41 g, 74%): $^1$H NMR (300 MHz, DMSO-d$_6$): δ 7.20 (m, 1H), 6.92 (m, 1H), 6.78 (m, 1H), 6.67 (s, 2H), 6.03 (d, J=3.0 Hz, 1H), 5.64 (d, J=3.0 Hz, 1H), 5.18 (s, 2H), 4.38 (d, J=9.0 Hz, 2H), 4.11 (m, 4H), 3.38 (s, 3H), 3.25 (m, 1H), 2.19 (s, 6H), 1.24 (m, 6H), 1.16 (m, 6H); TLC conditions: Uniplate silica gel, 250 microns; Mobile phase=hexanes-acetone (6:4); R$_f$=0.35.

Step c:

To a stirred solution of diethyl [3,5-dimethyl-4-(3'-iso-propyl-4'-methoxymethoxybenzylhydroxy)phenoxy]methylphosphonate (0.32 g, 0.66 mmol) in dichloromethane (8.0 mL) at 0° C. was added Dess-Martin periodinane (2.08 mL, 0.99 mmol, 0.48 M solution in CH$_2$Cl$_2$). The reaction mixture was stirred room temperature for 16 h, concentrated, diluted with diethyl ether (10.0 mL). To the solution was added a solution of 580 mg of Na$_2$S$_2$O$_3$ pentahydrate in 60 mL saturated NaHCO$_3$). After 15 min, the reaction mixture was diluted with ethyl acetate and water and washed with saturated NaHCO$_3$ and brine. The organic layer was concentrated under reduced pressure. The crude product was purified by column chromatography on silica gel, eluting with ethyl acetate-hexanes (1:1) to afford diethyl [3,5-dimethyl-4-(3'-iso-propyl-4'-methoxymethoxybenzoyl)phenoxy] methylphosphonate as an oil (0.285 g, 89%): $^1$H NMR (300 MHz, DMSO-d$_6$): δ 7.22 (m, 1H), 7.43 (m, 1H), 7.13 (m, 1H), 6.85 (s, 2H), 5.35 (s, 2H), 4.49 (d, J=7.5 Hz, 2H), 4.16 (m, 4H), 3.43 (s, 3H), 3.27 (m, 1H), 2.02 (s, 6H), 1.29 (m, 6H), 1.20 (m, 6H); TLC conditions: Uniplate silica gel, 250 microns; Mobile phase=dichloromethane-methanol (3:97); R$_f$=0.52.

Step d:

To a solution of diethyl [3,5-dimethyl-4-(3'-iso-propyl-4'-methoxymethoxybenzoyl)phenoxy]methylphosphonate (0.075 g, 0.16 mmol) in CH$_2$Cl$_2$ (3.0 mL) at −30° C. was added bromotrimethylsilane (0.31 mL, 2.4 mmol). The reaction mixture was stirred at room temperature 16 h and the solvent was removed under reduced pressure. The residue was treated with acetonitrile-water (4:1, 5.0 mL) and sonicated. The solvents were removed under reduced pressure. The residue was dissolved in 1 N NaOH and extracted with dichloromethane and ethyl acetate. The aqueous layer was acidified with 2 N HCl and extracted with ethyl acetate. The organic layer was dried over MgSO$_4$, filtered and concentrated under reduced pressure to afford [3,5-dimethyl-4-(4'-hydroxy-3-iso-propylbenzoyl)phenoxy]methylphosphonic acid as an pink solid (0.05 g, 84%): mp 138° C.; LC-MS m/z=379 [C$_{19}$H$_{23}$O$_6$P+H]$^+$; $^1$H NMR (300 MHz, DMSO-d$_6$): δ 10.50 (s, 1H), 7.64 (s, 1H), 7.27 (m, 1H), 6.87 (m, 1H), 6.78 (m, 1H), 4.18 (m, 2H), 3.18 (m, 1H), 2.00 (s, 6H), 3.11 (m, 1H), 1.17 (d, J=6.0 Hz, 6H); HPLC conditions: Column =3 Chromolith SpeedRODs RP-18e, 100×4.6 mm; Mobile phase=Solvent A (Acetonitrile)=HPLC grade acetonitrile; Solvent B (buffer)=20 mM ammonium phosphate buffer (pH 6.1, 0.018 M NH$_4$H$_2$PO$_4$/0.002 M (NH$_4$)$_2$HPO$_4$) with 5% acetonitrile. Flow rate=4 mL/min; UV@ 255 nm. Retention time in minutes. (rt=5.30, 95% purity).

Example 26

Compound 26: 2-[3,5-dimethyl-4-(3'-iso-propyl-4'-hydroxybenzyl)-phenoxy]ethylphosphonic acid Step a:

To a stirring solution of 3,5-dimethyl-4-(3'-iso-propyl-4'-methoxymethoxymethylbenzyl)phenol (1.00 g, 3.18 mmol, Chiellini et al., *Bioorg. Med. Chem. Lett.* 10:2607 (2000)) in DMF (30.0 mL) was added Cs$_2$CO$_3$ (5.18 g, 15.90 mmol) followed by 1,2-dibromoethane (1.64 g, 19.08 mmol). The reaction mixture was stirred at 60° C. for 2 d, diluted with ethyl acetate and washed with water (20 mL×4) and brine. The organic layer was dried over MgSO$_4$, filtered and concentrated under reduced pressure. The crude product was purified by column chromatography on silica gel, eluting with ethyl acetate-hexanes (1:19) to afford 1-(2-bromoethoxy)-4-(3'-iso-propyl-4'-methoxymethoxybenzyl)-3,5-dimethylbenzene as an oil (0.26 g, 16%): $^1$H NMR (300 MHz, CDCl$_3$): δ 6.94 (m, 2H), 6.67 (m, 3H), 5.18 (s, 2H), 4.32 (m, 2H), 3.95 (s, 2H), 3.68 (m, 2H), 3.51 (s, 3H), 3.37 (s, 3H), 3.32 (m, 1H), 2.26 (s, 6H), 1.22 (d, J=6.0 Hz, 6H); TLC conditions: Uniplate silica gel, 250 microns; Mobile phase=hexanes-ethyl acetate (4:1); R$_f$=0.91.

Step b:

A mixture of 1-(2-bromoethoxy)-4-(3'-iso-propyl-4'-methoxymethoxybenzyl)-3,5-dimethylbenzene (0.15 g, 0.36 mmol) and triethylphosphite (0.18 g, 1.07 mmol) in DMF (2.0 mL) was heated under reflux for 4 h. The reaction mixture was cooled to rt, diluted with ethyl acetate and extracted with water (10 mL×4) and brine. The organic layer was dried over MgSO$_4$, filtered and concentrated under reduced pressure. The residue was purified by column chromatography on silica gel, eluting with acetone-hexanes (1:1) to afford diethyl 2-[3,5-dimethyl-4-(3'-iso-propyl-4'-methoxymethoxybenzyl)phenoxy]ethylphosphonate as an oil (0.085 g, 50%): $^1$H NMR (300 MHz, DMSO-d$_6$): δ 6.96 (m, 1H), 6.89 (m, 1H), 6.62 (m, 3H), 5.16 (s, 2H), 4.12 (m, 2H), 4.07 (m, 4H) 3.86 (s, 2H), 3.37 (s, 3H), 3.22 (m, 1H), 2.30 (m, 2H), 2.17 (s, 6H), 1.25 (m, 6H), 1.12 (d, J=6.0 Hz, 6H); TLC conditions: Uniplate silica gel, 250 microns; Mobile phase=ethyl acetate-hexanes (3:7); R$_f$=0.10.

Step c:

Deprotection of diethyl 2-[3,5-dimethyl-4-(3'-iso-propyl-4'-methoxymethoxybenzyl)phenoxy]ethylphosphonate with bromotrimethylsilane afforded 2-[3,5-dimethyl-4-(4'-hydroxy-3'-iso-propylbenzyl)phenoxy]ethylphosphonic acid as a brown oil (0.055 g, 87%): mp: 58-61° C.; LC-MS m/z=379, [C$_{20}$H$_{27}$O$_5$P+H]$^+$; $^1$H NMR (300 MHz, CD$_3$OD): δ 6.84 (s, 1H), 6.66 (s, 2H), 6.56 (m, 2H), 4.26 (m, 2H), 3.90 (s, 2H), 3.22 (m, 1H), 2.30 (m, 1H), 2.22 (s, 6H), 1.15 (d, J=6.0 Hz, 6H); Anal. Calcd for (C$_{20}$H$_{27}$O$_5$P+0.6H$_2$O): C, 61.72; H, 7.30. Found: C, 61.96, H, 7.73.

Example 27

Compound 27: [3,5-dimethyl-4-(4'-fluoro-3'-iso-propylbenzyl)phenoxy]-methylphosphonic acid Step a:

To a solution of 2-bromopropene (6.0 g, 49.60 mmol) in diethyl ether (200 mL) at −78° C. was added t-butyllithium (36.0 mL). The reaction mixture was stirred at −78° C. for 3 h and to it was added tributyltin chloride (16.1 g, 49.60 mmol). The reaction mixture was allowed to warm up to room temperature and stirred for 16 h. The reaction mixture was filtered through a plug of Celite and the filtrate was washed with saturated NH$_4$Cl. The organic layer was dried over MgSO$_4$, filtered and concentrated to afford the crude product as colorless oil that was used for next step without further purification.

Step b:

To a solution of 3-bromo-4-fluorobenzaldehyde (1.23 g, 6.04 mmol) in dioxane (20 mL) was added the product obtained from step a followed by Pd(Ph$_3$)$_2$Cl$_2$. The reaction mixture was heated at 110° C. for 16 h, cooled to room temperature and filtered through a plug of Celite. The solvent was removed under reduced pressure and the crude product was purified by column chromatography on silica gel, eluting with ethyl acetate-hexanes (1:19) to afford 4-fluoro-3-isopropenylbenzaldehyde (500 mg, 50%): $^1$H NMR (300 MHz, CDCl$_3$): δ 7.89 (m, 1H), 7.82 (m, 1H), 7.24 (m, 1H), 5.36 (s, 2H), 2.21 (s, 3H). TLC conditions: Uniplate silica gel, 250 microns; Mobile phase=ethyl acetate-hexanes (1:19); R$_f$=0.60.

Step c:

To a solution of 4-bromo-3,5-dimethyl-triisopropylsilanoxybenzene (1.29 g, 3.6 mmol, Chiellini et al., *Bioorg. Med. Chem. Lett.* 10:2607 (2000)) in THF at −78° C. was added n-butyllithium (1.58 mL, 3.96 mmol, 2.5 M in THF). After 30 min, a solution of 4-fluoro-3-isopropenylbenzaldehyde (500 mg, 3.0 mmol) in THF was added. The reaction mixture was stirred at −78° C. for 1 h, allowed to warm to room temperature, diluted with EtOAc and quenched with water. The organic layer was dried over MgSO$_4$, filtered and concentrated to afford crude 1-(2,6-dimethyl-4-triisopropylsilanyloxyphenyl)-1-(4'-fluoro-3'-isopropenylphenyl)methanol as an oil: $^1$H NMR (200 MHz, CDCl$_3$): δ 7.18 (m, 1H), 7.02 (m, 1H), 6.94 (m, 1H), 6.56 (s, 2H), 6.22 (s, 1H), 5.18 (m, 2H), 2.20 (s, 6H), 2.08 (s, 3H), 1.25 (m, 3H), 1.11 (m, 18).

Step d:

A solution of 1-(2,6-dimethyl-4-triisopropylsilanyloxyphenyl)-1-(4'-fluoro-3'-isopropenylphenyl)methanol (1.2 g, 2.71 mmol) and Pd/C (0.1 g, 10%) in EtOH/HOAc (9:1, 10 mL) was stirred under a H$_2$ atmosphere for 16 h. The reaction mixture was filtered through a plug of Celite and concentrated to afford the crude 3,5-dimethyl-4-(4'-fluoro-3'-isopropylbenzyl)triisopropylsilanoxybenzene that was used for the next step without further purification.

Step e:

To a solution of 3,5-dimethyl-4-(4'-fluoro-3'-iso-propylbenzyl)triisopropylsilanoxybenzene in THF (10 mL) at 0° C. was added TBAF (1 M, 4.0 mL). The reaction mixture was stirred for 3 h, diluted with ethyl acetate 920 mL) and quenched with water (10 mL). The organic layer was dried over MgSO$_4$, filtered and concentrated under reduced pressure. The crude product was purified by column chromatography on silica gel, eluting with ethyl acetate-hexanes (1:9) to afford 3,5-dimethyl-4-(4'-fluoro-3'-iso-propylbenzyl)phenol (450 mg, 61% for two steps): $^1$H NMR (300 MHz, CDCl$_3$): δ 6.97 (d, J=7.4 Hz, 1H), 6.86 (m, 1H), 6.69 (m, 1H), 6.60 (s, 2H), 3.95 (s, 2H), 3.20 (m, 1H), 2.22 (s, 6H), 1.25 (d, J=6.4 Hz, 6H). TLC conditions: Uniplate silica gel, 250 microns; Mobile phase=ethyl acetate-hexanes (1:9); R$_f$=0.50.

Step f:

[3,5-Dimethyl-4-(4'-fluoro-3'-iso-propylbenzyl)phenoxy]methyl-phosphonic acid was prepared from 3,5-dimethyl-4-(4'-fluoro-3'-iso-propylbenzyl)phenol following the same procedure as described in compound 7, step b: $^1$H NMR (300 MHz, DMSO-d$_6$): δ 7.03 (m, 1H), 6.93 (m, 1H), 6.71 (s, 2H), 6.64 (m, 1H), 4.03 (d, J=10.2 Hz, 2H), 3.89 (s, 2H), 3.09 (m, 1H), 2.15 (s, 6H), 1.16 (d, J=6.6 Hz, 6H). mp: >200° C.; LC-MS m/z=367 [C$_{19}$H$_{24}$FO$_4$P+H]$^+$; Anal. Calcd for (C$_{19}$H$_{24}$FO$_4$P+0.4H$_2$O): C, 61.09; H, 6.69. Found: C, 60.85; H, 6.32.

Using the appropriate starting material, compound 27-1 was prepared in an analogous manner to that described for the synthesis of compound 27.

Compound 27-1: [3,5-dichloro-4-(4'-fluoro-3'-iso-propyl-benzyl)-phenoxy]methylphosphonic acid Intermediate (2,6-dichloro-4-triisopropylsilanyloxy-phenyl)-(4-fluoro-3-iso-propyl-phenyl)-methanol was prepared by the procedure described for the synthesis of compound 27, steps a, b, c, d as an oil (520 mg, 98%): $^1$H NMR (300 MHz, CDCl$_3$): δ 7.24 (m, 1H), 6.98 (m, 2H), 6.91 (s, 2H), 6.52 (s, 1H), 4.48 (s, 1H), 3.24 (m, 1H), 1.25 (m, 3H), 1.15 (s, 24H). TLC conditions: Uniplate silica gel, 250 microns; Mobile phase=ethyl acetate-hexanes (1:19); R$_f$=0.86.

Step d:

To a solution of (2,6-dimethyl-4-triisopropylsilanyloxyphenyl)-(4-fluoro-3-iso-propyl-phenyl)-methanol (520 mg, 1.08 mmol) in CH$_2$Cl$_2$ (10 mL) was added TFA (1.53 M, 0.7 mL) followed by triethylsilane (0.6 mL, 3.77 mmol) at r.t. After stirring for 2 h, the reaction mixture was diluted with EtOAc and water and the layers were separated. The aqueous layer was further extracted with EtOAc. The combined organic layers were washed with Sat. NaHCO$_3$, water and brine, dried over MgSO$_4$, filtered and concentrated. The residue was purified by column chromatography (silica gel, hexanes) to provide 3,5-dichloro-4-(4'-fluoro-3'-iso-propyl-benzyl)-phenoxy]-triisopropylsilane as a colorless liquid (360 mg, 72%): $^1$H NMR (300 MHz, CDCl$_3$): δ 7.11 (m, 1H), 6.91 (m, 4H), 4.21 (s, 2H), 3.19 (m, 1H), 1.24 (m, 3H), 1.17 (m, 24H). TLC conditions: Uniplate silica gel, 250 microns; Mobile phase=hexanes; R$_f$=0.68.

Intermediate 3,5-dichloro-4-(4'-fluoro-3'-iso-propyl-benzyl)-phenoxy]-triisopropylsilane was transformed into the title compound by the procedure described for the synthesis of compound 35, steps e, f and h to give a white solid (55 mg, 35%): $^1$H NMR (300 MHz, DMSO-d$_6$): δ 7.22 (s, 2H), 7.18 (m, 1H), 7.04 (m, 1H), 6.87 (m, 1H), 4.22 (d, J=9.6 Hz, 2H), 6.60 (s, 2H), 3.12 (m, 1H), 1.19 (d, J=6.9 Hz, 6H); mp=132~135, LC-MS m/z=408 [C$_{17}$H$_{18}$Cl$_2$FO$_4$P+H]$^+$; Anal. Calcd for (C$_{17}$H$_{18}$Cl$_2$FO$_4$P+0.2H$_2$O): C, 49.70; H, 4.51. Found: C, 49.58; H, 4.24.

Example 28

Compound 28: trans-2-[3,5-dimethyl-4-(4'-hydroxy-3'-iso-propylphenoxy)-phenyl]vinylphosphonic acid Step a:

To a mixture of bis(4-methoxy-3-iso-propylphenyl)iodonium tetrafluoroborate (4.80 g, 9.38 mmol) and copper powder (0.79 g, 12.52 mmol) in CH$_2$Cl$_2$ (15.0 mL) at 0° C. was added a solution of triethylamine (0.96 mL, 6.89 mmol) and 3,5-dimethyl-4-hydroxybenzaldehyde (0.94 g, 6.26 mmol) in dichloromethane (15.0 mL). The reaction mixture was stirred at room temperature for 3 d and filtered through a Celite plug. The solvent was removed under reduced pressure and the residue was purified by column chromatography on silica gel, eluting with acetone-hexanes (1:19) to afford 3,5-dimethyl-4-(3'-iso-propyl-4'-methoxyphenoxy)benzaldehyde as an oil (2.00 g, 100%): $^1$H NMR (300 MHz, DMSO-d$_6$): δ 9.96 (s, 1H), 7.75 (s, 2H), 6.85 (m, 1H), 6.73 (m, 1H), 6.36 (m, 1H), 3.74 (s, 3H), 3.19 (m, 1H), 2.15 (s, 6H), 1.12 (d, J=6.0 Hz, 6H); TLC conditions: Uniplate silica gel, 250 microns; Mobile phase=hexanes-acetone (17:3); R$_f$=0.51.

Step b:

To a mixture of tetraethyl methylenediphosphonate (0.20 mL, 0.80 mmol) and THF (7.0 mL) at 0° C. was added sodium hydride (0.033 g, 0.804 mmol, 60% dispersion in oil). The reaction mixture was stirred at room temperature for 30 min and to it was added 3,5-dimethyl-4-(3'-iso-propyl-4'-methoxyphenoxy)benzaldehyde (0.20 g, 0.67 mmol). The reaction mixture was stirred at room temperature for 1 h, quenched with cold aqueous solution of NH$_4$Cl, diluted with ethyl acetate and washed with water and brine. The solvent was removed under reduced pressure and the residue was purified by preparatory TLC on silica gel, eluting with acetone-hexanes (1:4) to afford diethyl trans-2-[3,5-dimethyl-4-(3'-iso-propyl-4'-methoxyphenoxy)phenyl] vinylphosphonate as an oil (0.21 g, 74%): $^1$H NMR (300 MHz, DMSO-d$_6$): δ 7.53 (s, 2H), 7.32 (m, 2H), 6.84 (m, 1H), 6.74 (m, 1H), 6.59 (m, 2H), 6.36 (m, 1 H), 4.00 (m, 4 H), 3.73 (s, 3 H), 3.20 (m, 1 H), 2.07 (s, 6 H), 1.27 (m, 6 H), 1.10 (d, J=6.0 Hz, 6 H); TLC conditions: Uniplate silica gel, 250 microns; Mobile phase=hexanes-acetone (4:1); R$_f$=0.13.

Step c:

To a solution of diethyl trans-2-[3,5-dimethyl-4-(3'-iso-propyl-4'-methoxyphenoxy)phenyl]vinylphosphonate (0.22 g, 0.50 mmol) in CH$_2$Cl$_2$ (5.0 mL) at −30° C. was added bromotrimethylsilane (0.66 mL, 5.00 mmol). The reaction mixture was stirred at room temperature 16 h and the solvent was removed under reduced pressure. The residue was dissolved in dichloromethane (5.0 mL) and cooled to −78° C. To it was added BBr$_3$ (1.49 mL, 1.49 mmol, 1.0 M solution in CH$_2$Cl$_2$). The reaction mixture was stirred at −78° C. for 3 h, allowed to warm to room temperature and stirred for 16 h. The reaction mixture was poured into ice, concentrated, and extracted with ethyl acetate. The organic solution was washed with 2% HCl (20 mL) and water (20 mL×3), dried over MgSO$_4$ and filtered. The solvent was removed under reduced pressure to afford trans-2-[3,5-dimethyl-4-(4'-hydroxy-3'-iso-propylphenoxy)phenyl]vinylphosphonic acid as an off-white solid (0.08 g, 44% over two steps): mp 92-94° C.; LC-MS m/z=363 [C$_{19}$H$_{23}$O$_5$P+H]$^+$; $^1$H NMR (300 MHz, CD$_3$OD): δ 7.35 (s, 2 H), 7.10 (s, 1 H), 6.65 (s, 2 H), 6.32 (m, 2 H), 3.21 (m, 1 H), 2.12 (s, 6 H), 1.15 (d, J=6.0 Hz, 6 H); HPLC conditions: Column=3 Chromolith SpeedRODs RP-18e, 100×4.6 mm; Mobile phase=Solvent A (Acetonitrile)=HPLC grade acetonitrile; Solvent B (buffer)=20 mM ammonium phosphate buffer (pH 6.1, 0.018 M NH$_4$H$_2$PO$_4$/0.002 M (NH$_4$)$_2$HPO$_4$) with 5% acetonitrile. Flow rate=4 mL/min; UV@ 255 nm. Retention time in minutes. (rt=5.71, 98% purity).

Example 29

Compound 29: 3-[3,5-dimethyl-4-(4'-hydroxy-3'-iso-propylphenoxy)phenyl]-propylphosphonic acid Step a:

To a mixture of triethyl phosphonoacetate (0.16 mL, 0.80 mmol) in THF (7.0 mL) at 0° C. was added NaH (0.033 g, 0.804 mmol, 60% dispersion in oil). The reaction mixture was stirred room temperature for 30 min and to it was added 3,5-dimethyl-4-(3-iso-propyl-4-methoxyphenoxy)benzaldehyde (0.20 g, 0.67 mmol, Example 28, step a). The reaction mixture was stirred at room temperature for 1 h, quenched with cold saturated NH$_4$Cl, diluted with ethyl acetate and washed with water and brine. The solvent was removed under reduced pressure and the residue was purified by preparatory TLC on silica gel, eluting with acetone-hexanes (3:17) to afford ethyl trans-3-[3,5-dimethyl-4-(3'-iso-propyl-4'-methoxyphenoxy)phenyl]acrylate as an oil (0.24 g, 97%): $^1$H NMR (300 MHz, DMSO-d$_6$): δ 7.60 (m, 3 H), 6.83 (m, 1 H), 6.76 (m, 1 H), 6.60 (m, 1 H), 6.36 (m, 1 H), 4.21 (m, 4 H), 3.73 (s, 3 H), 3.21 (m, 1H), 2.08 (s, 6 H), 1.27 (m, 6 H), 1.12 (d, J=6.0 Hz, 6 H); TLC conditions: Uniplate silica gel, 250 microns; Mobile phase=hexanes-acetone (4:1); R$_f$=0.62.

Step b:

To a mixture of ethyl trans-3-[3,5-dimethyl-4-(3'-iso-propyl-4'-methoxyphenoxy)phenyl]acrylate (1.10 g, 3.35 mmol) in THF (20.0 mL) at 0° C. was added DIBAL-H (4.68 mL, 4.68 mmol, 1.0 M solution in THF). The reaction mixture was stirred at room temperature for 2 h, quenched with cold 1 N HCl, diluted with ethyl acetate and washed with water and brine. The solvent was removed under reduced pressure and the residue was purified by column chromatography on silica gel, eluting with acetone-hexanes (1:9) to afford trans-3-[3, 5-dimethyl 4-(3'-iso-propyl-4'-methoxyphenoxy)phenyl]- prop-2-en-1-ol as an oil (0.50 g, 81%): $^1$H NMR (300 MHz, DMSO-d$_6$): δ 7.22 (s, 2 H), 6.97 (m, 0.5 H), 6.84 (m, 1.5 H), 6.73 (m, 1 H), 6.36 (m, 2 H), 4.87 (m, 1 H), 4.14 (m, 2 H), 3.73 (s, 3 H), 3.21 (m, 1 H), 2.05 (s, 6 H), 1.11 (d, J=6.0 Hz, 6 H); TLC conditions: Uniplate silica gel, 250 microns; Mobile phase=hexanes-acetone (17:3); R$_f$=0.11.

Step c:

To a mixture of trans-3-[3,5-dimethyl 4-(3'-iso-propyl-4'-methoxyphenoxy)phenyl]-prop-2-en-1-ol (0.50 g, 1.53 mmol) in methanol (15.0 mL) was added 10% Pd/C (0.10 g, 20% wt/wt). The reaction mixture was stirred under H$_2$ (balloon) at room temperature for 6 h and filtered through a plug of Celite. The solvent was removed under reduced pressure and the residue was purified by column chromatography on silica gel, eluting with acetone-hexanes (3:7) to afford 3-[3,5-dimethyl 4-(3'-iso-propyl-4'-methoxyphenoxy)phenyl]propanol as an oil (0.36 g, 72%): $^1$H NMR (300 MHz, DMSO-d$_6$): δ 6.97 (s, 2 H), 6.82 (m, 1 H), 6.74 (m, 1 H), 6.30 (m, 1 H), 4.49 (m, 1 H), 3.73 (s, 3 H), 3.43 (m, 2 H), 3.21 (m, 1 H), 2.57 (m, 2 H), 2.03 (s, 6 H), 1.73 (m, 2 H), 1.11 (d, J=6.0 Hz, 6 H); TLC conditions: Uniplate silica gel, 250 microns; Mobile phase=hexanes-acetone (17:3); R$_f$=0.26.

Step d:

To a stirred solution of triphenylphosphine (0.36 g, 1.39 mmol) and CBr$_4$ (0.46 g, 1.39 mmol) in diethyl ether (12.0 mL) at room temperature was added 3-[3,5-dimethyl 4-(3'-iso-propyl-4'-methoxyphenoxy)phenyl]propanol (0.35 g, 1.06 mmol). The reaction mixture was stirred for 16 h, filtered and concentrated under reduced pressure. The crude product was purified by column chromatography on silica gel, eluting with acetone-hexanes (1:9) to afford 1-bromo-3-[3,5-dimethyl 4-(3'-iso-propyl-4'-methoxyphenoxy)-phenyl]propane as an oil (0.30 g, 72%): $^1$H NMR (300 MHz, DMSO-d$_6$): δ 7.00 (s, 2 H), 6.83 (m, 1 H), 6.80 (m, 1 H), 6.31 (m, 1 H), 3.73 (s, 3 H), 3.53 (m, 2 H), 3.20 (m, 1 H), 2.70 (m, 2 H), 2.12 (m, 2 H), 2.03 (s, 6 H), 1.11 (d, J=6.0 Hz, 6 H); TLC conditions: Uniplate silica gel, 250 microns; Mobile phase=hexanes-acetone (4:1); R$_f$=0.75.

Step e:

A mixture of 1-bromo-3-[3,5-dimethyl 4-(3'-iso-propyl-4'-methoxyphenoxy)phenyl]propane (0.30 g, 0.77 mmol) and triethylphosphite (0.39 g, 2.31 mmol) in DMF (7.0 mL) was heated under reflux for 2.5 h and cooled to room temperature. The mixture was diluted with ethyl acetate and washed with water and brine. The organic layer was concentrated under reduced pressure and the residue was purified by column chromatography on silica gel, eluting with acetone-hexanes (1:3) to afford diethyl 3-[3,5-dimethyl 4-(3'-iso-propyl-4'-methoxyphenoxy)phenyl]propylphosphonate as an oil (0.11 g, 32%): $^1$H NMR (300 MHz, DMSO-d$_6$): δ 6.97 (s, 2 H), 6.83 (d, J=9.0 Hz, 1 H), 6.72 (d, J=3.0 Hz, 1 H), 6.32 (m, 1 H), 3.99 (m, 4 H), 3.73 (s, 3H), 3.35 (m, 2 H), 3.17 (m, 1 H), 2.62 (m, 2 H), 2.02 (s, 6 H), 1.75 (m, 4 H), 1.23 (m, 6 H), 1.10 (d, J=6.0 Hz, 6 H); TLC conditions: Uniplate silica gel, 250 microns; Mobile phase=acetone-hexanes (1:4); R$_f$=0.17.

Step f:

To a solution of diethyl 3-[3,5-dimethyl-4-(3'-iso-propyl-4'-methoxyphenoxy)phenyl]propylphosphonate (0.10 g, 0.22 mmol) in CH$_2$Cl$_2$ (5.0 mL) at −30° C. was added bromotrimethylsilane (0.30 mL, 2.23 mmol). The reaction mixture was stirred at room temperature 16 h and the solvent was removed under reduced pressure. The residue was dissolved in dichloromethane (3.0 mL) and cooled to −78° C. To it was added BBr$_3$ (0.66 mL, 0.66 mmol, 1.0 M solution in CH$_2$Cl$_2$). The reaction mixture was stirred at −78° C. for 3 h, allowed to warm to room temperature and stirred for 16 h. The reaction mixture was poured into ice, concentrated and extracted with ethyl acetate (10 mL). The organic solution was washed with 0.5 M HCl (20 mL×2) and water (20 mL×2), dried over MgSO$_4$, filtered and concentrated under reduced pressure to afford 3-[3,5-dimethyl 4-(4'-hydroxy-3'-iso-propylphenoxy)phenyl]propylphosphonic acid as a white solid (0.50 g, 60% over two steps): mp: 60-63° C.; LC-MS m/z=379 [C$_{20}$H$_{27}$O$_5$P+H]$^+$; $^1$H NMR (200 MHz, DMSO-d$_6$): δ 8.80 (s, 1 H), 6.85 (s, 2 H), 6.56 (m, 2 H), 6.10 (m, 1H), 3.05 (m, 1 H), 2.40 (m, 2 H), 1.90 (s, 6 H), 1.49 (m, 2 H), 1.33 (s, 2 H), 1.03 (d, J=6.0 Hz, 6 H); Anal. Calcd for (C$_{20}$H$_{27}$O$_5$P+1.1H$_2$O): C, 60.32; H, 7.39. Found: C, 60.19H, 7.32.

Example 30

Compound 30: 2-[3,5-dimethyl-4-(3'-iso-propyl-4'-methoxyphenoxy)-phenyl]ethylphosphonic acid Step a:

A solution of diethyl trans-2-[3,5-dimethyl-4-(3'-iso-propyl-4'-methoxyphenoxy)phenyl]vinylphosphonate (1.77 g, 4.10 mmol, Example 28, step b) and Pd/C (177 mg) in EtOH/HOAc (10 mL, 9:1)) was stirred under a H$_2$ atmosphere for 5 h. The reaction mixture was filtrated through a plug of Celite and the solvent was removed under reduced pressure. The residue was purified by column chromatography on silica gel, eluting with ethyl acetate-hexanes (1:1) to afford diethyl 2-[3,5-dimethyl-4-(3'-iso-propyl-4'-methoxyphenoxy)phenyl]ethylphosphonate (1.29 g, 74%): $^1$H NMR (300 MHz, CDCl$_3$): δ 6.94 (s, 2 H), 6.81 (d, J=3.0 Hz, 1 H), 6.68 (d, J=8.7 Hz, 1H), 6.36 (m, 1 H), 4.15 (m, 4 H), 3.30 (m, 1 H), 2.88 (m, 2 H), 2.13 (s, 6 H), 2.05 (m, 2 H), 1.37 (m, 6 H), 1.21 (d, J=6.9 Hz, 6 H). TLC conditions: Uniplate silica gel, 250 microns; Mobile phase=ethyl acetate-hexanes (1:9); R$_f$=0.35.

Step b:

Deprotection of diethyl 2-[3,5-dimethyl-4-(3'-iso-propyl-4'-methoxyphenoxy)phenyl]ethylphosphonate with bromotrimethylsilane afforded 2-[3,5-dimethyl-4-(3'-iso-propyl-4'-methoxyphenoxy)phenyl]-ethylphosphonic acid: $^1$H NMR (300 MHz, DMSO-d$_6$): δ 6.98 (s, 2 H), 6.78 (d, J=9.3 Hz, 1 H), 6.72 (d, J=2.7 Hz, 1 H), 6.26 (m, 1 H), 3.70 (s, 3 H), 3.16 (m, 1 H), 2.71 (m, 2 H), 2.00 (s, 6 H), 1.81 (m, 2 H), 1.10 (d, J=6.6 Hz, 6 H). LC-MS m/z=379 [C$_{20}$H$_{27}$O$_5$P+H]$^+$; Anal. Calcd for (C$_{20}$H$_{27}$O$_5$P+0.7H$_2$O): C, 61.43; H, 7.32. Found: C, 61.59; H, 7.60.

Example 31

Compound 31: [3,5-dimethyl-4-(4'-hydroxy-3'-iso-propylphenoxy)phenoxy]-methylphosphonic acid To a solution of 3,5-dimethyl-4-(3'-iso-propyl-4'-methoxyphenoxy)benzaldehyde (0.18 g, 0.60 mmol, Example 28, step a) in dichloromethane (6.0 mL) at 0° C. was added m-chloroperoxybenzoic acid (0.22 g, 0.905 mmol). The reaction mixture was stirred at room temperature for 16 h. The solvent was removed under reduced pressure and the residue was diluted with ethyl acetate. The organic solution was washed with saturated sodium bicarbonate (2×10 mL) and water. The solvent was removed under reduced pressure and the residue was dissolved in methanol (5 mL). To the solution was added 1 N NaOH (1.81 mL, 1.81 mmol) and the reaction mixture was stirred at room temperature for 4 h. The reaction mixture was diluted with ethyl acetate, acidified with 2 N HCl and washed with brine. The solvent was evaporated and the residue was purified by preparatory TLC eluting with acetone-hexanes (1:4) to afford 3,5-dimethyl-4-(3'-iso-propyl-4'-methoxyphenoxy)phenol as an oil (0.08 g, 47%): $^1$H NMR (200 MHz, DMSO-d$_6$): δ 9.17 (s, 1 H), 6.82 (m, 1 H), 6.70 (m, 1 H), 6.51 (s, 2 H), 6.32 (m, 1 H), 3.71 (s, 3 H), 3.18 (m, 1 H), 1.95 (s, 6 H), 1.12 (d, J=6.0 Hz, 6 H); TLC conditions: Uniplate silica gel, 250 microns; Mobile phase=hexanes-acetone (4:1); R$_f$=0.44.

Intermediate 3,5-dimethyl-4-(3'-iso-propyl-4'-methoxyphenoxy)-phenol was converted to [3,5-dimethyl-4-(3'-iso-propyl-4'-methoxyphenoxy)phenoxy]methylphosphonic acid following the procedure described for the synthesis of compound 8: mp 60-64° C.; LC-MS m/z=367 [C$_{18}$H$_{23}$O$_6$P+H]$^+$; $^1$H NMR (200 MHz, DMSO-d$_6$): δ 8.88 (s, 1 H), 6.76 (s, 2H), 6.60 (m, 2 H), 6.17 (m, 1 H), 4.04 (d, J=15.0 Hz, 2 H), 3.13 (m, 1 H), 2.01 (s, 6 H), 1.10 (d, J=6.0 Hz, 6 H); Anal. Calcd for (C$_{18}$H$_{23}$O$_6$P+0.7H$_2$O): C, 57.05; H, 6.49. Found: C, 57.10H, 6.63.

Example 32

Compound 32: 3-[3,5-dimethyl-4-(4'-hydroxy-3'-isopropylphenoxy)]-phenyl-2-oxopropylphosphonic acid Step a:

To a stirred solution of 3,5-dimethyl-4-(3'-iso-propyl-4'-methoxyphenoxy) benzaldehyde (4.1 g, 15.2 mmol, Example 28, step a) in methanol (35 mL) at 0° C. was slowly added NaBH$_4$ (1.16 g, 30.5 mmol). The reaction mixture was stirred at room temperature for 5 h and the solvent was removed under reduced pressure. The residue was dissolved in ethyl acetate (150 mL), washed with brine, dried over Na$_2$SO$_4$ and concentrated under reduced pressure. The crude product was purified by column chromatography on silica gel, eluting with ethyl acetate-hexanes (2:4) to afford 3,5-dimethyl-4-(3'-iso-propyl-4'-methoxyphenoxy)benzyl alcohol as a white solid (3.4 g, 83%, m.p.: 78-80° C.): $^1$H NMR (300 MHz, CDCl$_3$): δ 7.12 (s, 2 H), 6.80 (d, J=3.3 Hz, 2 H), 6.67 (d, J=9.0 Hz, 1 H), 6.36 (dd, J=3.0, 8.7 Hz, 1 H), 4.68 (s, 2 H), 3.80 (s, 3 H), 3.35-3.25 (m, 1 H), 2.16 (s, 6 H), 1.19 (d, J=7.2 Hz, 6H); TLC conditions: Uniplate silica gel, 250 microns; mobile phase=ethyl acetate-hexanes (2:4); R$_f$=0.5.

Step b:

To a stirred solution of 3,5-dimethyl-4-(3'-iso-propyl-4'-methoxyphenoxy)benzyl alcohol (1.0 g, 3.4 mmol) in DME (10 mL) at 0° C. was added phosphorous tribromide (1.8 g, 0.5 mL, 6.8 mmol). The reaction mixture was stirred at 0° C. for 5 h, quenched with methanol (2 mL) and stirred for 30 min. The reaction mixture was poured into ice water and extracted with ether (100 mL). The organic layer was washed with brine, dried over Na$_2$SO$_4$, filtered and concentrated under reduced pressure to afford crude 3,5-dimethyl-4-(3'-iso-propyl-4'-methoxyphenoxy)benzyl bromide as an oil (1.02 g, 82%): $^1$H NMR (300 MHz, CDCl$_3$): δ 7.15 (s, 2 H), 6.81 (d, J=3.0 Hz, 1 H), 6.67 (d, J=9.0 Hz, 1 H), 6.34 (dd, J=3.0, 8.7 Hz, 1 H), 4.51 (s, 2 H), 3.80 (s, 3H), 3.40-3.25 (m, 1 H), 2.15 (s, 6 H), 1.20 (d, J=7.2 Hz, 6 H); TLC conditions: Uniplate silica gel, 250 microns; mobile phase=ethyl acetate-hexanes (2:4); R$_f$=0.7.

Step c:

To a stirred solution of sodium cyanide (0.23 g, 4.69 mmol) in H$_2$O (2 mL) at room temperature was added a solution of 3,5-dimethyl-4-(3'-iso-propyl-4'-methoxyphenoxy)benzyl bromide (0.85 g, 2.34 mmol) in ethanol (5 mL). The reaction mixture was heated at 80° C. for 2 h, cooled to room temperature, and poured into ice water (100 mL). The mixture was stirred for 1 h and extracted with ethyl acetate (2×100 mL). The combined organic layers were washed with water and brine, dried over Na$_2$SO$_4$, filtered and concentrated under reduced pressure. The crude product was purified by column chromatography on silica gel, eluting with ethyl acetate-hexanes (1:4) to afford 3,5-dimethyl-4-(3'-iso-propyl-4'-methoxyphenoxy)phenyl-acetonitrile as a brown solid (0.64 g, 85%, m.p.: 56-58° C.): $^1$H NMR (300 MHz, CDCl$_3$): δ 7.07 (s, 2 H), 6.78 (d, J=3.3 Hz, 1 H), 6.68 (d, J=9.0 Hz, 1H), 6.35 (dd, J=3.0, 8.7 Hz, 1 H), 3.80 (s, 3 H), 3.73 (s, 2 H), 3.40-3.25 (m, 1 H), 2.16 (s, 6 H), 1.19 (d, J=7.2 Hz, 6 H); TLC conditions: Uniplate silica gel, 250 microns; mobile phase=ethyl acetate-hexanes (1:4); R$_f$=0.5.

Step d:

To a stirred solution of 3,5-dimethyl-4-(3'-iso-propyl-4'-methoxyphenoxy)phenylacetonitrile (0.75 g, 2.42 mmol) in acetic acid (7 mL) was added a 50% solution of H$_2$SO$_4$ (14 mL). The reaction mixture was heated at 105° C., for 3 h, cooled to room temperature and poured into ice water (100 mL). The mixture was stirred for 1 h and extracted with ethyl acetate (3×50 mL). The combined organic layers were washed with water and brine, dried over Na$_2$SO$_4$, filtered and concentrated under reduced pressure to afford 3,5-dimethyl-4-(3'-iso-propyl-4'-methoxyphenoxy)phenylacetic acid as a brownish solid (0.62 g, 85%, m.p.: 118-120° C.): $^1$H NMR (300 MHz, CDCl$_3$): δ 7.11 (s, 2 H), 6.82 (d, J=2.7 Hz, 1 H), 6.80 (d, J=8.7 Hz, 1 H), 6.37 (dd, J=3.3, 8.7 Hz, 1 H), 3.80 (s, 3 H), 3.61 (s, 2 H), 3.38-3.25 (m, 1 H), 2.11 (s, 6 H), 1.17 (d, J=7.2 Hz, 6 H); TLC conditions: Uniplate silica gel, 250 microns; mobile phase=ethyl acetate-hexanes (1:1); R$_f$=0.2.

Step e:

To a stirred cold solution of methanol (15 mL) and acetyl chloride (3 mL, 86.0 mmol) at 0° C. was added dropwise a solution of 3,5-dimethyl-4-(3'-iso-propyl-4'-methoxyphenoxy)phenylacetic acid (0.7 g, 4.3 mmol) in methanol (5 mL). The reaction mixture was heated under reflux for 5 h and cooled to room temperature. The solvent was removed under reduced pressure and the residue was dissolved in ethyl acetate (100 mL). The organic solution was washed with water and brine, dried over Na$_2$SO$_4$, filtered and concentrated under reduced pressure. The crude product was triturated with hexane, filtered and dried under reduced pressure to afford methyl 3,5-dimethyl-4-(3'-iso-propyl-4'-methoxyphenoxy)phenylacetate as a yellow solid (0.69 g, 95%): $^1$H NMR (300 MHz, CDCl$_3$): δ 7.02 (s, 2 H), 6.82 (d, J=2.7 Hz, 1 H), 6.66 (d, J=8.7 Hz, 1 H), 6.38 (dd, J=3.3, 8.7 Hz, 1 H), 3.79 (s, 3 H), 3.75 (s, 3 H), 3.60 (s, 2 H), 3.28-3.25 (m, 1 H), 2.14 (s, 6 H), 1.20 (d, J=7.2 Hz, 6 H); TLC conditions: Uniplate silica gel, 250 microns; mobile phase=ethyl acetate-hexanes (1:1); R$_f$=0.6.

Step f:

3-[3,5-dimethyl-4-(4'-hydroxy-3'-iso-propylphenoxy) phenyl]-2-oxopropylphosphonic acid was prepared from methyl-3,5-dimethyl-4-(3'-iso-propyl-4'-methoxyphenoxy) phenylacetate following the same procedure as described in compound 21: mp: 80-82° C.; $^1$H NMR (300 MHz, CDCl$_3$): δ 6.85 (s, 2 H), 6.51 (d, J=2.1 Hz, 1 H), 6.48 (d, J=8.4 Hz, 1 H), 6.14 (dd, J=3.0, 9.0 Hz, 1 H), 4.80 (s, 2 H), 3.80 (s, 2 H), 3.20-3.10 (m, 1 H), 2.99 (d, J=22.5 Hz, 1 H), 1.97 (s, 6 H), 1.03 (d, J=6.9 Hz, 6 H); LC-MS m/z=393 [C$_{20}$H$_{25}$O$_6$P+H]$^+$; HPLC conditions: ODSAQ AQ-303-5 column; mobile phase=CH$_3$OH:5% TFA(7:3) flow rate=1.0 mL/min; detection=UV @ 254 nm retention time in min: 11.19; Anal Calcd for (C$_{20}$H$_{25}$O$_6$P+0.2 CH$_2$Cl$_2$): C, 58.82; H, 6.22. Found: C, 58.75; H, 6.30.

Example 33

Compound 33: [3,5-dimethyl-4-(4'-Hydroxy-3'-iso-propyl-phenyl)-methoxymethyl]phenoxy]methylphosphonic acid Step a:

To a solution of (2,6-dimethyl-4-triisopropylsilanyloxyphenyl)-(3-iso-propyl-4-methoxymethoxyphenyl)methanol (1.60 g, 3.29 mmol, Chiellini et al., *Bioorg. Med. Chem. Lett.* 10:2607 (2000)) in THF (30.0 mL) at 0° C. was added TBAF (4.93 mL, 4.93 mmol, 1.0 M solution in THF). The reaction mixture was stirred at room temperature for 60 min, diluted with diethyl ether (10.0 mL) and washed with water (20 mL×2). The organic layer was dried over $MgSO_4$ and concentrated under reduced pressure. The crude product was purified by column chromatography on silica gel, eluting with ethyl acetate-hexanes (1:4) to afford 3,5-dimethyl-4-[(3'-iso-propyl-4'-methoxymethoxyphenyl)-hydroxymethyl]phenol as a white solid (1.00 g, 92%): $^1$H NMR (300 MHz, DMSO-$d_6$): δ 9.05 (s, 1 H), 7.17 (m, 1 H), 6.90 (m, 1 H), 6.77 (m, 1 H), 6.37 (s, 2 H), 5.97 (d, J=6.0 Hz, 1 H), 5.51 (d, J=6.0 Hz, 1 H) 5.15 (s, 2 H), 3.36 (s, 3 H), 3.23 (m, 1 H), 2.10 (s, 6 H), 1.16 (m, 6 H); TLC conditions: Uniplate silica gel, 250 microns; Mobile phase=hexanes-ethyl acetate (4:1); $R_f$=0.17.

Step b:

To a mixture of 3,5-dimethyl-4-[(3'-iso-propyl-4'-methoxymethoxyphenyl)-hydroxymethyl]phenol (0.380 g, 1.15 mmol) in DMF (10.0 mL) at 0° C. was added $Cs_2CO_3$ (1.87 g, 5.75 mmol). After 5 min, trifluoromethanesulfonic acid diethoxyphosphorylmethyl ester (0.24 g, 1.15 mmol) was added. The reaction mixture was stirred at room temperature for 16 h, quenched with 1 N HCl, diluted with ethyl acetate and extracted with water (10 mL×4). The organic layer was dried over $MgSO_4$ and concentrated under reduced pressure. The crude product was purified by column chromatography on silica gel, eluting with acetone-hexanes (1:4) to afford diethyl [3,5-dimethyl-4-[(3'-iso-propyl-4'-methoxymethoxyphenyl)-hydroxymethyl]phenoxy]methylphosphonate as an oil (0.41 g, 74%): $^1$H NMR (300 MHz, DMSO-$d_6$): δ 7.20 (m, 1 H), 6.92 (m, 1 H), 6.78 (m, 1 H), 6.67 (s, 2 H), 6.03 (d, J=3.0 Hz, 1 H), 5.64 (d, J=3.0 Hz, 1 H), 5.18 (s, 2 H), 4.38 (d, J=9.0 Hz, 2 H), 4.11 (m, 4 H), 3.38 (s, 3 H), 3.25 (m, 1 H), 2.19 (s, 6 H), 1.24 (m, 6 H), 1.16 (m, 6 H); TLC conditions: Uniplate silica gel, 250 microns; Mobile phase=hexanes-acetone (6:4); $R_f$=0.35.

Step c:

To a solution of diethyl [3,5-dimethyl-4-[(3'-iso-propyl-4'-methoxymethoxyphenyl)-hydroxymethyl]phenoxy]methylphosphonate (0.200 g, 0.42 mmol) in MeOH (6.0 mL) at 0° C. was added 2 M HCl (2.1 mL, 4.20 mmol). The reaction mixture was stirred at 0° C. for 3 h and at room temperature for 16 h. The reaction mixture was diluted with ethyl acetate (10.0 mL) and washed with water (20 mL×2). The organic layer was dried over $MgSO_4$ and concentrated under reduced pressure. The crude product was purified by column chromatography on silica gel, eluting with acetone-hexanes (1:1) to afford diethyl [3,5-dimethyl-4-[(4'-hydroxy-3'-iso-propylphenyl)methoxymethyl]phenoxy]methylphosphonate as an oil (0.125 g, 69%): $^1$H NMR (300 MHz, DMSO-$d_6$): δ 9.16 (s, 1 H), 7.03 (s, 1 H), 6.71 (s, 2 H), 6.59 (m, 2 H), 5.63 (s, 2 H), 4.41 (d, J=15.0 Hz, 2 H), 4.11 (m, 4 H) 3.20 (s, 3 H), 2.17 (s, 6 H), 1.21 (m, 6 H), 1.11 (m, 6 H); TLC conditions: Uniplate silica gel, 250 microns; Mobile phase=hexanes-acetone (1:1); $R_f$=0.50.

Step d:

To a solution of diethyl [3,5-dimethyl-4-[(4'-hydroxy-3'-iso-propylphenyl)methoxymethyl]phenoxy]methylphosphonate (0.065 g, 0.15 mmol) and 1,1,1,3,3,3-hexamethyldisilazane (0.38 mL, 1.80 mmol) in $CH_2Cl_2$ (3.0 mL) at −30° C. was added bromotrimethylsilane (0.12 mL, 0.90 mmol). The reaction mixture was stirred at room temperature 16 h and the solvent was removed under reduced pressure. The residue was treated with acetonitrile-water (4:1, 5.0 mL×3) and sonicated. The solvent was removed under reduced pressure and the residue was dissolved in 1 M NaOH (5 mL). The aqueous solution was extracted with ethyl acetate (5 mL×2) and acidified with 2 M HCl. The mixture was diluted with ethyl acetate and washed several times with water. The organic layer was dried over $MgSO_4$ and concentrated under reduced pressure to afford the title compound as a red powder (0.035 g, 62%): $^1$H NMR (300 MHz, $D_2O$): δ 7.03 (s, 1 H), 6.78-6.67 (m, 4 H), 6.14 (s, 1 H), 4.02 (d, J=10.5 Hz, 2 H), 3.21 (s, 3 H), 2.09 (s, 6 H), 1.01 (m, 6 H); HPLC conditions: Column=3 Chromolith SpeedRODs RP-18e, 100×4.6 mm; Mobile phase=Solvent A (Acetonitrile)=HPLC grade acetonitrile; Solvent B (buffer)=20 mM ammonium phosphate buffer (pH 6.1, 0.018 M $NH_4H_2PO_4$/0.002 M $(NH_4)_2HPO_4$) with 5% acetonitrile. Flow rate=4 mL/min; UV@255 μm. Retention time in minutes. (rt=5.70, 93% purity).

Example 34

Compound 34: [3,5-dimethyl-4-(4'-hydroxy-3'-iodobenzyl)phenoxy]-methylphosphonic acid Step a To a mixture of diethyl [3,5-dimethyl-4-(4'-methoxymethoxy-benzyl)phenoxy]methylphosphonate (0.26 g, 0.61 mmol, prepared from commercially available 4-bromophenol according to the procedure described in compound 7) in methanol (3.0 mL) at 0° C. was added 2 N HCl (1.0 mL). The reaction mixture was stirred at room temperature for 24 h, quenched with water (10.0 mL) and extracted with ethyl acetate (10.0 mL). The organic layer was dried over $MgSO_4$, filtered and concentrated under reduced pressure to afford diethyl [3,5-dimethyl-4-(4'-hydroxybenzyl)phenoxy]methyl-phosphonate (0.22 g, 95%) as colorless oil: $^1$H NMR (300 MHz, DMSO-$d_6$): δ 9.11 (s, 1 H), 6.60-6.80 (m, 6 H), 4.35 (d, J=14.7 Hz, 2 H), 4.11 (m, 4 H), 3.80 (s, 2 H), 2.15 (s, 6 H), 1.25 (t, J=10.5 Hz, 2 H); TLC conditions: Uniplate silica gel, 250 microns; Mobile phase=acetone-hexanes (1:1); $R_f$=0.40.

[3,5-Dimethyl-4-(4'-hydroxy-3'-iodobenzyl)phenoxy]methyl-phosphonic acid was prepared from diethyl [3,5-dimethyl-4-(4'-hydroxybenzyl)phenoxy]methylphosphonate according to the procedure described in compound 2 steps f and g: $^1$H NMR (300 MHz, $CD_3OD$): δ 7.27 (d, J=2.4 Hz, 1 H), 6.83 (dd, J=8.1, 2.1 Hz, 1 H), 6.76 (s, 2 H), 6.72 (d, J=8.1 Hz, 1 H), 4.23 (d, J=10.2 Hz, 2 H), 3.91 (s, 2 H), 2.23 (s, 6 H); LC-MS m/z=449 $[C_{16}H_{18}IO_5P+H]^+$; Anal Calcd for $(C_{16}H_{18}IO_5P+0.7H_2O)$: C, 41.70; H, 4.24. Found: C, 41.73; H, 4.56.

Example 35

Compound 35: [3,5-dimethyl-4-(3'-carboxyl-4'-hydroxy-benzyl)phenoxy]-methylphosphonic acid Step a:

To the suspension of NaH (3.25 g, 0.135 mol) in DMF (150 mL) was added 4-hydroxy-benzaldehyde (15.0 g, 0.123 mol) in DMF (10 mL) at 0° C., 5 min. later the reaction mixture became a cake. The heterogeneous mixture was stirred at 0° C. for 30 min. MOMCl (9.96 g, 0.123 mol) was added slowly and the reaction mixture was allowed to warm up to r.t. After stirring at r.t. for 16 h, the volatiles were removed under vacuum. The residue was partitioned between ethyl acetate and water and the water layer was further extracted with ethyl acetate. The combined ethyl acetate extracts were dried over $MgSO_4$, filtered and concentrated. The residue was purified by column chromatography on silica gel (ethyl acetate-hexanes; 1:4) to afford 4-methoxymethoxy-benzaldehyde (19.0 g, 93%): $^1$H NMR (300 MHz, $CDCl_3$): δ 9.94 (s, 1 H), 7.88 (m, 2H), 7.18 (m, 2H), 5.29 (s, 2H), 3.53 (s, 2H); TLC conditions: Uniplate silica gel, 250 microns; Mobile phase=ethyl acetate-hexanes (1:4); $R_f$=0.86.

Step b:

To a solution of (4-bromo-3,5-dimethyl-phenoxy)triisopropylsilane (8.0 g, 23.30 mmol) in THF (50 mL) was added a solution of n-butyllithium (2.5 M in THF, 90 mL) at −78° C. The heterogeneous mixture was stirred at −78° C. for 1 h A solution of 4-methoxymethoxy-benzaldehyde (3.09 g, 18.58 mmol) in THF (5 mL) was added and the mixture was stirred at −78° C. for 1 h then warmed up to r.t. The reaction was then diluted with ethyl acetate and water, the layers were separated and the aqueous layer was extracted with ethyl acetate. The combined organic extracts were dried ($MgSO_4$), filtered and concentrated to afford crude (2,6-dimethyl-4-triisopropylsilanyloxyphenyl)-(4-methoxymethoxyphenyl)methanol. Carried on to the next step without further purification.

Step c:

A degassed solution of crude (2,6-dimethyl-4-triisopropyl-silanyloxyphenyl)-(4-methoxymethoxyphenyl)methanol (12.0 g, 26.84 mmol) and Pd/C (1.2 g) in EtOAc/HOAc (19/1) was stirred under an atmosphere of hydrogen (1 atm) at r.t. After 5 h, the catalyst was filtered through a pad of Celite, rinsed with ethyl acetate and the combined filtrates concentrated under reduced pressure. The residue was purified by column chromatography on silica gel (ethyl acetate-hexanes; 1:9) to afford 4-(2,6-dimethyl-4-triisopropylsilanyloxybenzyl)-methoxymethoxybenzene (4.0 g, 41.5% for two steps): $^1$H NMR (300 MHz, $CDCl_3$): δ 6.93 (s, 4 H), 6.63 (s, 2H), 5.16 (s, 2H), 3.94 (s, 2H), 3.50 (m, 3H), 1.58 (s, 6H), 1.29 (m, 3H), 1.13 (m, 18H). TLC conditions: Uniplate silica gel, 250 microns; Mobile phase=ethyl acetate-hexanes (1:19); $R_f$=0.80.

Step d:

To a solution of 4-(2,6-dimethyl-4-triisopropylsilanyloxybenzyl)-methoxymethoxybenzene (2.0 g, 4.66 mmol) in ether was added TMEDA (1.05 mL, 6.99 mmol), followed by nBuLi (2.5 M in THF, 2.8 mL) at −20° C. The reaction mixture was warmed up to 0° C. and stirred for 1 h DMF (0.72 mL, 9.32 mmol) was then added and after stirring at 0° C. for 2 h, the reaction mixture was quenched with a saturated solution of $NH_4Cl$ and diluted with EtOAc. The water layer was extracted with EtOAc and the combined organic extracts were dried ($MgSO_4$), filtered and concentrated to give the crude product 5-(2,6-dimethyl-4-triisopropylsilanyloxybenzyl)-2-methoxymethoxy-benzaldehyde (2.1 g, 98%): $^1$H NMR (300 MHz, d6-DMSO): δ 10.33 (s, 1H), 7.24 (m, 3H), 6.58 (s, 2H), 5.31 (s, 2H), 3.91 (s, 2H), 3.33 (s, 6H), 1.23 (m, 3H), 1.06 (m, 18H). TLC conditions: Uniplate silica gel, 250 microns; Mobile phase=ethyl acetate-hexanes (1:9); $R_f$=0.55.

Step e:

To a solution of 5-(2,6-dimethyl-4-triisopropylsilanyloxybenzyl)-2-methoxymethoxy-benzaldehyde (1.4 g, 3.07 mmol) in THF (15 mL) was added TBAF (1 M, 3.68 mL) at 0° C. After stirring at r.t. for 2 h, the reaction mixture was diluted with EtOAc and water. The water layer was extracted with EtOAc and the combined organic extracts were dried ($MgSO_4$), filtered and concentrated. The residue was purified by column chromatography on silica gel (ethyl acetate-hexanes; 1:9) to afford 5-(4-hydroxy-2,6-dimethylbenzyl)-2-methoxymethoxybenzaldehyde (590 mg, 64% for two steps): $^1$H NMR (200 MHz, $CDCl_3$): δ 10.45 (s, 1H), 7.54 (s, 1H), 7.27 (m, 1H), 7.09 (m, 1H), 6.56(s, 2H), 5.25 (s, 2H), 3.92 (s, 2H), 3.50 (s, 3H), 2.16 (s, 6H). TLC conditions: Uniplate silica gel, 250 microns; Mobile phase=ethyl acetate-hexanes (1:9); $R_f$=0.68.

Step f:

To a solution of 5-(4-hydroxy-2,6-dimethylbenzyl)-2-methoxymethoxybenzaldehyde (590 mg, 1.97 mmol) in DMF (10 mL) was added $Cs_2CO_3$ (3.2 g, 9.83 mmol), followed by trifluoromethanesulfonic acid diethoxy-phosphorylmethyl ester (649 mg, 2.16 mmol) at r.t. After stirring at r.t. for 16 h, the reaction mixture was concentrated under reduced pressure and the residue was partitioned between EtOAc and water. The water layer was extracted with EtOAc and the combined organic extracts were dried ($MgSO_4$), filtered and concentrated. The residue was purified by column chromatography on silica gel (ethyl acetate-hexanes; 1:1) to afford diethyl [4-(3'-formyl-4'-methoxymethoxybenzyl)-3,5-dimethylphenoxy]methyl-phosphonate (650 mg, 72%): $^1$H NMR (300 MHz, $CDCl_3$): δ 10.42 (s, 1H), 7.51 (s, 1H), 7.09 (m, 2H), 6.67 (s, 2H), 5.25 (s, 2H), 4.26 (m, 6H), 3.94 (s, 2H), 3.50 (s, 3H), 2.19 (s, 6H), 1.37 (m, 6H). TLC conditions: Uniplate silica gel, 250 microns; Mobile phase=ethyl acetate-hexanes (1:1); $R_f$=0.55.

Step g:

To a solution of [4-(3'-formyl-4'-methoxymethoxybenzyl)-3,5-dimethylphenoxy]methylphosphonate (650 mg, 1.44 mmol) in THF (1.0 mL) at r.t. was added a solution of $NaH_2PO_4$ (52 mg, 0.43 mmol) in water (0.2 mL), 30% $H_2O_2$ (30%, 0.16 mL) followed by a solution of sodium chlorite (245 mg, 2.17 mmol) in water (1.0 mL). After stirring at r.t. for 30 min., the reaction mixture was diluted with EtOAc and water. The water layer was extracted with EtOAc and the combined organic extracts were washed with water, brine, dried ($MgSO_4$), filtered and concentrated to afford diethyl [3,5-dimethyl-4-(3'-carboxyl-4'-hydroxybenzyl)phenoxy] methylphosphonate as yellow solid (585 mg, 86.9%): $^1$H NMR (300 MHz, $CDCl_3$): δ 7.91 (m, 1H), 7.11 (m, 2H), 6.68 (s, 2H), 4.25 (m, 6H), 3.96 (s, 2H), 3.54 (s, 3H), 2.19 (s, 6H), 1.37 (m, 6H). TLC conditions: Uniplate silica gel, 250 microns; Mobile phase=MeOH-ethyl acetate (1:9); $R_f$=0.2.

Step h:

To the solution of diethyl [3,5-dimethyl-4-(3'-carboxyl-4'-hydroxy-benzyl)phenoxy]methylphosphonate (100 mg, 0.21 mmol) in $CH_2Cl_2$ (10 mL) was added TMSBr (0.28 mL, 2.10 mmol) at r.t. After stirring at r.t. for 16 h, the reaction mixture was concentrated and the residue was suspended in MeOH. After stirring for 2 h, the volatiles were removed and the residue was azeotropped with $CH_2Cl_2$ twice to provide [3,5-dimethyl-4-(3'-carboxyl-4'-hydroxybenzyl)phenoxy]methylphosphonic acid as a white solid (48 mg, 61.5%): mp. >200° C.; $^1$H NMR (200 MHz, DMSO-$d_6$): δ 7.38 (d, J=2.1 Hz, 1H), 7.17 (m, 1H), 6.87 (d, J=8.4 Hz, 1H), 6.74 (s, 2H), 4.06 (d, J=10.2 Hz, 2H), 3.89 (s, 2H), 2.18 (s, 6H). mp>200, LC-MS m/z=367 $[C_{17}H_{19}O_7P+H]$.$^+$; Anal. Calcd. for ($C_{17}H_{19}O_7P+0.4H_2O$): C, 54.67; H, 5.34. Found: C, 54.57; H, 5.60.

Example 36

Compound 36: [3,5-dimethyl-4-(4'-hydroxy-3'-iso-propylcarbamoylbenzyl)-phenoxy]methylphosphonic acid Step a:

To a solution of diethyl [3,5-dimethyl-4-(3'-carboxyl-4'-hydroxy-benzyl)phenoxy]methylphosphonate (compound 35, step f; 122 mg, 0.262 mmol) in DMF (5.0 mL) was added EDCI (60 mg, 0.314 mmol), HOAT (53 mg, 0.393 mmol), diisopropylethylamine (0.23 mL, 1.31 mmol) and isopropylamine (0.03 mL, 0.288 mmol). After stirring at r.t. for 16 h, the reaction mixture was concentrated under reduced pressure and the residue was partitioned between EtOAc and a saturated solution of NaHCO$_3$. The aqueous layer was extracted with EtOAc and the combined organic extracts were washed with water, brine, dried (MgSO$_4$), filtered and concentrated. The residue was purified by column chromatography on silica gel (ethyl acetate-hexanes; 1:1) to afford diethyl [3,5-dimethyl-4-(4'-hydroxy-3'-iso-propylcarbamoylbenzyl)-phenoxy]methylphosphonic acid as yellowish liquid (40 mg, 30%). TLC conditions: Uniplate silica gel, 250 microns; Mobile phase=ethyl acetate-hexanes (1:1); R$_f$=0.45.

Step b:

The title compound was prepared by the procedure described for the synthesis of compound 35, step f as an off-white solid (30 mg, 93.7%); mp.: 90° C., dec; $^1$H NMR (300 MHz, DMSO-d$_6$): δ 8.52 (d, J=7.5 Hz, 1H), 7.77 (d, J=1.5 Hz, 1H), 6.73(m, 4H), 4.14 (m, 1H), 4.06 (d, J=10.2 Hz, 2H), 3.88 (s, 2H), 2.18 (s, 6H), 1.21 (d, J=6.9 Hz, 6H). mp: decomposed at 90, LC-MS m/z=408 [C$_{20}$H$_{26}$NO$_6$P+H]$^+$; Anal. Calcd for (C$_{20}$H$_{26}$NO$_6$P+0.26 acetone+1.4 HBr): C, 46.58; H, 5.45; N, 2.61. Found: C, 46.49; H, 5.84; N, 2.93.

Example 37

Compound 37: [3,5-dimethyl-4-(4'-hydroxy-3'-phenethylcarbamoylbenzyl)-phenoxy]methylphosphonic acid Step a:

5-(2,6-dimethyl-4-triisopropylsilanyloxybenzyl)-2-methoxymethoxy benzaldehyde (example 35; step e) was transformed into 5-(2,6-dimethyl-4-triisopropylsilanyloxybenzyl)-2-methoxymethoxybenzoic acid by the procedure used for the synthesis of compound 35, step g: yellow solid (360 mg, 86.9%); $^1$H NMR (200 MHz, CDCl$_3$): δ 7.94 (s, 1H), 7.08 (m, 2H), 6.60 (s, 2H), 5.36 (s, 2H), 3.95 (s, 2H), 3.53 (s, 3H), 2.14 (s, 6H), 1.26 (m, 3H), 1.14 (m, 18H); TLC conditions: Uniplate silica gel, 250 microns; Mobile phase=MeOH-ethyl acetate (1:9); R$_f$=0.45.

Step b:

N-phenethyl-5-(2,6-dimethyl-4-triisopropylsilanyloxy-benzyl)-2-methoxymethoxybenzamide was prepared by the procedure used for the synthesis of compound 36, step a: colorless liquid (330 mg, 75%); $^1$H NMR (300 MHz, CDCl$_3$): δ 8.05 (d, J=2.4 Hz, 1H), 7.84 (m, 1H), 7.82 (m, 5H), 6.97 (d, J=9.0 Hz, 1H), 6.64(m, 1H), 6.61 (s, 2H), 5.01 (s, 2H), 3.97 (s, 2H), 3.82 (m, 2H), 3.30 (s, 3H), 2.97 (m, 2H), 2.18 (s, 6H), 1.28 (m, 3H), 1.14 (m, 18H). TLC conditions: Uniplate silica gel, 250 microns; Mobile phase=ethyl acetate-hexanes (1:1); R$_f$=0.55.

Step c:

N-phenethyl-5-(2,6-dimethyl-4-hydoxybenzyl)-2-methoxymethoxy-benzamide was prepared by the procedure used for the synthesis of compound 35, step e: (170 mg, 70%); TLC conditions: Uniplate silica gel, 250 microns; Mobile phase=ethyl acetate-hexanes (1:1); R$_f$=0.45.

Step d:

Diethyl[3,5-dimethyl-4-(4'-methoxymethoxy-3'-phenethylcarbamoyl-benzyl)phenoxy]methylphosphonate was prepared by the procedure used for the synthesis of compound 35, step f: (185 mg, 80%); $^1$H NMR (300 MHz, CDCl$_3$): δ 7.98 (d, J=2.1 Hz, 1H), 7.85 (m, 1H), 7.32 (m, 5H), 7.01 (d, J=5.4 Hz, 1H), 6.91(m, 1H), 6.69 (s, 2H), 4.29 (m, 4H), 3.98 (s, 2H), 3.81 (m, 2H), 3.31 (s, 3H), 2.96 (m, 2H), 2.22 (s, 6H), 1.41 (m, 6H). TLC conditions: Uniplate silica gel, 250 microns; Mobile phase=ethyl acetate-hexanes (1:1); R$_f$=0.52.

Step e:

The title compound was prepared by the procedure used for the synthesis of compound 35, step h: white solid (40 mg, 48.8%): mp.: 100° C., dec; $^1$H NMR (300 MHz, DMSO-d$_6$): δ 8.85 (m, 1H), 7.67 (d, J=2.1 Hz, 1H), 7.32 (m, 5H), 6.86 (m, 2H), 6.78(s, 2H), 4.10 (d, J=10.5 Hz, 2H), 3.91 (s, 2H), 3.57 (m, 2H), 2.92 (m, 2H), 2.24 (s, 6H). mp: decomposed at 100, LC-MS m/z=470 [C$_{25}$H$_{28}$NO$_6$P+H]$^+$; Anal. Calcd for (C$_{25}$H$_{28}$NO$_6$P+0.9 HBr): C, 55.37; H, 5.37; N,

Example 38

Compound 38: [4-(3'-benzyl-4'-hydroxy-benzyl)-3,5-dimethylphenoxy]-methylphosphonic acid Step a:

To a stirring solution of bromobenzene (0.45 g, 2.89 mmol) in THF (20 mL) at −78° C. was added n-BuLi (1.16 mL, 2.5 M in hexanes). The mixture was stirred at −78° C. for 1 h and a solution of 5-(2,6-dimethyl-4-triisopropylsilanyloxybenzyl)-2-methoxymethoxybenzaldehyde (example 35; step e, 1.2 g, 2.63 mmol) was added. The reaction mixture was stirred at −78° C. for 1 h, allowed to warm to room temperature and stirred for 1 h. The reaction mixture was quenched with saturated NH$_4$Cl and diluted with diethyl ether. The organic layer was dried over Na$_2$SO$_4$, filtered and concentrated under reduced pressure to afford [5-(2,6-dimethyl-4-triisopropylsilanyloxy-benzyl)-2-methoxymethoxy-phenyl]-phenyl-methanol as yellow oil (1.4 g, 99.6%): $^1$H NMR (200 MHz, DMSO-d$_6$): δ 7.23 (m, 6 H), 6.85 (d, J=8.8 Hz, 1 H), 6.68 (m, 1 H), 6.56 (s, 2 H), 5.92 (d, J=4.0 Hz, 1 H), 5.62 (d, J=4.0 Hz, 1 H), 5.10 (q, J=4.0 Hz, 2 H), 3.84 (s, 2 H), 3.23 (s, 3 H), 2.11 (s, 6 H), 1.23 (m, 3 H), 1.06 (d, J=6.4 Hz, 18 H); TLC conditions: Uniplate silica gel, 250 microns; Mobile phase=15% ethyl acetate in hexanes; R$_f$=0.50.

Step b:

To a solution of [5-(2,6-dimethyl-4-triisopropylsilanyloxy-benzyl)-2-methoxymethoxy-phenyl]-phenyl-methanol (1.4 g, 2.6 mmol) in ethyl acetate (20 mL) and acetic acid (1.5 mL) was added Pd/C (0.15 g). The mixture was stirred under H$_2$ atmosphere for 16 h. The mixture was filtered through a celite plug. The solvent was removed under reduced pressure. The residue was dissolved in CH$_2$Cl$_2$ (26 mL), ethyl-diisopropyl-amine (0.69 mL, 3.95 mmol) and chloromethyl methyl ether (0.26 mL, 3.42 mmol) were added. The reaction mixture was refluxed for 16 h and quenched with water. The organic layer was dried over Na$_2$SO$_4$, filtered and concentrated under reduced pressure. The crude product was purified by column chromatography on silica gel, eluting with ethyl acetate-hexanes (15:75) to afford [4-(3'-benzyl-4'-methoxymethoxy-benzyl)-3,5-dimethyl-phenoxy]-triisopropylsilane as an oil (0.9 g, 66%): $^1$H NMR (200 MHz, DMSO-d$_6$): δ 7.20 (m, 5 H), 6.90 (d, J=8.4 Hz, 1 H), 6.79 (s, 1 H), 6.70 (m, 1 H), 6.54 (s, 2 H), 5.12 (s, 2 H), 3.83 (s, 2 H), 3.81 (s, 2 H), 3.25 (s, 3 H), 2.09 (s, 6 H), 1.23 (m, 3 H), 1.06 (d, J=6.6 Hz, 18 H); TLC conditions: Uniplate silica gel, 250 microns; Mobile phase=15% ethyl acetate in hexanes; $R_f$=0.66.

Step c:

To a stirring solution of [4-(3'-benzyl-4'-methoxymethoxy-benzyl)-3,5-dimethyl-phenoxy]-triisopropylsilane (0.9 g, 1.73 mmol) in THF (20 mL) at room temperature was added tetrabutylammonium fluoride (2.3 mL, 1.0 M in THF). The reaction mixture was stirred at room temperature for 1 h, diluted with diethyl ether and washed with water (30 mL×2). The solvent was removed under reduced pressure. The crude product was purified by column chromatography on silica gel, eluting with ethyl acetate-hexanes (1:1) to afford 4-(3'-benzyl-4'-methoxymethoxy-benzyl)-3,5-dimethyl-phenol as a light yellow oil (0.6 g, 86%): $^1$H NMR (200 MHz, DMSO-$d_6$): δ 8.98 (s, 1 H), 7.16 (m, 5 H), 6.87 (m, 2 H), 6.70 (m, 1 H), 6.43 (s, 2 H), 5.12 (s, 2 H), 3.85 (s, 2 H), 3.76 (s, 2 H), 3.24 (s, 3 H), 2.06 (s, 6 H); TLC conditions: Uniplate silica gel, 250 microns; Mobile phase=20% ethyl acetate in hexanes; $R_f$=0.34.

Step d:

Diethyl [4-(3'-benzyl-4'-methoxymethoxy-benzyl)-3,5-dimethyl-phenoxy]methylphosphonate was prepared by the procedure used for the synthesis of compound 35, step f as a light yellow oil (0.09 g, 64%): $^1$H NMR (200 MHz, DMSO-$d_6$): δ 7.22 (m, 5 H), 6.87 (m, 2 H), 6.70 (m, 3 H), 5.12 (s, 2 H), 4.35 (d, J=10 Hz, 2 H), 4.11 (m, 4 H), 3.85 (s, 2 H), 3.82 (s, 2 H), 3.24 (s, 3 H), 2.13 (s, 6 H), 1.25 (t, J=7 Hz, 6 H); TLC conditions: Uniplate silica gel, 250 microns; Mobile phase=40% ethyl acetate in hexanes; $R_f$=0.27.

Step e:

The title compound was prepared by the procedure used for the synthesis of compound 35, step h as a white foam (32 mg, 44%): $^1$H NMR (200 MHz, DMSO-$d_6$): δ 9.14 (s, 1 H), 7.21 (m, 5 H), 6.67 (m, 4 H), 6.56 (m, 1 H), 4.02 (d, J=10.2 Hz, 2 H), 3.78 (s, 2 H), 3.75 (s, 2 H), 2.12 (s, 6 H); LC-MS m/z=413 $[C_{23}H_{25}O_5P+H]^+$; Anal Calcd for ($C_{23}H_{25}O_5P$+0.2 Et$_2$O+ 0.6H$_2$O): C, 65.26; H, 6.49. Found: C, 65.07; H, 6.38.

Example 39

Compound 39: [3,5-dimethyl-4-[3'-(4-fluoro-benzoyl)-4'-hydroxy-benzyl]phenoxy]methylphosphonic acid Step a:

[5-(2,6-dimethyl-4-triisopropylsilanyloxy-benzyl)-2-methoxymethoxy-phenyl]-(4-fluoro-phenyl)-methanol was prepared by the procedure used for the synthesis of example 38, step a as an oil (0.68 g, 56%): $^1$H NMR (200 MHz, DMSO-$d_6$): δ 7.26 (m, 3 H), 7.06 (m, 2 H), 6.85 (d, J=8.4 Hz, 1 H), 6.71 (m, 1 H), 6.56 (s, 2 H), 5.91 (d, J=4.0 Hz, 1 H), 5.68 (d, J=4.0 Hz, 1H), 5.10 (q, J=3.4 Hz, 2 H), 3.84 (s, 2 H), 3.22 (s, 3 H), 2.11 (s, 6 H), 1.23 (m, 3 H), 1.06 (d, J=6.2 Hz, 18 H); TLC conditions: Uniplate silica gel, 250 microns; Mobile phase=15% ethyl acetate in hexanes; $R_f$=0.26.

Step b:

To a stirring solution of [5-(2,6-dimethyl-4-triisopropylsilanyloxy-benzyl)-2-methoxymethoxy-phenyl]-(4-fluoro-phenyl)-methanol (0.68 g, 1.2 mmol) in dichloromethane (25 mL) at 0° C. was added Dess-Martin periodinane (3.9 mL, 0.48 M solution in CH$_2$Cl$_2$). The reaction mixture was stirred at room temperature for 4 h, concentrated, diluted with ethyl acetate. To the solution was added a solution of Na$_2$S$_2$O$_3$ pentahydrate (50 mg) in 60 mL saturated NaHCO$_3$. After 15 min, the organic layer was dried over Na$_2$SO$_4$, filtered and concentrated under reduced pressure to afford crude 5-(2,6-dimethyl-4-triisopropylsilanyloxy-benzyl)-(4-fluorobenzoyl)-2-methoxymethoxy-phenyl as an oil (0.68 g, 100%): $^1$H NMR (200 MHz, DMSO-$d_6$): δ 7.72 (m, 2 H), 7.33 (m, 2 H), 7.12 (m, 2 H), 6.86 (s, 1 H), 6.56 (s, 2 H), 5.04 (s, 2 H), 3.92 (s, 2 H), 3.14 (s, 3 H), 2.13 (s, 6 H), 1.21 (m, 3 H), 1.03 (d, J=6.2 Hz, 18 H); TLC conditions: Uniplate silica gel, 250 microns; Mobile phase=20% ethyl acetate in hexanes; $R_f$=0.26.

Step c:

To a stirring solution of 4-(2',6'-dimethyl-4'-triisopropylsilanyloxy-benzyl)-2-(4-fluorobenzoyl)-phenol was prepared by the procedure used for the synthesis of example 35 step c as a white solid (0.42 g, 86%): mp 140-142° C.; $^1$H NMR (300 MHz, DMSO-$d_6$): δ 9.05 (s, 1 H), 7.78 (m, 2 H), 7.36 (m, 2 H), 7.13 (m, 2 H), 6.95 (d, J=1.5 Hz, 1 H), 6.47 (s, 2 H), 5.05 (s, 2 H), 3.90 (s, 2 H), 3.15 (s, 3 H), 2.12 (s, 6 H); TLC conditions: Uniplate silica gel, 250 microns; Mobile phase=20% ethyl acetate in hexanes; $R_f$=0.63.

Step d:

Diethyl[3,5-dimethyl-4-[3'-(4-fluoro-benzoyl)-4'-hydroxy-benzyl]-phenoxy]methylphosphonate was prepared by the procedure used for the synthesis of example 35 step f as a light yellow oil (0.054 g, 19%): $^1$H NMR (300 MHz, DMSO-$d_6$): δ 7.76 (m, 2 H), 7.36 (m, 2 H), 7.13 (m, 2 H), 6.94 (d, J=1.5 Hz, 1 H), 6.77 (s, 2 H), 5.05 (s, 2 H), 4.36 (d, J=9.6 Hz, 2 H), 4.11 (m, 4 H), 3.95 (s, 2 H), 3.15 (s, 3 H), 2.20 (s, 6 H), 1.25 (m, 6 H); TLC conditions: Uniplate silica gel, 250 microns; Mobile phase=67% ethyl acetate in hexanes; $R_f$=0.37.

Step d:

The title compound was prepared by the procedure used for the synthesis of example 35 step h as a yellow foam (22 mg, 50%): $^1$H NMR (200 MHz, DMSO-$d_6$): δ 10.14 (s, 1 H), 7.74 (m, 2 H), 7.31 (m, 2 H), 7.03 (m, 1H), 6.92 (m, 2 H), 6.69 (s, 2 H), 4.02 (d, J=10.6 Hz, 2 H), 3.87 (s, 2 H), 2.16 (s, 6 H); LC-MS m/z=445 $[C_{23}H_{22}FO_6P+H]^+$; Anal Calcd for ($C_{23}H_{22}FO_6P$+0.2 Et$_2$O+0.3 CF$_3$COOH): C, 59.39; H, 4.96. Found: C, 59.62; H, 4.64.

Example 40

Compound 40: [3,5-dimethyl-4-[3'-(4-fluoro-benzyl)-4'-hydroxy-benzyl]-phenoxy]methylphosphonic acid Step a:

To a stirring solution of diethyl [3,5-dimethyl-4-[3'-(4-fluoro-benzyl)-4'-hydroxy-benzyl]phenoxy]methylphosphonic acid (0.13 g, 0.24 mmol) in MeOH (8 mL) at 0° C. was added NaBH$_4$ (90 mg, 2.4 mmol). The reaction mixture was stirred at room temperature for 16 h. The solvent was removed under reduced pressure and the residue was partitioned between ethyl acetate and water. The organic layer was dried over Na$_2$SO$_4$, filtered and concentrated under reduced pressure to afford diethyl [3,5-dimethyl-4-[3'-(4-fluorophenyl-hydroxymethyl)-4'-hydroxy-benzyl]phenoxy]methylphosphonic acid as an oil (0.13 g, 100%). This crude product was dissolved in CH$_2$Cl$_2$ (10 mL) and Et$_3$SiH (0.38 mL, 2.4 mmol) and TFA (0.18 mL, 2.4 mmol) were added. The reaction mixture was stirred at room temperature for 16 h. The solvent was removed under reduced pressure and the residue was partitioned between ethyl acetate and saturated NaHCO$_3$. The organic layer was dried over Na$_2$SO$_4$, filtered and concentrated under reduced pressure. The crude product was purified by column chromatography on silica gel, eluting with ethyl acetate to afford diethyl [3,5-dimethyl-4-[3'-(4-fluoro-benzyl)-4'-hydroxy-benzyl]phenoxy]methylphosphonate as an oil (80 mg, 69%): $^1$H NMR (200 MHz, DMSO-$d_6$): δ 9.18

(s, 1 H), 7.13 (m, 4 H), 6.67 (m, 5 H), 4.33 (d, J=10 Hz, 2 H), 4.11 (m, 4H), 3.76 (s, 4 H), 2.12 (s, 6 H), 1.25 (t, J=7 Hz, 6 H). TLC conditions: Uniplate silica gel, 250 microns; Mobile phase=ethyl acetate; $R_f$=0.5.

Step b:

The title compound was prepared by the procedure used for the synthesis of example 35 step h as a yellow solid (60 mg, 85%): $^1$H NMR (200 MHz, DMSO-$d_6$): δ 9.11 (s, 1 H), 7.13 (m, 4 H), 6.63 (m, 5 H), 4.01 (d, J=10.2 Hz, 2 H), 3.76 (s, 4 H), 2.12 (s, 6 H); LC-MS m/z=431 $[C_{23}H_{24}FO_5P+H]^+$; Anal Calcd for ($C_{23}H_{24}FO_5P$+0.6$H_2O$+0.2 $Et_2O$): C, 62.68; H, 6.01. Found: C, 62.31; H, 6.16; mp: 169-171° C.

Example 41

Compound 41: [3,5-dimethyl-4-[3'-benzyl-4'-hydroxy-benzyl]benzoyl]-methylphosphonic acid Step a:

To a solution of 4-(3'-benzyl-4'-methoxymethoxy-benzyl)-3,5-dimethyl-phenol (example 38, step c, 0.5 g, 1.38 mmol) and DMAP (0.67 g, 5.52 mmol) in $CH_2Cl_2$ (20 mL) at 0° C. was slowly added trifluoromethanesulfonyl anhydride (0.35 mL, 2.1 mmol). The reaction mixture was stirred at 0° C. for 2 h and quenched by water (10 mL). The organic layer was dried over $Na_2SO_4$, filtered and concentrated under reduced pressure to afford 4-(3'-benzyl-4'-methoxymethoxy-benzyl)-3,5-dimethyl-phenyl trifluoromethanesulfonate as an oil (0.5 g, 73%): $^1$H NMR (300 MHz, DMSO-$d_6$): δ 7.14-7.28 (m, 7 H), 6.94 (d, J=8.4 Hz, 1 H), 6.85 (d, J=2.4 Hz, 1 H), 6.70 (m, 1 H), 5.15 (s, 2 H), 3.94 (s, 2 H), 3.88 (s, 2 H), 3.27 (s, 3H), 2.24 (s, 6 H); TLC conditions: Uniplate silica gel, 250 microns; Mobile phase=ethyl acetate-hexanes (15:75); $R_f$=0.55.

Step b:

To a solution of 4-(3'-benzyl-4'-methoxymethoxy-benzyl)-3,5-dimethyl-phenyl trifluoromethanesulfonate (0.5 g, 1 mmol) in DMF (8 mL) in a bomb apparatus was added MeOH (0.82 mL, 20 mmol), $Pd(OAc)_2$ (23 mg, 0.1 mmol), bis-(diphenyphosphino)propane (42 mg, 0.1 mmol) and TEA (0.28 mL, 2 mmol). 60 psi of CO was then infused and the reaction mixture was stirred at 90° C. for 16 h. The cooled bomb was vented and the reaction mixture was poured into cold 1N HCl, extracted with EtOAc twice, the combined EtOAc were washed with brine, dried over $MgSO_4$, filtrated and concentrated. The residue was purified by column chromatography on silica gel, eluting with ethyl acetate-hexanes (15:75) to afford methyl 4-(3'-benzyl-4'-methoxymethoxy-benzyl)-3,5-dimethyl-benzoate as a yellow oil (360 mg, 88%): $^1$H NMR (300 MHz, DMSO-$d_6$): δ 7.66 (s, 2 H), 7.16 (m, 5 H), 6.90 (m, 2 H), 6.71 (m, 1 H), 5.15 (s, 2 H), 3.98 (s, 2 H), 3.87 (s, 2 H), 3.85 (s, 3 H), 3.26 (s, 3 H), 2.25 (s, 6 H). TLC conditions: Uniplate silica gel, 250 microns; Mobile phase=ethyl acetate-hexanes (15:75); $R_f$=0.50.

Step c:

To a stirring solution of diethyl methylphosphonate (0.39 mL, 2.67 mmol) in THF (10 mL) at −78° C. was added n-BuLi (2.5 M in hexanes, 1.07 mL), the reaction mixture was stirred at −78° C. for 1 h, then methyl 4-(3'-benzyl-4'-methoxymethoxy-benzyl)-3,5-dimethyl-benzoate (360 mg, 0.89 mmol) in THF (10 mL) was added at the same temperature. The reaction mixture was stirred at −78° C. for 1.5 h, then at room temperature for 1 h. The reaction mixture was quenched with saturated $NH_4Cl$ and diluted with diethyl ether. The organic layer was dried over $Na_2SO_4$, filtered and concentrated under reduced pressure. The residue was purified by column chromatography on silica-gel, eluting with ethyl acetate to afford diethyl [3,5-dimethyl-4-[3'-benzyl-4'-hydroxy-benzyl]benzoyl]methylphosphonate as a light yellow oil (350 mg, 75%): $^1$H NMR (300 MHz, DMSO-$d_6$): δ 7.72 (s, 2 H), 7.16 (m, 5H), 6.92 (m, 2 H), 6.71 (m, 1 H), 5.14 (s, 2 H), 4.04 (m, 6 H), 3.99 (s, 2 H), 3.82 (d, J=22.2 Hz, 2 H), 3.26 (s, 3 H), 2.27 (s, 6 H), 1.19 (t, J=7.5 Hz, 6 H). TLC conditions: Uniplate silica gel, 250 microns; Mobile phase=ethyl acetate-hexanes (2:1); $R_f$=0.35.

Step d:

The title compound was prepared by the procedure described for the synthesis of example 35, step h as a white foam (55 mg, 88%): $^1$H NMR (200 MHz, DMSO-$d_6$): δ 9.21 (s, 1 H), 7.66 (s, 2 H), 7.21 (m, 5 H), 6.65 (m, 2 H), 6.55 (m, 1 H), 3.89 (s, 2 H), 3.79 (s, 2 H), 3.45 (d, J=22.8 Hz, 2 H), 2.16 (s, 6H); LC-MS m/z=425 $[C_{24}H_{25}O_5P+H]^+$; Anal Calcd for ($C_{24}H_{25}O_5P$+1.6$H_2O$): C, 63.60; H, 6.27. Found: C, 63.87; H, 6.43.

Using the appropriate starting material, compounds 41-1 to 41-3 were prepared in an analogous manner to that described for the synthesis of compound 41.

Compound 41-1: 2-[3,5-dimethyl-4-(4'-fluoro-3'-iso-propyl-benzyl)phenyl]-2-oxo-ethylphosphonic acid The title compound was prepared from 3,5-dimethyl-4-(4'-fluoro-3'-iso-propyl-benzyl)-phenol (compound 27, step e) by the procedure described for the synthesis of compound 41 as a white solid (106 mg, 81.5%): $^1$H NMR (300 MHz, DMSO-$d_6$): δ 7.70 (s, 2H), 7.10 (m, 1H), 6.98 (m, 1H), 6.65 (m, 1H), 4.00 (s, 2H), 3.48 (d, J=22.4 Hz, 2H), 3.09 (m, 1H), 2.26 (s, 6H), 1.17 (d, J=7.0 Hz, 6 H). mp=138~140, LC-MS m/z=379 $[C_{20}H_{24}FO_4P+H]^+$; Anal. Calcd for ($C_{20}H_{24}FO_4P$): C, 63.49; H, 6.39. Found: C, 63.40; H, 6.63.

Compound 41-3: 2-[3,5-dichloro-4-(4-fluoro-iso-propyl-benzyl)-phenyl]-2-oxo-ethylphosphonic acid 3,5-Dichloro-4-(4-fluoro-3-iso-propyl-benzyl)-phenol, intermediate for the synthesis of compound 27-2, was transformed into the title compound by the procedure described for the synthesis of compound 41 to give a white solid (65 mg, 82%): $^1$H NMR (300 MHz, DMSO-$d_6$): δ 8.08 (s, 2H), 7.25 (m, 1H), 7.05 (m, 1H), 6.90 (m, 1H), 4.32 (s, 2H), 3.60 (d, J=22.5 Hz, 2H), 3.12 (m, 1H), 1.20 (d, J=6.9 Hz, 6H). mp=132~134, LC-MS m/z=417 $[C_{18}H_{18}Cl_2FO_4P+H]^+$; Anal. Calcd for ($C_{18}H_{18}Cl_2FO_4P$): C, 51.57; H, 4.33. Found: C, 51.37; H, 4.65.

Example 42

Compound 42: 2-[3,5-dimethyl-4-[3'-benzyl-4'-hydroxy-benzyl]phenyl]-ethylphosphonic acid Step a:

To a stirring solution of diethyl [3,5-dimethyl-4-[3'-benzyl-4'-hydroxy-benzyl]benzoyl]methylphosphonate (example 41, step c, 0.27 g, 0.52 mmol) in MeOH (10 mL) at 0° C. was added $NaBH_4$ (78 mg, 2.1 mmol). The reaction mixture was stirred at room temperature for 4 h. The solvent was removed under reduced pressure and the residue was partitioned between ethyl acetate and water. The organic layer was dried over $Na_2SO_4$, filtered and concentrated under reduced pressure to afford diethyl 2-[4-(3'-benzyl-4'-methoxymethoxy-benzyl)-3,5-dimethyl-phenyl]-2-hydroxy-ethyl-phosphonate as an oil (0.27 g, 100%): $^1$H NMR (300 MHz, DMSO-$d_6$): δ 7.18 (m, 5 H), 7.03 (s, 2 H), 6.93 (m, 2 H), 6.70 (m, 1 H), 5.39 (d, J=4.5 Hz, 1 H), 5.14 (s, 2H), 4.80 (m, 1 H), 3.85 (m, 8 H), 3.26 (s, 3H), 2.18 (s, 6H), 1.19 (m, 6 H). TLC conditions: Uniplate silica gel, 250 microns; Mobile phase=ethyl acetate-hexanes (2:1); $R_f$=0.29.

Step b:

To a stirring solution of diethyl 2-[4-(3'-benzyl-4'-methoxymethoxy-benzyl)-3,5-dimethyl-phenyl]-2-hydroxy-ethyl-phosphonate (0.24 g, 0.46 mmol) in $CH_2Cl_2$ (10 mL) at room temperature was added $Et_3SiH$ (0.34 mL, 2.1 mmol) and TFA (0.4 mL, 5.4 mmol). The reaction mixture was stirred at room temperature for 16 h. The solvent was removed under reduced pressure and the residue was partitioned between ethyl acetate and saturated $NaHCO_3$. The organic layer was dried over $Na_2SO_4$, filtered and concentrated under reduced pressure. The crude product was purified by column chromatography on silica gel, eluting with ethyl acetate-hexanes (3:1) to afford 2-[4-(3'-benzyl-4'-hydroxy-benzyl)-3,5-dimethyl-phenyl]ethylphosphonate as an oil (55 mg, 26%): $^1$H NMR (300 MHz, DMSO-$d_6$): δ 9.16 (s, 1 H), 7.22 (m, 5 H), 6.91 (s, 2 H), 6.76(s, 1 H), 6.62 (m, 2 H), 4.00 (m, 4 H), 3.80 (s, 4 H), 2.68 (m, 2 H), 2.14 (s, 6 H), 2.06 (m, 2H), 1.23 (m, 6 H). TLC conditions: Uniplate silica gel, 250 microns; Mobile phase=ethyl acetate-hexanes (2:1); $R_f$=0.33.

Step c:

The title compound was prepared by the procedure described for the synthesis of example 35, step h as a light yellow solid (28 mg, 58%): mp: 168-170° C.; $^1$H NMR (200 MHz, DMSO-$d_6$): δ 9.11 (s, 1 H), 7.19 (m, 5 H), 6.85 (s, 2 H), 6.63 (m, 3 H), 3.77 (s, 4 H), 2.66 (m, 2 H), 2.12 (s, 6 H), 1.76 (m, 2 H); LC-MS m/z=411 $[C_{24}H_{27}O_4P+H]^+$; Anal Calcd for ($C_{24}H_{27}O_4P+1.6H_2O$): C, 68.14; H, 6.77. Found: C, 68.19; H, 6.55.

Compound 42-1: 2-[3,5-dimethyl-4-(4'-fluoro-3'-iso-propyl-benzyl)phenyl]-ethylphosphonic acid Step a:

Intermediate diethyl 2-[3,5-dimethyl-4-(4'-fluoro-3'-iso-propyl-benzyl)phenyl]-2-oxo-ethylphosphonate for the synthesis of compound 41-1 was transformed into diethyl 2-[3,5-dimethyl-4-(4'-fluoro-3'-iso-propyl-benzyl)phenyl]-2-hydroxy-ethylphosphonate by the procedure described for the synthesis of compound 42, step a to give a yellow liquid (580 mg, 96.2%): $^1$H NMR (300 MHz, $CDCl_3$): δ 7.12 (s, 2H), 6.99 (m, 1H), 6.84 (m, 1H), 6.66 (m, 1H), 5.09 (s, 1H), 4.19 (m, 4H), 4.01 (s, 1H), 3.18 (m, 1H), 2.22 (s, 6H), 2.20 (m, 2H), 1.36 (m, 6H), 1.25 (d, J=6.4 Hz, 6H). TLC conditions: Uniplate silica gel, 250 microns; Mobile phase=ethyl acetate-hexanes (4:1); $R_f$=0.58.

Step b:

A degassed solution of diethyl 2-[3,5-dimethyl-4-(4'-fluoro-3'-iso-propyl-benzyl)phenyl]-2-hydroxy-ethylphosphonate (500 mg, 1.15 mmol) and Pd/C (50 mg) in EtOH/HOAc(19/1) was stirred under 1 atmosphere of hydrogen at r.t. After 5 h, the catalyst was filtered through a pad of celite and concentrated. The residue was purified by column chromatography (silica gel, ethyl acetate-hexanes; 9:1) to afford diethyl 2-[3,5-dimethyl-4-(4'-fluoro-3'-iso-propyl-benzyl)phenyl]ethylphosphonate (450 mg, 93.5%): $^1$H NMR (300 MHz, $CDCl_3$): δ 6.99 (s, 1H), 6.98 (s, 2H), 6.88 (m, 1H), 6.66 (m, 1H), 4.65 (m, 4H), 3.99 (s, 2H), 3.19 (m, 1H), 2.88 (m, 2H), 2.24 (s, 6H), 2.10 (m, 2H), 1.51 (m, 6H), 1.25 (d, J=6.9 Hz, 6H). TLC conditions: Uniplate silica gel, 250 microns; Mobile phase=ethyl acetate-hexanes (1:1); $R_f$=0.53.

Step c:

Diethyl2-[3,5-dimethyl-4-(4'-fluoro-3'-iso-propyl-benzyl)phenyl]-ethylphosphonate was transformed into the title compound by the procedure described for the synthesis of compound 35, step h to give a white solid (60 mg, 35%): $^1$H NMR (300 MHz, DMSO-$d_6$): δ 7.09 (m, 1H), 6.98 (m, 1H), 6.92 (s, 2H), 6.66 (m, 1H), 3.94 (s, 2H), 3.95 (s, 2H), 3.11 (m, 1H), 2.70 (m, 2H), 2.18 (s, 6H), 1.80 (m, 2H), 1.19 (d, J=7.2 Hz, 6H). mp=116~118, LC-MS m/z=365 $[C_{20}H_{26}FO_3P+H]^+$; Anal. Calcd for ($C_{20}H_{26}FO_3P$): C, 65.92; H, 7.19. Found: C, 65.68; H, 7.19.

Example 43

Compound 43: [3,5-dimethyl-4-S-[(4'-hydroxy-3'-iso-propylphenyl)-sulfanyl]phenoxy]methylphosphonate Step a:

A mixture of 3,5-Dimethyl-4-iodophenol (2.0 g, 8.06 mmol), potassium carbonate (3.33 g, 24.2 mmol) and methyl iodine (602 μl, 9.67 mmol) in DMF (20 mL) under a nitrogen atmosphere was heated at 65° C., with stirring for 16 hours. The cooled reaction was diluted with ethyl acetate (50 mL), filtered into a sep-funnel and washed with water (2×25 mL) then brine (25 mL). The organics were dried over sodium sulfate, filtered and the solvent removed under reduced pressure to give (1.68 g, 79%); $^1$H NMR (300 MHz, DMSO-$d_6$): δ 6.79(s, 2H), 3.72(s, 3H), 2.37(s, 6H); TLC conditions: Uniplate silica gel, 250 microns; Mobile phase=5% ethyl acetate in hexane; $R_f$=0.47.

Step b:

Copper iodine (70 mg, 0.37 mmol), neocuprinine (80 mg, 0.37 mmol) and potassium t-butoxide (470 mg, 4.05 mmol) were added in this order to a solution of 4-methoxy-3-iso-propyl-thiophenol (U.S. Pat. No. 6,747,048 B2, 600 mg, 2.3 mmol) and 3,5-dimethyl-4-iodoanisole (678 mg, 3.72 mmol) in toluene (10 mL). After refluxing overnight, the cooled reaction mixture was poured into ethyl acetate (50 mL) and washed twice with 1 N HCl then brine. The organics were dried over sodium sulfate, filtered and concentrated under reduced pressure. The residue was purified by column chromatography (silica gel, hexane/ethyl acetate 100:0 to 40:1) to give 3,5-dimethyl-4-(3'-iso-propyl-4'-methoxyphenylsulfanyl)anisole (0.358 g, 49%); $^1$H NMR (200 MHz, DMSO-$d_6$): δ 6.87-6.80(m, 4H), 6.56(m, 1H), 3.76(s, 3H), 3.71(s, 3H), 3.15(m, 1H), 2.34(s, 6H), 1.06(d, 6H, J=7 Hz); TLC conditions: Uniplate silica gel, 250 microns; Mobile phase=25% ethyl acetate in hexane; $R_f$=0.36

Step c:

3,5-dimethyl-4-(4'-hydroxy-3'-iso-propyl-phenylsulfanyl)phenol was prepared from 2,5-dimethyl-4-(3'-iso-propyl-4'-methoxy-phenylsulfanyl)-anisole according to the procedure described in example 8, step d. $^1$H NMR (300 MHz, DMSO-$d_6$): δ 9.58(bs, 1H), 9.21(bs, 1H), 6.77(m, 1H), 6.63(m, 3H), 6.46(dd, 1H, J=2.7 Hz and J=8.1 Hz), 3.09(m, 1H), 2.28(s, 6H), 1.06(d, 6H, J=7.2 Hz); TLC conditions: Uniplate silica gel, 250 microns; Mobile phase=ethyl acetate 25% in hexane; $R_f$=0.12

Step d:

Diethyl[3,5-Dimethyl-4-(4'-hydroxy-3'-iso-propyl-phenylsulfanyl)-phenoxy]methyl phosphonate was prepared according to the procedure described in compound 8, step e: $^1$H NMR (300 MHz, DMSO-$d_6$): δ 9.26(s, 1H), 6.92(s, 2H), 6.81(d, 1H, J=2.4 Hz), 6.65(d, 1H, J=8.4 Hz), 6.47(dd, 1H, J=2.1 Hz and J=8 Hz), 4.42(d, 2H, J=10 Hz), 4.11(m, 4H), 3.10(m, 1H), 2.35(s, 6H), 1.25(m, 6H), 1.06(d, 6H, J=2.9 Hz); TLC conditions: Uniplate silica gel, 250 microns; Mobile phase=ethyl acetate 50% in hexane; $R_f$=0.12

Step e:

The title compound was prepared according to the procedure described in compound 8, step f: $^1$H NMR (300 MHz, DMSO-$d_6$): δ 9.22 (s, 1H), 6.88 (s, 2H), 6.81 (d, J=2.1 Hz, 1H), 6.64 (d, J=8.4 Hz, 1H), 6.46 (dd, J=2 Hz and J=8.2 Hz, 1H), 4.08 (d, J=10.2 Hz, 2H), 3.10 (m, 1H), 2.34 (s, 6H), 1.07 (d, J=6.6H, 6Hz); LC-MS m/z=381 [$C_{18}H_{23}O_5PS-H$]$^-$; TLC conditions: Uniplate silica gel, 250 microns; Mobile phase=IPA/NH$_4$OH/H$_2$O [7:1:2]; $R_f$=0.53; HPLC, YMC Pack ODS-AQ, AQ 302, 150 mm×4.6 mm, S 5 μm, 12 nm, flow 2 mL/min, solvent A: 0.05% TFA aqueous, Solvent B: acetonitrile/0.05% TFA, Gradient 20% B to 70% B in 13 min—hold 1 min at 70% B—gradient to 100% B in 6 min. Rt=10.23 min.

Example 44

Compound 44: [3,5-dimethyl-4-[4'-hydroxy-3'-(iso-propylsulfonyl)benzyl]-phenoxy]methylphosphonic acid Step a:

Triisopropyl-[3,5-dimethyl-4-(4'-methoxymethoxy-3'-iso-propyl-sulfanylbenzyl)-phenoxy]silane was synthesized according to the procedure described in example 35, step d using di-iso-propyl disulfide as the electrophile. The product of this reaction was carried in the next step as a mixture of desired product and starting material triisopropyl-[3,5-dimethyl-4-(4'-methoxymethoxybenzyl)-phenoxy]silane: $^1$H NMR (200 MHz, DMSO-$d_6$): δ 1.15 (d, J=6.4 Hz, 6H); TLC conditions: Uniplate silica gel, 250 microns; Mobile phase=5% ethyl acetate in hexane; $R_f$=0.32

Step b:

3,5-Dimethyl-4-(4'-methoxymethoxy-3'-iso-propylsulfanylbenzyl)-phenol was prepared according to the procedure described in example 35, step e. The product of this reaction was carried on as a mixture of desired product and 3,5-dimethyl 4-(4'-methoxymethoxybenzyl)phenol: $^1$H NMR (200 MHz, DMSO-$d_6$): δ 1.16 (d, J=9.9 Hz, 6H); TLC conditions: Uniplate silica gel, 250 microns; Mobile phase=5% ethyl acetate in hexane; $R_f$=0.25

Step c:

Diethyl-[3,5-dimethyl-4-(4'-methoxymethoxy-3'-iso-propylsulfanyl-benzyl)phenoxy]methylphosphonate was prepared according to the procedure described in example 8, step e and carried on as a mixture of desired product and diethyl [3,5-dimethyl 4-(4'-methoxymethoxybenzyl)-phenoxy]methylphosphonate: $^1$H NMR (200 MHz, DMSO-$d_6$): δ 4.36 (d, 2H, J=15 Hz), 4.11 (m, 4H), 1.26 (t, 6H, J=10.8 Hz), 1.16 (d, 6H, J=9.9 Hz); LC-MS m/z=465 [$C_{23}H_{36}O_6PS+H$]$^+$; TLC conditions: Uniplate silica gel, 250 microns; Mobile phase=50% ethyl acetate in hexane; $R_f$=0.12

Step d:

A mixture diethyl [3,5-dimethyl 4-(4'-methoxymethoxy-3'-iso-propylsulfanylbenzyl)phenoxy]methylphosphonate (0.200 g, 0.402 mmol), saturated sodium bicarbonate (1 Ml) and mCPBA 50%-60% (0.173 g, 1.01 mmol) in dichloromethane (5 mL) was stirred overnight at room temperature. The layers were separated and the organics were dried over sodium sulfate, filtered and concentrated under reduced pressure. The residue was purified by preparative TLC (2000 μm, 5% hexanes in ethyl acetate) to give diethyl [3,5-dimethyl-4-[4'-methoxymethoxy-3'-(iso-propyl sulfonyl)benzyl]phenoxy]-methylphosphonate (0.090 g, 42%); $^1$H NMR (200 MHz, DMSO-$d_6$): δ 7.42 (s, 1H), 7.24 (s, 2H), 6.77 (s, 2H), 5.32 (s, 2H), 4.36 (d, J=10 Hz, 2H), 4.11 (m, 4H), 3.96 (s, 2H), 3.69 (m, 1H), 3.39 (s, 3H), 2.16 (s, 6H), 1.26 (t, J=7 Hz, 6H), 1.12 (d, J=7 Hz, 6H); TLC conditions: Uniplate silica gel, 250 microns; Mobile phase=ethyl acetate; $R_f$=0.28

Step e:

The title compound was prepared according to the described for example 8, step f (0.057 g, 82); $^1$H NMR (200 MHz, DMSO-$d_6$): δ 10.89 (bs, 1H), 7.31 (s, 1H), 7.12 (dd, J=5.8, 2.2 Hz, 1H z), 6.93 (d, J=8 H, 1H z), 6.72 (s, 2H), 4.04 (d, J=10.2 H, 2H z), 3.89 (s, 2H), 3.64 (m, 1H), 2.15 (s, 6H), 1.11 (d, J=7 Hz, 6H); LC-MS m/z=427 [$C_{19}H_{25}O_7PS-H$]$^-$; TLC conditions: Uniplate silica gel, 250 microns; Mobile phase=iso-propyl alcohol/NH$_4$OH/H$_2$O [7:1:2]; $R_f$=0.53; Anal. Calcd for ($C_{18}H_{23}O_5PS$+1 M H$_2$O+0.1 M EtOAc) C, 51.18; H, 6.15. Found: C, 51.01; H, 5.94.

Example 45

Compound 45: [4,6-Dimethyl-5-(4'-hydroxy-3'-iso-propyl)benzyl]-benzofuran-2-phosphonic Acid Step a:

To a mixture of 3,5-dimethyl-4-(4'-methoxymethoxy-3'-iso-propylbenzyl)phenol (1.0 g, 3.18 mmol, Chiellini et al., Bioorg. Med. Chem. Lett. 10:2607 (2000)) in $C_2H_5$OH (30.0 mL) and 40% aqueous methylamine (6.20 mL) at 0° C. was added a solution of potassium iodide (2.5 g, 15.0 mmol) and iodine (0.98 g, 3.82 mmol) in H$_2$O (6.20 mL). The reaction mixture was stirred at 0° C. for 1 h, quenched with water and extracted with ethyl acetate (2×30 mL). The organic layers were dried over MgSO$_4$, filtered and concentrated under reduced pressure. The crude product was purified by column chromatography on silica gel, eluting with 20% ethyl acetate in hexanes to afford 3,5-dimethyl-2-iodo-4-(4'-methoxymethoxy-3'-iso-propylbenzyl)phenol as white solid: $^1$H NMR (300 MHz, CD$_3$OD): δ 6.93 (m, 2 H), 6.65 (m, 2 H), 5.18 (s, 2 H), 4.05 (s, 2 H), 3.48 (s, 3 H), 3.30 (m, 1 H), 2.41 (s, 3 H), 2.19 (s, 3 H), 1.18 (d, J=6.6 Hz, 6 H); TLC conditions: Uniplate silica gel, 250 microns; Mobile phase=ethyl acetate-hexanes (1:5); $R_f$=0.60.

Step b:

To a mixture of Cu$_2$O (0.08 g, 0.57 mmol) in DMF (2.0 mL) was added a solution of diethyl ethynylphosphonate (0.11 g, 0.68 mmol) in DMF (0.5 mL) followed by a solution of 3,5-dimethyl-2-iodo-4-(4'-methoxymethoxy-3'-iso-propylbenzyl)phenol in diisopropylethylamine (0.40 mL) and DMF (1.0 mL). The reaction mixture was heated at 90° C. for 48 h, cooled to room temperature and filtered through a Celite plug. The solution was diluted with water (30 mL) and extracted with ethyl acetate (30 mL). The organic layer was separated, dried over MgSO$_4$. The solvent was removed under reduced pressure and the crude product was purified by column chromatography on silica gel, eluting with 50% ethyl acetate in hexanes to afford diethyl [4,6-Dimethyl-5-(4'-hydroxy-3'-iso-propyl)benzyl]benzofuran-2-phosphonate (0.07 g, 26%) as colorless oil: $^1$H NMR (300 MHz, CD$_3$OD): δ 7.66 (dd, J=8.1, 2.4 Hz, 1 H), 7.35 (s, 1 H), 6.97 (d, J=2.1 Hz, 1 H), 6.92 (d, J=8.1 Hz, 1 H), 6.64 (dd, J=8.1, 2.1 Hz, 1 H), 5.18 (s, 2 H), 4.24 (m, 4 H), 4.14 (s, 2 H), 3.47 (s, 3 H), 3.30 (m, 1 H), 2.49 (s, 3 H), 2.39 (s, 3 H), 1.40 (t, J=6.0 Hz, 6 H), 1.14 (d, J=6.6 Hz, 6 H); TLC conditions: Uniplate silica gel, 250 microns; Mobile phase=ethyl acetate-hexanes (1:1); $R_f$=0.50.

Step c:

[4,6-Dimethyl-5-(4'-hydroxy-3'-iso-propyl)benzyl]benzofuran-2-phosphonic acid was prepared from diethyl [4,6-Dimethyl-5-(4'-hydroxy-3'-iso-propyl)benzyl]benzofuran-2-phosphonate according to the procedure described in example 7, step b: mp: 180-182° C.; $^1$H NMR (300 MHz, CD$_3$OD): δ 7.44 (dd, J=8.1, 2.4 Hz, 1 H), 7.30 (s, 1 H), 6.85

(d, J=2.1 Hz, 1H), 6.61 (d, J=8.1 Hz, 1 H), 6.55 (d, J=8.1 Hz, 1 H), 4.08 (s, 2 H), 3.24 (m, 1 H), 2.46 (s, 3 H), 2.37 (s, 3 H), 1.14 (d, J=6.6 Hz, 6 H); LC-MS m/z=375 $[C_{20}H_{23}O_5P+H]^+$; Anal. Calcd for ($C_{20}H_{23}O_5P+0.7H_2O+0.1$ $CH_3OH$): C, 61.87; H, 6.41. Found: C, 61.80; H, 6.60.

Example 46

Compound 46: [3,5-Dimethyl-4-(4'-hydroxy-3'-iso-propylbenzyl)-2-iodophenoxy]methylphosphonic Acid The title compound was prepared from 3,5-dimethyl-4-(3'-iso-propyl-4'-methoxymethoxy)benzyl-2-iodophenol (compound 45, step a) according to the procedure described in example 7: $^1$H NMR (300 MHz, DMSO-$d_6$): δ 9.00 (s, 1 H), 6.87 (d, J=3.9 Hz, 1 H), 6.61 (d, J=12.0 Hz, 1 H), 6.40 (d, J=12.6 Hz, 1 H), 4.32 (d, J=10.2 Hz, 2 H), 3.94 (s, 2 H), 3.12 (m, 1 H), 2.36 (s, 3 H), 2.21 (s, 3 H); LC-MS m/z=491 $[C_{19}H_{24}IO_5P+H]^+$; Anal Calcd for $C_{19}H_{24}IO_5P$: C, 46.55; H, 4.93. Found: C, 46.93; H, 4.99.

Example 47

Compound 47: [3,5-Dimethyl 4-(4'-hydroxy-3'-iso-propylbenzyl)-phenylamino]methylphosphonic Acid Step a:
A solution of 3,5-dimethyl-4-(4'-methoxymethoxy-3'-iso-propylbenzyl)-trifluoromethanesulfonyloxyphenyl (2.04 g, 4.57 mmol, intermediate for the synthesis of compound 24-1), triethylamine (1.27 mL, 9.14 mmol), 1,3-bis(diphenylphosphino)propane (0.19 mL, 0.45 mmol), MeOH (3.71 mL, 91.40 mmol), and Pd(OAc)$_2$ (0.102 g, 0.46 mmol) in DMF (25 mL) was heated at 90° C. under 60 psi of CO in a Parr reactor for 16 h. The reaction mixture was cooled to 0° C., diluted with ethyl acetate (25 mL) and washed with H$_2$O (25 mL×2). The organic solution was dried over Na$_2$SO$_4$, filtered, and concentrated under reduced pressure. The crude product was purified by column chromatography on silica gel, eluting with ethyl acetate-hexanes (1:4) to afford methyl 3,5-dimethyl-4-(4'-methoxymethoxy-3'-iso-propylbenzyl) benzoate as an oil (1.52 g, 93%): $^1$H NMR (300 MHz, DMSO-$d_6$): δ 7.68 (s, 2 H), 6.97 (m, 1 H), 6.91 (m, 2 H), 6.20 (m, 1 H), 5.16 (s, 2 H), 4.01 (s, 3 H), 3.85 (s, 3 H), 3.21 (m, 1 H), 2.28 (s, 6 H), 1.14 (d, J=6.0 Hz, 6 H); TLC conditions: Uniplate silica gel, 250 microns; Mobile phase=ethyl acetate-hexanes (1:4); $R_f$=0.42.

Step b:
To a stirring solution of methyl 3,5-dimethyl-4-(4'-methoxymethoxy-3'-iso-propylbenzyl)benzoate (0.750 g, 2.11 mmol) in MeOH (20.0 mL) at 0° C. was added 1 M NaOH (12.64 mL, 12.64 mmol). The reaction mixture was heated at 50° C. for 16 h, cooled to 0° C. and acidified with 2 N HCl. The mixture was extracted with ethyl acetate (20 mL) and washed with H$_2$O (10 mL×2.). The solvent was removed under reduced pressure to afford 3,5-dimethyl-4-(4'-methoxymethoxy-3'-iso-propylbenzyl)benzoic acid as white solid (0.71 g, 98%): $^1$H NMR (300 MHz, DMSO-$d_6$): δ 12.76 (s, 1 H), 7.65 (s, 2 H), 6.98 (m, 1 H), 6.91 (m, 1 H), 6.60 (m, 1 H), 5.17 (s, 2 H), 4.00 (s, 2 H), 3.37 (s, 3 H), 3.23 (m, 1 H), 2.27 (s, 6 H), 1.14 (d, J=6.0 Hz, 6 H); TLC conditions: Uniplate silica gel, 250 microns; Mobile phase=hexanes-ethyl acetate (4:1); $R_f$=0.00.

Step c:
To a suspension of 3,5-dimethyl-4-(4'-methoxymethoxy-3'-iso-propylbenzyl)benzoic acid (0.70 g, 2.04 mmol), tert-butanol (0.756 mg, 10.22 mmol) and triethylamine (0.71 g, 5.11 mmol) in toluene (30 mL) was added diphenylphosphoryl azide (0.44 mL, 2.04 mmol). The reaction mixture was heated under reflux for 16 h, cooled to room temperature and poured into a cold solution of 0.25 M HCl (30 mL). The mixture was diluted with ethyl acetate and washed with H$_2$O (30 mL). The organic layer was separated and concentrated under reduced pressure. The crude product was purified by column chromatography on silica gel, eluting with ethyl acetate-hexanes (1:9) to afford t-butyl N-3,5-dimethyl-4-(4'-methoxymethoxy-3'-iso-propylbenzyl)carbamate as a yellow oil (0.63 g, 75%): $^1$H NMR (300 MHz, DMSO-$d_6$): δ 9.16 (s, 1 H), 7.16 (s, 2 H), 6.96 (m, 1 H), 6.90 (m, 1 H), 6.62 (m, 1 H), 5.16 (s, 2 H), 3.86 (s, 2 H), 3.37 (s, 3 H), 3.22 (m, 1 H), 2.15 (s, 6 H), 1.48 (m, 9 H), 1.23 (d, J=6.0 Hz, 6 H); TLC conditions: Uniplate silica gel, 250 microns; Mobile phase=ethyl acetate-hexanes (3:7); $R_f$=0.72.

Step d:
To a mixture of t-butyl N-3,5-dimethyl-4-(4'-methoxymethoxy-3'-iso-propylbenzyl)carbamate (0.315 g, 0.76 mmol) in THF (8.0 mL) at −78° C. was added lithium diisopropylamide (0.46 g, 0.91 mmol, 2.0 M solution in THF/heptane/ethylbenzene). The reaction mixture was stirred at −78° C. for 20 min and trifluoromethanesulfonic acid diethoxyphosphorylmethyl ester (0.16 g, 0.76 mmol) was added. The reaction mixture was stirred at −78° C. for 1 h, allowed to warm to room temperature and stirred for 4 h. The reaction mixture was quenched with 2.5 M aqueous ammonium chloride and diluted with ethyl acetate. The organic layer was washed with saturated aqueous ammonium chloride (8.0 mL), H$_2$O (8.0 mL) and brine (8.0 mL). The organic solution was dried over MgSO$_4$, filtered and concentrated under reduced pressure. The crude product was purified by column chromatography on silica gel, eluting with ethyl acetate-hexanes (1:1) to afford diethyl N-t-butoxycarbonyl-[3,5-dimethyl-4-(4'-methoxymethoxy-3'-iso-propylbenzyl) phenylamino]methyl phosphonate as an oil (0.21 g, 49%): $^1$H NMR (300 MHz, DMSO-$d_6$): δ 7.00 (s, 2 H), 6.94 (m, 1 H), 6.90 (m, 1 H), 6.64 (m, 1 H), 5.16 (s, 2 H), 4.09 (d, J=6.0 Hz, 2 H), 4.00 (m, 4 H), 3.8 (m, 2 H), 3.37 (s, 3 H), 3.22 (m, 1 H), 2.20 (s, 6 H), 1.40 (s, 9 H), 1.27 (m, 6 H), 1.13 (m, 6 H); TLC conditions: Uniplate silica gel, 250 microns; Mobile phase=ethyl acetate-hexanes (3:2); $R_f$=0.20

Step e:
To a stirring solution of diethyl N-t-butoxycarbonyl-[3,5-dimethyl-4-(4'-methoxymethoxy-3'-iso-propylbenzyl)phenylamino]methylphosphonate (0.19 g, 0.34 mmol) in MeOH (4.0 mL) at 0° C. was added 2 M HCl (1.68 mL, 3.37 mmol). The reaction mixture was allowed to warm to room temperature and stirred for 48 h. The reaction mixture was cooled to 0° C., neutralized with NaHCO$_3$, diluted with ethyl acetate (20 mL) and washed with H$_2$O (10 mL×2). The organic solution was dried over MgSO$_4$, filtered and concentrated under reduced pressure. The residue was purified by column chromatography on silica gel, eluting with ethyl acetate-hexanes (3:2) to afford diethyl [3,5-dimethyl-4-(4'-hydroxy-3'-iso-propylbenzyl)phenylamino]methylphosphonate as a white solid (0.07 g, 51%): $^1$H NMR (300 MHz, DMSO-$d_6$): δ 8.95 (s, 1H), 6.84 (m, 1 H), 6.63 (m, 1 H), 6.50 (m, 1 H), 6.45 (s, 2 H), 5.39 (m, 1 H), 4.06 (s, 6 H), 3.74 (s, 2 H), 3.51 (m, 2 H), 3.13 (m, 1 H), 2.09 (s, 6 H), 1.20 (m, 6 H), 1.11 (d, J=6.0 Hz, 6 H); TLC conditions: Uniplate silica gel, 250 microns; Mobile phase=ethyl acetate-hexanes (4:1); $R_f$=0.29.

Step f:
To a solution of diethyl [3,5-dimethyl-4-(4'-hydroxy-3'-iso-propylbenzyl)phenylamino]methylphosphonate (0.070 g, 0.17 mmol) in CH$_2$Cl$_2$ (3.0 mL) at −30° C. was added bromotrimethylsilane (0.28 mL, 2.08 mmol). The reaction mixture was stirred at room temperature for 16 h and the solvent was removed under reduced pressure. The residue was treated with acetonitrile-water (4:1, 5.0 mL) and stirred at 38° C. for 30 min. The solvent was removed under reduced pressure. The residue was dissolved in ethyl acetate and washed with H$_2$O. The organic solution was dried over MgSO$_4$, filtered and concentrated under reduced pressure to afford the title compound as an off-white powder (0.050 g, 79%); mp: 147-150° C.; $^1$H NMR (300 MHz, DMSO-d$_6$): δ 8.97 (s, 1 H), 6.86 (m, 1 H), 6.59 (m, 1 H), 6.49 (m, 1 H), 6.45 (s, 2 H), 3.74 (s, 2 H), 3.20 (d, J=12.0 Hz, 2 H), 3.13 (m, 1 H), 2.10 (s, 6 H), 1.12 (d, J=6.0 Hz, 6 H); LC-MS m/z=364 [C$_{19}$H$_{26}$NO$_4$P–H]$^+$; Anal. Calcd for (C$_{19}$H$_{26}$NO$_4$P+ 1.0H$_2$O+0.2 HBr+0.2 CH$_3$CO$_2$CH$_2$CH$_3$): C, 57.28; H, 7.23; N, 3.37; Br, 3.85. Found: C, 57.60; H, 7.33; N, 3.12; Br, 3.48.

Example 48

Compound 48: [4-(3'-cyclopropyl-4'-hydroxybenzyl)-3,5-dimethylphenoxy]-methylphosphonic acid Step a:
To a suspension of methyltriphosphonium bromide (4.81 g, 13.46 mmol) in THF (10.0 mL) at 0° C. was added n-butyllithium (4.30 g, 10.76 mmol, 2.5 M solution in hexane). The reaction mixture was stirred at 0° C. for 1 h and to it was added a solution of 5-(2,6-dimethyl-4-triisopropylsilanyloxybenzyl)-2-methoxymethoxy-benzaldehyde (1.23 g, 2.69 mmol, intermediate for the synthesis of Example 35, step d) in THF (5.0 mL). The reaction mixture was stirred at room temperature for 2.5 h, cooled to 0° C. and quenched with saturated ammonium chloride (15.0 mL). The mixture was extracted with ethyl acetate (20 mL), washed with H$_2$O (25 mL×2) and concentrated under reduced pressure. The crude product was purified by column chromatography on silica gel, eluting with ethyl acetate-hexanes (1:50) to afford triisopropyl-[3,5-dimethyl-4-(4'-methoxymethoxy-3'-vinylbenzyl)phenoxy]silane as oil (1.19 g, 97%): $^1$H NMR (300 MHz, DMSO-d$_6$): δ 7.12 (m, 1 H), 7.00-6.93 (m, 2 H), 6.80 (m, 1 H), 6.59 (s, 2 H), 5.62 (d, J=18.0 Hz, 1 H), 5.24 (d, J=12.0 Hz, 1 H), 5.19 (s, 2 H), 3.88 (s, 2 H), 3.37 (s, 3 H), 2.15 (s, 6 H), 1.37 (s, 1 H), 1.21 (m, 3 H), 1.08 (d, J=4.5 Hz, 18 H); TLC conditions: Uniplate silica gel, 250 microns; Mobile phase=ethyl acetate-hexanes (1:5); R$_f$=0.74.

Step b:
A mixture of copper powder (0.094 g, 1.48 mmol) and iodine (0.005 g, 0.016 mmol) in benzene (2.3 mL) was stirred at room temperature for 10 min. To it was added a solution of triisopropyl-[3,5-dimethyl-4-(4'-methoxymethoxy-3'-vinylbenzyl)phenoxy]silane (0.15 g, 0.33 mmol) in benzene (1.0 mL) followed by diiodomethane (0.053 mL, 0.66 mmol). The reaction mixture was heated at 70° C. for 144 h, cooled to room temperature and filtered through a Celite plug. The solvent was removed under reduced pressure to afford triisopropy-[4-(3'-cyclopropyl-4'-methoxymethoxybenzyl)-3,5-dimethylphenoxy]silane as oil (0.14 g, 91%): $^1$H NMR (300 MHz, DMSO-d$_6$): δ 6.92 (m, 1 H), 6.67 (m, 1 H), 6.58 (s, 2 H), 6.43 (s, 1 H), 5.18 (s, 2 H), 3.82 (s, 2 H), 3.39 (s, 3 H), 2.14 (s, 6 H), 1.26 (m, 3 H), 1.08 (d, J=4.5 Hz, 18 H), 0.87 (m, 2 H), 0.46 (m, 2 H); TLC conditions: Uniplate silica gel, 250 microns; Mobile phase=ethyl acetate-hexanes (1:5); R$_f$=0.74.

Step c:
To a mixture of triisopropy-[3,5-dimethyl-4-(3'-cyclopropyl-4'-methoxymethoxybenzyl)phenoxy]silane (0.38 g, 0.81 mmol) in THF (10.0 mL) at 0° C. was added TBAF (1.22 mL, 0.81 mmol, 1.0 M in THF). The reaction mixture was stirred at room temperature for 1 h, diluted with diethyl ether (20 mL) and washed with H$_2$O (20 mL×2). The organic solution was dried over MgSO$_4$, filtered and concentrated under reduced pressure. The crude product was purified by column chromatography on silica gel, eluting with ethyl acetate-hexanes (1:9) to afford 4-(3'-cyclopropyl-4'-methoxymethoxybenzyl)-3,5-dimethylphenol as an oil (0.18 g, 71%): $^1$H NMR (300 MHz, DMSO-d$_6$): δ 9.01 (s, 1 H), 6.90 (m, 1 H), 6.61 (m, 1 H), 6.58 (s, 1 H), 6.46 (s, 2 H), 5.17 (s, 2 H), 3.77 (s, 2 H), 3.39 (s, 3 H), 2.11 (s, 6H), 0.87 (m, 2 H), 0.51 (m, 2 H); TLC conditions: Uniplate silica gel, 250 microns; Mobile phase=ethyl acetate-hexanes (1:9); R$_f$=0.47.

Step d:
To a mixture of 4-(3'-cyclopropyl-4'-methoxymethoxybenzyl)-3,5-dimethylphenol (0.16 g, 0.53 mmol) and Cs$_2$CO$_3$ (0.859 g, 2.64 mmol) in DMF (6.0 mL) at 0° C. was added trifluoromethanesulfonic acid diethoxyphosphorylmethyl ester (0.11 g, 0.53 mmol). The reaction mixture was stirred at 0° C. for 5 h, allowed to warm to room temperature and stirred for 16 h. The reaction mixture was cooled to 0° C., quenched with cold 1 N HCl and extracted with ethyl acetate (8.0 mL). The organic solution was dried over MgSO$_4$, filtered and concentrated under reduced pressure. The crude product was purified by column chromatography on silica gel, eluting with ethyl acetate-hexanes (1:1) to afford diethyl [4-(3'-cyclopropyl-4'-methoxymethoxybenzyl)-3,5-dimethylphenoxy]methylphosphonate as oil (0.10 g, 28%): $^1$H NMR (300 MHz, DMSO-d$_6$): δ 6.90 (m, 1 H), 6.75 (s, 2 H), 6.59 (m, 2 H), 5.17 (s, 2 H), 4.39 (d, J=9.0 Hz, 2 H), 4.15 (m, 4 H), 3.83 (s, 2H), 3.39 (s, 3 H), 2.19 (s, 6 H), 2.09 (m, 1 H), 1.24 (m, 6 H), 0.87 (m, 2 H), 0.52 (m, 2 H); TLC conditions: Uniplate silica gel, 250 microns; Mobile phase=ethyl acetate-hexanes (4:1); R$_f$=0.25

Step e:
To a solution of diethyl [4-(3'-cyclopropyl-4'-methoxymethoxybenzyl)-3,5-dimethylphenoxy]methylphosphonate (0.090 g, 0.19 mmol) in CH$_2$Cl$_2$ (3.0 mL) at –30° C. was added bromotrimethylsilane (0.26 mL, 1.94 mmol). The reaction mixture was stirred at room temperature 16 h and the solvent was removed under reduced pressure. The residue was treated with acetonitrile-water (4:1, 5.0 mL), stirred at 38° C. for 30 min and concentrated under reduced pressure. The residue was dissolved in ethyl acetate and washed with H$_2$O. The organic solution was dried over MgSO$_4$, filtered and concentrated under reduced pressure to afford the title compound as an off-white powder (0.040 g, 57%); mp: 153-156° C.; $^1$H NMR (300 MHz, DMSO-d$_6$): δ 9.02 (s, 1 H), 6.67 (s, 2 H), 6.58 (m, 1 H), 6.41 (m, 2 H), 4.00 (d, J=10.5 Hz, 2 H), 3.75 (s, 2 H), 2.13 (s, 6 H), 1.98 (m, 1 H), 0.81 (m, 2 H), 0.47 (m, 2 H); LC-MS m/z=362 [C$_{19}$H$_{23}$O$_5$P–H]$^+$; Anal. Calcd for (C$_{19}$H$_{23}$O$_5$P+0.9H$_2$O): C, 60.28; H, 6.60. Found: C, 60.40; H, 6.92.

Example 49

Compound 49: [4-(3'-Dimethylamino-4'-hydroxybenzyl)-3,5-dimethyl-phenoxy]methylphosphonic acid Step a:
To a stirring solution of 4-bromo-2-nitro-phenol (6 g, 27.52 mmol) in MeOH (150 mL) at room temperature was added a suspension of Na$_2$S$_2$O$_4$ (29 g, 165.13 mmol). The mixture was stirred at room temperature for 3 hrs, filtered and concentrated down. The residue was partitioned between EtOAc and water. The organic layer was collected and dried over Na$_2$SO$_4$, filtered and concentrated under reduced pressure to afford crude 2-amino-4-bromo-phenol as a yellow solid (3.9 g, 75%): $^1$H NMR (200 MHz, DMSO-d$_6$): δ 9.27 (s, 1H), 6.70 (d, J=2.2 Hz, 1 H), 6.50 (m, 2 H), 4.79 (s, 2 H); TLC conditions: Uniplate silica gel, 250 microns; Mobile phase=20% ethyl acetate in hexanes; R$_f$=0.35.

Step b:

2-Amino-4-bromo-phenol (3.9 g, 20.74 mmol) was dissolved into AcOH (120 mL) and heated to 40° C. To this stirring solution at 40° C. was added (HCHO)n (1.9 g, 62.23 mmol), followed by NaBH$_3$CN (3.9 g, 62.23 mmol). The reaction mixture was stirred for 1 hr at 40° C., then another (HCHO)n (1.9 g, 62.23 mmol) and NaBH$_3$CN (3.9 g, 62.23 mmol) were added. The mixture was stirred for 16 hrs at 40° C. The solvent was removed under reduced pressure. The residues were partitioned between EtOAc and water. The organic layer was collected and dried over Na$_2$SO$_4$, filtered and concentrated under reduced pressure. The crude product was purified by column chromatography on silica gel, eluting with ethyl acetate-hexanes (30:70) to afford 4-bromo-2-dimethylamino-phenol as a light yellow solid (3.7 g, 83%): $^1$H NMR (300 MHz, DMSO-d$_6$): δ 9.44 (s, 1 H), 6.92 (m, 2 H), 6.71 (d, J=8.4 Hz, 1 H), 2.69 (s, 6 H); TLC conditions: Uniplate silica gel, 250 microns; Mobile phase=20% ethyl acetate in hexanes; R$_f$=0.57.

Step c:

To a stirring solution of 4-bromo-2-dimethylamino-phenol (3.7 g, 17.13 mmol) in CH$_2$Cl$_2$ (100 mL) at room temperature was added ethyl-diisopropyl-amine (4.47 mL, 25.7 mmol) and chloro-methoxy-methane (1.69 mL, 22.27 mmol). The mixture was refluxed for 16 hrs, added water. The organic layer was collected and dried over Na$_2$SO$_4$, filtered and concentrated under reduced pressure to afford crude N-(5-bromo-2-methoxymethoxyphenyl)dimethylamine as a red oil (4.4 g, 99%): $^1$H NMR (200 MHz, DMSO-d$_6$): 6.96 (m, 3 H), 5.17 (s, 2 H), 3.40 (s, 3 H), 2.72 (s, 6H); TLC conditions: Uniplate silica gel, 250 microns; Mobile phase=15% ethyl acetate in hexanes; R$_f$=0.59.

Step d:

To a stirring solution of N-(5-bromo-2-methoxymethoxyphenyl)dimethylamine (3.4 g, 13.07 mmol) in THF (80 mL) at −78° C. was added n-BuLi (5.22 mL, 2.5 M in hexanes). The mixture was stirred at −78° C. for 1 hr and a solution of 2,6-dimethyl-4-triisopropylsilanyloxy-benzaldehyde (3.6 g, 11.77 mmol) was added. The reaction mixture was stirred at −78° C. for 1 hr, allowed to warm to room temperature and stirred for 1 hr. The reaction mixture was quenched with saturated NH$_4$Cl and diluted with diethyl ether. The organic layer was dried over Na$_2$SO$_4$, filtered and concentrated under reduced pressure. The crude product was purified by column chromatography on silica gel, eluting with ethyl acetate-hexanes (30:70) to afford (3-dimethylamino-4-methoxymethoxy-phenyl)-(2,6-dimethyl-4-triisopropyl silanyloxyphenyl)methanol as a yellow oil (4 g, 63%): $^1$H NMR (300 MHz, DMSO-d$_6$): δ 6.89 (d, J=8.4 Hz, 1 H), 6.79 (s, 1 H), 6.61 (m, 1 H), 6.51 (s, 2H), 6.01 (d, J=4.0 Hz, 1 H), 5.65 (d, J=4.0 Hz, 1 H), 5.14 (s, 2 H), 3.41 (s, 3H), 2.64 (s, 6 H), 2.17 (s, 6 H), 1.24 (m, 3 H), 1.08 (d, J=7.2 Hz, 18 H); TLC conditions: Uniplate silica gel, 250 microns; Mobile phase=25% ethyl acetate in hexanes; R$_f$=0.27.

Step e:

To a stirring solution of (3-dimethylamino-4-methoxymethoxy-phenyl)-(2,6-dimethyl-4-triisopropylsilanyloxy-phenyl)-methanol (3.4 g, 6.97 mmol) in CH$_2$Cl$_2$ (150 mL) at room temperature was added Et$_3$SiH (5.6 mL, 34.85 mmol) and TFA (2.6 mL, 34.85 mmol). The reaction mixture was stirred at room temperature for 6 hrs. The solvent was removed under reduced pressure and the residue was partitioned between ethyl acetate and saturated NaHCO$_3$. The organic layer was dried over Na$_2$SO$_4$, filtered and concentrated under reduced pressure. The crude product was purified by column chromatography on silica gel, eluting with ethyl acetate-hexanes (3:7) to afford N-[5-(2',6'-dimethyl-4'-triisopropylsilanyloxybenzyl)-2-methoxy-methoxyphenyl]dimethylamine as a yellow oil (3 g, 91%): $^1$H NMR (300 MHz, DMSO-d$_6$): δ 6.86 (d, J=8.1 Hz, 1 H), 6.59 (s, 2 H), 6.54 (d, J=2.1 Hz, 1 H), 6.41 (m, 1 H), 5.12 (s, 2 H), 3.85 (s, 2 H), 3.40 (s, 3 H), 2.64 (s, 6H), 2.15 (s, 6 H), 1.26 (m, 3 H), 1.08 (d, J=7.2 Hz, 18 H); TLC conditions: Uniplate silica gel, 250 microns; Mobile phase=ethyl acetate-hexanes (25:75); R$_f$=0.54.

Step f:

To a stirring solution of N-[5-(2',6'-dimethyl-4'-triisopropylsilanyloxybenzyl)-2-methoxymethoxyphenyl]dimethylamine (3 g, 6.36 mmol) in THF (60 mL) at room temperature was added tetrabutylammonium fluoride (9.54 mL, 1.0 M in THF). The reaction mixture was stirred at room temperature for 2 hr, diluted with diethyl ether and washed with water (30 mL×2). The solvent was removed under reduced pressure. The crude product was purified by column chromatography on silica gel, eluting with ethyl acetate-hexanes (1:1) to afford 4-(3'-dimethylamino-4'-methoxymethoxybenzyl)-3,5-dimethylphenol as a light yellow oil (1.8 g, 90%): $^1$H NMR (300 MHz, DMSO-d$_6$): δ 9.01 (s, 1 H), δ 6.85 (d, J=8.1 Hz, 1H), 6.63 (d, J=2.1 Hz, 1 H), 6.47 (s, 2 H), 6.35 (m, 1 H), 5.12 (s, 2 H), 3.80 (s, 2 H), 3.40 (s, 3 H), 2.67 (s, 6 H), 2.17 (s, 6 H), TLC conditions: Uniplate silica gel, 250 microns; Mobile phase=30% ethyl acetate in hexanes; R$_f$=0.28.

Step g:

To a stirring solution of 4-(3'-dimethylamino-4'-methoxymethoxybenzyl)-3,5-dimethylphenol (0.525 g, 1.66 mmol) in DMF (18 mL) at 0° C. was added NaH (80 mg, 1.99 mmol, 60%) and stirred for 1 hr at room temperature. Diethyl tosyloxymethylphosphonate (0.7 g, 2.16 mmol) was added and the mixture was stirred for 16 hrs at room temperature. The solvent was removed under reduced pressure, and the residue was partitioned between EtOAc and sat. NaHCO$_3$. The organic layer was dried over Na$_2$SO$_4$, filtered and concentrated under reduced pressure. The crude product was purified by column chromatography on silica gel, eluting with ethyl acetate-hexanes (8:2) to afford diethyl [4-(3'-dimethylamino-4'-methoxymethoxybenzyl)-3,5-dimethylphenoxy] methylphosphonate as a light yellow oil (0.5 g, 65%): $^1$H NMR (300 MHz, DMSO-d$_6$): δ 6.85 (d, J=8.1 Hz, 1 H), 6.76 (s, 2 H), 6.64 (d, J=2.1 Hz, 1 H), 6.34 (m, 1 H), 5.12 (s, 2 H), 4.38 (d, J=9.8 Hz, 2 H), 4.14 (m, 4 H), 3.86 (s, 2 H), 3.40 (s, 3 H), 2.67 (s, 6H), 2.19 (s, 6 H), 1.25 (t, J=7.0 Hz, 6 H); TLC conditions: Uniplate silica gel, 250 microns; Mobile phase=ethyl acetate-hexanes (6:4); R$_f$=0.43.

Step h:

To a stirring solution of diethyl [4-(3'-dimethylamino-4'-methoxymethoxybenzyl)-3,5-dimethylphenoxy]methylphosphonate (0.48 g, 1.03 mmol) in MeOH (6 mL) and water (1 mL) at room temperature was added HCl (1.03 mL, 10 N), and heated at 100° C. for 5 min by microwave. The solvent was removed under reduced pressure, and the residue was partitioned between EtOAc and sat. NaHCO$_3$. The organic layer was dried over Na$_2$SO$_4$, filtered and concentrated under reduced pressure. The crude product was purified by column chromatography on silica gel, eluting with ethyl acetate-CH$_2$Cl$_2$ (3:1) to afford diethyl [4-(3'-dimethylamino-4'-hydroxybenzyl)-3,5-dimethyl-phenoxy]methylphosphonate as a light yellow oil (0.29 g, 67%): $^1$H NMR (200 MHz, DMSO-d$_6$): δ 8.77 (s, 1 H), δ 6.72 (s, 2H), 6.57 (m, 2 H), 6.26 (m, 1 H), 4.35 (d, J=9.8 Hz, 2 H), 4.13 (m, 4 H), 3.79 (s, 2 H), 2.60 (s, 6 H), 2.17 (s, 6 H), 1.25 (t, J=7.0 Hz, 6 H); TLC conditions: Uniplate silica gel, 250 microns; Mobile phase=ethyl acetate-$CH_2Cl_2$ (1:3); $R_f$=0.49.

Step i:

The title compound was prepared according to the procedure described for the synthesis of compound 8, step f. $^1$H NMR (300 MHz, DMSO-$d_6$): δ 7.34 (s, 1 H), 6.92 (d, J=8.7 Hz, 1 H), 6.79 (m, 1 H), 6.73 (s, 2 H), 4.03 (d, J=10.2 Hz, 2 H), 3.88 (s, 2 H), 3.13 (s, 6 H), 2.17 (s, 6 H); mp: degasses at 90° C.; LC-MS m/z=366 [C18H24NO5P+H]$^+$; Anal Calcd for (C18H24NO5P+1.4HBr +0.4H$_2$O+0.1MeOH): C, 44.45; H, 5.48; N, 2.86; Br, 22.87. Found: C, 44.64; H, 5.67; N, 2.65; Br, 22.74.

Example 50

Compound 50: [4-(3'-Benzyloxycarbonylamino-4'-hydroxybenzyl)-3,5-dimethyl-phenoxy]methylphosphonic acid Step a:

To a stirring solution of diethyl [3,5-dimethyl-4-(3'-carboxyl-4'-methoxymethoxybenzyl)phenoxy]methylphosphonate (0.36 g, 0.77 mmol) in toluene (20 mL) at room temperature was added diphenylphosphoryl azide (0.17 mL, 0.77 mmol), triethylamine (0.2 mL, 1.4 mmol) and benzyl alcohol (0.4 mL, 3.85 mmol). The mixture was refluxed for 16 hrs. The solvent was removed under reduced pressure, and the residue was partitioned between EtOAc and sat. NH$_4$Cl. The organic layer was dried over Na$_2$SO$_4$, filtered and concentrated under reduced pressure. The crude product was purified by column chromatography on silica gel, eluting with ethyl acetate to afford diethyl [4-(3'-benzyloxycarbonylamino-4'-methoxymethoxybenzyl)-3,5-dimethylphenoxy]methylphosphonate as a light yellow oil (0.4 g, 91%): $^1$H NMR (300 MHz, DMSO-$d_6$): δ 8.60 (s, 1 H), 7.38 (m, 6 H), 6.99 (d, J=8.4 Hz, 1 H), 6.76 (s, 2 H), 6.65 (m, 1 H), 5.13 (s, 2 H), 5.12 (s, 2 H), 4.37 (d, J=9.6 Hz, 2 H), 4.13 (m, 4 H), 3.87 (s, 2 H), 3.37 (s, 3 H), 2.19 (s, 6 H), 1.27 (t, J=6.9 Hz, 6 H); TLC conditions: Uniplate silica gel, 250 microns; Mobile phase=75% ethyl acetate in hexanes; $R_f$=0.45.

Step b:

To a stirring solution of diethyl [4-(3'-benzyloxycarbonylamino-4'-methoxymethoxy-benzyl)-3,5-dimethylphenoxy]methylphosphonic (0.1 g, 0.175 mmol) in MeOH (2 mL) at room temperature was added HCl (0.18 mL, 10 N), and the reaction mixture was heated at 100° C. for 5 min by microwave. The solvent was removed under reduced pressure, and the residue was partitioned between EtOAc and sat. NaHCO$_3$. The organic layer was dried over Na$_2$SO$_4$, filtered and concentrated under reduced pressure. The crude product was purified by column chromatography on silica gel, eluting with ethyl acetate to afford diethyl [4-(3'-benzyloxycarbonylamino-4'-hydroxybenzyl)-3,5-dimethylphenoxy]methylphosphonate as a light yellow oil (0.076 g, 82%): $^1$H NMR (300 MHz, DMSO-$d_6$): δ 9.48 (s, 1 H), 8.34 (s, 1 H), 7.38 (m, 6 H), 6.71 (m, 3 H), 6.53 (m, 1 H), 5.11 (s, 2 H), 4.37 (d, J=9.6 Hz, 2 H), 4.13 (m, 4 H), 3.82 (s, 2 H), 2.19 (s, 6 H), 1.27 (t, J=6.9 Hz, 6 H); TLC conditions: Uniplate silica gel, 250 microns; Mobile phase=75% ethyl acetate in hexanes; $R_f$=0.40.

Step c:

To a stirring solution of diethyl [4-(3'-benzyloxycarbonylamino-4'-hydroxybenzyl)-3,5-dimethylphenoxy]methylphosphonic (0.076 g, 0.144 mmol) in CH$_2$Cl$_2$ (8 mL) at room temperature was added hexamethyldisilazane (0.28 mL, 1.27 mmol) and bromotrimethylsilane (0.15 mL, 1.15 mmol). The reaction mixture was stirred at room temperature for 16 hrs. The solvent was removed under reduced pressure, and the residue was partitioned between EtOAc and water. The organic layer was dried over Na$_2$SO$_4$, filtered and concentrated under reduced pressure. The crude product was washed by CH$_2$Cl$_2$ to afford the title compound as a white amorphous solid (0.03 g, 44%): $^1$H NMR (300 MHz, DMSO-$d_6$): δ 9.41 (s, 1 H), 8.30 (s, 1H), 7.33 (m, 6 H), 6.66 (m, 3 H), 6.48 (m, 1 H), 5.08 (s, 2 H), 3.97 (d, J=10.2 Hz, 2 H), 3.77 (s, 2 H), 2.13 (s, 6 H). mp: shrink at 180° C. LC-MS m/z=472 [C24H26NO7P+H]$^+$; Anal Calcd for (C24H26NO7P+ 1.1H$_2$O): C, 58.68; H, 5.79; N, 2.85. Found: C, 58.44; H, 5.89; N, 2.77.

Example 51

Compound 51-1: [3,5-dimethyl-4-(4'-Hydroxy-3'-methanesulfonylamino-benzyl)phenoxy]methylphosphonic acid Step a:

To a solution of diethyl [4-(3'-benzyloxycarbonylamino-4'-methoxymethoxybenzyl)-3,5-dimethylphenoxy]methylphosphonic (0.33 g, 0.58 mmol) in EtOH (20 mL) at room temperature was added Pd/C (50 mg). The reaction mixture was stirred at room temperature under 50 psi H$_2$ for 16 hrs then filtered through Celite®. The solvent was removed under reduced pressure to afford diethyl [4-(3'-amino-4'-methoxymethoxybenzyl)-3,5-dimethylphenoxy]methylphosphonate as a colorless oil (0.25 g, 99%): $^1$H NMR (300 MHz, DMSO-$d_6$): δ 6.76 (m, 3 H), 6.29 (d, J=2.4 Hz, 1 H), 6.12 (m, 1 H), 5.07 (s, 2 H), 4.69 (s, 2 H), 4.35 (d, J=10.2 Hz, 2 H), 4.12 (m, 4 H), 3.76 (s, 2 H), 3.39 (s, 3 H), 2.19 (s, 6 H), 1.27 (t, J=7 Hz, 6 H); TLC conditions: Uniplate silica gel, 250 microns; Mobile phase=75% ethyl acetate in hexanes; $R_f$=0.51.

Step b:

To a stirring solution of diethyl [4-(3'-amino-4'-methoxymethoxybenzyl)-3,5-dimethyl-phenoxy]methylphosphonic (0.13 g, 0.3 mmol) in CH$_2$Cl$_2$ (10 mL) at room temperature was added pyridine (0.037 mL, 0.45 mmol) and methanesulfonyl chloride (0.026 mL, 0.33 mmol). The reaction mixture was stirred at room temperature for 16 hrs. then partitioned between CH$_2$Cl$_2$ and water. The organic layer was dried over Na$_2$SO$_4$, filtered and concentrated under reduced pressure. The crude product was purified by column chromatography on silica gel, eluting with ethyl acetate to afford diethyl [3,5-dimethyl-4-(3'-methanesulfonylamino-4'-methoxymethoxy-benzyl)phenoxy]methylphosphonate as a light yellow oil (0.12 g, 77%): $^1$H NMR (300 MHz, DMSO-$d_6$): δ 8.91 (s, 1 H), 7.02 (d, J=8.4 Hz, 1 H), 6.96 (d, J=2.1 Hz, 1 H), 6.76 (m, 3 H), 5.18 (s, 2 H), 4.37 (d, J=9.9 Hz, 2 H), 4.16 (m, 4 H), 3.87 (s, 2 H), 3.41 (s, 3 H), 2.93 (s, 3 H), 2.19 (s, 6 H), 1.27 (t, J=6.9 Hz, 6 H); TLC conditions: Uniplate silica gel, 250 microns; Mobile phase=75% ethyl acetate in hexanes; $R_f$=0.42.

Step c:

To a stirring solution of diethyl[3,5-dimethyl-4-(3'-methanesulfonylamino-4'-methoxymethoxybenzyl)phenoxy]methyl-phosphonate (0.12 g, 0.23 mmol) in MeOH (2 mL) at room temperature was added HCl (1.2 mL, 2 N), and the reaction mixture was heated at 100° C. for 5 min by microwave. The solvent was removed under reduced pressure, and the residue was partitioned between EtOAc and sat. NaHCO$_3$. The organic layer was dried over Na$_2$SO$_4$, filtered and concentrated under reduced pressure. The crude product was purified by column chromatography on silica gel, eluting with ethyl acetate to afford diethyl[3,5-dimethyl-4-(4'-hydroxy-3'- methanesulfonylaminobenzyl) phenoxy]methylphosphonate as a white solid (0.08 g, 74%): $^1$H NMR (300 MHz, DMSO-d$_6$): δ 6.85 (d, J=1.8 Hz, 1 H), 6.76 (m, 3 H), 6.63 (m, 1 H), 4.37 (d, J=9.9 Hz, 2 H), 4.14 (m, 4 H), 3.82 (s, 2 H), 2.89 (s, 3 H), 2.18 (s, 6 H), 1.27 (t, J=6.9 Hz, 6 H); TLC conditions: Uniplate silica gel, 250 microns; Mobile phase=ethyl acetate; R$_f$=0.42.

Step d:

The title compound was prepared according to the procedure described in example 8, step f, (60 mg, 85%): $^1$H NMR (200 MHz, DMSO-d$_6$): δ 9.61 (s, 1 H), 8.61 (s, 1 H), 6.74 (m, 5 H), 4.02 (d, J=10.2 Hz, 2 H), 3.80 (s, 2 H), 2.88 (s, 3 H), 2.16 (s, 6 H); mp: shrinks at 200° C.; LC-MS m/z=416 [C17H22NO7PS+H]$^+$; Anal Calcd for (C17H22NO7PS+ 0.1MeOH+0.8H$_2$O): C, 47.43; H, 5.59; N, 3.23. Found: C, 47.57; H, 5.68; N, 3.10.

Using the appropriate starting materials, compounds 51-2 was prepared in an analogous manner to that described for the synthesis of compound 51-1

Compound 51-2: [3,5-Dimethyl-4-(4'-hydroxy-3'-trifluoroacetyl-aminobenzyl)phenoxy]methylphosphonic acid $^1$H NMR (200 MHz, DMSO-d$_6$): δ 10.41 (s, 1 H), 9.71 (s, 1 H), 6.95 (s, 1 H), 6.74 (m, 4 H), 4.03 (d, J=10.2 Hz, 2 H), 3.83 (s, 2 H), 2.16 (s, 6 H); mp: 170-172° C.; LC-MS m/z=434 [C18H19F3NO6P+H]$^+$; Anal Calcd for (C18H19F3NO6P+ 0.4H$_2$O): C, 49.08; H, 4.53; N, 3.18. Found: C, 49.26; H, 4.75; N, 2.83.

Compound 51-3: [3,5-dimethyl-4-(4'-Hydroxy-3'-isobutyrylaminobenzyl) phenoxy]methylphosphonic acid Step a:

Diethyl (3'-amino-4'-hydroxybenzyl)-3,5-dimethylphenoxy]-methylphosphonate was prepared according to the procedure described for the synthesis of example 51-1, step c: $^1$H NMR (200 MHz, DMSO-d$_6$): δ 8.70 (s, 1 H), 6.71 (s, 2 H), 6.48 (d, J=7.6 Hz, 1 H), 6.19 (s, 1 H), 6.01 (m, 1 H), 4.38 (s, 2 H), 4.33 (d, J=9.6 Hz, 2 H), 4.12 (m, 4 H), 3.70 (s, 2 H), 2.16 (s, 6 H), 1.23 (t, J=7.4 Hz, 6 H); TLC conditions: Uniplate silica gel, 250 microns; Mobile phase=75% ethyl acetate in hexanes; R$_f$=0.46.

Step b:

To a stirring solution of diethyl (3'-amino-4'-hydroxybenzyl)-3,5-dimethylphenoxy]methylphosphonate (0.046 g, 0.12 mmol) in THF (5 mL) at 0° C. was added pyridine (0.015 mL, 0.18 mmol) and isobutyric anhydride (0.021 mL, 0.13 mmol). The reaction mixture was stirred at 50° C. for 16 hrs. It was added EtOAc and water. The organic layer was dried over Na$_2$SO$_4$, filtered and concentrated under reduced pressure. The crude product was purified by column chromatography on silica gel, eluting with ethyl acetate to afford diethyl [3,5-dimethyl-4-(4'-hydroxy-3'-isobutyrylaminobenzyl) phenoxy]methylphosphonate as a yellow oil (0.046 g, 83%): $^1$H NMR (300 MHz, DMSO-d$_6$): δ 9.55 (s, 1 H), 9.22 (s, 1 H), 7.36 (s, 1 H), 6.73 (m, 3 H), 6.58 (m, 1 H), 4.36 (d, J=9.6 Hz, 2 H), 4.13 (m, 4 H), 3.82 (s, 2 H), 2.73 (m, 1 H), 2.19 (s, 6 H), 1.27 (t, J=6.9 Hz, 6 H), 1.07 (d, J=6.9 Hz, 6 H); TLC conditions: Uniplate silica gel, 250 microns; Mobile phase=80% ethyl acetate in hexanes; R$_f$=0.37.

Step c:

The title compound was prepared according to the procedure described for the synthesis of example 8, step f: $^1$H NMR (200 MHz, DMSO-d$_6$): δ 9.51 (s, 1 H), 9.22 (s, 1 H), 7.33 (s, 1 H), 6.72 (m, 3 H), 6.58 (m, 1 H), 4.03 (d, J=10.2 Hz, 2 H), 3.80 (s, 2 H), 2.71 (m, 1 H), 2.17 (s, 6 H), 1.06 (d, J=7.0 Hz, 6H); LC-MS m/z=408 [C20H26NO6P+H]$^+$; Anal Calcd for (C20H26NO6P+0.9H$_2$O+0.45HBr): C, 52.22; H, 6.19; N, 3.04; Br, 7.82. Found: C, 52.31; H, 6.42; N, 2.66; Br, 7.60.

Example 52

Compound 52: [3,5-dimethyl-4-(4'-Hydroxy-3'-isopropylbenzyl)-benzenesulfonyl]methylphosphonic acid Step a:

To a stirring solution of 3,5-dimethyl-4-(4'-methoxymethoxy-3'-iso-propylbenzyl)phenylamine (0.5 g, 1.6 mmol) at 80° C. in dimethyldisulfide (5 mL) was added isoamylnitrite (0.86 mL, 6.4 mmol). The reaction mixture was stirred at 80° C. for 1 h. The solvent was removed under reduced pressure. The crude product was purified by column chromatography on silica gel, eluting with ethyl acetate-hexanes (1:3) to afford 3,5-dimethyl-4-(4'-methoxymethoxy-3'-iso-propylbenzyl)methylsulfanylbenzene as a light yellow oil (0.24 g, 44%): $^1$H NMR (300 MHz, CDCl$_3$-d$_1$): δ 6.90-6.94 (m, 4H), 6.62 (m, 1 H), 5.19 (s, 2 H), 3.97 (s, 2 H), 3.50 (s, 3 H), 3.31 (m, 1 H), 2.52 (s, 3 H), 2.25 (s, 6 H) 1.20 (d, J=6.9 Hz, 6 H). TLC conditions: Uniplate silica gel, 250 microns; Mobile phase=ethyl acetate-hexanes (1:2); R$_f$=0.73.

Step b:

To a stirring solution of 3,5-dimethyl-4-(4'-methoxymethoxy-3'-iso-propylbenzyl)methylsulfanylbenzene (0.24 g, 0.7 mmol) at room temperature in CH$_2$Cl$_2$ (10 mL) was added m-CPBA (0.42 g, 2.45 mmol). The reaction mixture was stirred at room temperature for 16 hrs. It was quenched by sat. Na$_2$SO$_3$. The organic layer was washed by sat. NaHCO$_3$ and dried over Na$_2$SO$_4$, filtered and concentrated under reduced pressure to afford 3,5-dimethyl-4-(4'-methoxymethoxy-3'-iso-propylbenzyl)methylsulfonylbenzene as a light yellow oil (0.23 g, 87%): $^1$H NMR (200 MHz, CDCl$_3$-d$_1$): δ 7.62 (s, 2 H), 6.88 (m, 2 H), 6.55 (m, 1 H), 5.16 (s, 2 H), 4.10 (s, 2 H), 3.46 (s, 3 H), 3.28 (m, 1 H), 3.06 (s, 3 H), 2.33 (s, 6 H) 1.17 (d, J=6.9 Hz, 6 H). TLC conditions: Uniplate silica gel, 250 microns; Mobile phase=ethyl acetate-hexanes (1:2); R$_f$=0.46.

Step c:

To a stirring solution of 3,5-dimethyl-4-(4'-methoxymethoxy-3'-iso-propylbenzyl)methylsulfonylbenzene (0.23 mL, 0.61 mmol) in THF (10 mL) at −78° C. was added n-BuLi (2.5 M in hexanes, 0.29 mL), the reaction mixture was stirred at −78° C. for 1 hr and at 0° C. for 40 min, then diethyl phosphorochloridate (0.11 mL, 0.73 mmol) was added at 0° C. The reaction mixture was stirred at room temperature for 1 hr. The reaction mixture was quenched with saturated NH$_4$Cl and diluted with diethyl ether. The organic layer was dried over Na$_2$SO$_4$, filtered and concentrated under reduced pressure. The residue was purified by column chromatography on silica gel, eluting with ethyl acetate to afford diethyl [3,5-dimethyl-4-(4'-methoxymethoxy-3'-iso-propylbenzyl)phenylsulfonyl]methylphosphonate as a light yellow oil (130 mg, 42%): $^1$H NMR (200 MHz, DMSO-d$_6$): δ 7.63 (s, 2H), 7.00 (d, J=3.0 Hz, 1 H), 6.88 (d, J=8.4 Hz, 1 H), 6.60 (dd, J=3.0, 8.4 Hz, 1 H), 5.15 (s, 2 H), 4.36 (d, J=17.2 Hz, 2 H), 3.97 (m, 6 H), 3.36 (s, 3 H), 3.22 (m, 1 H), 2.31 (s, 6 H), 1.19 (m, 12 H). TLC conditions: Uniplate silica gel, 250 microns; Mobile phase=ethyl acetate-hexanes (3:1); R$_f$=0.43.

Step d:

The title compound was prepared by the procedure described for the synthesis of example 8, step f: $^1$H NMR (200

MHz, DMSO-d$_6$): δ 9.08 (s, 1H), 7.61 (s, 2 H), 6.89 (d, J=3.0 Hz, 1 H), 6.62 (d, J=8.0 Hz, 1 H), 6.43 (d, J=3.0, 8.0 Hz, 1 H), 3.96 (s, 2 H), 3.85 (d, J=16.6 Hz, 2 H), 3.13 (m, 1 H), 2.28 (s, 6 H), 1.10 (d, J=6.8 Hz, 6 H); LC-MS m/z=413 [C19H25O6PS+H]$^+$; Anal Calcd for (C19H25O6PS+ 1.0H$_2$O+0.15HBr +0.2Et$_2$O): C, 51.99; H, 6.42; Br, 2.62. Found: C, 51.67; H, 6.50; Br, 2.62.

Example 53

Compound 53: [3,5-dimethyl-4-(4'-Hydroxy-3'-iso-propylphenoxy)-benzenesulfonyl]methylphosphonic acid Step a:
To a stirring solution of 4-bromo-2,6-dimethylphenol (6 g, 29.85 mmol) in CH$_2$Cl$_2$ (80 mL) at 0° C. was added imidazole (4.1 g, 59.70 mmol) and triisopropylsilyl chloride (7.1 mL, 32.84 mmol). The reaction mixture was stirred at room temperature for 16 hrs. The solvent was removed under reduced pressure and the residue was partitioned between ethyl acetate and water. The organic layer was dried over Na$_2$SO$_4$, filtered and concentrated under reduced pressure. The crude product was purified by column chromatography on silica gel, eluting with ethyl acetate-hexanes (1:9) to afford (4-bromo-2,6-dimethylphenoxy)triisopropylsilane as a colorless oil (1.6 g, 15%): $^1$H NMR (300 MHz, DMSO-d$_6$): δ 7.19 (s, 2 H), 2.20 (s, 6 H), 1.29 (m, 3 H), 1.10 (d, J=7.2 Hz, 18 H). TLC conditions: Uniplate silica gel, 250 microns; Mobile phase=ethyl acetate-hexanes (5:95); R$_f$=0.70.

Step b:
To a stirring solution of (4-bromo-2,6-dimethylphenoxy)-triisopropylsilane (0.5 g, 1.4 mmol) in THF (15 mL) at −78° C. was added n-BuLi (2.5 M in hexanes, 0.56 mL), the reaction mixture was stirred at −78° C. for 1 hr, then dimethyldisulfide (0.16 mL, 1.82 mmol) was added at −78° C. The reaction mixture was stirred at room temperature for 1 h and quenched with saturated NH$_4$Cl and diluted with diethyl ether. The organic layer was dried over Na$_2$SO$_4$, filtered and concentrated under reduced pressure to afford crude (2,6-dimethyl-4-methylsulfanylphenoxy)triisopropyl-silane as an oil (0.46 g, 100%): $^1$H NMR (300 MHz, DMSO-d$_6$): δ 6.92 (s, 2 H), 2.41 (s, 3 H), 2.20 (s, 6 H), 1.29 (m, 3 H), 1.10 (d, J=7.2 Hz, 18 H). TLC conditions: Uniplate silica gel, 250 microns; Mobile phase=ethyl acetate-hexanes (2:98); R$_f$=0.57.

Step c:
To a stirring solution of (2,6-dimethyl-4-methylsulfanylphenoxy)triisopropyl-silane (0.46 g, 1.4 mmol) in CH$_2$Cl$_2$ (15 mL) at room temperature was added m-CPBA (0.85 g, 4.9 mmol). The reaction mixture was stirred at room temperature for 16 hrs. It was quenched by sat. Na$_2$SO$_3$. The organic layer was washed by sat. NaHCO$_3$ and dried over Na$_2$SO$_4$, filtered and concentrated under reduced pressure to afford crude (2,6-dimethyl-4-methanesulfonylphenoxy)triisopropylsilane as an oil (0.47 g, 94%): $^1$H NMR (200 MHz, DMSO-d$_6$): δ 7.57 (s, 2 H), 3.14 (s, 3 H), 2.28 (s, 6H), 1.19 (m, 3 H), 1.10 (d, J=7.2 Hz, 18 H). TLC conditions: Uniplate silica gel, 250 microns; Mobile phase=ethyl acetate-hexanes (5:95); R$_f$=0.49.

Step d:
To a stirring solution of (2,6-dimethyl-4-methanesulfonylphenoxy)triisopropylsilane (0.47 g, 1.32 mmol) in THF (15 mL) at −78° C. was added n-BuLi (2.5 M in hexanes, 0.58 mL), the reaction mixture was stirred at −78° C. for 1 hr, then diethyl phosphorochloridate (0.25 mL, 1.72 mmol) was added at −78° C. The reaction mixture was stirred at room temperature for 16 hrs. The reaction mixture was quenched with saturated NH$_4$Cl and diluted with diethyl ether. The organic layer was dried over Na$_2$SO$_4$, filtered and concentrated under reduced pressure. The residue was purified by column chromatography on silica gel, eluting with ethyl acetate-hexanes (1:1) to afford diethyl (3,5-dimethyl-4-triisopropylsilanyloxy-benzenesulfonyl)methylphosphonate as a colorless oil (0.1 g, 15%): $^1$H NMR (200 MHz, CDCl$_3$-d$_6$): δ 7.57 (s, 2 H), 4.17 (m, 4 H), 3.71 (d, J=17.2 Hz, 2H), 2.29 (s, 6 H), 1.33 (m, 9 H), 1.10 (d, J=7.2 Hz, 18 H). TLC conditions: Uniplate silica gel, 250 microns; Mobile phase=ethyl acetate-hexanes (1:1); R$_f$=0.45.

Step e:
To a stirring solution diethyl (3,5-dimethyl-4-triisopropylsilanyloxy-benzenesulfonyl)methylphosphonate in THF (3 mL) at room temperature was added TBAF (0.3 mL, 1 M in THF). It was stirred at room temperature for 2 hrs. The solvent was removed under reduced pressure and the residue was partitioned between ethyl acetate and water. The organic layer was dried over Na$_2$SO$_4$, filtered and concentrated under reduced pressure. The crude product was purified by column chromatography on silica gel, eluting with ethyl acetate-hexanes (5:1) to afford diethyl (3,5-dimethyl-4-hydroxybenzenesulfonyl)methylphosphonate as a light yellow oil (70 mg, 100%): $^1$H NMR (300 MHz, CDCl$_3$-d$_6$): δ 7.54 (s, 2 H), 4.12 (m, 4 H), 3.65 (d, J=16.8 Hz, 2 H), 2.22 (s, 6 H), 1.22 (d, J=7.2 Hz, 6 H). TLC conditions: Uniplate silica gel, 250 microns; Mobile phase=ethyl acetate-hexanes (5:1); R$_f$=0.44.

Step f:
To a stirring mixture of bis(4-methoxy-3-iso-propylphenyl)iodonium tetrafluoroborate (0.15 g, 0.3 mmol) and copper powder (16 mg, 0.26 mmol) in CH$_2$Cl$_2$ (5 mL) at 0° C. was added a solution of triethylamine (0.031 mL, 0.22 mmol) and diethyl (3,5-dimethyl-4-hydroxybenzenesulfonyl)-methylphosphonate (70 mg, 0.2 mmol) in CH$_2$Cl$_2$ (2 mL). The reaction mixture was stirred at room temperature for 16 hrs and filtered through a Celite plug. The solvent was removed under reduced pressure and the crude product was purified by column chromatography on silica gel, eluting with ethyl acetate-hexanes (5:1) to afford diethyl[3,5-dimethyl-4-(4'-methoxy-3'-iso-propylphenoxy)benzenesulfonyl]methylphosphonate as a light yellow oil (40 mg, 41%): $^1$H NMR (200 MHz, DMSO-d$_6$): δ 7.76 (s, 2 H), 6.79 (m, 2 H), 6.35 (m, 1 H), 4.44 (d, J=16.8 Hz, 2 H), 4.02 (m, 4 H), 3.73 (s, 3 H), 3.18 (m,1 H), 2.14 (s, 6 H), 1.15 (m, 12 H); TLC conditions: Uniplate silica gel, 250 microns; Mobile phase=ethyl acetate-hexanes (3:2); R$_f$=0.49.

Step g:
The title compound was prepared according to the procedure described for the synthesis of example 22, step d, (40 mg, 0.083 mmol): $^1$H NMR (200 MHz, DMSO-d$_6$): δ 9.02 (s, 1 H), 7.70 (s, 2 H), 6.67 (m, 2 H), 6.19 (dd, J=3.0, 8.4 Hz, 1 H), 3.72 (d, J=15.8 Hz, 2 H), 3.14 (m, 1 H), 2.09 (s, 6 H), 1.11 (d, J=6.6 Hz, 6 H); LC-MS m/z=415 [C18H23O7PS+H]$^+$; Anal Calcd for (C18H23O7PS+1.3H$_2$O+0.1EtOAc): C, 49.48; H, 5.96. Found: C, 49.18; H, 5.67.

Example 54

Compound 54: [3,5-Dimethyl-4-(4'-hydroxy-3'-iso-propylphenoxy)-benzenesulfanyl]methylphosphonic acid Step a:
To a stirring solution of (2,6-dimethyl-4-methylsulfanylphenoxy)triisopropylsilane (2.18 g, 6.72 mmol) in CCl$_4$ (25 mL) at room temperature was added N-chlorosuccinimide (0.99 g, 7.39 mmol). The reaction mixture was stirred at room temperature for 16 hrs and filtered through a Celite plug. The solvent was removed under reduced pressure to afford crude (4-chloromethylsulfanyl-2,6-dimethylphenoxy)triisopropylsilane as an oil (2.4 g, 100%). This crude oil was dissolved into phosphorous acid triethyl ester (1.5 mL). It was heated at 180° C. for 30 min by microwave. The solvent was removed under reduced pressure and the residue was purified by column chromatography on silica gel, eluting with ethyl acetate-hexanes (1:1) to afford diethyl (3,5-dimethyl-4-triisopropyl-silanyloxy-phenylsulfanyl)methylphosphonate as a yellow oil (1.6 g, 52%): $^1$H NMR (200 MHz, DMSO-d$_6$): δ 7.09 (s, 2 H), 4.98 (m, 4 H), 3.31 (d, J=13.8 Hz, 2 H), 2.17 (s, 6 H), 1.25 (m, 9 H), 1.09 (d, J=7.0 Hz, 18 H). TLC conditions: Uniplate silica gel, 250 microns; Mobile phase=ethyl acetate/Hexanes (2:3); R$_f$=0.45.

Step b:

The title compound was prepared according to the procedure described for the synthesis of example 53, steps e, f and g: $^1$H NMR (300 MHz, DMSO-d$_6$): δ 8.91 (s, 1 H), 7.16 (s, 2 H), 6.64 (m, 2 H), 6.21 (dd, J=3.3, 8.7 Hz, 1H), 4.13 (m, 3 H), 2.02 (s, 6 H), 1.11 (d, J=6.9 Hz, 6 H); LC-MS m/z=383 [C18H23O5PS+H]$^+$; Anal Calcd for (C18H23O5PS+ 0.15TFA+0.2Et$_2$O): C, 55.00; H, 5.98. Found: C, 54.88; H, 5.76.

Example 55

Compound 55: [3,5-Dimethyl-4-(4'-hydroxy-3'-methylsulfanyl-benzyl)-phenoxy]methylphosphonic acid Step a:

To a stirring solution of diethyl [3,5-dimethyl-4-(3'-amino-4'-methoxymethoxybenzyl)phenoxy]methylphosphonate (Example 51, step a; 0.29 g, 0.66 mmol) at 80° C. in dimethyldisulfide (3 mL) was added isoamyl nitrite (0.4 mL, 2.64 mmol). The reaction mixture was stirred at 80° C. for 1 h. The solvent was removed under reduced pressure. The crude product was purified by column chromatography on silica gel, eluting with ethyl acetate-hexanes (1:1) to afford diethyl [3,5-dimethyl-4-(3'-methylsulfanyl-4'-methoxymethoxy-benzyl)phenoxy]methylphosphonate as a red oil (0.12 g, 39%): $^1$H NMR (200 MHz, DMSO-d$_6$): δ 6.91 (d, J=8.4 Hz, 1 H), 6.86 (d, J=2.1 Hz, 1 H), 6.75 (s, 2 H), 6.58 (dd, J=2.2, 8.4 Hz, 1 H), 5.16 (s, 2 H), 4.36 (d, J=10.0 Hz, 2 H), 4.11 (m, 4 H), 3.89 (s, 2 H), 3.37 (s, 3 H), 2.30 (s, 3H), 2.17 (s, 6 H), 1.25 (t, J=7.0 Hz, 6 H); TLC conditions: Uniplate silica gel, 250 microns; Mobile phase=50% ethyl acetate in hexanes; R$_f$=0.61.

Step b:

The title compound was prepared according to the procedure described for the synthesis of example 8, step f as a yellow foam (40 mg, 42%). $^1$H NMR (300 MHz, DMSO-d$_6$): δ 9.58 (s, 1 H), 6.80 (d, J=2.1 Hz, 1 H), 6.72 (s, 2 H), 6.66 (d, J=8.4 Hz, 1 H), 6.50 (dd, J=2.1, 8.4 Hz, 1 H), 4.06 (d, J=10.2 Hz, 2 H), 3.84 (s, 2 H), 2.28 (s, 3 H), 2.18 (s, 6 H); LC-MS m/z=369 [C$_{17}$H$_{21}$O$_5$PS+H]$^+$; Anal Calcd for (C$_{17}$H$_{21}$O$_5$PS+ 0.1EtOAc+0.1TFA): C, 54.40; H, 5.68. Found: C, 54.65; H, 5.33.

Example 56

Compound 56: 3,5-Dicyano-4-(4'-hydroxy-3'-iso-propylphenoxy]-methylphosphonate

Step a:

To a solution of 4-benzoyloxyphenol (0.2 g, 0.93 mmol) in dichloromethane (9.3 mL) at 0° C. was added bis(pyridine) iodonium tetrafluoroborate (0.76 g, 2.06 mmol). The reaction mixture was stirred at room temperature for 1 h. The solvent was removed under reduced pressure and the residue was purified by column chromatography on silica gel, eluting with acetone-hexanes (1:9) to afford 4-benzoyloxy-3,5-diiodophenol as an off-white solid (0.22 g, 50%): $^1$H NMR (300 MHz, DMSO-d$_6$): δ 9.60 (s, 1 H), 8.06 (m, 2 H), 7.72 (s, 2 H), 7.59 (m, 3 H); TLC conditions: Uniplate silica gel, 250 microns; Mobile phase=hexanes-acetone (4:1); R$_f$=0.45.

Step b:

To a mixture of bis(4-methoxy-3-iso-propylphenyl)iodonium tetrafluoroborate (0.77 g, 1.51 mmol) and copper powder (0.13 g, 2.01 mmol) in CH$_2$Cl$_2$ (4.4 mL) at 0° C. was added a solution of TEA (0.15 mL, 1.10 mmol) and 4-benzoyloxy-3,5-diiodophenol (0.47 g, 1.00 mmol) in dichloromethane (4.0 mL). The reaction mixture was stirred at room temperature for 24 h and filtered through a Celite plug. The solvent was removed under reduced pressure and the residue was purified by column chromatography on silica gel, eluting with acetone-hexanes (1:9) to afford 3,5-diiodo-4-(4'-methoxy-3'-iso-propylphenoxy)phenyl benzoate as an off-white solid (0.61 g, 98%): $^1$H NMR (300 MHz, DMSO-d$_6$): δ 8.10 (m, 2H), 7.96 (s, 2 H), 7.73 (m, 1 H), 7.60 (m, 2 H), 6.85 (d, J=9.0 Hz, 1H), 6.73 (d, J=3.0 Hz, 1H), 6.35 (m, 1 H), 3.74 (s, 3 H), 3.21 (m, 1 H), 1.13 (d, J=6.0 Hz, 6 H); TLC conditions: Uniplate silica gel, 250 microns; Mobile phase=hexanes-acetone (1:9); R$_f$=0.42.

Step c:

To a stirred solution of 3,5-diiodo-4-(4'-methoxy-3'-iso-propylphenoxy)phenyl benzoate (0.4 g, 0.76 mmol) in DMF (5.0 mL) at rt was added CuCN (0.27 g, 3.0 mmol). The reaction mixture was heated at 160° C. for 5 min under microwave irradiation, the reaction mixture was cool to room temperature and poured into 1N HCl (50 mL) and extracted with ethyl acetate (100 mL×2). The organic layers were dried over Na$_2$SO$_4$, filtered and concentrated under reduced pressure. The residue was purified by column chromatography on silica gel, eluting with ethyl acetate-hexanes (3:7) to afford 3,5-dicyano-4-(4'-methoxy-3'-iso-propylphenoxy)phenol as a viscous oil (105 mg, 35%): $^1$H NMR (300 MHz, CDCl$_3$): δ 7.35 (s, 2 H), 6.99 (d, J=3.0 Hz, 1 H), 6.78 (d, J=8.7 Hz, 1 H), 6.99 (dd, J=3.0, 8.7 Hz, 1 H), 3.84 (s, 3 H), 3.38-3.30 (m, 1 H), 1.21 (d, J=6.9 Hz, 6 H); TLC conditions: Uniplate silica gel, 250 microns; Mobile phase=hexanes-ethyl acetate (7:3); R$_f$=0.38.

Step d:

3,5-dicyano-4-(4'-hydroxy-3'-iso-propylphenoxy)phenol was prepared according to the procedure described for the synthesis of compound 54, step d (132 mg, 32%): $^1$H NMR (300 MHz, CD$_3$OD) δ 7.38 (s, 2 H), 6.81 (d, J=3.0 Hz, 1 H), 6.70 (d, J=9.0 Hz, 1 H), 6.52 (dd, J=9.0, 3.0 Hz, 1 H), 3.26 (heptuplet, J=7.0 Hz, 1 H), 1.18 (d, J=7.0 Hz, 6 H); TLC conditions: Merck silica gel, 250 microns; Mobile phase=hexanes-ethyl acetate (1:1), R$_f$=0.35.

Step e:

Diethyl trifluoromethanesulfonyloxymethylphosphonate (148 mg, 0.5 mmol) was added to an heterogeneous mixture of 3,5-dicyano-4-(4'-hydroxy-3'-iso-propylphenoxy)phenol (132 mg, 0.45 mmol) and cesium carbonate (440 mg, 1.35 mmol) in DMF at rt. After stirring at rt for 1 week, the reaction mixture was diluted with ethyl acetate and the pH lowered to 1 with 1 N hydrochloric acid. The organics were washed with water then brine, dried over sodium sulfate and concentrated under reduced pressure. The residue was purified by column chromatography (silica gel, hexanes/ethyl acetate 50/50 to 0/100) to give diethyl 3,5-dicyano-4-(4'-hydroxy-3'-iso-propylphenoxy)methylphosphonate (44 mg, 22%): $^1$H NMR (300 MHz, CDCl$_3$) δ 7.42 (s, 2H), 6.73 (d, J=3.0 Hz, 1H), 6.68 (d, J=9.0 Hz, 1H), 6.57 (dd, J=9.0, 3.0 Hz, 1H), 4.35-4.20 (m, 6H), 3.23 (heptuplet, J=7.0 Hz, 1H), 1.38 (t, J=7.0 Hz, 6H), 1.18 (d, J=7.0 Hz, 6H); TLC conditions: Merck silica gel, 250 microns; Mobile phase=hexanes-ethyl acetate (1:1), $R_f$=0.2.

Step f:

The title compound was prepared by the procedure described for the synthesis of compound 8, step f (18 mg, 47%): $^1$H NMR (300 MHz, CD$_3$OD) δ 7.74 (s, 2H), 6.85 (d, J=3.0 Hz, 1H), 6.72 (d, J=9.0 Hz, 1H), 6.56 (dd, J=9.0, 3.0 Hz, 1H), 4.35 (d, J=6.8 Hz 2H), 3.27 (heptuplet, J=7.0 Hz, 1H), 1.18 (d, J=7.0 Hz, 6H); Anal. Calcd for (C$_{18}$H$_{17}$N$_2$O$_6$P+1.4H$_2$O): C, 52.28; H, 4.83; N, 6.77. Found: C, 52.55; H, 4.90; N, 6.12.

Example 57

Compound 57: [4,6-dichloro-3-fluoro-5-(4'-hydroxy-3'-iso-propylphenoxy)-pyrid-2-yloxy]methyl phosphonic acid Step a:

To a stirring solution of 3,5-dichloro-2,6-difluoro-4-(4'-methoxymethoxy-3'-iso-propyl-phenoxy)-pyridine (0.11 g, 0.29 mmol) and diethyl hydroxymethyl-phosphonate (0.045 mL, 0.31 mmol) in THF (3 mL) at 0° C. was added NaH (13 mg, 0.31 mmol). The reaction mixture was stirred at room temperature for 16 hrs, diluted with EtOAc and washed with water (30 mL×2). The solvent was removed under reduced pressure. The crude product was purified by column chromatography on silica gel, eluting with ethyl acetate-hexanes (2:1) to afford diethyl [4,6-dichloro-3-fluoro-5-(4'-hydroxy-3'-iso-propylphenoxy)-pyrid-2-yloxy]methyl phosphonate as a yellow oil (43 mg, 28%): $^1$H NMR (300 MHz, DMSO-d$_6$): δ 7.00 (d, J=9.0 Hz, 1 H), 6.96 (d, J=3.3 Hz, 1 H), 6.67 (dd, J=3.3, 9.0 Hz, 1 H), 5.19 (s, 2 H), 4.77 (d, J=8.1 Hz, 2 H), 4.15 (m, 4 H), 3.40 (s, 3 H), 3.28 (m, 1 H), 1.27 (t, J=7.2 Hz, 6H), 1.17 (d, J=6.6 Hz, 6 H); TLC conditions: Uniplate silica gel, 250 microns; Mobile phase=66% ethyl acetate in hexanes; $R_f$=0.31.

Step b:

The title compound was prepared according to the procedure described for the synthesis of example 8, step f as a white solid (30 mg, 71%): mp: 139-141° C.; $^1$H NMR (200 MHz, DMSO-d$_6$): δ 9.22 (s, 1 H), 6.84 (d, J=2.8 Hz, 1H), 6.68 (d, J=8.8 Hz, 1 H), 6.47 (dd, J=2.8, 8.8 Hz, 1 H), 4.46 (d, J=8.8 Hz, 2 H), 3.17 (m, 1 H), 1.13 (d, J=6.6 Hz, 6 H); LC-MS m/z=427 [C$_{15}$H$_{15}$Cl$_2$FNO$_6$P+H]$^+$; Anal Calcd for (C$_{15}$H$_{15}$C$_2$FNO$_6$P+0.5H$_2$O): C, 41.40; H, 3.71; N, 3.22. Found: C, 41.09; H, 3.87; N, 2.89.

Example 58

Compound 58: [4-(4'-Acetoxy-3'-iso-propylbenzyl)-3,5-dimethylphenoxy]-methylphosphonic acid A mixture of [3,5-Dimethyl-4-(4'-hydroxy-3'-iso-propylbenzyl)] phenoxy]methyl phosphonic acid (5.0 g, 13.7 mmol) and acetic anhydride (5.0 g, 48.9 mmol) in toluene (70 mL) was stirred at 20° C. for 3 hrs. Water (5 mL) was added and the mixture was stirred 1 hr. The solvent was removed under reduced pressure. Toluene (50 mL) was added to the residue then removed under reduced pressure. Toluene addition and evaporation was repeated twice more. The resulting solid was dried under vacuum at 45° C. to give the title compound (5.6 g, 100%). A purified sample (420 mg) was obtained by stirring the crude product in boiling isopropyl ether, cooling to 20° C., collecting the solid by filtration, and drying under vacuum. mp: 169-172° C.; $^1$H NMR (300 MHz, DMSO-d$_6$): δ 7.06 (d, J=2.1 Hz, 1H), 6.85 (d, J=8.4 Hz, 1H), 6.70 (s, 2H), 6.65 (dd, J=9.0 and 2.4 Hz, 1H), 4.02 (d, J=10.2 Hz, 2H), 3.90 (s, 2H), 2.94-2.84 (m, 1H), 2.25 (s, 3H), 2.15 (s, 6H), 1.07 (d, J=6.9 Hz, 6H). Anal. Calcd for (C$_{21}$H$_{27}$O$_6$P): C, 62.06; H, 6.70. Found: C, 62.22; H, 6.82.

Example 59

Cis and Trans (S)-2-[(4-(4'-Acetoxy-3'-iso-propyl-benzyl)-3,5-dimethylphenoxy)methyl]-4-(3-chlorophenyl)-2-oxo-2λ$^5$-[1,3,2]-dioxaphosphonane A solution of oxalyl chloride (3.0 g, 23.6 mmol) in dichloromethane (14 mL) was added over 20 minutes to a stirring suspension of [4-(4'-acetoxy-3'-iso-propylbenzyl)-3,5-dimethylphenoxy]methylphosphonic acid (3.2 g, 7.88 mmol) in dichloromethane (50 mL). The resulting solution was stirred at 20° C. for 1 hr. then the solvent was removed under reduced pressure. Dichloromethane (30 mL) was added to the residue then evaporated under reduced pressure. The resulting oil was dissolved in THF (32 mL) and the solution was added over 40 minutes to a stirring solution of (S)-1-(3-chlorophenyl)-1,3-propanediol (1.5 g, 7.88 mmol) and triethylamine (2.4 g, 23.6 mmol) in THF (32 mL) while keeping the temperature below −70° C. The reaction mixture was stirred at −70° C. for 2 hrs. then warmed to 15° C. To the reaction mixture was added 0.5 M aqueous HCl (32 mL) and ethyl acetate (32 mL). The phases were separated and the aqueous layer was extracted with ethyl acetate (32 mL). The combined organic layers were washed with brine, dried over magnesium sulfate, and filtered. The solvent was removed under reduced pressure. The crude product was purified by chromatography on silica gel, eluting with ethyl acetate-hexanes (50%-100%) to afford:

Compound 59-trans: (610 mg, 14%): $^1$H NMR (300 MHz, DMSO-d$_6$): δ 7.48-7.36 (m, 4H), 7.07 (d, J=2.1 Hz, 1H), 6.85 (d, J=8.4 Hz, 1H), 6.83 (s, 2H), 6.64 (dd, J=9.0 and 2.0 Hz, 1H), 5.85-5.82, (m, 1H), 4.74-4.68 (m, 1H), 4.61 (d, J=9.3 Hz, 2H), 4.52-4.42 (m, 1H), 3.92 (s, 2H), 2.94-2.85 (m, 1H), 2.25 (s, 3H), 2.24-2.20 (m, 2H), 2.17 (s, 6H), 1.07 (d, J=6.9 Hz, 6H). TLC conditions: Uniplate silica gel, 250 microns; Mobile phase=dichloromethane-acetone (9:1); $R_f$=0.5.

Compound 59-cis: (2.5 g, 57%): $^1$H NMR (300 MHz, DMSO-d$_6$): δ 7.47 (m, 1H), 7.38-7.26 (m, 3H), 7.06 (d, J=2.1 Hz, 1H), 6.85 (d, J=8.7 Hz, 1H), 6.76 (s, 2H), 6.67 (dd, J=8.1 and 2.1 Hz, 1 H), 5.76-5.72 (m, 1H), 4.61-4.36 (m, 4H), 3.92 (s, 2H), 2.94-2.85 (m, 1H), 2.25 (s, 3H), 2.20-2.19 (m, 2H), 2.16 (s, 6H), 1.07 (d, J=6.9 Hz, 6H). TLC conditions: Uniplate silica gel, 250 microns; Mobile phase=dichloromethane-acetone (9:1); $R_f$=0.35; Anal Calcd for (C$_{30}$H$_{34}$ClO$_6$P+0.13H$_2$O): C, 64.42; H, 6.17. Found: C, 64.12; H, 6.07.

Example 60

Compound 60: [4-(4'-Hydroxy-3'-iso-propyl-2'-methylbenzyl)-3-methylphenoxy]methylphosphonic acid Step a:

To a stirring solution of 1-bromo-3-iso-propyl-4-methoxy-2-methyl-benzene (compound 7-16, step c; 0.7 g, 2.88 mmol) in THF (20 mL) at −78° C. was added n-BuLi (1.6 mL, 2.5 M in hexanes). The mixture was stirred at −78° C. for 1 hr and 4-methoxy-2-methyl-benzaldehyde (0.37 mL, 2.74 mmol) was added. The reaction mixture was stirred at −78° C. for 1 hr, allowed to warm to room temperature and stirred for 1 hr. The reaction mixture was quenched with saturated NH$_4$Cl and diluted with diethyl ether. The organic layer was dried over Na$_2$SO$_4$, filtered and concentrated under reduced pressure to afford crude (4'-methoxy-3'-iso-propyl-2'-methylphenyl)-(4-methoxy-2-methylphenyl)-methanol as a light yellow oil (1.0 g, 100%). This crude oil was dissolved into EtOAc (25 mL) and AcOH (5 mL) and Pd/C (0.1 g) was added. After stirring at rt for 6 hours, the reaction mixture was filtered through the Celite and concentrated under reduced pressure to afford crude 4-(4'-methoxy-2'-methyl-3'-iso-propylbenzyl)-3-methyl-anisole as a yellow oil (0.8 g, 93%): $^1$H NMR (300 MHz, DMSO-d$_6$): δ 6.88-6.80 (m, 5 H), 3.77 (s, 2 H), 3.74 (s, 3 H), 3.71 (s, 3. H), 3.34 (m, 1 H), 2.22 (s, 3 H), 2.14 (s, 3 H), 1.28 (d, J=6.9 Hz, 6 H); TLC conditions: Uniplate silica gel, 250 microns; Mobile phase=8% ethyl acetate in hexanes; R$_f$=0.56.

Step b:

To a stirring solution of 4-(4'-methoxy-2'-methyl-3'-iso-propylbenzyl)-3-methyl-anisole (0.8 g, 2.68 mmol) in CH$_2$Cl$_2$ (10 mL) at −20° C. was added BBr$_3$ (10.7 mL, 1M in CH$_2$Cl$_2$). The reaction mixture was stirred at room temperature for 16 hrs. Ice was add and the mixture was diluted with CH$_2$Cl$_2$. The organic layer was dried over Na$_2$SO$_4$, filtered and concentrated under reduced pressure. The crude product was purified by column chromatography on silica gel, eluting with ethyl acetate/hexanes (1:1) to afford 4-(4'-hydroxy-2'-methyl-3'-iso-propylbenzyl)-3-methylphenol as a yellow solid (0.54 g, 75%): $^1$H NMR (200 MHz, DMSO-d$_6$): δ 9.03 (s, 1 H), 8.84 (s, 1 H), 6.41-6.60 (m, 5 H), 3.65 (s, 2 H), 3.33 (m, 1 H), 2.12 (s, 3 H), 2.08 (s, 3 H), 1.27 (d, J=6.9 Hz, 6 H); TLC conditions: Uniplate silica gel, 250 microns; Mobile phase=20% ethyl acetate in hexanes; R$_f$=0.31.

Step c:

To a solution of 44-(4'-hydroxy-2'-methyl-3'-iso-propylbenzyl)-3-methylphenol (0.54 g, 2 mmol) in DMF (15 mL) at room temperature was added Cs$_2$CO$_3$ (2.6 g, 8 mmol) and diethyl trifluoromethanesulfonyloxymethylphosphonate (0.66 g, 2.2 mmol). The reaction mixture was stirred at room temperature for 1 hr. The solvent was removed under reduced pressure and the residue was partitioned between ethyl acetate and saturated NaHCO$_3$. The organic layer was dried over Na$_2$SO$_4$, filtered and concentrated under reduced pressure. The crude product was purified by column chromatography on silica gel, eluting with ethyl acetate-hexanes (4:1) to afford diethyl [4-(4'-hydroxy-3'-iso-propyl-2'-methylbenzyl)-3-methylphenoxy]methylphosphonate as a colorless oil (0.14 g, 17%): $^1$H NMR (300 MHz, DMSO-d$_6$): δ 8.89 (s, 1 H), 6.86 (d, J=2.7 Hz, 1H), 6.76 (dd, J=2.7, 9.0 Hz, 1 H), 6.67 (d, J=9.0 Hz, 1 H), 6.51 (m, 2 H), 4.36 (d, J=9.6 Hz, 2 H), 4.11 (m, 4 H), 3.73 (s, 2 H), 3.34 (m, 1 H), 2.22 (s, 3 H), 2.09 (s, 3 H), 1.27 (m, 12 H); TLC conditions: Uniplate silica gel, 250 microns; Mobile phase=66% ethyl acetate in hexanes; R$_f$=0.45.

Step d:

The title compound was prepared according to the procedure described for the synthesis of example 8, step f as a white solid (80 mg, 67%): $^1$H NMR (300 MHz, DMSO-d$_6$): 8.88 (s, 1 H), 6.85 (d, J=2.1 Hz, 1 H), 6.73 (dd, J=2.1, 8.7 Hz, 1 H), 6.66 (d, J=8.7 Hz, 1 H), 6.51 (m, 2 H), 4.02 (d, J=10.2 Hz, 2 H), 3.73 (s, 2 H), 3.34 (m, 1 H), 2.22 (s, 3 H), 2.10 (s, 3 H), 1.30 (d, J=6.9 Hz, 6 H); mp: 166-168° C.; LC-MS m/z=363 [C19H25O5P−H]$^−$; Anal Calcd for (C19H25O5P+0.13HBr): C, 60.87; H, 6.76; Br, 2.77. Found: C, 61.19; H, 6.84; Br, 3.10.

Example 61

Compound 61-1: [4-(4'-hydroxy-3'-iso-propylbenzyl)-2,3,5-trimethylphenoxy]methylphosphonic Acid Step a:

A mixture of 3,5-dimethyl-2-iodo-4-(4'-methoxymethoxy-3'-iso-propylbenzyl)phenol (compound 47, step a; 1.0 g, 2.27 mmol) and PdCl$_2$(PPh$_3$)$_2$ (0.10 g, 0.14 mmol) in TEA (1.6 mL) and methanol (8.0 mL) was heated under a CO atmosphere (60 psi) at 80° C. for 72 h. The reaction mixture was cooled to room temperature and filtered through a Celite plug. The solvent was removed under reduced pressure and the crude product was purified by column chromatography on silica gel, eluting with 10% ethyl acetate in hexanes to afford methyl 2,4-dimethyl-6-hydroxy-3-(4'-methoxymethoxy-3'-iso-propylbenzyl)benzoate (0.32 g, 38%): $^1$H NMR (300 MHz, CD$_3$OD): δ 6.93 (m, 2 H), 6.67 (s, 2 H), 5.18 (s, 1 H), 3.98 (s, 2 H), 3.92 (s, 3 H), 3.48 (s, 3 H), 3.30 (m, 1 H), 2.22 (m, 6 H), 1.18 (d, J=6.9 Hz, 6 H); TLC conditions: Uniplate silica gel, 250 microns; Mobile phase=ethyl acetate-hexanes (1:5); R$_f$=0.60.

Step b:

To a solution of methyl 2,4-dimethyl-6-hydroxy-3-(4'-methoxymethoxy-3'-iso-propylbenzyl)benzoate in ethanol-water (3.0 mL, 95:5) at room temperature was added NaBH$_4$. The reaction mixture was heated at 80° C. for 4 h and cooled to room temperature. The reaction mixture was quenched with aqueous NH$_4$Cl and extracted with ether. The organic layer was dried over MgSO$_4$, filtered and concentrated under reduced pressure. The crude product was purified by column chromatography on silica gel, eluting with 30% acetone in hexanes to afford 2,4-dimethyl-6-hydroxy-3-(4'-methoxymethoxy-3'-iso-propylbenzyl)benzyl alcohol: $^1$H NMR (300 MHz, CD$_3$OD): δ 6.97 (d, J=2.4 Hz, 1 H), 6.92 (d, J=13.2 Hz, 1 H), 6.68 (dd, J=13.2, 2.4 Hz, 1 H), 6.59 (s, 1 H), 5.17 (s, 2 H), 4.78 (s, 2 H), 3.96 (s, 2H), 3.47 (s, 3 H), 3.30 (m, 1H), 2.24 (s, 3 H), 2.19 (s, 3 H), 1.18 (d, J=10.8 Hz, 6 H); TLC conditions: Uniplate silica gel, 250 microns; Mobile phase=acetone-hexanes (3:7); R$_f$=0.40.

Step c:

A mixture of 2,4-dimethyl-6-hydroxy-3-(4'-methoxymethoxy-3'-iso-propylbenzyl)benzyl alcohol ((0.20 g, 0.58 mmol) and Pd—C (0.08 g, 10%) in ethyl acetate-acetic acid (3.5 mL, 95:5) was stirred at room temperature under a H$_2$ atmosphere for 6 h. The reaction mixture was filtered through a Celite plug and the solvent was removed under reduced pressure to afford 4-(4'-methoxymethoxy-3'-iso-propylbenzyl)-2,3,5-trimethylphenol (0.19 g, 100%) as colorless oil: $^1$H NMR (300 MHz, CD$_3$OD): δ 6.94 (m, 1H), 6.91 (d, J=13.2 Hz, 1 H), 6.68 (dd, J=13.2, 2.4 Hz, 1 H), 6.55 (s, 1 H), 5.17 (s, 2 H), 3.95 (s, 2 H), 3.47 (s, 3 H), 3.30 (m, 1 H), 2.19 (s, 3 H), 2.16 (s, 3 H), 2.11 (s, 3 H), 1.17 (d, J=10.8 Hz, 6 H); TLC conditions: Uniplate silica gel, 250 microns; Mobile phase=acetone-hexanes (3:7); R$_f$=0.60.

The title compound was prepared according to the procedure described for the synthesis of compound 7: mp: 56.0-58.0° C.; $^1$H NMR (300 MHz, CD$_3$OD): δ 6.85 (d, J=2.4 Hz, 1 H), 6.76 (s, 1 H), 6.60 (d, J=12.0 Hz, 1 H), 6.52 (dd, J=12.6, 2.4 Hz, 1 H), 4.22 (d, J=10.2 Hz, 2 H), 3.94 (s, 2 H), 3.23 (m, 1 H), 2.25 (s, 3 H), 2.24 (s, 3 H), 2.15 (s, 3 H), 1.17 (d, J=10.8 Hz, 6 H); LC-MS m/z=379 [C$_{20}$H$_{27}$O$_5$P+H]$^+$; Anal Calcd for [C$_{20}$H$_{27}$O$_5$P+1.1H$_2$O]: C, 60.32; H, 7.39. Found: C, 60.05; H, 7.14.

Example 62

Compound 62: [6-iodo-4-(4'-hydroxy-3'-iso-propyl-benzyl)-2,3,5-trimethylphenoxy]methylphosphonic Acid

[6-Iodo-4-(4'-hydroxy-3'-iso-propylbenzyl)-2,3,5-trimethylphenoxy] methylphosphonic acid was prepared from 4-(4'-methoxymethoxy-3'-iso-propylbenzyl)-2,3,5-trimethylphenol (compound 61-1, step c) was prepared according to the procedure described for the synthesis of compound 45, step a and transformed into the title compound according to the procedure described for the synthesis of compound 7-1: mp: 185-187° C.; $^1$H NMR (300 MHz, CD$_3$OD): δ 6.88 (d, J=2.4 Hz, 1 H), 6.61 (d, J=12.3 Hz, 1 H), 6.50 (d, J=2.4 Hz, 1 H), 4.14 (d, J=10.5 Hz, 1 H), 4.09 (s, 2 H), 3.24 (m, 1 H), 2.46 (s, 3 H), 2.39 (s, 3 H), 2.19 (s, 3 H), 1.18 (d, J=6.9 Hz, 6 H); LC-MS m/z=504 [C$_{20}$H$_{27}$O$_5$P]$^+$; Anal. Calcd for (C$_{20}$H$_{26}$IO$_5$P+0.8H$_2$O): C, 46.26; H, 5.41. Found: C, 46.48; H, 5.78.

Example 63

Compound 63: [3-Bromo-4-(4'-hydroxy-3'-iso-propylphenoxy)-5-trifluoromethyl-phenylamino]methylphosphonic acid Step a:
Intermediate 1,5-dibromo-2-(3'-iso-propyl-4'-methoxyphenoxy)-3-trifluoromethyl-benzene was prepared from 2,4-dibromo-6-trifluoromethyl-phenol (*J. Amer. Chem. Soc.*, 1947, 2346) according to the procedure described for the synthesis of compound 4, step a: $^1$H NMR (200 MHz, DMSO-d$_6$): δ 8.39 (m, 1 H), 8.07 (m, 1 H), 6.85 (m, 2 H), 6.45 (m, 1 H), 3.73 (s, 3 H), 3.15 (m, 1 H), 1.08 (d, J=10.5 Hz, 6 H); TLC conditions: Uniplate silica gel, 250 microns; Mobile phase=hexanes; R$_f$=0.54.

Step b:
To a mixture of Pd(OAc)$_2$ (0.031 g, 0.14 mmol) in toluene (40 mL) at rt was added (+/−)2,2'-bis(diphenylphosphino)-1,1'-binaphthyl (0.13 mL, 0.21 mmol). The reaction mixture was stirred at rt for several minutes and Cs$_2$CO$_3$ (3.62 g, 11.10 mmol), 1,5-dibromo-2-(3'-iso-propyl-4'-methoxyphenoxy)-3-trifluoromethyl-benzene (1.30 g, 2.77 mmol, dissolved in 10 mL toluene), and diethyl aminomethylphosphonate oxalate (0.76 g, 2.97 mmol) were added. The reaction mixture was stirred at 100° C. for 16 h. The solution was cooled to rt, diluted with diethyl ether (25 mL), filtered and concentrated. The crude product was purified by column chromatography on silica gel, eluting with ethyl acetate-hexanes (1:1) to afford diethyl [3-bromo-4-(4'-methoxy-3'-iso-propyl-phenoxy)-5-trifluoromethylphenylamino]methylphosphonate as an oil (0.28 g, 18%): $^1$H NMR (300 MHz, DMSO-d$_6$): δ 7.33 (m, 1 H), 7.16 (m, 1H), 6.85 (m, 1 H), 6.65 (m, 1 H), 6.55 (m, 1 H), 6.39 (m, 1 H), 4.08 (m, 4 H), 3.74 (s, 3 H), 3.68 (m, 2 H), 3.21 (m, 1 H), 1.19 (m, 6 H), 1.11 (d, J=6.0 Hz, 6 H); TLC conditions: Uniplate silica gel, 250 microns; Mobile phase=ethyl acetate-hexanes (4:1); R$_f$=0.25.

Step c:
The title compound was prepared according to the procedure described for the synthesis of Example 19, step e: mp: 98-102° C.; $^1$H NMR (300 MHz, CD$_3$OD): δ 7.11 (m, 1 H), 6.95 (m, 2 H), 6.48 (m, 1 H), 6.45 (m, 1 H), 6.20 (m, 1 H), 3.41 (d, J=12.0 Hz, 2 H), 3.12 (m, 1 H), 1.17 (m, 18 H), 1.04 (d, J=6.0 Hz, 6 H); LC-MS m/z=484 [C$_{17}$H$_{18}$BrF$_3$NO$_5$P−H]$^+$; HPLC conditions: Column=Shimadzu LC-A8, SPD-10A; YMC Pack RP-18 filter, 150×4.6; Mobile phase=Solvent A Acetonitrile/0.05% TFA; Solvent B=H$_2$O/0.05% TFA. Gradient: 0 min: 20% B; 13 min: 70% B; 16 min: 100% B; 18 min: 20% B. Flow rate=2.0 mL/min; UV@ 254 nm. rt=9.16 min.

Example 64

Compound 64: [3,5-Dimethyl-4-[4'-hydroxy-3'-(3-trifluoromethylphenoxy)-benzyl]phenoxy]methylphosphonic acid Step a:
To 5-(2,6-dimethyl-4-triisopropylsilanyloxybenzyl)-2-methoxy-methoxy-benzaldehyde (compound 15, step e; 0.460 g, 1.01 mmol) in dichloromethane 30 mL was add mCPBA (0.870 g, 2.52 mmol) and saturated sodium bicarbonate solution (2 mL). After stirring at rt overnight, the reaction mixture was poured into dichloromethane 50 mL and washed 3× with 10 mL of saturated aqueous sodium bicarbonate. The dichloromethane was dried over sodium sulfate, filtered and concentrated under reduced pressure. The resulting residue was combined with methanol (10 mL) and 2 mL of 1 N NaOH and stirred for 1.5 hours at room temperature. The reaction was acidified with 12 N HCl (pH<3) and poured into 50 mL ethyl acetate. The layers were separated and the organics were dried over sodium sulfate, filtered and concentrated. Flash column chromatography using silica and a step gradient of hexane/ethyl acetate [20:1], hexane/ethyl acetate [9:1] provided 5-(2,6-dimethyl-4-triisopropylsilanyloxybenzyl)-2-methoxymethoxy-phenol (0.189 g, 42%): $^1$H NMR (300 MHz, DMSO-d$_6$): δ 8.95(s, 1H), 6.86(d, 1H, J=8.1 Hz), 6.56(s, 2H), 6.41(d, 1H, J=2.1 Hz), 6.34(dd, 1H, J=2.1 Hz and J=8.7 Hz), 5.05(s, 2H), 3.78(s, 2H), 3.38(s, 3H), 2.13(s, 6H), 1.11(m, 3H), 1.00(m, 18H); Uniplate silica gel, 250 microns; Mobile phase=10% ethyl acetate in hexane: Rf=0.15

Step b:
(2,6-Dimethyl-4-triisopropylsilanyloxybenzyl)-4-methoxymethoxy-3-(3-trifluoromethylphenoxy)benzene was prepared from 5-(2,6-dimethyl-4-triisopropylsilanyloxybenzyl)-2-methoxymethoxy-phenol according to the procedure described in Dominic M. T. Chan et al. *Tetrahedron Lett.* 39:2933-2936 (1998), (0.070 g, 37%) $^1$H NMR (300 MHz, DMSO-d$_6$): δ 7.53(t, 1H, J=7.8 Hz), 7.35(d, 1H, J=7.8 Hz), 7.21-7.10(m, 2H), 6.98(s, 1H), 6.89(m, 1H), 6.59(m, 1H), 6.64(s, 2H), 5.09(s, 2H), 3.89(s, 2H), 3.18(s, 3H), 2.11(s, 6H), 1.16(m, 3 H), 1.01(m, 18H); Uniplate silica gel, 250 microns; Mobile phase=10% ethyl acetate in hexane: Rf=0.47

Step c:
3,5-Dimethyl-4-[4'-methoxymethoxy-3'-(3-trifluoromethylphenoxy)-benzyl]phenol was synthesized according to the procedure described for the synthesis of compound 35, step e, (0.059 g, 100%); $^1$H NMR (300 MHz, DMSO-d$_6$): δ 9.02(s, 1H), 7.55(t, 1H, J=7.8 Hz), 7.38(1H, d, J=8.4 Hz), 7.14(m, 2H), 7.02(s, 1H), 6.88(dd, 1H, J=1.5 Hz and J=6.6 Hz), 6.72(d, 1H, 2.1 Hz), 6.44(s, 2H), 5.08(s, 2H), 3.85(s, 2H), 3.18(s, 3H), 2.08(s, 6H); (Uniplate silica gel, 250 microns; Mobile phase=25% ethyl acetate in hexane: Rf=0.28

Step d:
Diethyl[3,5-dimethyl-4-[4'-methoxymethoxy-3'-(3-trifluoromethyl-phenoxy)benzyl]phenoxy]methylphosphonate was prepared according to the procedure described for the synthesis of compound 8, steps e (0.015 g, 15%); $^1$H NMR (300 MHz, DMSO-d$_6$): δ 7.55(t, 1H, J=8.4 Hz), 7.37(d, 1H, J=7.5 Hz), 7.14(m, 2H), 7.02(s, 1H), 6.86(dd, 1H, J=1.7 Hz and J=7 Hz), 6.73(s, 2H), 5.08(s, 2H), 4.34(d, 2H, J=9.9 Hz), 4.09(m, 4H), 3.91(s, 2H), 3.18(s, 3H), 2.18(s, 6H), 1.24(t, 6H, J=7 Hz); Uniplate silica gel, 250 microns; Mobile phase=25% hexane in ethyl acetate: Rf=0.2

Step e:

The title compound was prepared according to the procedure described for the synthesis of compound 8, steps f, (0.022 g, 90%); $^1$H NMR (300 MHz, DMSO-d$_6$): δ 9.48(s, 1H), 7.53(t, 1H, J=7.8 Hz), 7.34(d, 1H, J=7.2 Hz), 7.07(d, 1H, J=9 Hz), 7.01(s, 1H), 6.90(d, 1H, J=8.4 Hz), 6.71(m, 4H), 4.00(d, 2H, J=10.2 Hz), 3.84(s, 2H), 2.15(s, 6H); LC-MS m/z=481 [C$_{23}$H$_{22}$F$_3$O$_6$P–H]$^-$; Uniplate silica gel, 250 microns; Mobile phase=isopropyl alcohol/water/ammonium hydroxide [7:2:1]: Rf=0.47; HPLC, zorbax, XDB-C8, 150 mm×4.6 mm, 5 um, flow 1 mL/min, solvent A: 0.05 M KH$_2$PO$_4$ aqueous pH 6.2, Solvent B: acetonitrile, Gradient 40% B to 60% B over 11 min then 60% B. total run time 12 min. RT 1.87 min; Anal Calcd for (C$_{23}$H$_{22}$F$_3$O$_6$P+0.3 M H$_2$O+0.1 M EtOAc) C, 56.60; H, 4.70. Found: C, 56.68; H, 3.97.

Example 65

Compound 65-1: 2,6-diiodo-3,5-dimethyl-[4-(4'-hydroxy-3'-iso-propylbenzyl)phenoxy]methyl phosphonic acid Step a:

To a stirred solution of 3,5-dimethyl-4-(4'-methoxymethoxy-3'-iso-propylbenzyl)phenol (0.22 g, 0.70 mmol), (Chiellini et al., *Bioorg. Med. Chem. Lett.* 10:2607 (2000)) in EtOH (6.2 mL) and CH$_3$NH$_2$ 40% in water (2.5 mL) was added iodine (0.39 g, 1.54 mmol) and KI (0.25 g 1.54 mmol) in H$_2$O (3 mL) at 0° C. The reaction mixture was stirred at room temperature for 16 h, quenched with brine (50 mL) and extracted with ethyl acetate (50 mL×2). The combined organic layers were dried over Na$_2$SO$_4$, filtered and concentrated under reduced pressure. The crude product was purified by column chromatography on silica gel, eluting with ethyl acetate-hexanes (1:4) to afford 2,6-diiodo-3,5-dimethyl-4-(4'-methoxymethoxy-3'-iso-propylbenzyl)phenol as a colorless oil (198 mg, 50%): $^1$H NMR (300 MHz, CDCl$_3$): δ 6.97 (d, J=2.1 Hz, 1 H), 6.92 (d, J=5.6 Hz, 1 H), 6.59 (dd, J=2.4, 8.4 Hz, 1 H), 6.0 (s, 1 H), 5.19 (s, 2 H), 4.16 (s, 2 H), 3.50 (s, 3 H), 3.35-3.30 (m, 1 H), 2.48 (s, 6 H), 1.21 (d, J=6.9 Hz, 6H); TLC conditions: Uniplate silica gel, 250 microns; Mobile phase=hexanes-ethyl acetate (4:1); R$_f$=0.62.

Step b:

To a stirred solution of 2,6-diiodo-3,5-dimethyl-4-(3'-iso-propyl-4'-methoxymethoxybenzyl)phenol (0.2 g, 0.35 mmol) in DMF (3.0 mL) at 0° C. was added Cs$_2$CO$_3$ (0.34 g, 1.05 mmol). After 10-min, diethyl trifluoromethanesulfonyloxymethyl phosphonate (0.1 g, 0.35 mmol) was added. The reaction mixture was stirred at 0° C. for 1 h, allowed to warm to room temperature and stirred for 16 h. The reaction mixture was quenched with 1 N HCl, diluted with ethyl acetate, and washed with water (10 mL×4) and brine. The organic layer was concentrated under reduced pressure and the crude product was purified by column chromatography on silica gel, eluting with ethyl acetate-hexanes (2:3) as mobile phase to afford diethyl [2,6 diiodo-3,5-dimethyl-4-(3'-iso-propyl-4'-methoxymethoxybenzyl)phenoxy]methyl-phosphonate as an oil (0.21 g, 85%): $^1$H NMR (300 MHz, CDCl$_3$): δ 6.96 (d, J=2.4 Hz, 1 H), 6.92 (d, J=8.4 Hz, 1 H), 6.56 (dd, J=2.1, 8.4 Hz, 1 H), 5.18 (s, 2 H), 4.45-4.35 (m, 6 H), 4.18 (s, 2 H), 3.50 (s, 3 H), 3.39-3.25 (m, 1 H), 2.49 (s, 6 H), 1.47 (t, J=6.9 Hz, 6 H), 1.20 (d, J=6.9 Hz, 6H); TLC conditions: Uniplate silica gel, 250 microns; Mobile phase=hexanes-ethyl acetate (1:1); R$_f$=0.35.

Step c:

To a solution of diethyl [2,6-diiodo-3,5-dimethyl-4-(3'-iso-propyl-4'-methoxymethoxybenzyl)phenoxy]methylphosphonate (0.14 g, 0.19 mmol) in CH$_2$Cl$_2$ (4.0 mL) at 0° C. was added bromotrimethylsilane (0.31 mL, 1.9 mmol). The reaction mixture was stirred at room temperature for 16 h and the solvent was removed under reduced pressure. The residue was treated with methanol and water (4:1, 5.0 mL) and the solvents were removed under reduced pressure. The residue was treated with acetonitrile and filtered to afford 2,6-diiodo-3,5-dimethyl-[4-(4'-hydroxy-3'-iso-propylbenzyl)phenoxy]-methyl phosphonic acid as white solid (97 mg, 80%): mp 236° C.; $^1$H NMR (300 MHz, CD$_3$OD): δ 6.87 (s, 1 H), 6.62 (d, J=7.8 Hz, 1 H), 6.46 (d, J=8.7 Hz, 1 H), 4.31 (d, J=10.8 Hz, 2 H), 4.19 (s, 2 H), 3.35-3.18 (m, 1 H), 2.50 (s, 6 H), 1.17 (d, J=6.9 Hz, 6 H); LC-MS m/z=616 [C$_{19}$H$_{23}$I$_2$O$_5$P]+; HPLC conditions: ODSAQ AQ-303-5 column; mobile phase=CH$_3$OH:0.05% TFA (7:3) flow rate=1.0 mL/min; detection=UV @ 280 nm retention time in min: 13.82; Anal Calcd for (C$_{20}$H$_{25}$O$_6$P+0.9H$_2$O): C, 36.09; H, 3.95. Found: C, 35.80; H, 4.22.

Using the appropriate starting material, compounds 65-2 was prepared in an analogous manner to that described for the synthesis of compound 65-1.

Compound 65-2: 2,6-dibromo-3,5-dimethyl-[4-(4'-hydroxy-3'-iso-propylbenzyl)phenoxy]methyl phosphonic acid Step a To a stirred solution of 3,5-dimethyl-4-(4'-methoxymethoxy-3'-iso-propylbenzyl)phenol (0.2 g, 0.63 mmol), (Chiellini et al., *Bioorg. Med. Chem. Lett.* 10:2607 (2000)) in EtOH (6.0 mL) and CH$_3$NH$_2$ 40% in water (2.5 mL) was added bromine (0.25 g, 1.59 mmol) and KBr (0.11 g 1.59 mmol) in H$_2$O (2 mL) at 0° C. The reaction mixture was stirred at room temperature for 16 h, quenched with water (50 mL) and extracted with ethyl acetate (50 mL×2). The combined organic layers were dried over Na$_2$SO$_4$, filtered and concentrated under reduced pressure. The crude product was purified by column chromatography on silica gel, eluting with ethyl acetate-hexanes (1:9) to afford 2,6-dibromo-3,5-dimethyl-4-(4'-methoxymethoxy-3'-iso-propylbenzyl)phenol as a white solid (0.18 g, 60%): $^1$H NMR (300 MHz, CDCl$_3$): δ 6.97 (d, J=2.1 Hz, 1 H), 6.92 (d, J=8.4 Hz, 1 H), 6.60 (dd, J=2.4, 8.7 Hz, 1 H), 6.0 (s, 1 H), 5.19 (s, 2 H), 4.08 (s, 2 H), 3.50 (s, 3 H), 3.35-3.30 (m, 1 H), 2.38 (s, 6 H), 1.21 (d, J=6.0 Hz, 6 H); TLC conditions: Uniplate silica gel, 250 microns; Mobile phase=hexanes-ethyl acetate (4:1); R$_f$=0.62.

Step b:

The title compound was prepared according to the procedure described for the synthesis of example 45, step b and c: as a white solid (0.15 g, 80%) mp 190° C.; $^1$H NMR (300 MHz, CD$_3$OD): δ 6.88 (d, J=2.1 Hz, 1 H), 6.62 (d, J=8.4 Hz, 1 H), 6.46 (dd, J=2.4, 8.7 Hz, 1 H), 4.27 (d, J=10.5 Hz, 2 H), 4.12 (s, 2 H), 3.35-3.18 (m, 1 H), 2.40 (s, 6 H), 1.17 (d, J=6.9 Hz, 6 H); LC-MS m/z=523 [C$_{19}$H$_{23}$I$_2$O$_5$P+H]$^+$; HPLC conditions: ODSAQ AQ-12S05146W column; mobile phase=0.05% TFA/CH$_3$CN:0.05% TFA/H$_2$O (1:1) flow rate=1.0 mL/min; detection=UV @ 254 nm retention time in min: 10.45; Anal Calcd for (C$_{20}$H$_{23}$Br$_2$O$_5$P): C, 43:70; H, 4.44. Found: C, 43.78; H, 4.46.

Example 66

Compound 66: 4,6-Dimethyl-4-(4'-hydroxy-3'-iso-propylphenoxy)-indolephosphonic acid Step a:

A solution of sodium nitrite (155 mg, 2.24 mmol) in water (1 mL) was added to a suspension of 3,5-dimethyl-4-(4'-methoxy-3'-iso-propylphenoxy)-aniline (*J. Med. Chem.* 38:695 (1995), 640 mg, 2.24 mmol) in ethanol (3 mL) and concentrated hydrochloric acid (12 M, 1.12 mL, 13.44 mmol) at 0° C. The yellow heterogeneous solution slowly turns to an orange clear solution. After stirring at 0° C. for 30 minutes, a solution of tin dichloride (1.53 g, 8.06 mmol) in hydrochloric acid (12 M, 1.3 mL, 15.68 mmol) was added. The orange solution turned green and a white precipitate formed. Ethanol (3 mL) was added to dissolve most of the precipitate and the heterogeneous reaction mixture was stirred at 0° C. After 2 hours, water was added and the precipitate collected by filtration. The sticky solid was dissolved in ethyl acetate and washed with water, 1 N sodium hydroxide then brine. The organics were dried over sodium sulfate, concentrated under reduced pressure and the residue was purified by column chromatography (silica gel, dichloromethane/methanol 95/5 to 90/10) to give 3,5-dimethyl-4-(4'-methoxy-3'-iso-propylphenoxy)-phenyl hydrazine (305 mg, 45%): $^1$H NMR (300 MHz, CDCl$_3$) δ 6.77 (d, J=3.0 Hz, 1H), 6.67 (d, J=9.0 Hz, 1 H) 6.58 (s, 2H), 6.37 (dd, J=9.0, 3.0 Hz, 1H), 3.77 (s, 3H), 3.27 (heptuplet, J=6.9 Hz, 1H), 2.09 (s, 3H), 1.18 (d, J=6.9 Hz, 6H); TLC conditions: Merck silica gel, 250 microns; Mobile phase=dichloromethane-methanol (9:1), R$_f$=0.6.

Step b:

Diethyl acetylphosphonate (183 mg, 1.02 mmol) was added to a yellow solution of hydrazine in toluene at rt. After stirring 10 minutes at rt, polyphosphoric acid (PPA, 0.4 g) was added and the turbid reaction mixture was placed in an oil bath at 115° C. After refluxing for 5 minutes, the cooled brown biphasic solution was partitioned between ethyl acetate and water and the organic layer was washed with water then brine, dried over sodium sulfate, concentrated under reduced pressure and the residue purified by column chromatography (silica gel, hexanes/ethyl acetate 70/30 to 20/80) to give diethyl 5,6-dimethyl-4-(4'-methoxy-3'-iso-propylphenoxy)indolephosphonate (276 mg, 61%): $^1$H NMR (300 MHz, CDCl$_3$) δ (s, 1H, exchangeable with D$_2$O), 7.17 (s, 1H), 7.07 (m, 1H), 6.83 (d, J=3.0 Hz, 1H), 6.65 (d, J=9.0 Hz, 1H), 6.34 (dd, J=9.0, 3.0 Hz, 1H), 4.30-4.08 (m, 4H), 3.77 (s, 3H), 3.28 (heptuplet, J=6.9 Hz, 1H), 2.35 (s, 3H), 2.24 (s, 3H), 1.37 (t, J=7.1 Hz, 6H), 1.18 (d, J=6.9 Hz, 6H); TLC conditions: Merck silica gel, 250 microns; Mobile phase=dichloromethane-methanol (9:1); R$_f$=0.55.

Step c:

5,6-Dimethyl-4-(4'-hydroxy-3'-iso-propylphenoxy)indolephosphonic acid was prepared according to the procedure described for the synthesis of example 8, step f (100 mg, 51%): $^1$H NMR (300 MHz, CD$_3$OD) δ 7.14 (s, 1H), 6.97 (s, 1H), 6.75 (d, J=9.0 Hz, 1H), 6.68 (d, J=3.0 Hz, 1H), 6.35 (dd, J=9.0, 3.0 Hz, 1H), 3.75 (s, 3H), 3.25 (heptuplet, J=6.9 Hz, 1H), 2.27 (s, 3H), 2.16 (s, 3H), 1.11 (d, J=6.9 Hz, 6H); LC-MS m/z=390.4 [C$_{20}$H$_{24}$NO$_5$P+H]$^+$.

Step d:

A solution of boron tribromide (1 M in dichloromethane, 1.3 mL, 1.3 mmol) was added to a solution of 5,6-dimethyl-4-(4'-methoxy-3'-iso-propylphenoxy)indolephosphonic acid (100 mg, 0.26 mmol) in dichloromethane (10 mL) at −78° C. The ice bath was removed and the reaction mixture was warmed to rt. After stirring at rt overnight, the reaction mixture was quenched with ice, diluted with ethyl acetate and washed with water then brine, dried over sodium sulfate and concentrated under reduced pressure to give the title compound (86.3 mg, 80%): $^1$H NMR (300 MHz, CD$_3$OD) δ 7.18 (s, 1H), 6.97 (d, J=3.0 Hz, 1H), 6.60 (s, 1H), 6.57 (d, J=9.0 Hz, 1H), 6.26 (dd, J=9.0, 3.0 Hz, 1H), 3.22 (heptuplet, J=6.9 Hz, 1H), 2.28 (s, 3H), 2.18 (s, 3H), 1.12 (d, J=6.9 Hz, 6H); Anal. Calcd for (C$_{19}$H$_{22}$NO$_5$P+1.5H$_2$O+0.1 C$_3$H$_6$O): C, 56.79; H, 6.32; N, 3.43. Found: C, 56.61; H, 5.92; N, 3.22.

Example 67

Compound 67: 2-[3,5-dibromo-4-(4'-hydroxy-3'-isopropylphenoxy)phenyl]-ethylphosphonic Acid Step a:

To a solution of dimethyl methylphosphonate (0.06 g, 0.48 mmol) in THF (3.0 mL) at −78° C. was slowly added LDA (0.25 mL, 2 M in THF). After 30 min, a solution of 3,5-dibromo-4-(3'-isopropyl-4'-methoxyphenoxy)benzyl bromide (0.20 g, 0.40 mmol, intermediate for the synthesis of compound 19-1) in THF was added. The reaction mixture was stirred at −78° C. for 5 min, allowed to warm to room temperature and stirred for 2 h. The reaction mixture was quenched with aqueous NH$_4$Cl (10.0 mL) and extracted with ether (10.0 mL). The organic layer was dried over MgSO$_4$, filtered and concentrated under reduced pressure. The crude product was purified by column chromatography on silica gel, eluting with 50% acetone in hexanes to afford dimethyl 2-[3,5-dibromo-4-(4'-methoxy-3'-isopropylphenoxy)phenyl]ethylphosphonate (0.09 g, 43%) as a colorless oil: $^1$H NMR (300 MHz, CD$_3$OD): δ 7.64 (s, 2 H), 6.82 (d, J=10.0 Hz, 1H), 6.75 (d, J=4.2 Hz, 1H), 6.44 (dd, J=2.8, 10.2 Hz, 1H), 3.79 (d, J=2.8 Hz, 6H), 3.76 (s, 3H), 3.30 (m, 1H), 2.94 (m, 2H), 2.23 (m, 2H), 1.17 (d, J=7.0 Hz, 6H); LC-MS m/z=537 [C$_{20}$H$_{25}$Br$_2$O$_5$P+H]$^+$; TLC conditions: Uniplate silica gel, 250 microns; Mobile phase=acetone-hexanes (1:1); R$_f$=0.50.

Step b:

The title compound was prepared from dimethyl 2-[3,5-dibromo-4-(4'-methoxy-3'-isopropylphenoxy)phenyl]ethylphosphonate according to the procedure described for the synthesis of compound 4, step b: mp: 56-59° C.; $^1$H NMR (200 MHz, DMSO-d$_6$): δ 9.02 (s, 1H), 7.65 (s, 2H), 6.64 (m, 2H), 6.21 (dd, J=2.8, 10.2 Hz, 1H), 3.14 (m, 1H), 2.79 (m, 2H), 1.87 (m, 2H), 1.11 (d, J=7.0 Hz, 6H); LC-MS m/z=495 [C$_{17}$H$_{19}$ Br$_2$O$_5$P+H]$^+$; Anal. Calcd for (C$_{17}$H$_{19}$Br$_2$O$_5$P+ 0.5H$_2$O): C, 40.58; H, 4.01. Found: C, 40.26; H, 4.22.

Example 68

Compound 68: [3,5-Dimethyl-4-(4'-hydroxy-3'-iso-propylbenzyl)benzyl]-phosphonic Acid Step a:

To a solution of methyl 3,5-methyl-4-(3'-isopropyl-4'-methoxymethoxybenzyl)benzoate 1.80 g, 5.0 mmol, Example 47, step a ) in THF (30.0 mL) at 0° C. was slowly added DIBAL (12.6 mL, 12.6 mmol). The reaction mixture was stirred at 0° C. for 2 h and quenched with potassium sodium tartrate. The reaction mixture was diluted with hexanes and stirred at room temperature for 2 h. The organic layer was separated, dried over MgSO$_4$, filtered and concentrated under reduced pressure. The crude product was dissolved in ether (95.0 mL) and slowly added to a solution of carbon tetrabromide and PPh$_3$ in ether (20.0 mL). The reaction mixture was stirred at room temperature for 16 h and filtered through a Celite plug. The solvent was removed under reduced pressure and the crude product was purified by column chromatography on silica gel, eluting with 10% ethyl acetate in hexanes to afford 3,5-dimethyl-4-(3'-isopropyl-4'-methoxymethoxybenzyl)-benzyl bromide (1.82 g, 93%) as white solid: $^1$H NMR (300 MHz, CD$_3$OD): δ 7.13 (s, 2H), 6.93 (m, 2H), 6.67 (d, J=7.2 Hz, 1H), 5.17 (s, 2H), 4.54 (s, 2H), 4.02 (s, 2H), 3.48 (s, 3H), 3.31 (m, 1H), 2.25 (s, 6H), 1.17 (d, J=7.0 Hz, 6H); TLC conditions: Uniplate silica gel, 250 microns; Mobile phase=ethyl acetate-hexanes (1:9); R$_f$=0.8.

Step b:

To a solution of 3,5-dimethyl-4-(3'-isopropyl-4'-methoxymethoxybenzyl)benzyl bromide (0.60 g, 1.53 mmol) in DMF (5.0 mL) at room temperature was slowly added a solution of trimethylphosphite (0.57 g, 4.60 mmol) in DMF (1.0 mL). The reaction mixture was stirred at 140° C. for 3 h and cooled to room temperature. The mixture was quenched with water (10 mL) and extracted with ethyl acetate (10 mL). The organic layer was dried over MgSO$_4$, filtered and concentrated under reduced pressure. The crude product was purified by column chromatography on silica gel, eluting with 50% acetone in hexanes to afford dimethyl 2-[3,5-dibromo-4-(4'-methoxymethoxy-3'-isopropylphenoxy)]benzylphosphonate (0.20 g, 31%) as colorless oil: $^1$H NMR (300 MHz, CD$_3$OD): δ 7.04 (d, J=2.4 Hz, 2H), 6.93 (m, 2H), 6.69(d, J=7.2 Hz, 1H), 5.17 (s, 2H), 4.01 (s, 2H), 3.72 (d, J=10.2 Hz, 6H), 3.28 (m, 1H), 3.22 (d, J=21.3 Hz, 2H), 2.25 (s, 6H), 1.17 (d, J=7.0 Hz, 6H); TLC conditions: Uniplate silica gel, 250 microns; Mobile phase=acetone-hexanes (1:1); R$_f$=0.5.

Step c:

The title compound was prepared from dimethyl [3,5-dibromo-4-(4'-hydroxy-3'-isopropylphenoxy)benzyl]phosphonate according to the procedure described for the synthesis of compound 7, step b: mp: 60-63; $^1$H NMR (300 MHz, CD$_3$OD): δ 7.03 (s, 2H), 6.93 (m, 2H), 6.09(s, 1H), 6.58 (m, 2H), 3.95 (s, 2H), 3.23 (m, 1H), 3.08 (d, J=21.0 Hz, 2H), 2.24 (s, 6H), 1.17 (d, J=7.0 Hz, 6H); LC-MS m/z=349 [C$_{19}$H$_{25}$O$_4$P+H]$^+$; Anal. Calcd for (C$_{19}$H$_{25}$O$_4$P+0.6H$_2$O): C, 63.47; H, 7.55. Found: C, 63.53; H, 7.35.

Example 69

Compound 69: [3,5-dimethyl-4-(4'-hydroxy-3'-isopropylbenzyl)phenoxy]-methylphosphonic acid monomethyl ester Step a:

A solution of [3,5-dimethyl-4-(4'-hydroxy-3'-iso-propylbenzyl)-phenoxy]methylphosphonic acid (compound 7, 105 mg, 0.29 mmol), oxalyl chloride (0.5 mL) and DMF (2 drops) in dichloromethane was refluxed for 2 hours then concentrated under reduced pressure and azeotroped twice with dichloromethane. The residue was taken in dichloromethane and triethylamine (0.16 mL, 1.2 mmol) followed by methanol (1 mL) were added at rt. After stirring at rt for 2 hours, the reaction mixture was quenched with brine, diluted with ethyl acetate, washed with 1 N sodium hydroxide, then brine. The organics were dried over sodium sulfate, concentrated under reduced pressure and the residue purified by column chromatography (silica gel, dichloromethane/methanol 96/4 to 92/8) to give dimethyl [3,5-dimethyl-4-(4'-hydroxy-3'-iso-propylbenzyl)phenoxy]methylphosphonate (75 mg, 70%): $^1$H NMR (200 MHz, CDCl$_3$) δ 6.92 (d, J=3.0 Hz, 1 H), 6.68 (s, 2H), 6.66 (d, J=9.0 Hz, 1H), 6.52 (dd, J=9.0, 3.0 Hz, 1H), 4.31 (d, J=10.2 Hz, 2H), 3.89 (d, J=11.0 Hz, 6H), 3.15 (heptuplet, J=7.0 Hz, 1H), 2.19 (s, 6H), 1.21 (d, J=7.0 Hz, 6H); TLC conditions: Merck silica gel, 250 microns; Mobile phase=dichloromethane-methanol (9:1); R$_f$=0.65.

Step b:

A 1 N solution of sodium hydroxide (1 mL, 1 mmol) was added to a solution of dimethyl [3,5-dimethyl-4-(4'-hydroxy-3'-iso-propylbenzyl)-phenoxy]methylphosphonate (75 mg, 0.19 mmol) in THF at rt. The biphasic solution was stirred at rt for 24 hours then diluted with ethyl acetate and extracted twice with 1 N sodium hydroxide. The combined aqueous extracts were acidified to pH 1 with concentrated hydrochloric acid and extracted twice with ethyl acetate. The combined organic extracts were dried over sodium sulfate and concentrated under reduced pressure to give the title compound (55 mg, 76%): $^1$H NMR (200 MHz, CDCl$_3$) δ 6.92 (d, J=3.0 Hz, 1H), 6.68 (s, 2H), 6.60-6.4 (m, 2H), 4.31 (d, J=10.2 Hz, 2H), 3.89 (d, J=11.0 Hz, 3H), 3.15 (heptuplet, J=7.0 Hz, 1H), 2.19 (s, 6H), 1.21 (d, J=7.0 Hz, 6H); LC-MS m/z=379.4 [C$_{20}$H$_{27}$O$_5$P+H]$^+$; Anal. Calcd for (C$_{20}$H$_{27}$O$_5$P+0.4H$_2$O): C, 62.30; H, 7.27. Found: C, 62.20; H, 7.51.

Compound 69-1: [3,5-dimethyl-4-(4'-hydroxy-3'-isopropylbenzyl) phenoxy]methylphosphonic acid monoethyl ester Step a:

Diethyl[3,5-dimethyl-4-(4'-hydroxy-3'-isopropylbenzyl) phenoxy]-methylphosphonate was prepared from diethyl [3,5-dimethyl-4-(4'-methoxymethoxy-3'-iso-propylbenzyl) phenoxy]methylphosphonate (Example 7, step a) according to the procedure described for the synthesis of compound 7-14, step a: $^1$H NMR (300 MHz, DMSO-d$_6$): δ 9.00 (s, 1H), 6.85 (m, 1H), 6.74 (s, 2H), 6.63 (m, 1H), 6.48 (m, 1H), 4.36 (d, J=9.0 Hz, 2H), 4.13 (m, 4H), 3.81 (s, 2H), 3.14 (m, 1H), 2.18 (s, 6H), 1.27 (m, 6H), 1.12 (d, J=6.0 Hz, 6H); TLC conditions: Uniplate silica gel, 250 microns; Mobile phase=hexanes-ethyl acetate (1:4); R$_f$=0.40.

Step b:

The title compound was prepared according to the procedure described for the synthesis of compound 69, step b: $^1$H NMR (300 MHz, DMSO-d$_6$): δ 9.00 (s, 1H), 6.85 (m, 1H), 6.73 (s, 2H), 6.61 (m, 1H), 6.48 (m, 1H), 4.21 (d, J=9.0 Hz, 2H), 4.06 (m, 2H), 3.81 (s, 2H), 3.14 (m, 1H), 2.18 (s, 6H), 1.24 (m, 3H), 1.12 (d, J=6.0 Hz, 6H); LC-MS m/z=393 [C$_{21}$H$_{29}$O$_5$P−H]$^+$; Anal. Calcd for (C$_{21}$H$_{29}$O$_5$P+0.1H$_2$O): C, 63.98; H, 7.47. Found: C, 63.93, H, 7.07. HPLC conditions: Column=Agilent zorbax RP18, 150×3.0 mm; Mobile phase=Solvent B (Acetonitrile)=HPLC grade acetonitrile; Solvent A (buffer)=20 mM potassium phosphate buffer (pH 4.7). Flow rate=0.75 mL/min; UV@ 254 nm. rt=13.98 min).

Compound 69-2: [3,5-dibromo-4-(4'-hydroxy-3'-isopropylphenoxy)benzyl]-phosphonic Acid Monomethyl Ester Step a:

To a solution of [3,5-dimethyl-4-(3'-isopropyl-4'-methoxyphenoxy)]benzyl bromide (intermediate for the synthesis of compound 19-1, 0.20 g, 0.40 mmol) in DMF (2.5 mL) at room temperature was slowly added a solution of trimethylphosphite (0.57 g, 4.60 mmol) in DMF (0.5 mL). The reaction mixture was stirred at 140° C. for 3 h and cooled to room temperature. The mixture was quenched with water (10 mL) and extracted with ethyl acetate (10 mL). The organic layer was dried over MgSO$_4$, filtered and concentrated under reduced pressure. The crude product was purified by column chromatography on silica gel, eluting with 50% acetone in hexanes to afford dimethyl [3,5-dibromo-4-(3'-isopropyl-4'- methoxyphenoxy)benzyl]phosphonate (0.10 g, 49%) as colorless oil: $^1$H NMR (300 MHz, CD$_3$OD): δ 7.68 (s, 2H), 6.83 (d, J=7.2 Hz, 1H), 6.72 (s, 1H), 6.45 (d, J=7.2 Hz, 1H), 3.81 (s, 6H), 3.77 (s, 3H), 3.38 (d, J=10.2 Hz, 2H), 3.28 (m, 1H), 1.17 (d, J=7.0 Hz, 6H); TLC conditions: Uniplate silica gel, 250 microns; Mobile phase=acetone-hexanes (1:1); R$_f$=0.5.

Step b

To a solution dimethyl [3,5-dibromo-4-(3'-isopropyl-4'-methoxyphenoxy)benzyl]phosphonate (0.22 g, 0.42 mmol) in CH$_2$Cl$_2$ (3.0 mL) at −78° C. was slowly added BBr$_3$ (0.63 mL, 0.63 mmol). After 5 min, the reaction mixture was allowed to warm to room temperature and stirred for 3 h. The reaction mixture was quenched with ice-water and extracted with ethyl acetate (10 mL). The organic layer was dried over MgSO$_4$, filtered and concentrated under reduced pressure. The crude product was purified by column chromatography on silica gel, eluting with 50% acetone in hexanes to afford dimethyl [3,5-dibromo-4-(4'-hydroxy-3'-isopropylphenoxy)-benzyl]phosphonate (0.06 g, 28%) as white solid: $^1$H NMR (200 MHz, DMSO-d$_6$): δ 9.07 (s, 1H), 7.67 (d, J=2.2 Hz, 1H), 6.65 (m, 2H), 6.22 (dd, J=2.8, 10.2 Hz, 1H), 3.64 (d, J=11.0 Hz, 6H), 3.40 (d, J=15.0, 2H), 3.18 (m, 1H), 1.10 (d, J=7.0 Hz, 6H); TLC conditions: Uniplate silica gel, 250 microns; Mobile phase=acetone-hexanes (1:1); R$_f$=0.3.

Step c

The title compound was prepared according to the procedure described for the synthesis of compound 69, step b: mp: 56-59° C.; $^1$H NMR (200 MHz, DMSO-d$_6$): δ 9.05 (s, 1H), 6.75 (s, 2H), 7.66 (d, J=2.2 Hz, 1H), 6.66 (m, 2H), 6.22 (dd, J=2.8, 10.2 Hz, 1H), 3.57 (d, J=11.0 Hz, 3H), 3.12-3.23 (m, 3H), 1.10 (d, J=7.0 Hz, 6H); LC-MS m/z=495 [C$_{17}$H$_{19}$Br$_2$O$_5$P+H]$^+$; Anal. Calcd for (C$_{17}$H$_{19}$Br$_2$O$_5$P): C, 41.32; H, 3.88. Found: C, 41.55; H, 4.02.

Compound 69-3: [3,5-Dimethyl-4-(4'-hydroxy-3'-isopropylbenzyl)benzyl]-phosphonic Acid Monomethyl ester The title compound was prepared from dimethyl 2-[3,5-dibromo-4-(4'-methoxymethoxy-3'-isopropylphenoxy)]benzylphosphonate (compound 68, step b) according to the procedure described for the synthesis of compound 7-14, step a followed by compound 69, step b: mp: 72-75; $^1$H NMR (300 MHz, CD$_3$OD): δ 7.01 (d, J=2.1 Hz, 2H), 6.84 (d, J=2.1 Hz, 1H), 6.54 (m, 2H), 3.94 (s, 2H), 3.65 (d, J=10.8 Hz, 3H), 3.21 (m, 1H), 3.09 (d, J=21.0 Hz, 2H), 2.23 (s, 6H), 1.13 (d, J=7.0 Hz, 6H); LC-MS m/z=361 [C$_{20}$H$_{27}$O$_4$P−H]$^+$; Anal. Calcd for (C$_{20}$H$_{27}$O$_4$P+0.2H$_2$O): C, 65.63; H, 7.55. Found: C, 65.70; H, 7.44.

Compound 69-4: [3,5-dibromo-4-(4'-hydroxy-3'-isopropylphenoxy)-phenylamino]-methylphosphonic acid monomethyl ester Step a:

To a stirring mixture of t-butyl [3,5-dibromo-4-(3'-isopropyl-4'-methoxymethoxyphenoxy)phenyl]carbamate (compound 84, step f, 0.15 g, 0.28 mmol) and acetonitrile (4.0 mL) was added Cs$_2$CO$_3$ (0.179 g, 0.55 mmol) followed by dimethyl 4-chloro-benzenesulfonyloxymethylphosphonate (0.087 g, 0.28 mmol). The reaction mixture was stirred at 40° C. for 16 h and the solvent evaporated. The reaction mixture was partitioned with ethyl acetate and H$_2$O, the organic layer was concentrated and the crude was purified by preparatory thin-layer chromatography on silica gel, eluting with ethyl acetate-hexanes (3:2) to afford dimethyl N-tert-butoxycarbonyl-[3,5-dibromo-4-(3'-isopropyl-4'-methoxymethoxyphenoxy)phenylamino]-methylphosphonate as an oil (0.040 g, 22%): $^1$H NMR (300 MHz, DMSO-d$_6$): δ 7.88 (s, 2 H), 7.03 (m, 1 H), 6.72 (m, 1 H), 6.46 (m, 1 H), 5.18 (s, 2 H), 4.25 (m, 2 H), 3.64 (d, J=9.0 Hz, 6 H), 3.41 (s, 3 H), 3.27 (m, 1 H), 1.44 (s, 9 H), 1.15 (d, J=6.0 Hz, 6 H); TLC conditions: Uniplate silica gel, 250 microns; Mobile phase=ethyl acetate-hexanes (4:1); R$_f$=0.42

Step b:

To a mixture of N-tert-butoxycarbonyl-[3,5-dibromo-4-(3'-isopropyl-4'-methoxymethoxyphenoxy)phenylamino] methylphosphonate (0.27 g, 0.41 mmol) in methanol (6.0 mL) was added 3 N HCl (0.68 mL, 2.03 mmol). The reaction mixture was heated with microwave radiation at 100° C. in a sealed vial for 5 minutes. The solvent was removed and the residue was partitioned with ethyl acetate and water. The organic layer was coevaporated with methanol and concentrated under reduced pressure to afford N-tert-butoxycarbonyl-[3,5-dibromo-4-(4'-hydroxy-3'-isopropyl-phenoxy)-phenylamino]methylphosphonate (0.075 g, 87%) as a solid: $^1$H NMR (300 MHz, DMSO-d$_6$): δ 8.90 (s, 1 H), 7.09 (s, 2 H), 6.65 (m, 2 H), 6.28 (m, 2 H), 3.70 (m, 6 H), 3.66 (m, 2 H), 3.19 (m, 1 H), 1.14 (d, J=6.0 Hz, 6 H); TLC conditions: Uniplate silica gel, 250 microns; Mobile phase=ethyl acetate-hexanes (4:1); R$_f$=0.25

Step c:

To a stirred solution of N-tert-butoxycarbonyl-[3,5-dibromo-4-(4'-hydroxy-3'-isopropyl-phenoxy)phenylamino] methylphosphonate (0.075 g, 0.14 mmol) in THF (2.0 mL) was added 1 M NaOH (0.70 mL, 0.86 mmol). The reaction mixture was stirred at rt for 16 h, then heated at 40° C. for 5 hrs. The reaction mixture was cooled to 0° C., treated 2 N HCl (pH~1), diluted with ethyl acetate and H$_2$O, partitioned, and the organic layer was extracted with H$_2$O. The organic layer was filtered and concentrated to afford the title compound as a grey solid (0.070 g, 96%): $^1$H NMR (300 MHz, DMSO-d$_6$): δ 8.97 (s, 1 H), 7.07 (s, 2 H), 6.65 (m, 2 H), 6.25 (m, 1 H), 3.64 (m, 2 H), 3.42 (s, 3 H), 3.16 (m, 1 H), 1.14 (d, J=6.0 Hz, 6 H); LC-MS m/z=510 [C$_{17}$H$_{20}$Br$_2$NO$_5$P−H]$^+$; HPLC conditions: Column=Shimadzu LC-A8, SPD-10A; YMC Pack RP-18 filter, 150×4.6; Mobile phase=Solvent A Acetonitrile/0.05% TFA; Solvent B=H$_2$O/0.05% TFA. Flow rate=2.0 mL/min; UV@ 254 nm. Retention time in minutes. (rt=8.81/20.00, 93% purity).

Compound 69-5: [(3,5-Dimethyl-4-[3'-(4-fluorobenzyl)-4'-hydroxybenzyl]-phenylamino)methyl]methylphosphonic acid monomethyl ester Prepared from benzyl N-[3,5-dimethyl-4-(3'-(4-fluorobenzyl)-4'-methoxymethoxybenzyl)phenyl]carbamate (compound 79, step b) according to the procedure described for the synthesis of compound 69-4: $^1$H NMR (300 MHz, DMSO-d$_6$): δ 9.15 (s, 1 H), 7.01-7.22 (m, 4 H), 6.76 (s, 1 H), 6.67 (d, J=8.1 Hz, 1 H), 6.58 (d, J=8.1 Hz, 1 H), 6.40 (s, 2 H), 3.79 (s, 2 H), 3.71 (s, 2 H), 3.58 (d, J=10.5 Hz, 3 H), 3.29 (m, 2 H), 2.07 (s, 6 H); LC-MS m/z=444 [C24H27FNO4P+H]$^+$; Anal Calcd for (C24H27FNO4P+2.2H$_2$O): C, 59.67; H, 6.55; N, 2.90. Found: C, 59.40; H, 6.24; N, 3.31.

Compound 69-6: [3,5-dibromo-4-(4'-hydroxy-3'-isopropylphenoxy)-phenoxy]methylphosphonic acid monomethylester Step a:

To a stirring mixture of DMF (20.0 mL) and NaH (0.074 g, 1.86 mmol) at 0° C. was added 3,5-dibromo-4-(3-isopropyl-4-hydroxy-phenoxy)phenol (Intermediate for the synthesis of compound 8-1, 0.75 g, 1.86 mmol) dissolved in DMF (2.0 mL). The reaction mixture was allowed to stir at rt for 1 hr and cooled to 0° C. Dimethyl 4-chloro-benzenesulfonyloxymethylphosphonate (0.11 g, 0.36 mmol) was added and the reaction mixture was stirred at rt for 16 h. The reaction was quenched with ice $H_2O$, the pH was adjusted to 1 with 2 M HCl, and the mixture was partitioned with ethyl acetate and $H_2O$. The organic layer was concentrated and coevaporated with acetone (2×). The residue was treated with a hexane/ethyl acetate mixture and sonicated to afford dimethyl [3,5-dibromo-4-(4-hydroxy-3-iso-propyl-phenoxy)phenoxy]methylphosphonate as a white solid precipitate (0.070 g, 34%): $^1$H NMR (200 MHz, DMSO-$d_6$): δ 9.00 (s, 1H), 7.47 (s, 2H), 6.65 (m, 2H), 6.23 (m, 1H), 4.60 (d, J=10.0 Hz, 2H), 3.75 (d, J=10.0 Hz, 6H), 3.12 (m, 1H), 1.09 (d, J=6.0 Hz, 6 H); TLC conditions: Uniplate silica gel, 250 microns; Mobile phase=ethyl acetate; $R_f$=0.60

Step b:

To a stirred solution of dimethyl [3,5-dibromo-4-(4-hydroxy-3-iso-propyl-phenoxy)phenoxy]methylphosphonate (0.155 g, 0.30 mmol) in THF (4.0 mL) was added 2 M NaOH (0.89 mL, 1.77 mmol). The reaction mixture was stirred at rt for 48 h, cooled to 0° C., treated with conc. HCl (pH~1), and partitioned with ethyl acetate and $H_2O$. The organic layer was extracted with $H_2O$ (1×). The organic layer was concentrated, dissolved in acetone, filtered and concentrated to afford the title compound as an off-white solid (0.110 g, 73%): $^1$H NMR (300 MHz, DMSO-$d_6$): δ 9.03 (s, 1 H), 7.47 (s, 2H), 6.66 (m, 2H), 6.27 (m, 1H), 4.41 (d, J=9.0 Hz, 2H), 3.69 (d, J=9.0 Hz, 3H), 3.17 (m, 1H), 1.14 (d, J=6.0 Hz, 6H); LC-MS m/z=510 $[C_{17}H_{19}Br_2O_6P-H]^+$.

Example 70

Compound 70: [3,5-dimethyl-4-(4'-hydroxy-3'-isopropylbenzyl)-phenoxymethyl]methylphosphinic acid Step a:

Solid sodium hydroxide (400 mg, 10 mmol) was added to a solution of diethyl[3,5-dimethyl-4-(4'-methoxymethoxy-3'-iso-propylbenzyl)phenoxy]-methylphosphonate (compound 7, step a, 500 mg, 1.08 mmol) in THF (6 mL) and water (2 mL). The biphasic mixture was stirred at rt for 2 days, then diluted with ethyl acetate and washed with brine then 1 N hydrochloric acid, dried ($Na_2SO_4$) and concentrated under reduced pressure. The crude material was carried over without purification: $^1$H NMR (300 MHz, CDCl$_3$) δ 6.96 (d, J=2.1 Hz, 1H), 6.91 (d, J=8.1 Hz, 1H), 6.71 (s, 2H), 6.66 (dd, J=8.1, 2.1 Hz, 1H), 5.12 (s, 2H), 4.4-4.2 (m, 4H), 3.94 (s, 2H), 3.51 (s, 3H), 3.31 (heptuplet, J=7.0 Hz, 1H), 2.23 (s, 6H), 1.41 (t, J=7.0 Hz, 3H), 1.21 (d, J=7.0 Hz, 6 H).

Step b:

Thionyl chloride (120 µL, 1.62 mmol) was added to a solution of crude [3,5-dimethyl-4-(4'-methoxymethoxy-3'-iso-propylbenzyl)phenoxy]-methylphosphonic acid monoethyl ester (1.08 mmol) and pyridine (510 µL, 6.48 mmol) in dichloromethane at rt. After stirring at rt for 18 hours, the yellow solution was concentrated under reduced pressure. The yellow oil was dissolved in THF (10 mL) and the solution cooled to −78° C. A solution of MeMgBr in THF (3M, 1.1 mL, 3.3 mmol) was added to the solution of chloridate at −78° C. After stirring at −78° C. for 15 min, the reaction mixture was quenched at −78° C. with acetic acid (324 µL, 5.4 mmol), diluted with ethyl acetate and washed successively with saturated solution of sodium bicarbonate, a 10% solution of copper sulfate, brine, dried ($Na_2SO_4$) and concentrated under reduced pressure. The residue was purified by column chromatography (silica gel, ethyl acetate/methanol 99/1 to 95/5) to give ethyl [3,5-dimethyl-4-(4'-methoxymethoxy-3'-isopropylbenzyl)phenoxymethyl] methylphosphinate (318 mg, 68%): $^1$H NMR (300 MHz, CDCl$_3$) δ 6.98 (s, 1H), 6.92 (d, J=8.4 Hz, 1H), 6.70 (s, 2H), 6.66 (d, J=8.4 Hz, 1H), 5.19 (s, 2H), 4.4-4.2 (m, 4H), 3.96 (s, 2H), 3.51 (s, 3H), 3.33 (heptuplet, J=7.0 Hz, 1H), 2.26 (s, 6H), 1.68 (d, J=15 Hz, 3H), 1.4 (t, J=7.0 Hz, 3H), 1.22 (d, J=7.0 Hz, 6H); TLC conditions: Merck silica gel, 250 microns; Mobile phase=dichloromethane-methanol (9:1); $R_f$=0.5.

Step c:

The title compound was prepared according to the procedure described for the synthesis of compound 7, step b, (225.8 mg): $^1$H NMR (300 MHz, DMSO d$_6$) δ 9.00 (s, 1H), 6.86 (d, J=1.8 Hz, 1H), 6.73 (s, 2H), 6.63 (d, J=8.4 Hz, 2H), 6.46 (dd, J=8.4, 1.8 Hz, 1H), 4.11 (d, J=8.4 Hz, 4H), 3.82 (s, 2H), 3.51 (s, 3H), 3.14 (heptuplet, J=7.0 Hz, 1H), 2.19 (s, 6H), 1.43 (d, J=14.7 Hz, 3H), 1.12 (d, J=7.0 Hz, 6H); LC-MS m/z=363.1 $[C_{20}H_{27}O_4P+H]^+$; Anal. Calcd for ($C_{20}H_{27}O_4P$+0.2$H_2O$): C, 65.63; H, 7.55. Found: C, 65.47; H, 7.57.

Example 71

Compound 71: [3,5-Dibromo-4-(4'-hydroxy-3'-isopropylphenoxy)benzyl]-methylphosphinic Acid Step a:

To a solution of 3,5-dibromo-4-(3'-isopropyl-4'-methoxylphenoxy)benzyl bromide (intermediate for the synthesis of compound 19-1, 0.30 g, 0.60 mmol) in DMF (4.0 mL) at room temperature was slowly added a solution of diethyl methylphosphonite (0.25 g, 1.8 mmol) in DMF (0.5 mL). The reaction mixture was stirred at 100° C. for 3 h and cooled to room temperature. The mixture was quenched with water (10 mL) and extracted with ethyl acetate (10 mL). The organic layer was dried over MgSO$_4$, filtered and concentrated under reduced pressure. The crude product was purified by column chromatography on silica gel, eluting with 50% acetone in hexanes to afford ethyl [3,5-dibromo-4-(3'-isopropyl-4'-methoxyphenoxy)benzyl]methylphosphinate (0.29 g, 92%) as a colorless oil: $^1$H NMR (200 MHz, DMSO-$d_6$): δ 7.69 (d, J=2.8 Hz, 1 H), 6.84 (d, J=10 Hz, 1H), 6.73 (d, J=4.2 Hz, 1H), 6.40 (dd, J=2.8, 10.2 Hz, 1H), 3.98 (m, 2H), 3.73 (s, 3H), 3.20 (m, 1H), 1.38 (d, J=10.2 Hz, 3H), 1.19 (t, J=7.8 Hz, 3H), 1.11 (d, J=7.0 Hz, 6 H); LC-MS m/z=521 $[C_{20}H_{25}Br_2O_4P+H]^+$; TLC conditions: Uniplate silica gel, 250 microns; Mobile phase=acetone-hexanes (1:1); $R_f$=0.50.

Step b:

The title compound was prepared according to the procedure described for the synthesis of compound 4, step b: mp: 61-63° C.; $^1$H NMR (200 MHz, DMSO-$d_6$): δ 9.05 (s, 1 H), 7.65 (d, J=2.4 Hz, 2H), 6.67 (m, 2H), 6.23 (dd, J=2.8, 10.2 Hz, 1H), 3.36 (d, J=10.2 Hz, 3H), 3.14 (m, 1H), 1.28 (d, J=10.2 Hz, 3H), 1.11 (d, J=7.0 Hz, 6 H); LC-MS m/z=479 $[C_{17}H_{19}Br_2O_4P+H]^+$; Anal. Calcd for ($C_{17}H_{1}$ g $Br_2O_4P$): C, 42.71; H, 4.01. Found: C, 42.45; H, 4.40.

Example 72

Compound 72: [3,5-Dimethyl-4-(4'-hydroxy-3'-isopropylbenzyl)-benzyl]methylphosphinic Acid Step a:

To a solution of [3,5-dimethyl-4-(3'-isopropyl-4'-methoxymethoxybenzyl)]benzyl bromide (compound 68, step a, 0.25 g, 0.64 mmol) in DMF (4.0 mL) at room temperature was slowly added a solution of diethyl methylphosphite (0.26 g, 1.92 mmol) in DMF (1.0 mL). The reaction mixture was stirred at 110° C. for 2 h and cooled to room temperature. The mixture was quenched with water (10 mL) and extracted with ethyl acetate (10 mL). The organic layer was dried over MgSO$_4$, filtered and concentrated under reduced pressure. The crude product was purified by column chromatography on silica gel, eluting with 80% acetone in hexanes to afford ethyl [3,5-dimethyl-4-(3'-isopropyl-4'-methoxymethoxybenzyl)benzyl]-methylphosphinate (0.18 g, 70%) as colorless oil: $^1$H NMR (300 MHz, CD$_3$OD): δ 7.04 (d, J=2.4 Hz, 2H), 6.91 (m, 2H), 6.72 (d, J=7.2 Hz, 1H), 5.18 (s, 2H), 4.07 (m, 2H), 4.01 (s, 2H), 3.47 (s, 3H), 3.28 (m, 1H), 3.22 (d, J=21.3 Hz, 2H), 2.25 (s, 6H), 1.45 (d, J=14.1 Hz, 3 H), 1.17 (d, J=7.0 Hz, 6 H); TLC conditions: Uniplate silica gel, 250 microns; Mobile phase=acetone-hexanes (1:1); R$_f$=0.3.

Step b:
The title compound was prepared according to the procedure described for the synthesis of compound 7, step b: mp: 170-173; $^1$H NMR (300 MHz, CD$_3$OD): δ 6.97 (s, 2H), 6.79 (s, 1H), 6.52 (m, 2H), 3.91 (s, 2H), 3.20 (m, 1H), 3.09 (d, J=17.7 Hz, 2H), 2.20 (s, 6H), 1.37 (d, J=14.1 Hz, 3H), 1.10 (d, J=7.0 Hz, 6H); LC-MS m/z=347 [C$_{20}$H$_{27}$O$_3$P+H]$^+$; Anal. Calcd for (C$_{20}$H$_{27}$O$_3$P+0.3H$_2$O): C, 68.28; H, 7.91. Found: C, 68.33; H, 9.11.

Example 73

Compound 73: [3,5-Dimethyl-4-(4'-hydroxy-3'-isopropylbenzyl)benzyl]-ethylphosphinic Acid Step a:
To a solution of 3,5-dibromo-4-(3'-isopropyl-4'-methoxylphenoxy)benzyl bromide (intermediate for the synthesis of compound 19-1, 0.19 g, 0.39 mmol) in DMF (3.0 mL) at room temperature was slowly added a solution of diethyl ethylphosphite (0.17 g, 1.17 mmol) in DMF. The reaction mixture was stirred at 100° C. for 2 h and cooled to room temperature. The mixture was quenched with water (10 mL) and extracted with ethyl acetate (10 mL). The organic layer was dried over MgSO$_4$, filtered and concentrated under reduced pressure. The crude product was purified by column chromatography on silica gel, eluting with 50% acetone in hexanes to afford diethyl [3,5-dibromo-4-(4'-hydroxy-3'-isopropylphenoxy)benzyl]-ethylphosphinate (0.19 g, 93%) as colorless oil: $^1$H NMR (300 MHz, CD$_3$OD): δ 7.70 (d, J=2.8 Hz, 2H), 6.84 (d, J=10 Hz, 1H), 6.71 (d, J=4.2 Hz, 1H), 6.48 (dd, J=2.8, 10.2 Hz, 1H), 4.09 (m, 2H), 3.81 (s, 3H), 3.30 (m, 3H), 1.84 (m, 2H), 1.13-1.40 (m, 12H); TLC conditions: Uniplate silica gel, 250 microns; Mobile phase=acetone-hexanes (1:1); R$_f$=0.50.

Step b:
The title compound was prepared according to the procedure described for the synthesis of compound 4, step b: mp: 80-83° C.; $^1$H NMR (300 MHz, CD$_3$OD): δ 7.68 (d, J=2.8 Hz, 2H), 6.64 (m, 2H), 6.36 (dd, J=2.8, 10.2 Hz, 1H), 3.33 (m, 1H), 3.24 (d, J=15.6 Hz, 2H), 1.76 (m, 2H), 1.19 (m, 9H); LC-MS m/z=493 [C$_{18}$H$_{21}$Br$_2$O$_4$P+H]$^+$; Anal. Calcd for (C$_{18}$H$_{21}$Br$_2$O$_4$P): C, 43.93; H, 4.30. Found: C, 43.56; H, 4.26.

Example 74

Compound 74: ethyl [(4-methylphenyl)sulfonyloxymethyl]-methylphosphinate

Step a:
To a stirred solution of diethyl (4-methylphenyl)-sulfonyloxymethylphosphonate (intermediate for the synthesis of compound 7, 2.00 g, 6.21 mmol) in benzene (20.0 mL) was added phosphorous pentachloride (1.55 mL, 7.45 mmol) and the reaction mixture was refluxed until homogenous, then stirred at rt overnight. The solvents were removed and the residue was coevaporated with toluene (2×). The crude was used as is in the next step.

Step b:
To the crude ethyl (4-methylphenyl)sulfonyloxymethylphosphinate monochloridate (2.00 g, 6.39 mmol) in dry THF (30.0 mL) at −78° C. was added MeMgBr (2.20 mL, 6.97 mmol, 3.0 M in diethyl ether). The reaction was quenched immediately after the MeMgBr addition with 1 mL of acetic acid. The reaction mixture was diluted with ethyl acetate and H$_2$O and the organic layer was washed twice with saturated aqueous NaHCO$_3$ and once with H$_2$O. The organic layer was concentrated and coevaporated with MeOH. The product was obtained by precipitation from hexanes to afford the title compound as a white solid (1.40 g, 77% over two steps): $^1$H NMR (200 MHz, DMSO-d$_6$): δ 7.85 (m, 2H), 7.52 (m, 2H), 4.30 (d, J=12.0 Hz, 2H), 3.90 (m, 2H), 2.40 (s, 3H), 1.45 (d, J=21.0 Hz, 3H), 1.15 (m, 3H); TLC conditions: Uniplate silica gel, 250 microns; Mobile phase=ethyl acetate-methanol (9:1); R$_f$=0.27.

Example 75

Compound 75: [3,5-Dimethyl-4-(4'-hydroxy-3'-methylsulfanylbenzyl)-phenoxy]methylphosphonic acid monomethyl ester Step a:
To a stirring solution of triisopropyl-[3,5-dimethyl-4-(4'-methoxymethoxybenzyl)phenoxy]silane (1.2 g, 2.8 mmol) and TMEDA (0.51 mL, 3.42 mmol) in ether (25 mL) at −20° C. was added n-BuLi (1.37 mL, 2.5 M in hexanes). The mixture was stirred at −20° C. for 1 h and methyldisulfanylmethane (0.5 mL, 5.6 mmol) was added. The reaction mixture was stirred at −20° C. for 1 h, allowed to warm to room temperature and stirred for 4 h. The reaction mixture was quenched with saturated NH$_4$Cl and diluted with diethyl ether. The organic layer was dried over Na$_2$SO$_4$, filtered and concentrated under reduced pressure to afford triisopropyl-[3,5-dimethyl-4-(4'-methoxymethoxy-3'-methylsulfanylbenzyl)phenoxy]silane as a yellow oil (1.3 g, 98%): $^1$H NMR (300 MHz, DMSO-d$_6$): δ 6.95 (d, J=8.1 Hz, 1H), 6.78 (d, J=2.1 Hz, 1H), 6.4 (dd, J=2.1, 8.1 Hz, 1H), 6.60 (s, 2H), 5.19 (s, 2H), 3.90 (s, 2H), 3.35 (s, 3H), 2.27 (s, 3H), 2.14 (s, 6H), 1.25 (m, 3H), 1.09 (d, J=6.9 Hz, 18H); TLC conditions: Uniplate silica gel, 250 microns; Mobile phase=15% ethyl acetate in hexanes; R$_f$=0.46.

Step b:
To a stirring solution of triisopropyl-[3,5-dimethyl-4-(4'-methoxymethoxy-3'-methylsulfanylbenzyl)phenoxy]silane (1.3 g, 2.74 mmol) in THF (20 mL) at room temperature was added tetrabutylammonium fluoride (3.4 mL, 1.0 M in THF). The reaction mixture was stirred at room temperature for 2 h, diluted with diethyl ether and washed with water (30 mL×2). The solvent was removed under reduced pressure. The crude product was purified by column chromatography on silica gel, eluting with ethyl acetate-hexanes (4:6) to afford 3,5-dimethyl-4-(4'-methoxymethoxy-3'-methylsulfanylbenzyl)phenol as a white solid (0.75 g, 86%): $^1$H NMR (300 MHz, DMSO-d$_6$): δ 9.04 (s, 1H), 6.93 (d, J=8.4 Hz 1H), 6.86 (d, J=1.2 Hz 1H), 6.61 (dd, J=1.2, 8.4 Hz, 1H), 6.49 (s, 2H), 5.19 (s, 2H), 3.86 (s, 2H), 3.40 (s, 3H), 2.32 (s, 3H), 2.12 (s, 6H); TLC conditions: Uniplate silica gel, 250 microns; Mobile phase=30% ethyl acetate in hexanes; R$_f$=0.45.

Step c:
To a solution of 3,5-dimethyl-4-(4'-methoxymethoxy-3'-methylsulfanylbenzyl)phenol (0.54 g, 1.7 mmol) in CH$_3$CN (20 mL) at room temperature was added Cs$_2$CO$_3$ (0.82 g, 2.54 mmol) and dimethyl (4-chlorophenylsulfonyloxy)methylphosphonate (0.54 g, 1.7 mmol). The reaction mixture was refluxed for 16 h. The solvent was removed under reduced pressure and the residue was partitioned between ethyl acetate and saturated NaHCO$_3$. The organic layer was dried over Na$_2$SO$_4$, filtered and concentrated under reduced pressure. The crude product was purified by column chromatography on silica gel, eluting with ethyl acetate-hexanes (4:1) to afford dimethyl [3,5-dimethyl-4-(4'-methoxymethoxy-3'-methylsulfanylbenzyl)phenoxy]methylphosphonate as a colorless oil (0.3 g, 40%): $^1$H NMR (200 MHz, DMSO-d$_6$): δ 6.89 (m, 2H), 6.75 (s, 2H), 6.58 (m, 1H), 5.16 (s, 2H), 4.42 (d, J=10.0 Hz, 2H), 3.89 (s, 2H), 3.73 (d, J=10.6 Hz, 6H), 3.37 (s, 3H), 2.30 (s, 3H), 2.17 (s, 6H); TLC conditions: Uniplate silica gel, 250 microns; Mobile phase=80% ethyl acetate in hexanes; R$_f$=0.31.

Step d:

To a stirring solution of dimethyl [3,5-dimethyl-4-(4'-methoxymethoxy-3'-methylsulfanylbenzyl)phenoxy]methylphosphonate (0.051 g, 0.12 mmol) in MeOH (1.5 mL) at room temperature was added HCl (0.93 mL, 1 N), and heated at 100° C. for 5 min by microwave. The solvent was removed under reduced pressure, and the residue was partitioned between EtOAc and sat. NaHCO$_3$. The organic layer was dried over Na$_2$SO$_4$, filtered and concentrated under reduced pressure. The crude product was purified by column chromatography on silica gel, eluting with ethyl acetate to afford dimethyl[3,5-dimethyl-4-(4'-hydroxy-3-methylsulfanylbenzyl)phenoxy]-methylphosphonate as a colorless oil (0.037 g, 80%): $^1$H NMR (200 MHz, DMSO-d$_6$): δ 9.57 (s, 1H), δ 6.74 (m, 3H), 6.63 (d, J=8.0 Hz, 1H), 6.49 (m, 1H), 4.42 (d, J=9.8 Hz, 2H), 3.83 (s, 2H), 3.72 (d, J=10.3 Hz, 6H), 2.26 (s, 3H), 2.16 (s, 6H); TLC conditions: Uniplate silica gel, 250 microns; Mobile phase=ethyl acetate; R$_f$=0.45.

Step e:

To a stirring solution of dimethyl [3,5-dimethyl-4-(4'-hydroxy-3-methylsulfanylbenzyl)phenoxy]methylphosphonate (0.037 g, 0.093 mmol) in THF (3 mL) at room temperature was added NaOH (0.37 mL, 1 N), and stirred for 48 h at room temperature. It was acidified by 1 N HCl to pH=2, and the mixture was partitioned between EtOAc and sat. NaHCO$_3$. The organic layer was dried over Na$_2$SO$_4$, filtered and concentrated under reduced pressure to afford the title compound as a light brown foam (0.030 g, 84%): $^1$H NMR (200 MHz, DMSO-d$_6$): δ 9.61 (s, 1H), 6.78 (s, 1H), 6.64 (m, 3H), 6.46 (d, J=8.0 Hz, 1H), 3.96 (d, J=9.2 Hz, 2H), 3.81 (s, 2H), 3.51 (d, J=9.8 Hz, 3H), 2.26 (s, 3H), 2.14 (s, 6H); LC-MS m/z=383 [C$_{18}$H$_{23}$O$_5$PS+H]$^+$; Anal Calcd for (C$_{18}$H$_{23}$O$_5$PS+ 0.1H$_2$O+0.4CH$_2$Cl$_2$): C, 52.85; H, 5.78. Found: C, 52.68; H, 5.45.

Example 76

Compound 76: [3,5-Dimethyl-4-(4'-hydroxy-3'-methanesulfonylbenzyl)-phenoxy]methylphosphonic acid monomethyl ester Step a:

To a stirring solution of dimethyl [3,5-dimethyl-4-(4'-methoxymethoxy-3'-methylsulfanylbenzyl)phenoxy]methylphosphonate (compound 75, step c, 0.25 g, 0.57 mmol) in CH$_2$Cl$_2$ (15 mL) at room temperature was added m-CPBA (0.34 g, 2 mmol). The mixture was stirred for 16 h at room temperature, quenched with saturated Na$_2$SO$_3$ and diluted with CH$_2$Cl$_2$. The organic layer was collected and dried over Na$_2$SO$_4$, filtered and concentrated under reduced pressure.

The crude product was purified by column chromatography on silica gel, eluting with ethyl acetate to afford dimethyl [3,5-dimethyl-4-(3'-methanesulfonyl-4'-methoxymethoxybenzyl)phenoxy]methylphosphonate as a colorless oil (0.14 g, 53%): $^1$H NMR (200 MHz, DMSO-d$_6$): δ 7.43 (s, 1H), 7.25 (s, 2H), 6.77 (s, 2H), 5.35 (s, 2H), 4.43 (d, J=10.0 Hz, 2H), 3.95 (s, 2H), 3.73 (d, J=10.6 Hz, 6H), 3.41 (s, 3H), 3.25 (s, 3H), 2.17 (s, 6H); TLC conditions: Uniplate silica gel, 250 microns; Mobile phase=ethyl acetate; R$_f$=0.31.

Step b:

To a stirring solution of dimethyl [3,5-dimethyl-4-(3'-methanesulfonyl-4'-methoxymethoxybenzyl)phenoxy]methylphosphonate (0.14 g, 0.3 mmol) in MeOH (2 mL) at room temperature was added HCl (0.3 mL, 10 N), and heated at 100° C. for 5 min by microwave. The solvent was removed under reduced pressure, and the residue was partitioned between EtOAc and sat. NaHCO$_3$. The organic layer was dried over Na$_2$SO$_4$, filtered and concentrated under reduced pressure. The crude product was purified by column chromatography on silica gel, eluting with methanol-ethyl acetate (5:95) to afford dimethyl [3,5-dimethyl-4-(4'-hydroxy-3'-methanesulfonylbenzyl)phenoxy]methylphosphonate as a colorless oil (0.042 g, 33%): $^1$H NMR (200 MHz, DMSO-d$_6$): δ 10.87 (s, 1H), 7.30 (d, J=1.8 Hz, 1H), 7.13 (dd, J=1.8, 8.4 Hz, 1H), 6.92 (d, J=8.4 Hz, 1H), 6.76 (s, 2H), 4.42 (d, J=10.0 Hz, 2 Hz), 3.89 (s, 2H), 3.74 (d, J=10.6 Hz, 6H), 3.19 (s, 3H), 2.16 (s, 6H); TLC conditions: Uniplate silica gel, 250 microns; Mobile phase=5% methanol in ethyl acetate; R$_f$=0.42.

Step c:

To a stirring solution of dimethyl [3,5-dimethyl-4-(4'-hydroxy-3'-methanesulfonylbenzyl)phenoxy]methylphosphonate (0.042 g, 0.098 mmol) in THF (3 mL) at room temperature was added NaOH (0.39 mL, 1 N), and stirred for 48 h at room temperature. It was acidified by 1 N HCl to pH=2, and the mixture was partitioned between EtOAc and sat. NaHCO$_3$. The organic layer was dried over Na$_2$SO$_4$, filtered and concentrated under reduced pressure to afford the title compound as a light yellow foam (0.016 g, 39%): $^1$H NMR (200 MHz, DMSO-d$_6$): δ 10.96 (s, 1H), 7.34 (d, J=1.8 Hz, 1H), 7.11 (dd, J=1.8, 8.4 Hz, 1H), 6.95 (d, J=8.4 Hz, 1H), 6.71 (s, 2H), 4.07 (d, J=9.6 Hz, 2H), 3.88 (s, 2H), 3.58 (d, J=10.4 Hz, 3 H), 3.19 (s, 3H), 2.15 (s, 6H); LC-MS m/z=415 [C$_{18}$H$_{23}$O$_7$PS+H]$^+$; Anal Calcd for (C$_{18}$H$_{23}$O$_7$PS+1.1H$_2$O): C, 49.79; H, 5.86. Found: C, 49.47; H, 5.73.

Example 77

Compound 77: [(3,5-dimethyl-4-(4-hydroxy-3-methanesulfonylbenzyl)-phenoxy)methyl]methylphosphinic acid Step a:

To a solution of 3,5-dimethyl-4-(4'-methoxymethoxy-3'-methylsulfanylbenzyl)phenol (compound 75, step b, 0.11 g, 0.35 mmol) in CH$_3$CN (5 mL) at room temperature was added Cs$_2$CO$_3$ (0.17 g, 0.52 mmol) and ethyl [(4-methylphenyl)sulfonyloxymethyl]methylphosphinate (compound 74, 0.1 g, 0.35 mmol). The reaction mixture was refluxed for 16 h. The solvent was removed under reduced pressure and the residue was partitioned between ethyl acetate and saturated NaHCO$_3$. The organic layer was dried over Na$_2$SO$_4$, filtered and concentrated under reduced pressure. The crude product was purified by column chromatography on silica gel, eluting with ethyl acetate to afford ethyl [(3,5-dimethyl-4-(4'-methoxymethoxy-3'-methylsulfanylbenzyl)phenoxy)methyl]methylphosphinate as a colorless oil (0.3 g, 91%): $^1$H NMR (200

MHz, DMSO-$d_6$): δ 6.89 (m, 2H), 6.76 (s, 2H), 6.56 (dd, J=1.8, 8.4 Hz, 1H), 5.16 (s, 2H), 4.27 (m, 2H), 4.04 (m, 2H), 3.89 (s, 2H), 3.37 (s, 3H), 2.30 (s, 3H), 2.17 (s, 6H), 1.51 (d, J=14.6 Hz, 3H), 1.23 (t, J=7.0 Hz, 3 H); TLC conditions: Uniplate silica gel, 250 microns; Mobile phase=ethyl acetate; $R_f$=0.32.

Step b:

To a stirring solution of ethyl [(3,5-dimethyl-4-(4'-methoxymethoxy-3'-methylsulfanylbenzyl)phenoxy)methyl]methylphosphinate (0.14 g, 0.32 mmol) in $CH_2Cl_2$ (10 mL) at room temperature was added m-CPBA (0.19 g, 1.12 mmol). The mixture was stirred for 16 h at room temperature, quenched with saturated $Na_2SO_3$ and diluted with $CH_2Cl_2$. The organic layer was collected and dried over $Na_2SO_4$, filtered and concentrated under reduced pressure. The crude product was purified by column chromatography on silica gel, eluting with ethyl acetate to afford ethyl [(3,5-dimethyl-4-(3'-methanesulfonyl-4'-methoxymethoxybenzyl)phenoxy)methyl] methylphosphinate as a colorless oil (0.07 g, 47%): $^1$H NMR (200 MHz, DMSO-$d_6$): δ 7.42 (s, 1H), 7.25 (s, 2H), 6.78 (s, 2H), 5.35 (s, 2H), 4.27 (m, 2H), 4.04 (m, 2H), 3.95 (s, 2H), 3.41 (s, 3H), 3.25 (s, 3H), 2.17 (s, 6H), 1.51 (d, J=14.6 Hz, 3H), 1.23 (t, J=7.0 Hz, 3H); TLC conditions: Uniplate silica gel, 250 microns; Mobile phase=5% methanol in ethyl acetate; $R_f$=0.32.

Step c:

To a stirring solution of ethyl [(3,5-dimethyl-4-(3'-methanesulfonyl-4'-methoxymethoxybenzyl)phenoxy)methyl] methylphosphinate (0.07 g, 0.15 mmol) in $CH_2Cl_2$ (6 mL) at −20° C. was added TMSBr (0.2 mL, 1.5 mmol). The mixture was stirred for 16 h at room temperature and concentrated under reduced pressure. The residue was added MeOH and stirred for 1 h at room temperature. The solution was concentrated under reduced pressure to afford the title compound as a light pink foam (0.04 g, 67%): $^1$H NMR (200 MHz, DMSO-$d_6$): δ 10.84 (s, 1H), 7.31 (d, J=1.8 Hz, 1H), 7.17 (dd, J=1.8, 8.4 Hz, 1H), 6.95 (d, J=8.4 Hz, 1H), 6.74 (s, 2H), 4.08 (d, J=8.4 Hz, 2H), 3.89 (s, 2H), 3.19 (s, 3H), 2.16 (s, 6H), 1.39 (d, J=14.6 Hz, 3H); LC-MS m/z=399 [C18H23O6PS+H]$^+$; Anal Calcd for (C18H23O6PS+0.2$CH_2Cl_2$+1.8$H_2O$): C, 48.81; H, 6.08. Found: C, 48.52; H, 6.22.

Example 78

Compound 78: 2-[3,5-Dimethyl-4-(3'-(4-fluorobenzyl)-4'-hydroxybenzyl)-phenyl]ethylphosphonic acid monomethyl ester Step a:

To a solution of 4-bromophenol (13.84 gm, 0.08 Mol), 4-fluorobenzyl alcohol (8.68 gm, 0.08 Mol), and 120 mL of dichloroethane was added zinc bromide (21 gm, 0.09 Mol). The reaction mixture was stirred at 60° C. for 24 h, filtered and concentrated under reduced pressure. Pure product was obtained by flash chromatography using $SiO_2$, dichloromethane/hexane [1:1] as eluant to give 4-bromo-2-(4-fluorobenzyl)phenol (9.25 g, 41%) as colorless oil: $^1$H NMR (200 MHz, DMSO-$d_6$): δ 9.79 (s, 1H), 7.16 (m, 5H), 6.74 (d, J=8.8 Hz, 1H), 3.82 (s, 2H); TLC conditions: Uniplate silica gel, 250 microns; Mobile phase=methylene chloride-hexanes (1:1); $R_f$=0.38.

Step b:

To a stirring solution of 4-bromo-2-(4-fluorobenzyl)phenol (16 g, 59.9 mmol) in $CH_2Cl_2$ (200 mL) at room temperature was added ethyl-diisopropyl-amine (15.6 mL, 89.85 mmol) and chloro-methoxy-methyl ether (6.1 mL, 79.67 mmol). After stirring at reflux for 16 h, water was added and the mixture was partitioned with ethyl acetate. The organic layer was collected and dried over $Na_2SO_4$, filtered and concentrated under reduced pressure. The crude product was purified by column chromatography on silica gel, eluting with ethyl acetate-hexanes (1:9) to afford 4-bromo-2-(4-fluorobenzyl)methoxymethoxybenzene as a light yellow oil (16.4 g, 88%): $^1$H NMR (200 MHz, DMSO-$d_6$): 6.96-7.40 (m, 7H), 5.20 (s, 2H), 3.89 (s, 2H), 3.26 (s, 3H); TLC conditions: Uniplate silica gel, 250 microns; Mobile phase=6% ethyl acetate in hexanes; $R_f$=0.79.

Step c:

To a stirring solution of 4-bromo-2-(4-fluoro-benzyl)methoxymethoxybenzene (6.2 g, 19.93 mmol) in THF (80 mL) at −78° C. was added n-BuLi (8.8 mL, 2.5 M in hexanes). The mixture was stirred at −78° C. for 1 h and 2,6-dimethyl-4-triisopropylsilanyloxy-benzaldehyde (6.11 g, 19.93 mmol) was added. The reaction mixture was stirred at −78° C. for 1 h, allowed to warm to room temperature and stirred for 1 h. The reaction mixture was quenched with saturated $NH_4Cl$ and diluted with diethyl ether. The organic layer was dried over $Na_2SO_4$, filtered and concentrated under reduced pressure. The crude product was purified by column chromatography on silica gel, eluting with ethyl acetate-hexanes (1:9) to afford (2,6-dimethyl-4-triisopropylsilanyloxyphenyl)-[3-(4-fluorobenzyl)-4-methoxymethoxyphenyl] methanol as a light yellow oil (8.3 g, 75%): $^1$H NMR (200 MHz, DMSO-$d_6$): δ 6.88-7.20 (m, 7H), 6.47 (s, 2H), 5.97 (d, J=4.0 Hz, 1H), 5.65 (d, J=4.0 Hz, 1H), 5.14 (s, 2H), 3.85 (s, 2H), 3.25 (s, 3H), 2.11 (s, 6H), 1.24 (m, 3H), 1.08 (d, J=7.2 Hz, 18H); TLC conditions: Uniplate silica gel, 250 microns; Mobile phase=10% ethyl acetate in hexanes; $R_f$=0.47.

Step d:

To a stirring solution of (2,6-dimethyl-4-triisopropylsilanyloxyphenyl)-[3-(4-fluorobenzyl)-4-methoxymethoxyphenyl]methanol (8.3 g, 15.01 mmol) in $CH_2Cl_2$ (150 mL) at room temperature was added $Et_3SiH$ (9.6 mL, 60.04 mmol) and TFA (4.5 mL, 60.04 mmol). The reaction mixture was stirred at room temperature for 6 h. The solvent was removed under reduced pressure and the residue was partitioned between ethyl acetate and saturated $NaHCO_3$. The organic layer was dried over $Na_2SO_4$, filtered and concentrated under reduced pressure. Then to this stirring solution of crude product in $CH_2Cl_2$ (150 mL) at room temperature was added ethyl-diisopropyl-amine (2.6 mL, 15.01 mmol) and chloro-methoxy-methyl ether (1 mL, 13.51 mmol). The mixture was refluxed for 16 h, added water. The organic layer was dried over $Na_2SO_4$, filtered and concentrated under reduced pressure. The crude product was purified by column chromatography on silica gel, eluting with ethyl acetate-hexanes (1:9) to afford [3,5-dimethyl-4-(3'-(4-fluorobenzyl)-4'-methoxymethoxybenzyl)phenoxy]triisopropylsilane as a light yellow oil (7 g, 87%): $^1$H NMR (200 MHz, DMSO-$d_6$): δ 6.66-7.19 (m, 7H), 6.54 (s, 2H), 5.12 (s, 2H), 3.82 (s, 4H), 3.25 (s, 3H), 2.11 (s, 6H), 1.23 (m, 3H), 1.06 (d, J=7.2 Hz, 18H); TLC conditions: Uniplate silica gel, 250 microns; Mobile phase ethyl acetate-hexanes (1:9); $R_f$=0.68.

Step e:

To a stirring solution of [3,5-dimethyl-4-(3'-(4-fluorobenzyl)-4'-methoxymethoxybenzyl)phenoxy]triisopropylsilane (7 g, 13.04 mmol) in THF (100 mL) at room temperature was added tetrabutylammonium fluoride (16.3 mL, 1.0 M in THF). The reaction mixture was stirred at room temperature for 2 h, diluted with diethyl ether and washed with water (30 mL×2). The solvent was removed under reduced pressure. The crude product was purified by column chromatography on silica gel, eluting with ethyl acetate-hexanes (3:7) to afford 3,5-dimethyl-4-[3'-(4-fluorobenzyl)-4'-methoxymethoxybenzyl]-phenol as a colorless oil (4.6 g, 93%): $^1$H NMR (200 MHz, DMSO-d$_6$): δ 6.99 (s, 1H), δ 7.13 (m, 4H), 6.85 (m, 2H), 6.67 (m, 1H), 6.43 (s, 2H), 5.12 (s, 2H), 3.84 (s, 2H), 3.76 (s, 2H), 3.24 (s, 3H), 2.07 (s, 6H), TLC conditions: Uniplate silica gel, 250 microns; Mobile phase=ethyl acetate-hexanes (15:85); R$_f$=0.45.

Step f:

To a solution of 3,5-dimethyl-4-[3'-(4-fluorobenzyl)-4'-methoxymethoxybenzyl]phenol (4.6 g, 12.09 mmol) and DMAP (4.4 g, 36.27 mmol) in CH$_2$Cl$_2$ (100 mL) at 0° C. was slowly added trifluoromethanesulfonyl anhydride (3.1 mL, 18.14 mmol). The reaction mixture was stirred at 0° C. for 2 h and quenched with water (60 mL). The organic layer was dried over Na$_2$SO$_4$, filtered and concentrated under reduced pressure. The crude product was purified by column chromatography on silica gel, eluting with ethyl acetate-hexanes (15:85) to afford 3,5-dimethyl-4-[3'-(4-fluorobenzyl)-4'-methoxymethoxybenzyl]phenyl trifluoromethanesulfonate as a colorless oil (5.8 g, 94%): $^1$H NMR (200 MHz, DMSO-d$_6$): δ 6.91-7.28 (m, 7H), 6.80 (s, 1H), 6.69 (d, J=8.4 Hz, 1H), 5.15 (s, 2H), 3.91 (s, 2H), 3.84 (s, 2H), 3.25 (s, 3H), 2.22 (s, 6H); TLC conditions: Uniplate silica gel, 250 microns; Mobile phase=ethyl acetate-hexanes (15:85); R$_f$=0.65.

Step g:

To a solution of 3,5-dimethyl-4-[3'-(4-fluorobenzyl)-4'-methoxymethoxybenzyl]phenyl trifluoromethanesulfonate (5.8 g, 11.32 mmol) in DMF (80 mL) in a bomb apparatus was added MeOH (9.2 mL, 226.4 mmol), Pd(OAc)$_2$ (0.25 g, 1.13 mmol), DPPP (0.47 g, 1.13 mmol) and TEA (3.2 mL, 22.64 mmol). 60 psi of CO was then infused and the reaction mixture was stirred at 90° C. for 16 h. The bomb was cooled to 0° C., vented, its content poured into cold 1 N HCl and extracted with EtOAc twice. The combined EtOAc extracts were washed with brine, dried over MgSO$_4$, filtered and concentrated. The residue was purified by column chromatography on silica gel, eluting with ethyl acetate-hexanes (15:85) to afford methyl 3,5-dimethyl-4-[3'-(4-fluorobenzyl)-4'-methoxymethoxybenzyl]benzoate as a colorless oil (4.8 g, 100%): $^1$H NMR (200 MHz, DMSO-d$_6$): δ 7.64 (s, 2H), 6.68-7.25 (m, 7H), 5.13 (s, 2H), 3.97 (s, 2H), 3.83 (s, 5H), 3.24 (s, 3H), 2.23 (s, 6H). TLC conditions: Uniplate silica gel, 250 microns; Mobile phase=ethyl acetate-hexanes (15:75); R$_f$=0.52.

Step h:

To a stirring solution of dimethyl methylphosphonate (1.44 mL, 13.26 mmol) in THF (60 mL) at −78° C. was added n-BuLi (2.5 M in hexanes, 5.3 mL), the reaction mixture was stirred at −78° C. for 1 h, then 3,5-dimethyl-4-[3'-(4-fluorobenzyl)-4'-methoxymethoxybenzyl]benzoate (1.4 g, 3.31 mmol) in THF (10 mL) was added at the same temperature. The reaction mixture was stirred at −78° C. for 1.5 h, then at room temperature for 1 h. The reaction mixture was quenched with saturated NH$_4$Cl and diluted with diethyl ether. The organic layer was dried over Na$_2$SO$_4$, filtered and concentrated under reduced pressure. The residue was purified by column chromatography on silica gel, eluting with ethyl acetate to afford dimethyl [2-(3,5-dimethyl-4-(3'-(4-fluorobenzyl)-4'-methoxymethoxybenzyl)phenyl)-2-oxo-ethyl]phosphonate as a light yellow oil (1.53 g, 90%): $^1$H NMR (200 MHz, DMSO-d$_6$): δ 7.70 (s, 2H), 6.66-7.22 (m, 7H), 5.14 (s, 2H), 3.97 (s, 2H), 3.84 (s, 2H), 3.82 (d, J=22.4 Hz, 2H), 3.65 (d, J=11.0 Hz, 6H), 3.24 (s, 3H), 2.25 (s, 6H). TLC conditions: Uniplate silica gel, 250 microns; Mobile phase=ethyl acetate-hexanes (4:1); R$_f$=0.35.

Step i:

To a stirring solution of dimethyl [2-(3,5-dimethyl-4-(3'-(4-fluorobenzyl)-4'-methoxymethoxybenzyl)phenyl)-2-oxo-ethyl]phosphonate (1.34 g, 2.6 mmol) in MeOH (60 mL) at 0° C. was added NaBH$_4$ (0.49 g, 13.02 mmol). The reaction mixture was stirred at room temperature for 16 h. The solvent was removed under reduced pressure and the residue was partitioned between ethyl acetate and water. The organic layer was dried over Na$_2$SO$_4$, filtered and concentrated under reduced pressure to afford crude dimethyl [2-(3,5-dimethyl-4-(3'-(4-fluorobenzyl)-4'-methoxymethoxybenzyl)phenyl)-2-hydroxy-ethyl]phosphonate as a light yellow oil (1.4 g, 100%): $^1$H NMR (200 MHz, DMSO-d$_6$): δ 7.11 (m, 6H), 6.89 (m, 2H), 6.67 (m, 1H), 5.44 (d, J=4.2 Hz, 1H), 5.12 (s, 2H), 4.80 (m, 1H), 3.87 (s, 2H), 3.84 (s, 2H), 3.55 (m, 8H), 3.22 (s, 3H), 2.17 (s, 6H). TLC conditions: Uniplate silica gel, 250 microns; Mobile phase=ethyl acetate; R$_f$=0.41.

Step j:

To a stirring solution of [2-(3,5-dimethyl-4-(3'-(4-fluorobenzyl)-4'-methoxymethoxybenzyl)phenyl)-2-hydroxy-ethyl]phosphonate (1.4 g, 2.7 mmol) in CH$_2$Cl$_2$ (80 mL) at room temperature in EtOAc (20 mL) and AcOH (2 mL) was added Pd/C (0.2 g), and the reaction mixture was stirred under 50 PSI H$_2$ at room temperature for 16 h. The mixture was filtered through a celite plug. The solvent was removed under reduced pressure. The residue was purified by column chromatography on silica gel, eluting with ethyl acetate to afford dimethyl 2-[3,5-dimethyl-4-(3'-(4-fluorobenzyl)-4'-methoxymethoxy-benzyl)phenyl]ethylphosphonate as a colorless oil (0.37 g, 27%): $^1$H NMR (200 MHz, DMSO-d$_6$): δ 6.81-7.22 (m, 8H), 6.69 (m, 1H), 5.12 (s, 2H), 3.84 (s, 4H), 3.62 (d, J=10.6 Hz, 6H), 3.24 (s, 3H), 2.65 (m, 2H), 2.14 (s, 6H), 2.02 (m, 2H). TLC conditions: Uniplate silica gel, 250 microns; Mobile phase=ethyl acetate; R$_f$=0.49.

Step k:

To a stirring solution of dimethyl 2-[3,5-dimethyl-4-(3'-(4-fluorobenzyl)-4'-methoxymethoxybenzyl)phenyl]ethylphosphonate (0.32 g, 0.64 mmol) in MeOH (4 mL) at room temperature was added HCl (2.1 mL, 3 N), and heated at 100° C. for 5 min by microwave. The solvent was removed under reduced pressure, and the residue was partitioned between EtOAc and sat. NaHCO$_3$. The organic layer was dried over Na$_2$SO$_4$, filtered and concentrated under reduced pressure. The crude product was purified by column chromatography on silica gel, eluting with ethyl acetate to afford dimethyl 2-[3,5-dimethyl-4-(3'-(4-fluorobenzyl)-4'-hydroxybenzyl)phenyl]-ethylphosphonate as a colorless oil (0.27 g, 92%): $^1$H NMR (200 MHz, DMSO-d$_6$): δ 9.19 (s, 1H), 6.98-7.22 (m, 4H), 6.89 (s, 2H), 6.63 (m, 3H), 3.79 (s, 2H), 3.76 (s, 2H), 3.62 (d, J=10.8 Hz, 6H), 2.65 (m, 2H), 2.13 (s, 6H), 2.02 (m, 2H). TLC conditions: Uniplate silica gel, 250 microns; Mobile phase=ethyl acetate; R$_f$=0.44.

Step l:

To a stirring solution of dimethyl 2-[3,5-dimethyl-4-(3'-(4-fluorobenzyl)-4'-hydroxybenzyl)phenyl]ethylphosphonate (0.27 g, 0.59 mmol) in THF (10 mL) at room temperature was added NaOH (2.4 mL, 1 N), and the reaction mixture was brought to reflux, After 48 h, 1 N HCl was added to pH=2, and the mixture was partitioned between EtOAc and sat. NaHCO$_3$. The organic layer was dried over Na$_2$SO$_4$, filtered and concentrated under reduced pressure to afford the title compound as a light yellow solid (0.2 g, 77%): $^1$H NMR (300 MHz, DMSO-d$_6$): 9.18 (s, 1H), 6.88-7.22 (m, 4H), 6.86 (s, 2H), 6.71 (d, J=2.1 Hz, 1H), 6.65 (d, J=8.1 Hz, 1H), 6.55 (dd, J=2.1, 8.1 Hz, 1H), 3.78 (s, 2H), 3.76 (s, 2H), 3.52 (d, J=11.1 Hz, 3H), 2.65 (m, 2H), 2.11 (s, 6H), 1.84 (m, 2H); mp: 125-127° C.; LC-MS m/z=443 [C25H28FO4P+H]$^+$; Anal Calcd for (C25H28FO4P+0.5H$_2$O): C, 66.51; H, 6.47. Found: C, 66.23; H, 6.61.

Example 79

Compound 79: [(3,5-Dimethyl-4-[3'-(4-fluorobenzyl)-4'-hydroxybenzyl]-phenylamino)methyl]methylphosphinic acid Step a:

To a stirring solution of afford methyl 3,5-dimethyl-4-[3'-(4-fluorobenzyl)-4'-methoxymethoxybenzyl]benzoate (compound 78, step f, 2.8 g, 6.63 mmol) in MeOH (80 mL) at 0° C. was added NaOH (27 mL, 1 N). After heating at 50° C. for 16 h, the solvent was removed under reduced pressure and the residue was acidified with 1 N HCl to pH=1, and the mixture was extracted with EtOAc. The organic layer was dried over $Na_2SO_4$, filtered and concentrated under reduced pressure to afford 3,5-dimethyl-4-[3'-(4-fluorobenzyl)-4'-methoxymethoxybenzyl]benzoic acid as white solid (2.7 g, 100%): $^1$H NMR (300 MHz, DMSO-$d_6$): 12.71 (s, 1H), 7.64 (s, 2H), 7.01-7.22 (m, 4H), 6.95 (d, J=8.4 Hz, 1H), 6.85 (d, J=2.1 Hz, 1H), 6.73 (dd, J=2.1, 8.4 Hz, 1H), 5.15 (s, 2H), 3.98 (s, 2H), 3.86 (s, 2H), 3.27 (s, 3H), 2.25 (s, 6H).

Step b

To a solution of 3,5-dimethyl-4-[3'-(4-fluorobenzyl)-4'-methoxymethoxybenzyl]benzoic acid (2.3 g, 5.63 mmol) in toluene (80 mL) was added diphenylphosphoryl azide (1.22 mL, 5.63 mmol), triethylamine (1.57 mL, 11.26 mmol) and BnOH (2.9 mL, 28.15 mmol) at room temperature. The mixture was refluxed for 16 h. The solvent was removed under reduced pressure, and the residue was partitioned between EtOAc and sat. $NH_4Cl$. The organic layer was dried over $Na_2SO_4$, filtered and concentrated under reduced pressure. The crude product was purified by column chromatography on silica gel, eluting with ethyl acetate-hexanes (1:1) to afford benzyl N-[3,5-dimethyl-4-(3'-(4-fluorobenzyl)-4'-methoxymethoxybenzyl)phenyl]carbamate as a yellow oil (2.9 g, 100%): $^1$H NMR (300 MHz, DMSO-$d_6$): δ 9.59 (s, 1H), 7.01-7.44 (m, 11H), 6.92 (d, J=8.7 Hz, 1H), 6.86 (d, J=1.8 Hz, 1H), 6.76 (dd, J=1.8, 8.7 Hz, 1H), 5.15 (s, 2H), 5.14 (s, 2H), 3.87 (s, 2H), 3.85 (s, 2H), 3.27 (s, 3H), 2.14 (s, 6H); TLC conditions: Uniplate silica gel, 250 microns; Mobile phase=15% ethyl acetate in hexanes; $R_f$=0.55.

Step c:

To a solution of benzyl N-[3,5-dimethyl-4-(3'-(4-fluorobenzyl)-4'-methoxymethoxybenzyl)phenyl]carbamate (0.62 g, 1.21 mmol) in $CH_3CN$ (10 mL) at room temperature was added $Cs_2CO_3$ (0.79 g, 2.42 mmol) and ethyl [(4-methylphenyl)sulfonyloxymethyl]methylphosphinate (compound 74, 0.35 g, 1.21 mmol). The reaction mixture was refluxed for 16 h. The solvent was removed under reduced pressure and the residue was partitioned between ethyl acetate and saturated $NaHCO_3$. The organic layer was dried over $Na_2SO_4$, filtered and concentrated under reduced pressure. The crude product was purified by column chromatography on silica gel, eluting with ethyl acetate to afford ethyl [(N-benzyloxycarbonyl-3,5-dimethyl-4-(3'-(4-fluorobenzyl)-4'-methoxymethoxybenzyl)phenylamino)methyl]methylphosphinate as a colorless oil (0.065 g, 8.5%): $^1$H NMR (300 MHz, DMSO-$d_6$): δ 7.01-7.44 (m, 11H), 6.92 (d, J=8.4 Hz, 1H), 6.89 (d, J=2.1 Hz, 1H), 6.73 (dd, J=2.1, 8.4 Hz, 1H), 5.15 (s, 2H), 5.14 (s, 2H), 4.08 (d, J=6.9 Hz, 2H), 3.91 (s, 2H), 3.85 (m, 3H), 3.63 (m, 1H), 3.27 (s, 3H), 2.18 (s, 6H), 1.32 (d, J=14.4 Hz, 3H), 1.01 (t, J=7.0 Hz, 3H); TLC conditions: Uniplate silica gel, 250 microns; Mobile phase=ethyl acetate-hexanes (4:1); $R_f$=0.39.

Step d:

To a solution of ethyl [(N-benzyloxycarbonyl-3,5-dimethyl-4-(3'-(4-fluorobenzyl)-4'-methoxymethoxybenzyl) phenylamino)methyl] methylphosphinate (0.065 g, 0.1 mmol) in EtOH (30 mL) at room temperature was added Pd/C (0.04 g) and the reaction mixture was stirred under 50 PSI $H_2$ at room temperature for 16 h. The mixture was filtered through a Celite plug. The solvent was removed under reduced pressure and the residue (0.045 g, 0.09 mmol) was dissolved into $CH_2Cl_2$ (8 mL). TMSBr (0.12 mL, 0.9 mmol) was then added at −20° C. The reaction mixture was stirred at room temperature for 16 h and concentrated under reduced pressure. MeOH was added to the residue and the solution was stirred at room temperature. After 1 h, the solution was concentrated under reduced pressure and purified by Prep. LC-MS to afford the title compound as a white solid (0.014 g, 36%): $^1$H NMR (300 MHz, DMSO-$d_6$): δ 9.15 (s, 1H), 7.01-7.22 (m, 4H), 6.77 (d, J=2.1 Hz, 1H), 6.67 (d, J=8.1 Hz, 1H), 6.59 (dd, J=2.1, 8.1 Hz, 1H), 6.41 (s, 2H), 3.79 (s, 2H), 3.71 (s, 2H), 3.25 (d, J=10.2 Hz, 2H), 2.16 (s, 6H), 1.37 (d, J=14.1 Hz, 3H); LC-MS m/z=428 [C24H27FNO3P+H]$^+$; Anal Calcd for (C24H27FNO3P+1.6H$_2$O): C, 63.18; H, 6.67; N, 3.07. Found: C, 62.87; H, 6.50; N, 2.96.

Example 80

Compound 80: [(3,5-Dichloro-4-(3'-(4-fluorobenzyl)-4'-hydroxybenzyl)-phenoxy)methyl]methylphosphonic acid Step a:

4-[(4-Benzyloxy-2,6-dichlorophenyl)[3-(4-fluorobenzyl)-4-methoxy-methoxyphenyl]methanol was prepared from 2,6-dichloro-4-benzyloxybenzaldehyde (*Organic Letters* 4:2833 (2002)) according to the procedure described for the synthesis of compound 78, step c. (0.58 gm, 20%); $^1$H NMR (200 MHz, DMSO-$d_6$): δ 7.38 (m, 5H), 7.13 (m, 7H), 6.95 (s, 2H), 6.32 (d, J=4.8 Hz, 1H), 5.97 (d, J=4.4 Hz, 1H), 5.15 (s, 4H), 3.88 (s, 2H), 3.26 (s, 3H); TLC conditions: Uniplate silica gel, 250 microns; Mobile phase=ethyl acetate-hexanes (3:1); $R_f$=0.45.

Step b:

5-Benzyloxy-1,3-dichloro-2-[3'-(4-fluorobenzyl)-4'-methoxymethoxy-benzyl]benzene was synthesized by combining (1.21 gm, 2.48 mmol) starting material, with dichloromethane 30 mL, TFA (0.92 mL, 12.4 mmol), and triethylsilane (2 mL, 12.4 mmol). The reaction was stirred at r.t for 1.5 h in an ice/water bath, poured into dichloromethane 50 mL, washed 1× with 50 mL $NaHCO_3$, 1× with 25 mL $H_2O$, 1× with 25 mL HCl. The organics were dried over $Na_2SO_4$, filtered and concentrated under reduced pressure. (1.172 gm, 100%); NMR (300 MHz, DMSO-$d_6$): δ 7.37 (m, 5H), 7.15 (m, 4H), 7.08 (m, 4H), 6.94 (m, 2H), 5.14 (s, 4H), 4.06 (s, 2H), 3.85 (s, 2H), 3.25 (s, 3H); TLC conditions: Uniplate silica gel, 250 microns; Mobile phase=hexanes-ethyl acetate (3:1); $R_f$=0.40.

Step c:

3,5-Dichloro-4-[3'-(4-fluorobenzyl)-4'-methoxymethoxybenzyl]-phenol was prepared according to the procedure described for the synthesis of compound 35, step c. (0.183 gm, 40%); $^1$H NMR (300 MHz, DMSO-$d_6$): δ 10.27 (bs, 1H), 7.23 (m, 4H), 7.10 (m, 4H), 6.86 (m, 2H), 6.84 (m, 3H), 5.14 (s, 2H), 4.02 (s, 2H), 3.85 (s, 2H), 3.25 (s, 3H); TLC conditions: Uniplate silica gel, 250 microns; Mobile phase=hexanes-ethyl acetate (3:1); $R_f$=0.32.

Step d:

To a solution of 3,5-dichloro-4-[3'-(4-fluorobenzyl)-4'-methoxymethoxybenzyl]phenol (0.08 gm, 0.19 mmol), acetonitrile (3 mL), ethyl [(4-methylphenyl)sulfonyloxymethyl]methylphosphinate (compound 74, 0.105 gm, 0.38 mmol), was added cesium carbonate (0.153 gm, 0.47 mmol). The reaction was heated at reflux for 2 hours, then stirred over night at r.t. The reaction was filter into 25 ml ethyl acetate, washed 1× with brine, dried over $Na_2SO_4$, filtered and concentrated. Ethyl [(3,5-dichloro-4-(3-(4-fluorobenzyl)-4-hydroxybenzyl)phenoxy)methyl]methylphosphinate was obtained by prep plate TLC using a 2 mm×20×20 cm $SiO_2$ plate eluted with ethyl acetate. (0.06 gm, 60%); $^1$H NMR (300 MHz, DMSO-$d_6$): δ 7.23 (s, 2H), 7.17 (m, 2H), 7.07 (t, J=8.7 Hz, 2H), 6.95 (m, 2H), 6.86 (m, 1H), 5.14 (s, 2H), 4.41 (m, 2H), 4.07 (s, 2H), 4.04 (m, 2H), 3.86 (s, 2H), 3.25 (s, 3H); $^{31}$P NMR (121.4 MHz, DMSO-$d_6$): δ 46.13; TLC conditions: Uniplate silica gel, 250 microns; ethyl acetate; $R_f$=0.22.

Step e:

Title compound was prepared according to the procedure described for the synthesis of compound 7, step b (0.032 gm, 62%); $^1$H NMR (300 MHz, DMSO-$d_6$): δ 9.27 (s, 1H), 7.18 (m, 4H), 7.06 (t, J=8.7 Hz, 2H), 6.84 (d, J=1.8 Hz, 1H), 6.71 (m, 2H), 4.20 (d, J=8.1 Hz, 2H), 4.01 (s, 2H), 3.78 (s, 2H), 1.39 (d, J=14.7 Hz, 3H); TLC conditions: Uniplate silica gel, 250 microns; isopropanol/AcOH/$H_2O$ [7:2:1]; $R_f$=0.65; LC-MS m/z=467 $[C_{22}H_{20}Cl_2FO_4P+H]^-$; Anal Calcd for ($C_{22}H_{20}Cl_2FO_4P+0.1H_2O$): C, 56.09; H, 4.32. Found: C, 55.94; H, 4.15.

Example 81

Compound 81: [3,5-Dichloro-4-(3'-(4-fluorobenzyl)-4'-hydroxybenzyl)-phenoxy]methyl phosphonic acid monomethyl ester Step a:

Dimethyl[3,5-dichloro-4-(3'-(4-fluorobenzyl)-4'-methoxymethyl-benzyl)phenoxy]methylphosphonate was prepared from 3,5-dichloro-4-[3'-(4-fluorobenzyl)-4'-hydroxybenzyl]phenol according to the procedure described for the synthesis of compound 75, step b (0.091 gm, 69%); $^1$H NMR (200 MHz, DMSO-$d_6$): δ 7.26 (s, 2H), 7.10 (m, 2H), 6.92 (m, 5H), 5.10 (s, 2H), 4.25 (d, J=10.6 Hz, 2H), 4.07 (s, 2H), 3.85 (s, 3H), 3.74 (d, J=11 Hz, 2H), 3.25 (s, 3H); TLC conditions: Uniplate silica gel, 250 microns; ethyl acetate-hexane [3:1]; $R_f$=0.32.

Step b

Dimethyl[3,5-dichloro-4-(3'-(4-fluorobenzyl)-4'-hydroxybenzyl)-phenoxy]methylphosphonate was prepared according to the procedure described for the synthesis of compound 7-14, step a (0.093 gm, 81%); $^1$H NMR (300 MHz, DMSO-$d_6$): δ 9.27 (s, 1H), 7.18 (m, 4H), 7.06 (t, J=9 Hz, 2H), 6.84 (s, 1H), 6.69 (m, 2H), 4.57 (d, J=10 Hz, 2H), 4.02 (s, 2H), 3.78 (s, 2H), 3.73 (d, J=11 Hz, 6H); TLC conditions: Uniplate silica gel, 250 microns; ethyl acetate-hexane [3:1]; $R_f$=0.23.

Step c:

A solution of dimethyl [3,5-dichloro-4-(3'-(4-fluorobenzyl)-4'-hydroxybenzyl)phenoxy]methyl phosphonate (compound 80, step , 0.093 gm, 0.18 mmol), THF (3 mL), and 1 N NaOH (0.75 mL) was heated at reflux for 12 h. The reaction was allowed to cool, concentrated under reduced pressure and diluted to a volume of 20 mL with $H_2O$. The liquor was washed with 2× with 10 mL of ethyl acetate, then acidified using conc. HCl to pH 3. The acidic solution was extracted with 2×10 mL of diethyl ether. The ether was dried over $Na_2SO_4$, filtered and concentrated under reduced pressure to afford the title compound (0.063 gm, 72%); $^1$H NMR (200 MHz, DMSO-$d_6$): δ 9.28 (s, 1H), 7.10 (m, 4H), 6.85 (s, 1H), 6.70 (s, 2H), 4.36 (d, J=10 Hz, 2H), 4.01 (s, 2H), 3.77 (s, 2H), 3.64 (d, J=10.5 Hz, 3H); TLC conditions: Uniplate silica gel, 250 microns; isopropanol/AcOH/$H_2O$ [7:2:1]; $R_f$=0.72; LC-MS m/z 485 $[C_{22}H_{20}Cl_2FO_5P+H]^+$; Anal Calcd for ($C_{22}H_{20}Cl_2FO_5P$): C, 54.45; H, 4.15. Found: C, 54.45; H, 4.12.

Example 82

Compound 82: [3,5-Dibromo-4-(3'-(4-fluorobenzyl)-4'-hydroxyphenoxy]-methylphosphonic acid monomethyl ester Step a:

A mixture of 4-bromo-2-(4-fluorobenzyl)phenol (compound 78, step a, 6.0 gm, 21.4 mmol), 1.2 g of palladium on activated carbon (10%) and 100 mL of methanol in a glass reaction vessel was shaken at 50 psi $H_2$ over night, filtered and concentrated under reduced pressure. The resulting light orange oil was dissolved in 180 mL dichloromethane and washed 1× with $NaHCO_3$ saturated solution. The organic was dried over $Na_2SO_4$, filtered and concentrated under reduced pressure to afford 2-(4-fluorobenzyl)phenol (4.52 gm, 100%): $^1$H NMR (200 MHz, DMSO-$d_6$): δ 9.39 (s, 1H), 7.22 (m, 2H), 7.02 (m, 3H), 6.74 (m, 2H), 3.84 (s, 2H); TLC conditions: Uniplate silica gel, 250 microns; Mobile phase=methylene chloride-hexanes (1:1); $R_f$=0.32.

Step b:

A mixture of 2-(4-fluorobenzyl)phenol (4.51 gm, 22.41 mmol), DMF (60 mL), potassium carbonate (7.78 gm, 56.02 mmol) and methyl iodine (1.67 mL, 26.81 mmol) was stirred at rt for 16 h. The reaction was poured into 150 mL ethyl acetate, filtered, washed 3× with 50 mL $H_2O$, 1× with 100 m]L brine, dried over $Na_2SO_4$, filtered and concentrated under reduced pressure to afford 2-(4-fluorobenzyl)anisole (4.27 gm, 88%); $^1$H NMR (200 MHz, DMSO-$d_6$): δ 7.11(m, 7H), 3.88(s, 2H), 3.76(s, 3H); TLC conditions: Uniplate silica gel, 250 microns; methylene chloride-hexanes (1:1); $R_f$=0.64.

Step c:

Bis[3-(4-fluorobenzyl)-4-methoxy]iodonium tetrafluoroborate was prepared from 2-(4-fluorobenzyl)anisole using the procedure from (Yokoyama et al. *J. Med. Chem.* 38:695 (1995)). (5.49 gm, 40%); $^1$H NMR (200 MHz, DMSO-$d_6$): δ 7.94 (m, 4H), 7.15 (m, 12H), 3.86 (s, 4H), 3.25 (s, 6H); TLC conditions: Uniplate silica gel, 250 microns; dichloromethane-methanol [10:1]; $R_f$=0.53.

Step d:

3,5-Dibromo-4-[3'-(4-fluorobenzyl)-4'-methoxyphenoxy] phenyl benzoate was prepared from bis[3-(4-fluorobenzyl)-4-methoxy]iodonium tetrafluoroborate and 3-benzoyloxy-2, 6-dibromophenol according to the procedure described for the synthesis of compound 4, step a (2.15 gm, 63%); $^1$H NMR (200 MHz, DMSO-$d_6$): δ 8.13(dd, J=6.8, 1 Hz, 2Hz), 7.90(s, 2H), 7.75(d, J=7.2 Hz, 1H), 7.63(t, J=7 Hz, 2H), 7.19(m, 4H), 6.92(d, J=8.8 Hz, 1H), 6.76(d, J=3 Hz, 1H), 6.51(dd, J=6, 2.2 Hz, 1H), 3.87(s, 2H), 3.74(s, 3H); TLC conditions: Uniplate silica gel, 250 microns; hexane-acetone [20:1]; $R_f$=0.24.

Step e:

To a mixture of 3,5-dibromo-4-[3'-(4-fluorobenzyl)-4'-methoxyphenoxy]phenyl benzoate (2.14 gm, 3.75 mmol) in THF 60 mL was added 1 N NaOH 20 mL. The reaction was stirred at r.t overnight, then poured into 120 mL ethyl acetate. The aqueous layer was removed and the organic was washed 2× with aqueous $NaHCO_3$, 1× with 1 N HCl 30 mL. The ethyl acetate was dried over $Na_2SO_4$, filtered and concentrated under reduced pressure to give 3,5-dibromo-4-[3'-(4-fluorobenzyl)-4'-methoxyphenoxy]phenol (1.68 gm, 93%); $^1$H NMR (300 MHz, DMSO-$d_6$): δ 10.27 (s, 1H), 7.20 (m, 2H), 7.05 (m, 4H), 6.87 (d, J=9 Hz, 1H), 6.65 (d, J=3.3 Hz, 1H), 6.46 (dd, J=9, 3 Hz, 1H), 3.84 (s, 2H), 3.71 (s, 3H); TLC conditions: Uniplate silica gel, 250 microns; hexane-ethyl acetate [3:1]; $R_f$=0.65.

Step f:

To a stirred solution of 3,5-dibromo-4-[3'-(4-fluorobenzyl)-4'-methoxyphenoxy]phenol (1.66 gm, 3.44 mmol), dichloromethane 100 mL, was added boron tribromide (8.6 mL, 8.60 mmol) in an ice/water bath. The reaction was stirred overnight under a nitrogen atmosphere. The reaction was diluted with ethyl acetate 60 mL, filtered and washed with water 2× with 10 mL and brine 3×10 mL. The ethyl acetate was dried over $Na_2SO_4$, filtered and concentrated under reduced pressure. 3,5-Dibromo-4-[3'-(4-fluorobenzyl)-4'-hydroxyphenoxy]phenol (1.06 gm, 66%) was obtained by flash chromatography using $SiO_2$ eluted with a step gradient of hexane-ethyl acetate[3:1] 2L and hexane-ethyl acetate [3:2]; $^1$H NMR (300 MHz, DMSO-$d_6$): δ 10.24 (s, 1H), 9.14 (s, 1H), 7.22 (m, 2H), 7.08 (m, 4H), 6.69 (td, J=8.7 Hz, 1H), 6.54 (d, J=3.3 Hz, 1H), 6.55 (dd, J=8.4, 3.3 Hz, 1H), 6.35 (dd, J=9, 3 Hz, 1H), 3.80 (s, 2H); TLC conditions: Uniplate silica gel, 250 microns; Mobile phase=methylene chloride-hexanes (1:1); $R_f$=0.55.

Step g:

To a stirred solution of 3,5-dibromo-4-[3'-(4-fluorobenzyl)-4'-hydroxyphenoxy] phenol (0.237 gm, 0.51 mmol), DMF 8 mL, cesium carbonate (0.824, 2.53 mmol) in an ice/water bath was added diethyl trifluoromethylsulfonyloxymethylphosphonate (0.122 gm, 0.41 mmol). The reaction was stir overnight under a nitrogen atmosphere. The reaction was diluted with ethyl acetate 60 mL, filtered and washed with water 2× with 10 mL and brine 3×10 mL. The ethyl acetate was dried over $Na_2SO_4$, filtered and concentrated under reduced pressure. Diethyl [3,5-dibromo-4-(3'-(4-fluorobenzyl)-4'-hydroxyphenoxy]methylphosphonate (0.124 g, 39%) was obtained by prep plate TLC using a 2 mm×20 cm×20 cm prep plate eluted with ethyl acetate; $^1$H NMR (300 MHz, DMSO-$d_6$): δ 9.18 (s, 1H), 7.47 (s, 2H), 7.22 (t, J=5.7 Hz, 2H), 7.07 (t, J=9 Hz, 2H), 6.70 (d, J=8.7 Hz, 1H), 6.55 (d, J=3.3 Hz, 1H), 6.35 (dd, J=9 Hz and J=3 Hz, 1H), 4.54 (d, J=8.7 Hz, 2H), 4.11 (q, J=7.2 Hz, 4H), 3.80 (s, 2H), 1.26 (t, J=7.2 Hz, 6H); $^{31}$P NMR (121 MHz, DMSO-$d_6$): δ 18.87 (s, 1 P); TLC conditions: Uniplate silica gel, 250 microns; Mobile phase=ethyl acetate; $R_f$=0.42.

Step h:

To a stirred solution of diethyl [3,5-dibromo-4-(3'-(4-fluorobenzyl)-4'-hydroxyphenoxy)phenoxy]methylphosphonate (0.134 g, 0.22 mmol) in $CH_2Cl_2$ (5 mL) at 0° C. was added TMSBr (0.24 g, 0.2 mL). The reaction mixture was stirred at 0° C. for 30 min, allowed to warm to room temperature. The reaction mixture was stirred at room temperature for 16 h and the solvent was removed under reduced pressure. The residue was co-evaporated 3×5 mL dichloromethane and 1×5 mL methanol to give [3,5-dibromo-4-(3'-(4-fluorobenzyl)-4'-hydroxyphenoxy)phenoxy]methylphosphonic acid as a white foam (0.124 g, 100%); $^1$H NMR (300 MHz, DMSO-$d_6$): δ 7.35 (s, 2H), 7.23 (m, 2H), 7.06 (t, J=9 Hz, 2H), 6.70 (d, J=8.4 Hz, 1H), 6.58 (d, J=3.3 Hz, 1H), 6.32 (dd, J=9 Hz and J=3 Hz 1H), 3.92 (d, J=8.7 Hz), 3.79 (s, 2H); LC-MS m/z=561 $[C_{20}H_{16}Br_2FO_6P-H]^-$.

Step i:

Dimethyl [3,5-dibromo-4-(3'-(4-fluorobenzyl)-4'-hydroxyphenoxy)-phenoxy]methylphosphonate was prepared from [3,5-dibromo-4-(3'-(4-fluorobenzyl)-4'-hydroxyphenoxy)phenoxy]methylphosphonic acid according to the procedure described for the synthesis of compound 69, step a (0.089 gm, 66%): $^1$H NMR (300 MHz, DMSO-$d_6$): δ 9.19 (s, 1H), 7.48 (s, 2H), 7.22 (m, 2H), 7.07 (t, J=9 Hz, 2H), 6.70 (d, J=9 Hz, 1H), 6.55 (dd, J=3.3 Hz, 1H), 6.34 (dd, J=3 Hz and J=9 Hz, 1H), 4.59 (d, J=9.9 Hz, 2H), 3.80 (s, 2H), 3.75 (d, J=10.5 Hz, 6H); TLC conditions: Uniplate silica gel, 250 microns; Mobile phase=ethyl acetate; $R_f$=0.40.

Step j:

Title compound was prepared from dimethyl [3,5-dibromo-4-(3'-(4-fluorobenzyl)-4'-hydroxyphenoxy)phenoxy] methylphosphonate according to the procedure described for the synthesis of compound 81, step c (0.064 gm, 80%); $^1$H NMR (200 MHz, DMSO-$d_6$): δ 9.19 (s, 1H), 7.44 (s, 2H), 7.22 (t, J=8 Hz, 2H), 7.07 (t, J=8 Hz, 2H), 6.70 (d, J=8.8 Hz, 1H), 6.57 (d, J=3 Hz, 1H), 6.34 (dd, J=8.8, 3 Hz, 1H), 4.33 (d, J=10 Hz, 2H), 3.80 (s, 2H), 3.63 (d, J=11 Hz, 3H); TLC conditions: Uniplate silica gel, 250 microns; isopropanol/AcOH/$H_2O$ [7:2:1]; $R_f$=0.74; LC-MS m/z 575 $[C_{21}H_{18}Br_2FO_6P-H]^-$; Anal Calcd for $(C_{21}H_{18}Br_2FO_6P)$: C, 43.78; H, 3.15. Found: C, 43.66; H, 3.09.

Example 83

Compound 83: [3,5-dimethyl-4-(5'-iodo-4'-hydroxy-3'-iso-propylbenzyl)-phenoxy]methylphosphonic acid Step a:

Diethyl [3,5-dimethyl-4-(5'-iodo-4'-hydroxy-3'-iso-propylbenzyl) phenoxy]methylphosphonate was prepared from diethyl [3,5-dimethyl-4-(4'-hydroxy-3'-iso-propylbenzyl) phenoxy]methylphosphonate (compound 69-1, step a) was prepared according to the procedure described for the synthesis of compound 13-15-cis: $^1$H NMR (300 MHz, $CD_3OD$): δ 7.06 (d, J=2.4 Hz, 1H), 6.89 (d, J=2.4 Hz, 1H), 6.77 (s, 2H), 4.42 (d, J=11.2 Hz, 2H), 4.28 (m, 4H), 3.93 (s, 2H), 3.28 (m, 1H), 2.24 (s, 6H), 1.40 (t, J=7.2 Hz, 6H), 1.17 (d, J=7.0 Hz, 6H); TLC conditions: Uniplate silica gel, 250 microns; Mobile phase=acetone-hexanes (1:1); $R_f$=0.6.

Step b:

The title compound was prepared according to the procedure described for the synthesis of compound 7, step b: mp: 195-198° C.; 7.06 (d, J=2.4 Hz, 1H), 6.89 (d, J=2.4 Hz, 1H), 6.77 (s, 2H), 4.24 (d, J=11.2 Hz, 2H), 3.92 (s, 2H), 3.25 (m, 1H), 2.23 (s, 6H), 1.17 (d, J=7.0 Hz, 6H); LC-MS m/z=491 $[C_{19}H_{24}IO_5P+H]^+$; Anal. Calcd for $(C_{19}H_{24}IO_5P)$: C, 46.55; H, 4.93. Found: C, 46.66; H, 5.26.

Example 84

Compound 84: [(3,5-dibromo-4-(4'-hydroxy-3'-iso-propylphenoxy)-phenylamino)methyl]methylphosphinic acid Step a:

To a stirred solution of bis(4-methoxyphenyl)iodonium tetrafluoroborate (3.14 g, 6.12 mmol, Yokoyama et al. *J. Med. Chem.* 38:695 (1995)) and copper powder (0.52 g, 8.12 mmol) in $CH_2Cl_2$ (12.0 mL) at 0° C. was added a solution of 2,6-dibromo-4-nitrophenol (1.20 g, 4.04 mmol) and $Et_3N$ (0.62 mL, 4.48 mmol) in $CH_2Cl_2$ (8.0 mL). The reaction was wrapped in aluminum foil (darkness), stirred at room temperature for 216 h and filtered through a Celite plug. The filtrate was concentrated and purified by column chromatography on silica gel, eluting with acetone-hexanes (3:97) to afford 3,5-dibromo-4-(3'-isopropyl-4'-methoxyphenoxy)nitrobenzene as an orange solid (1.95 g, 100%): $^1$H NMR (300 MHz, DMSO-$d_6$): δ 8.60 (s, 2H), 6.82 (m, 2H), 6.44 (m, 1H), 3.73 (s, 3H), 3.12 (m, 1H), 1.13 (d, J=6.0 Hz, 6H); TLC conditions: Uniplate silica gel, 250 microns; Mobile phase=ethyl acetate-hexanes (3:47); $R_f$=0.45.

Step b:

To a stirred solution of 3,5-dibromo-4-(3'-isopropyl-4'-methoxyphenoxy)-nitrobenzene (1.37 g, 2.98 mmol) in $CH_2Cl_2$ (30.0 mL) at −78° C. was added $BBr_3$ (8.93 mL, 8.93 mmol, 1 M solution in $CH_2Cl_2$). The reaction mixture was stirred at room temperature for 2.5 h, quenched with ice/water, and stirred cold for several minutes. The reaction mixture was diluted with $CH_2Cl_2$ and $H_2O$, partitioned, and the aqueous solution was extracted with $CH_2Cl_2$. The combined organic layers were concentrated under reduced pressure and the residue was purified by column chromatography on silica gel, eluting with ethyl acetate-hexanes (1:10) to afford 3,5-dibromo-4-(4'-hydroxy-3'-isopropylphenoxy)nitrobenzene as a solid (1.20 g, 90%): $^1$H NMR (300 MHz, DMSO-$d_6$): δ 9.19 (s, 1H), 8.64 (s, 2H), 6.73 (m, 2H), 6.37 (m, 1H), 3.12 (m, 1H), 1.16 (d, J=6.0 Hz, 6H); TLC conditions: Uniplate silica gel, 250 microns; Mobile phase=ethyl acetate-hexanes (1:5); $R_f$=0.46.

Step c:

To a stirred solution of 3,5-dibromo-4-(4'-hydroxy-3'-isopropylphenoxy)nitrobenzene (0.43 g, 0.96 mmol) in $CH_2Cl_2$ (9.0 mL) at 0° C. was added diisopropylethylamine (0.50 mL, 2.89 mmol) and the reaction mixture was stirred for several minutes. Chloromethylmethyl ether (0.15 mL, 1.92 mmol) was added and the solution was refluxed for 16 h, cooled to 0° C., quenched with $H_2O$ and partitioned between $CH_2Cl_2$ and $H_2O$. The organic layer was concentrated under reduced pressure and coevaporated with methanol and toluene to afford 3,5-dibromo-2-(3'-isopropyl-4'-methoxymethoxyphenoxy)nitrobenzene as a glass (0.430 g, 91%): $^1$H NMR (300 MHz, DMSO-$d_6$): δ 8.65 (s, 2H), 7.00 (m, 1H), 6.86 (m, 1H), 6.48 (m, 1H), 5.19 (s, 2H), 3.41 (s, 3H), 3.14 (m, 1H), 1.17 (d, J=6.0 Hz, 6H); TLC conditions: Uniplate silica gel, 250 microns; Mobile phase=ethyl acetate-hexanes (1:5); $R_f$=0.50.

Step d:

To a stirred suspension of 3,5-dibromo-2-(3'-isopropyl-4'-methoxymethoxyphenoxy)nitrobenzene (0.72 g, 1.47 mmol) in $MeOH/H_2O$ (15.0 mL/3.0 mL) was added $Na_2S_2O_4$ (2.56 g, 14.68 mmol). The reaction mixture was stirred at room temperature for 20 min and the methanol was evaporated under reduced pressure. The reaction mixture was diluted with diethyl ether and $H_2O$, partitioned, and the aqueous solution was treated with 1:1 saturated aqueous $NaHCO_3$/brine. The treated aqueous layer was then extracted with ethyl acetate. The organic layers were then combined, washed with $H_2O$ (2×), concentrated, then coevaporated with MeOH (2×) to afford 3,5-dibromo-4-(3'-isopropyl-4'-methoxymethoxyphenoxy)aniline as a solid (0.60 g, 89%): $^1$H NMR (300 MHz, DMSO-$d_6$): δ 6.93 (m, 3H), 6.72 (m, 1H), 6.40 (m, 1H), 5.16 (s, 2H), 3.40 (s, 3H), 3.21 (m, 1H), 1.15 (d, J=6.0 Hz, 6H); TLC conditions: Uniplate silica gel, 250 microns; Mobile phase=ethyl acetate-hexanes (1:5); $R_f$=0.27.

Step e:

To a stirred suspension of 3,5-dibromo-4-(3'-isopropyl-4'-methoxymethoxyphenoxy)aniline (0.50 g, 1.12 mmol) in THF (12.0 mL) was added t-BOC anhydride (0.61 g, 2.80 mmol), dimethylaminopyridine (0.025 g, 5% wt/wt), and t-BuOH (0.25 g, 3.36 mmol). The reaction mixture was stirred at reflux for 1 h and the solvent was evaporated under reduced pressure. The reaction mixture was diluted with ethyl acetate and $H_2O$, partitioned, and the organic layer was concentrated. The residue was purified by column chromatography on silica gel, eluting with ethyl acetate-hexanes (1:10) to afford t-butyl N-t-butoxycarbonyl-[3,5-dibromo-4-(3'-isopropyl-4'-methoxymethoxyphenoxy)phenyl]carbamate as a solid (0.62 g, 86%): $^1$H NMR (300 MHz, DMSO-$d_6$): δ 7.84 (s, 2H), 7.04 (m, 1H), 6.66 (m, 1H), 6.51 (m, 1H), 5.18 (s, 2H), 3.41 (s, 3H), 3.15 (m, 1H), 1.22 (s, 18H), 1.13 (d, J=6.0 Hz, 6H); TLC conditions: Uniplate silica gel, 250 microns; Mobile phase=ethyl acetate-hexanes (1:5); $R_f$=0.68.

Step f:

To a stirred solution of t-butyl N-t-butoxycarbonyl-[3,5-dibromo-4-(3'-isopropyl-4'-methoxymethoxyphenoxy)phenyl]carbamate (0.62 g, 0.96 mmol) in methanol (20.0 mL) was added 2 M NaOH (2.88 mL, 5.77 mmol). The reaction mixture was stirred at rt for 4.5 h and the solvent was evaporated under reduced pressure. The reaction mixture was treated with saturated aqueous ammonium chloride, diluted with ethyl acetate and $H_2O$, partitioned, and the aqueous layer was extracted with ethyl acetate. The combined organic layers were dried over $MgSO_4$, and concentrated to afford t-butyl [3,5-dibromo-4-(3'-isopropyl-4'-methoxymethoxyphenoxy)phenyl]carbamate as an oil (0.62 g, 86%): $^1$H NMR (300 MHz, DMSO-$d_6$): δ 9.79 (s, 1H), 7.87 (s, 2H), 6.97 (m, 1H), 6.77 (m, 1H), 6.39 (m, 1H), 5.17 (s, 2H), 3.41 (s, 3H), 3.14 (m, 1H), 1.50 (s, 9H), 1.17 (d, J=6.0 Hz, 6H); TLC conditions: Uniplate silica gel, 250 microns; Mobile phase=ethyl acetate-hexanes (1:5); $R_f$=0.68.

Step g:

To a stirring mixture of t-butyl [3,5-dibromo-4-(3'-isopropyl-4'-methoxymethoxyphenoxy)phenyl]carbamate (0.11 g, 0.20 mmol) and acetonitrile (3.0 mL) was added $Cs_2CO_3$ (0.859 g, 2.64 mmol) followed by ethyl [(4-methylphenyl)sulfonyloxymethyl]methylphosphinate (compound 74, 0.059 g, 0.20 mmol). The reaction mixture was stirred at reflux for 16 h then partitioned with ethyl acetate and $H_2O$. The organic layer was concentrated and the crude product was purified by preparatory thin-layer chromatography on silica gel, eluting with ethyl acetate-hexanes (4:1) to afford ethyl N-t-butoxycarbonyl-[(3,5-dibromo-4-(3'-isopropyl-4'-methoxymethoxyphenoxy)phenylamino)methyl]methylphosphinate as an oil (0.053 g, 39%): $^1$H NMR (300 MHz, DMSO-$d_6$): δ 7.88 (s, 2H), 6.99 (m, 1H), 6.72 (m, 1H), 6.47 (m, 1H), 5.18 (s, 2H), 4.13 (m, 2H), 3.93 (m, 1H), 3.75 (m, 1H), 3.41 (s, 3H), 3.14 (m, 1H), 1.43 (s, 9H), 1.12 (d, J=6.0 Hz, 6H); TLC conditions: Uniplate silica gel, 250 microns; Mobile phase=ethyl acetate-hexanes (4:1); $R_f$=0.17.

Step h:

To a mixture of ethyl N-t-butoxycarbonyl-[(3,5-dibromo-4-(3'-isopropyl-4'-methoxymethoxyphenoxy)phenylamino)methyl] methylphosphinate (0.27 g, 0.41 mmol) in methanol (6.0 mL) was added 3 N HCl (0.68 mL, 2.03 mmol). The reaction mixture was heated with microwave radiation at 100° C. in a sealed vial for 5 minutes. The solvent was removed and the residue was partitioned with ethyl acetate and brine, partitioned, and the aqueous solution was extracted with ethyl acetate. The combined organic layers were coevaporated with methanol and concentrated under reduced pressure. The crude residue was purified by preparatory thin-layer chromatography on silica gel, eluting with methanol-ethyl acetate (5:95) to afford ethyl [(3,5-dibromo-4-(4'-hydroxy-3'-isopropylphenoxy)-phenylamino)methyl] methylphosphinate (0.16 g, 77%) as an oil: $^1$H NMR (300 MHz, DMSO-$d_6$): δ 8.97 (s, 1H), 7.11 (s, 2H), 6.65 (m, 2H), 6.26 (m, 2H), 4.06 (m, 2H), 3.55 (m, 2H), 3.14 (m, 1H), 1.48 (d, J=6.0 Hz, 6H), 1.22 (m, 3H), 1.12 (d, J=6.0 Hz, 6H); TLC conditions: Uniplate silica gel, 250 microns; Mobile phase=methanol-ethyl acetate (5:95); $R_f$=0.35.

Step i:

To a solution of ethyl [(3,5-dibromo-4-(4'-hydroxy-3'isopropylphenoxy)phenylamino)methyl]methylphosphinate (0.08 g, 0.16 mmol) in $CH_2Cl_2$ (2.0 mL) at −30° C. was added bromotrimethylsilane (0.21 mL, 1.55 mmol). The reaction mixture was stirred at −30° C. for 4 h, then rt for 12 h and the solvent was removed under reduced pressure. The residue was treated with acetonitrile-H$_2$O (4:1, 5.0 mL) and stirred at 38° C. for 30 min. The solvent was removed under reduced pressure. The residue was dissolved in ethyl acetate and washed with H$_2$O. The organic solution was filtered and concentrated under reduced pressure to afford the title compound as an off-white powder (0.076 g, 100%); $^1$H NMR (300 MHz, CD$_3$OD): δ 6.92 (s, 2H), 6.51 (m, 2H), 6.20 (m, 1H), 3.38 (m, 2H), 3.12 (m, 1H), 1.43 (d, J=15.0 Hz, 3H), 1.05 (d, J=6.0 Hz, 6H); LC-MS m/z=494 [C$_{17}$H$_{20}$Br$_2$NO$_4$P−H]$^+$; HPLC conditions: Column=Shimadzu LC-A8, SPD-10A; YMC Pack RP-18 filter, 150×4.6; Mobile phase=Solvent A Acetonitrile/0.05% TFA; Solvent B=H$_2$O/0.05% TFA. Flow rate=2.0 mL/min; UV@ 254 nm. rt=14.52 min Example 85

Compound 85: 2-[3,5-Dimethyl-4-(3'-(4-fluorobenzyl)-4'-hydroxybenzyl)-phenyl]ethylphosphonic acid The title compound was prepared from dimethyl 2-[3,5-Dimethyl-4-(3'-(4-fluorobenzyl)-4'-hydroxybenzyl)phenyl] ethylphosphonate (compound 78, step k) according to the procedure described for the synthesis of compound 7, step b (40 mg, 100%): $^1$H NMR (200 MHz, DMSO-d$_6$): δ 9.17 (s, 1H), 7.11 (m, 4H), 6.85 (s, 2H), 6.53-6.73 (m, 3H), 3.76 (s, 4H), 2.64 (m, 2H), 2.12 (s, 6H), 1.78 (m, 2H); LC-MS m/z=429 [C$_{24}$H$_{26}$FO$_4$P+H]$^+$; Anal Calcd for (C$_{24}$H$_{26}$FO$_4$P+ 2.3H$_2$O): C, 61.35; H, 6.56. Found: C, 61.04; H, 6.36.

Example 86

Compound 86: dimethyl [2-(3,5-dimethyl-4-(3'-(4-fluorobenzyl)-4'-methoxymethoxybenzyl)phenyl)-2-oxo-ethyl]phosphonic acid The title compound was prepared from (60 mg, 94%) from dimethyl [2-(3,5-dimethyl-4-(3'-(4-fluorobenzyl)-4'-methoxymethoxybenzyl)phenyl)-2-oxo-ethyl]phosphonate (compound 78, step h) according to the procedure described for the synthesis of compound 7, step b (60 mg, 94%): $^1$H NMR (300 MHz, DMSO-d$_6$): δ 9.23 (s, 1H), 7.66 (s, 2H), 7.15 (m, 2H), 7.07 (m, 2H), 6.76 (d, J=2.1 Hz, 1H), 6.66 (d, J=8.1 Hz, 1H), 6.55 (dd, J=2.1, 8.1 Hz, 1H), 3.90 (s, 2H), 3.77 (s, 2H), 3.47 (d, J=22.5 Hz, 2H), 2.23 (s, 6H); LC-MS m/z=443 [C$_{24}$H$_{24}$FO$_5$P+H]$^+$; Anal Calcd for (C$_{24}$H$_{24}$FO$_5$P+0.1HBr+ 0.2EtOAc+0.8H$_2$O): C, 61.73; H, 5.70; Br, 1.66. Found: C, 61.59; H, 5.64; Br, 1.84.

Example 87

Compound 87: [4-(4'-Hydroxy-3'-methanesulfonyl-benzyl)-3,5-dimethyl-phenoxymethyl]-phosphonic acid The title compound was prepared from (compound 76, step a) according to the procedure described for the synthesis of compound 7, step b: $^1$H NMR (200 MHz, DMSO-d$_6$): δ 10.82 (s, 1H), 7.33 (d, J=2.0 Hz, 1H), 7.11 (dd, J=2.0, 8.4 Hz, 1H), 6.95 (d, J=8.4 Hz, 1H), 6.72 (s, 2H,), 4.03 (d, J=10.2 Hz, 2H), 3.88 (s, 2H), 3.20 (s, 3H), 2.15 (s, 6H); LC-MS m/z=401 [C$_{17}$H$_{21}$O$_7$PS+H]$^+$; Anal Calcd for (C$_{17}$H$_{21}$O$_7$PS+0.8H$_2$O): C, 49.23; H, 5.49. Found: C, 49.11; H, 5.61.

Example 88

Compound 88: [(3,5-dibromo-4-(4'-hydroxy-3'-iso-propylphenoxy)-phenoxy)methyl]methylphosphinic acid Step a:
To a stirring mixture of DMF (20.0 mL) and NaH (0.074 g, 1.86 mmol) at 0° C. was added 3,5-dibromo-4-(3-isopropyl-4-hydroxyphenoxy)phenol (Intermediate for the synthesis of compound 8-1, 0.75 g, 1.86 mmol) dissolved in DMF (2.0 mL). The reaction mixture was allowed to stir at rt 1 hr and cooled to 0° C. To the stirred mixture was ethyl [(4-methylphenyl)sulfonyloxymethyl]methylphosphinate (compound 74, 0.52 g, 1.77 mmol) and the reaction was stirred at rt for 16 h. The reaction was quenched with ice/H$_2$O and the solvent was evaporated. The pH was adjusted to 1 with 2 M HCl and the mixture was partitioned with ethyl acetate and H$_2$O. The aqueous solution was extracted with ethyl acetate and the combined organic layers were concentrated under reduced pressure was purified by column chromatography on silica gel, eluting with ethyl acetate-hexanes (9:1) to afford crude product mixture (555 mg) and recovered starting material (270 mg). The crude product residue was treated with acetone to afford ethyl [(3,5-dibromo-4-(4'-hydroxy-3'-iso-propylphenoxy)phenoxy)methyl] methylphosphinate as a white solid (0.23 g, 24%): $^1$H NMR (200 MHz, DMSO-d$_6$): δ 9.03 (s, 1H), 7.50 (s, 2H), 6.67 (m, 2H), 6.27 (m, 1H), 4.49 (m, 2H), 4.02 (m, 2H), 3.14 (m, 1H), 1.58 (d, J=16.0 Hz, 3H); 1.23 (m, 3H), 1.12 (d, J=6.0 Hz, 6H); TLC conditions: Uniplate silica gel, 250 microns; Mobile phase=ethyl acetate; R$_f$=0.26

Step b:
To a stirring suspension of ethyl [(3,5-dibromo-4-(4'-hydroxy-3'-iso-propylphenoxy)phenoxy)methyl]methylphosphinate (0.24, 0.45 mmol) in CH$_2$Cl$_2$ (6.0 mL) at −30° C. was added bromotrimethylsilane (0.59 mL, 4.50 mmol). The reaction mixture was stirred at rt for 16 h and the solvent was removed under reduced pressure. The residue was treated with acetonitrile-H$_2$O (5:1, 5.0 mL) and stirred at 38° C. for 20 min. The solvent was removed under reduced pressure. The residue was dissolved in ethyl acetate and washed with H$_2$O. The organic solution was concentrated, coevaporated with MeOH, and filtered to afford the title compound as a white powder (0.215 g, 97%); $^1$H NMR (200 MHz, DMSO-d$_6$): δ 9.02 (s, 1H), 7.47 (s, 2H), 6.63 (m, 2H), 6.26 (m, 1H), 4.26 (d, J=12.0 Hz, 2H), 3.14 (m, 1H), 1.45 (d, J=14.0 Hz, 3H), 1.12 (d, J=6.0 Hz, 6H); LC-MS m/z=495 [C$_{17}$H$_{20}$Br$_2$O$_5$P−H]$^+$; Anal. Calcd for (C$_{17}$H$_{20}$Br$_2$O$_5$P+ 0.2H$_2$O+0.1 CH$_3$COCH$_3$): C, 41.27; H, 4.00 Found: C, 41.22; H, 4.06 HPLC conditions: Column =Shimadzu LC-A8, SPD-10A; YMC Pack RP-18 filter, 150×4.6; Mobile phase=Solvent A Acetonitrile/0.05% TFA; Solvent B=H$_2$O/ 0.05% TFA. Flow rate=2.0 mL/min; UV@254 nm. Retention time. (rt=8.93 min).

Example 89

Compound 89: [4-(5'-bromo-6'-hydroxynapthyl)-3,5-dimethylphenoxy]-methylphosphonic acid Step a:
To a stirred solution of 6-methoxy-1-napthol (Kasturi, T. R. Arunachalum, T. *Can. Journal. Chem.* 3625 (1968), 3.0 g, 17.2 mmol) in anhydrous CH$_2$Cl$_2$ (50 mL) at −40° C. was added Et$_3$N (4.66 mL, 34.4 mmol) and the reaction mixture was stirred at −40° C. for 15 min. The trifluoromethanesulfonyl anhydride (5.8 g, 20.6. mmol) CH$_2$Cl$_2$ in (5 mL) was added and the reaction mixture was stirred for 2 h at −10° C. and for 30 min at room temperature. The reaction mixture was quenched with saturated NaHCO$_3$ (50 mL) and extracted with CH$_2$Cl$_2$ (2×100 mL). The combined organic layers were washed with water and brine, dried over Na$_2$SO$_4$, filtered and concentrated under reduced pressure. The crude product was purified by column chromatography on silica gel, eluting with ethyl acetate-hexanes (1:9) to afford 6-methoxy-1-napthyl trifluoromethanesulfonate as a colorless oil (5.10 g, 92%): $^1$H NMR (300 MHz, CDCl$_3$): δ 8.0 (d, J=9.0 Hz, 1H), 7.77 (d, J=8.4 Hz, 1H), 7.44 (t, J=8.1 Hz, 1H), 7.35-7.32 (m, 2H), 7.22 (s, 1H), 3.98 (s, 3H); TLC conditions: Uniplate silica gel, 250 microns; mobile phase=ethyl acetate-hexanes (1:4); R$_f$=0.6.

Step b:

A mixture of 6-methoxy-1-napthyl trifluoromethanesulfonate (0.85 g, 2.6 mmol), bis-picolinato-diborane (1.07 g, 3.95 mmol) and anhydrous potassium acetate (0.77 g, 7.8 mmol) in DMSO (30 mL) was degassed by nitrogen sparge for 30 min and PdCl$_2$dppf.dichloromethane (0.43 g, 0.52 mmol) was added. The reaction mixture was heated to 85° C. for 4 h. The reaction mixture was filtered through a Celite plug and washed with ethyl acetate (2×50 mL) and concentrated under reduced pressure. The crude product was purified by column chromatography on silica gel, eluting with ethyl acetate-hexanes (1:4) to afford 1,1,2,2-tetramethyl-6-methoxynapthyl-1-boronate as a pale yellow solid (0.64 g, 86%): $^1$H NMR (300 MHz, CDCl$_3$): δ 8.69 (d, J=9.3 Hz, 1H), 7.98 (d, J=7.8 Hz, 1H), 7.85 (d, J=7.8 Hz, 1H), 7.46 (dd, J=1.5, 6.6 Hz, 1H), 7.22 (dd, J=2.4, 9.0 Hz, 1H), 7.16 (d, J=2.4 Hz 1H), 3.96 (s, 3H), 1.45 (s, 12H); TLC conditions: Uniplate silica gel, 250 microns; mobile phase=ethyl acetate-hexanes (1:4); R$_f$=0.65.

Step c:

To a stirred suspension of NaH (0.5 g, 22.0 mmol) in anhydrous DMF (20 mL) at 0° C. was added 3,5-dimethyl-4-bromophenol (2.2 g, 11.0 mmol) in DMF (5 mL) followed by diethyl tosyloxymethylphosphonate (3.9 g, 24.2 mmol) in DMF (5.0 mL) 30 min later. The reaction mixture was stirred for 14 h at room temperature and poured into water (30 mL). The aqueous solution was extracted with ethyl acetate (2×100 mL) and the combined organic layers were washed with brine, dried over Na$_2$SO$_4$, filtered and concentrated under reduced pressure. The crude product was purified by column chromatography on silica gel, eluting with ethyl acetate-hexanes (2:3) to afford diethyl (3,5-dimethyl-4-bromophenoxy)methylphosphonate as a syrup. (1.85 g, 48%): $^1$H NMR (300 MHz, CDCl$_3$): δ 6.88 (s, 2H), 4.15-4.25 (m, 6H), 2.41 (s, 2H), 1.40 (t, J=6.0 Hz, 6H); LC-MS m/z=351[α]$_3$H$_{20}$BrO$_4$P+H]$^+$; TLC conditions: Uniplate silica gel, 250 microns; mobile phase=ethyl acetate-hexanes (2:3); R$_f$=0.3.

Step d:

To a stirred solution of 1,1,2,2-tetramethyl-6-methoxynapthyl-1-boronate (0.5 g, 1.76 mmol) and diethyl (3,5-dimethyl-4-bromophenoxy)methylphosphonate (0.675 g, 1.93 mmol) in anhydrous DME (40 mL) degassed by nitrogen for 10 min. Palladium tetrakis(triphenylphosphine) (0.4 g, 0.35 mmol) and an aqueous solution of sodium carbonate (0.55 g, 5.28 mmol) in water (10 mL) were added. The reaction mixture was heated 85° C. for 24 h. and the reaction mixture was poured into water (30 mL). The aqueous solution was extracted with ethyl acetate (2×100 mL) and the combined organic layers were washed with brine, dried over Na$_2$SO$_4$, filtered and concentrated under reduced pressure. The crude product was purified by column chromatography on silica gel, eluting with ethyl acetate-hexanes (1:2) to afford diethyl [3,5-dimethyl-4-(6'-methoxynapthyl)phenoxy]methylphosphonate as a syrup. (0.45 g, 45%): $^1$H NMR (300 MHz, CDCl$_3$): δ 7.77 (d, J=8.1 Hz, 1H), 7.52 (t, J=7.2 Hz, 1H), 7.27 (d, J=6.0 Hz, 1H), 7.24-7.23 (m, 2H), 7.13 (d, J=1.5 Hz, 1H), 7.05 (dd, J=2.7, 9.0 Hz, 1H), 6.81 (s, 2H), 4.34-4.27 (m, 6H), 3.96 (s, 3H), 1.91 (s, 6H), 1.42 (t, J=5.1 Hz, 6H); LC-MS m/z=429 [C$_{24}$H$_{29}$O$_5$P+H]$^+$; TLC conditions: Uniplate silica gel, 250 microns; mobile phase=ethyl acetate-hexanes (2:3); R$_f$=0.3.

Step e:

To a stirred solution of diethyl [3,5-dimethyl-4-(6'-methoxynapthyl)phenoxy]methylphosphonate (130 mg, 0.30 mmol) in anhydrous CH$_2$Cl$_2$ (10 mL) was added bromine (50 mg, 0.32 mmol), the solution was stirred for 30 min. and the reaction mixture was washed with aqueous sodium bisulfate. The resulting solution was extracted with CH$_2$Cl$_2$ (2×50 mL) and the combined organic layers were washed with saturated NaHCO$_3$ (25 mL), dried over Na$_2$SO$_4$, filtered and concentrated under reduced pressure. The crude product was purified by column chromatography on silica gel, eluting with ethyl acetate-hexanes (2:3) to afford diethyl [4-(5'-bromo-6'-methoxynapthyl)-3,5-dimethylphenoxy]methylphosphonate as a brownish solid (140 mg, 93%): $^1$H NMR (300 MHz, CDCl$_3$): δ 8.30 (d, J=8.0 Hz, 1H), 7.65 (t, J=7.2 Hz, 1H), 7.34-7.32 (m, 2H), 7.20-7.15 (m, 2H), 6.82 (s, 2H), 4.39-4.29 (m, 6H), 4.04 (s, 3H), 1.90 (s, 6H), 1.44 (t, J=6.9 Hz, 6H); LC-MS m/z=507 [C$_{24}$H$_{28}$BrO$_5$P]+; TLC conditions: Uniplate silica gel, 250 microns; mobile phase=ethyl acetate-hexanes (2:3); R$_f$=0.28.

Step f:

To a stirred solution of diethyl [4-(5'-bromo-6'-methoxynapthyl)-3,5-dimethylphenoxy]methylphosphonate (130 mg, 0.25 mmol) in CH$_2$Cl$_2$ (5 mL) at 0° C. was added TMSBr (0.38 g, 0.35 mL, 2.5 mmol). The reaction mixture was stirred at 0° C. for 30 min, allowed to warm to room temperature and stirred for 16 h. The solvent was removed under reduced pressure, the residue was dissolved in CH$_3$OH (3 mL) and the solvent was removed under reduced pressure. The residue was triturated with acetonitrile and dried under reduced pressure to afford [4-(5'-bromo-6'-methoxynapthyl)-3,5-dimethylphenoxy] methylphosphonic acid as a white solid (0.12 g 100%, crude): $^1$H NMR (300 MHz, CD$_3$OD): δ 8.12 (d, J=8.8 Hz, 1H), 7.55 (t, J=7.0 Hz, 1H), 7.13-6.92 (m, 3H), 6.80 (s, 2H), 4.20 (d, J=10.4 Hz, 2H), 3.96 (s, 3H), 1.91 (s, 6H); LC-MS m/z=451 [C$_{20}$H$_{20}$BrO$_5$P]$^+$;

Step g:

To a stirred solution of [4-(5'-bromo-6'-methoxynapthyl)-3,5-dimethylphenoxy]methylphosphonic acid (0.12 g, 0.26 mmol) in CH$_2$Cl$_2$ (5 mL) at −78° C. was added BBr$_3$ (0.1 g, 0.39 mmol) in CH$_2$Cl$_2$ (5 mL). The reaction mixture was stirred at rt for 3 h and poured into ice water (25 mL) and stirred for 1 h. The reaction mixture was extracted with ethyl acetate (2×50 mL). The combined organic layers were washed with water and brine, dried over Na$_2$SO$_4$, filtered and concentrated under reduced pressure. The crude product was recrystallized from CH$_2$Cl$_2$, filtered and dried under reduced pressure to afford the title compound as a yellow solid (70 mg, 92%, 94% pure): $^1$H NMR (200 MHz, CD$_3$OD): δ 8.14 (d, J=8.8 Hz, 1H), 7.39 (t, J=7.0 Hz, 1H), 7.15-6.99 (m, 3H), 6.81 (s, 2H), 4.19 (d, J=10.4 Hz, 2H), 1.81 (s, 6H); LC-MS m/z=437 [C$_{19}$H$_{18}$BrO$_5$P+H]$^+$; HPLC conditions: YMC pack ODS-AQ12SO$_{51546}$W column; mobile phase=TFA/ACN (0.05%) and TFA/H$_2$O (0.05%) flow rate=1.0 mL/min; detection=UV@254 nm retention time in min: 7.14; Anal Calcd: (MF:C$_{19}$H$_{18}$BrO$_5$P+0.8 CH$_2$Cl$_2$) Calcd: C, 47.36; H, 3.92, Found: C, 47.12; H, 3.58.

Example 90

Compound 90: [3,5-dichloro-4-(4-O-hydroxynapthyloxy)phenylamino]-methylphosphonic acid Step a:

To a stirred solution of 4-methoxy-1-napthol (0.5 g, 2.86 mmol) and 3,5-dichloro-4-iodonitrobenzene (1.0 g, 3.16 mmol) in DMSO (30 mL) at room temperature was added $K_2CO_3$ (0.6 g, 4.30 mmol). The reaction mixture was heated at 125° C. for 18 h, cooled to room temperature and poured into water. The aqueous layer was extracted with ethyl acetate (2×100 mL). The combined organic layers were washed with brine and water, dried over $Na_2SO_4$, filtered and concentrated under reduced pressure. The crude product was purified by column chromatography on silica gel, eluting with ethyl acetate-hexanes (1:9) to afford 3,5-dichloro-4-(4'-O-methoxynapthyloxy)-nitrobenzene as a yellow solid (0.8 g, 78%): $^1$H NMR (300 MHz, $CDCl_3$): δ 8.15 (s, 2H), 8.0-8.16 (m, 1H), 7.40-7.50 (m, 3H), 6.34 (d, J=8.4 Hz, 1H), 6.06 (d, J=8.4 Hz, 1H), 3.76 (s, 3H); TLC conditions: Uniplate silica gel, 250 microns; mobile phase=ethyl acetate-hexanes (1:4); $R_f$=0.7.

Step b:

A suspension of 3,5-dichloro-4-(4'-O-methoxynapthyloxy)-nitrobenzene (0.47 g, 2.6 mmol) in acetic acid (20 mL) and water (2 mL) was heated at 50° C. until all material was dissolved then cooled to rt. Iron powder (108 mg, 1.94 mmol) was added at room temperature and the reaction mixture was stirred overnight, filtered through a Celite plug and washed with EtOAc (100 mL). The filtrate was extracted with ethyl acetate (2×100 mL). The combined organic layers were washed with water and brine, dried over $Na_2SO_4$, filtered and concentrated under reduced pressure to give 3,5-dichloro-4-(4'-O-methoxynapthyloxy)aminobenzene as a brownish solid (0.32 g, 75%): $^1$H NMR (200 MHz, $CD_3OD$): δ 8.15 (dd, J=2.2, 5.8 Hz, 1H), 8.0 (dd, J=2.2, 5.8 Hz, 1H), 7.37-7.31 (m, 2H), 6.58 (s, 1H), 6.45 (d, J=8.4 Hz, 1H), 6.07 (d, J=8.4 Hz, 1H), 3.73 (s, 3H);TLC conditions: Uniplate silica gel, 250 microns; mobile phase=ethyl acetate-hexanes (2:3); $R_f$=0.3.

Step c:

To a stirred solution of 3,5-dichloro-4-(4'-O-methoxynapthyloxy)aminobenzene (14, 0.3 g, 0.90 mmol) in $CH_2Cl_2$ (10 mL) at 0° C. were added $Et_3N$ (0.27 g, 2.25 mmol), $(Boc)_2O$ (0.21 g, 1.0 mmol) and a catalytic amount of DMAP (25 mg). The reaction mixture was stirred at rt for 4 h and quenched with water (15 mL). The reaction mixture was extracted with $CH_2Cl_2$ (2×50 mL). The combined organic layers were washed with water and brine, dried over $Na_2SO_4$, filtered and concentrated under reduced pressure. The crude product was purified by column chromatography on silica gel, eluting with ethyl acetate-hexanes (2:8) to afford t-butyl N-[3,5-dichloro-4-(4'-O-methoxynapthyloxy)benzene]carbamate as a yellow solid (0.22 g, 58%): $^1$H NMR (300 MHz, $CDCl_3$): δ 8.21 (dd, J=2.2, 6.0 Hz, 1H), 8.04 (d, J=2.2, 6.0 Hz, 1H) 7.43-7.36 (m, 2H), 7.07 (s, 2H), 6.33 (d, J=8.4 Hz, 1H), 6.07 (d, J=8.4 Hz, 1H), 3.74 (s, 3H), 1.32 (s, 9H).

Step d:

To a stirred solution of t-butyl N-[3,5-dichloro-4-(4'-O-methoxynapthyloxy)benzene]carbamate (0.22 g, 0.5 mmol) in anhydrous acetonitrile (15 mL) at room temperature were added $Cs_2CO_3$ (0.33 g, 1.0 mmol) and diethyl tosyloxymethylphosphonate (0.16 g, 0.5 mmol). The reaction mixture was heated at 80° C. for 8 h and cool to room temperature, then poured into water (20 mL). The aqueous solution was extracted with ethyl acetate (2×50 mL) and the combined organic layers were washed with brine, dried over $Na_2SO_4$, filtered and concentrated under reduced pressure. The crude product was purified by column chromatography on silica gel, eluting with ethyl acetate-hexanes (1:1) to afford diethyl N-t-butoxycarbonyl-[3,5-dichloro-4-(4-O-methoxynapthyloxy)phenylamino]methylphosphonate as a viscous. (145 mg, 50%): $^1$H NMR (200 MHz, $CDCl_3$): δ 8.21 (dd, J=1.8, 7.4 Hz, 1H), 8.04 (dd, J=2.0, 6.2 Hz, 1H), 7.43-7.36 (m, 2H), 7.24 (s, 2H), 6.33 (d, J=8.4 Hz, 1H), 6.07 (d, J=8.4 Hz, 1H), 4.0-3.86 (m, 6H), 3.75 (s, 3H), 1.29 (s, 12H), 1.11 (t, J=6.9 Hz, 6H); LC-MS m/z=584 $[C_{28}H_{34}Cl_2NO_6P+2]^+$; TLC conditions: Uniplate silica gel, 250 microns; mobile phase=ethyl acetate-hexanes (1:1); $R_f$=0.3.

Step e:

[3,5-dichloro-4-(4-O-methoxynapthyloxy)phenylamino]methyl-phosphonic acid was prepared from diethyl N-t-butoxycarbonyl-[3,5-dichloro-4-(4-O-methoxynapthyloxy)phenylamino]methylphosphonate according to the procedure described for the synthesis of compound 89, step f; brownish solid (92 mg, 100%): $^1$H NMR (200 MHz, $CD_3OD$): δ 8.13 (dd, J=2.2, 6.6 Hz, 1H), 7.99 (dd, J=2.6, 6.0 Hz, 1H), 7.40-7.31 (m, 2H), 6.67 (s, 2H), 6.44 (d, J=8.4 Hz, 1H), 6.07 (d, J=8.4 Hz, 1H), 3.74 (s, 3H), 3.27 (d, J=12.0 Hz, 2H); LC-MS m/z=427 $[C_{18}H_{16}Cl_2NO_5P+H]^+$;

Step f:

The title compound was prepared from [3,5-dichloro-4-(4-O-methoxynapthyloxy)phenylamino]methylphosphonic acid according to the procedure described for the synthesis of compound 89, step g; brown solid (38 mg, 40%): $^1$H NMR (200 MHz, $CD_3OD$): δ 8.09 (dd, J=2.2, 6.6 Hz, 1H), 7.95 (dd, J=2.6, 6.0 Hz, 1H), 7.33-7.28 (m, 2H), 6.64 (s, 2H), 6.35 (d, J=8.4 Hz, 1H), 5.97 (d, J=8.4 Hz, 1H), 3.21 (d, J=12.0 Hz, 2H); LC-MS m/z=414 $[α]_7H_{14}Cl_2NO_5P+H]^+$; HPLC conditions: YMC pack ODS-AQ12S051546W column; mobile phase=TFA/ACN (0.05%) and TFA/$H_2O$ (0.05%) flow rate=1.0 mL/min; detection=UV@254 nm retention time in min: 9.58; Anal Calcd: (MF:$C_{17}H_{14}Cl_2NO_5P+1.0H_2O$) Calcd: C, 47.24, H, 3.73; N, 3.24 Found: C, 47.35; H, 3.51; N, 3.00.

Example 91

Compound 91:

[(3,5-dichloro-4-(4-O-hydroxynapthyloxy)phenylamino)-methyl]methylphosphinic acid Step a:

Ethyl N-t-butoxycarbonyl-[(3,5-dichloro-4-(4-O-methoxynapthyloxy)-phenylamino)methyl]methylphosphinate was prepared from t-butyl N-[3,5-dichloro-4-(4'-O-methoxynapthyloxy)benzene]carbamate (compound 90, step c) and ethyl [(4-methylphenyl)sulfonyloxymethyl]methylphosphinate (compound 74) according to the procedure described for the synthesis of compound 90, step d; syrup (80 mg, 29%): $^1$H NMR (200 MHz, $CDCl_3$): δ 8.21 (dd, J=1.8, 7.4 Hz, 1H), 8.04 (dd, J=2.0, 6.2 Hz, 1H), 7.45-7.36 (m, 2H), 7.26 (s, 2H), 6.33 (d, J=8.4 Hz, 1H), 6.06 (d, J=8.4 Hz, 1H), 4.0-3.86 (m, 4H), 3.75 (s, 3H), 1.35 (d, J=13.8 Hz, 3H), 1.29 (s, 12H), 1.07 (t, J=6.9 Hz, 3H); LC-MS m/z=555 $[C_{26}H_{32}Cl_2NO_6P+H]^+$; TLC conditions: Uniplate silica gel, 250 microns; mobile phase=ethyl acetate-hexanes (1:1); $R_f$=0.3.

Step b:

[(3,5-dichloro-4-(4-O-methoxynapthyloxy)phenylamino)methyl]-methylphosphinic acid was prepared from ethyl [(3,5-dichloro-4-(4'-O-methoxynapthyloxy)phenylamino)methyl]methylphosphinate according to the procedure described for the synthesis of compound 89, step f; brown solid (50 mg, 88%): $^1$H NMR (200 MHz, $CD_3OD$): δ 8.12

(dd, J=2.2, 6.6 Hz, 1H), 7.98 (dd, J=2.6, 6.0 Hz, 1H), 7.41-7.31 (m, 2H), 6.69 (s, 2H), 6.45 (d, J=8.4 Hz, 1H), 6.07 (d, J=8.4 Hz, 1H), 3.74 (s, 3H), 3.29 (d, J=12.0 Hz, 2H), 1.38 (d, J=14.0 Hz, 3H); LC-MS m/z=427 $[C_{18}H_{16}Cl_2NO_5P+H]^+$

Step c:

The title compound was prepared from [(3,5-dichloro-4-(4-O-methoxynapthyloxy)phenylamino)methyl]methylphosphinic acid according to the procedure described for the synthesis of compound 89, step g; brownish solid (24 mg, 50%): $^1$H NMR (200 MHz, DMSO-$d_6$): δ 9.58 (s, 1H), 8.01 (d, J=7.8 Hz, 1H), 7.89 (d, J=7.8 Hz, 1H), 7.48-7.34 (m, 2H), 6.73 (s, 2H), 6.43 (d, J=8.0 Hz, 1H), 5.99 (d, J=8.0 Hz, 1H), 3.13 (d, J=10.4 Hz, 2H) 1.14 (d, J=13.8 Hz, 3H); LC-MS m/z=412 $[C_{18}H_{16}Cl_2NO_5P+H]^+$.

Example 92

Compound 92: [(3,5-Dibromo-4-(3'-(4-fluorobenzyl)-4'-hydroxyphenoxy)-methyl]methylphosphinic acid Step a Ethyl [(3,5-Dibromo-4-(4'-hydroxy-3'-(4-fluorobenzyl)phenoxy)methyl]methyl phosphinate was prepared from 3,5-dibromo-4-[3'-(4-fluorobenzyl)-4'-hydroxyphenoxy] phenol (compound 82, step g) and ethyl [(4-methylphenyl)sulfonyloxymethyl]methylphosphinate (compound 74) according to the procedure described for the synthesis of compound 77, step a; (0.014.8 gm, 14%); $^1$H NMR (200 MHz, $CD_3OD$): δ 7.18 (s, 2H), 6.944 (m, 2H), 6.74 (t, J=8.6 Hz, 2H), 6.48 (d, J=8.8 Hz, 1H), 6.70 (m, 2H), 4.23 (dd, J=5, 8.6 Hz, 2H), 3.96 (m, 2H), 3.65 (s, 2H), 1.46 (d, 3H, J=14.6 Hz), 1.16 (t, J=7 Hz, 3H); TLC conditions: Uniplate silica gel, 250 microns; ethyl acetate; $R_f$=0.18; LC-MS m/z 589 $[C_{23}H_{22}Br_2FO_5P+H]^+$.

Step b:

The title compound was prepared according to the procedure described for the synthesis of compound 7, step b; (0.010 gm, 81%); $^1$H NMR (200 MHz, $CD_3OD$): δ 7.36 (s, 2H), 7.14 (m, 2H), 6.94 (t, J=8.8 Hz, 2H), 6.65 (d, J=8.4 Hz, 1H), 6.70 (m, 2H), 4.28 (d, J=8.6 Hz, 2H), 3.96 (m, 2H), 3.85 (s, 2H), 1.65 (d, 3H, J=15.2 Hz); TLC conditions: Uniplate silica gel, 250 microns; IPA/AcOH/$H_2O$ [7:2:1]; $R_f$=0.73; LC-MS m/z 559 $[C_{21}H_{18}Br_2FO_5P-H]^-$.

Example 93

Compound 93: [3,5-Dimethyl-4-(3'-Isopropyl-1'H-indol-5'-ylmethyl)-phenoxy]methylphosphonic acid Step a:

To the suspension of 4-bromophenylhydrazine hydrochloride (6.0 g mg, 26.85 mmol) in water was added 3.5 M NaOH (11.5 ml, 40.82 mmol), followed by isovaleraldehyde (2.77 g, 32.21 mmol). The reaction was stirred for 10 min, then the reaction was acidified with AcOH (25 ml). The reaction was stirred further for 30 min, and toluene was then added to extract the product twice. The combined toluene layer was washed with Sat. $NaHCO_3$, dried over $MgSO_4$, filtrated and concentrated to afford N-(4-bromo-phenyl)-N'-(3-methylbutyl)-hydrazide (7.6 g, 100%): $^1$H NMR (200 MHz, $CDCl_3$): δ 9.63 (s, 1H), 7.07 (d, J=8.6 Hz, 1H), 6.97 (m, 1H), 6.62 (d, J=8.6 Hz, 2H), 1.88 (m, 2H), 1.60 (m, 1H), 0.71 (d, J=6.6 Hz, 6H).

Step b:

To the solution of N-(4-bromo-phenyl)-N'-(3-methyl-butyl)-hydrazide (7.6 g, 31.54 mmol) in xylene (150 ml) was added $ZnCl_2$ (5.16 g, 37.84 mmol). Tet the reaction was refluxed for 1.5 hrs, then concentrated, and the residue was partitioned between toluene and sat. $NaHCO_3$. The organic layer was collected and the water layer was further extracted with toluene once. The combined organic layers was dried over $MgSO_4$, filtrated and concentrated. The residue was purified by column chromatography on silica gel, eluting with ethyl acetate-hexanes (1:9) to afford 5-bromo-3-isopropyl-1H-indole (4.55 g, 60.9%): $^1$H NMR (300 MHz, $CDCl_3$): δ 8.72 (s, 1H), 8.57 (s, 1H), 8.05 (m, 2H), 7.77 (s, 1H), 3.95 (m, 1H), 2.15 (d, J=6.6 Hz, 6H). TLC conditions: Uniplate silica gel, 250 microns; Mobile phase=ethyl acetate-hexanes (1:9); $R_f$=0.51.

Step c:

To a suspension of NaH (509 mg, 20.16 mmol) in THF (50 ml) was added 5-bromo-3-isopropyl-1H-indole (4.55 g, 19.20 mmol). The reaction mixture was stirred at r.t. for 30 min, and TIPSCl was then added at r.t. The reaction was stirred further for 1 hr, diluted with EtOAc, and water was added to quench the reaction. The organic layer was collected and the water layer was further extracted with EtOAC once. The combined organic layer was dried over $MgSO_4$, filtrated and concentrated. The residue was purified by column chromatography on silica gel, eluting with hexane to afford 5-bromo-3-isopropyl-1-triisopropylsilyl-1H-indole (5.1 g, 67.6%): $^1$H NMR (200 MHz, $CDCl_3$): δ 7.53 (d, J=1.8 Hz, 1H), 7.13 (d, J=8.8 Hz, 1H), 6.99 (m, 1H), 6.76(s, 1H), 2.92 (m, 1H), 1.44 (m, 3H), 1.14 (d, J=6.6 Hz, 6H), 0.93 (d, J=7.4 Hz, 18H). TLC conditions: Uniplate silica gel, 250 microns; Mobile phase=Hexane (1:9); $R_f$=0.65.

Step d:

(2,6-Dimethyl-4-triisopropylsilanyloxyphenyl)-(3-isopropyl-1-triisopropylsilyl-1H-indol-5-yl)-methanol was prepared from 5-bromo-3-isopropyl-1-triisopropylsilyl-1H-indole and 2,6-Dimethyl-4-triisopropylsilanyloxybenzaldehyde according to the procedure described for the synthesis of compound 27, step c; brown oil (2.44 g, 77.2%): $^1$H NMR (200 MHz, $CDCl_3$): δ 7.47 (s, 1H), 7.36 (d, J=8.8 Hz, 1H), 6.98 (d, J=8.8 Hz, 1H), 6.93 (s, 1H), 6.58 (s, 2H), 6.40 (d, J=3.6 Hz, 1H), 3.10 (m, 1H), 2.24 (s, 6H), 1.69 (m, 6H), 1.28 (d, J=6.6 Hz, 6H), 1.12 (d, J=6.2 Hz, 36H). TLC conditions: Uniplate silica gel, 250 microns; Mobile phase=ethyl acetate-hexanes (1:19); $R_f$=0.62.

Step e:

To a solution of (2,6-dimethyl-4-triisopropylsilanyloxyphenyl)-(3-isopropyl-1-triisopropylsilyl-1H-indol-5-yl)-methanol (1.86 g, 3.0 mmol) in $CH_2Cl_2$ (20 ml) was added tiethylsilane (1.74 g, 15.0 mmol), followed by AcOH (1.11 ml), then TFA (1.11 ml, 15.0 mmol). The reaction was stirred at r.t. for 1 hr, the reaction mixture was diluted with EtOAc and water and the layers were separated. The EtOAc layer was collected and the water layer was further extracted with EtOAc once. The combined organic layers was washed with Sat. $NaHCO_3$, water and brine, dried over $MgSO_4$, filtrated and concentrated. The residue was purified by column chromatography on silica gel, eluting with ethyl acetate-hexanes (1:49) to afford 5-(2,6-dimethyl-4-triisopropylsilyloxybenzyl)-3-isopropyl-1H-indole (1.0 g, 74.6%): $^1$H NMR (200 MHz, $CDCl_3$): δ 7.59 (s, 1H), 7.02 (d, J=8.2 Hz, 1H), 6.97 (s, 1H), 6.70 (s, 1H), 6.63 (d, J=8.2 Hz, 1H), 3.89 (s, 2H), 2.88 (m, 1H), 2.01 (s, 6H), 1.2 (m, 3H), 1.05 (d, J=6.6 Hz, 6H), 0.99 (d, J=6.2 Hz, 18H). TLC conditions: Uniplate silica gel, 250 microns; Mobile phase=ethyl acetate-hexanes (1:49); $R_f$=0.70.

Step f:

3,5-Dimethyl-4-(3-isopropyl-1H-indol-5-ylmethyl)phenol was prepared according to the procedure described for the synthesis of compound 35, step e; yellow oil (420 mg, 64%):

$^1$H NMR (200 MHz, CDCl$_3$): δ 7.61 (s, 1H), 7.06 (s, 1H), 7.02 (d, J=8.0 Hz, 1H), 6.72 (s, 1H), 6.63 (d, J=8.2 Hz, 2H), 6.38 (s, 2H), 3.89 (s, 2H), 2.93 (s, 1H), 2.04 (s, 6H), 1.05 (d, J=7.2 Hz, 6H). TLC conditions: Uniplate silica gel, 250 microns; Mobile phase=ethyl acetate-hexanes (1:3); R$_f$=0.65.

Step g:

Diethyl [3,5-dimethyl-4-(3'-isopropyl-1'H-indol-5'-ylmethyl)-phenoxy]methylphosphonate was prepared by the procedure used for the synthesis of compound 35, step f as a colorless oil (130 mg, 43%): $^1$H NMR (200 MHz, CDCl$_3$): δ 7.82 (s, 1H), 7.23 (s, 1H), 7.20 (d, J=8.8 Hz, 1H), 6.90 (s, 1H), 6.79 (d, J=8.8 Hz, 1H), 6.68(s, 2H), 4.11 (m, 6H), 4.09 (s, 2H), 3.07 (m, 1H), 2.24 (s, 6H), 1.28 (m, 12H). TLC conditions: Uniplate silica gel, 250 microns; Mobile phase=ethyl acetate-hexanes (1:1); R$_f$=0.65.

Step h:

The title compound was prepared according to the procedure described for the synthesis of compound 35, step h; yellow foam (50 mg, 63.6%): $^1$H NMR (200 MHz, DMSO-d$_6$): δ 10.60 (s, 1H), 7.18 (D, J=8.0 Hz, 1H), 7.13 (s, 1H), 6.98 (s, 1H), 6.71 (s, 2H), 6.63 (d, J=8.0 Hz, 1H), 4.02 (m, 4H), 3.02 (m, 1H), 2.20 (s, 6H), 1.22 (d, J=7.0 Hz, 6H). LC-MS m/z=388 [C$_{21}$H$_{26}$NO$_4$P+H]$^+$; Anal. Calcd for (C$_{21}$H$_{26}$NO$_4$P+0.5 HBr): C, 58.95; H, 6.24; N, 3.27. Found: C, 58.99; H, 6.42; N, 3.20.

Example 94

Compound 94: Methylphosphonic acid mono-[3,5-dimethyl-4-(4'-hydroxy-3'-isopropylbenzyl)benzyl] ester Step a:

To a solution of 3,5-dimethyl-4-(3'-iso-propyl-4'-methoxymethoxybenzyl)phenol (example 38, step c, 1.11 g, 3.52 mmol) and DMAP (1.72 g, 14.1 mmol) in CH$_2$Cl$_2$ (27 mL) at 0° C. was slowly added trifluoromethanesulfonyl anhydride (0.89 mL, 5.27 mmol). The reaction mixture was stirred at 0° C. for 2 h and quenched by water (10 mL). The organic layer was dried over Na$_2$SO$_4$, filtered and concentrated under reduced pressure to afford 3,5-dimethyl-4-(3'-iso-propyl-4'-methoxymethoxybenzyl)-phenyl trifluoromethanesulfonate as an oil (1.39 g, 89%): $^1$H NMR (300 MHz, DMSO-d$_6$): δ 7.14-7.28 (m, 7H), 6.94 (d, J=8.4 Hz, 1H), 6.85 (d, J=2.4 Hz, 1H), 6.70 (m, 1H), 5.15 (s, 2H), 3.94 (s, 2H), 3.88 (s, 2H), 3.27 (s, 3H), 2.24 (s, 6H); TLC conditions: Uniplate silica gel, 250 microns; Mobile phase=ethyl acetate-hexanes (15:85); R$_f$=0.55.

Step b:

To a solution of 3,5-dimethyl-4-(3'-iso-propyl-4'-methoxymethoxy-benzyl)phenyl trifluoromethanesulfonate (1.36 g, 3.05 mmol) in DMF (15.3 mL) in a bomb apparatus was added MeOH (2.5 mL, 61.6 mmol), Pd(OAc)$_2$ (68 mg, 0.3 mmol), bis-(diphenyphosphino)propane (138 mg, 0.3 mmol) and Et$_3$N (0.85 mL, 6.1 mmol). 60 psi of CO was then infused and the reaction mixture was stirred at 90° C. for 16 h. The cooled bomb was vented and the reaction mixture was poured into cold 1N HCl, extracted with EtOAc twice, the combined EtOAc were washed with brine, dried over Na$_2$SO$_4$, filtrated and concentrated. The residue was purified by column chromatography on silica gel, eluting with ethyl acetate-hexanes (1:9) to afford methyl 3,5-dimethyl-4-(3'-iso-propyl-4'-methoxymethoxybenzyl)benzoate as a yellow oil (1.00 g, 92.3%): $^1$H NMR (300 MHz, DMSO-d$_6$): δ 7.66 (s, 2H), 7.16 (m, 5H), 6.90 (m, 2H), 6.71 (m, 1H), 5.15 (s, 2H), 3.98 (s, 2H), 3.87 (s, 2H), 3.85 (s, 3H), 3.26 (s, 3H), 2.25 (s, 6H). TLC conditions: Uniplate silica gel, 250 microns; Mobile phase=ethyl acetate-hexanes (15:85); R$_f$=0.50.

Step c:

To a mixture of methyl 3,5-dimethyl-4-(3'-iso-propyl-4'-methoxymethoxybenzyl)benzoate (1.00 g, 2.81 mmol) in THF (11.3 mL) at 0° C. was added a solution of DIBAL-H (8.44 mL, 8.44 mmol, 1.0 M solution in hexanes). The reaction mixture was stirred at room temperature for 16 h, quenched with cold 1 N HCl and diluted with ethyl acetate. The organic layer was washed with 1 N HCl and brine, dried over Na$_2$SO$_4$, filtered and concentrated under reduced pressure to afford 3,5-dimethyl-4-(3'-iso-propyl-4'-methoxymethoxy-benzyl)benzyl alcohol as an off-white solid (0.75 g, 81.3%): $^1$H NMR (300 MHz, DMSO-d$_6$): δ 7.54 (s, 2H), 6.81 (m, 2H), 6.40 (m, 1H), 5.51 (m, 1H), 4.54 (d, J=6.0 Hz, 2H), 3.75 (s, 3H), 3.21 (m, 1H), 1.13 (d, J=6.0 Hz, 6H); TLC conditions: Uniplate silica gel, 250 microns; Mobile phase=ethyl acetate-hexanes (15:85); R$_f$=0.27.

Step d:

To a mixture of 3,5-dimethyl-4-(3'-iso-propyl-4'-methoxymethoxy-benzyl)benzyl alcohol (0.26 g, 0.79 mmol) in dichloromethane (1.5 mL) was added TEA (0.11 mL, 0.79 mmol) and a solution of methylphosphonic dichloride (0.11 g, 0.79 mmol) in dichloromethane (0.5 mL). The reaction mixture was stirred at room temperature for 2.75 h, filtered to remove salts, and the filtrate was then concentrated to remove dichloromethane. The reaction mixture was taken up in ethyl acetate, and extracted into 1N NaOH (2×10 mL). The basic layer was then acidified to pH=2 with 1N HCl and extracted into ethyl acetate (2×10 mL). The organic layer was dried over Na$_2$SO$_4$, filtered and concentrated under reduced pressure. The residue was then purified by preparative TLC 500 μm silica gel plate eluted with methanol/ethyl acetate [3:7] to give methylphosphonic acid mono-[3,5-dimethyl-4-(3'-iso-propyl-4'-methoxymethoxy-benzyl)benzyl] ester (55 mg, 17.1%): $^1$H NMR (300 MHz, CDCl$_3$): δ 7.07 (s, 2H), 6.94 (s, 1H), 6.88 (d, J=8.4 Hz, 1H), 6.62 (d, J=6.0 Hz, 1H), 5.14 (s, 2H), 5.00 (d, J=7.5 Hz, 2H), 3.96 (s, 2H), 3.46 (s, 3H), 3.30-3.26 (m, J=13.8 Hz, 1H), 2.24 (s, 6H), 1.56 (d, J=18.3 Hz, 3H), 1.19 (d, J=7.2 Hz, 6H); TLC conditions: Uniplate silica gel, 250 microns; Mobile phase=ethyl acetate; R$_f$=0.05.

Step e:

To a mixture of methylphosphonic acid mono-[3,5-dimethyl-4-(3'-isopropyl-4'-methoxymethoxy-benzyl)benzyl] ester (40 mg, 0.10 mmol) in methanol (0.98 mL) was added 1N HCl (0.49 mL, 0.49 mmol). The reaction mixture was stirred at room temperature for 7 days and concentrated to remove methanol. The reaction mixture was taken up in ethyl acetate (5 mL) and 1N HCl (5 mL). The organic layer was rinsed with H$_2$O, brine, dried over Na$_2$SO$_4$, filtered and concentrated under reduced pressure. The residue was then purified by preparative TLC 250 μm silica gel plate eluted with methanol-ethyl acetate [5:95] to give the title compound (7.0 mg, 19.6%): $^1$H NMR (200 MHz, DMSO-d$_6$): δ 9.02 (s, 1H), 7.04 (s, 2H), 6.85 (s, 1H), 6.63 (d, J=8.2 Hz, 1H), 6.46 (d, J=7.0 Hz, 1H), 4.85 (d, J=7.8 Hz, 2H), 3.87 (s, 2H), 3.16 (m, J=14.4 Hz, 1H), 2.20 (s, 6H), 1.38 (d, J=17.2 Hz, 3H), 1.11 (d, J=7.0 Hz, 6H); TLC conditions: Uniplate silica gel, 250 microns; Mobile phase=methanol-ethyl acetate [3:7]; R$_f$=0.70.

Compound 94-1: Phosphoric acid [3,5-dimethyl-4-(4'-hydroxy-3'-isopropylbenzyl) benzyl] ester methyl ester Step a:

To a mixture of 3,5-dimethyl-4-(3'-iso-propyl-4'-methoxymethoxybenzyl) benzyl alcohol (0.10 g, 0.30 mmol) in methanol (1.5 mL) was added 1N HCl (1.5 mL, 1.5 mmol). The reaction mixture was stirred at 45° C. for 16 h, then cooled to room temperature and concentrated to remove methanol. The reaction mixture was partitioned between ethyl acetate and water. The aqueous layer was extracted twice with ethyl acetate. The organic layer was dried over Na$_2$SO$_4$, filtered and concentrated under reduced pressure. 3,5-dimethyl-4-(3'-iso-propyl-4'-hydroxybenzyl)benzyl alcohol (73 mg, 84.5%) was used without further purification: $^1$H NMR (300 MHz, CDCl$_3$): δ 7.06 (s, 2H), 6.95 (s, 1H), 6.57 (m, J=5.1 Hz, 2H), 4.64 (s, 2H), 3.96 (s, 2H), 3.17 (m, J=14.1 Hz, 1H), 2.25 (s, 6H), 1.22 (d, J=2.7 Hz, 6H); TLC conditions: Uniplate silica gel, 250 microns; Mobile phase=ethyl acetate-hexanes [1:1]; R$_f$=0.54.

Step b:

To a mixture of 3,5-dimethyl-4-(3'-iso-propyl-4'-hydroxybenzyl)-benzyl alcohol (73 mg, 0.26 mmol) in tetrahydrofuran (2.0 mL) was added t-BuMgCl (0.26 mL, 1.0 M in THF, 0.26 mmol) and dimethyl chlorophosphate (0.03 mL, 0.26 mmol). The reaction mixture was stirred at 45° C. for 16 h, then cooled to room temperature and concentrated to remove dichloromethane. The reaction mixture was taken up in ethyl acetate, and extracted into 1N NaOH (2×10 mL). The basic layer was then acidified to pH=2 with 1N HCl and extracted into ethyl acetate (2×10 mL). The organic layer was dried over Na$_2$SO$_4$, filtered and concentrated under reduced pressure. The residue was then purified by preparative TLC 500 μm silica gel plate eluted with ethyl acetate-hexanes [7:3] to give phosphoric acid [3,5-dimethyl-4-(3'-iso-propyl-4'-hydroxybenzyl)benzyl] ester dimethyl ester (31 mg, 30.7%): $^1$H NMR (300 MHz, CDCl$_3$): δ 7.11 (d, J=9.3 Hz, 2H), 7.05 (s, 2H), 7.00 (s, 1H), 6.67 (d, J=10.5 Hz, 1H), 4.62 (s, 2H), 3.98 (s, 2H), 3.85 (s, 3H), 3.82 (s, 3H), 3.30 (m, J=13.8 Hz, 1H), 2.22 (s, 6H), 1.20 (d, J=6.9 Hz, 6H); TLC conditions: Uniplate silica gel, 250 microns; Mobile phase=ethyl acetate-hexanes [1:1]; R$_f$=0.24.

Step c:

To a solution of phosphoric acid [3,5-dimethyl-4-(3'-iso-propyl-4'-hydroxybenzyl)benzyl] ester dimethyl ester (31 mg, 0.08 mmol) in THF (0.4 mL) was added 1N NaOH (0.4 mL, 0.40 mmol). The reaction mixture was stirred at 60° C. for 16 h, then cooled to room temperature and concentrated to remove solvent. The reaction mixture was taken up in ethyl acetate and extracted into 1N NaOH (2×10 mL). The basic layer was then acidified to pH=2 with 1N HCl and extracted into ethyl acetate (2×10 mL). The organic layer was dried over Na$_2$SO$_4$, filtered and concentrated under reduced pressure to give the title compound (3.1 mg, 10.4%): $^1$H NMR (300 MHz, CDCl$_3$): δ 7.07 (m, 3H), 6.99 (s, 1H), 6.64 (d, J=8.4 Hz, 2H), 4.63 (s, 2H), 3.99 (s, 2H), 3.79 (d, J=11.4 Hz, 3H), 3.29 (m, 1H), 2.22 (s, 6H), 1.17 (d, J=6.6 Hz, 6H); LC-MS m/z=377.4 [C$_{20}$H$_{27}$O$_5$P−H]$^-$; TLC conditions: Uniplate silica gel, 250 microns; Mobile phase=methanol-ethyl acetate [3:7]; R$_f$=0.45.

Example 95

Compound 95: [4-(4-Hydroxy-3-isopropyl-benzyl)-3,5-dimethyl-phenoxymethyl]phosphamic acid Step a:

To a solution of [3,5-dimethyl-4-(4'-hydroxy-3'-isopropylbenzyl)-phenoxy]methylphosphonic acid (compound 7, 0.49 g, 1.36 mmol) in acetonitrile (13.6 mL), was added diisopropylethylamine (0.90 mL, 5.43 mmol) and benzyl bromide (0.65 mL, 5.43 mmol). The reaction mixture was stirred at 80° C. for 16 h, then cooled to room temperature and concentrated to remove dichloromethane. The reaction mixture was taken up in ethyl acetate, rinsed with water, a saturated solution of sodium bicarbonate, and brine. The organic layer was dried over Na$_2$SO$_4$, filtered and concentrated under reduced pressure. The residue was then purified by column chromatography on silica gel, eluted with ethyl acetate-hexanes [1:9] to give dibenzyl [3,5-dimethyl-4-(4'-hydroxy-3'-isopropylbenzyl)phenoxy]methylphosphonate (0.50 g, 0.92 mmol): $^1$H NMR (200 MHz, DMSO-d$_6$): δ 9.00 (s, 1H), 7.37 (m, J=6.6 Hz, 5H), 6.83 (s, 1H), 6.70 (s, 2H), 6.61 (d, J=8.6 Hz, 2H), 6.44 (d, J=8.2 Hz, 1H), 5.14 (d, J=8.2 Hz, 2H), 4.50 (d, J=9.8 Hz, 2H), 3.79 (s, 2H), 3.14 (m, J=13.2 Hz, 1H), 2.15 (s, 6H), 1.10 (d, J=7.0 Hz, 6H), ; TLC conditions: Uniplate silica gel, 250 microns; Mobile phase=ethyl acetate-hexanes [1:1]; R$_f$=0.77.

Step b:

To a solution of dibenzyl [3,5-dimethyl-4-(4'-hydroxy-3'-isopropylbenzyl)phenoxy]methylphosphonate (0.50 g, 0.92 mmol) in tetrahydrofuran (4.6 mL), was added 1N NaOH (4.6 mL, 4.6 mmol). The reaction mixture was allowed to stir at room temperature for 16 h. The reaction mixture was diluted in ethyl acetate and 1N NaOH. The organic layer was extracted with water, and then the pH was adjusted to pH=12 with 1N NaOH. The aqueous layer was then extracted with ethyl acetate. The organic layer was dried over Na$_2$SO$_4$, filtered and concentrated under reduced pressure to give [3,5-dimethyl-4-(4'-hydroxy-3'-isopropylbenzyl)phenoxy]methyl-phosphonic acid monobenzyl ester (0.45 g, 100%) as a yellow foam: $^1$H NMR (200 MHz, DMSO-d$_6$): δ 9.12 (s, 1H), 7.35 (m, J=31.4 Hz, 5H), 6.84 (s, 1H), 6.64 (d, J=10.2 Hz, 1H), 6.59 (s, 2H), 6.44 (d, J=8.0 Hz, 1H), 4.83 (d, J=7.0 Hz, 2H), 3.77 (m, J=9.2 Hz, 4H), 3.15 (m, J=14.0 Hz, 1H), 2.13 (s, 6H), 1.11 (d, J=7.0 Hz, 6H); TLC conditions: Uniplate silica gel, 250 microns; Mobile phase=ethyl acetate-hexanes [1:1]; R$_f$=0.04.

Step c:

To a mixture of [3,5-dimethyl-4-(4'-hydroxy-3'-isopropylbenzyl)-phenoxy]methylphosphonic acid monobenzyl ester (108 mg, 0.238 mmol) and DMF (0.1 mL, 1.29 mmol) in dichloromethane (1.0 mL) at 0° C., was added oxalyl chloride (0.04 mL, 0.476 mmol). After 3 h, the reaction mixture was concentrated under reduced pressure, redissolved in dichloromethane (1.5 mL), and cooled to −78° C. To the reaction mixture triethylamine (0.07 mL, 0.476 mmol) was added, followed by liquid ammonia at −78° C. (0.25 mL). The reaction mixture was stirred in a sealed vial warming to room temperature over 16 h. The vial was cooled to 0° C., vented and concentrated under reduced pressure. The reaction mixture was taken up in ethyl acetate and 1N NaOH. The organic layer was dried over Na$_2$SO$_4$, filtered and concentrated under reduced pressure. The residue was then purified by preparative TLC 1000 μm silica gel plate eluted with ethyl acetate to give [3,5-dimethyl-4-(4'-hydroxy-3'-isopropylbenzyl)phenoxy]-methylphosphamic benzyl ester (18 mg, 16.7%): $^1$H NMR (300 MHz, CDCl$_3$): δ 7.40 (m, 5H), 6.93 (s, 1H), 6.65 (d, J=8.1 Hz, 1H), 6.61 (s, 2H), 6.51 (d, J=8.4 Hz, 1H), 5.17 (d, J=8.1 Hz, 2H), 4.28 (dd, J=10.5, 5.4 Hz, 2H), 3.89 (s, 2H), 3.22 (m, 1H), 2.19 (s, 6H), 1.22 (d, J=6.6 Hz, 6H); LC-MS m/z=454.4 [C$_{26}$H$_{32}$NO$_4$P+H]$^+$; TLC conditions: Uniplate silica gel, 250 microns; Mobile phase=ethyl acetate; R$_f$=0.56.

Step d:

The title compound is obtained from [3,5-dimethyl-4-(4'-hydroxy-3'-isopropylbenzyl)phenoxy]methylphosphamic benzyl ester according to the procedure described by Valentijn et al., SYNLETT, 9:663 (1991).

Compound 95-2: N-methyl-[3,5-dimethyl-4-(4'-hydroxy-3'-isopropylbenzyl)phenoxy]methylphosphamic benzyl ester To a mixture of [3,5-dimethyl-4-(4'-hydroxy-3'-isopropylbenzyl)-phenoxy]methylphosphonic acid monobenzyl ester (108 mg, 0.238 mmol) and DMF (0.1 mL, 1.29 mmol) in dichloromethane (1.0 mL) at 0° C., was added oxalyl chloride (0.04 mL, 0.476 mmol). After 3 h, the reaction mixture was concentrated under reduced pressure, redissolved in dichloromethane (1.5 mL), and cooled to −78° C. To the reaction mixture triethylamine (0.07 mL, 0.476 mmol) was added, followed by methylamine (0.24 mL, 2.0 M solution in THF, 0.476 mmol) at −78° C. (0.25 mL). The reaction mixture was stirred, warming to room temperature over 16 h, then concentrated under reduced pressure. The reaction mixture was taken up in ethyl acetate and 1N NaOH. The organic layer was dried over $Na_2SO_4$, filtered and concentrated under reduced pressure. The residue was then purified by preparative TLC 1000 μm silica gel plate eluted with ethyl acetate to give N-methyl-[3,5-dimethyl-4-(4'-hydroxy-3'-isopropylbenzyl) phenoxy]methylphosphamic benzyl ester (23 mg, 20.7%): $^1$H NMR (300 MHz, $CDCl_3$): δ 7.39 (m, 5H), 6.92 (s, 1H), 6.63 (s, 2H), 6.62 (d, J=8.1 Hz, 1H), 6.51 (d, J=2.1 Hz, 1H), 5.14 (m, 2H), 5.05 (s, 1H), 4.30 (dd, J=10.2, 3.6 Hz, 2H), 3.89 (s, 3H), 3.19 (m, 1H), 2.71 (d, J=10.8 Hz, 3H), 2.19 (s, 6H), 1.22 (d, J=6.9 Hz, 6H); LC-MS m/z=468.4 $[C_{27}H_{34}NO_4P+H]^+$; TLC conditions: Uniplate silica gel, 250 microns; Mobile phase=ethyl acetate; $R_f$=0.44.

Step b:

The title compound is obtained from N-methyl [3,5-dimethyl-4-(4'-hydroxy-3'-isopropylbenzyl)phenoxy]methylphosphamic benzyl ester according to the procedure described by Valentijn et al., *SYNLETT*, 9:663 (1991).

Example 96

Compound 96: [(3,5-Dimethyl-4-(3'-Isopropyl-1'H-indol-5'-ylmethyl)-phenoxy)methyl]methylphosphinic acid Step a:

To the solution of 3,5-dimethyl-4-(3-isopropyl-1H-indol-5-ylmethyl)phenol (compound 93, step f, 200 mg, 0.683 mmol) in acetonitrile (10 ml) was added $Cs_2CO_3$ (450 mg, 1.365 mmol), followed by ethyl [(4-methylphenyl)sulfonyloxymethyl]methylphosphinate (compound 74, 200 mg, 0.683 mmol) at r.t, the reaction mixture was then heated to reflux overnight. The second day, concentrated down, the residue was partitioned between EtOAc and water, collected the org. layer, water layer was further extracted with EtOAc once, the combined org. layer was dried over $MgSO_4$, filtrated and concentrated. The residue was purified by column chromatography on silica gel, eluting with ethyl MeOH— EtOAc (1:49) to afford ethyl [(3,5-dimethyl-4-(3'-Isopropyl-1'H-indol-5'-ylmethyl)phenoxy)methyl]-methylphosphinate (131 mg, 46.4%): $^1$H NMR (300 MHz, $CDCl_3$): δ 7.85 (s, 1H), 7.26 (s, 1H), 7.24 (d, J=8.4 Hz, 1H), 6.95 (s, 1H), 6.84 (d, J=8.4 Hz, 1H), 6.72 (s, 2H), 4.20 (m, 4H), 4.14 (s, 2H), 3.15 (m, 1H), 2.30 (s, 1H), 1.67 (d, J=14.7 Hz, 3H), 1.40 (m, 3H), 1.34 (d, J=6.6 Hz, 6H). TLC conditions: Uniplate silica gel, 250 microns; Mobile phase=ethyl acetate; $R_f$=0.33.

Step b:

The title compound was prepared from ethyl [(3,5-dimethyl-4-(3'-Isopropyl-1'H-indol-5'-ylmethyl)phenoxy)methyl]methylphosphinate according to the procedure described for the synthesis of compound 93, step h; (100 mg, 81.3%): $^1$H NMR (300 MHz, DMSO-$d_6$): δ 10.58 (s, 1H), 7.17 (d, J=8.4 Hz, 1H), 7.13 (s, 1H), 6.98 (d, J=1.8 Hz, 1H), 6.72 (s, 2H), 6.67 (dd, J=8.4, 1.8 Hz, 1H), 4.08 (d, J=8.4 Hz, 2H), 3.99 (s, 2H), 2.98 (m, 1H), 2.19 (s, 6H), 1.40 (d, J=14.4 Hz, 3H), 1.22 (d, J=6.9 Hz, 6H). LC-MS m/z=386 $[C_{22}H_{28}NO_3P+H]^+$; Anal. Calcd for $(C_{21}H_{26}NO_4P+0.2$ HBr): C, 65.79; H, 7.08; N, 3.49. Found: C, 65.97; H, 7.28; N, 3.30.

$CH_2Cl_2$: dichloromethane
DMF: dimethylformamide
TEA: triethylamine
THF: tetrahydrofuran
TFA: trifluoroacetic acid
$MgSO_4$: magnesium sulfate
TBSCl: t-butyldimethylsilyl chloride
$H_2O$: water
DMSO: dimethyl sulfoxide
$CH_3CN$: acetonitrile For the purposes of clarity and brevity compounds are referred to by compound numbers (from the Table below) in the biological examples below.

| Structure | Compound Number |
|---|---|
| 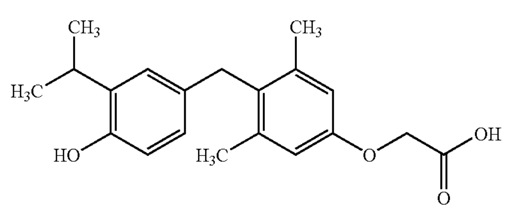 | 17 |
| 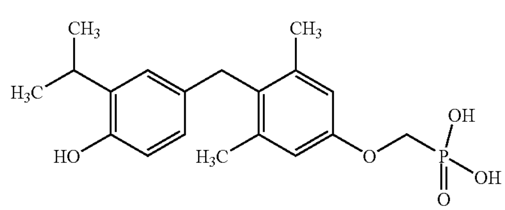 | 7 |

-continued

| Structure | Compound Number |
|---|---|
| 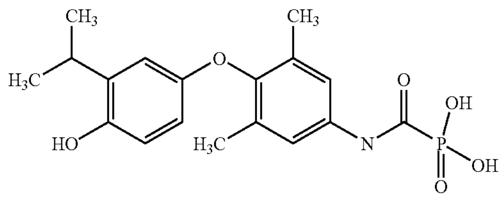 | 1 |
| 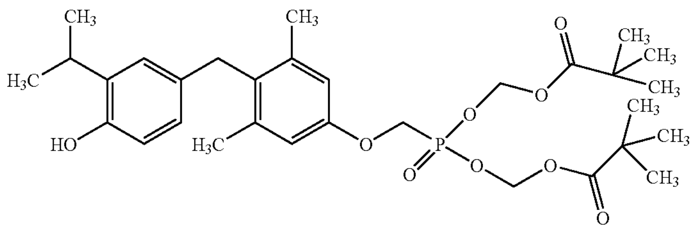 | 12-1 |
| 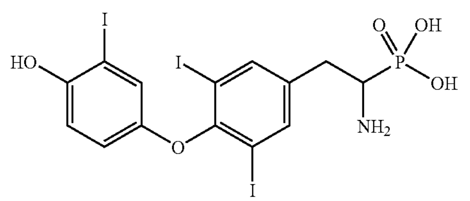 | 2 |
| 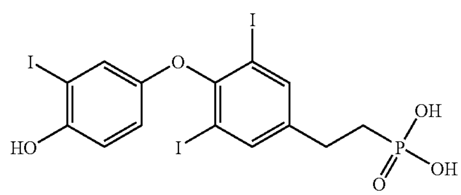 | 3 |
| 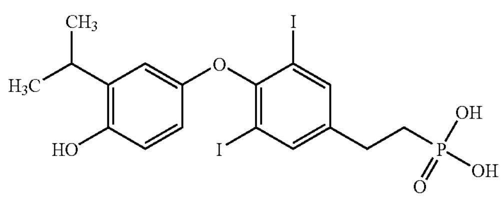 | 4 |
| 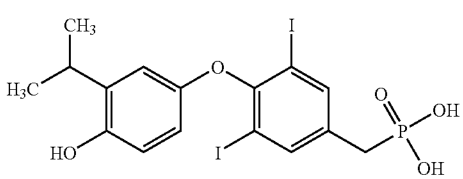 | 5 |
| 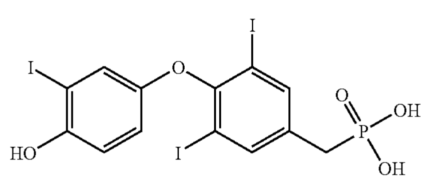 | 6 |
| 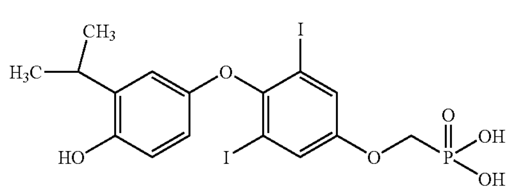 | 8 |

-continued
| Structure | Compound Number |
|---|---|
| 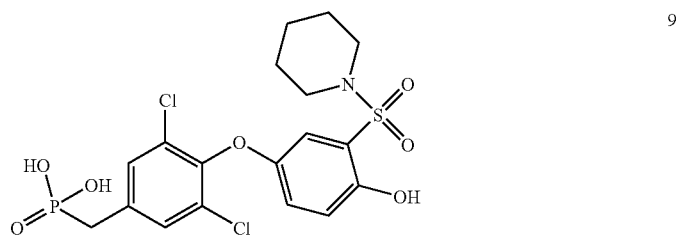 | 9 |
| 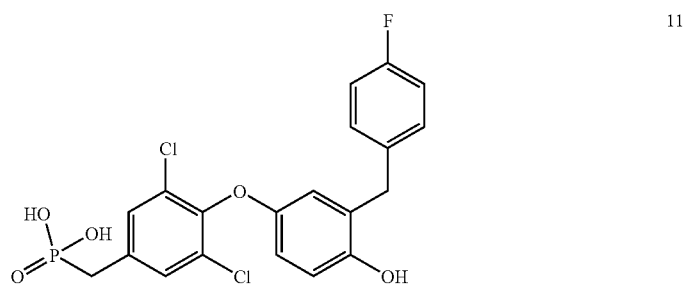 | 11 |
| 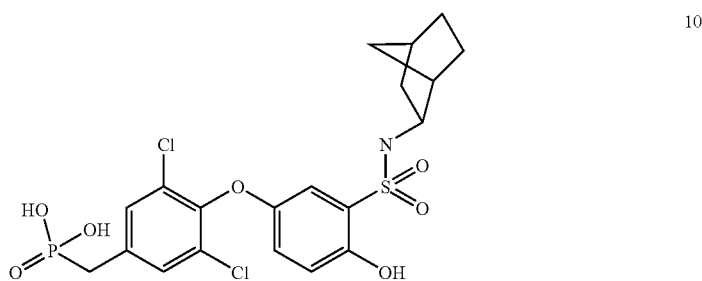 | 10 |
| 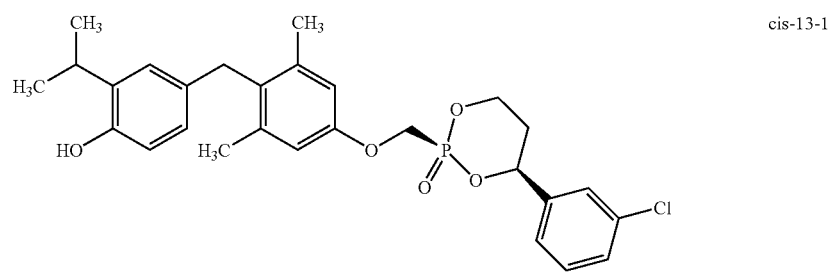 | cis-13-1 |
| 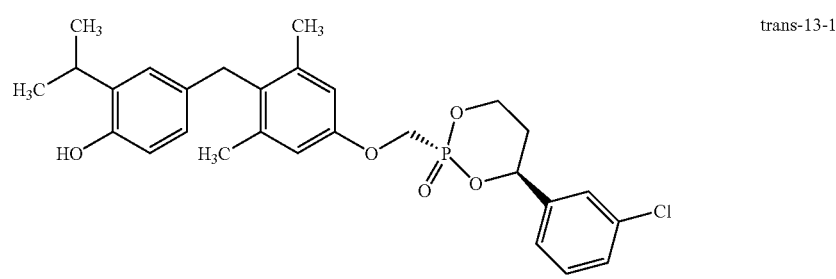 | trans-13-1 |

| Structure | Compound Number |
|---|---|
| Chiral | cis-13-6 |
| Chiral | cis-13-2 |
| Chiral | trans-13-2 |
| Chiral | cis-13-3 |
| Chiral | trans-13-3 |

-continued
| Structure | Compound Number |
|---|---|
| 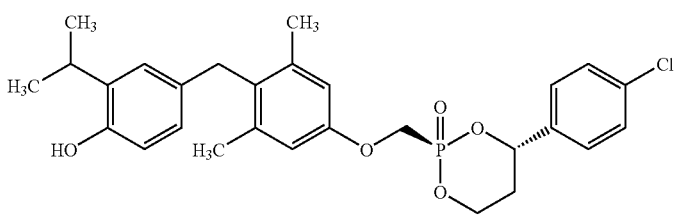 Chiral | trans-13-6 |
| 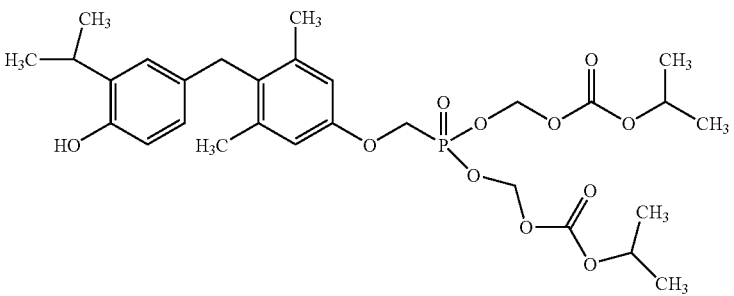 | 12-3 |
| 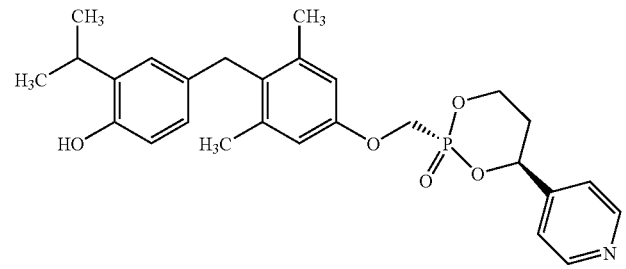 | trans-13-5 |
| 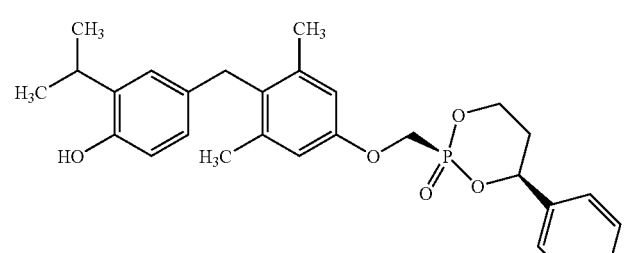 | cis-13-5 |
| 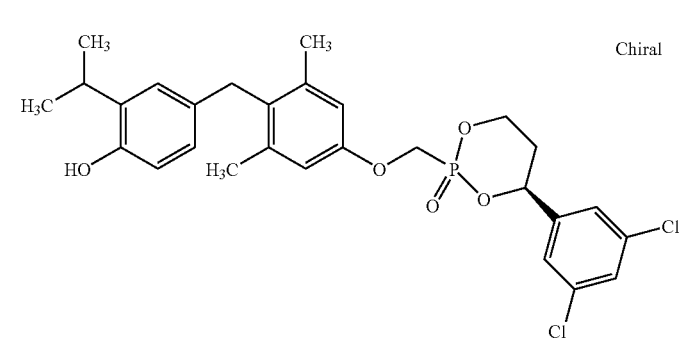 Chiral | trans-13-7 |

| Structure | Compound Number |
|---|---|
| | trans-13-4 (Chiral) |
| | cis-13-4 (Chiral) |
| | 12-2 |
| | cis-13-7 (Chiral) |
| | 14 |

| Structure | Compound Number |
|---|---|
| 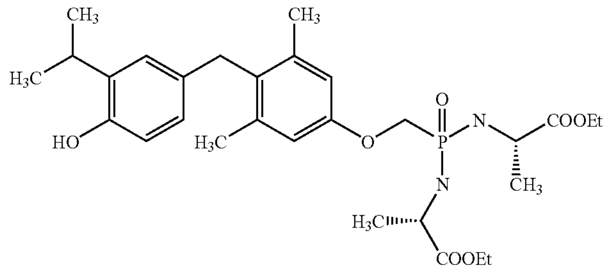 | 15-1 |
| 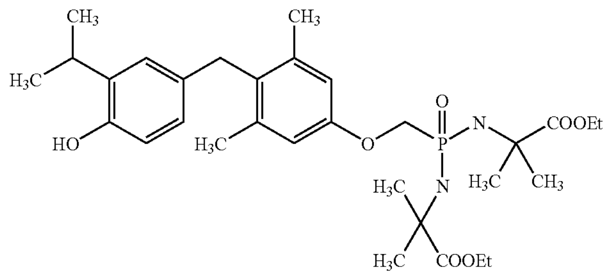 | 15-2 |
| 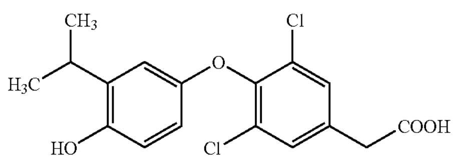 | 18 |
| 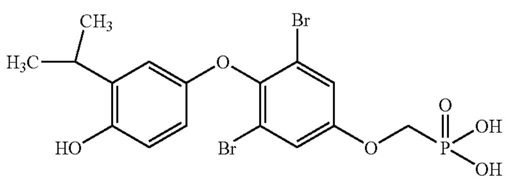 | 8-1 |
| 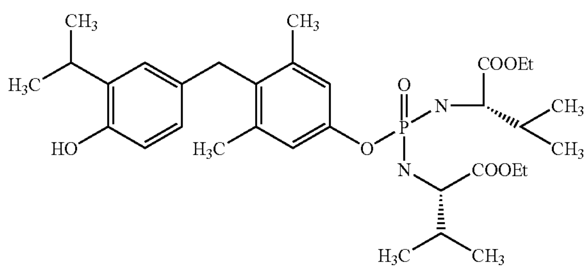 | 15-3 |
| 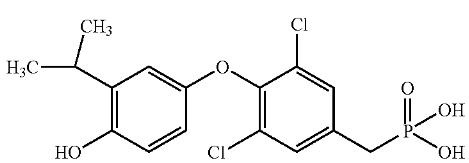 | 19 |
| 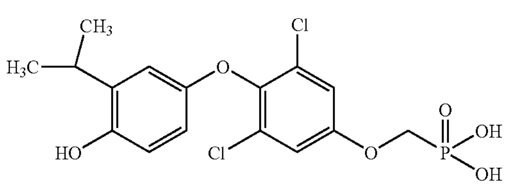 | 8-2 |

-continued

| Structure | Compound Number |
|---|---|
| (structure) | 24-1 |
| (structure) | 7-5 |
| (structure) | 25 |
| (structure) | 22 |
| (structure) | 21 |
| (structure) | 7-6 |
| (structure) | 24-2 |
| (structure) | 19-1 |

| Structure | Compound Number |
|---|---|
| 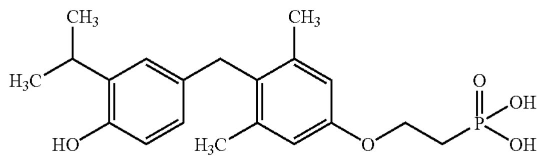 | 26 |
| 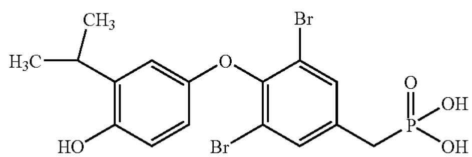 | 19-2 |
| 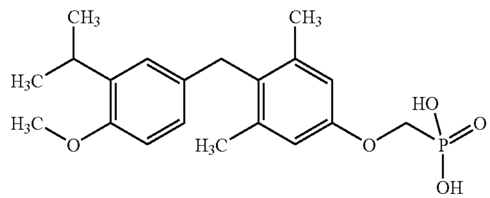 | 7-4 |
| 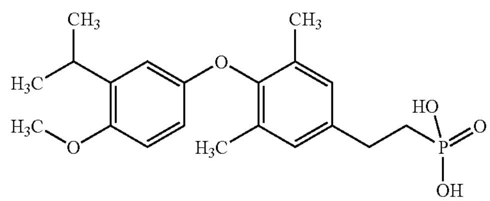 | 30 |
| 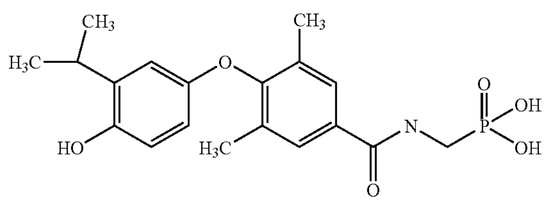 | 23 |
| 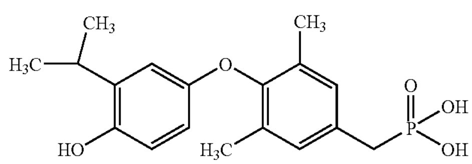 | 19-3 |
| 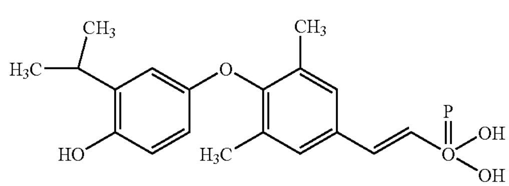 | 28 |
| 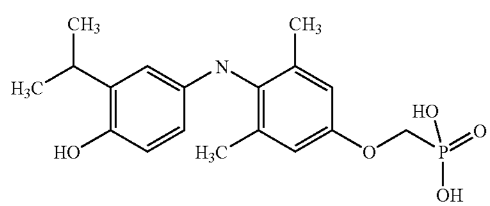 | 20 |

-continued

| Structure | Compound Number |
|---|---|
| 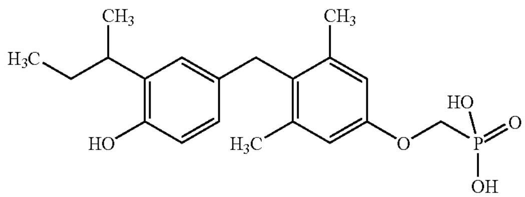 | 7-3 |
| 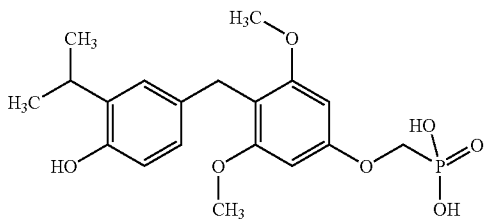 | 7-2 |
| 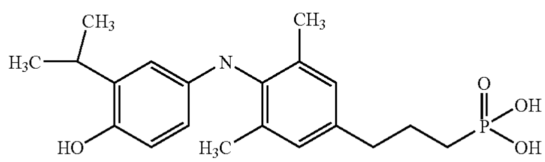 | 29 |
| 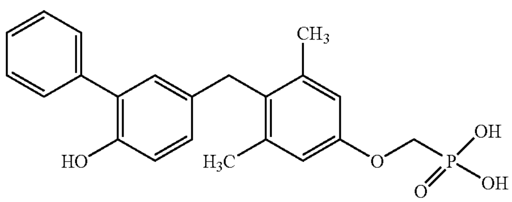 | 7-1 |
| 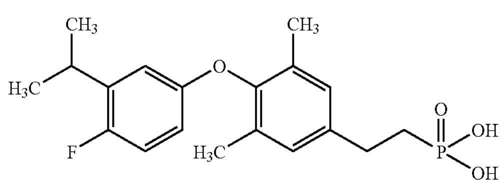 | 32 |
| 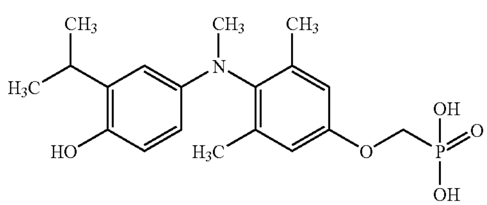 | 20-1 |
| 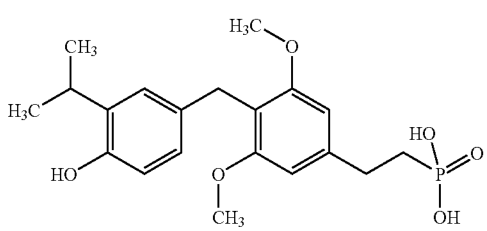 | 24 |

| Structure | Compound Number |
|---|---|
| 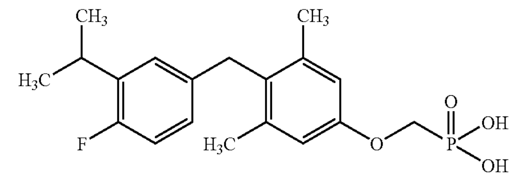 | 27 |
| 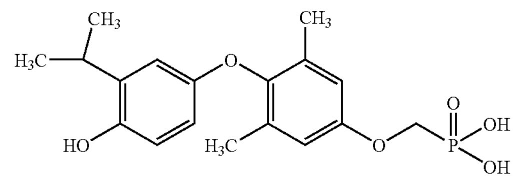 | 31 |
| 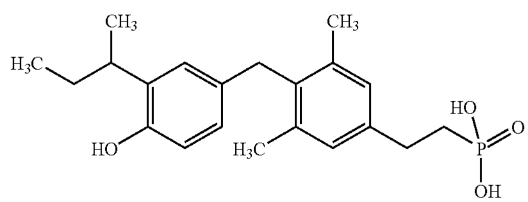 | 24-3 |
| 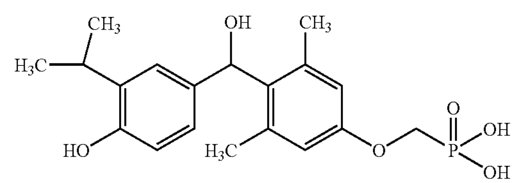 | 33 |
| 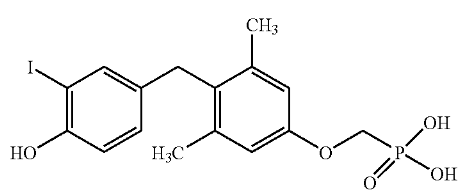 | 34 |
| 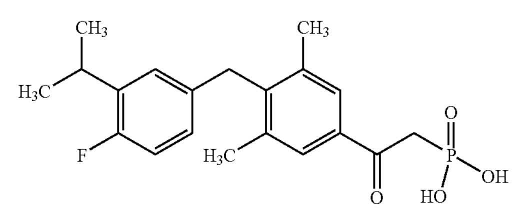 | 41-2 |
| 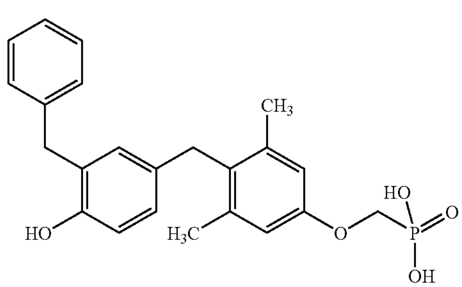 | 38 |

| Structure | Compound Number |
|---|---|
| 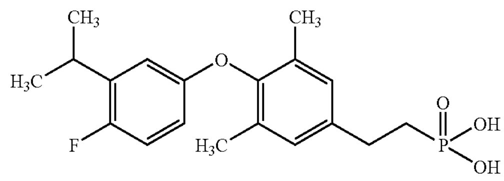 | 42-2 |
| 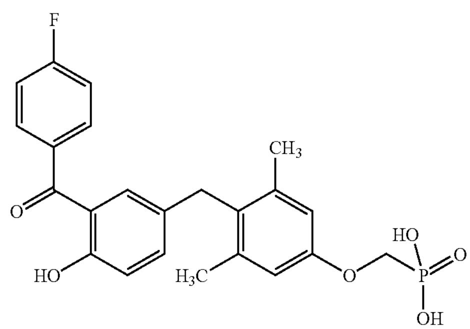 | 39 |
| 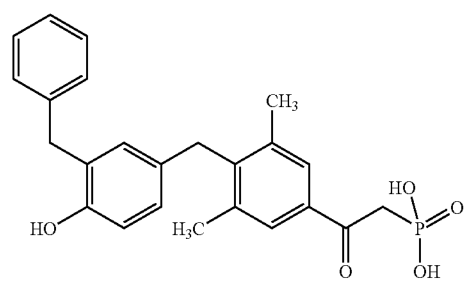 | 41 |
| 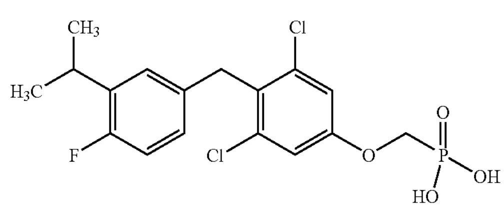 | 27-2 |
| 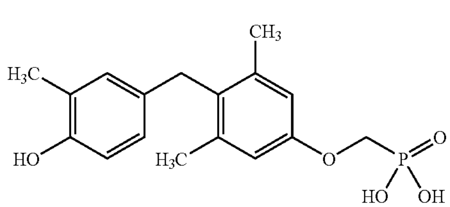 | 7-7 |
| 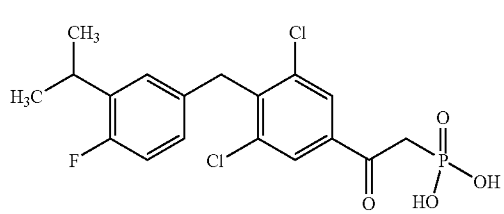 | 41-3 |

| Structure | Compound Number |
|---|---|
| 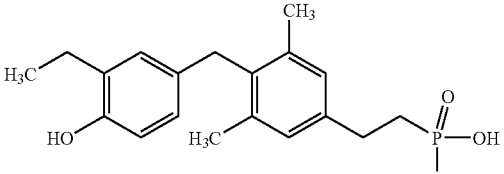 | 24-4 |
| 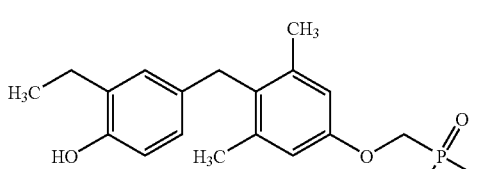 | 7-8 |
| 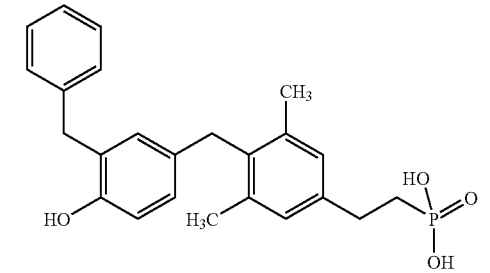 | 42 |
| 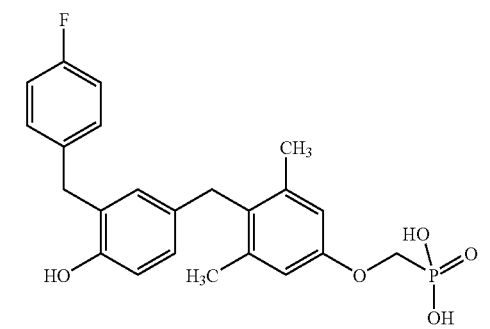 | 40 |
| 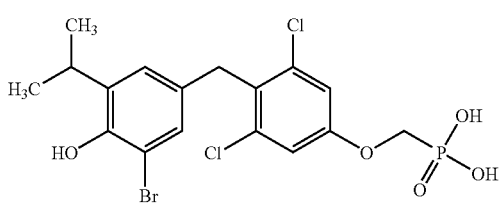 | 7-14 |
| 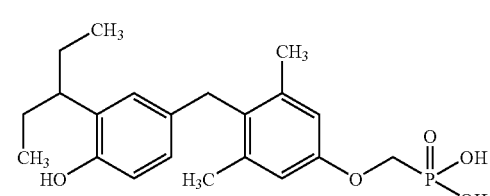 | 7-9 |

-continued

| Structure | Compound Number |
|---|---|
| 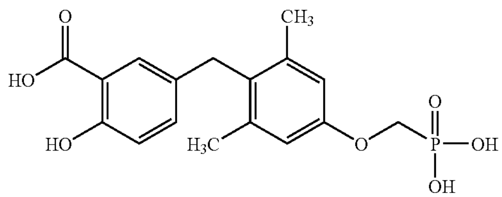 | 35 |
| 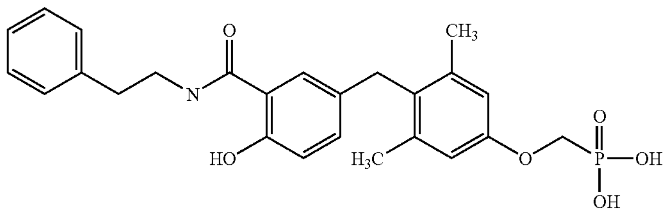 | 37 |
| 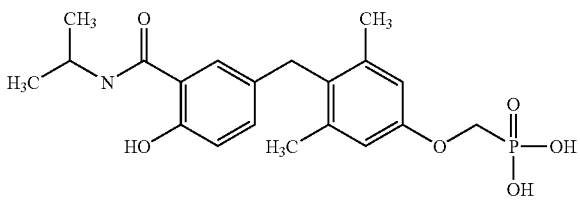 | 36 |
| 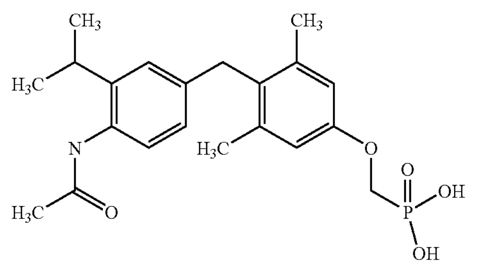 | 7-12 |
| 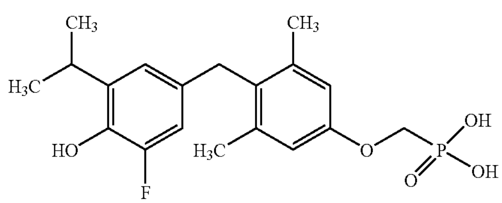 | 7-11 |
| 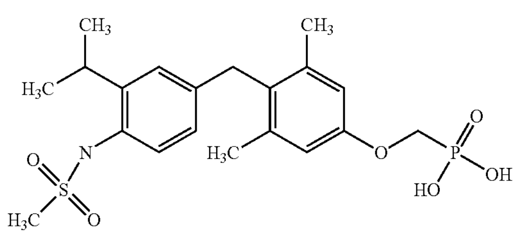 | 7-13 |
| 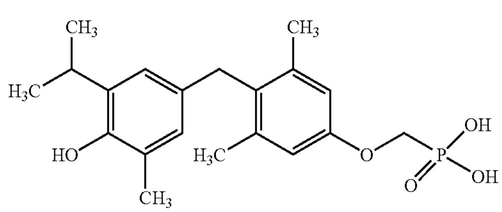 | 7-10 |

-continued

| Structure | Compound Number |
|---|---|
| 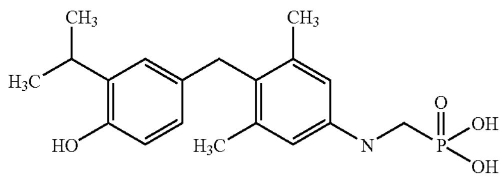 | 47 |
| BrH | 49 |
| 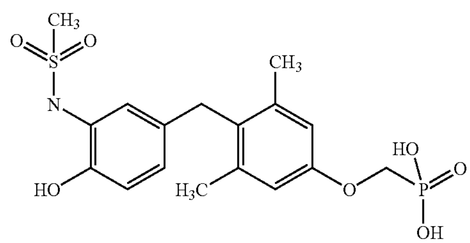 | 51-1 |
| 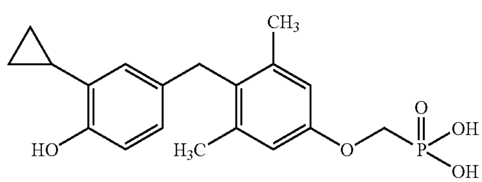 | 48 |
| 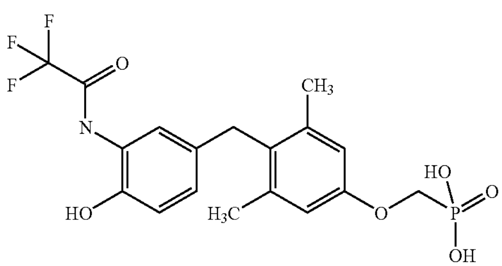 | 51-2 |
| 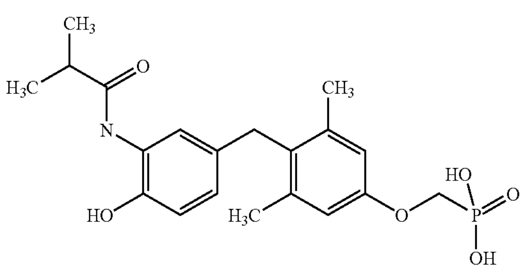 | 51-3 |
| 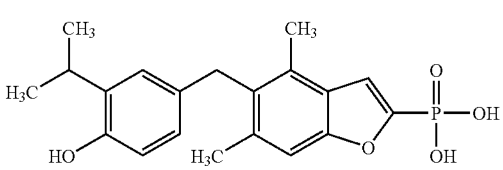 | 45 |

| Structure | Compound Number |
|---|---|
| 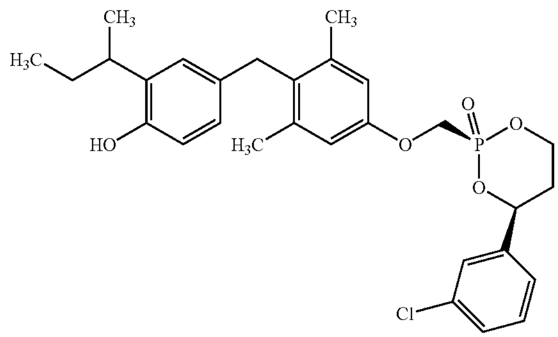 | 13-8 |
| 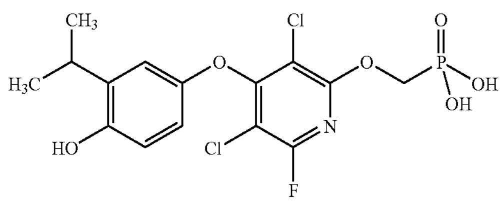 | 57 |
| 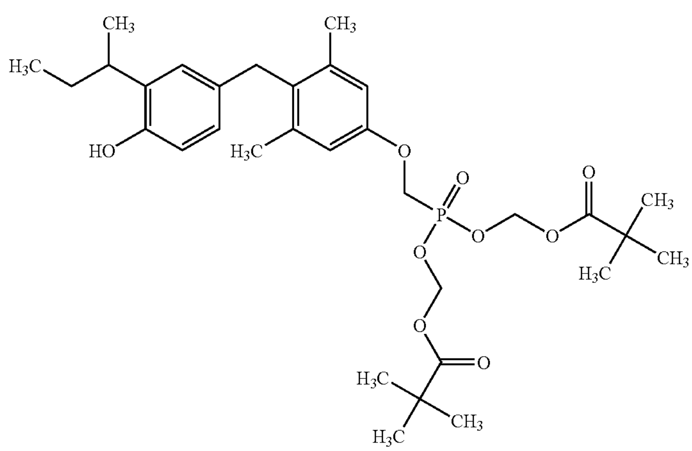 | 12-4 |
| 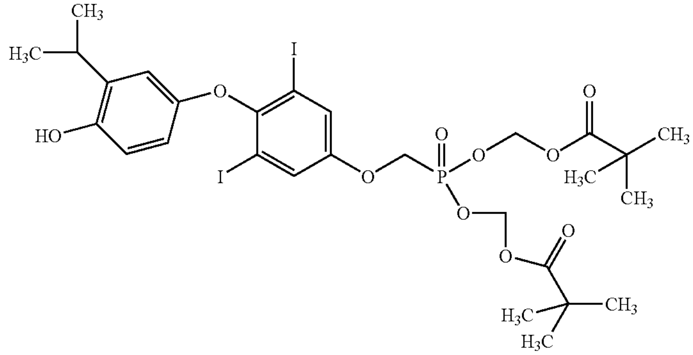 | 12-7 |

-continued
| Structure | Compound Number |
|---|---|
| 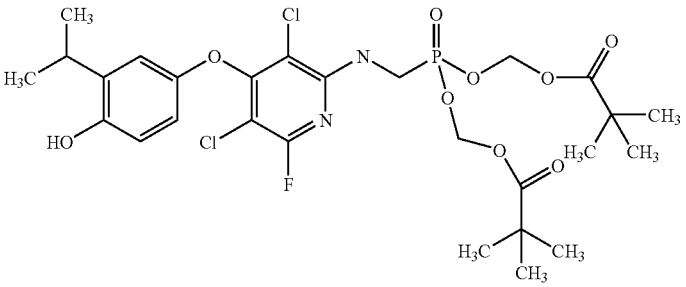 | 12-9 |
| 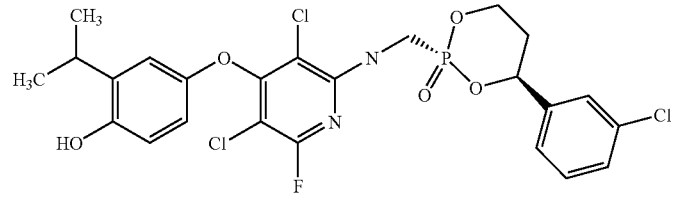 | 13-12-trans |
| 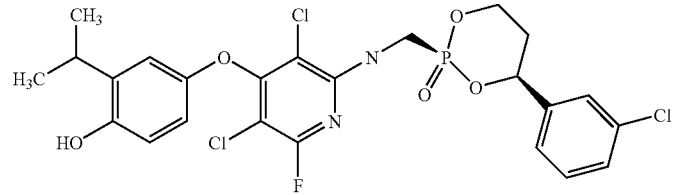 | 13-12-cis |
| 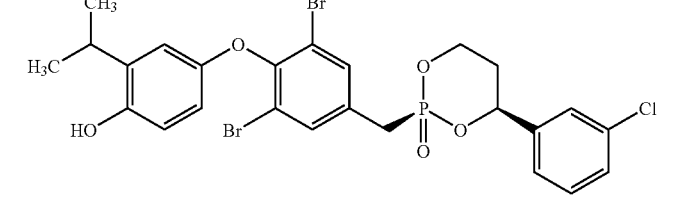 | 13-9 |
| 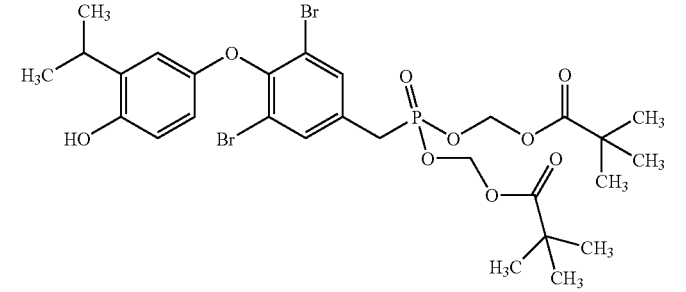 | 12-5 |
| 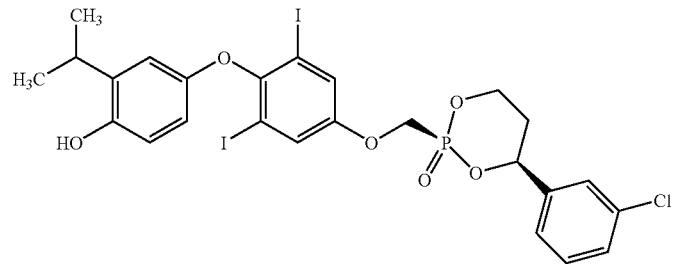 | 13-10 |

-continued

| Structure | Compound Number |
|---|---|
| 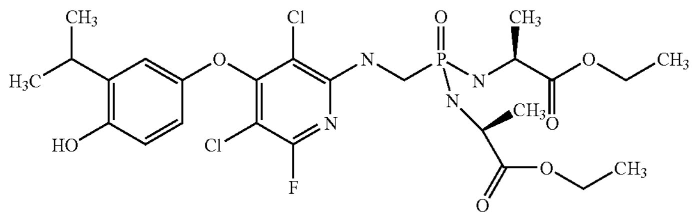 | 15-6 |
| 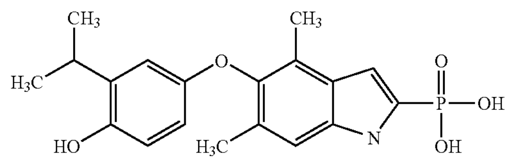 | 66 |
| 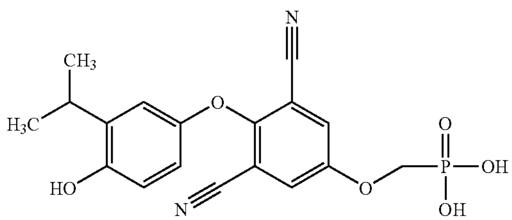 | 56 |
| 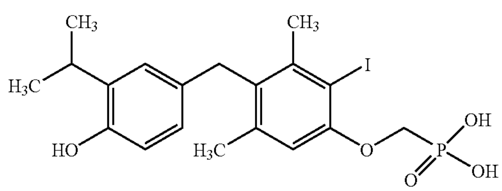 | 46 |
| 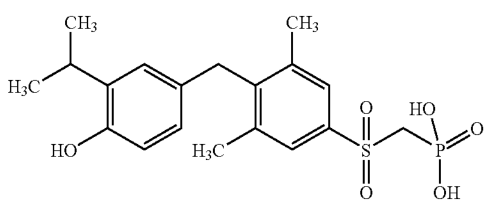 | 52 |
| 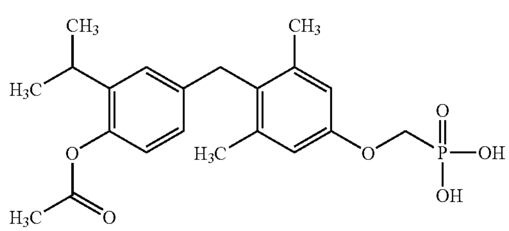 | 58 |
| 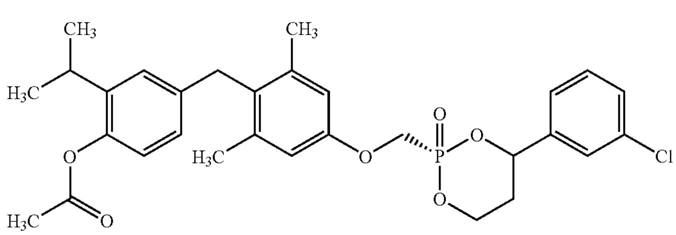 | 59 |

-continued

| Structure | Compound Number |
|---|---|
| 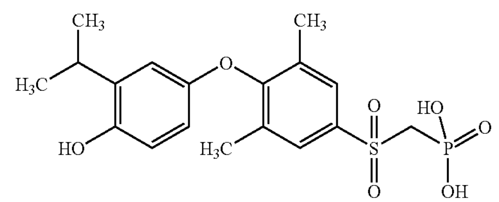 | 53 |
| 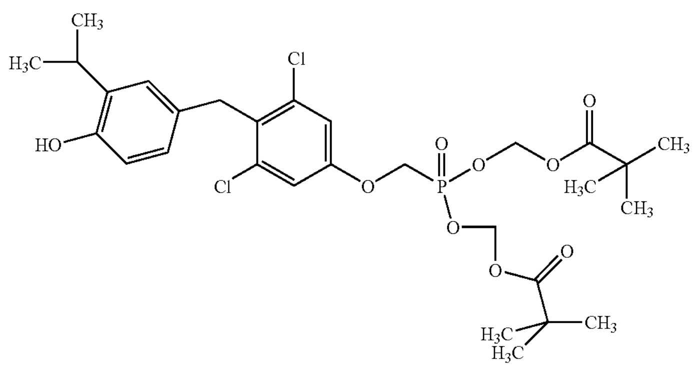 | 12-8 |
| 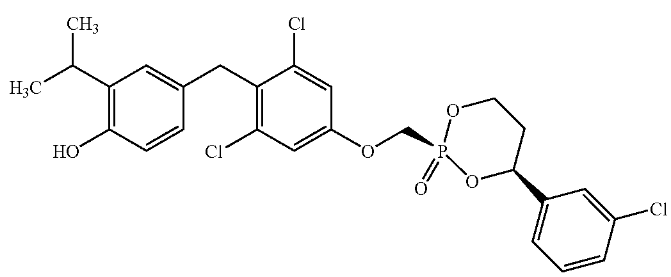 | 13-11 |
| 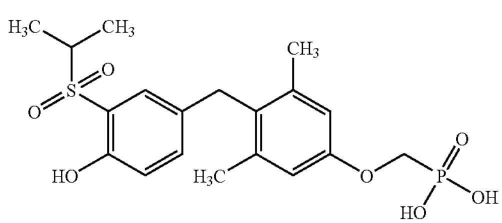 | 44 |
| 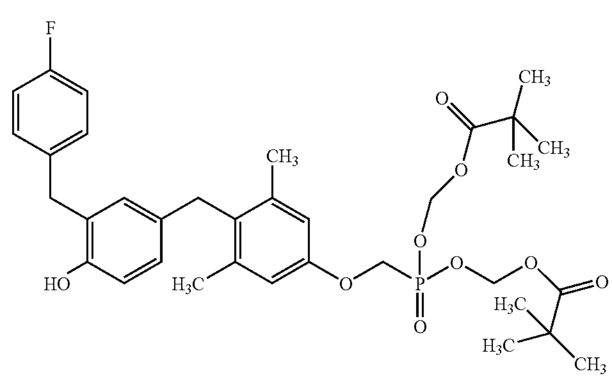 | 12-6 |

-continued

| Structure | Compound Number |
|---|---|
| 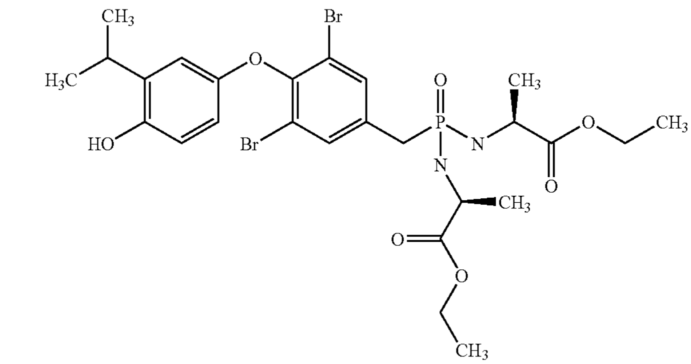 | 15-5 |
| 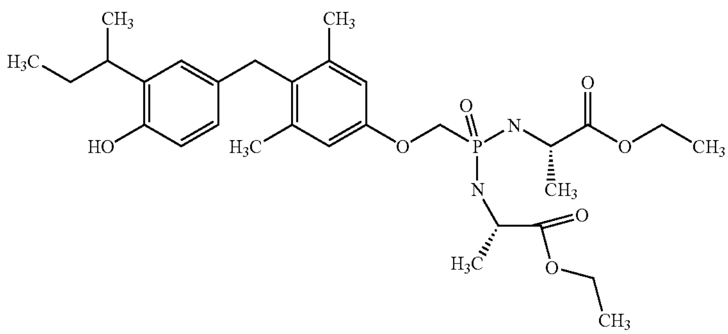 | 15-4 |
| 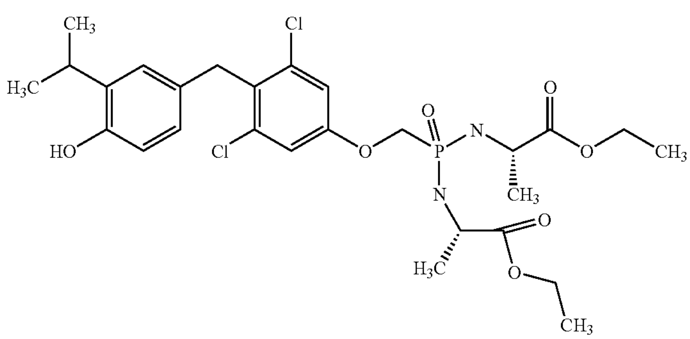 | 15-7 |
| 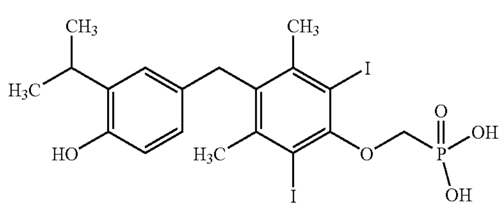 | 65-1 |
| 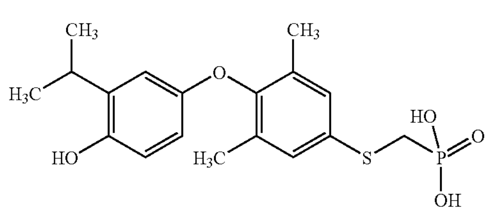 | 54 |

| Structure | Compound Number |
|---|---|
| (structure) | 50 |
| (structure) | 43 |
| (structure) | 63 |
| (structure) | 65-2 |
| (structure) | 7-16 |
| (structure) | 61 |

-continued
| Structure | Compound Number |
|---|---|
| 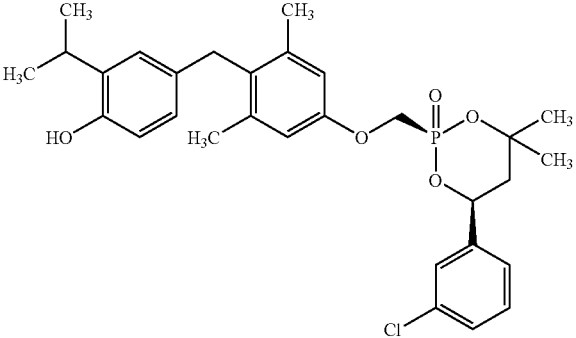 | 13-13-cis |
| 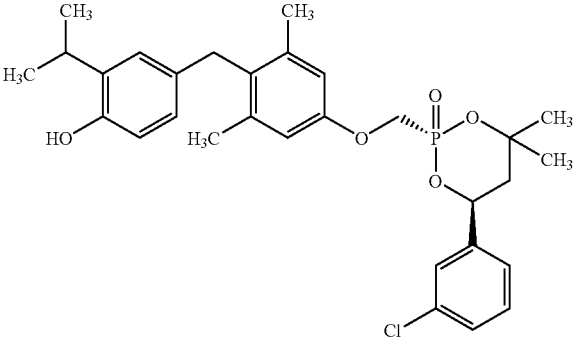 | 13-13-trans |
| 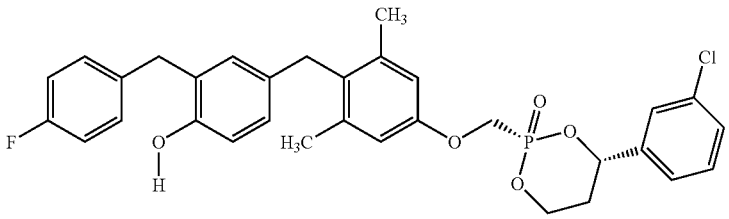 | 13-14-cis |
| 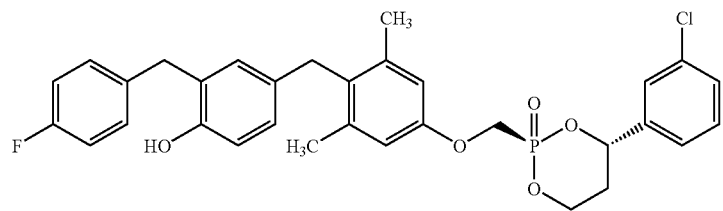 | 13-14-trans |
| 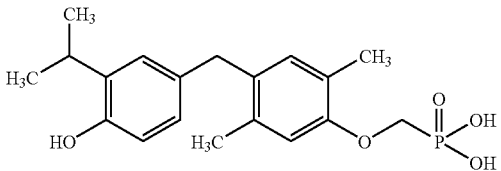 | 7-17 |

| Structure | Compound Number |
|---|---|
| 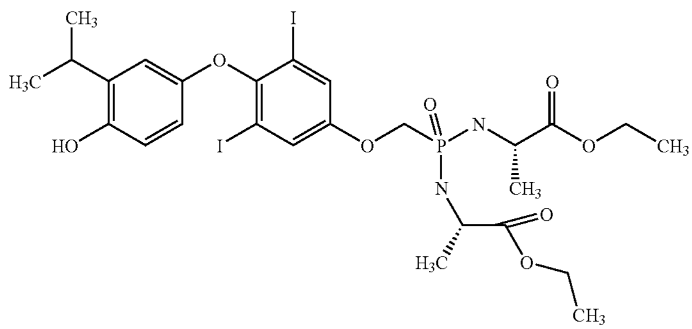 | 15-8 |
| 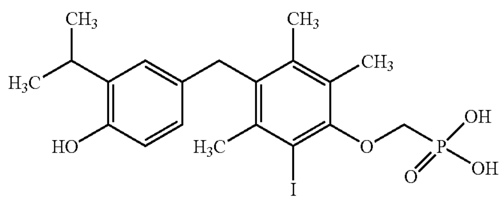 | 62 |
| 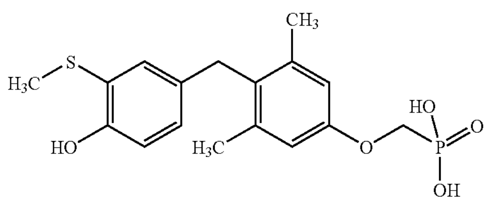 | 55 |
| 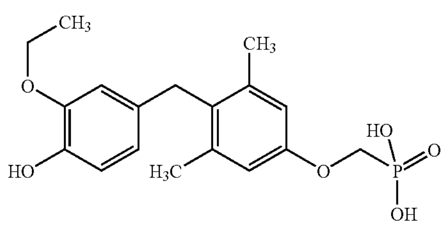 | 7-15 |
| 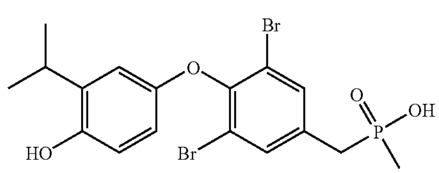 | 71 |
| 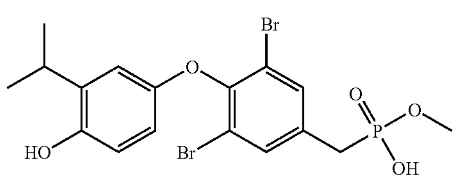 | 69-2 |
| 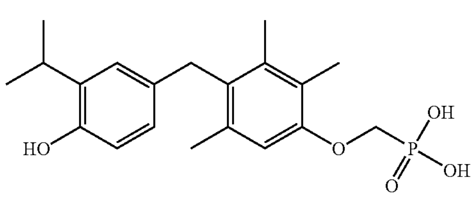 | 61 |

| Structure | Compound Number |
|---|---|
| (structure) | 69 |
| (structure) | 22-1 |
| (structure) | 70 |
| (structure) | 67 |
| (structure) | 66 |

Examples of use of the method of the invention includes the following. It will be understood that these examples are exemplary and that the method of the invention is not limited solely to these examples.

For the purposes of clarity and brevity, chemical compounds are referred to as synthetic example numbers in the biological examples below.

Example A

Receptor Binding

The purpose of these studies was to determine the affinity of T3 and various thyromimetics for human thyroid hormone receptors TRα1 and TRβ1.

Methods: Baculoviruses expressing TRα1, TRβ1 and RXRα were generated using cDNA and other reagents from Invitrogen (Carlsbad, Calif.). To produce TR/RXR heterodimer proteins, the sf9 insect cells were first grown to a density of $1\text{-}5\times10^5$ cells/mL. TRα1 or TRβ1 and RXRα baculovirus stocks were added to the cell culture with a ratio of 1 to 1 (multiplicity of infection=10). The cells were harvested three days after the infection. The cells were lysed in assay buffer (50 mM NaCl, 10% Glycerol, 20 mM tris, pH 7.6 2 mM EDTA, 5 mM β-mercaptoethanol and 1.25% CHAPS) and the lysates were assayed for T3 binding as follows: $^{125}$I-T3 was incubated with the lysates of TR and RXR recombinant baculoviruses coinfected cells (50 μl) in assay buffer for one h and then the $^{125}$I-T3-TR/RXR complex was separated from free $^{125}$I-T3 by a mini-gel-filtration (Sephadex G50) column. The bound $^{125}$I-T3 was counted with a scintillation counter.

Binding of compounds to either the TRα1 or TRβ1 were also performed by means of scintillation proximity assays (SPA). The SPA assay, a common method used for the quantitation of receptor-ligand equilibria, makes use of special beads coated with a scintillant and a capture molecule, copper, which binds to the histidine-tagged α or β receptor. When labeled T3 is mixed with receptor and the SPA beads, radioactive counts are observed only when the complex of protein and radiolabeled ligand is captured on the surface of the bead. Displacement curves were also generated with labeled T3 and increasing concentrations of unlabeled thyromimetics of interest.

Figure 1B:
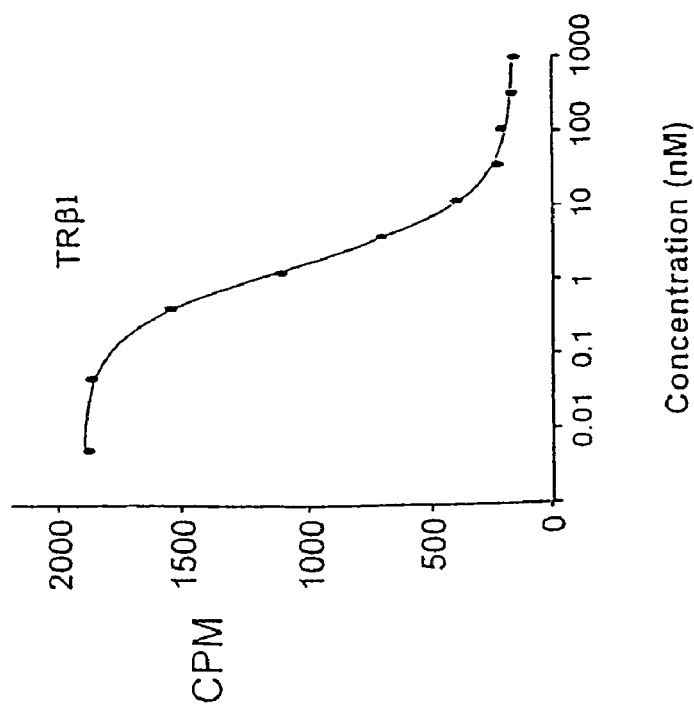
FIG. 1b depicts the binding of T3 to the Rβ1 receptor using a homologous displacement reaction.
Figure 1C:
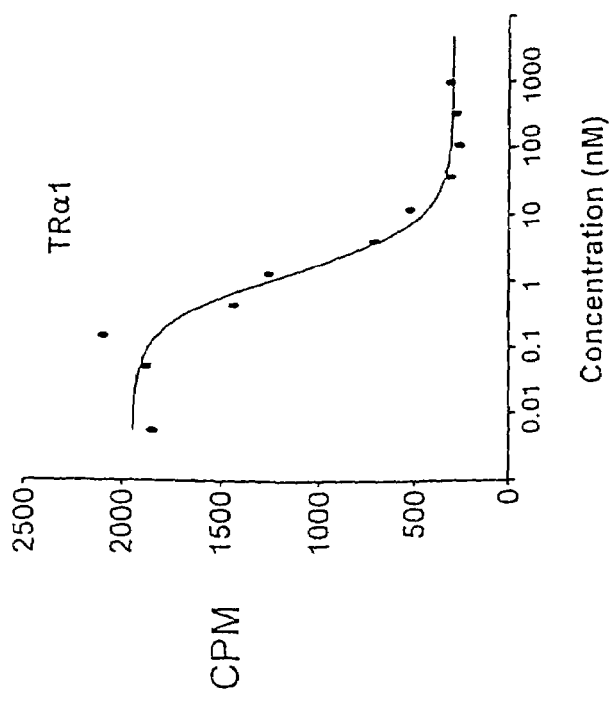
FIG. 1c depicts the binding of Compound 17 to the TRα1 receptor using a heterologous displacement reaction.
Figure 1D:
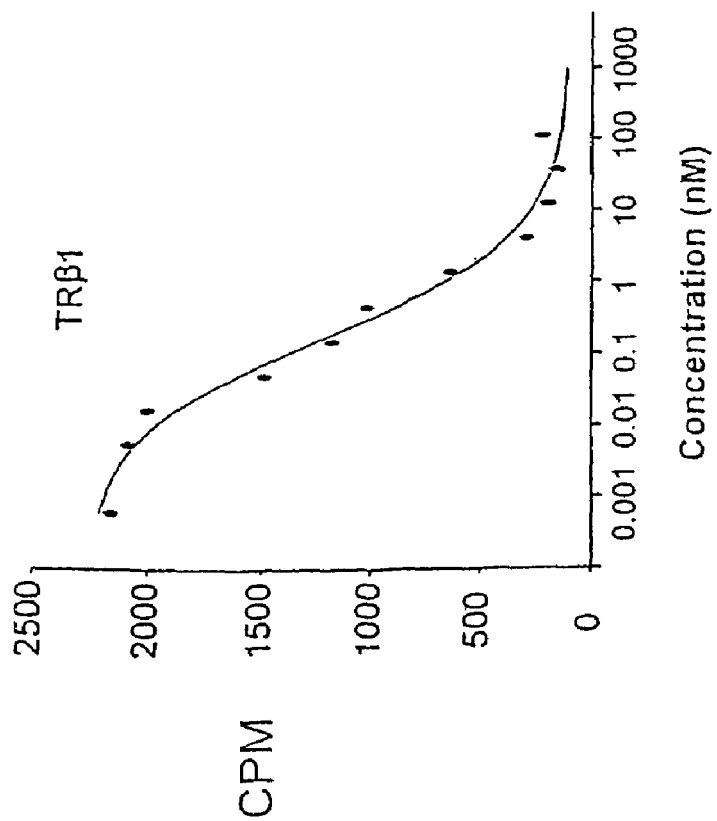
FIG. 1d depicts the binding of Compound 17 to the TRβ1 receptor using a heterologous displacement reaction.
Figure 1E:
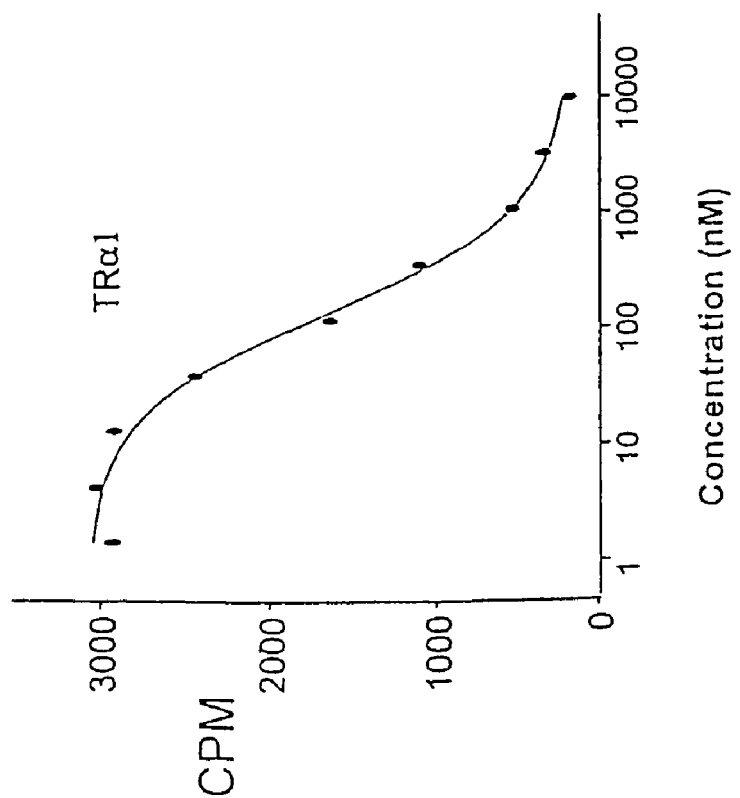
FIG. 1e depicts the binding of Compound 7 to the TRα1 receptor using a heterologous displacement reaction.
Figure 1F:
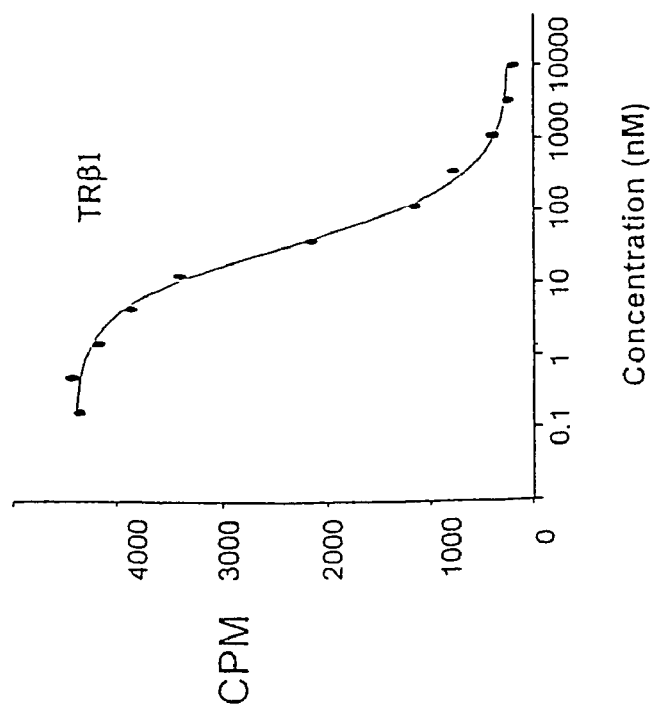
FIG. 1*f* depicts the binding of Compound 7 to the TRβ1 receptor using a heterologous displacement reaction.

Results: Examples of representative T3 binding results using the gel filtration method are shown in FIG. 1(a). SPA assay results for T3 are shown in FIGS. 1(b) and 1(c). Table 3 below shows the SPA data generated with various thyromimetics of interest. Binding results for T3 demonstrated a Kd=0.29 nM for TRα and a Kd=0.67 nM for TRβ.

TABLE 3

| Compound | Ki TRα (nM) | Ki TRβ (nM) |
| --- | --- | --- |
| 17 | 1.21 | 0.29 |
| 1 | 285 | 36.1 |
| 12-1 | 1666 | 662 |
| 3 | 46 | 5.42 |
| 6 | 16 | 26 |
| 9 | 350 | 204 |
| 11 | 121 | 30.3 |
| 13-1-cis | 2583 | 1979 |
| 13-1-trans | 1744 | 1322 |
| 13-6-cis | 4710 | 3589 |
| 13-2-cis | 488 | 419 |
| 13-2-trans | 1354 | 469 |
| 13-3-cis | 2837 | 3431 |
| 13-3-trans | 2006 | 2456 |
| 13-6-trans | 1526 | 1574 |
| 13-5-trans | 354 | 281 |
| 13-5-cis | 4432 | 1008 |
| 13-7-trans | 1554 | 3798 |
| 13-4-trans | 2129 | 1815 |
| 13-4-cis | 5531 | 1521 |
| 13-7-cis | 49632 | 45135 |
| 7 | 58 | 3.3 |
| 2 | 1416 | 271 |
| 4 | 14.1 | 0.99 |
| 5 | 1.84 | 0.84 |
| 8 | 3.74 | 0.97 |
| 10 | >2000 | >2000 |
| 8-1 | 18.6 | 2.51 |
| 15-3 | >2000 | >2000 |
| 19 | 304 | 52 |
| 8-2 | 114 | 20 |
| 24-1 | 378 | 31 |
| 7-5 | 67 | 9.5 |
| 25 | >2000 | 363 |
| 22 | 186 | 31 |
| 21 | >1400 | >180 |
| 7-6 | 98 | 7.6 |
| 24-2 | >2000 | 24 |
| 26 | 594 | 87 |
| 19-2 | 343 | 20 |
| 7-4 | >2000 | >2000 |
| 30 | >2000 | >2000 |
| 23 | >2000 | >2000 |
| 19-3 | 1760 | 128 |
| 28 | 375 | 14.0 |
| 20 | >2000 | >2000 |
| 7-3 | 31 | 6.6 |
| 7-2 | >2000 | 146 |
| 29 | 661 | 47 |
| 7-1 | 1166 | 106 |
| 32 | 284 | 96 |
| 24 | >2000 | >2000 |
| 27 | >2000 | >2000 |
| 31 | 540 | 73 |
| 24-3 | 113 | 2.87 |
| 33 | 267 | 16.7 |
| 34 | 118 | 6.5 |
| 41-2 | >2000 | >2000 |
| 38 | 254 | 5.4 |
| 42-2 | >2000 | >2000 |
| 39 | >2000 | 58 |
| 7-7 | 898 | 90 |
| 41-3 | >2000 | 280 |
| 24-4 | >2000 | 92 |
| 7-8 | 62 | 9.7 |
| 42 | 794 | 16.2 |
| 40 | 30 | 1.1 |
| 7-14 | 429 | 52 |
| 7-9 | 110 | 5.4 |
| 35 | >2000 | >2000 |
| 37 | 294 | 23 |
| 36 | >2000 | 106 |
| 7-12 | >2000 | 61 |
| 12-3 | 738 | 156 |
| 41 | >2000 | 181 |
| 7-10 | 112 | 48 |
| 47 | 24.3 | 2.5 |
| 48 | 128.6 | 9 |
| 45 | 216 | 14 |
| 46 | 20 | 2 |
| 52 | >2000 | 48 |
| 44 | 832 | 44 |
| 54 | 143 | 42 |
| 43 | 363 | 108 |
| 71 | 4 | 0.4 |
| 69-2 | 2.8 | 0.8 |
| 61 | 42.7 | 1.4 |
| 69 | 13.5 | 3 |
| 22-1 | 10.3 | 1.5 |
| 70 | 183 | 5.4 |
| 67 | 37 | 1.8 |
| 66 | 863.2 | 121 |

Conclusion: The parent thyromimetics tested had good to excellent affinity for the TRα1 and/or TRβ1 receptors. The prodrugs had poor affinity for the receptors and are therefore unlikely to exert a thyromimetic effect until activated in the liver.

Example B

Subacute Studies in Normal Mice/Rats Demonstrating Liver versus Heart Selectivity of Phosphonic Acid and Carboxylic Acid T3 Mimetics The purpose of these studies was to compare the difference in efficacy, cardiac effects and endocrine effects between T3 and T3 mimetics that are carboxylic acids and T3 mimetics that are phosphonic acids. In one example, T3 and Compounds 7 and 17, which differ only in that for Compound 7X is —P(O)OH$_2$ and for Compound 17X is —C(O)OH, were compared. Efficacy endpoints include serum cholesterol, liver mitochondrial glycerol phosphate dehydrogenase (mGPDH) activity and the expression of relevant liver genes (e.g., the LDL-receptor, apoB, cpt-1, spot14 and apoAI). Safety parameters include heart weight, heart rate, heart mGPDH activity, the expression and key genes involved in cardiac structure and function (e.g., Serca2, HCN2, Kv1.5, MHCα, MHCβ, Alpha1c), and standard plasma chemistry analysis (liver enzymes, electrolytes, creatinine). Endocrine effects are monitored by analysis of serum thyroid stimulating hormone (TSH). [Taylor et al., *Mol Pharmacol* 52(3): 542-7 (1997); Weitzel et al., *Eur J Biochem* 268(14):4095-4103 (2001)]

Methods: mGPDH activity was analyzed in isolated mitochondria using 2-(4-iodophenyl)-3-(4-nitrophenyl)-5-phenyl tetrazolium chloride as the terminal electron acceptor (Gardner R S, Analytical Biochemistry 59:272 (1974)). Commercially available GPDH was used in each assay as a standard (Sigma, St. Louis, Mo.). Changes in levels of mRNA for liver and heart genes are analyzed using reverse transcriptase followed by real-time PCR analysis. The analysis is performed using an iCycler instrument (Biorad) and appropriate primers by means of standard methodology [e.g., Schwab D A et al. (2000) *Life Sciences* 66: 1683-94]. The amounts of mRNA are normalized to an internal control, typically, cyclophilin. Serum TSH is measured using an enzyme immunoassay (EIA) kit designed for rat TSH (Amersham Pharmacia Biotech, Arlington Heights, Ill.). Serum cholesterol is analyzed using a commercially available enzymatic kit (Sigma Diagnostics, St. Louis, Mo.).

Normal rats (Sprague-Dawley) were maintained on a standard diet. Compounds 7 and 17, or T3 were administered by continuous infusion using an osmotic pump (Alzet; subcutaneous implant) at a dose of 1 mg/kg/day. The compounds were dissolved in 0.1N NaOH solution and the pH adjusted to 7.4-8.0. The compounds were brought up to an appropriate volume using PBS and BSA to maintain solubility within the pump. The compounds were chemically stable in the excipient at 37° C. for 7 days.

Results: Compound 7, a phosphonic acid T3 mimetic, produced a significant thyromimetic effect in the liver equivalent to that of T3 or Compound 17, a carboxylic acid T3 mimetic, without producing any significant effect in the heart. Compound 17 produced a significant thyromimetic effect comparable to that of T3 in both organs. Values are expressed as percent of control. (Table 4)

TABLE 4

|  | Liver GPDH | Heart GPDH | Heart Weight |
|---|---|---|---|
| control | 100 | 100 | 100 |
| T3 | 406 | 284 | 146 |
| Compound 17 | 426 | 277 | 134 |
| Compound 7 | 399 | 112 | 108 |

Conclusion: Based on mGPDH enzyme activity, Compound 7 had significant thyromimetic activity in the liver and none in the heart. In addition, Compound 7 did not cause cardiac hypertrophy. T3 and Compound 17, in contrast, did not show liver-selective thyromimetic effects. Thus, the results demonstrate that phosphonic acid T3 mimetics have a greater selectivity for the heart in terms of drug activity and distribution than carboxylic acid T3 mimetics.

Example C

Subacute Studies in ZDF Rats Demonstrating Improved Therapeutic Index for Phosphonic Acid Containing T3 Mimetics ZDF rats were treated with either Compound 18 (a carboxylic acid T3 mimetic) or Compound cis-13-1 (a HepDirect prodrug of a phosphonic acid T3 mimetic) for 28 days dosed orally once a day. Compound 18 was administered at doses up to 5 mg/kg/d. Compound cis-13-1 was administered at doses up to 50 mg/kg/d. We reasoned that the ZDF rat, as a metabolically challenged animal model, would be more sensitive to the potential adverse cardiac effects of thyromimetics than a normal, cholesterol-fed rat. At sacrifice, heart rate, and the first derivative of left ventricular pressure (LV dP/dt) were measured with a Millar catheter inserted into the left ventricle. The therapeutic index (TI) for Compound 18 in the cholesterol-fed rat was 40 with respect to heart rate increases (Grover et al. PNAS 2003). The measurement of TI was a dose that ED15 for heart rate, i.e., a dose that increased heart rate greater than or equal to 15% compared to the ED50 for cholesterol lowering. The therapeutic index for Compound 18 in the ZDF rats with respect to heart rate was 0.4, indicating that the model is much more sensitive to cardiac effects than a non-metabolically challenged animal. Additionally, the TI for LV dP/dt was 0.15. An increase in LV dP/dt of 25% was the value used in the TI calculation. The most sensitive measure of cardiac effects in this animal was LV dP/dt. ZDF rats treated with Compound cis-13-1 showed no changes in any of the parameters measured. Since we only dosed up to 50 mg/kg/d, we do not know the exact therapeutic index for some of these parameters. However, the TI improvement over Compound 18 is listed in the table below:

| Parameter | TI Improvement |
|---|---|
| ED15 HR | >39 |
| ED25 LV dP/dt | >102 |

The reason that the TI is listed as greater than, i.e., ">" is that the doses of Compound cis-13-1 were not high enough to reach the 15% or 25% threshold even at 50 mg/kg/d. By extrapolation with the cholesterol-fed rat for the Compound 18 data, the ZDF rats were 100-times more sensitive to the cardiac effects of the compound (a TI of ED15 HR/ED50 cholesterol from 40 in the normal rat to 0.4 in the ZDF rat). Therefore we calculate that the TI in a non-metabolically challenged animal would be >3900 with respect to heart rate and >10,000 with respect to LV dP/dt. We chose not to dose at such high levels at this time since the results from the ZDF animals demonstrated a significantly improved safety window. Thus the compounds of the present invention demonstrate a TI that is unexpected and vastly superior than carboxylic acid T3 mimetics.

Example D

Subacute Studies in Cholesterol-fed Rats

The cholesterol-fed rat is an animal model of hypercholesterolemia generated by feeding the animals a diet with high cholesterol content. The purpose of these studies was to evaluate the effects of Compounds 7 and 17 on serum cholesterol (an efficacy parameter) and on heart weight and heart mGPDH activity (potential toxicity parameters).

Methods: Rats were maintained on a diet containing 1.5% cholesterol and 0.5% cholic acid for 2 weeks prior to initiation of treatment. Serum cholesterol values were assessed and the animals randomized into groups for treatment. Serum cholesterol was analyzed using a commercially available enzymatic kit (Sigma Diagnostics, St. Louis, Mo.). Compound 17 and Compound 7 at various concentrations were administered IP once-a-day for seven days.

Figure 2A:
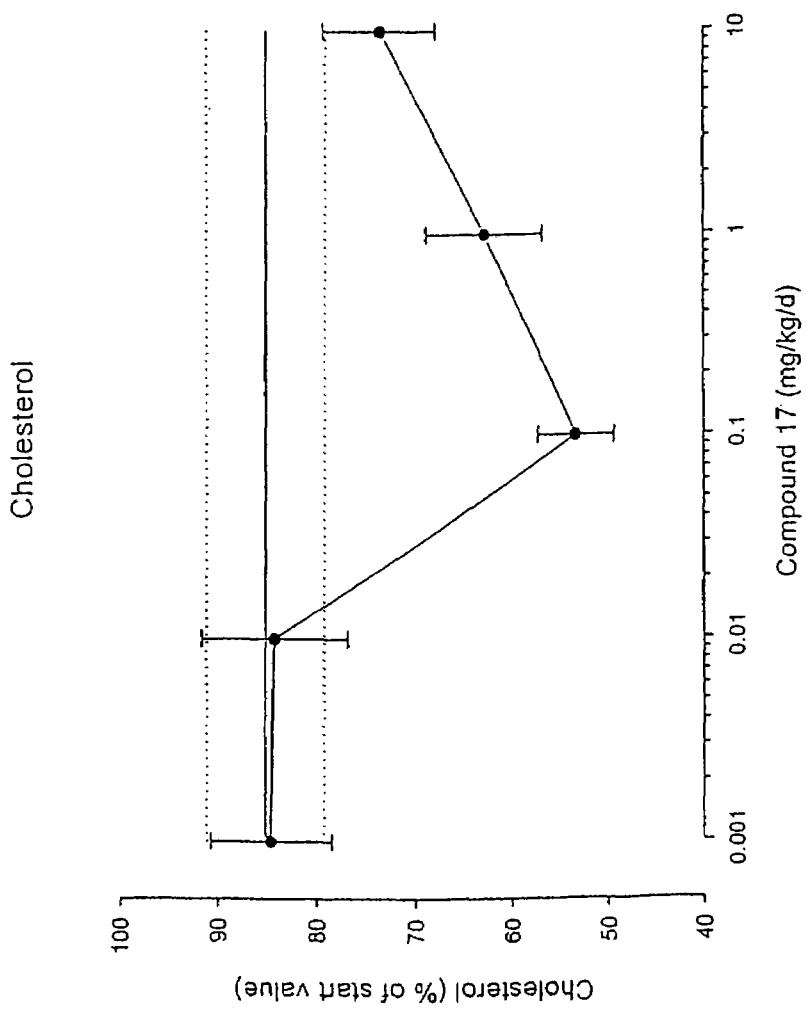
FIG. 2*a* depicts the dose response of serum cholesterol levels to Compound 17 in cholesterol fed rats.
Figure 2B:
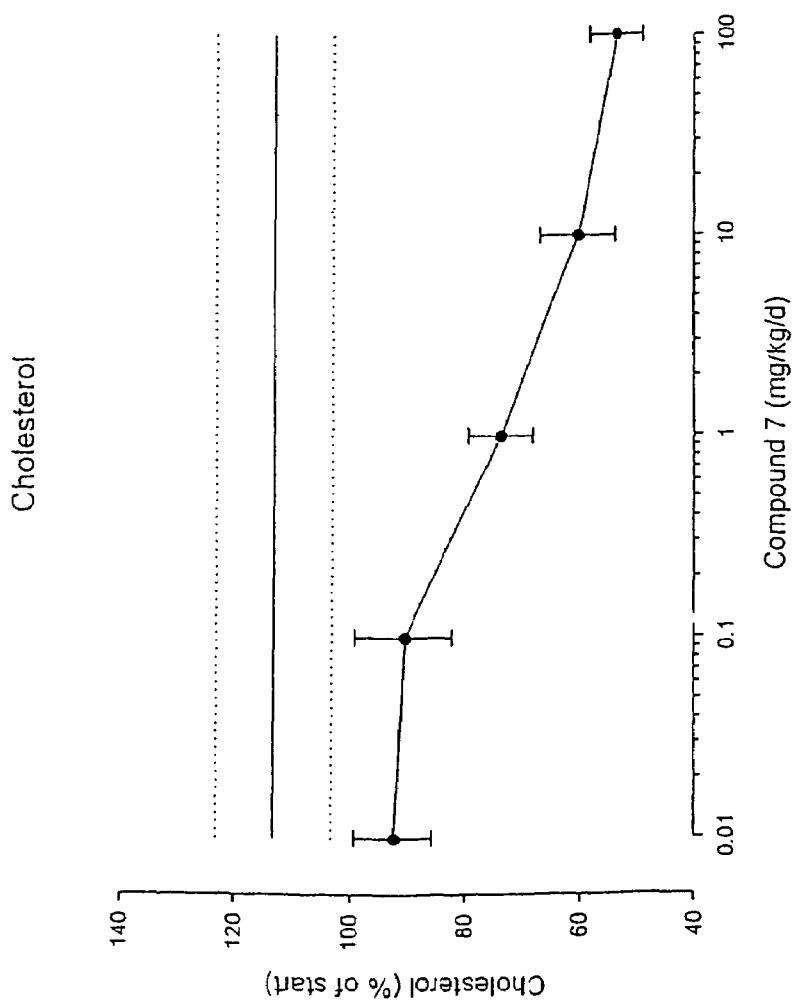
FIG. 2*b* depicts the dose response of serum cholesterol levels to Compound 7 in cholesterol fed rats.
Figure 3A:
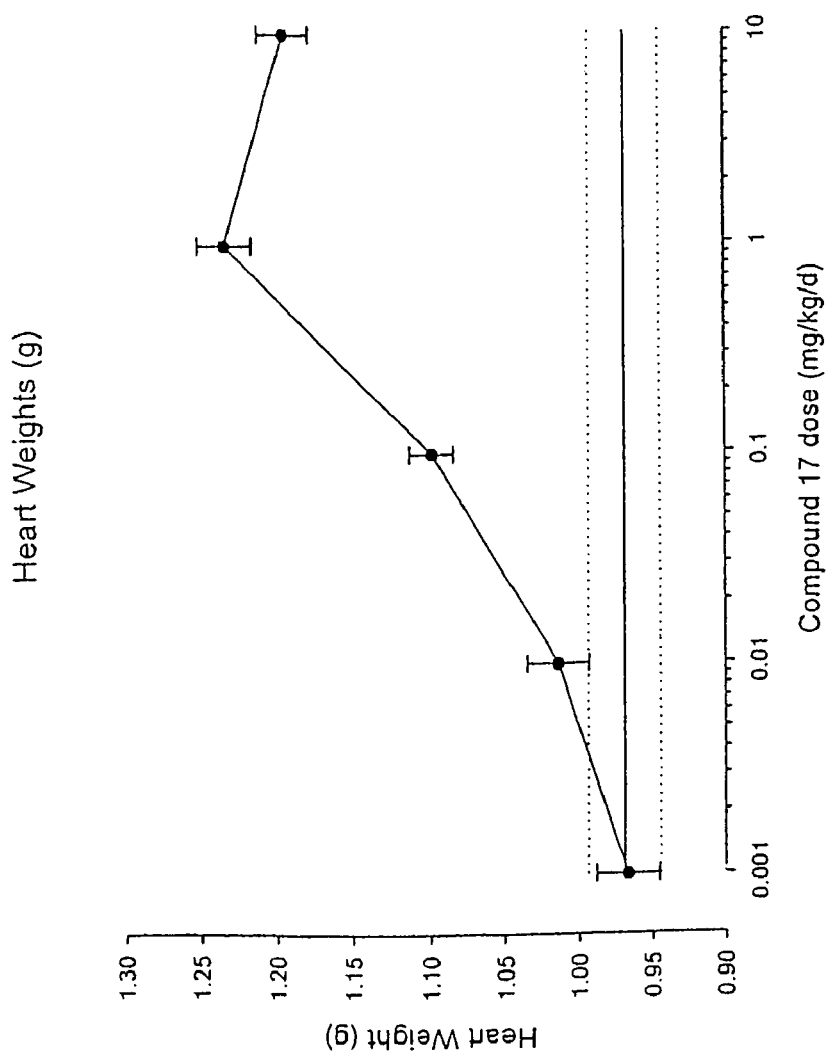
FIG. 3*a* depicts the effect of Compound 17 on the weight of the heart in cholesterol fed rats.
Figure 3B:
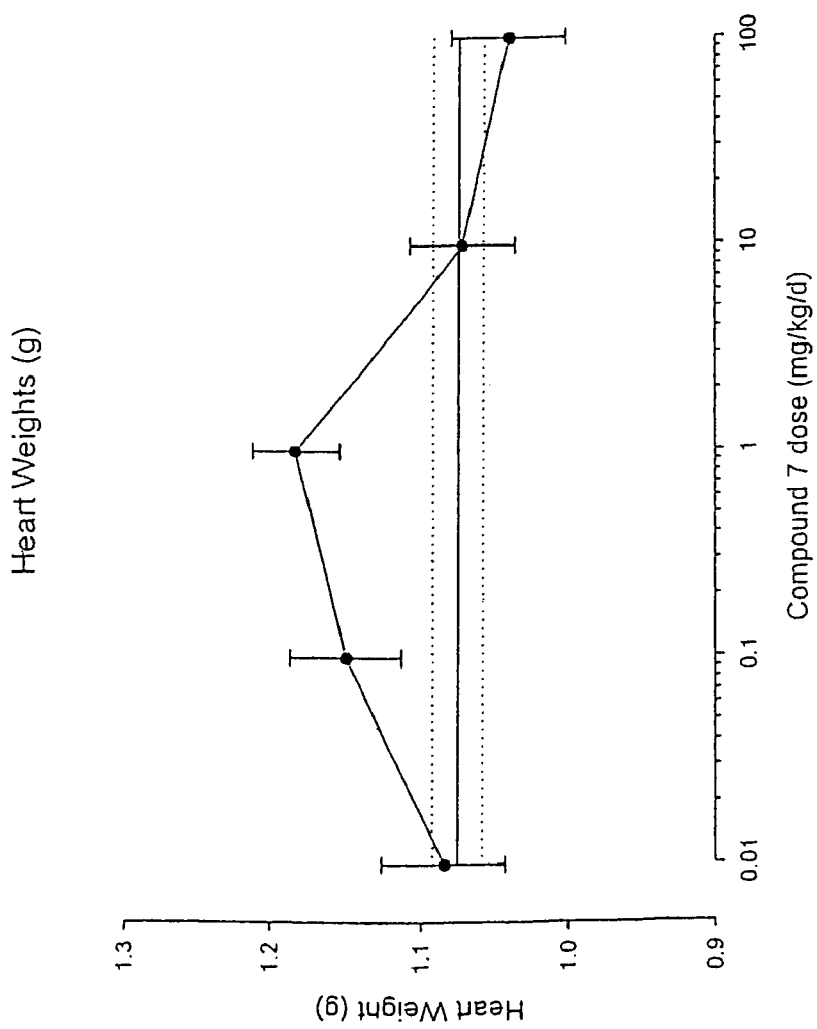
FIG. 3*b* depicts the effect of Compound 7 on the weight of the heart in cholesterol fed rats.
Figure 4A:
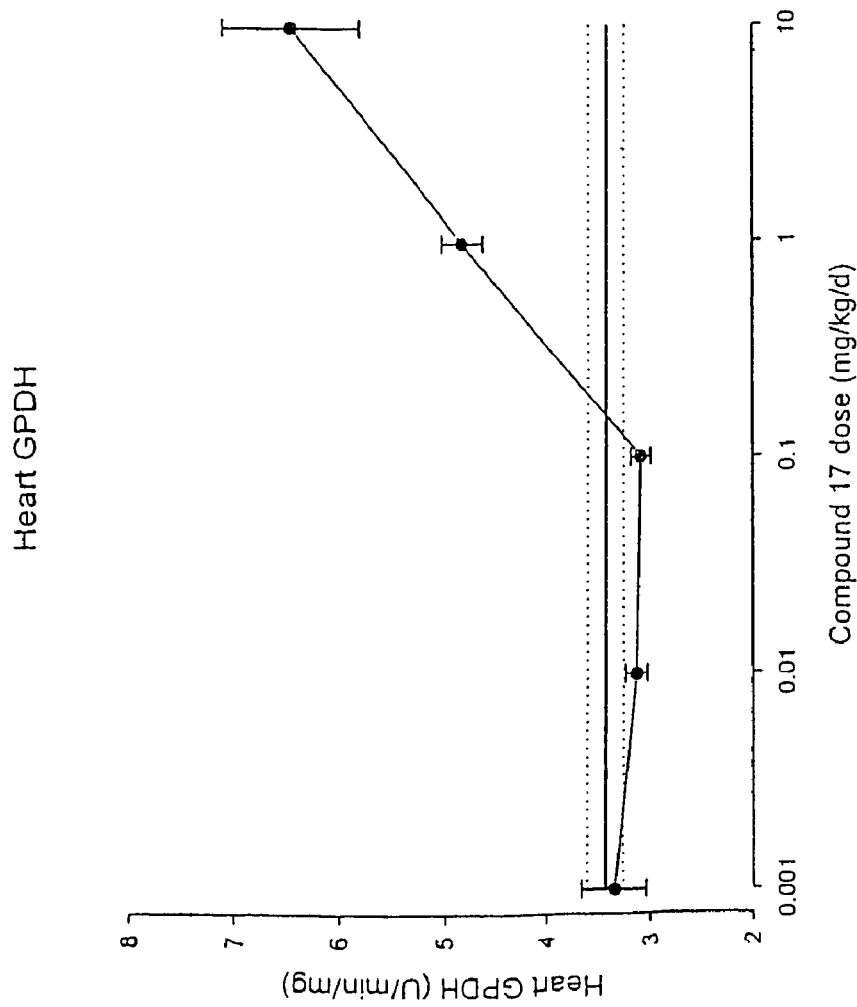
FIG. 4*a* depicts the effect of Compound 17 on cardiac GPDH activity in cholesterol fed rats.
Figure 4B:
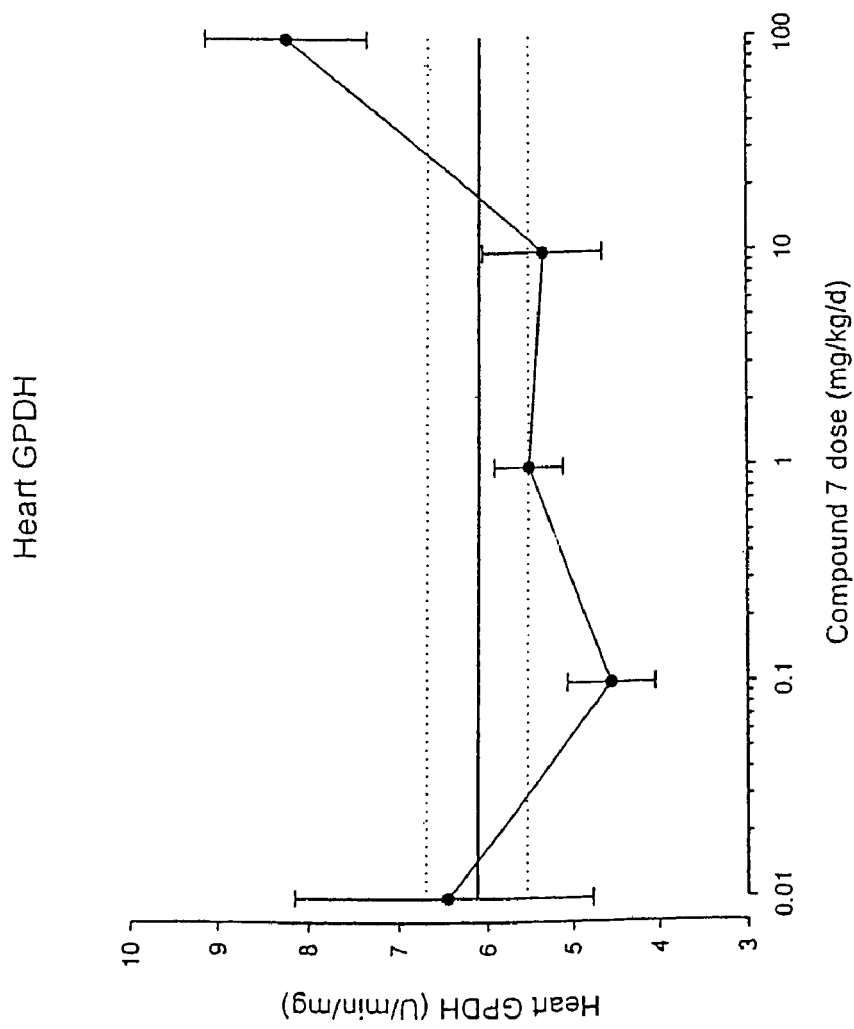
FIG. 4*b* depicts the effect of Compound 7 on cardiac GPDH activity in cholesterol fed rats.

Results: Doses of 0.1-1 mg/kg/day Compound 17 significantly decreased serum cholesterol. Doses of Compound 7 from 1-100 mg/kg/day significantly decreased serum cholesterol. The decreases of serum cholesterol at 1 mg/kg/day were identical for Compound 17 and Compound 7 (see FIG. 2). Undesirable cardiac hypertrophy was observed with Compound 17 at all doses which significantly decreased serum cholesterol, 0.1-1 mg/kg/day. No cardiac hypertrophy was observed with Compound 7 (see FIG. 3). Cardiac GPDH activity was also increased by Compound 17 at 1 mg/kg/day whereas a trend towards increased heart GPDH activity was observed with compound 7 only at 100 mg/kg (see FIG. 4). No adverse cardiac effects were observed with Compound 7 at any dose. These studies also indicate that cardiac weight is more sensitive to thyromimetic effects than GPDH activity.

Conclusion: There is no separation between efficacy (cholesterol lowering) and toxicity (cardiac hypertrophy, induction of heart GPDH) for compound 17. Compound 7, in contrast, showed a therapeutic window of 10-to 100-fold. Thus, the results demonstrate that phosphonic acid T3 mimetics have a greater therapeutic window than carboxylic acid T3 mimetics.

Example E

Microsome/Primary Hepatocyte Stability Studies i. Prodrug Activation in Rat Liver Microsomes The purpose of these studies was to determine the kinetics of activation of prodrugs of thyromimetics in microsomal preparations. Microsomes contain the P450 enzyme that is required for the activation of many of the prodrugs prepared. The Km, Vmax, and intrinsic clearance values determined are measures of prodrug affinity for the microsomal enzymes, the rate at which the prodrug is activated, and the catalytic efficiency with which the prodrug is activated, respectively.

Methods: Activation of prodrugs by dexamethasone treated rat hepatocyte microsomes. Microsomes were isolated by standard differential centrifugation methods from dexamethasone-treated rats. The treatment is to increase cytochrome P450-3A (CYP3A4) activity. Induction of CYP3A4 was confirmed by an increase in testosterone hydroxylation.

Various concentrations of HepDirect™ Compound 7 were incubated with rat hepatocytes microsomes. Compound 7 formation was analyzed by HPLC using UV-Vis detection. Kinetic parameters ($V_{max}$ and $K_m$) were calculated from the transformed data and the intrinsic clearance calculated from the kinetic parameters.

Results and conclusion: Table 5 shows that prodrugs of Compound 7 are well activated in rat liver microsomes and have good affinity for the microsomal enzyme(s) catalyzing their activation:

TABLE 5

| Compound | Vmax (pmol/min/mg) | Km (µM) | CLint (µL/min/mg) |
|---|---|---|---|
| 13-1-cis | 1746 | 31 | 56 |
| 13-6-cis | 598 | 10 | 62 |
| 13-2-cis | 694 | 8 | 86 |
| 13-3-cis | 2118 | 46 | 46 |
| 13-5-cis | 3266 | 113 | 29 |
| 12-3 | 775 | 14 | 54 |
| 13-4-cis | 2983 | 100 | 30 | ii. Activation of Prodrug by Human Liver S9

Prodrugs are tested for conversion to their respective parent compounds by human liver S9. The S9 fraction is a fraction that contains both cytosolic and microsomal protein.

Method: Reaction mixtures (0.5 mL at 37° C.) consist of 0.2 M potassium phosphate pH 7.4, 13 mM glucose-6-phosphate, 2.2 mM NADP$^+$, 1 unit of glucose-6-phosphate dehydrogenase, 0-2.5 mg/mL human liver S9 fraction (In Vitro Technologies, Inc.), and up to 250 µM of prodrug. The activation of the prodrugs to the respective parent compounds is monitored by reverse phase HPLC or LC-MS/MS (Example F).

Results: The rate of formation of the parent compound is measured. The enzyme kinetic parameters of $V_{max}$, $K_m$, and intrinsic clearance $CL_{int}$ are calculated.

Conclusion: Prodrugs of T3 mimetics are readily activated to their respective parent compound by human liver S9.

iii. Activation of Prodrug in Isolated Rat Hepatocytes

The purpose of these studies was to monitor the uptake and activation of the prodrugs of T3 mimetics to their respective active species in fresh, isolated rat hepatocytes.

Method: Hepatocytes are prepared from fed Sprague-Dawley rats (250-300 g) according to the procedure of Berry and Friend (Berry, M. N., Friend, D. S. *J. Cell Biol.* 43, 506-520 (1969)) as modified by Groen (Groen, A. K. et al., *Eur J. Biochem* 122, 87-93 (1982)). Hepatocytes (60 mg wet weight/mL) are incubated in 1 mL Krebs-bicarbonate buffer containing 10 mM glucose, and 1 mg/mL BSA. Incubations are carried out in a 95% oxygen, 5% carbon dioxide atmosphere in closed, 50-mL Falcon tubes submerged in a rapidly shaking water bath (37° C.). Prodrugs are dissolved in DMSO to yield 10 mM stock solutions, and then diluted into the cell suspension to yield a final concentration of 100 µM. At appropriate time points over the course of 1 h, aliquots of the cell suspension are removed and spun through a silicon/mineral oil layer into 10% perchloric acid. The cell extracts in the acid layers are neutralized, and the intracellular prodrug metabolite content analyzed by reverse phase HPLC or LC-MS/MS (Example F). The AUC of the active species in the hepatocytes is calculated from the concentration-time profile of parent compound.

Results: Results are shown in Table 6 below:

TABLE 6

| Compound | AUC (0-2 h) (nmole * h/g) |
|---|---|
| Compound 13-1-cis | 967 |
| Compound 13-6-cis | 433 |
| Compound 13-2-cis | 533 |
| Compound 3-3-cis | 459 |
| Compound 13-5-cis | 1988 |
| Compound-13-7-cis | 806 |
| Compound 13-4-cis | 784 |

Conclusion: Prodrugs of T3 mimetics are readily taken up and activated to their active species in fresh rat hepatocytes.

Example F

Oral Bioavailability/Efficacy Studies in Normal Rats i. Oral Bioavailability The oral bioavailability (OBAV) of Compound 12-1, a bis POM prodrug of Compound 7, was estimated by comparison of the dose-normalized area under the curve (AUC) of the plasma concentration-time profile of Compound 7 following IV and PO administration of Compound 7 and Compound 12-1, respectively, to normal rats.

Method: Groups of non-fasted male SD rats were administered either 5 mg/kg of Compound 7 by IV bolus or 20 mg/kg of Compound 12-1 by oral gavage. Prior to drug administration, the rats were catheterized at the tail artery to facilitate blood collection. Plasma samples were obtained at pre-specified time points following dosing, extracted with 1.5 volumes of methanol, and then assayed by an LC-UV method using a C18 column eluted with a gradient of 20% to 45% v/v acetonitrile in a potassium phosphate buffer pH 6.2 over 15 min with UV absorbance monitoring at 280 nm. The AUC values were determined noncompartmentally from the plasma concentration-time plots by trapezoidal summation to the last measurable time point.

In another experiment the OBAV of Compound 19-2, a phosphonic acid T3 mimetic, was assessed using catheterized rats. Plasma levels of compound were analyzed by HPLC and the AUCs for the i.v. dose of 5 mg/kg and the p.o. dose of 20 mg/kg were compared. The maximum OBAV for Compound 19-2 was 0.003%. Typically, compounds that are taken forward as an oral drug candidate have OBAV values of at least 15-20%, when tested in an animal model. This minimal requirement for OBAV in a genetically homogenous model system insures that exposure can be accurately monitored when humans are treated with the compound. Furthermore, in a genetically variable background such as humans, the variability for a compound with low OBAV in genetically homogenous model systems, can be widely variable, leading some subjects to have much higher than anticipated exposure, while other subjects have no exposure. OBAV of Compound cis-13-1 is calculated to be 25% when AUC's of Compound cis-13-1 are used and to be 40-50% when comparing the AUC's of Compound 7 using serial plasma samples of a i.v. administered compound versus a p.o. administered compound. The liver levels at 1.5 h post-dosing of Compound 7 and prodrugs thereof are listed in Table 7, example F (ii).

Results: Compound 12-1 was adequately absorbed in the rat with an estimated OBAV of 25%. Following oral administration of the prodrug, the plasma concentrations of the generated Compound 7 ($C_{max}$=1.2±0.2 µg/mL at a $T_{max}$=3±1 hr) were sustained over an 8 h period ($t_{1/2}$=6±6 hr). Compound 19-2 was not adequately absorbed.

Conclusion: Adequate systemic exposure of Compound 7 was maintained over 8 h after an oral administration of Compound 12-1 to rats.

ii. Liver Distribution Following Oral Administration

Liver levels of Compound 7 were assessed in normal rats following oral administration of the HepDirect™ or other prodrugs. The levels were used to estimate potential efficacy. Liver levels were assessed by LC-MS using the 363.3/63.0 peak area to estimate levels of Compound 7 generated by orally administered prodrugs.

Results: Results are shown in Table 7.

TABLE 7

| Compound | Liver Levels (ug/g) (10 mg/kg@1.5 h) |
|---|---|
| Compound 7 | Not Detected |
| Compound 12-1 | 1.39 |
| Compound 13-1-cis | 0.98 |
| Compound 13-6-cis | 0.39 |
| Compound 13-2-cis | 0.25 |
| Compound 13-3-cis | 0.77 |
| Compound 12-2 | 0.67 |
| Compound 13-5-cis | 0.56 |
| Compound 13-7-cis | 0.23 |
| Compound 13-4-cis | 0.32 |

Conclusion: All compounds tested produced adequate liver levels of compound 7. All are predicted to induce thyromimetic effects in vivo following oral administration.

Example G

Oxygen Consumption Study

Thermogenesis is a measurement of energy consumption. Compounds that increase thermogenesis are likely to increase caloric expenditure and thereby cause body weight loss and its associated benefits to metabolic status (e.g., insulin sensitivity). Thermogenesis is assessed in subcellular fractions of various tissues, isolated cells, whole tissues, or in whole animals using changes in oxygen consumption as the endpoint. Oxygen is used up when calories are burned by various metabolic processes.

Methods: Animals are dosed once or several times a day via a parenteral or oral route for a treatment period ranging from 1 day to several weeks. Oxygen consumption is measured following a single or multiple days of treatment.

Mitochondrial thermogenesis is measured polargraphically with a Clark-type oxygen electrode using mitochondria isolated from various tissues, including liver. Mitochondria are isolated by differential centrifugation. As those skilled in the art are familiar, state 3 respiration or cytochrome c oxidase activity are measured in isolated mitochondria. The mitochondria are incubated at 30° C. in a buffered medium containing 80 mM KCl, 50 mM HEPES, 5 mM KH2PO4, 1 mM EGTA, 0.1% (w/v) fatty acid-free bovine serum albumin (BSA), pH 7.0 in the presence of 10 mM succinate, 3/75 µM rotenone and 0.3 mM ADP (Iossa, S, *FEBS Letters,* 544: 133-7 (2003)).

Oxygen consumption rates are measured in isolated hepatocytes using a portable Clark-type oxygen electrode placed in the hepatocyte medium. Hepatocytes are isolated from liver using a two-step collagenase perfusion (Berry, M. N., Friend, D. S. *J. Cell Biol.* 43: 506-520 (1969)) as modified by Groen (Groen, A. K. et al., *Eur J. Biochem* 122: 87-93 (1982)). Non-parenchymal cells are removed using a Percoll gradient and the cells are resuspended in tissue culture medium in a spinner flask. The oxygen consumption of the cells is measured over time once the system is sealed.

Oxygen consumption is measured in isolated perfused liver (Fernandez, V., *Toxicol Lett.* 69:205-10(1993)). Liver is perfused in situ and oxygen consumption is calculated by measuring the difference between the oxygen saturation of the inflow buffer and the outflow buffer maintained at a constant flow.

In one assay, whole animal oxygen consumption is measured using an indirect calorimeter (Oxymax, Columbus Instruments, Columbus, Ohio). Animals are removed from their cages and placed in the chambers. The resting oxygen consumption is measured in animals during periods of inactivity as measured by activity monitors. The oxygen consumption is calculated based on the flow through the chamber and the difference in oxygen partial pressures at the inflow and outlet ports. Carbon dioxide ($CO_2$) efflux is also measured in parallel using a $CO_2$ electrode.

Male Sprague Dawley rats were treated with 3, 10, or 30 mg/kg/d of Compound cis-13-1 orally for 14 days. Rats were placed in the FoxBox apparatus (Sable Systems, Las Vegas, Nev.), allowed to acclimate and the resting oxygen consumption was measured. The oxygen consumption rates were compared to pre-dose measurements taken on each individual animal. Oxygen consumption following treatment was 116, 125, 132% of the pre-dose rate, for 3, 10, and 30, respectively. Thus, the compounds of the present invention are useful in increasing oxygen consumption.

Example H

Tissue Distribution Studies

The tissue distribution and the pharmacokinetics of Compound 7 and the Compound 17 were assessed following IP administration to normal rats.

Method: In separate studies, the T3 mimetic phosphonate Compound 7 and its carboxylate analog Compound 17 were administered at 10 mg/kg to groups of male SD rats via the peritoneal cavity. At pre-selected time points following dosing, the rats were anesthetized using isofluorane and the peritoneal cavity was then opened and a blood sample was obtained from the abdominal vena cava. In addition, liver, kidney, and heart were excised and immersed in 3 volumes of cold 60% acetonitrile. The blood samples were briefly centrifuged and the plasma fraction was then extracted with 1.5 volumes of methanol, processed, and analyzed by LC-UV as described in Example G. The frozen liver, kidney, and heart tissue were homogenized in 60% v/v acetonitrile, centrifuged, and then analyzed by LC-UV. Pharmacokinetic parameters and AUC of the plasma and tissue concentration-time profiles were determined noncompartmentally by WinNonLin.

Results: The following plasma pharmacokinetics were calculated for Compound 17 and Compound 7 and shown in Table 8.

TABLE 8

| PARAMETER | UNIT | Compound 17 | Compound 7 |
|---|---|---|---|
| Dosing_time | hr | 0 | 0 |
| Rsq | | 0.9966 | 0.9893 |
| Tmax | hr | 0.3333 | 0.3333 |
| Cmax | μg/mL | 3.49 | 25.97 |
| Tlast | hr | 2 | 4 |
| Vz(observed)/F | L/kg | 2.2049 | 0.4008 |
| Cl(observed)/F | L/hr/kg | 3.3628 | 0.3006 |
| AUMClast | μg * hr^2/mL | 1.7683 | 33.7098 |

The AUC values of the plasma and tissue concentration-time profiles were calculated for Compound 17 and Compound 7 and shown in Table 9.

TABLE 9

| T3 Mimetic | Plasma AUC | Liver AUC | Heart AUC | Kidney AUC |
|---|---|---|---|---|
| Compound 17 | 2.8 μg·hr/mL | 48.5 nmol·hr/g | 27.6 nmol·hr/g | 1.1 nmol·hr/g |
| Compound 7 | 31.6 μg·hr/mL | 301.7 nmol·hr/g | 32.8 nmol·hr/g | 5.0 nmol·hr/g |

Conclusion: Compared to the phosphonic acid T3 mimetic (Compound 7), the carboxylic acid T3 mimetic (Compound 17) had significantly higher plasma clearance and volume of distribution in the rat. Substantially higher levels of Compound 7 measured in the liver indicated good penetration of the T3 mimetic phosphonate into the target organ. Compound 7 showed higher liver exposure relative to Compound 17. Thus, phosphonic acid T3 mimetics have greater liver specificity, as compared to heart tissue, than do carboxylic acid T3 mimetics.

Example I

Subacute Studies in Cholesterol fed Rats Cholesterol Reduction

The purpose of these studies was to evaluate the effects of a carboxylic acid T3 mimetic (Compound 18) a phosphonic acid T3 mimetic prodrug (Compound 13-1-cis) on serum cholesterol and TSH levels, hepatic and cardiac gene expression and enzyme activities, heart weight, and clinical chemistry parameters.

Methods: Rats were maintained on a diet containing 1.5% cholesterol and 0.5% cholic acid for 2 weeks prior to initiation of treatment. Serum cholesterol values were assessed and the animals randomized into groups for treatment. Serum cholesterol was analyzed using a commercially available enzymatic kit (Sigma Diagnostics, St. Louis, Mo.). Compound 13-1-cis and Compound 18 were administered PO once a day for seven days. Serum TSH is measured using an enzyme immunoassay (EIA) kit designed for rat TSH (Amersham Pharmacia Biotech, Arlington Heights, Ill.). Expression levels of liver genes (e.g., the LDL-receptor, apoB, cpt-1, spot14 and apoAI) and heart genes (e.g., Serca2, HCN2, Kvl.5, MHCα, MHCβ, Alpha1c) are quantified by Northern blot analysis or by RT-PCR. For Northern analyses, RNA is isolated from liver tissue by a guanidinium thiocyanate method, and total RNA is obtained using an RNeasy column (Quiagen). mRNA is separated on a 1% agarose gel and transferred to a nylon membrane. Oligonucleotides specific for the complementary gene sequences are used to make $^{32}$P-labeled probes (Multiprime DNA labeling systems, Amersham Pharmacia Biotech). Following hybridization of the probes to the nylon membranes, radioactivity is assessed on a blue film (Eastman Kodak Co,), and the resulting image quantified using the appropriate software. RT-PCR is performed using an iCycler instrument (Biorad) using appropriate primers by means of standard methodology [e.g., Schwab D A et al. (2000) *Life Sciences* 66: 1683-94]. GPDH activity in liver and heart are measured as described in Example B. The activities of PEPCK and glucose 6-phosphatase in liver are measured by means of direct enzymatic assays of homogenized liver tissue as described by Andrikopoulos S et al. (1993) *Diabetes* 42: 1731-1736. Alternatively, expression levels of the corresponding genes are determined by Northern blot analysis or RT-PCR as described above.

Figure 5:
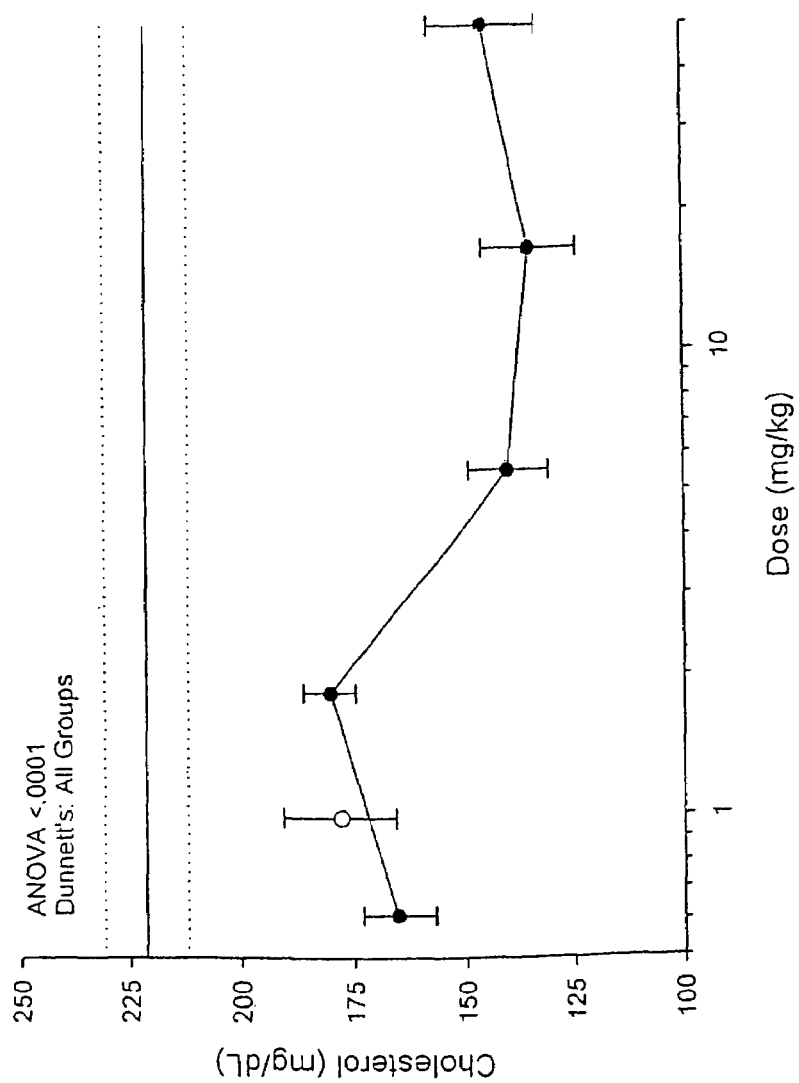
FIG. 5 depicts the dose response of serum cholesterol levels to Compound 13-1-cis in cholesterol-fed rats.

Results: Doses of 0.6-50 mg/kg/day of Compound 13-1-cis significantly decreased serum cholesterol (see FIG. 5). Compound 18 at 1 mg/kg/day significantly decreased serum cholesterol. No significant undesirable cardiac hypertrophy was observed with Compound 13-1-cis at any dose tested.

Conclusion: Compound 13-1 showed significant cholesterol lowering even at the lowest dose evaluated (0.6 mg/kg). Furthermore, no evidence of undesirable effects on heart weight was observed across the entire dose range tested (up to 50 mg/kg).

Example J

Decreases in Hepatic Fat Content Following Treatment with a Phosphonic Acid Thyromimetic Normal rats were chronically infused with Compound 7 for 7 days. Liver triglycerides were analyzed following lipid extraction by the Bligh Dyer method (Bligh EG and Dyer WJ, A rapid method of total lipid extraction and purification. Can J Med Sci. 1959 (August); 37(8):911-7, incorporated herein by reference). Total triglycerides were analyzed in the liver extracts by an enzymatic assay (Thermo Electron Corporation). Total lipid was normalized to initial liver weight and triglyceride content was normalized to liver weight. T3 administration would not be expected to decrease liver triglyceride content. Analysis of hepatic triglyceride content in the T3 infused rats showed no significant decrease in triglyceride content. There was a 4% reduction in liver triglycerides for this group and the results were not statistically significant. The Compound 7 infused animals demonstrated a decrease in hepatic triglyceride content of 64%, an unexpected and significantly different result.

In other experiments, Compound 7 was orally administered to ZDF rats for 28 days. Liver triglycerides were analyzed as described above. Total liver triglycerides were reduced in the treated animals 42% in the 2.5 mg/kg/d group. Histologic analysis of liver sections following H&E staining demonstrated a pronounced and diffuse microvesicular steatosis throughout the hepatic lobule in the vehicle treated group. The hepatic steatosis is a well known and described phenomenon for the ZDF rat, and therefore not attributable to vehicle treatment. There was a dose dependent reduction in the microvesicular steatosis and a noticeable appearance of intact cytoplasm within the hepatocytes consistent with a non-steatotic liver.

Example K

Effects of Phosphonic Acid T3 Mimetic Prodrugs In Vivo on Cholesterol

Another experimental assay was to evaluate the effects of prodrugs of phosphonic acid T3 mimetics of the present invention on serum cholesterol. Rats were made hypercholesterolemic by maintenance on a diet containing 1.5% cholesterol and 0.5% cholic acid for at least 2 weeks prior to initiation of treatment. Plasma cholesterol values were assessed prior to and following treatment and the effects of compound were expressed as a percentage change from the pre-dose cholesterol levels. Total cholesterol was analyzed using a commercially available enzymatic kit (Sigma Diagnostics, St. Louis, Mo.). Compounds were routinely tested for oral efficacy at a dose of 0.5 mg/kg/d. Hypercholesterolemic rats were treated with vehicle, Compound 13-1-cis (a Hep-Direct version of Compound 7), Compound 19-1 (a diethyl ester of Compound 19-2), Compound 13-9 (a HepDirect version of Compound 19-2), Compound 12-5 (a bisPom version of compound 19-2), or Compound 15-5 (a bisamidate version of Compound 19-2) at 0.5 mg/kg/d orally. Compound 13-1-cis has been extensively characterized and was used as the positive control for the assay. Vehicle, Compound 13-9 and Compound 19-1 failed to demonstrate cholesterol lowering in this assay while Compound 13-1-cis, Compound 12-5 and Compound 15-5 demonstrated a significant lowering of cholesterol. HepDirect versions of the phosphonic acid T3 mimetics normally show good results, however, diethyl ester versions of the phosphonic acid T3 mimetics of the present invention were found not to be suitable as prodrugs.

In another experiment, the efficacy of Compound 7 was compared to Compounds 12-9, cis-13-2 and 15-6, which are prodrugs of a compound that binds poorly to both TRα and TRβ (Ki of about 300 nM). Compound 7 was efficacious whereas Compounds 12-9, cis-13-2 and 15-6 were not efficacious in lowering cholesterol.

Table 10 (below) shows the results for additional compounds of the present invention assayed in the present method.

TABLE 10

|  | % Cholesterol Lowering |
|---|---|
| Compound delivered i.p (0.2 mg/kg/d) | |
| Untreated | −3.6 |
| Vehicle | −5.3 |
| 40 | −64.2 |
| 7-5 | −63.3 |
| 7-9 | −63.2 |
| 24-3 | −48.6 |
| 8-2 | −48.0 |
| 45 | −46.3 |
| 7-3 | −45.4 |
| 22 | −44.0 |
| 66 | −42.9 |
| 7 | −41.5 |
| 11 | −36.4 |
| 24-1 | −35.4 |
| 7-14 | −32.9 |
| 33 | −32.5 |
| 46 | −29.6 |
| 47 | −29.3 |
| 42 | −28.8 |
| 7-8 | −28.6 |
| 7-10 | −25.8 |
| 8 | −24.3 |
| 48 | −23.4 |
| 29 | −21.9 |
| 38 | −21.7 |
| 31 | −21.1 |
| 27 | −20.8 |
| 24-2 | −20.5 |
| 28 | −20.5 |
| 6 | −20.5 |
| 19 | −19 |
| 52 | −18.8 |
| 7-6 | −13.5 |
| 37 | −0.4 |
| Compound delivered p.o. (0.5 mg/kg/d) | |
| Untreated | −4.0 |
| Vehicle | −5.1 |
| 15-4 | −39.6 |
| 12-8 | −33.7 |
| 12-5 | −32.5 |
| cis-13-1 | −31.8 |
| 12-4 | −30.5 |
| 15-5 | −29.9 |
| 15-7 | −29.1 |
| 13-8 | −26.5 |
| 13-11 | −24.8 |
| 13-9 | −10.9 |
| 19-1 | −6.6 |
| 12-7 | −39.1 |
| 13-10 | −25.8 |
| 15-8 | −31.1 |
| Compound delivered p.o. (0.2 mg/kg/d) | |
| Vehicle | −5.1 |
| 71 | −54.4 |
| 69-2 | −49.9 |
| 69 | −41.9 |
| 45 | −40.4 |
| 7-9 | −38.4 |
| 7-5 | −38.0 |
| 7-3 | −36.5 |
| 61 | −33.7 |
| 70 | −32.8 |
| 8-1 | −32.2 |
| 40 | −27.3 |
| 46 | −23.8 |
| 8 | −20.6 |
| 22-1 | −19.9 |
| 67 | −17.0 |
| 22 | −16.5 |
| 66 | −12.5 |
| 7-1 | −12.2 |
| 11 | −5.1 |

Example L

Effects of Phosphonic Acid T3 Mimetic Prodrugs In Vivo on Circulating TSH

Another concern with synthetic thyromimetics is the suppression of the endogenous thyroid axis. Thyroid homeostasis is maintained by the action of thyroid releasing hormone (TRH) and thyroid stimulating hormone (TSH). TRH is produced in the paraventricular region of the hypothalamus (Dupre, S M et al, Endocrinology 145:2337-2345 (2004). TRH acts on the pituitary releasing TSH which then acts on the thyroid organ itself. The levels of TRH and TSH are controlled by a feed-back sensing mechanism so that low levels of thyroid hormone (TH) (T3 or T4) will cause an increase in TRH and TSH and elevated levels of TH will cause a suppression of TRH and TSH. Because TSH can be measured more readily than TRH, levels of TSH are tested as a measure of systemic effects of TH or synthetic thyromimetics. Decreased TSH levels are a concern because suppression of the thyroid axis could lead to systemic hypothyroidism. Although this particular side effect has been noted, it has typically been treated with less concern than the cardiac safety issues. However, new evidence indicates that, in addition to possible systemic hypothyroidism, which is a concern for any potential long-term therapy, TSH suppression will enhance osteoclast function leading to a decrease in bone mass and loss of bone structural integrity (Abe, E et al, Cell 115:151-62 (2003)). Therefore previous investigators have measured TSH levels when testing synthetic thyromimetics and have used a 30% decrease of TSH as the denominator in their therapeutic index calculations. The therapeutic index of TSH levels in cholesterol-fed rats, treated with either Compound 17 or Compound 18 (both carboxylic acid T3 mimetics) for 7 days, are 0.8 and 0.4, respectively. Therefore, both compounds suppress TSH as doses lower than that required to decrease circulating cholesterol. In ZDF rats treated with 50 mg/kg/d Compound 7 for 28 days, no statistically significant difference from vehicle was measured for TSH. However, 0.2 mg/kg/d of Compound 18 in 28 day treated ZDF rats, decreased TSH levels greater than 90%. In mice treated with 10 mg/kg/d Compound 7 for 77 days, no decrease in TSH was observed, indicating that Compound 7 can significantly decrease cholesterol levels without producing an adverse effect on the endogenous thyroid axis.

Example M

Effects of Phosphonic Acid T3 Mimetic Prodrugs In Vivo on Glucose

Plasma glucose in Compound 7 treated ZDF rats at sacrifice decreased from 618 mg/dL to 437 mg/dL following 4 weeks of treatment with Compound cis-13-1. The decrease was dose dependent. Blood glucose levels at those doses corresponded to 442 mg/dL and 243 mg/dL, respectively. Similar changes were also evident at two weeks, post-treatment. There was a dose-dependent decrease in the water consumption of the treated animals, which is consistent with an improvement in glycemic control.

Example N

T3 and T3 Mimetic Mediated Myosin Heavy Chain Gene Transcription in the Heart

An RT-PCR assay as disclosed in: Sara Danzi, Kaie Ojamaa, and Irwin Klein *Am J Physiol Heart Circ Physiol* 284: H2255-H2262, 2003 (incorporated herein by reference) is used to study both the time course and the mechanism for the triiodothyronine (T3)-induced transcription of the α- and β-myosin heavy chain (MHC) genes in vivo on the basis of the quantity of specific heterogeneous nuclear RNA (hnRNA). The temporal relationship of changes in transcriptional activity to the amount of α-MHC mRNA and the coordinated regulation of transcription of more than one gene in response to T3 and T3 mimetics are demonstrated. Analysis of a time course of T3 and T3 mimetics that are not liver specific show mediated induction of α-MHC hnRNA and repression of β-MHC hnRNA, whereas no significant affect is observed with compounds of the present invention at doses that are therapeutically useful.

Example O

Cardiovascular Activity of T3 Mimetics in the Rat

The objective of these experiments was to evaluate the effect of phosphonic acid containing T3 mimetics versus carboxylic acid containing T3 mimetics, on cardiovascular function (heart rate, inotropic state, and aortic pressure) in the Sprague Dawley (SD) rat model.

Method: Compound cis-13-1 (a HepDirect prodrug of Compound 7) was dissolved in PEG400 and administered daily to SD male rats (n=6/group) by oral gavage (1, 5, 10, 30, 50 mg/kg/day) at 1 ml/kg body weight. The control group (n=6) was given vehicle only. Compound 18 (a carboxylic acid T3 mimetic) was administered at 1 mg/kg p.o. as a positive control (n=6). On the 7th day after the start of dosing, animals were anesthetized with Isofluorane and the left ventricle cannulated with a high fidelity catheter tip transducer via the right carotid artery. Left ventricular pressure, its first derivative (LVdP/dt), lead I ECG, and heart rate (HR) triggered off the ECG waveform, were digitally recorded. LV dP/dt is a well accepted measure of ionotropic state. Systolic and diastolic aortic pressures were measured by retracting the catheter into the proximal aorta.

Results: Compared to vehicle treated animals, Compound 18 administration resulted in marked and statistically significant increases in HR, LV dP/dt, and systolic aortic pressure after 7 days of treatment. In contrast, HR, LV dP/dt, systolic and diastolic aortic pressures in all groups treated with Compound cis-13-1 were not significantly different compared to vehicle treated animals. Heart weight and heart weight normalized to body weight in Compound 18 treated animals were significantly increased compared to control animals. There were no significant changes in heart weight or heart weight/body weight ratios in Compound cis-13-1 treated groups.

Conclusions: It is concluded that Compound cis-13-1 when administered at doses up to 50 mg/kg/day for 7 days is devoid of significant chronotropic and inotropic effects in the normal SD rat. This stands in contrast to Compound 18 which is associated with marked effects when given at 1 mg/kg/day.

Example P

Continuous Infusion Study

Screening for thyromimetic activity was performed in normal rats maintained on a cholesterol-containing diet. Compounds were administered by continuous infusion using an osmotic pump at 1 mg/kg/day. The compounds were dissolved in 0.1N NaOH solution and the pH adjusted to 7.4-8.0. The compounds were chemically stable as an aqueous solution at 37° C. for 14 days.

Compounds 7, 69, 70, and 69-1 were compared to 17 and vehicle testing changes in heart rate, LV dP/dt, systolic and diastolic blood pressure, and reductions in total cholesterol. Compound 17 increased heart rate by 40% when analyzed at day 7 and the elevation was through d14. At the end-of-life it was demonstrated that Compound 17 also increased LV dP/dt by 71% and left ventricular weight. Systolic and diastolic blood pressure was also increased by 30%. Compound 17 produced a significant decrease in cholesterol when measured at day 7, but no significant decrease in cholesterol was observed at day 14. For some reason, Compound 17 ceased to produce a cholesterol-lowering effect at the longer time, while still maintaining adverse cardiovascular effects.

Compounds 7, 69, 70, and 69-1 demonstrated no changes in any of the cardiovascular parameters at either day 7 or day 14. Compounds 7, 69, 70, and 69-1 demonstrated cholesterol lowering effects at day 7 and at day 14. Reductions in cholesterol at day 7 were equivalent for all the compounds tested.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A compound of Formula VIII:

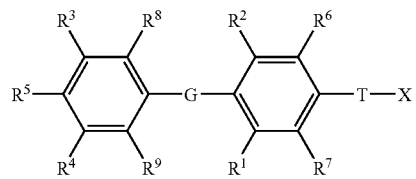

wherein:
G is —CH$_2$—;
T is —OCH$_2$—;
R$^1$ and R$^2$ are each independently selected from the group consisting of —Cl, —Br, —I, —CH$_3$, —CF$_3$, and CN;
R$^4$, R$^7$, R$^8$, and R$^9$ are hydrogen;
R$^6$ is hydrogen or —CH$_3$;
R$^3$ is selected from the group consisting of —C$_1$-C$_6$ alkyl, —C$_3$-C$_6$ cycloalkyl and —CH$_2$-phenyl optionally substituted on phenyl by halogen;
R$^5$ is —OH;
X is P(O)YR$^{11}$Y'R$^{11}$;
Y and Y' are —O— or —NH—;
when Y and Y' are —O—, R$^{11}$ attached to —O— is independently selected from the group consisting of —H, —C(R$^z$)$_2$—OC(O)R$^y$, —C(R$^z$)$_2$—O—C(O)OR$^y$, and optionally substituted CH$_2$ heterocycloalkyl
when Y and Y' are —NH— R$^{11}$ attached to —NH— is independently selected from the group consisting of H and —C(R$^x$)$_2$—COOR$^y$;
each R$^z$ is independently —H or C$_1$-C$_4$ alkyl;
R$^y$ is C$_1$-C$_4$ alkyl;
each R$^x$ is independently —H or C$_1$-C$_4$ alkyl;
or a pharmaceutically acceptable salt thereof.

2. The compound of claim 1, wherein R$^1$ and R$^2$ are each —CH$_3$.

3. The compound of claim 1, wherein Y and Y' are each —NH—.

4. The compound of claim 3, wherein R$^{11}$ attached to —NH— is —C(R$^x$)$_2$—COOR$^y$.

5. The compound of claim 1, wherein Y and Y' are —O—.

6. The compound of claim 5, wherein R$^{11}$ attached to —O— is —H or a pharmaceutically acceptable salt thereof.

7. The compound of claim 5, wherein R$^{11}$ attached to —O— is selected from the group consisting of —C(R$^z$)$_2$—OC(O)R$^y$ and —C(R$^z$)$_2$—O—C(O)OR$^y$.

8. A compound selected from the group consisting of:

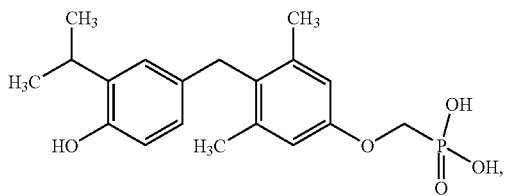

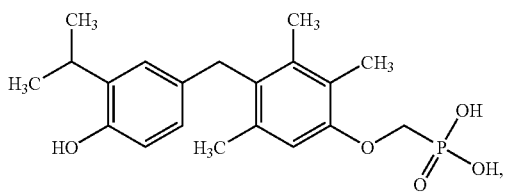

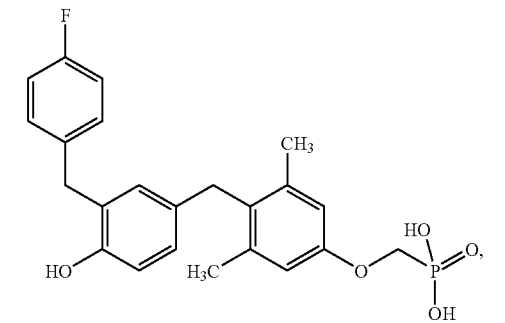

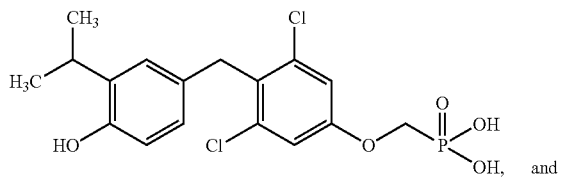

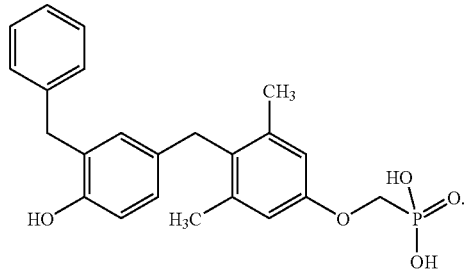

9. A compound:

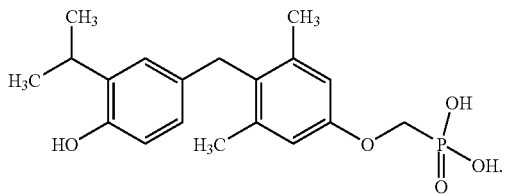

10. A compound:
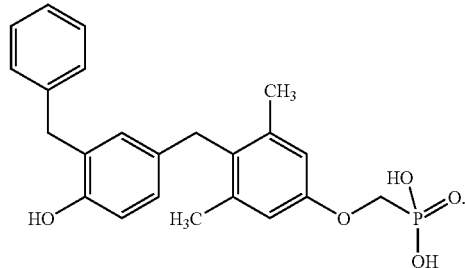
11. A compound selected from the group consisting of:
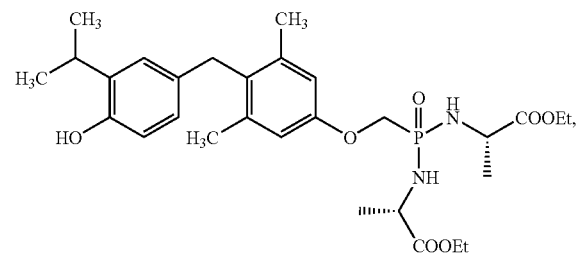
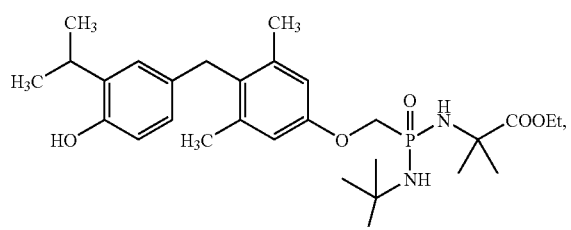
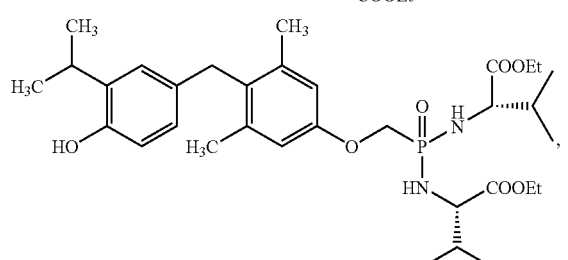
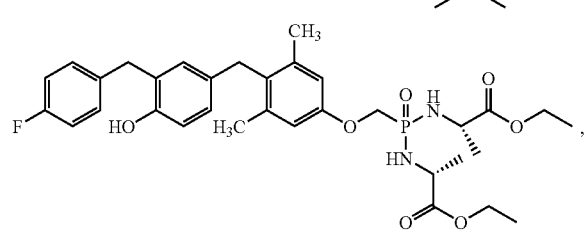
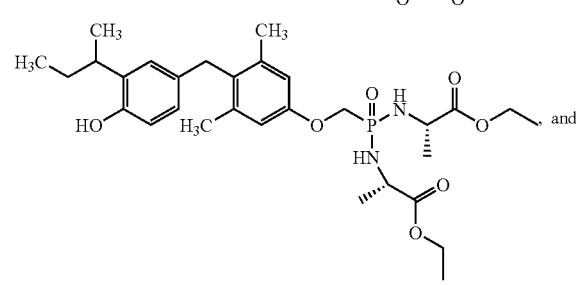
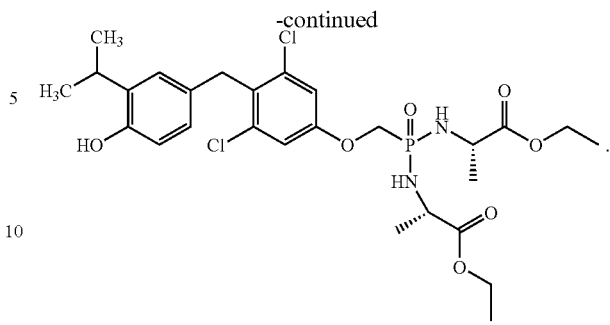
12. A compound selected from the group consisting of:
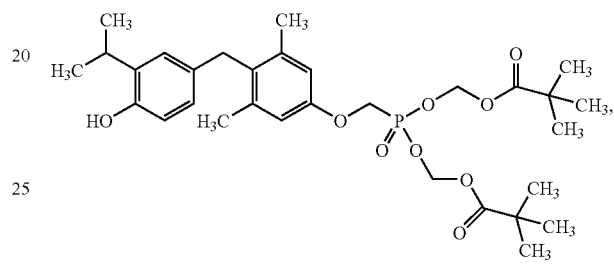
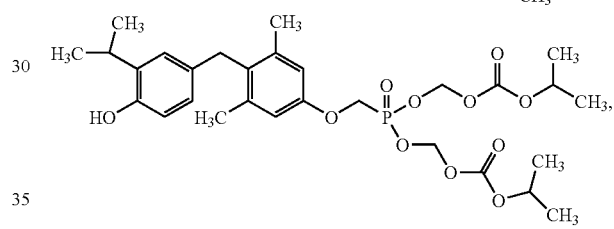
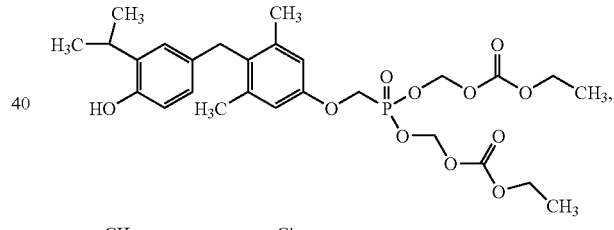
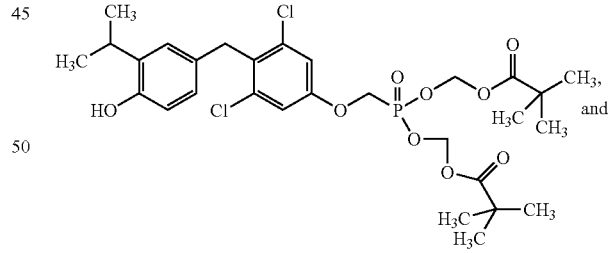
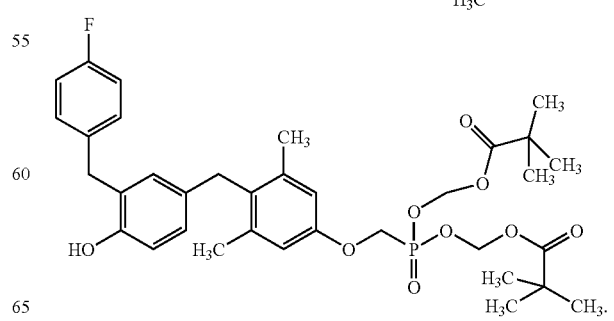

13. A pharmaceutical composition comprising a compound of any one of claims 1-12 and a pharmaceutically acceptable excipient, carrier, or diluent.

14. The pharmaceutical composition of claim 13 wherein said pharmaceutical composition in a form selected from the group consisting of a controlled release composition, transdermal patch, tablet, hard capsule, and soft capsule.

15. The pharmaceutical composition of claim 13 wherein said pharmaceutical composition comprises a crystalline form of said compound.

16. The pharmaceutical composition of claim 13 wherein said pharmaceutical composition comprises a salt form of said compound.

17. The pharmaceutical composition of claim 13 wherein said pharmaceutical composition is administered orally in a unit dose of about 0.375 μg/kg to 3.75 mg/kg.

18. The new pharamaceutical compostion of claim 13 wherein said pharmaceutical composition is administered orally in a total daily dose of about 0.375 μg/kg/day to about 3.75 mg/kg/day, equivalent of the free acid.

* * * * *